US009593306B2

(12) United States Patent
Davis et al.

(10) Patent No.: US 9,593,306 B2
(45) Date of Patent: Mar. 14, 2017

(54) DIFFERENTIATION OF PLURIPOTENT STEM CELLS

(75) Inventors: Janet Davis, Skillman, NJ (US); Jiajian Liu, Skillman, NJ (US); Christine Parmenter, Skillman, NJ (US); Pascal Ghislain André Bonnet, Beerse (BE)

(73) Assignee: Janssen Biotech, Inc., Horsham, PA (US)

( * ) Notice: Subject to any disclaimer, the term of this patent is extended or adjusted under 35 U.S.C. 154(b) by 81 days.

(21) Appl. No.: 13/434,409

(22) Filed: Mar. 29, 2012

(65) Prior Publication Data
US 2012/0196365 A1  Aug. 2, 2012

Related U.S. Application Data

(63) Continuation of application No. 12/494,789, filed on Jun. 30, 2009.

(60) Provisional application No. 61/076,900, filed on Jun. 30, 2008, provisional application No. 61/076,908, filed on Jun. 30, 2008, provisional application No. 61/076,915, filed on Jun. 30, 2008.

(51) Int. Cl.
*C12N 5/071* (2010.01)
*C12N 5/0735* (2010.01)

(52) U.S. Cl.
CPC ......... *C12N 5/0606* (2013.01); *C12N 5/0678* (2013.01)

(58) Field of Classification Search
None
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,083,903 A | 7/2000 | Adams et al. |
| 6,087,113 A | 7/2000 | Caplan et al. |
| 6,200,806 B1 | 3/2001 | Thomson |
| 6,261,549 B1 | 7/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 4/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |

(Continued)

FOREIGN PATENT DOCUMENTS

| | | |
|---|---|---|
| CN | 1389565 A | 7/2002 |
| CN | 1602351 A | 3/2005 |
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |

(Continued)

OTHER PUBLICATIONS

Ding et al., Proc. Natl. Acad. Sci. USA, 2003, 100: 7632-7637).*
Guan et al., Journal of combinatorial Chemistry, 2000, 2: 297-300.*
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.

(Continued)

*Primary Examiner* — Ileana Popa
(74) *Attorney, Agent, or Firm* — Lois A. Gianneschi

(57) ABSTRACT

The present invention is directed to methods to differentiate pluripotent stem cells. In particular, the present invention is directed to methods and compositions to differentiate pluripotent stem cells into cells expressing markers characteristic of the definitive endoderm lineage comprising culturing the pluripotent stem cells in medium comprising a sufficient amount of GDF-8 to cause the differentiation of the pluripotent stem cells into cells expressing markers characteristic of the definitive endoderm lineage.

13 Claims, 126 Drawing Sheets

(56) References Cited

U.S. PATENT DOCUMENTS

| | | | |
|---|---|---|---|
| 6,642,048 B2 | 11/2003 | Xu | |
| 6,656,488 B2 | 12/2003 | Yi et al. | |
| 6,670,127 B2 | 12/2003 | Evans | |
| 6,703,017 B1 | 3/2004 | Peck et al. | |
| 6,713,446 B2 | 3/2004 | Gupta | |
| 6,793,945 B2 | 9/2004 | Bathurst et al. | |
| 6,800,480 B1 | 10/2004 | Bodnar et al. | |
| 6,815,203 B1 | 11/2004 | Bonner-Weir et al. | |
| 6,958,319 B2 | 10/2005 | Gupta | |
| 6,987,110 B2 | 1/2006 | Zhang et al. | |
| 7,005,252 B1 | 2/2006 | Thomson et al. | |
| 7,033,831 B2 | 4/2006 | Fisk et al. | |
| 7,157,275 B2 | 1/2007 | Guarino et al. | |
| 7,297,539 B2 | 11/2007 | Mandalam et al. | |
| 7,326,572 B2 | 2/2008 | Fisk et al. | |
| 7,371,576 B2 | 5/2008 | Tsang et al. | |
| 7,410,798 B2 | 8/2008 | Mandalam et al. | |
| 7,413,734 B2 | 8/2008 | Mistry et al. | |
| 7,442,548 B2 | 10/2008 | Thomson et al. | |
| 7,449,334 B2 | 11/2008 | Thomson et al. | |
| 7,510,876 B2 | 3/2009 | D'Amour et al. | |
| 7,534,608 B2 | 5/2009 | Martinson et al. | |
| 7,569,385 B2 | 8/2009 | Haas | |
| 7,585,672 B2 | 9/2009 | Odorico et al. | |
| 7,704,738 B2 | 4/2010 | D'Amour et al. | |
| 7,993,920 B2 | 8/2011 | Martinson et al. | |
| 8,187,878 B2 † | 5/2012 | Dalton | |
| 2002/0072117 A1 | 6/2002 | Xu | |
| 2003/0082155 A1 | 5/2003 | Habener | |
| 2003/0138948 A1 | 7/2003 | Fisk et al. | |
| 2003/0180903 A1 | 9/2003 | Bryhan et al. | |
| 2004/0015805 A1 | 1/2004 | Kidd | |
| 2004/0058412 A1 | 3/2004 | Ho et al. | |
| 2004/0062753 A1 | 4/2004 | Rezania | |
| 2004/0106196 A1 | 6/2004 | Fraser et al. | |
| 2004/0121460 A1 | 6/2004 | Lumelsky et al. | |
| 2004/0121461 A1 | 6/2004 | Honmou et al. | |
| 2004/0132729 A1 | 7/2004 | Salituro et al. | |
| 2004/0161419 A1 | 8/2004 | Strom et al. | |
| 2004/0171623 A1 | 9/2004 | Reynolds et al. | |
| 2004/0209901 A1 | 10/2004 | Adams et al. | |
| 2004/0220393 A1 | 11/2004 | Ward et al. | |
| 2004/0241761 A1 | 12/2004 | Sarvetnick | |
| 2005/0037488 A1 | 2/2005 | Mitalipova | |
| 2005/0037491 A1 | 2/2005 | Mistry et al. | |
| 2005/0053588 A1 | 3/2005 | Yin et al. | |
| 2005/0054093 A1 | 3/2005 | Haas | |
| 2005/0054098 A1 | 3/2005 | Mistry et al. | |
| 2005/0054102 A1 | 3/2005 | Wobus et al. | |
| 2005/0058631 A1 | 3/2005 | Kihm et al. | |
| 2005/0063961 A1 | 3/2005 | Friedlander et al. | |
| 2005/0148070 A1 | 7/2005 | Thomson et al. | |
| 2005/0158852 A1 | 7/2005 | Wang et al. | |
| 2005/0187298 A1 | 8/2005 | Vasudevan et al. | |
| 2005/0208029 A1 | 9/2005 | Umezawa et al. | |
| 2005/0233446 A1 | 10/2005 | Parsons | |
| 2005/0244962 A1 | 11/2005 | Thomson et al. | |
| 2005/0260749 A1 | 11/2005 | Odorico et al. | |
| 2005/0266554 A1 | 12/2005 | D'Amour | |
| 2006/0003446 A1 | 1/2006 | Keller | |
| 2006/0030042 A1 | 2/2006 | Brivaniou et al. | |
| 2006/0040387 A1 | 2/2006 | Fisk | |
| 2006/0148081 A1 | 7/2006 | Kelly et al. | |
| 2006/0194315 A1 | 8/2006 | Condie et al. | |
| 2006/0194321 A1 | 8/2006 | Colman et al. | |
| 2006/0281174 A1 | 12/2006 | Xu et al. | |
| 2007/0010011 A1 | 1/2007 | Parsons | |
| 2007/0082397 A1 | 4/2007 | Hasson et al. | |
| 2007/0154981 A1 | 7/2007 | Hori et al. | |
| 2007/0155661 A1* | 7/2007 | Kim | 514/12 |
| 2007/0254359 A1* | 11/2007 | Rezania et al. | 435/325 |
| 2007/0259421 A1 | 11/2007 | D'Amour et al. | |
| 2007/0259423 A1 | 11/2007 | Odorico | |
| 2007/0264713 A1 | 11/2007 | Terstegge et al. | |
| 2008/0091234 A1 | 4/2008 | Kladakis et al. | |
| 2008/0241107 A1 | 10/2008 | Copland, III et al. | |
| 2008/0260700 A1 | 10/2008 | Accili et al. | |
| 2008/0267926 A1 | 10/2008 | Martinson et al. | |
| 2008/0268533 A1 | 10/2008 | Dalton et al. | |
| 2008/0268534 A1 | 10/2008 | Robins et al. | |
| 2009/0004152 A1 | 1/2009 | Martinson et al. | |
| 2009/0053182 A1 | 2/2009 | Ichim et al. | |
| 2009/0093055 A1 | 4/2009 | Fisk et al. | |
| 2009/0170198 A1 | 7/2009 | Rezania | |
| 2009/0203141 A1 | 8/2009 | Lin et al. | |
| 2009/0263896 A1 | 10/2009 | Kelly et al. | |
| 2009/0269845 A1 | 10/2009 | Rezania et al. | |
| 2009/0298178 A1 † | 12/2009 | D'Amour | |
| 2009/0325293 A1 | 12/2009 | Davis et al. | |
| 2010/0003749 A1 | 1/2010 | Uchida et al. | |
| 2010/0015100 A1 | 1/2010 | Xu | |
| 2010/0015711 A1 | 1/2010 | Davis et al. | |
| 2010/0028307 A1 | 2/2010 | O'Neil | |
| 2010/0093053 A1 | 4/2010 | Oh et al. | |
| 2010/0112691 A1 | 5/2010 | Green et al. | |
| 2010/0112693 A1 | 5/2010 | Rezania et al. | |
| 2010/0255580 A1 | 10/2010 | Rezania | |
| 2011/0014703 A1 | 1/2011 | Xu et al. | |
| 2011/0151560 A1 | 6/2011 | Xu | |
| 2011/0229441 A1 | 9/2011 | Benchoua et al. | |
| 2011/0281355 A1 | 11/2011 | Xu | |
| 2012/0045830 A1 | 2/2012 | Green et al. | |
| 2012/0052576 A1 | 3/2012 | Rezania | |
| 2012/0190111 A1 | 7/2012 | Davis et al. | |
| 2012/0264209 A1 | 10/2012 | Odorico et al. | |
| 2013/0189777 A1 | 7/2013 | Rezania | |
| 2013/0224156 A1 | 8/2013 | Takahashi et al. | |

FOREIGN PATENT DOCUMENTS

| | | |
|---|---|---|
| EP | 348969 B1 | 5/1993 |
| EP | 0617126 B1 | 9/1994 |
| EP | 0800829 B1 | 10/1997 |
| EP | 92302 B1 | 11/2006 |
| EP | WO 2007/003525 * | 1/2007 |
| EP | 1873237 A1 | 1/2008 |
| EP | 1391505 B1 | 1/2009 |
| EP | 2088190 A1 | 8/2009 |
| EP | 2479260 B1 | 6/2016 |
| GB | 2484873 B2 | 4/2014 |
| JP | 2005506074 A2 | 3/2005 |
| JP | 2006-500003 A2 | 1/2006 |
| JP | 2008500809 A2 | 1/2008 |
| JP | 2009513143 A2 | 4/2009 |
| KR | 10-2008-0020098 A | 3/2008 |
| RU | 2359671 C2 | 6/2009 |
| WO | 9219759 A2 | 2/1992 |
| WO | 9847892 A1 | 10/1998 |
| WO | 9920741 A1 | 4/1999 |
| WO | 0029549 A1 | 5/2000 |
| WO | 0123528 A1 | 4/2001 |
| WO | 0151616 A2 | 7/2001 |
| WO | 0181549 A3 | 11/2001 |
| WO | 0246183 A2 | 6/2002 |
| WO | 0246197 A1 | 6/2002 |
| WO | 02086107 A2 | 10/2002 |
| WO | 02092756 A2 | 11/2002 |
| WO | 03026584 A2 | 4/2003 |
| WO | 03029445 A1 | 4/2003 |
| WO | 03033697 A1 | 4/2003 |
| WO | 03042405 A2 | 5/2003 |
| WO | 03005049 A1 | 6/2003 |
| WO | 03054169 A1 | 7/2003 |
| WO | 03062405 A2 | 7/2003 |
| WO | 03095452 A1 | 11/2003 |
| WO | 03102134 A2 | 12/2003 |
| WO | 03103972 A1 | 12/2003 |
| WO | 2004011621 A2 | 2/2004 |
| WO | 2004016747 A2 | 2/2004 |
| WO | 2004044158 A2 | 5/2004 |
| WO | 2004050827 A2 | 6/2004 |
| WO | 2004055155 A2 | 7/2004 |
| WO | 2004073633 A1 | 9/2004 |
| WO | 2004087885 A2 | 10/2004 |

(56) References Cited

FOREIGN PATENT DOCUMENTS

| | | |
|---|---|---|
| WO | 2004090110 A2 | 10/2004 |
| WO | 2004067001 A1 | 12/2004 |
| WO | 2005001077 A2 | 1/2005 |
| WO | 2005080598 A1 | 1/2005 |
| WO | 2005014799 A1 | 2/2005 |
| WO | 2005017117 A2 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | 2005116073 A3 | 12/2005 |
| WO | 2006016999 A1 | 2/2006 |
| WO | 2006020919 A2 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006094286 A2 | 9/2006 |
| WO | 2006100490 A1 | 9/2006 |
| WO | 2006108361 A1 | 10/2006 |
| WO | 2006113470 A2 | 10/2006 |
| WO | 2006114098 A2 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007027157 A1 | 3/2007 |
| WO | 2007030870 A1 | 3/2007 |
| WO | 2007047509 A1 | 4/2007 |
| WO | 2007051038 A2 | 5/2007 |
| WO | 2007069666 A1 | 6/2007 |
| WO | 2007082963 A1 | 7/2007 |
| WO | 2007103282 A1 | 9/2007 |
| WO | 2007127927 A2 | 11/2007 |
| WO | 2007139929 A2 | 12/2007 |
| WO | 2007143193 A1 | 12/2007 |
| WO | 2007149182 A2 | 12/2007 |
| WO | 2008004990 A2 | 1/2008 |
| WO | 2008013664 A1 | 1/2008 |
| WO | 2008035110 A1 | 3/2008 |
| WO | 2008036447 A2 | 3/2008 |
| WO | 2008048647 A1 | 4/2008 |
| WO | 2008048671 A1 | 4/2008 |
| WO | 2008086005 A1 | 7/2008 |
| WO | 2008094597 A1 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | 2009048675 A1 | 4/2009 |
| WO | 2009061442 A1 | 5/2009 |
| WO | 2009070592 A1 | 6/2009 |
| WO | 2009096049 A1 | 8/2009 |
| WO | 2009096902 A1 | 8/2009 |
| WO | 2009101407 A2 | 8/2009 |
| WO | 2009105570 A2 | 8/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011067465 A1 | 6/2011 |
| WO | 2011108993 A1 | 9/2011 |
| WO | 2011123572 A1 | 10/2011 |
| WO | 2011139628 A1 | 11/2011 |
| WO | 2012019122 A2 | 2/2012 |
| WO | 2012117333 A1 | 9/2012 |
| WO | 2013055834 A2 | 4/2013 |
| WO | 2013184888 A1 | 12/2013 |
| WO | 2014152321 A1 | 9/2014 |

OTHER PUBLICATIONS

Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.

Ackermann, et al., Molecular Regulation of Pancreatic B-Cell Mass Development, Maintenance, and Expansion, Journal of Molecular Endocrinology, 2007, pp. 193-206, vol. 38.

Adams, J., Proteasome Inhibition in Cancer: Development of PS-341, Seminars in Oncology, 2001, pp. 613-619, vol. 28, No. 6.

Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.

Allegrucci, et al., Differences between Human Embryonic Stem Cell Lines, Human Reproduction Update, Aug. 26, 2006, pp. 1-18, Advance Access.

Almond, et al., The Proteasome: A Novel Target for Cancer Chemotherapy, Leukemia, 2002, pp. 433-443, vol. 16.

Amit et al., Human Feeder Layers for Human Embryonic Stem Cells, Biology of Reproduction, Jan. 22, 2003, 2150-2156, 68, No. 6, Society for the Study of Reproduction, Inc.

Amit, et al., Clonally Derived Human Embryonic Stem Cell Lines Maintain Pluripotency and Proliferative Potential for Prolonged Periods of Culture, Developmental Biology, 2000, pp. 271-278, vol. 227.

Amit, et al., Feeder Layer- and Serum-Free Culture of Human Embryonic Stem Cells, Biology of Reproduction, 2004, pp. 837-845, vol. 70.

Arai, et al., Purification of Recombinant Activin A Using the Second Follistatin Domain of Follistatin-Related Gene (FLRG), Protein Expression & Purification, 2006, pp. 78-82, vol. 49.

Armstrong, et al., The Role of PI3K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.

Baetge, Production of B-Cells from Human Embryonic Stem Cells, Diabetes, Obesity, Metabolism, 2008, pp. 186-194, vol. 10, Supplement 4.

Balsam, et al., Haematopoeitic Stem Cells Adopt Mature Haeatopoietic Fates in Ischaemic Myocardium, Nature, Apr. 8, 2004, pp. 668-673, Nature Publishing Group.

Barclay, et al., The Leucocyte Antigen Facts Book, The Leucocyte Antigen Facts Book, 1997, Textbook, 2[sup] edition, Academic Press.

Beltrami, et al., Adult Cardiac Stem Cells are Multipotent and Support Myocardial Regeneration, Cell, Sep. 19, 2003, pp. 763-776, vol. 114, Cell Press.

Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.

Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.

Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.

Bocian-Sobkowska, et al., Polyhormonal Aspect of the Endocrine Cells of the Human Fetal Pancreas, Histochem Cell Biol, 1999, pp. 147-153, vol. 112, Issue 2.

(56) References Cited

OTHER PUBLICATIONS

Bonner-Weir et al., In vitro cultivation of human islets from expanded ductal tissue, Proceedings of the National Academy of Sciences, Jul. 5, 2000, 7999-8004, 97-14, National Academy of Sciences.

Borowiak, et al., How to Make AB Cells, Current Opinion Cell Biology, 2009, pp. 727-732, vol. 21, Issue 6.

Braam, et al., Improved Genetic Manipulation of Human Embryonic Stem Cells, Nature Methods, May 2008, pp. 389-392, vol. 5, No. 5.

Brakenhoff et al., Development of a Human Interleukin-6 Receptor Antagonist, Journal of Biological Chemistry, Jan. 7, 1994, 86-93, 269-1, US.

Brambrink, et al., Sequential Expression of Pluripotency Markers During Direct Reprogramming of Mouse Somatic Cells, Cell Stem Cell, 2008, pp. 151-159, vol. 2.

Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.

Brevini, et al., No Shortcuts to Pig Embryonic Stem Cells, Theriogenology, 2010, pp. 544-550, vol. 74.

Bross, et al., Approval Summary for Bortezomib for Injection in the Treatment of Multiple Myeloma, Clinical Cancer Research, Jun. 15, 2004, pp. 3954-3964, vol. 10.

Brown, et al., Optimal Control of Blood Glucose: The Diabetic Patient or the Machine?, Science Translation Medicine, Apr. 14, 2010, pp. 1-5, vol. 2 Issue 27.

Burkard et al., Conditional Neuronal Nitric Oxide Synthase Overexpression Impairs Myocardial Contractility, Circulation Reseach, Jan. 18, 2007, pp. e32-e44, vol. 100.

Buzzard et al., Karyotype of human ES cells during extended culture, Nature, Apr. 1, 2004, 381-382, 22-4, Nature Publishing Group.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem Cells, Cell, May 30, 2003, pp. 643-655, vol. 113.

Chapple, et al., Unfolding Retinal Dystrophies: A Role for Molecular Chaperones?, Trends in Molecluar Medicine, 2001, pp. 414-421, vol. 7, No. 9.

Chen, et al., A Small Molecule that Directs Differentiation of Human ESCs into the Pancreatic Lineage, Nature Chemical Biology, Apr. 11, 2009, pp. 258-265, vol. 5, No. 4.

Chen, et al., Chemically Defined Conditions for Human iPSC Derivation and Culture, Nature Methods, 2011, pp. 424-429, vol. 8, Issue 5.

Chen, et al., Differentiation of Rat Marrow Mesencymal Stem Cells in Pancreatic Islet Beta-Cells, World Journal of Gastroenterology, Oct. 15, 2004, pp. 3016-3020.

Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.

Cheon, et al., Defined Feeder-Free Culture System of Human Embryonic Stem Cells, Biol Reprod, 2005, 105.046870, DOI10/1095.

Chung, et al., Human Embryonic Stem Cell Lines Generated without Embryo Destruction, Cell Stem Cell, 2008, pp. 113-117, vol. 2.

Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.

Crane, et al., An Embryogenic Model to Explain Cytogenetic Inconsistencies Observed in Chorionic Villus Versus Fetal Tissue, Prenatal Diagnosis, 1988, pp. 119-129, vol. 8.

Cresta, et al., Phase I Study of Bortezomib with Weekly Paclitaxel in Patients with Advanced Solid Tumours, European Journal of Cancer, 2008, pp. 1829-1834, vol. 44.

Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.

D'Amour et al., Efficient differentiation of human embryonic stem cells to definitive endoderm, Nature Biotechnology, Oct. 28, 2005, 1-8, :W.1038/nbt1163, Nature Publishing Group.

D'Amour et al., Production of pancreatic hormone-expressing endocrine cells from human embryonic stem cells, Nature Biotechnology, Oct. 19, 2006, 1392-1401, 24-11, Nature Publishing Group, US.

David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.

De Coppi, et al., Isolation of Amniotic Stem Cell Lines with Potential for Therapy, Nature Biotechnology, 2007, pp. 100-106, vol. 25, No. 1.

Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.

Donovan, et al., The End of the Beginning for Pluripotent Stem Cells, Nature, Nov. 2001, pp. 92-97, vol. 414.

Dorrell, et al., Editorial, Stem Cell Research, 2008, pp. 155-156, vol. 1.

Doyle, et al., Cell and Tissue Culture: Laboratory Procedures in Biotechnology, Cell and Tiossue Culture: Laboratory Procedures in Biotechnology, 1995, Textbook, Textbook, Wiley.

Draper, et al., Recurrent Gain of Chromosomes 17q and 12 in Cultured Human Embryonic Stem Cells, Nature Biotechnology, 2004, pp. 53-54, vol. 22, No. 1.

Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.

Dupont-Gillain, et al., Plasma-Oxidized Polystyrene: Wetting Properties and Surface Reconstruction, Langmuir, 2000, pp. 8194-8200, vol. 16.

Edlund, Pancreatic Organogenisis—Pancreatic Mechanisims and Implications for Therapy, Nature, Jul. 1, 2002, 524-532, 3, Nature Publishing Group, US.

Ellerstrom, et al., Derivation of a Xeno-Free Human Embryonic Stem Cell Line, Stem Cells, 2006, pp. 2170-2176, vol. 24.

Ellerstrom, et al., Facilitated Expansion of Human Embryonic Stem Cells by Single-Cell Enzymatic Dissociation, Stem Cells, 2007, pp. 1690-1696, vol. 25, No. 7.

Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.

Enzmann, et al., Enhanced Induction of RPE Lineage Markers in Pluripootent Neural Stem Cells Engrafted into the Adult Rat Subretinal Space, Investigative Ophthalmology & Visual Science, Dec. 2003, pp. 5417-5422, vol. 44, No. 12, Association for Research in Vision and Ophthamology.

Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.

Ezashi, et al., Low 02 Tensions and the Prevention of Differentiation of hES Cells, Proceedings of the National Academy of Sciences of USA, Mar. 29, 2005, pp. 4783-4788, vol. 102, No. 13.

Fauza, Amniotic Fluid and Placental Stem Cells, Ballieres Best Practice and Research Clinical Obsterics and Gynaecology, 2004, pp. 877-891, vol. 18, No. 6.

(56) References Cited

OTHER PUBLICATIONS

Fidler et al., Selective Immunomodulation by the Antineoplastic Agent Mitoxantrone, Journal of Immunology, Jul. 15, 1986, 727-732, 137-2, American Society of Immunologists, US.
Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.
Fok, et al., Shear-Controlled Single-Step Mouse Embryonic Stem Cell Expansion and Embryoid Body-Based Differentiation, Stem Cells, 2005, pp. 1333-1342, vol. 23.
Frandsen et al., Activin B mediated induction of Pdx1 in human embryonic stemcell derived embryoid bodies, Biochemical and Biophysical Research Communications, Aug. 15, 2007, 568-574, 362, Elsevier Inc.
Fung, et al., The Effect of Medical Therapy and Islet Cell Transplantation on Diabetic Nephropathy: An Interim Report, Transplantation, Jul. 15, 2007, pp. 17-22, vol. 84, No. 1.
Gadue, et al., Wnt and TGB-B Signaling are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gershengorn et al., Epithelial-to-Mesenchymal Transition Generates Proliferative Human Islet Precursor Cells, Science, Dec. 24, 2004, 2261-2264, 306, US.
Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, pp. 360-380, vol. 269.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.
Guo, et al., Stem Cells to Pancreatic B-Cells: New Sources for Diabetes Cell Therapy, Endocrine Reviews, May 2009, pp. 214-227, vol. 30, No. 3, The Endocrine Society.
Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.
Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.
Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.
Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.
Hasegawa, et al., A Method for the Selection of Human Embryonic Stem Cell Sublines with High Replating Efficiency After Single-Cell Dissociation, Stem Cells, 2006, pp. 2649-2660, vol. 24.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.
Henderson, et al., Preimplantation Human Embryos and Embryonic Stem Cells Show Comparable Expression of Stage-Specific Embryonic Antigens, Stem Cells, 2002, pp. 329-337, vol. 20.
Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.
Herzenberg, et al., Fluorescence-activated Cell Sorting, Scientific American, 1976, 108-117, 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Hichem Frigui, et al., A Robust Competitive Clustering Algorithm With Applications in Computer Vision, IEEE, May 1, 1999, 450-465, 21-5, IEEE, US.
Ho, et al., Animal Cell Bioreactors, Animal Cell Bioreactors, 1991, 1-512, Hardcover, Butterworth-Heinemann.
Hoehn, et al., Morphological and Biochemical Heterogeneity of Amniotic Fluid Cells in Culture, Methods in Cell Biology, 1982, pp. 11-34, vol. 26, Academic Press, Inc.
Hori, et al., Growth inhibitors promote differentiation of insulin-producing tissue from embryonic stem cells, Proceedings of the National Academy of Sciences, Dec. 10, 2002, 16105-16110, 99-25, National Academy of Sciences.
Hussain, et al., Stem-Cell Therapy for Diabetes Mellitus, Lancet, 2004, pp. 203-205, vol. 364.
Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.
Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.
Int Anker, et al., Amniotic Fluid as a Novel Source of Mesenchymal Stem Cells for Therapeutic Transplantation, Blood, Aug. 15, 2003, pp. 1548-1549, vol. 102, No. 4.
Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.
Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.
Jeon, et al., Endocrine Cell Clustering During Human Pancreas Development, J Histochem Cytochem, 2009, pp. 811-824, vol. 57, Issue 9.
Jiang, et al., Generation of Insulin-Producing Islet-Like Clusters from Human Embryonic Stem Cells, Stem Cells, 2007, pp. 1940-1953, vol. 25, Issue 8.
Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.
Kahan, Pancreatic Precursors and Differentiated Islet Cell Types from Murine Embryonic Stem Cells, Diabetes, Aug. 2003, pp. 2016-2042, vol. 52.
Kelly, et al., Cell-Surface Markers for the Isolation of Pancreatic Cell Types Derived from Human Embryonic Stem Cells, Nature Biotechnology, 2011, pp. 750-756, vol. 29, Issue 8.
Kicic, et al., Differentiation of Marrow Stromal Cells into Photoreceptors in the Rat Eye, The Journal of Neuroscience, Aug. 27, 2003, pp. 7742-7749, vol. 23, Issue 21.
Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.
Kinkel, et al., Cyp26 Enzymes Function in Endoderm to Regulate Pancreatic Field Size, PNAS, May 12, 2009, pp. 7864-7869, vol. 106, No. 19.
Kleinman et al., Basement Membrane Complexes with Biological Activity, Biochemistry, 1986, 312-318, 25, American Chemical Society.

(56) References Cited

OTHER PUBLICATIONS

Klimanskaya, et al., Human Embryonic Stem Cells Derived without Feeder Cells, Lancet, May 2005, pp. 1636-1641, vol. 365, No. 9471.
Koblas, et al., Differentiation of CD133-Positive Pancreatic Cells Into Insulin-Producing Islet-Like Cell Clusters, Transplantation Proceedings, 2008, pp. 415-418, vol. 40.
Kohen, et al., Characterization of Matrigel Interfaces During Defined Human Embryonic Stem Cell Culture, Biointerphases, Dec. 2009, pp. 6979.
Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.
Koyangi et al., Inhibition of the Rho/ROCK Pathway Reduces Apoptosis During Transplantatation of Embryonic Stem Cell-Derived Neural Precursors, Journal of Neurosciene Research, Sep. 7, 2007, 270-280, 86, Wiley-Liss, Inc.
Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.
Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.
Kron, et al., Expression of Human Activin C Protein in Insect Larvae Infected with a Recombinant Baculovirus, Journal of Virological Methods, 1998, pp. 9-14, vol. 72.
Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.
Ku et al., Committing Embryonic Stem Cells to Early Endocrine Pancreas In Vitro, Stem Cells, 2004, 1205-1217, 22, AlphaMed Press.
Kubo et al., Development of definitive endoderm from embryonic stem cells in culture, Development, 2004, 1651-1662, 131, The Company of Biologists.
Lanza, et al., Characteristics and Characterization of Human Pluripotent Stem Cells, Stem Cell Anthology, 2010, pp. 141, 142, 144 and 146, 1st Edition.
Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.
Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.
Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.
Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.
Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.
Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.
Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.
Levenstein et al., Basic Fibroblast Growth Factor Support of Human Embryonic Stem Cell Self-Renewal, Stem Cells, Nov. 10, 2005, 568-574, 24, AlphaMed Press.
Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.
Lilja et al., Cyclin-dependent Kinase 5 Promotes Insulin Exocytosis, Journal of Biological Chemistry, Jul. 6, 2001, 34199-34205, 36-7, JBC Papers in Press.
Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.
Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.
Loh, et al., Genomic Approaches to Deconstruct Puripotency, Annu Rev Genomics Hum Genet, 2011, pp. 165-185, vol. 12.
Ludwig, et al., Derivation of Human Embryonic Stem Cells in Defined Conditions, Nature Biotechnology, Feb. 2006, pp. 185-187, vol. 24 No. 2.
Lumelsky, et al., Differentiation of Embryonic Stem Cells to Insulin-Secreting Structures Similar to Pancreatic Islets, Science, 2001, 1389-1394, 292, HighWire Press.
Lund, et al., Cell Transplantation as a Treatment for Retinal Disease, Progress in Retinal and Eye Research, 2001, pp. 415-449, vol. 20, No. 4, Elsevier Science Ltd.
Lund, et al., Retinal Transplantation: Progress and Problems in Clinical Application, Journal of Leukocyte Biology, Aug. 2003, pp. 151-160, vol. 74.
Lyttle, et al., Transcription Factor Expression in the Developing Human Fetal Endocrine Pancreas, Diabetologica, 2008, pp. 1169-1180, vol. 51, Spring-Verlag.
MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.
Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.
Marshall, et al., Early Micro- and Macro-Angiopathy in the Streptozotocin, Research in Experimental Medicine, 1980, pp. 145-158, vol. 177, Springer-Verlag.
Marshall, et al., Isolation and Maintenance of Primate Embryonic Stem Cells, Methods in Molecular Biology, 2001, pp. 11-18, vol. 158.
Martin, et al., Bioreactors for Tissue Mass Culture: Design, Characterization, and Recent Advances, Biomaterials, Jul. 14, 2005, pp. 7481-7503, vol. 26.
Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.
McKiernan, et al., Directed Differentiation of Mouse Embryonic Stem Cells into Pancreatic-Like or Neuronal- and Glial-Like Phenotypes, Tissue Engineering, 2007, pp. 2419-2430, vol. 13, No. 10.
McLean et al., Activin A Efficiently Specifies Definitive Endoderm from Human Embryonic Stem Cells Only When Phosphatidylinositol 3-Kinase Signaling is Suppressed, Stem Cells, 2007, 29-38, 25, AlphaMed Press.
McLin, et al., Repression of WNT/(szligbeta)-6atenin Signaling in the Anterior Endoderm is Essential for Liver and Pancreas Development, Development, 2007, pp. 2207-2217, vol. 134, Issue 12.
Meijer, et al., Pharmacological Inhibitors of Glycogen Synthase Kinase 3, Trends in Pharmacological Sciences, Sep. 2004, pp. 471-480, vol. 25, No. 9.
Micallef et al., Retinoic Acid Induces Pdx1-Positive Endoderm in Differentiating Mouse Embryonic Stem Cells, Diabetes, Feb. 2005, 301-305, 54, American Diabetes Association.

(56) References Cited

OTHER PUBLICATIONS

Michael J. Borowitz, et al., Prognostic Significance of Fluorescence Intensity of Surface Marker . . . , Blood, Jun. 1, 1997, 3960-3966, 89-11, American Society of Hematology, Washington, D.C., US.

Miller, et al., The Pig as a Model for Human Nutrition, Annual Review of Nutrition, 1987, pp. 361-382, vol. 7, Annual Reviews Inc.

Milunsky, et al., Genetic Disorders and the Fetus: Diagnosis Prevention and Treatment, Pediatric and Developmental Pathology, 2011, pp. 84, vol. 14, Society for Pediatric Pathology.

Mitalipova, et al., Preserving the Genetic Integrity of Human Embyonic Stem Cells, Nature Biotechnology, 2005, pp. 19-20, vol. 23, No. 1.

Mitsui, et al., The Homeoprotein Nanog is Required for Maintenance of Pluripotency in Mouse Epiblast and ES Cells, Cell, May 30, 2003, pp. 631-642, vol. 113, Cell Press.

Miyamoto et al., Human Placenta Feeder Layers Support Undifferentiated Growth of Primate Embryonic Stem Cells, Stem Cells, 2004, 433-440, 22, AlphaMed Press.

Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.

Moore, et al., The Corneal Epithelial Stem Cell, DNA and Cell Biology, 2002, pp. 443-451, vol. 21, No. 5/6.

Moran, et al., Bidirectional-Barbed Sutured Knotless Running Anastomosis v Classic van Velthoven in a Model System, Journal of Endourology, 2007, pp. 1175-1177, vol. 21, No. 10.

Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.

Movassat, et al., Keratinocyte Growth Factor and Beta-Cell Differentiation in Human Fetal Pancreatic Endocrine Precursor Cells, Diabetologia, 2003, pp. 822-829, vol. 46.

Muchamuel, et al., Preclinical Pharmacology and in Vitro Characterization of PR-047, An Oral Inhibitor of the 20s Proteasome, Blood, Nov. 16, 2008, p. 1257, vol. 112, No. 11.

Munoz, et al., Conventional Pluripotency Markers are Unspecific for Bovine Embryonic-Derived Cell-Lines, Theriogenology, 2008, pp. 1159-1164, vol. 69.

Murtha, et al., Evaluation of a Novel Technique for Wound Closure Using a Barbed Suture, Cosmetic, Aug. 2, 2005, pp. 1769-1780, vol. 117, No. 6.

Nakagawa, et al., Generation of Induced Pluripotent Stem Cells without Myc from Mouse and Human Fibroblasts, Jan. 2008, pp. 101-106, vol. 26, No. 1.

Nakamura, et al., Ocular Surface Reconstruction Using Cultivated Mucosal Epithelial Stem Cells, Cornea, Oct. 2003, S75-S80, vol. 22, Supplement 1.

Nicholas et al., A Method for Single-Cell Sorting and Expansion of Genetically modified Human Embryonic Stem Cells, Stem Cells and Development, 2007, 109-117, 16, Mary Ann Liebert, Inc.

Nishimura, et al., Expression of MafA in Pancreatic Progenitors is Detrimental for Pancreatic Development, Developmental Biology, 2009, pp. 108-120, vol. 333.

Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.

Oh, et al., Human Embryonic Stem Cells: Technological Challenges Towards Therapy, Clinical and Experimental Pharmacology and Physiology, 2006, pp. 489-495, vol. 33.

Okita, et al., Generation of Germline-Competent Induced Pluripotent Stem Cells, Nature, Jul. 19, 2007, pp. 313-317, vol. 448.

Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.

Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.

Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.

Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.

Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.

Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.

Pangas, et al., Production and Purification of Recombinant Human Inhibin and Activin, Journal of Endocrinology, 2002, pp. 199-210, vol. 172.

Pardo, et al., Corning CellBIND Surface: An Improved Surface for Enhanced Cell Attachment, Corning Technical Report, 2005, 8 page report, XP002530385.

Paris, et al., Equine Embryos and Embryonic Stem Cells: Defining Reliable Markers of Pluripotency, Theriogeneology, 2010, pp. 516-524, vol. 74.

Peerani, et al., Niche-Mediated Control of Human Embryonic Stem Cell Self-Renewal and Differentiation, The EMBO Journal, 2007, pp. 4744-4755, vol. 26.

Peter O. Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.

Phillips, et al., Attachment and Growth of Human Embryonic Stem Cells on Microcarriers, Journal of Biotechnology, 2008, pp. 24-32, vol. 138.

Pouton, et al., Embryonic Stem Cells as a Source of Models for Drug Discovery, Nature Reviews Drug Discovery, Aug. 2007, pp. 1474-1776, vol. 6, No. 8.

Prichard, et al., Adult Adipose Derived Stem Cell Attachment to Biomaterials, Biomaterials, 2006, pp. 936-946, vol. 28, No. 6.

Prowse, et al., A Proteome Analysis of Conditioned Media from Human Neonatal Fibroblasts Used in the Maintenance of Human Embryonic Stem Cells, Proteomics, 2005, pp. 978-989, vol. 5.

Prusa, et al., Oct-4-Expressing Cells in Human Amniotic Fluid: a New Source for Stem Cell Research?, Human Reproduction, 2003, pp. 1489-1493, vol. 18, No. 7.

Rajagopal, et al., Insulin Staining of ES Cell Progeny from Insulin Uptake, Science, Jan. 17, 2003, pp. 363, vol. 299.

Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.

Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.

Rebollar, et al., Proliferation of Aligned Mammalian Cells on Laser-Nanostructured Polystyrene, Biomaterials, 2008, pp. 1796-1806, vol. 29.

Reisner, Growing Organs for Transplantation form Embryonic Precursor Tissues, Immunol. Res., 2007, pp. 261-273, vol. 38.

Reubinoff et al., Embryonic stem cell lines from human blastocysts: somatic differentiation in vitro, Nature Biotech, Apr. 18, 2000, 399-404, 18, Nature America Inc.

Rezania, Production of Functional Glucagon-Secreting-Cells from Human Embryonic Stem Cells, Diabetes, 2011, pp. 239-247, vol. 60, Issue 1.

Richards et al., Comparative Evaluation of Various Human Feeders for Prolonged Undifferentiated Growth of Human Embryonic Stem Cells, Stem Cells, 2003, 546-556, 21, AlphaMed Publlishing.

(56) References Cited

OTHER PUBLICATIONS

Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.
Ricordi et al., Automated Method for Isolation of Human Pancreatic Islets, Diabetes, Apr. 1988, 413-420, 37, American Diabetes Association.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adultmesenchymal Stem Cells in the CNS, Society for Neuroscience Abstract Viewer and Itineray Planner, 2002, XP002519394, Program 237.18.
Sato et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, 1357-1367, 13-6, IT.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Scullica, et al., Diagnosis and Classification of Macular Degenerations: an Approach Based on Retinal Function Testing, Documenta Ophthalmologica, 2001, pp. 237-250, vol. 102.
Seaberg et al., Clonal identification of multipotent precursors from adult ~ mouse pancreas that generate neural and pancreatic lineages, Nature Biotechnology, Sep. 2004, 1115-1124, 22, Nature Publishing Group.
Segev, et al., Differentiation of Human Embryonic Stem Cells into Insulin-Producing Clusters, Stem Cells, Jan. 1, 2004, pp. 265-274.
Shackleton, et al., Generation of a Functional Mammary Gland from a Single Stem Cell, Nature, Jan. 5, 2006, pp. 84-88, XP002567665, vol. 439.
Shamblott et al., Derivation of pluripotent stem cells from cultured human primordial germ cells, Developmental Biology, Nov. 1998, 13726-13731, 95, National Academy of Sciences.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.
Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.
Sherwood, et al., Transcriptional Dynamics of Endodermal Organ Formation, Developmental Dynamics, 2009, pp. 29-42, vol. 238, Issue 1.
Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.
Schindler et al., A synthetic nanofibrillar matrix promotes in vivo-like organization and morphogenesis for cells in culture, Biomaterials, Apr. 18, 2005, 5624-5631, 26, Elsevier.
Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.
Shiraki, et al., Guided Differentiation of Embryonic Stem Cells into Pdx1-Expressing Regional-Specific Definitive Endoderm, Stem Cells, 2008, pp. 874-885, vol. 26.
Sidhu et al., Derivation of Three Clones from Human Embryonic Stem Cell Lines by FACS Sorting and Their Characterization, Stem Cells and Development, 2006, 61-69, 15, Mary Ann Liebert, Inc.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.
Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.
Soria et al., Insulin-Secreting Cells Derived From Embryonic Stem Cells Normalize Glycemia in Streptozotocin-Induced Diabetic Mice, Diabetes, Feb. 2000, 1-6, 49, American Diabetes Association.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoic Acid Signaling is Required for a Critical Early Step in Zebrafish Pancreatic Development, Current Biology, 2002, pp. 1215-1220, vol. 12, Issue 14.
Stephen D. De Rosa, 11-color, 13-parameter flow cytometry: Identification of . . . , Nature, Feb. 1, 2001, 245-248, 7-2, Nature Publishing Group, US.
Stojkovic et al., An Autogeneic Feeder Cell System That Efficiently Supports Growth of Undifferentiated Human Embryonic Stem Cells, Stem Cells, 2005, 306-314, 23, AlphaMed Press.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Thomson et al., Embryonic Stem Cell Lines Derived from Human Blastocysts, Science, Nov. 6, 1998, 1145-1147, 282, HighWire Press.

(56) References Cited

OTHER PUBLICATIONS

Thomson et al., Isolation of a primate embryonic stem cell line, Developmental Biology, Aug. 1995, 7844-7848, 92, Proc. Natl. Acad. Sci, US.
Thomson et al., Primate Embryonic Stem Cells, Current Topics in Developmental Biology, 1998, 133-154, 38, Academic Press, US.
Tomita, et al., Bone Marrow-Derived Stem Cells Can Differentiate into Retinal Cells in Injured Rat Retina, Stem Cells, 2002, pp. 279-283, vol. 20.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tulachan et al., TGF-β isoform signaling regulates secondary transition and mesenchymal-induced endocrine development in the embryonic mouse pancreas, Developmental Biology, 2007, 508-521, 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos One, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediactric Surgery, Jan. 1988, 3-9, 23-1.
Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, 961-967, 4-1, Nature Reviews, US.
Van Der Windt, et al., The Chioce of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Vacuum Cell Seeding: a New Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structurs of Anthraquinones with their Effects onthe Suppression of Immune Responses, International Journal of Immunopharmacology, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, 972-980, 22, AlphaMed Press.
Xu, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Acitivity, The Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA is a Key Regulator of Glucose-Stimulated Insulin Secretion, Molecular and Cellular Biology, Jun. 2005, 4969-4976, 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.

(56) References Cited

OTHER PUBLICATIONS

Zhang, Jie, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 2003, 1-127, 1-127 (with English Abstract).
Zhang, et al., Highly Efficient Differentiation of Human ES Cells and iPS Cells into Mature Pancreatic Insulin-Producing Cells, Cell Research, 2009, pp. 429-438, vol. 19, Issue 14.
Zhao et al., The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.
Zhao, et al., Derivation and Characterization of Hepatic Progenitor Cells from Human Embryonic Stem Cells, PLoS One Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.
Abe, et al., Evidence That P13K, Rac, Rho, and Rho Kinase are Involved in Basic Fibroblast Growth Factor-Stimulated Fibroblast-Collagen Matrix Contraction, Journal of Cellular Biochemistry, 2007, pp. 1290-1299, vol. 102.
Ali, et al., Exploitation of Protein Kinase C: A Useful Target for Cancer Therapy, Cancer Treatment Reviews, 2009, pp. 1-8, vol. 35.
Assady, et al., Insulin Production by Human Embryonic Stem Cells, Diabetes, 2001, pp. 1691-1697, vol. 50.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.
Best, et al., Embryonic Stem Cells to Beta-Cells by Understanding Pancreas Development, Molecular and Cellular Endocrinology, 2008, pp. 86-94, vol. 288.
Brevini et al., Embryonic Stem Cells in Domestic Animals, Embryonic Stem Cells in Domestic Animals, 2010, pp. 544-550, vol. 74.
Cao, et al., High Glucose is Necessary for Complete Maturation of Pdx1-VP16-Expressing Hepatic Cells into Functional Insulin-Producing Cells, Diabetes, 2004, pp. 3168-3176, vol. 53.
Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.
Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.
Chetty, et al., A Simple Tool to Improve Pluripotent Stem Cell Differentiation, Nature Methods, 2013, pp. 553-558, vol. 10, No. 6.
Choi, et al., In Vitro Trans-Differentiation of Rat Mesenchymal Cells into Insulin-Producing Cells by Rat Pancreatic Extract, Biochemical and Biophysical Research Communications, 2005, pp. 1299-1305, vol. 330.
D'Amour, et al, Production of pancreatic hormone, Nature Biotechnology, 2006, pp. 1392-1401, vol. 24.
Dekker, et al., Adhesion of Endothelial Cells and Adsorption of Serum Proteins on Gas Plasma-Treated Polytetrafluoroethylene, Biomaterials, 1991, pp. 130-138, vol. 12.

Deramaudt, et al., The PDX1 Homeodomain Transcription Factor Negatively Regulates the Pancreatic Ductal Cell-specific Keratin 19 Promoter, Journal of Biological Chemistry, 2006, pp. 38385-38395, vol. 281, No. 50.
Dufour, et al., Development of an Ectopic Site for Islet Transplantation Using Biodegradable Scaffolds, Tissue Engineering, 2005, pp. 1323-1331, vol. 11, No. 9/10.
Florio, et al., Activin A Stimulates Insulin Secretion in Cultured Human Pancreatic Islets, J. Endocrinol. Invest., 2000, pp. 231-234, vol. 23.
Foster, et al., Differentiation of Transplanted Microencapsulated Fetal Pancreatic Cells, Experimental Transplantation, Jun. 15, 2007, pp. 1440-1448, vol. 83, No. 11.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Gibco, Solutions for Life Science Research and Drug Discovery, Catalogue Cell Culture Products, 2004-2005, pp. 1-4E, 281406 26 5 27.
Gittes, Developmental Biology of the Pancreas: A comprehensive Review, Developmental Biology, 2009, pp. 4-35, vol. 326, No. 1.
Gordon Weir, Do stem cells hold the key to creation of a cure for diabetes?, Diabetes Voice, 2008, pp. 29-31, Edition 53, No. 2.
Gregg Duester, Retionoic Acid Synthesis and Signaling During Early Organogenesis, Cell, 2008, pp. 921-931, vol. 134.
Hainsworth, et al., Retinal Capillar Basement Membrane Thickening in a Porcine Model of Diabetes Mellitus, Comp Med, 2002, pp. 523-529, vol. 52.
Hay, et al., Highly Efficient Differentiation of hESCs to Functional Hepatic Endoderm Requires ActivinA and Wnt3a Signaling, PNAS, 2008, pp. 12301-12306, vol. 105, No. 34.
Heinis, et al., HIF1a and Pancreatic Beta-Cell Development, The FASEB Journal, 2012, pp. 2734-2742, vol. 26.
Heinis, et al., Oxygen Tension Regulates Pancreatic Beta-Cell Differentiation Through Hypoxia-Inducible Factor 1x, Diabetes, 2010, pp. 662-669, vol. 59.
Heit, et al., Embryonic Stem Cells and Islet Replacement in Diabetes Mellitus, Pediatric Diabetes, 2004, pp. 5-15, vol. 5.
Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.
Herrera, Adult-Insulin- and Glucagon-Producing Cells Differentiate from Two Independent Cell Lineages, Development, 2000, pp. 2317-2322, vol. 127, No. 11.
Hoffman, et al., Characterization and Culture of Human Embryonic Stem Cells, Nature Biotechnology, 2005, pp. 699-708, vol. 23, No. 6.
Hosoya, et al., Induction of Differentiation of Undifferentiated Cells into Pancreatic Beta-Cells in Vertebrates, Int. J. Dev. Biol., 2012, pp. 313-323, vol. 56.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.
Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.
Jiang, et al., In Vitro Derivation of Functional Insulin-Producing Cells from Human Embryonic Stem Cells, Cell Research, 2007, pp. 333-344, vol. 17.
Karvonen, et al., Incidents of Childhood Type 1 Diabetes Worldwide, Diabetes Care, 2000, pp. 1516-1526, vol. 23, No. 10.
Konstantinova, et al., EphA-Ephrin-A-Mediated Beta Cell Communication Regulates Insulin Secretion from Pancreatic Islets, Cell, 2007, pp. 359-370, vol. 129.
Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.
Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.

(56) References Cited

OTHER PUBLICATIONS

Larsen, et al., Use of the Gootingen Minipig as a Model of Diabetes, with Special Focus on Type 1 Diabetes Research, ILAR Journal, 2004, pp. 303-313, vol. 45, No. 3.
Lee, et al., PKC-Inhibitors Sustain Self-Renewal of Mouse Embryonic Stem Cells Under Hypoxia in Vitro, Experimental and Molecular Medicine, Apr. 2010, pp. 294-301, vol. 43, No. 4.
Lee, et al., Protein Kinase A- and C-Induced Insulin Release from Ca2+-Insensitive Pools, Cellular Signalling, 2003, pp. 529-537, vol. 15.
Leon-Quinto, et al., In Vitro Directed Differentiation of Mouse Embryonic Stem Cells into Insulin-Producing Cells, Diabetologia, 2004, pp. 1442-1451, vol. 47, No. 8.
Li, et al., Pluripotency Can be Rapidly and Efficiently Induced in Human Amniotic Fluid-Derived Cells, Human Molecular Genetics, 2009, pp. 4340-4349, vol. 18, No. 22.
Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.
Mathis, et al., B-Cell Death During Progression to Diabetes, Nature, 2001, pp. 792-798, vol. 414.
Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.
Munoz, et al, Conventional pluripotency markers, Conventional pluripotency markers, Theriogenology, 2008, 1159-1164, vol. 69.
Amit, et al., Dynamic Suspension Culture for Scalable Expansion of Undifferentiated Human Pluripotent Stem Cells, Nature Protocols, Apr. 7, 2011, pp. 572-579, vol. 6, No. 5.
Baertschiger, et al., Mesenchymal Stem Cells Derived From Human Exocrine Pancreas Express Transcription Factors Implicated in Beta-Cell Development, Pancreas, 2008, pp. 75-84, vol. 37, No. 1.
Eguizabal, et al., Embryonic Stem Cells/Induced Pluripotent Stem Complete Meiosis from Human Induced Pluripotent Stem Cells, Stem Cells, 2011, pp. 1186-1195, vol. 29.
Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.
Harmon, et al., GDF11 Modulates NGN3+ Islet Progenitor Cell Number and Promotes B-Cell Differentiation in Pancreas Development, Development, 2004, pp. 6163-6174, vol. 131.
Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.
Ludwig et al., Defined Culture Media for Human Embryonic Stem Cells, Embryonic Stem Cells, 2007, pp. 1-16, Springer.
Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.
Nie, et al., Scalable Passaging of Adherent Human Pluripotent Stem Cells, PLOS One, 2014, pp. 1-9, vol. 9, Issue 1.
Park, et al., Effects of Activin A on Pancreatic Ductal Cells in Streptozotocin-Inducted Diabetic Rats, Experimental Transplantation, 2007, pp. 925-930, vol. 83.
Rajala, et al., Testing of Nine Different Xeno-free Culture Media for Human Embryonic Stem Cell Cultures, Human Reproduction, Jan. 24, 2007, pp. 1231-1238, vol. 22, No. 5.
Richards, et al., Development of Defined Media for the Serum-Free Expansion of Primary Keratinocytes and Human Embryonic Stem Cells, Tissue Engineering, 2008, pp. 221-232, vol. 14, No. 3.
Rowley, et al., Meeting Lot-Size Challenges of Manufacturing Adherent Cells for Therapy, Cell Therapies Manufacturing, 2012, pp. 16-22, vol. 10, No. 3.
Schulz, et al., A Scalable System for Production of Functional Pancreatic Progenitors from Human Embryonic Stem Cells, PLOS One, 2012, pp. 1-17, vol. 7, Issue 5.
Sneddon, et al., Self-Renewal of Embryonic-Stem-Cell-Derived Progenitors by Organ-Matched Mesenchyme, Nature, Nov. 29, 2012, pp. 765-770, vol. 491.
Stacpoole, et al., Efficient Derivation of Neural Precurosor Cells, Spinal Motor Neurons and Midbr, Nat Protoc, 2012, pp. 1-26, vol. 6, Issue 8.
Vieira, et al., Modulation of Neuronal Stem Cell Differentiation by Hypoxia and Reactive Oxygen Species, Progress in Neurobiology, 2011, pp. 444-455, vol. 93.
Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.
Yang, et al., Evaluation of Humam MSCs Cell Cycle, Viability and Differentiation in Micromass Culture, Biorheology, 2006, p. 489-496, vol. 43.
Zalzman, et al., Differentiation of Human Liver-Derived, Insulin-Producing Cells Toward the B-Cell Phenotype, Diabetes, 2005, pp. 2568-2575, vol. 54.
Zuscik, et al., Regulation of Chondrogenesis and Chondrocyte Differentiation by Stress, J Clin Invest, 2008, pp. 429-438, vol. 118, Issue 2.
Nostro, et al., Generation of Beta Cells from Human Pluripotent Stem Cells: Potential for Regenerative Medicine, Seminars in Cell & Developmental Biology, 2012, pp. 701-710, vol. 23.
Rezania, et al, Reversal of Diabetes with Insulin-Producing Cells Derived in vitro from Human Pluripotent Stem Cells, Nature Biotechnology, 2014, pp. 1121-1133, vol. 32, No. 11.
Thermofisher Scientific, B-27 Serum-Free Supplement (50x) Liquid, Technical Resources, 2016, URL:https://www.thermofisher.com/nl/en/home/technical-resources/media-formulation.250.html, retrieved from the internet.
Wachs, et al., High Efficacy of Clonal Growth and Expansion of Adult Neural Stem Cells, Laboratory Investigation, 2003, pp. 949-962, vol. 83, No. 7.

\* cited by examiner
† cited by third party

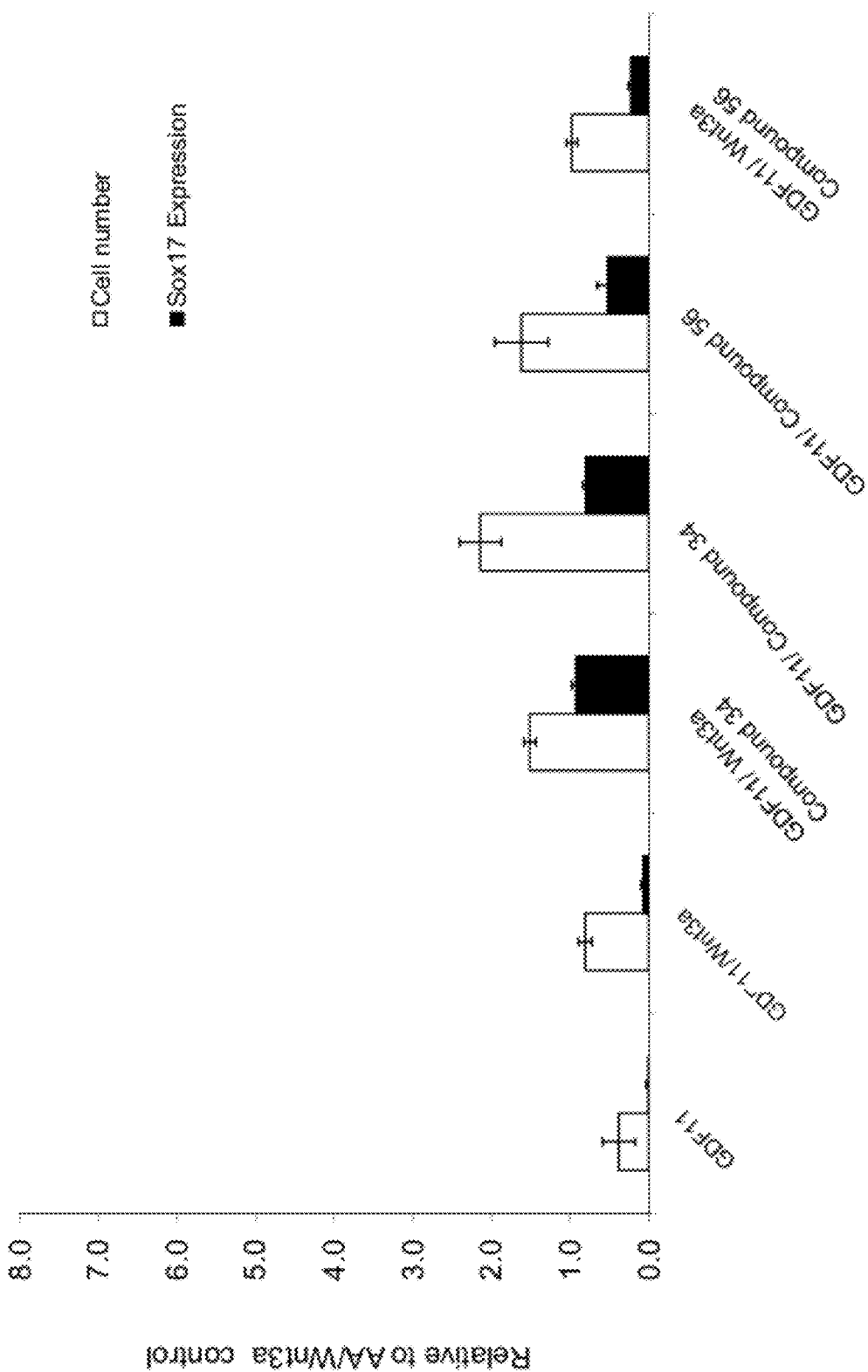

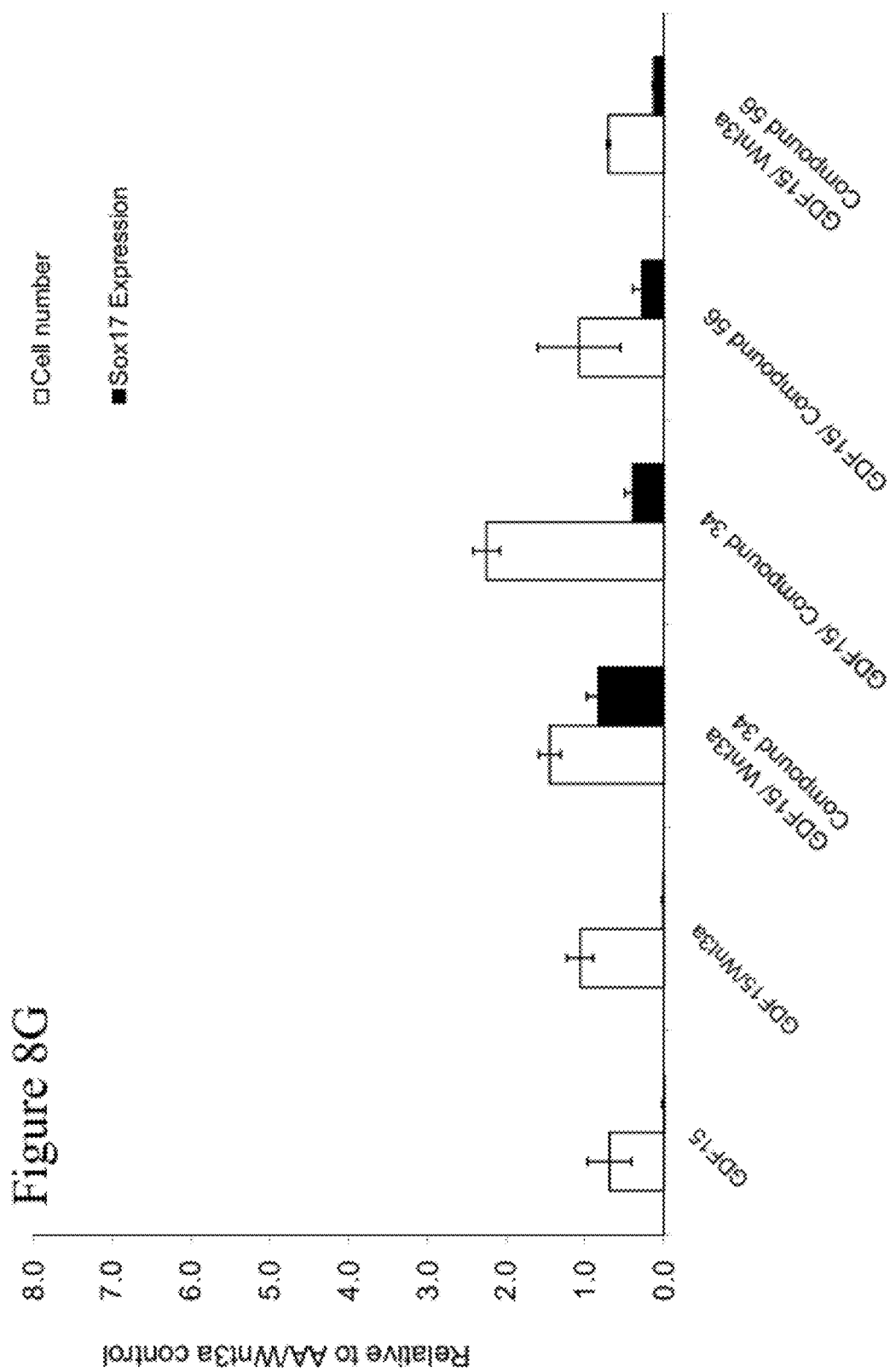

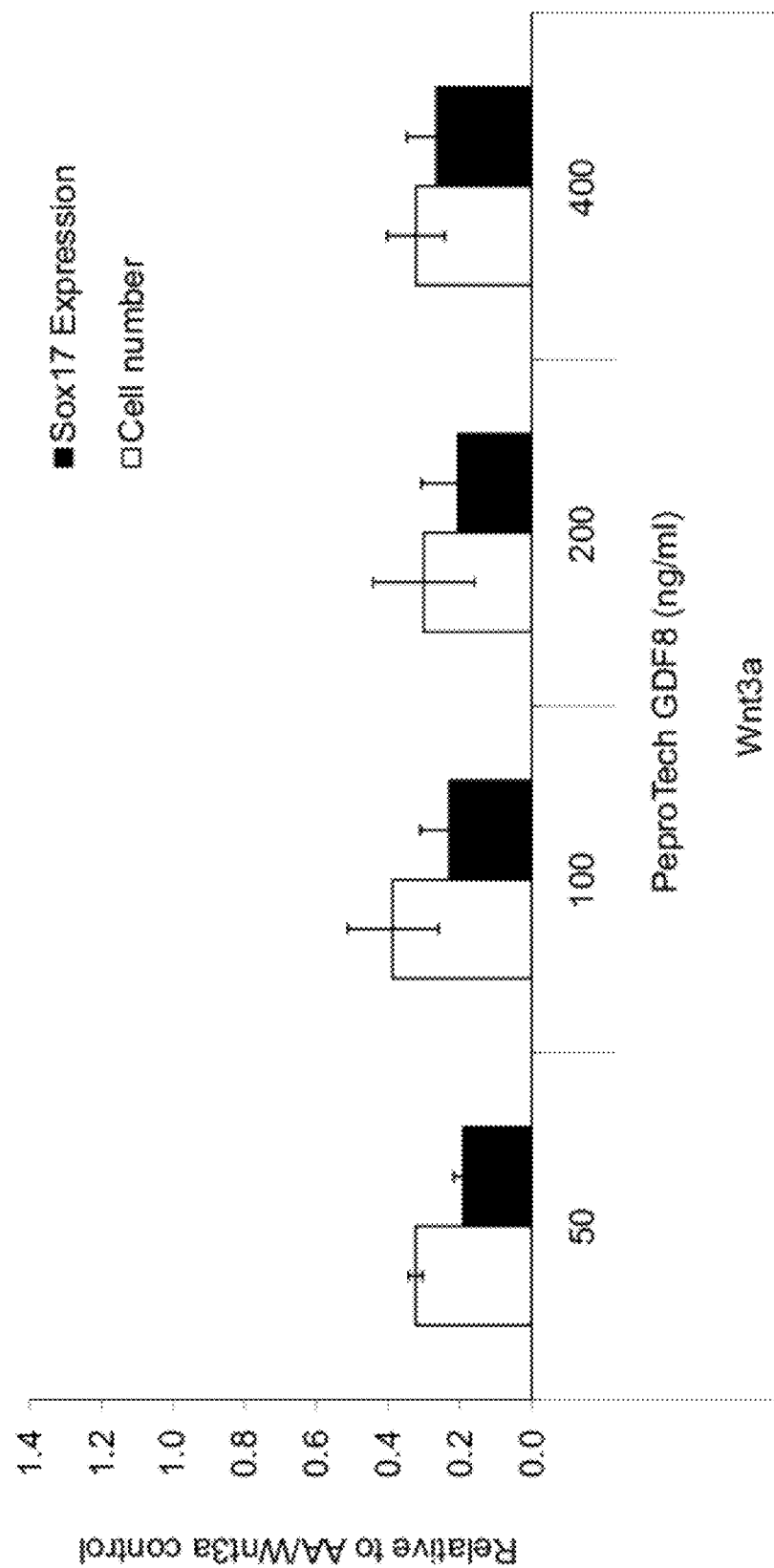

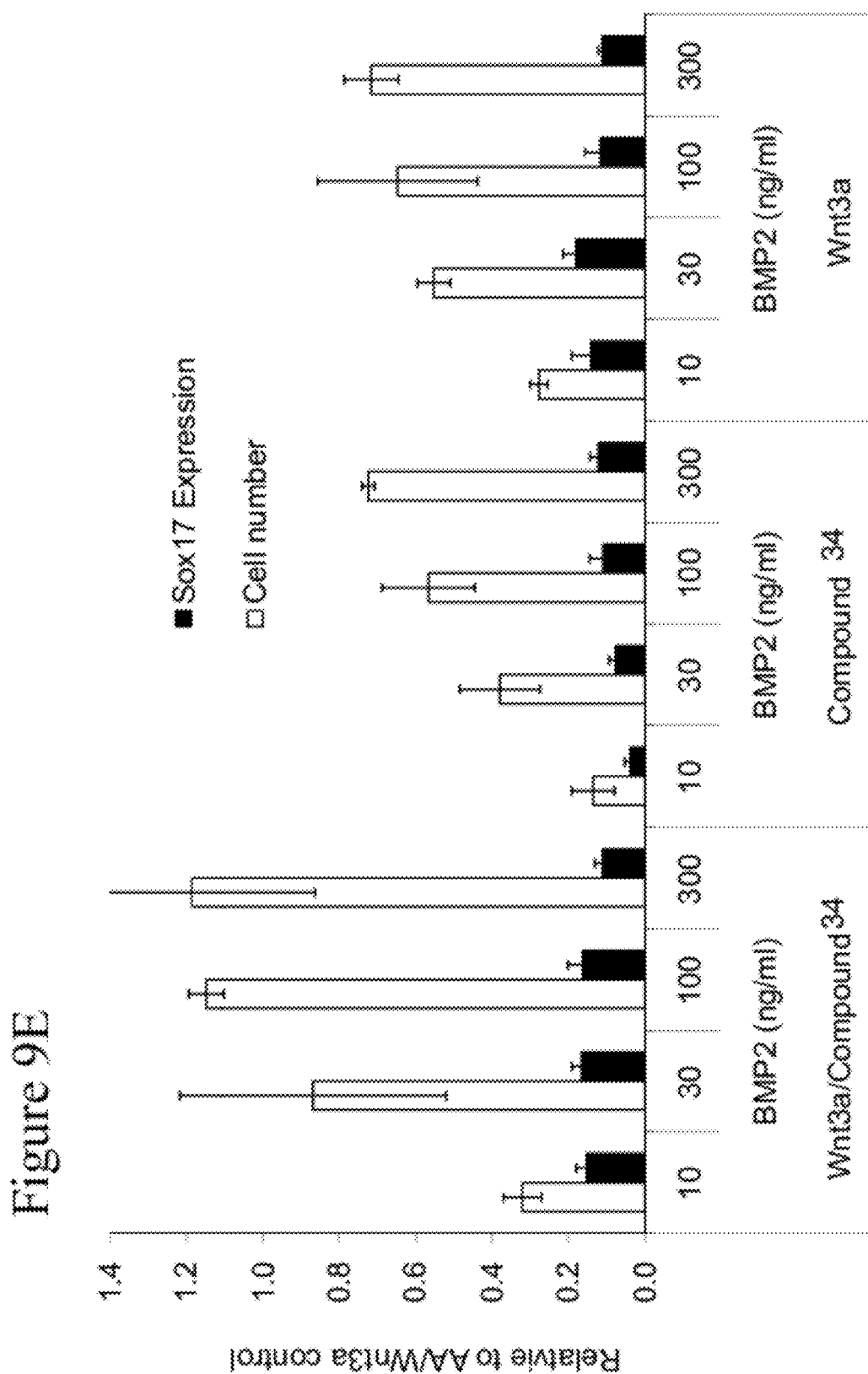

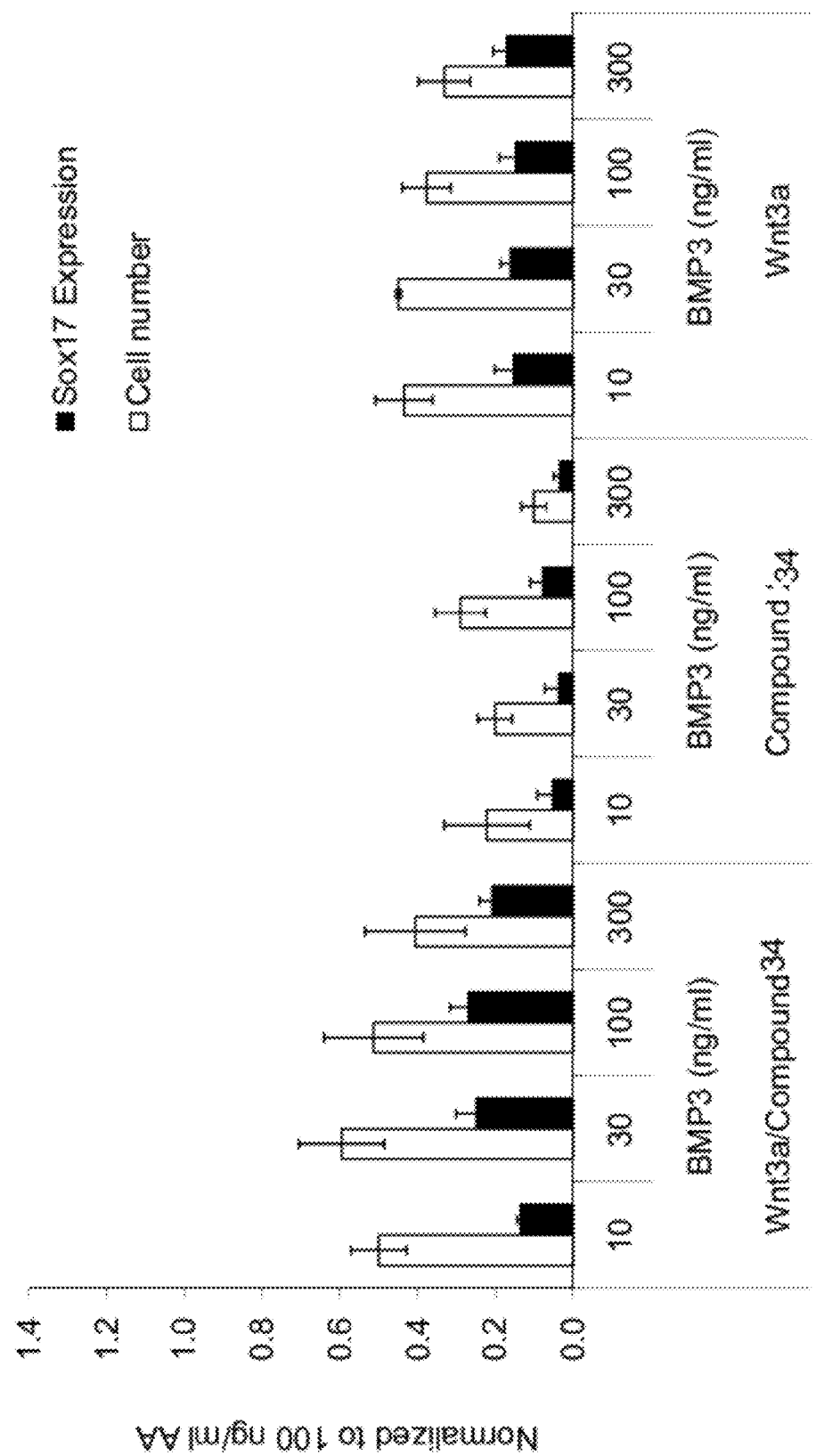

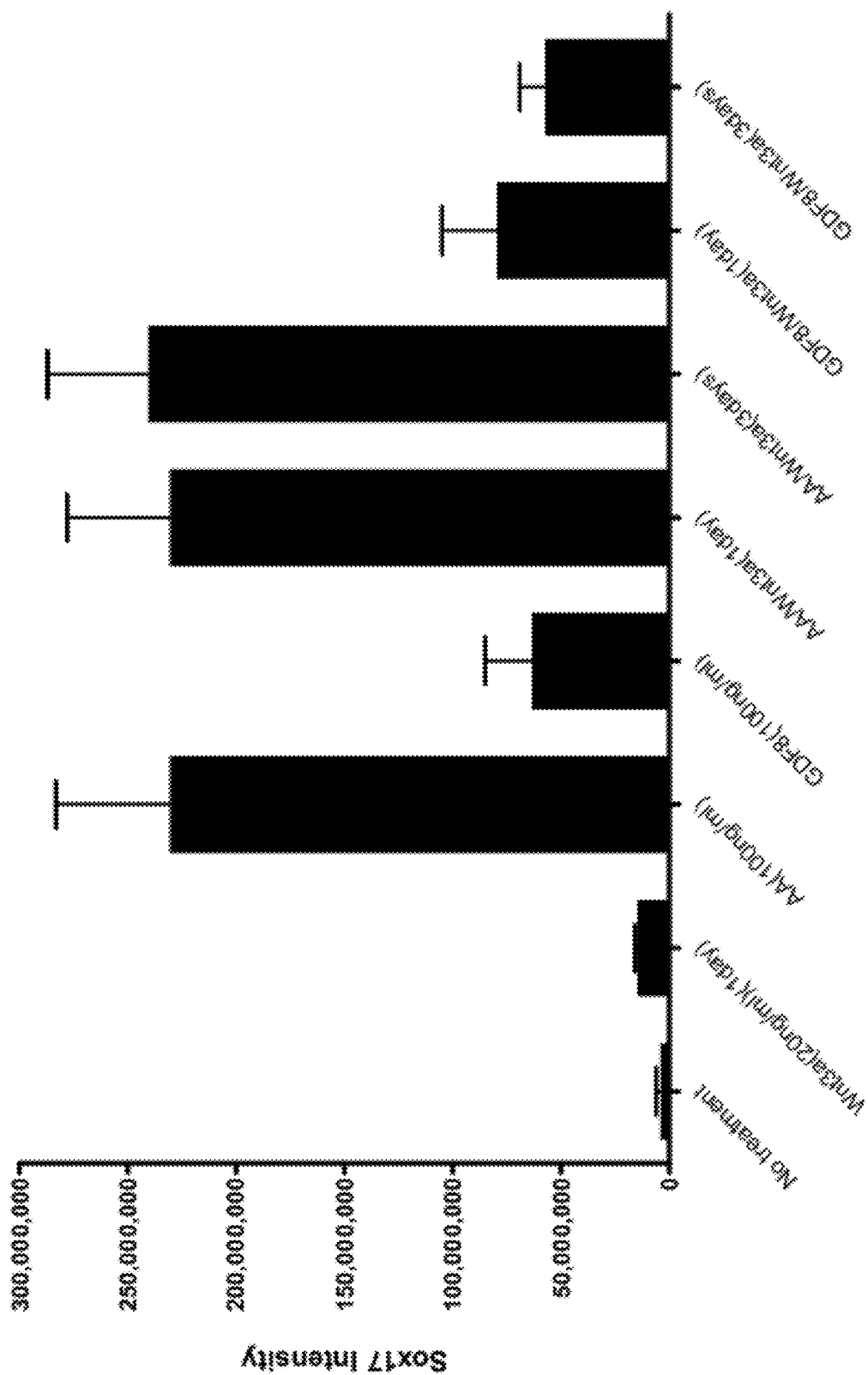

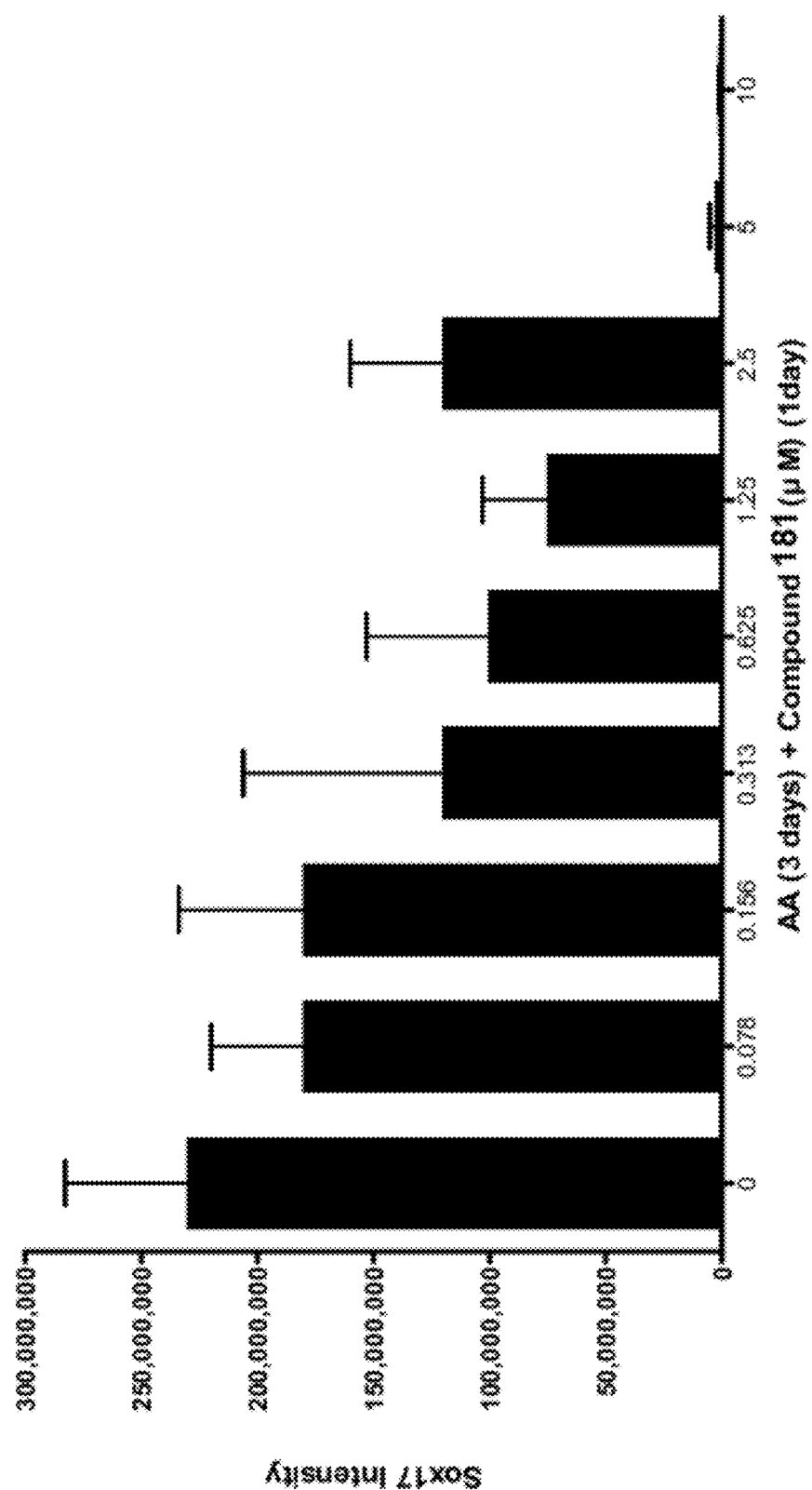

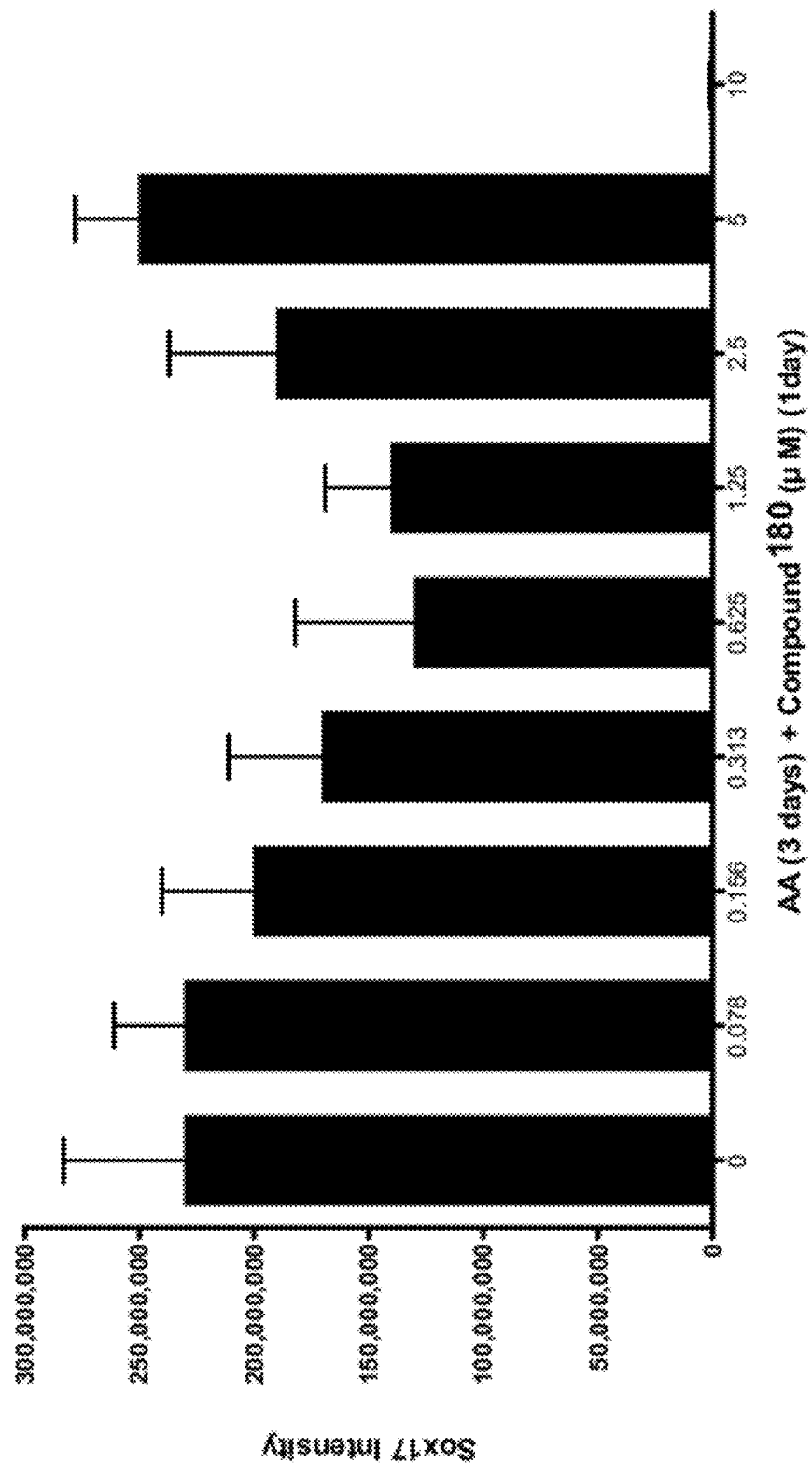

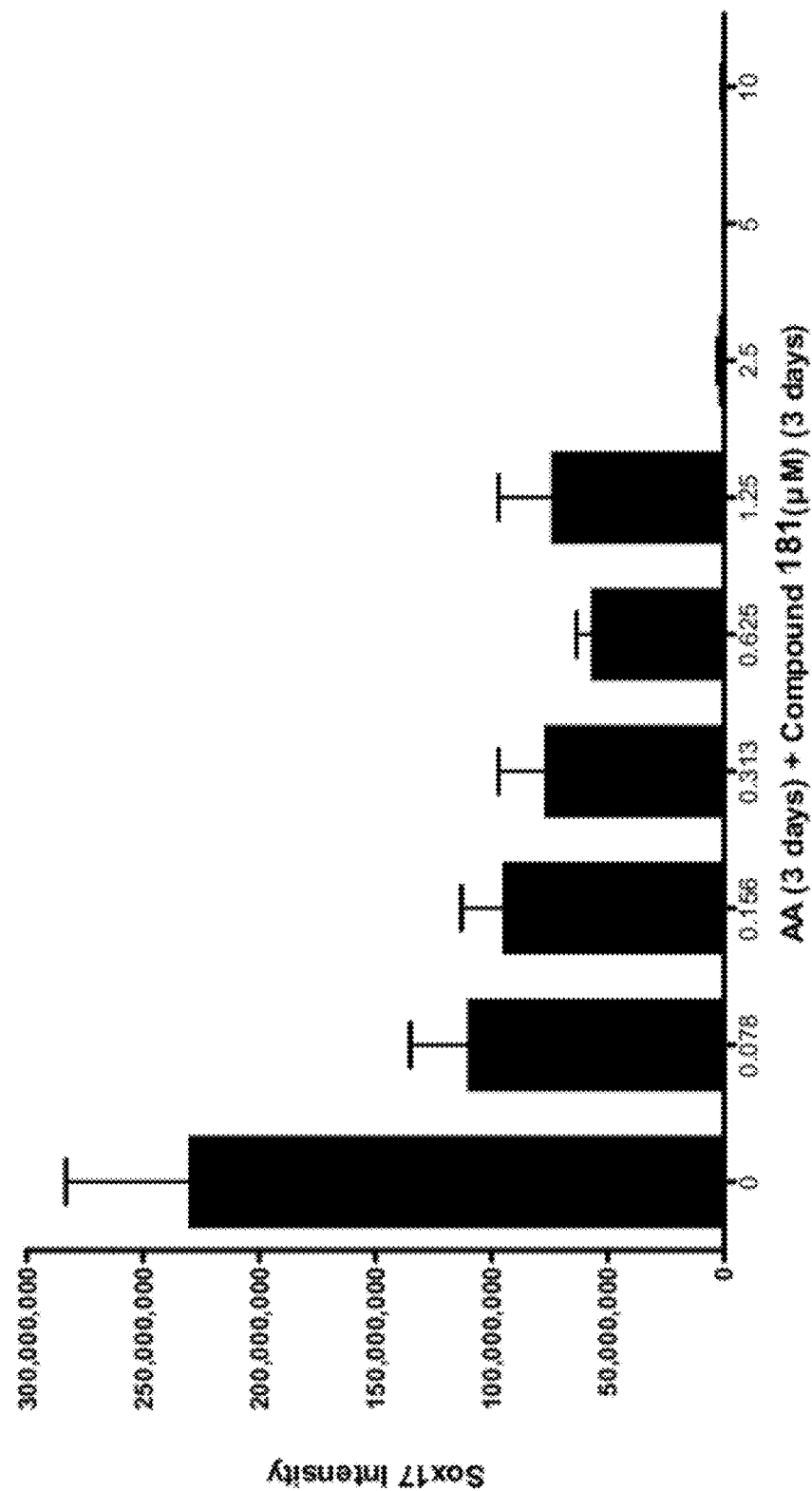

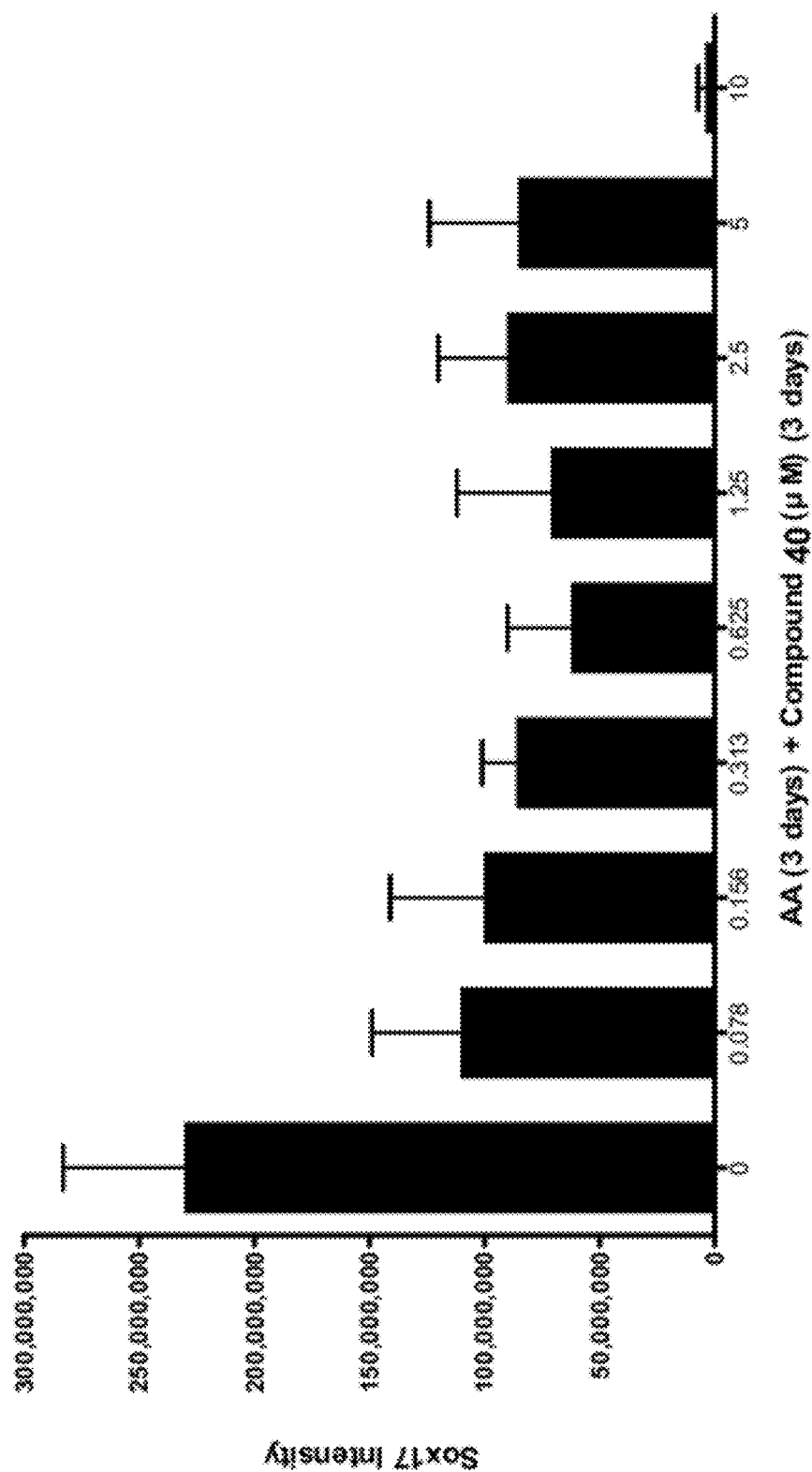

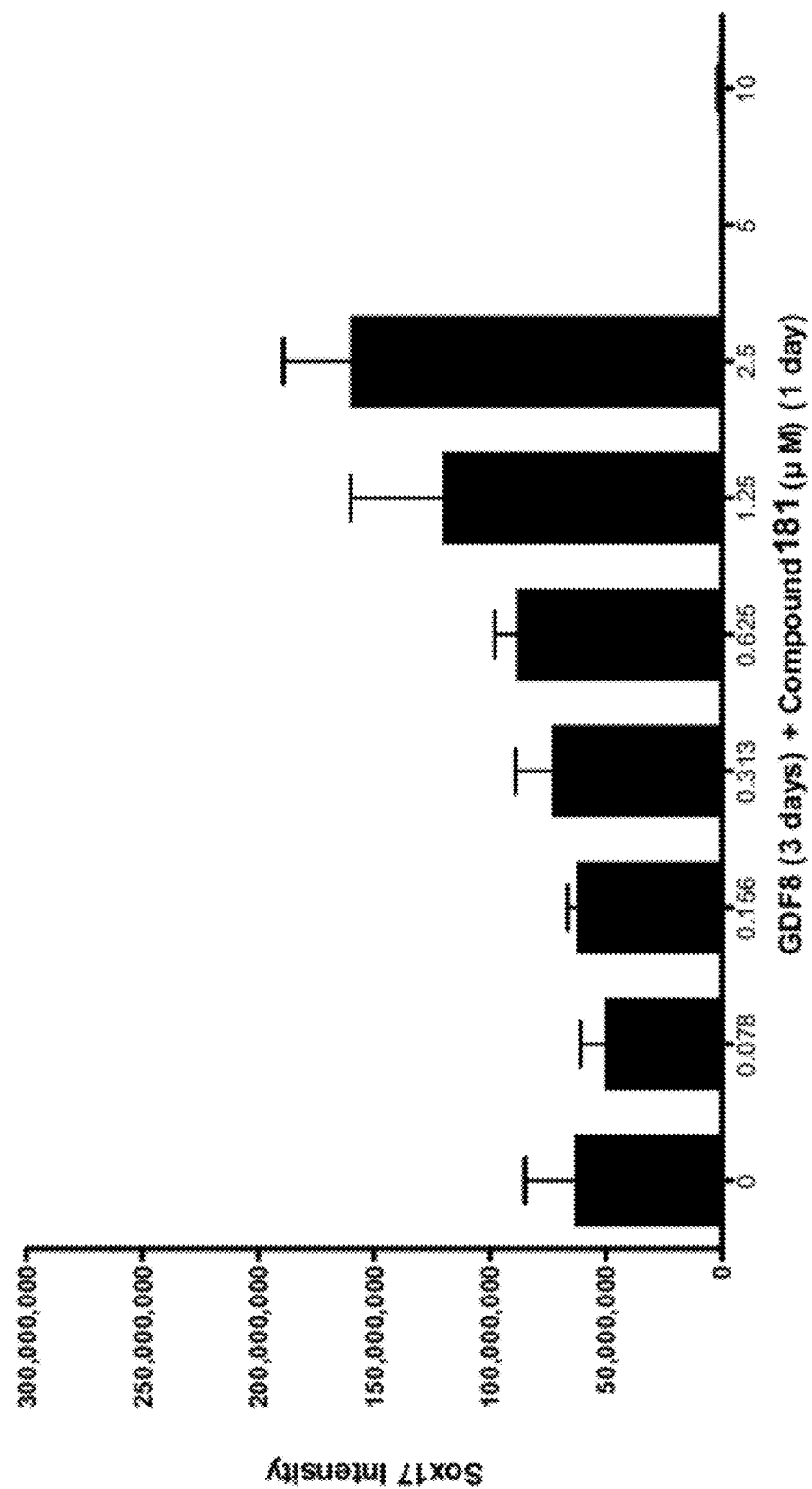

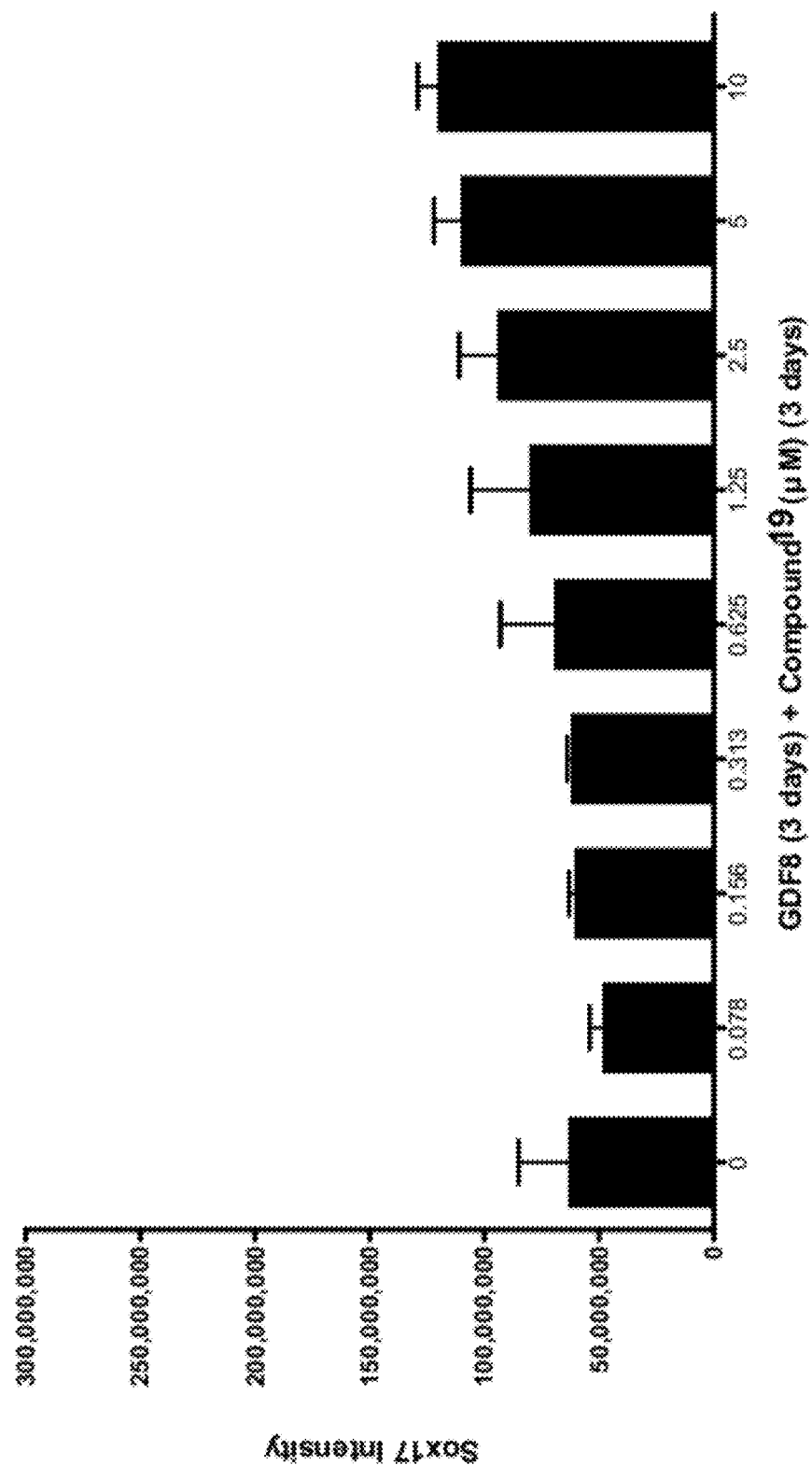

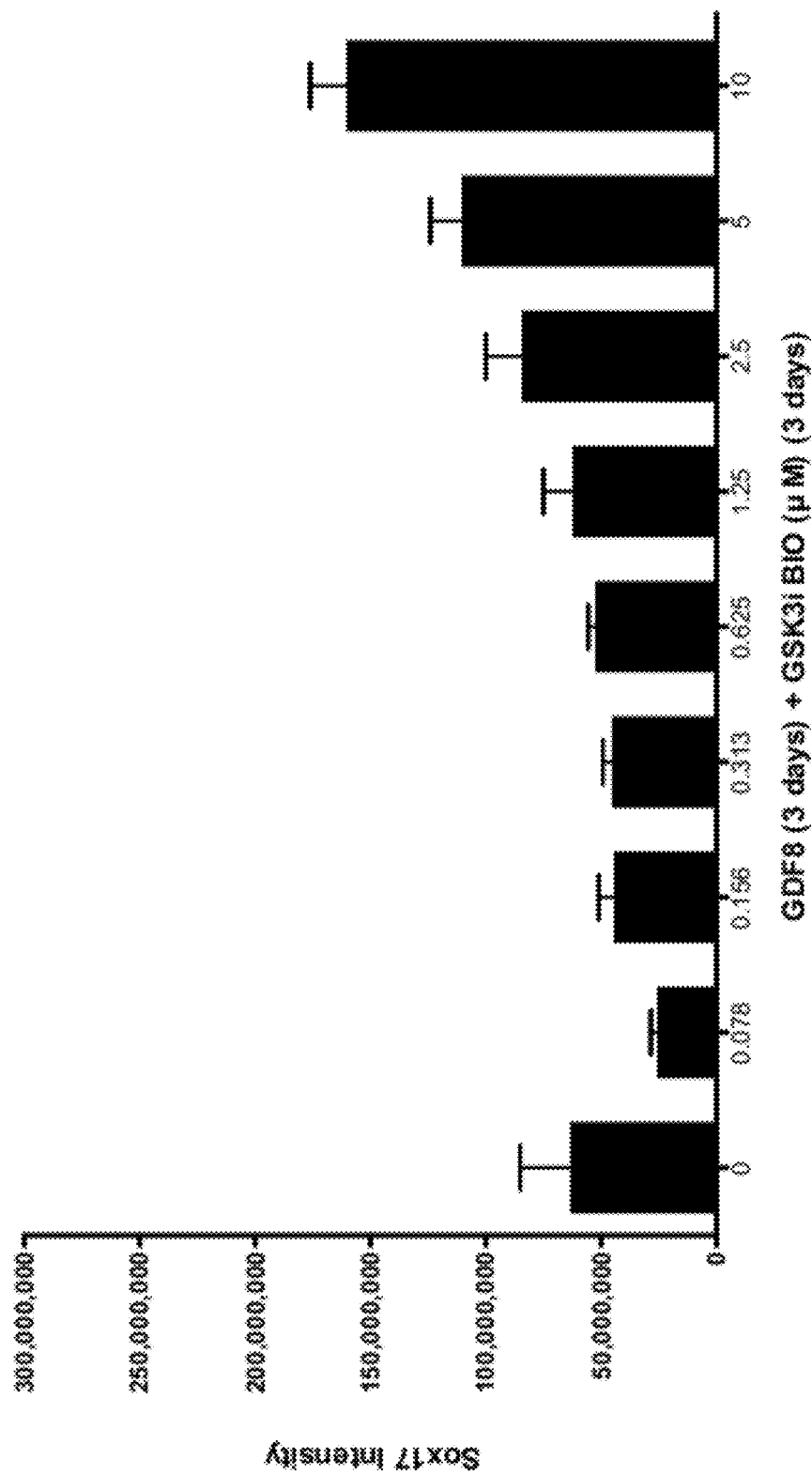

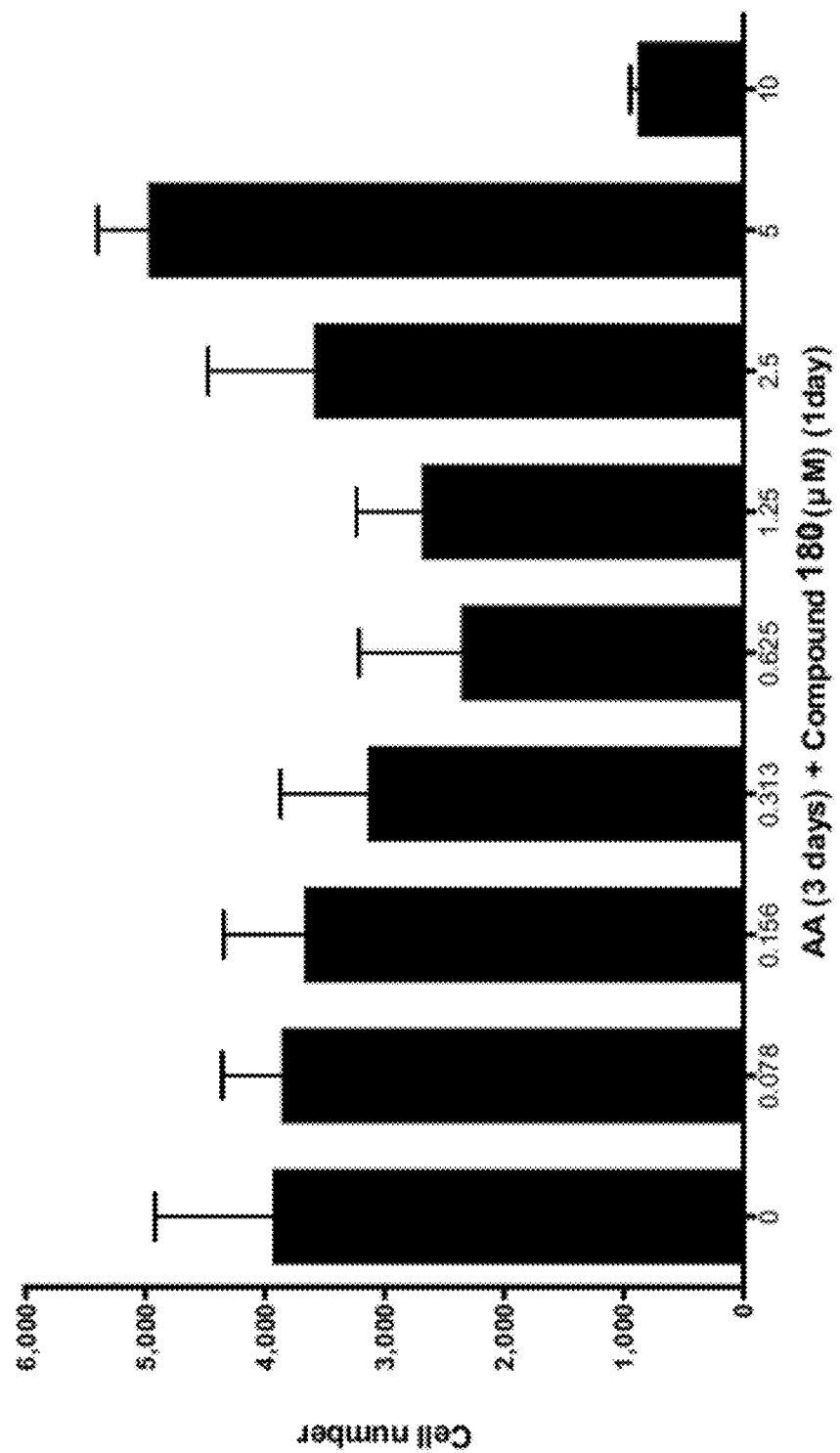

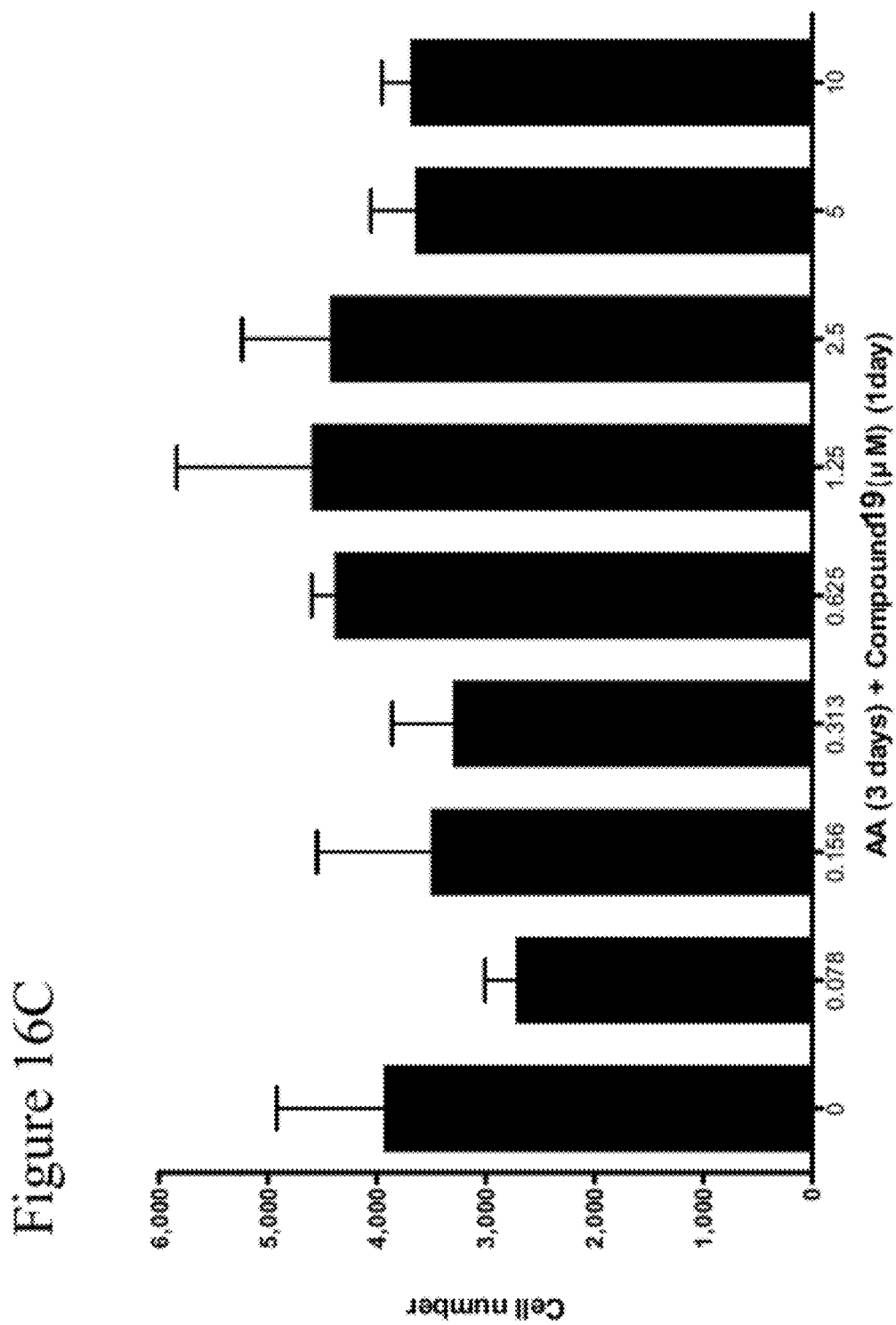

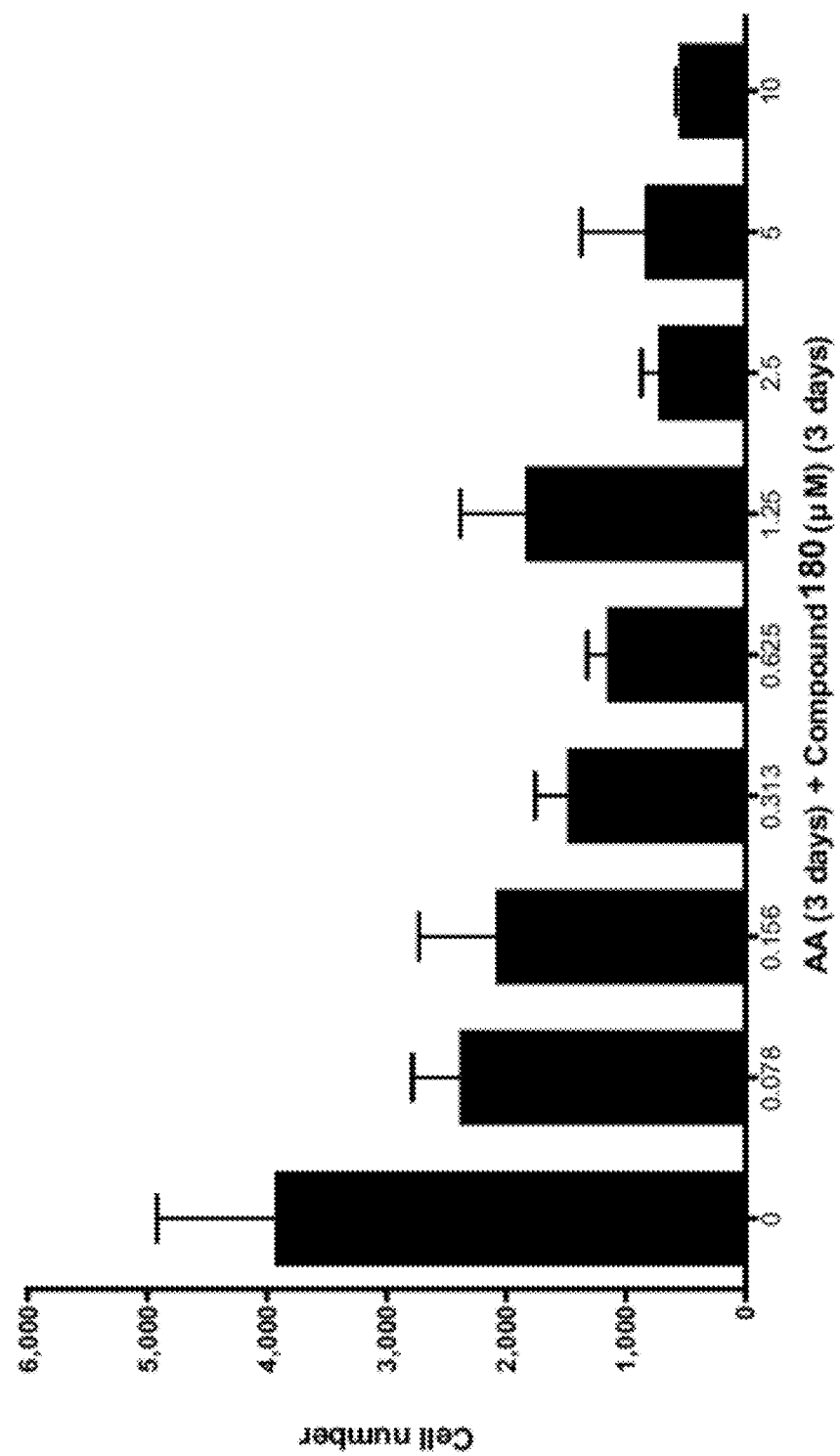

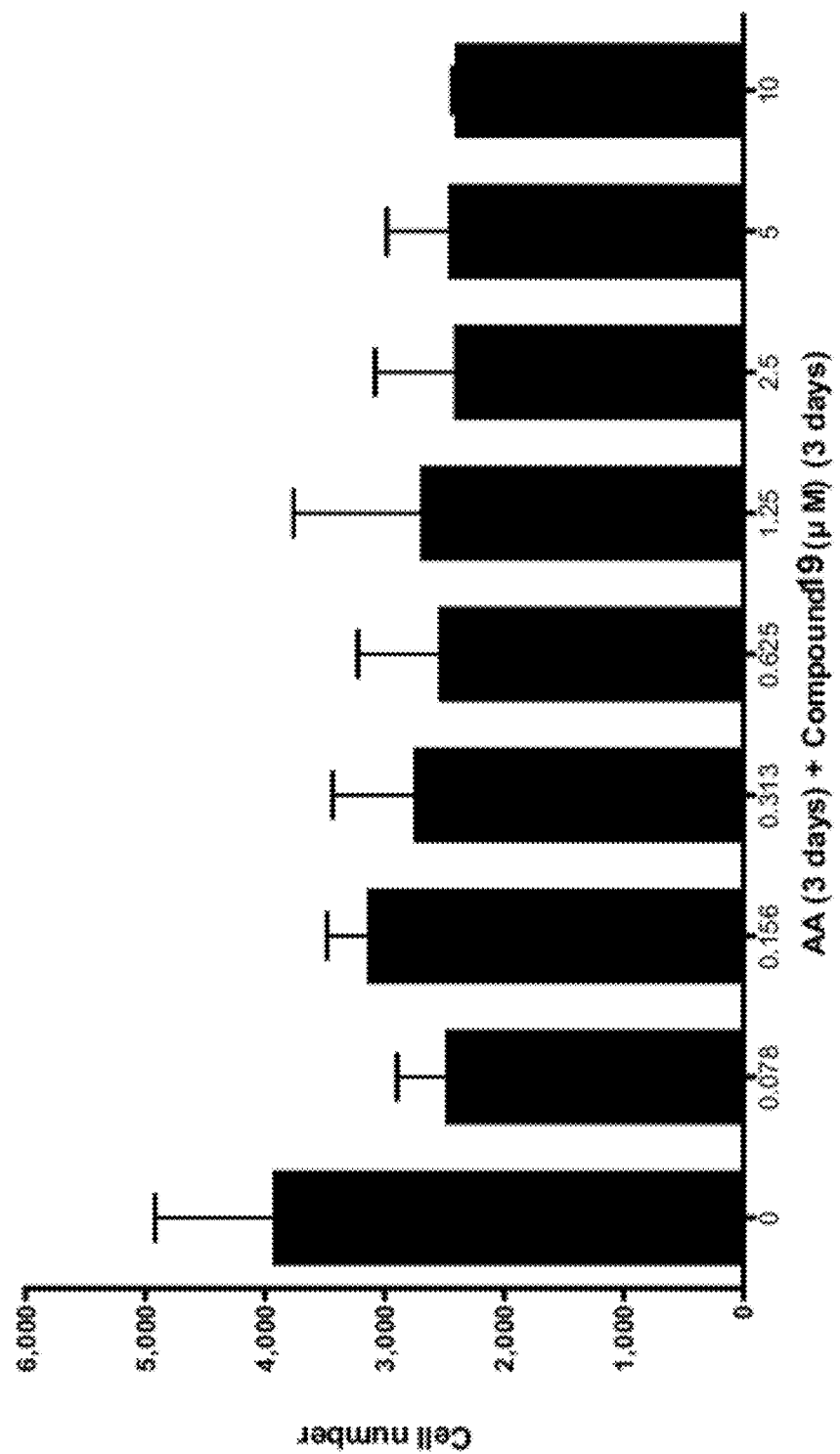

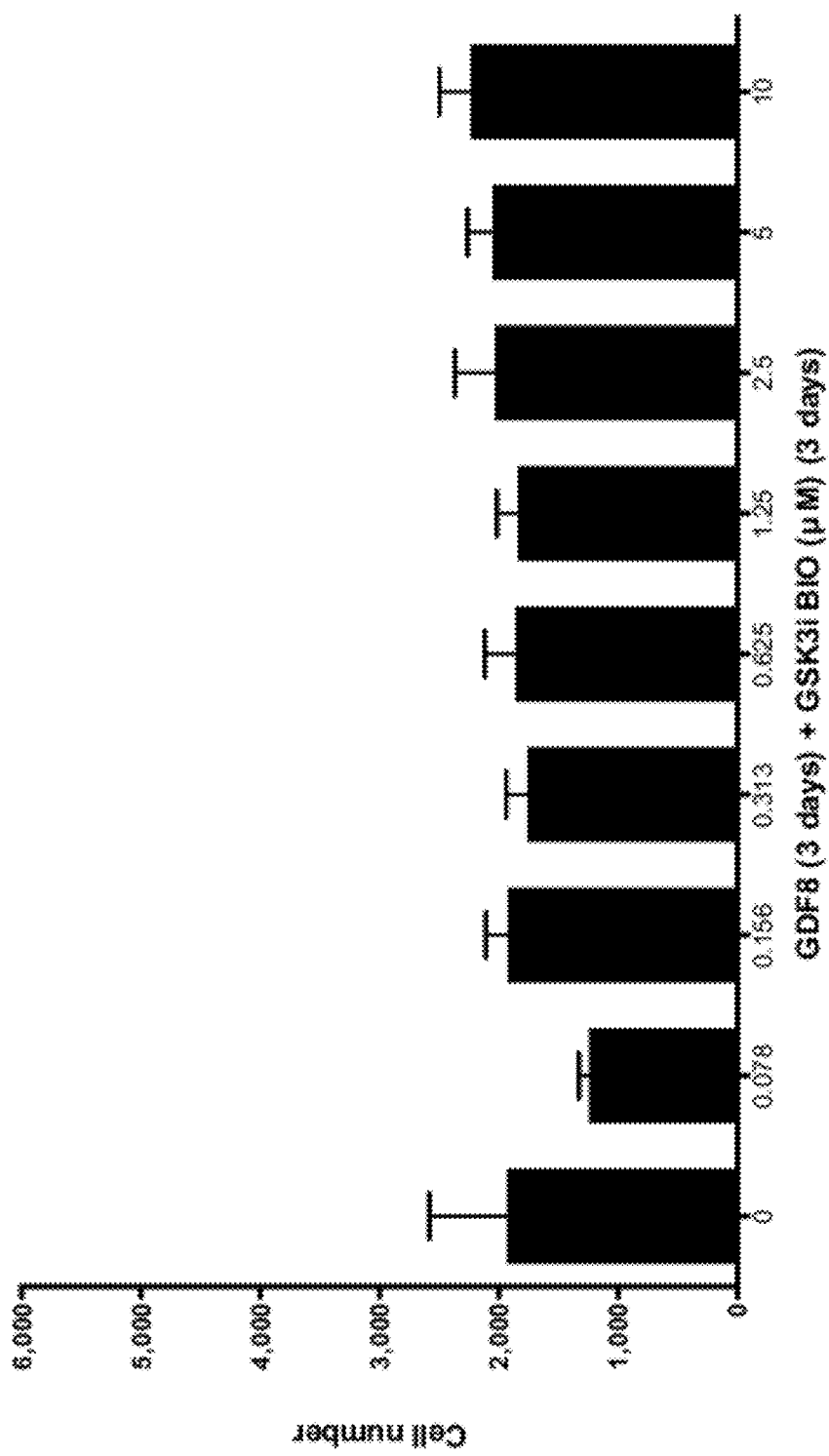

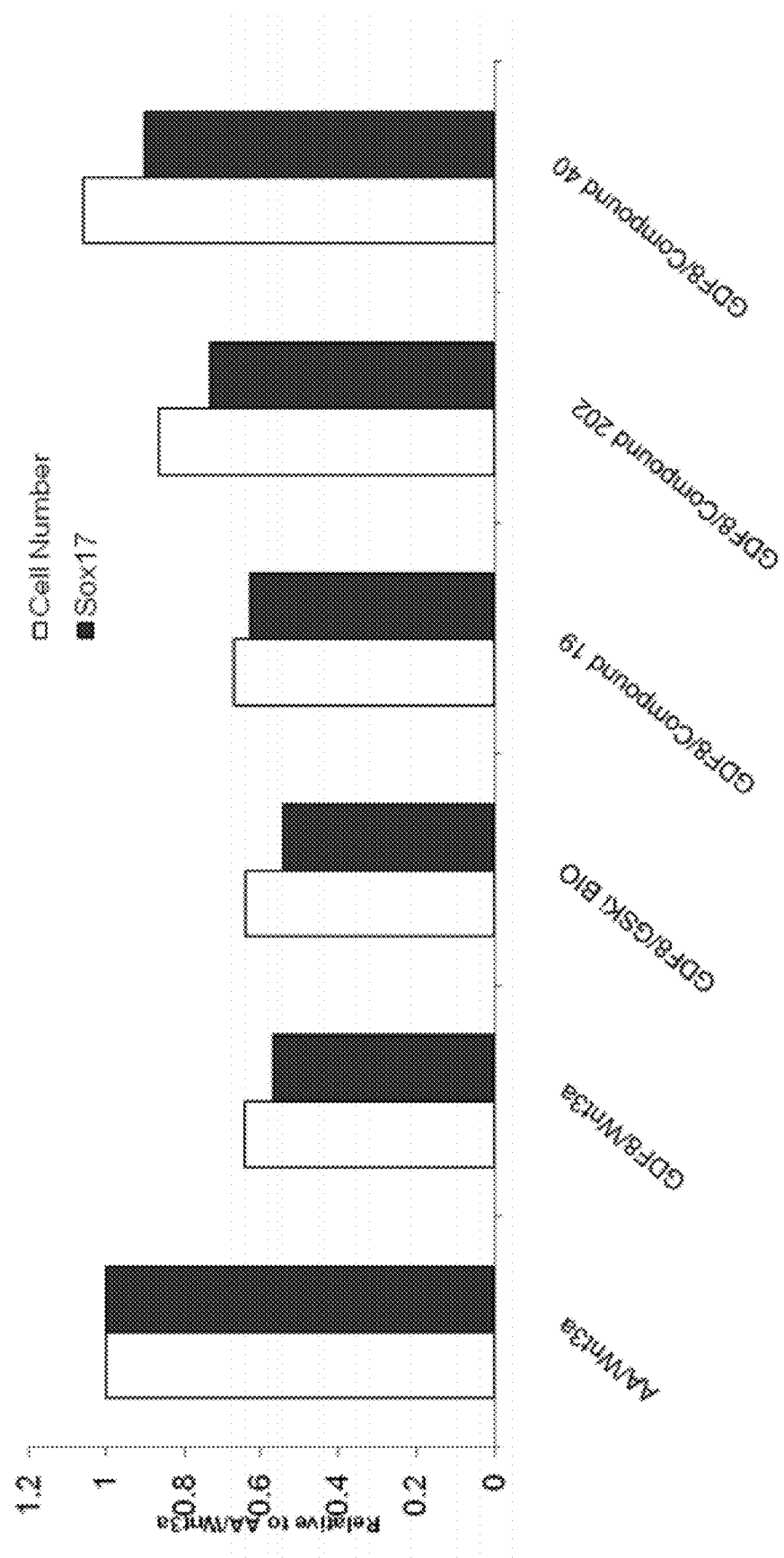

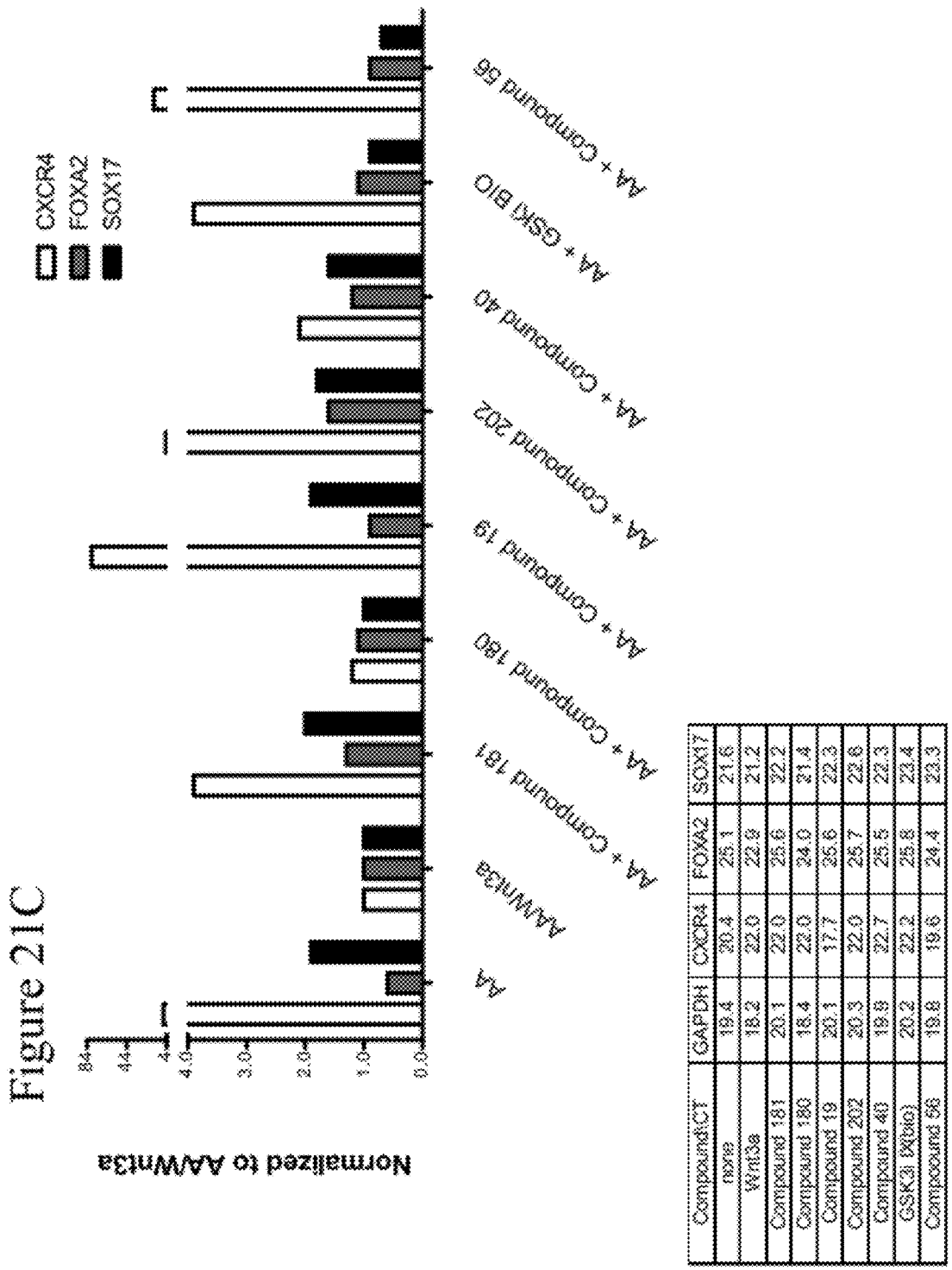

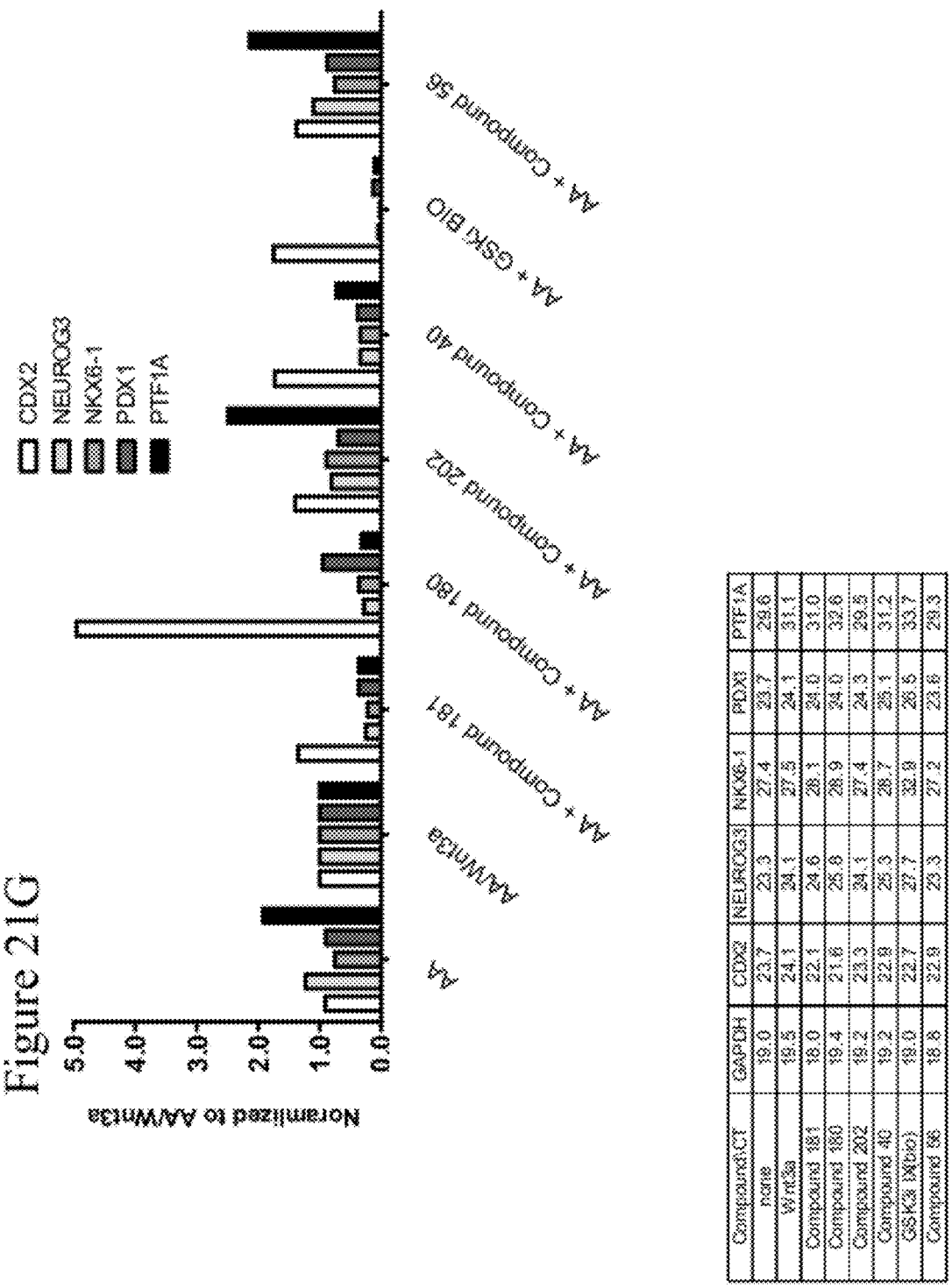

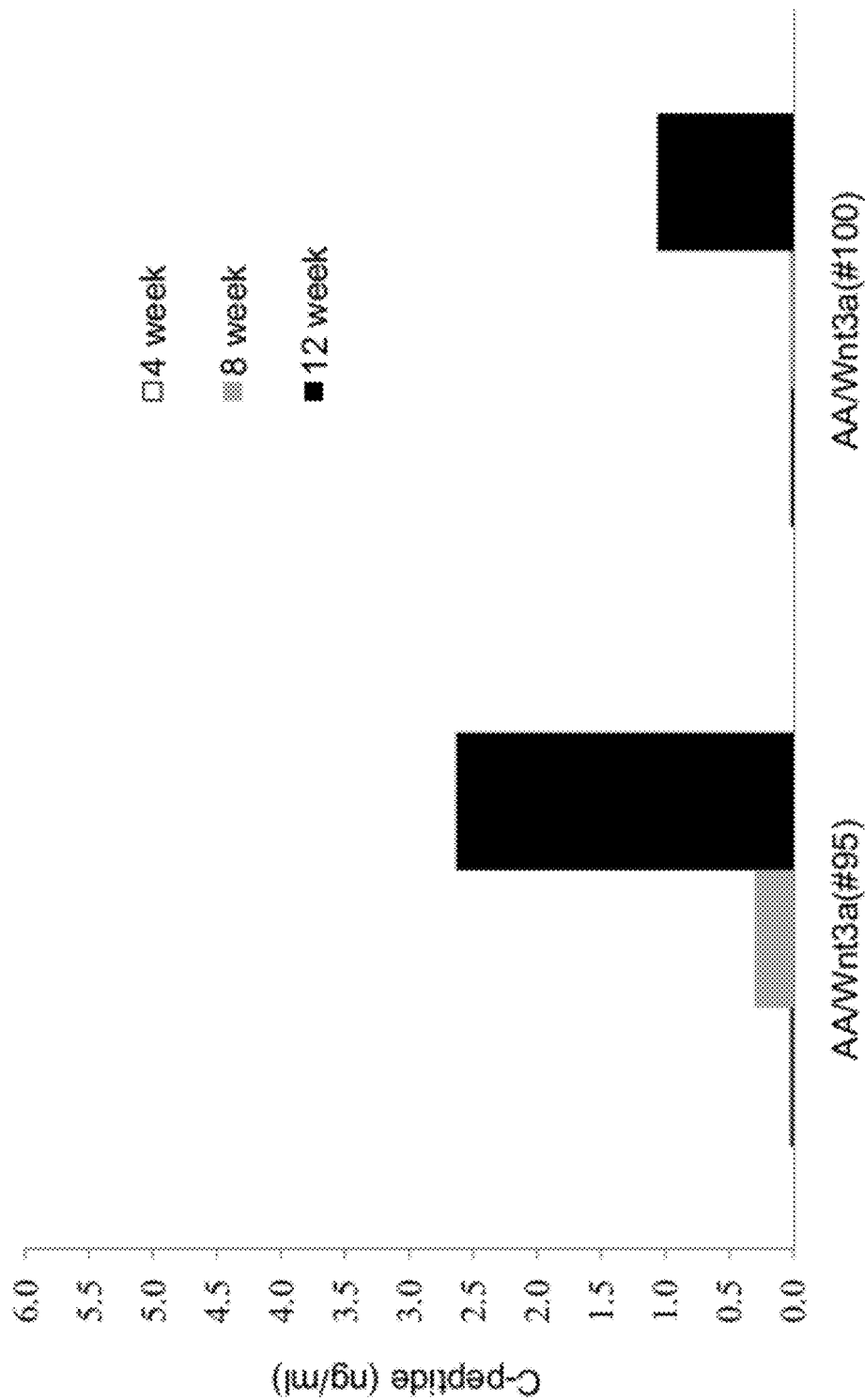

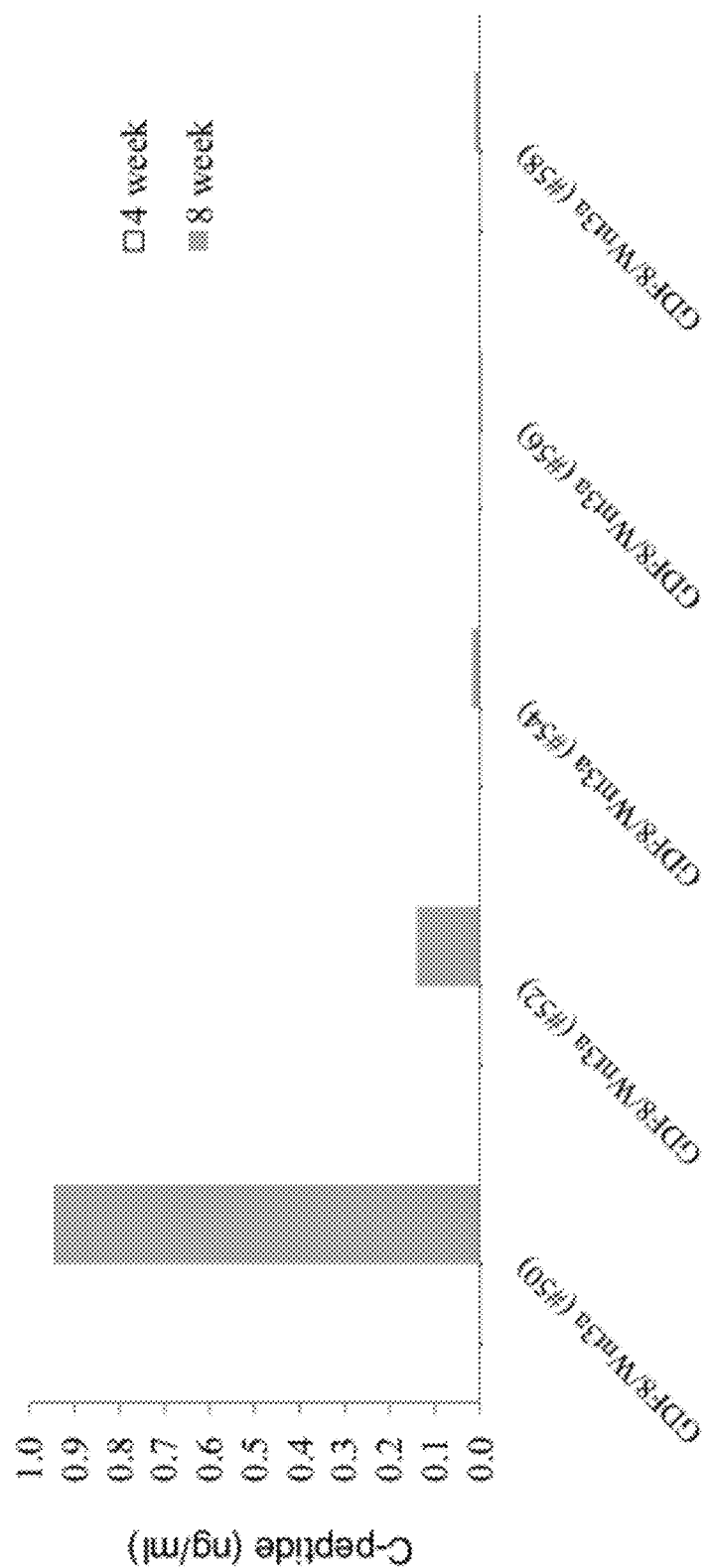

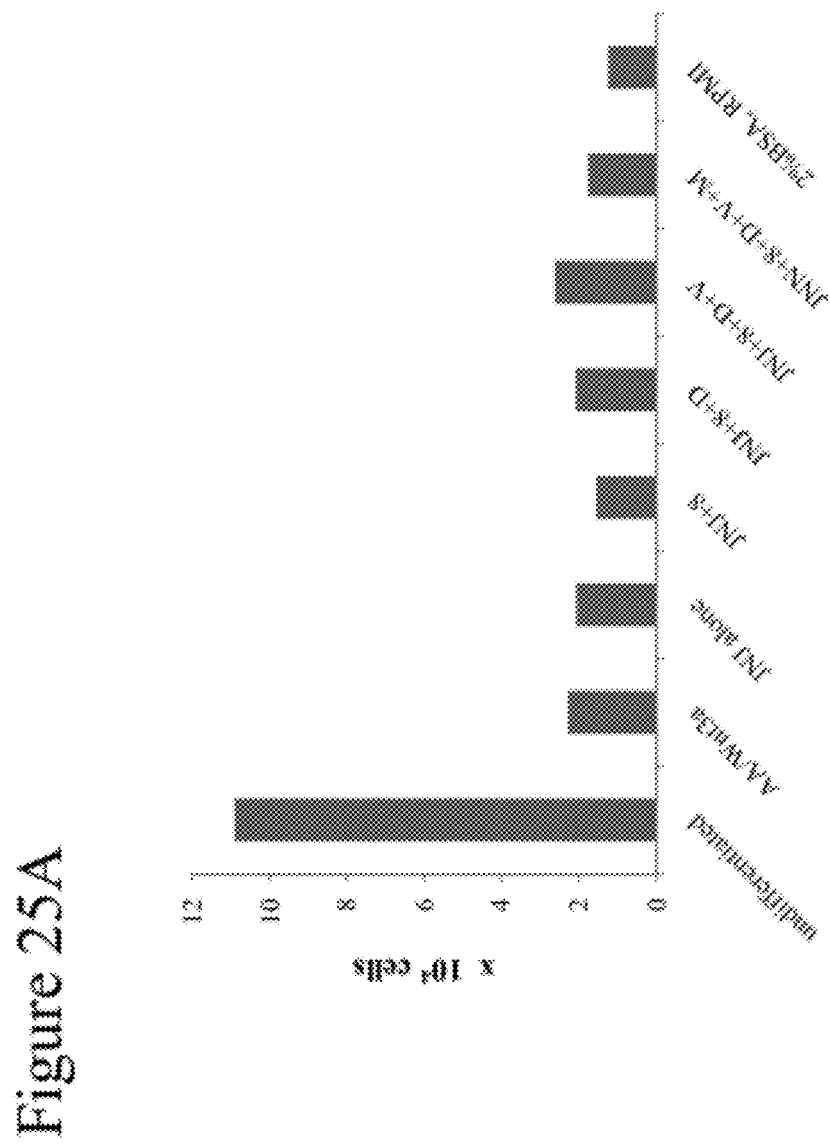

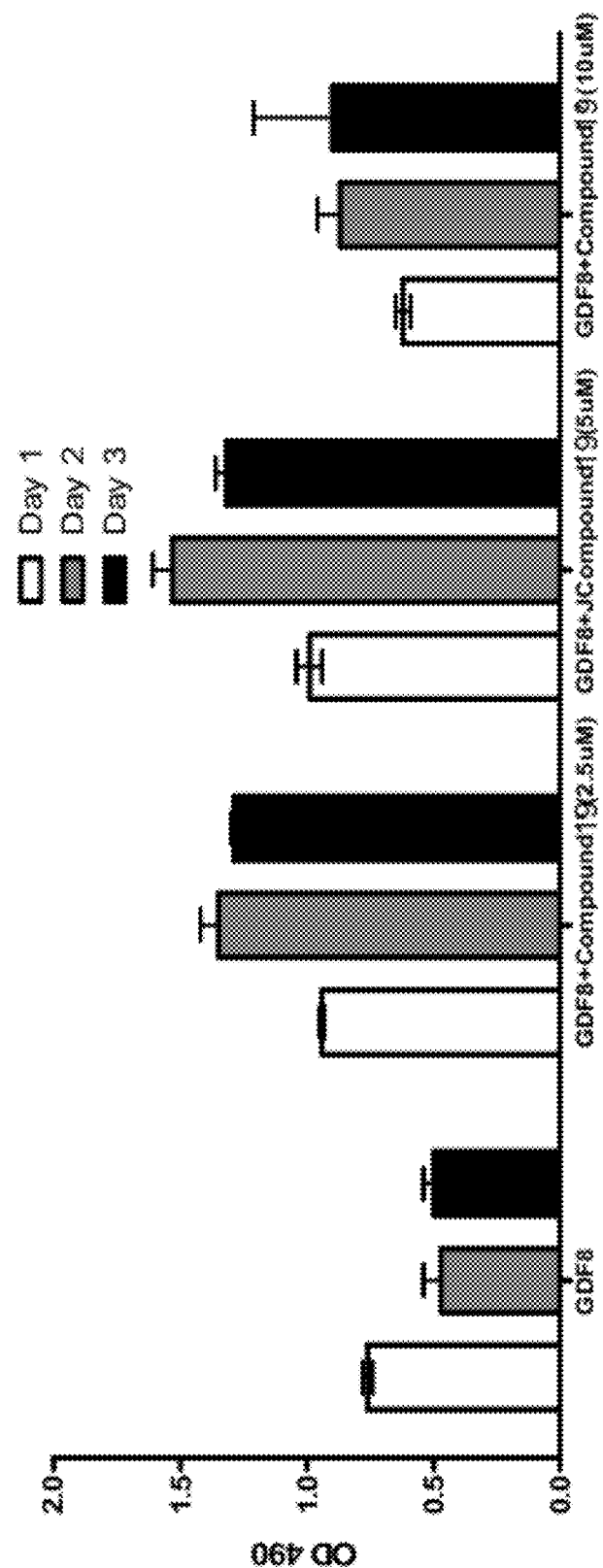

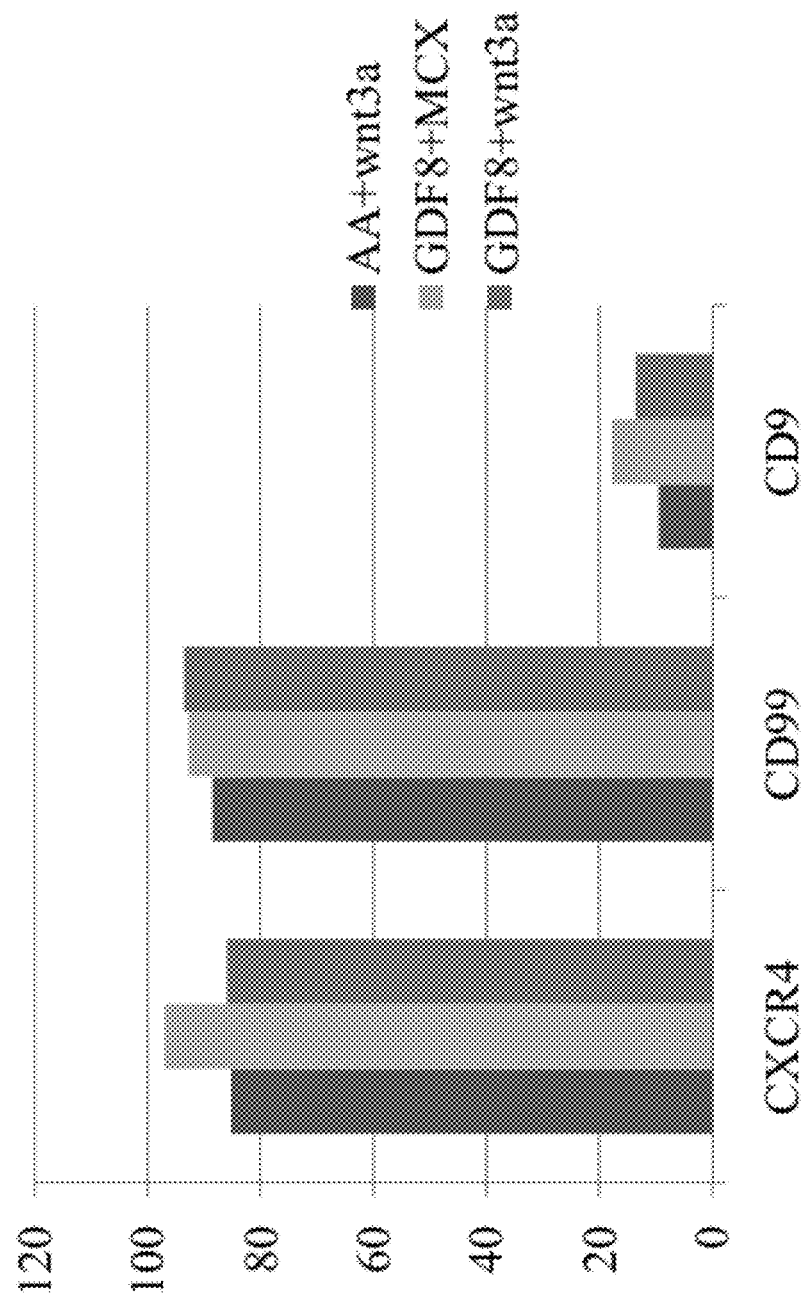

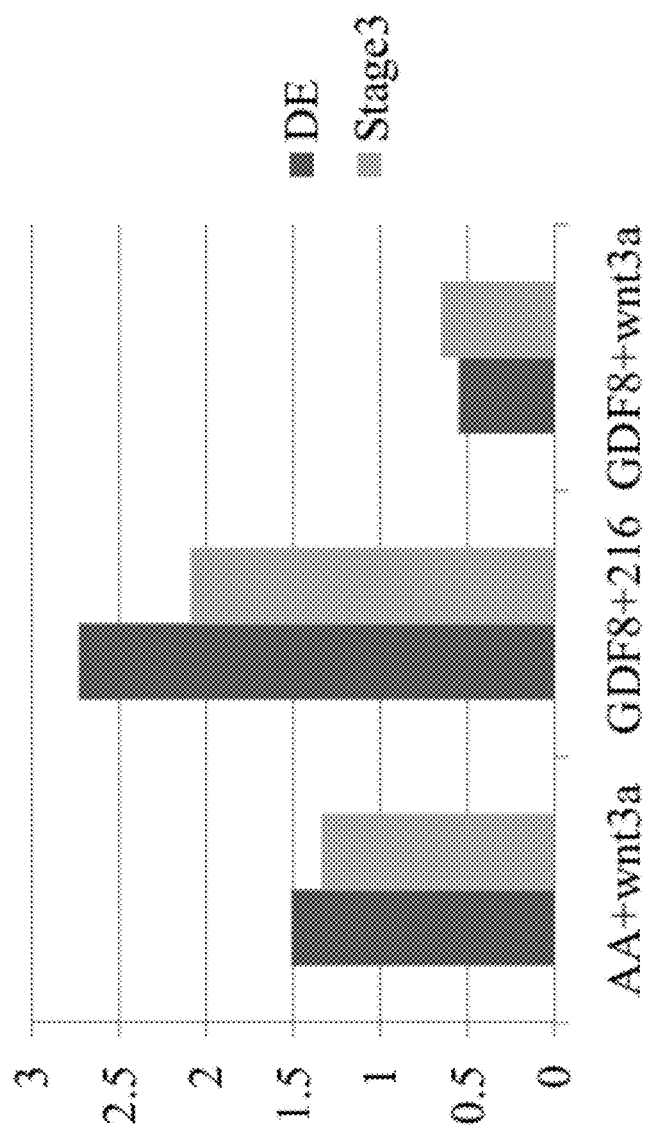

Figure 27D

| Stage 3 | AA+wnt | GDF8+MCX | GDF8+wnt |
|---|---|---|---|
| Pdx | 215 | 555 | 142 |
| Cdx2 | 1614 | 1567 | 965 |
| HNF4a | 339 | 210 | 267 |

Figure 27F

| Stage 4 | AA+wnt | GDF8+MCX | GDF8+wnt |
|---|---|---|---|
| Pdx | 276 | 545 | 71 |
| Cdx2 | 1971 | 2496 | 983 |
| HNF4a | 640 | 426 | 609 |

DIFFERENTIATION OF PLURIPOTENT STEM CELLS

CROSS REFERENCE TO RELATED APPLICATIONS

This application is a continuation of U.S. application Ser. No. 12/494,789, filed Jun. 30, 2009, currently pending, which claims priority to application Ser. No. 61/076,900, filed Jun. 30, 2008, application Ser. No. 61/076,908, filed Jun. 30, 2008, and application Ser. No. 61/076,915, filed Jun. 30, 2008. The complete disclosures of the aforementioned related patent applications are hereby incorporated by reference in their entirety.

FIELD OF THE INVENTION

The present invention is directed to methods to differentiate pluripotent stem cells. In particular, the present invention is directed to methods and compositions to differentiate pluripotent stem cells into cells expressing markers characteristic of the definitive endoderm lineage comprising culturing the pluripotent stem cells in medium comprising a sufficient amount of GDF-8 to cause the differentiation of the pluripotent stem cells into cells expressing markers characteristic of the definitive endoderm lineage.

BACKGROUND

Advances in cell-replacement therapy for Type 1 diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, for example, HNF-3beta, GATA4, MIXL1, CXCR4 and SOX17.

Formation of the pancreas arises from the differentiation of definitive endoderm into pancreatic endoderm. Cells of the pancreatic endoderm express the pancreatic-duodenal homeobox gene, PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

In one example, Hori et al. (PNAS 99: 16105, 2002) discloses that treatment of mouse embryonic stem cells with inhibitors of phosphoinositide 3-kinase (LY294002) produced cells that resembled β cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form Pdx1 positive pancreatic endoderm. Retinoic acid is most effective at inducing Pdx1 expression when added to cultures at day 4 of embryonic stem cell differentiation during a period corresponding to the end of gastrulation in the embryo (Diabetes 54:301, 2005).

Miyazaki et al. reports a mouse embryonic stem cell line over-expressing Pdx1. Their results show that exogenous Pdx1 expression clearly enhanced the expression of insulin, somatostatin, glucokinase, neurogenin3, p48, Pax6, and HNF6 genes in the resulting differentiated cells (Diabetes 53: 1030, 2004).

Skoudy et al. reports that activin A (a member of the TGF-β superfamily) up-regulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004).

Shiraki et al. studied the effects of growth factors that specifically enhance differentiation of embryonic stem cells into Pdx1 positive cells. They observed that TGFβ2 reproducibly yielded a higher proportion of Pdx1 positive cells (Genes Cells. 2005 June; 10(6): 503-16).

Gordon et al. demonstrated the induction of brachyury [positive]/HNF-3beta [positive] endoderm cells from mouse embryonic stem cells in the absence of serum and in the presence of activin along with an inhibitor of Wnt signaling (US 2006/0003446A 1).

Gordon et al. (PNAS, Vol 103, page 16806, 2006) states: "Wnt and TGF-beta/nodal/activin signaling simultaneously were required for the generation of the anterior primitive streak."

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (D'Amour K A et al. 2005). Transplanting these cells under the kidney capsule of mice resulted in differentiation into more mature cells with characteristics of some endodermal organs. Human embryonic stem cell-derived definitive endoderm cells can be further differentiated into PDX1 positive cells after addition of FGF-10 (US 2005/0266554A1).

D'Amour et al. (Nature Biotechnology—24, 1392-1401 (2006)) states: "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones."

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of n-butyrate and activin A. The cells were then cultured with TGF-β antagonists such as Noggin in combination with EGF or betacellulin to generate PDX1 positive cells. The terminal differentiation was induced by nicotinamide.

In one example, Benvenistry et al. states: "We conclude that over-expression of PDX1 enhanced expression of pancreatic enriched genes, induction of insulin expression may require additional signals that are only present in vivo" (Benvenistry et al, Stem Cells 2006; 24:1923-1930).

Activin A is a TGF-beta family member that exhibits a wide range of biological activities including regulation of cellular proliferation and differentiation, and promotion of neuronal survival. Isolation and purification of activin A is often complex and can often result in poor yields. For example, Pangas. S. A. and Woodruff, T. K states: "Inhibin and activin are protein hormones with diverse physiological roles including the regulation of pituitary FSH secretion. Like other members of the transforming growth factor-β gene family, they undergo processing from larger precursor molecules as well as assembly into functional dimers. Isolation of inhibin and activin from natural sources can only produce limited quantities of bioactive protein." (J. Endocrinol. 172 (2002) 199-210).

In another example, Arai, K. Y. et al states: "Activins are multifunctional growth factors belonging to the transforming growth factor-β superfamily. Isolation of activins from natural sources requires many steps and only produces limited quantities. Even though recombinant preparations have been used in recent studies, purification of recombinant activins still requires multiple steps." (Protein Expression and Purification 49 (2006) 78-82).

Therefore, there still remains a significant need for alternatives for activin A to facilitate the differentiation of pluripotent stem cells.

SUMMARY

In one embodiment, the present invention provides a method to differentiate pluripotent stem cells into cells expressing markers characteristic of the definitive endoderm lineage, comprising culturing the pluripotent stem cells in medium comprising a sufficient amount of GDF-8 to cause the differentiation of the pluripotent stem cells into cells expressing markers characteristic of the definitive endoderm lineage.

In one embodiment, the medium comprising a sufficient amount of GDF-8 also contains at least one other compound. In one embodiment, the at least one other compound is an aniline-pyridinotriazine. In an alternate embodiment, the at least one other compound is a cyclic aniline-pyridinotriazine.

BRIEF DESCRIPTION OF THE FIGURES

FIG. 5 shows the expression of PDX1 and CDX2 protein in cells following the third step of differentiation, according to the methods described in Example 12. H1 cells were treated for a total of three days with 100 ng/ml activin A or 200 ng/ml GDF-8 in combination with 20 ng/ml Wnt3a for the first day or 2.5 µM Compound 34 or 2.5 µM Compound 56 for all three days followed by subsequent differentiation through the second and third steps of differentiation. Protein expression and cell numbers, as determined with fluorescent antibody probes and high content analysis, are depicted for each treatment group. For comparative purposes, values are normalized relative to treatment with activin A/Wnt3a.

FIG. 6 shows the expression of PDX1 protein (white bars) and cell number (black bars) in cells following the fourth step of differentiation, according to the methods described in Example 12. H1 cells were treated for a total of three days with 100 ng/ml activin A or 200 ng/ml GDF-8 in combination with 20 ng/ml Wnt3a for the first day or 2.5 µM Compound 34 or 2.5 µM Compound 56 for all three days followed by subsequent differentiation through the second, third, and fourth steps of differentiation. Protein expression and cell numbers, as determined with fluorescent antibody probes and high content analysis, are depicted for each treatment group. For comparative purposes, values are normalized relative to treatment with activin A/Wnt3a.

FIG. 7 shows the protein expression for insulin and glucagon and cell number in cells differentiated according to the methods described in Example 12. H1 cells were treated for a total of three days with 100 ng/ml activin A or 200 ng/ml GDF-8 in combination with 20 ng/ml Wnt3a for the first day or 2.5 μM Compound 34 or 2.5 μM Compound 56 for all three days followed by subsequent differentiation through the second, third, fourth, and fifth steps of differentiation. Protein expression and cell numbers, as determined with fluorescent antibody probes and high content analysis, are depicted for each treatment group. For comparative purposes, values are normalized relative to treatment with activin A/Wnt3a.

FIG. 10 shows SOX17 protein expression in human embryonic stem cells after differentiation to definitive endoderm, according to the methods described in Example 15. H1 cells were treated for a total of three days in various timed exposures with 100 ng/ml of activin A or 100 ng/ml GDF-8 in combination with 20 ng/ml Wnt3a. SOX17 protein expression, as determined with fluorescent antibody probes and high content analysis, is shown as total intensity values for each treatment group, testing control conditions for differentiation with no growth factors added (no treatment), with Wnt3a alone, with activin A or GDF-8 alone, or with activin A/Wnt3a treatment or GDF-8/Wnt3a treatment, where Wnt3a was added only for the first day of assay or for all three days of assay as shown.

FIG. 20, panel A shows FACS analysis for the definitive endoderm marker, CXCR4, in cells after the first step of differentiation. CXCR4 expression was measured using a fluorescent antibody probe and flow cytometry, yielding the percentages of positive cells as shown. FIG. 20, panel B shows high content image analysis for normalized SOX17 protein expression (black bars) and recovered cell numbers (white bars) resulting from the first step of differentiation, testing the corresponding treatments shown. FIG. 20, panel C shows high content image analysis for relative cell numbers recovered from cultures treated through differentiation step 5. FIG. 20, panel D shows high content image analysis for glucagon protein expression from cultures treated through differentiation step 5. FIG. 20, panel E shows high content image analysis for insulin protein expression from cultures treated through differentiation step 5. FIG. 20, panel F shows the ratio of glucagon to insulin expression in cells from cultures treated through differentiation step 5. For comparison purposes, expression values in panels B, C, D, E, and F are normalized to the control treatment with activin A and Wnt3a during step 1.

FIG. 22, panel A shows FACS analysis for the definitive endoderm marker, CXCR4, in cells after the first step of differentiation. CXCR4 expression was measured using a fluorescent antibody probe and flow cytometry, yielding the percentages of positive cells as shown. In FIG. 22, panel B, normalized RT-PCR values for various differentiation markers in cells recovered after the fourth step of differentiation are shown corresponding to respective treatments using activin A/Wnt3a or GDF-8/Compound 40 or GDF-8/Compound 202 during the first step of differentiation.

DETAILED DESCRIPTION

Figure 1A:
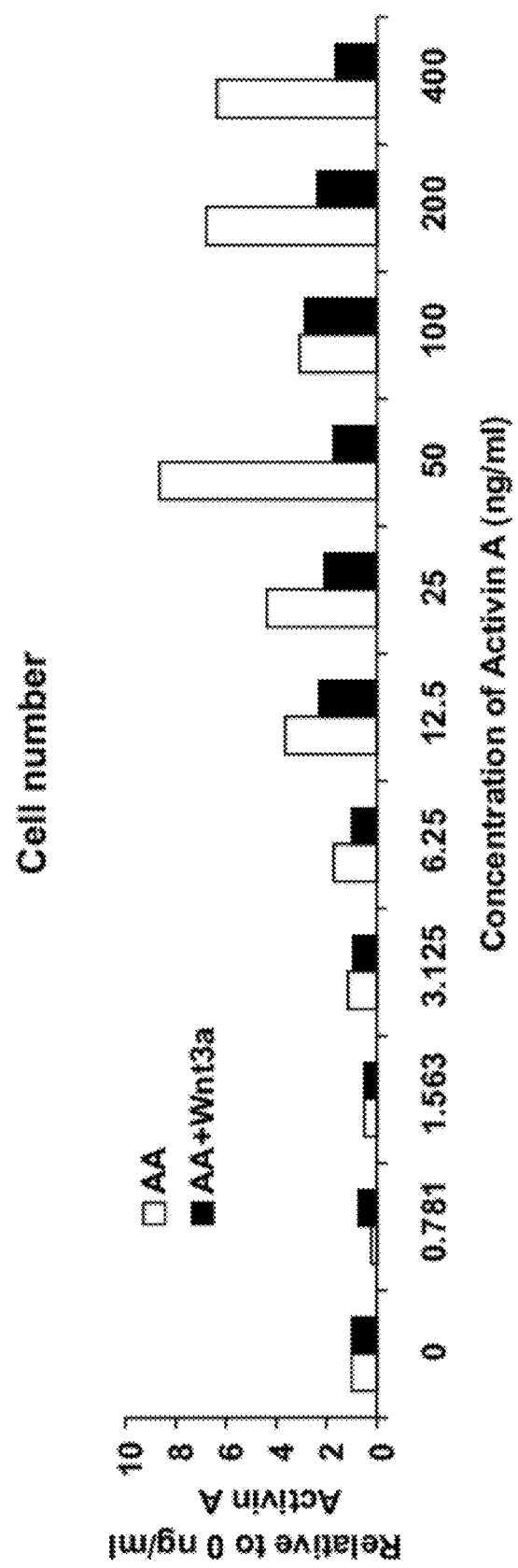
FIG. 1 shows the differentiation of H1 human embryonic stem cells into cells expressing markers characteristic of the definitive endoderm lineage. Differentiation was determined by measuring cell number (Panel A) and SOX17 intensity (Panel B) using an IN Cell Analyzer 1000 (GE Healthcare). Human embryonic stem cells were treated for a total of four days with medium containing 20 ng/ml Wnt3a plus activin A at the concentrations indicated (black bars) or medium lacking Wnt3a but with activin A at the concentrations indicated (white bars).

For clarity of disclosure, and not by way of limitation, the detailed description of the invention is divided into the following subsections that describe or illustrate certain features, embodiments, or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"β-cell lineage" refers to cells with positive gene expression for the transcription factor PDX-1 and at least one of the following transcription factors: NGN3, NKX2.2, NKX6.1, NEUROD, ISL1, HNF-3 beta, MAFA, PAX4, or PAX6. Cells expressing markers characteristic of the β cell lineage include β cells.

"Cells expressing markers characteristic of the definitive endoderm lineage", or "Stage 1 cells", or "Stage 1", as used herein, refers to cells expressing at least one of the following markers: SOX17, GATA4, HNF-3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage", as used herein, refers to cells expressing at least one of the following markers: PDX1, HNF-1 beta, PTF1 alpha, HNF6, or HB9. Cells expressing markers characteristic of the pancreatic endoderm lineage include pancreatic endoderm cells, primitive gut tube cells, and posterior foregut cells.

"Cells expressing markers characteristic of the pancreatic endocrine lineage", or "Stage 5 cells", or "Stage 5", as used herein, refers to cells expressing at least one of the following markers: NGN3, NEUROD, ISL1, PDX1, NKX6.1, PAX4, or PTF-1 alpha. Cells expressing markers characteristic of the pancreatic endocrine lineage include pancreatic endocrine cells, pancreatic hormone expressing cells, and pancreatic hormone secreting cells, and cells of the β-cell lineage.

"Definitive endoderm", as used herein, refers to cells which bear the characteristics of cells arising from the epiblast during gastrulation and which form the gastrointestinal tract and its derivatives. Definitive endoderm cells express the following markers: HNF-3 beta, GATA4, SOX-17, Cerberus, OTX2, goosecoid, C-Kit, CD99, or MIXL1.

"Extraembryonic endoderm", as used herein, refers to a population of cells expressing at least one of the following markers: SOX7, AFP, or SPARC.

"Markers", as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell", as used herein, refers to a cell expressing at least one of the following markers: CD48, eomesodermin (EOMES), SOX17, DKK4, HNF-3 beta, GSC, FGF17, or GATA-6.

"Pancreatic endocrine cell", or "pancreatic hormone expressing cell", as used herein, refers to a cell capable of expressing at least one of the following hormones: insulin, glucagon, somatostatin, and pancreatic polypeptide.

"Pancreatic endoderm cell", or "Stage 4 cells", or "Stage 4", as used herein, refers to a cell capable of expressing at least one of the following markers: NGN3, NEUROD, ISL1, PDX1, PAX4, or NKX2.2.

"Pancreatic hormone producing cell", as used herein, refers to a cell capable of producing at least one of the following hormones: insulin, glucagon, somatostatin, and pancreatic polypeptide.

"Pancreatic hormone secreting cell", as used herein, refers to a cell capable of secreting at least one of the following hormones: insulin, glucagon, somatostatin, and pancreatic polypeptide.

"Posterior foregut cell" or "Stage 3 cells", or "Stage 3", as used herein, refers to a cell capable of secreting at least one of the following markers: PDX1, HNF1, PTF-1 alpha, HNF6, HB-9, or PROX-1.

"Pre-primitive streak cell", as used herein, refers to a cell expressing at least one of the following markers: Nodal, or FGF8.

"Primitive gut tube cell" or "Stage 2 cells", or "Stage2", as used herein, refers to a cell capable of secreting at least one of the following markers: HNF1, HNF-4 alpha.

"Primitive streak cell", as used herein, refers to a cell expressing at least one of the following markers: Brachyury, Mix-like homeobox protein, or FGF4.

Isolation, Expansion, and Culture of Pluripotent Stem Cells

Characterization of Pluripotent Stem Cells

The pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10 to 12 weeks gestation. Non-limiting examples are established lines of human embryonic stem cells or human embryonic germ cells, such as, for example, the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

In one embodiment, pluripotent stem cells are prepared as described by Takahashi et al. (Cell 131: 1-12, 2007).

Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, the suitable culture substrate is MATRIGEL® (Becton Dickenson). MATRIGEL® is a soluble preparation from Engelbreth-Holm-Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma M7522; human recombinant basic fibroblast growth factor (bFGF), Gibco #13256-029.

Formation of Pancreatic Hormone Producing Cells from Pluripotent Stem Cells

In one embodiment, the present invention provides a method for producing pancreatic hormone producing cells from pluripotent stem cells, comprising the steps of:
a. Culturing pluripotent stem cells,
b. Differentiating the pluripotent stem cells into cells expressing markers characteristic of the definitive endoderm lineage,
c. Differentiating the cells expressing markers characteristic of the definitive endoderm lineage into cells expressing markers characteristic of the pancreatic endoderm lineage, and
d. Differentiating the cells expressing markers characteristic of the pancreatic endoderm lineage into cells expressing markers characteristic of the pancreatic endocrine lineage.

In one aspect of the present invention, the pancreatic endocrine cell is a pancreatic hormone producing cell. In an alternate aspect, the pancreatic endocrine cell is a cell expressing markers characteristic of the β-cell lineage. A cell expressing markers characteristic of the β-cell lineage expresses PDX1 and at least one of the following transcription factors: NGN3, NKX2.2, NKX6.1, NEUROD, ISL1, HNF-3 beta, MAFA, PAX4, or Pax6. In one aspect of the present invention, a cell expressing markers characteristic of the β-cell lineage is a β-cell.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FOXD3, Connexin43, Connexin45, OCT4, SOX2, Nanog, hTERT, UTF-1, ZFP42, SSEA-3, SSEA-4, Tra1-60, or Tra1-81.

The pluripotent stem cells may be cultured on a feeder cell layer. Alternatively, the pluripotent stem cells may be cultured on an extracellular matrix. The extracellular matrix may be a solubilized basement membrane preparation extracted from mouse sarcoma cells (as sold by BD. Biosciences under the trade name MATRIGEL™). Alternatively, the extracellular matrix may be growth factor-reduced MATRIGEL™. Alternatively, the extracellular matrix may be fibronectin. In an alternate embodiment, the pluripotent stem cells are cultured and differentiated on tissue culture substrate coated with human serum.

The extracellular matrix may be diluted prior to coating the tissue culture substrate. Examples of suitable methods for diluting the extracellular matrix and for coating the tissue culture substrate may be found in Kleinman, H. K., et al., Biochemistry 25:312 (1986), and Hadley, M. A. et al., J. Cell. Biol. 101:1511 (1985).

In one embodiment, the extracellular matrix is MATRIGEL™. In one embodiment, the tissue culture substrate is coated with MATRIGEL™ at a 1:10 dilution. In an alternate embodiment, the tissue culture substrate is coated with MATRIGEL™ at a 1:15 dilution. In an alternate embodiment, the tissue culture substrate is coated with MATRIGEL™ at a 1:30 dilution. In an alternate embodiment, the tissue culture substrate is coated with MATRIGEL™ at a 1:60 dilution.

In one embodiment, the extracellular matrix is growth factor-reduced MATRIGEL™. In one embodiment, the tissue culture substrate is coated with growth factor-reduced MATRIGEL™ at a 1:10 dilution. In an alternate embodiment, the tissue culture substrate is coated with growth factor-reduced MATRIGEL™ at a 1:15 dilution. In an alternate embodiment, the tissue culture substrate is coated with growth factor-reduced MATRIGEL™ at a 1:30 dilution. In an alternate embodiment, the tissue culture substrate is coated with growth factor-reduced MATRIGEL™ at a 1:60 dilution.

Markers characteristic of the definitive endoderm lineage are selected from the group consisting of SOX17, GATA4, HNF-3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of PDX1, HNF-1 beta, PTF1 alpha, HNF6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of the pancreatic endocrine lineage are selected from the group consisting of NGN3, NEUROD, ISL1, PDX1, NKX6.1, PAX4, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

Formation of Cells Expressing Markers Characteristic of the Definitive Endoderm Lineage In one aspect of the present invention, pluripotent stem cells may be differentiated into cells expressing markers characteristic of the definitive endoderm lineage by culturing the pluripotent stem cells in medium comprising a sufficient amount of GDF-8 to cause the differentiation of the pluripotent stem cells into cells expressing markers characteristic of the definitive endoderm lineage.

The pluripotent stem cells may be cultured in the medium containing a sufficient amount of GDF-8 for about one day to about seven days. Alternatively, the pluripotent stem cells may be cultured in the medium containing a sufficient amount of GDF-8 for about one day to about six days. Alternatively, the pluripotent stem cells may be cultured in the medium containing a sufficient amount of GDF-8 for about one day to about five days. Alternatively, the pluripotent stem cells may be cultured in the medium containing a sufficient amount of GDF-8 for about one day to about four days. Alternatively, the pluripotent stem cells may be cultured in the medium containing a sufficient amount of GDF-8 for about one day to about three days. Alternatively, the pluripotent stem cells may be cultured in the medium containing a sufficient amount of GDF-8 for about one day to about two days. Alternatively, the pluripotent stem cells may be cultured in the medium containing a sufficient amount of GDF-8 for about one day.

In one embodiment, the GDF-8 is used at a concentration from about 5 ng/ml to about 500 ng/ml. In an alternate embodiment, the GDF-8 is used at a concentration from about 5 ng/ml to about 50 ng/ml. In an alternate embodiment, the GDF-8 is used at a concentration from about 5 ng/ml to about 25 ng/ml. In an alternate embodiment, the GDF-8 is used at a concentration of about 25 ng/ml.

In one embodiment, the medium comprising a sufficient amount of GDF-8 also contains at least one other factor. In one embodiment, the at least one other factor is selected from the group consisting of: EGF, FGF4, PDGF-A, PDGF-B, PDGF-C, PDGF-D, VEGF, muscimol, PD98059, LY294002, U0124, U0126, and sodium butyrate.

In one embodiment, the EGF is used at a concentration from about 5 ng/ml to about 500 ng/ml. In an alternate embodiment, the EGF is used at a concentration from about 5 ng/ml to about 50 ng/ml. In an alternate embodiment, the EGF is used at a concentration of about 50 ng/ml.

In one embodiment, the FGF4 is used at a concentration from about 5 ng/ml to about 500 ng/ml. In an alternate embodiment, the FGF4 is used at a concentration from about 5 ng/ml to about 50 ng/ml. In an alternate embodiment, the FGF4 is used at a concentration of about 50 ng/ml.

In one embodiment, the PDGF-A is used at a concentration from about 5 ng/ml to about 500 ng/ml. In an alternate embodiment, the PDGF-A is used at a concentration from about 5 ng/ml to about 50 ng/ml. In an alternate embodiment, the PDGF-A is used at a concentration of about 50 ng/ml.

In one embodiment, the PDGF-B is used at a concentration from about 5 ng/ml to about 500 ng/ml. In an alternate embodiment, the PDGF-B is used at a concentration from about 5 ng/ml to about 50 ng/ml. In an alternate embodiment, the PDGF-B is used at a concentration of about 50 ng/ml.

In one embodiment, the PDGF-C is used at a concentration from about 5 ng/ml to about 500 ng/ml. In an alternate embodiment, the PDGF-C is used at a concentration from about 5 ng/ml to about 50 ng/ml. In an alternate embodiment, the PDGF-C is used at a concentration of about 50 ng/ml.

In one embodiment, the PDGF-D is used at a concentration from about 5 ng/ml to about 500 ng/ml. In an alternate embodiment, the PDGF-D is used at a concentration from about 5 ng/ml to about 50 ng/ml. In an alternate embodiment, the PDGF-D is used at a concentration of about 50 ng/ml.

In one embodiment, the VEGF is used at a concentration from about 5 ng/ml to about 500 ng/ml. In an alternate embodiment, the VEGF is used at a concentration from about 5 ng/ml to about 50 ng/ml. In an alternate embodiment, the VEGF is used at a concentration of about 50 ng/ml.

In one embodiment, the muscimol is used at a concentration from about 1 µM to about 200 µM. In an alternate embodiment, the muscimol is used at a concentration from about 1 µM to about 20 µM. In an alternate embodiment, the muscimol is used at a concentration of about 20 µM.

In one embodiment, the PD98059 is used at a concentration from about 0.1 µM to about 10 µM. In an alternate embodiment, the PD98059 is used at a concentration from about 0.1 µM to about 1 µM. In an alternate embodiment, the PD98059 is used at a concentration of about 1 µM.

In one embodiment, the LY294002 is used at a concentration from about 0.25 µM to about 25 µM. In an alternate embodiment, the LY294002 is used at a concentration from about 0.25 µM to about 2.5 µM. In an alternate embodiment, the LY294002 is used at a concentration of about 2.5 µM.

In one embodiment, the U0124 is used at a concentration from about 0.1 µM to about 10 µM. In an alternate embodiment, the U0124 is used at a concentration from about 0.1 µM to about 1 µM. In an alternate embodiment, the U0124 is used at a concentration of about 1 µM.

In one embodiment, the U0126 is used at a concentration from about 0.1 µM to about 10 µM. In an alternate embodiment, the U0126 is used at a concentration from about 0.1 µM to about 1 µM. In an alternate embodiment, the U0126 is used at a concentration of about 1 µM.

In one embodiment, the sodium butyrate is used at a concentration from about 0.05 µM to about 5 µM. In an alternate embodiment, the sodium butyrate is used at a concentration from about 0.05 µM to about 0.5 µM. In an alternate embodiment, the sodium butyrate is used at a concentration of about 0.5 µM.

In an alternate embodiment, the at least one other factor is selected from the group consisting of: an aniline-pyridinotriazine, a cyclic aniline-pyridinotriazine, N-{[1-(Phenylmethyl)azepan-4-yl]methyl}-2-pyridin-3-ylacetamide, 4-{[4-(4-{[2-(Pyridin-2-ylamino)ethyl]amino}-1,3,5-triazin-2-yl)pyridin-2-yl]oxy}butan-1-ol, 3-({3-[4-({2-[Methyl (pyridin-2-yl)amino]ethyl}amino)-1,3,5-triazin-2-yl]pyridin-2-yl}amino)propan-1-ol, N~4~-[2-(3-Fluorophenyl) ethyl]-N~2~-[3-(4-methylpiperazin-1-yl)propyl]pyrido[2,3-d]pyrimidine-2,4-diamine, 1-Methyl-N-[(4-pyridin-3-yl-2-{[3-(trifluoromethyl)phenyl]amino}-1,3-thiazol-5-yl) methyl]piperidine-4-carboxamide, 1,1-Dimethylethyl {2-[4-({5-[3-(3-hydroxypropyl)phenyl]-4H-1,2,4-triazol-3-yl}amino)phenyl]ethyl}carbamate, 1,1-Dimethylethyl {[3-({5-[5-(3-hydroxypropyl)-2-(methyloxy)phenyl]-1,3-oxazol-2-yl}amino)phenyl]methyl}carbamate, 1-({5-[6-({4-[(4-Methylpiperazin-1-yl)sulfonyl]phenyl}amino) pyrazin-2-yl]thiophen-2-yl}methyl)piperidin-4-ol, 1-({4-[6-({4-[(4-Methylpiperazin-1-yl)sulfonyl]phenyl}amino) pyrazin-2-yl]thiophen-2-yl}methyl)piperidine-4-carboxamide, and 2-{[4-(1-Methylethyl)phenyl]amino}-N-(2-thiophen-2-ylethyl)-7,8-dihydropyrido[4,3-d] pyrimidine-6(5H)-carboxamide.

The Compounds of the Present Invention

The present invention provides compounds that are capable of differentiating pluripotent stem cells into cells expressing markers characteristic of the definitive endoderm lineage.

In one embodiment, the compound that is capable of differentiating pluripotent stem cells into cells expressing markers characteristic of the definitive endoderm lineage is an aniline-pyridinotriazine of the Formula (1):

Formula (1)

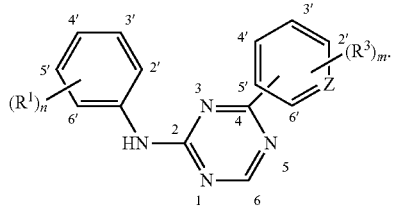

The N-oxide forms, the pharmaceutically acceptable addition salts and the stereochemically isomeric forms thereof, wherein:

m represents an integer from 1 to 4; n represents an integer from 1 to 4; Z represents N or C;

$R^1$ and $R^8$ each independently represent hydrogen, $Het^{14}$, cyano, halo, hydroxy, $C_{1-6}$alkoxy-, $C_{1-6}$alkyl-, mono- or di($C_{1-4}$alkyl)amino-carbonyl-, mono- or di($C_{1-4}$alkyl) amino-sulfonyl, $C_{1-6}$alkoxy-substituted with halo or $R^1$ represents $C_{1-6}$alkyl substituted with one or where possible two or more substituents selected from hydroxy or halo;

$R^2$ and $R^9$ each independently represents hydrogen, $C_{1-4}$alkyl, $C_{2-4}$alkenyl, $Het^3$, $Het^4$-$C_{1-4}$alkyl-, $Het^5$-$C_{1-4}$alkylcarbonyl-, mono- or di($C_{1-4}$alkyl)amino-$C_{1-4}$alkyl-carbonyl- or phenyl optionally substituted with one or where possible two or more substituents selected from hydrogen, hydroxy, amino or $C_{1-4}$alkyloxy-;

$R^3$ and $R^7$ each independently represent hydrogen, $C_{1-4}$alkyl, $Het^6$, $Het^7$-$C_{1-4}$alkyl-, $C_{2-4}$alkenylcarbonyl-optionally substituted with $Het^8$-$C_{1-4}$alkylaminocarbonyl-, $C_{2-4}$alkenylsulfonyl-, $C_{1-4}$lkyloxy$C_{1-4}$alkyl- or phenyl optionally substituted with one or where possible two or more substituents selected from hydrogen, hydroxy, amino or $C_{1-4}$alkyloxy-;

R4, R5, R6 and $R^{10}$ each independently represent hydrogen or $C_{1-4}$alkyl optionally substituted with hydroxy, $Het^9$ or $C_{1-4}$alkyloxy;

$Het^1$ and $Het^2$ each independently represent a heterocycle selected from pyrrolidinyl, piperidinyl, piperazinyl, pyridinyl, pyrimidinyl, pyrazinyl, imidazolidinyl or pyrazolidinyl wherein said $Het^1$ and $Het^2$ are optionally substituted with amino, hydroxy, $C_{1-4}$alkyl, hydroxy-$C_{1-4}$allcyl-, phenyl, phenyl-$C_{1-4}$alkyl-, $C_{1-4}$alkyl-oxy-$C_{1-4}$alkyl-mono- or di($C_{1-4}$alkyl) amino- or amino-carbonyl-;

$Het^3$ and $Het^6$ each independently represent, heterocycle selected from pyrrolidinyl or piperidinyl wherein said $Het^3$ and $Het^6$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^4$, $Het^7$ and $Het^9$ each independently represent a heterocycle selected from morpholinyl, pyrrolidinyl, piperazinyl or piperidinyl wherein said $Het^4$, $Het^7$ and $Het^9$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^5$ represents a heterocycle selected from morpholinyl, pyrrolidinyl, piperazinyl or pipendinyl wherein said $Het^5$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{10}$, $Het^{11}$ and $Het^{13}$ each independently represent a heterocycle selected from pyrrolidinyl, piperidinyl, piperazinyl, pyridinyl, pyrimidinyl, pyrazinyl, imidazolidinyl or pyrazolidinyl wherein said $Het^{10}$, $Het^{11}$ and $Het^{13}$ are optionally substituted with amino, hydroxy, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, amino-carbonyl- or mono- or di($C_{1-4}$alkyl) amino-;

$Het^{12}$ represents a heterocycle selected from pyrrolidinyl, piperidinyl, piperazinyl, pyridinyl, pyrimidinyl, pyrazinyl, imidazolidinyl or pyrazolidinyl wherein said $Het^{12}$ is optionally substituted with amino, hydroxy, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-; mono- or di($C_{1-4}$alkyl)amino- or amino-carbonyl-;

$Het^{14}$ represents a heterocycle selected from morpholinyl; pyrrolidinyl; piperazinyl; imidazolyl; pyrrolyl; 2,3,4-triazapyrrolyl; 1,2,3-triazolyl; pyrazolyl; or piperidinyl wherein said $Het^{14}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-; in particular $Het^{14}$ represents a heterocycle selected from morpholinyl; pyrrolidinyl; pyrrolyl; 2,3,4-triazapyrrolyl; piperazinyl or piperidinyl wherein said $Het^{14}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-; more particular $Het^{14}$ represents a heterocycle selected from morpholinyl; pyrrolidinyl; piperazinyl or piperidinyl wherein said $Het^{14}$ is optionally substituted with one or where possible two or more substituents selected from $C_{1-4}$alkyl, $C_{1-4}$cycloalkyl, hydroxy-$C_{1-4}$alkyl-, $C_{1-4}$alkyloxy$C_{1-4}$alkyl or polyhydroxy-$C_{1-4}$alkyl-.

In one embodiment, the aniline-pyridinotriazine is a compound of the Formula (1).

In one embodiment, the aniline-pyridinotriazine is a compound of the Formula (2).

Formula (2):

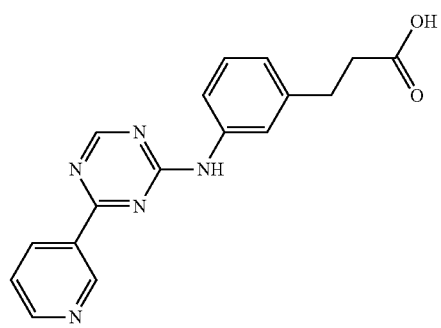

3-{3-[(4-Pyridin-3-yl-1,3,5-triazin-2-yl)amino]phenyl}propanoic acid. Referred to herein as "Compound 1."

In one embodiment, the aniline-pyridinotriazine is a compound of the Formula (3).

Formula (3):

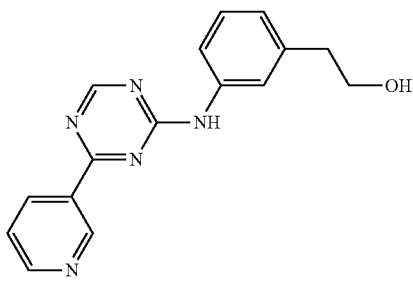

2-{3-[(4-Pyridin-3-yl-1,3,5-triazin-2-yl)amino]phenyl}ethanol. Referred to herein as "Compound 2".

In one embodiment, the aniline-pyridinotriazine is a compound of the Formula (4).

Formula (4):

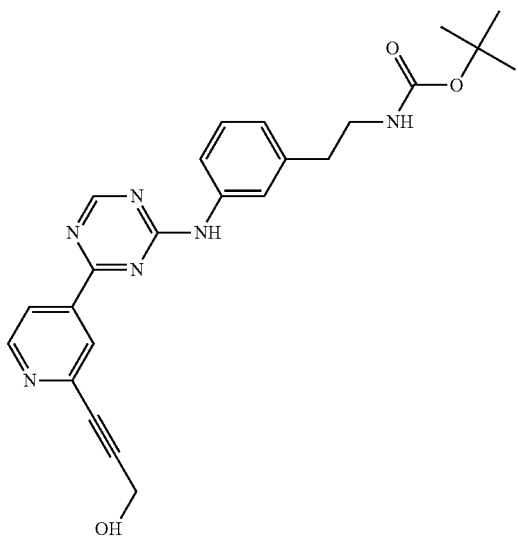

1,1-Dimethylethyl {2-[3-({4-[2-(3-hydroxyprop-1-yn-1-yl)pyridin-4-yl]-1,3,5-triazin-2-yl}amino)phenyl]ethyl}carbamate. Referred to herein as "Compound 3".

In one embodiment, the aniline-pyridinotriazine is a compound of the Formula (5).

Formula (5):

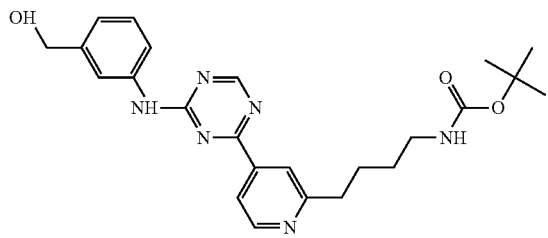

1,1-Dimethylethyl {4-[4-(4-{[3-(hydroxymethyl)phenyl]amino}-1,3,5-triazin-2-yl)pyridin-2-yl]butyl}carbamate. Referred to herein as "Compound 4".

In one embodiment, the aniline-pyridinotriazine is a compound of the Formula (6).

Formula (6):

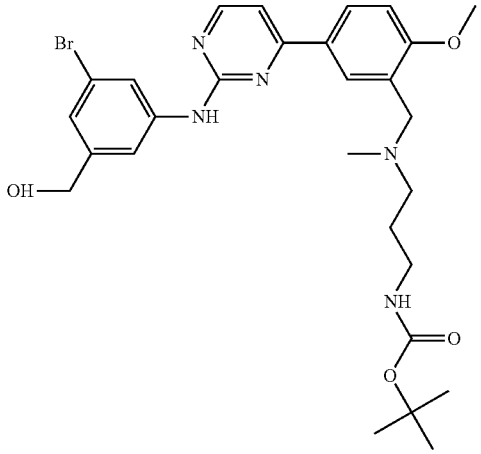

1,1-Dimethylethyl {3-[{[5-(2-{[3-bromo-5-(hydroxymethyl)phenyl]amino}pyrimidin-4-yl)-2-(methyloxy)phenyl]methyl}(methyl)amino]propyl}carbamate. Referred to herein as "Compound 5".

In one embodiment, the aniline-pyridinotriazine is a compound of the Formula (7).

Formula (7):

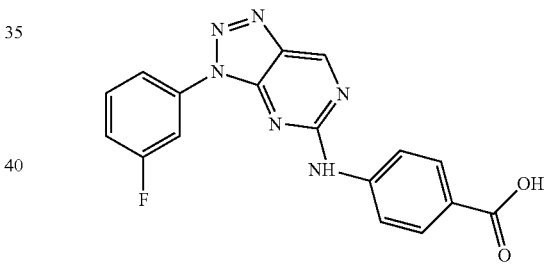

4-{[3-(3-Fluorophenyl)-3H-[1,2,3]triazolo[4,5-d]pyrimidin-5-yl]amino}benzoic acid. Referred to herein as "Compound 6".

In one embodiment, the aniline-pyridinotriazine is a compound of the Formula (8).

Formula (8):

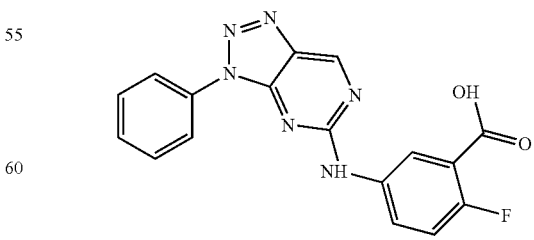

2-Fluoro-5-[(3-phenyl-3H-[1,2,3]triazolo[4,5-d]pyrimidin-5-yl)amino]benzoic acid. Referred to herein as "Compound 7".

In one embodiment, the aniline-pyridinotriazine is a compound of the Formula (9).

Formula (9):

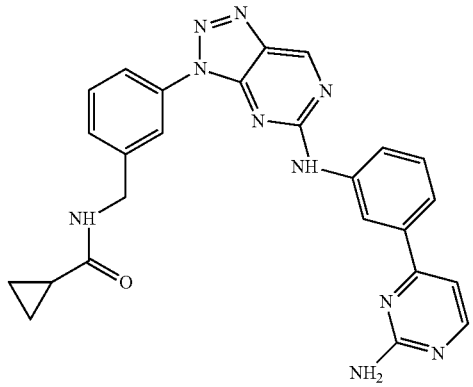

N-{[3-(5-{[3-(2-Aminopyrimidin-4-yl)phenyl]amino}-3H-[1,2,3]triazolo[4,5-d]pyrimidin-3-yl)phenyl]methyl}cyclopropanecarboxamide. Referred to herein as "Compound 8".

In one embodiment, the aniline-pyridinotriazine is a compound of the Formula (10).

Formula (10):

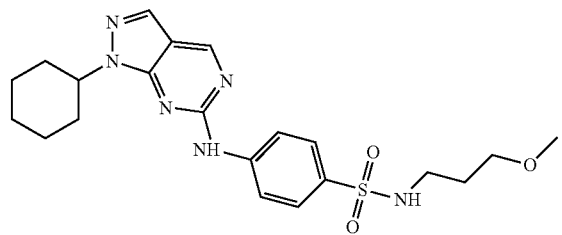

4-[(1-Cyclohexyl-1H-pyrazolo[3,4-d]pyrimidin-6-yl)amino]-N-[3-(methyloxy)propyl]benzenesulfonamide. Referred to herein as "Compound 9".

In one embodiment, the aniline-pyridinotriazine is a compound of the Formula (11).

Formula (11):

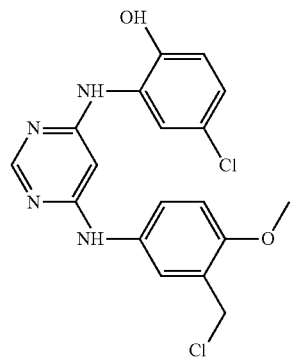

4-Chloro-2-[(6-{[3-(chloromethyl)-4-methoxyphenyl]amino}pyrimidin-4-yl)amino]phenol. Referred to herein as "Compound 10".

In one embodiment, the aniline-pyridinotriazine is a compound of the Formula (12).

Formula (12):

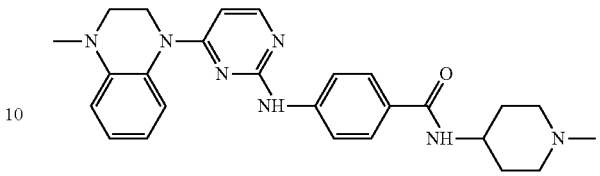

4-{[4-(4-Methyl-3,4-dihydroquinoxalin-1(2H)-yl)pyrimidin-2-yl]amino}-N-(1-methylpiperidin-4-yl)benzamide. Referred to herein as "Compound 11".

In one embodiment, the aniline-pyridinotriazine is a compound of the Formula (13).

Formula (13):

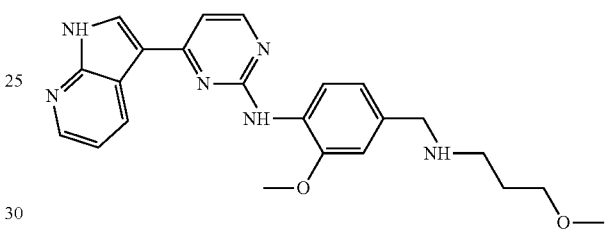

N-(2-Methoxy-4-{[(3-methoxypropyl)amino]methyl}phenyl)-4-(1H-pyrrolo[2,3-b]pyridin-3-yl)pyrimidin-2-amine. Referred to herein as "Compound 12".

In one embodiment, the compound that is capable of differentiating pluripotent stem cells into cells expressing markers characteristic of the definitive endoderm lineage is a cyclic aniline-pyridinotriazine of the Formula (14):

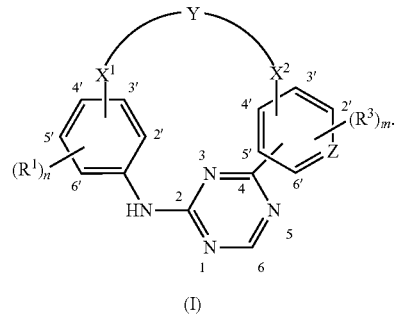

Formula (14)

The N-oxide forms, the pharmaceutically acceptable addition salts and the stereochemically isomeric forms thereof, wherein:

m represents an integer from 1 to 4; n represents an integer from 1 to 4; Z represents N or C;

Y represents -NR$^2$—C$_{1-6}$alkyl-CO—NR$^4$—, —C$_{1-4}$alkyl-NR$^9$—C$_{1-4}$alkyl-, C$_{1-6}$alkyl-CO-Het$^{10}$-, -Het$^{11}$-CO—C$_{1-6}$alkyl-, Het$^{12}$-C$_{1-6}$alkyl-, —CO-Het$^{13}$-C$_{1-6}$alkyl-, —CO—NR$^{10}$—C$_{1-6}$alkyl-,-Het$^1$-C$_{1-6}$alkyl-CO—NR$^5$—, or -Het$^2$-CO—NR$^6$— wherein the —C$_{1-6}$alkyl-linker in —NR$^2$—C$^{1-6}$alkyl-CO—NR$^4$— or -Het$^1$-C$_{1-6}$alkyl-CO—NR$^5$— is optionally substituted with one or where possible two or more substituents selected from hydroxy, methoxy, aminocarbonyl, halo, phenyl, indolyl, methylsulfide, thiol, hydroxyphenyl, cyanophenyl, amino and hydroxycarbonyl;

$X^1$ represents a direct bond, $C_{1-4}$alkyl, $C_{1-4}$alkyloxy-, $C_{1-4}$alkyl-CO—, $C_{2-4}$ alkenyl, $C_{2-4}$alkynyl, or $C_{1-4}$alkyl-$NR^3$—, wherein said $C_{1-4}$alkyl or $C_{2-4}$alkenyl is optionally substituted with one or where possible two or more halo substituents;

$X^2$ represents a direct bond, $C_{1-4}$alkyl, $C_{1-4}$alkyloxy-, $C_{1-4}$alkyl-CO—, $C_{2-4}$ alkenyl, $C_{2-4}$alkynyl, or $C_{1-4}$alkyl-$NR^7$—, wherein said $C_{1-4}$alkyl or $C_{2-4}$alkenyl is optionally substituted with one or where possible two or more halo substituents;

$R^1$ and $R^8$ each independently represent hydrogen, $Het^{14}$, cyano, halo, hydroxy, $C_{1-6}$alkoxy-, $C_{1-6}$alkyl-, mono- or di($C_{1-4}$alkyl)amino-carbonyl-, mono- or di($C_{1-4}$alkyl)amino-sulfonyl, $C_{1-6}$alkoxy-substituted with halo or $R^1$ represents $C_{1-6}$alkyl substituted with one or where possible two or more substituents selected from hydroxy or halo;

$R^2$ and $R^9$ each independently represents hydrogen, $C_{1-4}$alkyl, $C_{2-4}$alkenyl, $Het^3$, $Het^4$-$C_{1-4}$alkyl-, $Het^5$-$C_{1-4}$alkylcarbonyl-, mono- or di($C_{1-4}$alkyl)amino-$C_{1-4}$alkyl-carbonyl- or phenyl optionally substituted with one or where possible two or more substituents selected from hydrogen, hydroxy, amino or $C_{1-4}$alkyloxy-;

$R^3$ and $R^7$ each independently represent hydrogen, $C_{1-4}$alkyl, $Het^6$, $Het^7$-$C_{1-4}$alkyl-, $C_{2-4}$alkenylcarbonyl-optionally substituted with $Het^8$-$C_{1-4}$alkylaminocarbonyl-, $C_{2-4}$alkenylsulfonyl-, $C_{1-4}$lkyloxy$C_{1-4}$alkyl- or phenyl optionally substituted with one or where possible two or more substituents selected from hydrogen, hydroxy, amino or $C_{1-4}$alkyloxy-;

R4, R5, R6 and $R^{10}$ each independently represent hydrogen or $C_{1-4}$alkyl optionally substituted with hydroxy, $Het^9$ or $C_{1-4}$alkyloxy;

$Het^1$ and $Het^2$ each independently represent a heterocycle selected from pyrrolidinyl, piperidinyl, piperazinyl, pyridinyl, pyrimidinyl, pyrazinyl, imidazolidinyl or pyrazolidinyl wherein said $Het^1$ and $Het^2$ are optionally substituted with amino, hydroxy, $C_{1-4}$alkyl, hydroxy-$C_{1-4}$allcyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^3$ and $Het^6$ each independently represent, heterocycle selected from pyrrolidinyl or piperidinyl wherein said $Het^3$ and $Het^6$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^4$, $Het^7$ and $Het^9$ each independently represent a heterocycle selected from morpholinyl, pyrrolidinyl, piperazinyl or piperidinyl wherein said $Het^4$, $Het^7$ and $Het^9$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^5$ represents a heterocycle selected from morpholinyl, pyrrolidinyl, piperazinyl or pipendinyl wherein said $Het^5$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{10}$, $Het^{11}$ and $Het^{13}$ each independently represent a heterocycle selected from pyrrolidinyl, piperidinyl, piperazinyl, pyridinyl, pyrimidinyl, pyrazinyl, imidazolidinyl or pyrazolidinyl wherein said $Het^{10}$, $Het^{11}$ and $Het^{13}$ are optionally substituted with amino, hydroxy, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, amino-carbonyl- or mono- or di($C_{1-4}$alkyl) amino-;

$Het^{12}$ represents a heterocycle selected from pyrrolidinyl, piperidinyl, piperazinyl, pyridinyl, pyrimidinyl, pyrazinyl, imidazolidinyl or pyrazolidinyl wherein said $Het^{12}$ is optionally substituted with amino, hydroxy, hydroxy-$C_{1-4}$alkyl-, phenyl, phenyl-$C_{1-4}$alkyl-, $C_{1-4}$alkyl-oxy-$C_{1-4}$alkyl-; mono- or di($C_{1-4}$alkyl)amino- or amino-carbonyl-;

$Het^{14}$ represents a heterocycle selected from morpholinyl; pyrrolidinyl; piperazinyl; imidazolyl; pyrrolyl; 2,3,4-triazapyrrolyl; 1,2,3-triazolyl; pyrazolyl; or piperidinyl wherein said $Het^{14}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-; in particular $Het^{14}$ represents a heterocycle selected from morpholinyl; pyrrolidinyl; pyrrolyl; 2,3,4-triazapyrrolyl; piperazinyl or piperidinyl wherein said $Het^{14}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-; more particular $Het^{14}$ represents a heterocycle selected from morpholinyl; pyrrolidinyl; piperazinyl or piperidinyl wherein said $Het^{14}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$ alkyl-.

Compounds of Formula (7) are disclosed in WO2007/003525, assigned to Janssen Pharmaceutica N.V.

In one embodiment, the cyclic aniline-pyridinotriazine is a compound of the Formula (14).

In one embodiment, the cyclic aniline-pyridinotriazine is a compound of the Formula (15).

Formula (15):

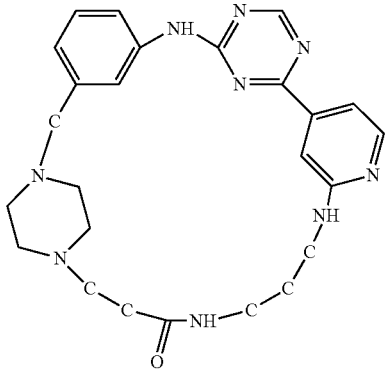

1,8,10,12,17,19,23,27,33-Nonaazapentacyclo[25.2.2.1~3, 7~.1~9,13~.1~14,18~]tetratriaconta-3(34),4,6,9(33),10,12, 14(32),15,17-nonaen-24-one. Referred to herein as "Compound 13".

In one embodiment, the cyclic aniline-pyridinotriazine is a compound of the Formula (16).

Formula (16):

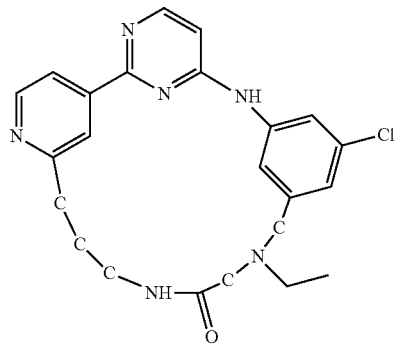

10-Chloro-14-ethyl-3,5,7,14,17,22,27-heptaazatetracyclo[19.3.1.1~2,6~.1~8,12~]heptacosa-1(25),2(27),3,5,8(26),9,11,21,23-nonaen-16-one. Referred to herein as "Compound 14".

In one embodiment, the cyclic aniline-pyridinotriazine is a compound of the Formula (17).

Formula (17):

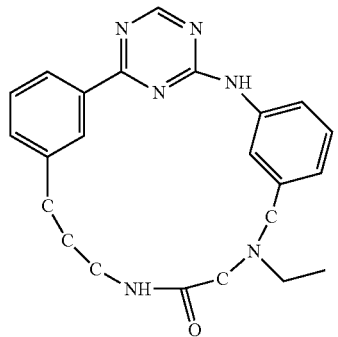

14-Ethyl-3,5,7,14,17,27-hexaazatetracyclo[19.3.1.1~2,6~.1~8,12~]heptacosa-1(25),2(27),3,5,8(26),9,11,21,23-nonaen-16-one. Referred to herein as "Compound 15".

In one embodiment, the cyclic aniline-pyridinotriazine is a compound of the Formula (18).

Formula (18):

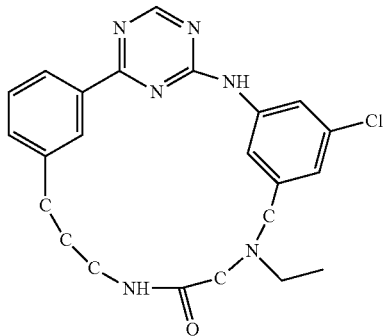

10-Chloro-14-ethyl-3,5,7,14,17,27-hexaazatetracyclo[19.3.1.1~2,6~.1~8,12~]heptacosa-1(25),2(27),3,5,8(26),9,11,21,23-nonaen-16-one. Referred to herein as "Compound 16".

In one embodiment, the cyclic aniline-pyridinotriazine is a compound of the Formula (19).

Formula (19):

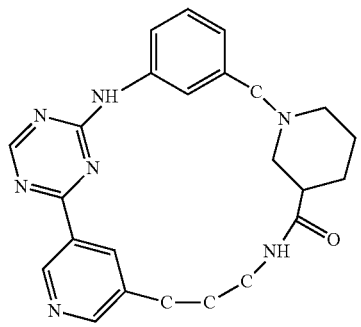

3,5,7,14,20,26,31-Heptaazapentacyclo[22.3.1.1~2,6~.1~8,12~.1~14,18~]hentriaconta-1(28),2(31),3,5,8(30),9,11,24,26-nonaen-19-one. Referred to herein as "Compound 17".

In one embodiment, the cyclic aniline-pyridinotriazine is a compound of the Formula (20).

Formula (20):

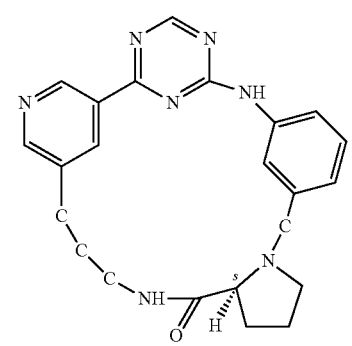

(18S)-3,5,7,14,20,26,30-Heptaazapentacyclo[22.3.1.1~2,6~.1~8,12~.0~14,18~]triaconta-1(28),2(30),3,5,8(29),9,11,24,26-nonaen-19-one. Referred to herein as "Compound 18".

In one embodiment, the cyclic aniline-pyridinotriazine is a compound of the Formula (21).

Formula (21):

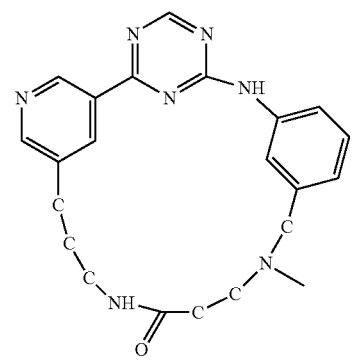

14-Methyl-3,5,7,14,18,24,28-heptaazatetracyclo[20.3.1.1~2,6~.1~8,12~]octacosa-1(26),2(28),3,5,8(27),9,11,22,24-nonaen-17-one. Referred to herein as "Compound 19".

In one embodiment, the cyclic aniline-pyridinotriazine is a compound of the Formula (22).

Formula (22):

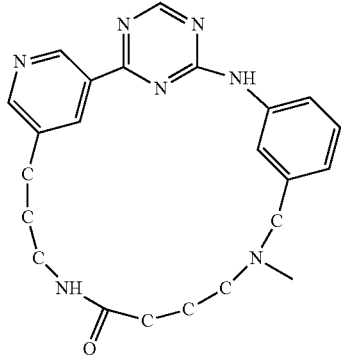

14-Methyl-3,5,7,14,19,25,29-heptaazatetracyclo[21.3.1.1~2,6~.1~8,12~]nonacosa-1(27),2(29),3,5,8(28),9,11,23,25-nonaen-18-one. Referred to herein as "Compound 20".

In one embodiment, the cyclic aniline-pyridinotriazine is a compound of the Formula (23).

Formula (23):

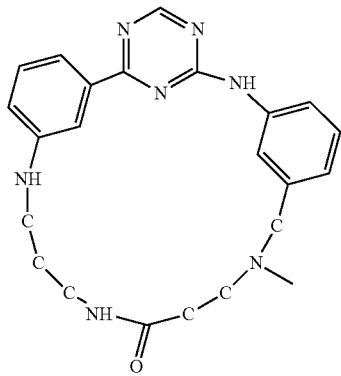

14-Methyl-3,5,7,14,18,22,29-heptaazatetracyclo[21.3.1.1~2,6~.1~8,12~]nonacosa-1(27),2(29),3,5,8(28),9,11,23,25-nonaen-17-one. Referred to herein as "Compound 21".

In one embodiment, the cyclic aniline-pyridinotriazine is a compound of the Formula (24).

Formula (24):

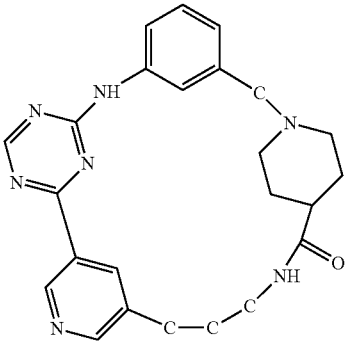

1,8,10,12,16,22,30-Heptaazapentacyclo[22.2.2.1~3,7~.1~9,13~.1~14,18~]hentriaconta-3(31),4,6,9(30),10,12,14(29),15,17-nonaen-23-one. Referred to herein as "Compound 22".

In one embodiment, the cyclic aniline-pyridinotriazine is a compound of the Formula (25).

Formula (25):

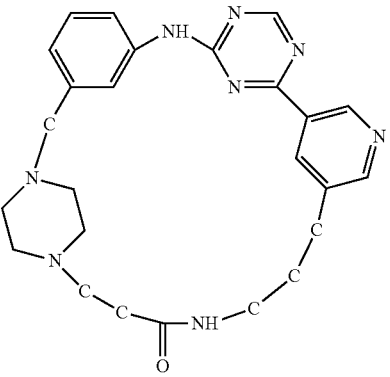

1,8,10,12,16,22,26,32-Octaazapentacyclo[24.2.2.1~3,7~.1~9,13~.1~14,18~]tritriaconta-3(33),4,6,9(32),10,12,14(31),15,17-nonaen-23-one. Referred to herein as "Compound 23".

In one embodiment, the cyclic aniline-pyridinotriazine is a compound of the Formula (26).

Formula (26):

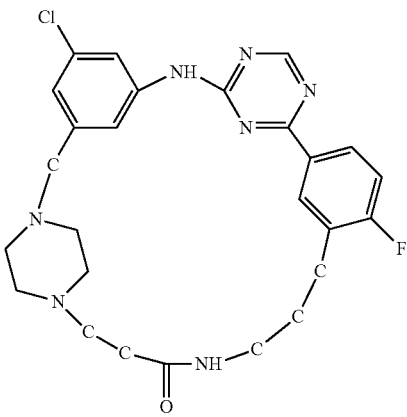

5-Chloro-17-fluoro-1,8,10,12,22,26,32-heptaazapentacyclo[24.2.2.1~3,7~.1~9,13~.1~14,18~]tritriaconta-3(33),4,6,9(32), 10,12,14(31),15,17-nonaen-23-one. Referred to herein as "Compound 24".

In one embodiment, the cyclic aniline-pyridinotriazine is a compound of the Formula (27).

Formula (27):

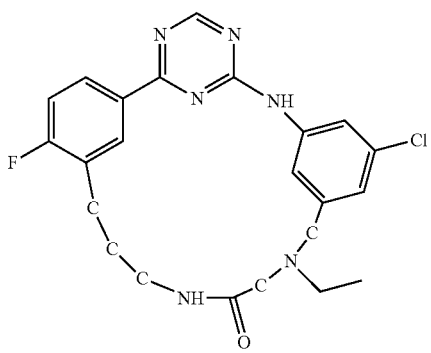

10-Chloro-14-ethyl-22-fluoro-3,5,7,14,17,27-hexaazatetracyclo[19.3.1.1~2,6~.1~8,12~]heptacosa-1(25),2(27),3,5,8(26),9,11,21,23-nonaen-16-one. Referred to herein as "Compound 25".

In one embodiment, the cyclic aniline-pyridinotriazine is a compound of the Formula (28).

Formula (28):

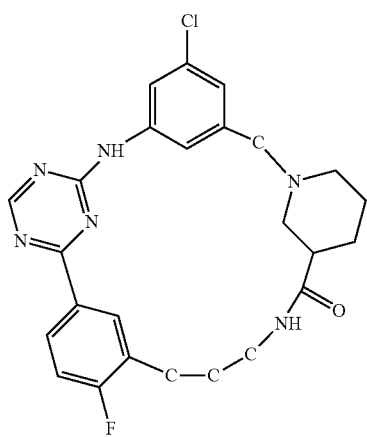

10-Chloro-25-fluoro-3,5,7,14,20,31-hexaazapentacyclo[22.3.1.1~2,6~.1~8,12~.1~14,18~]hentriaconta-1(28),2(31),3,5,8(30),9,11,24,26-nonaen-19-one. Referred to herein as "Compound 26".

In one embodiment, the cyclic aniline-pyridinotriazine is a compound of the Formula (29).

Formula (29):

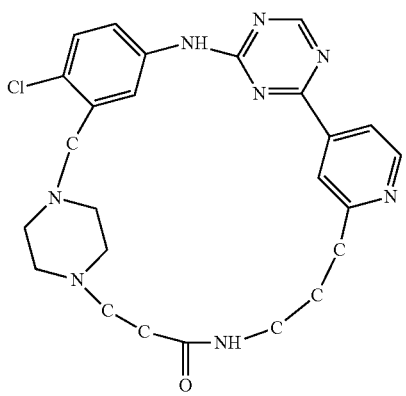

4-Chloro-1,8,10,12,17,22,26,32-octaazapentacyclo[24.2.2.1~3,7~.1~9,13~.1~14,18~]tritriaconta-3(33),4,6,9(32),10,12,14(31),15,17-nonaen-23-one. Referred to herein as "Compound 27".

In one embodiment, the cyclic aniline-pyridinotriazine is a compound of the Formula (30).

Formula (30):

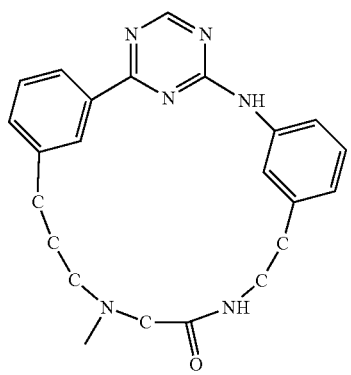

18-Methyl-3,5,7,15,18,28-hexaazatetracyclo[20.3.1.1~2,6~1~8,12~]octacosa-1(26),2(28),3,5,8(27),9,11,22,24-nonaen-16-one. Referred to herein as "Compound 28".

In one embodiment, the cyclic aniline-pyridinotriazine is a compound of the Formula (31).

Formula (31):

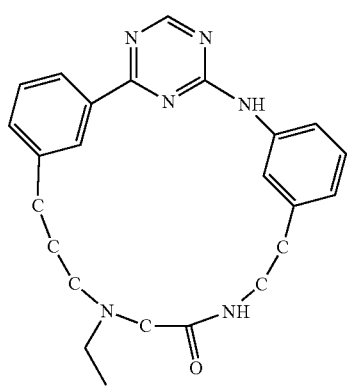

18-Ethyl-3,5,7,15,18,28-hexaazatetracyclo[20.3.1.1~2,6~.1~8,12~]octacosa-1(26),2(28),3,5,8(27),9,11,22,24-nonaen-16-one. Referred to herein as "Compound 29".

In one embodiment, the cyclic aniline-pyridinotriazine is a compound of the Formula (32).

Formula (32):

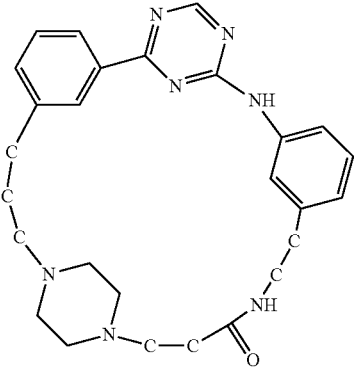

1,8,10,12,17,19,23,27,33-Nonaazapentacyclo[25.2.2.1~3,7~.1~9,13~.1-14,18~]tetratriaconta-3(34),4,6,9(33),10,12,14(32),15,17-nonaen-24-one. Referred to herein as "Compound 30".

In one embodiment, the cyclic aniline-pyridinotriazine is a compound of the Formula (33).

Formula (33):

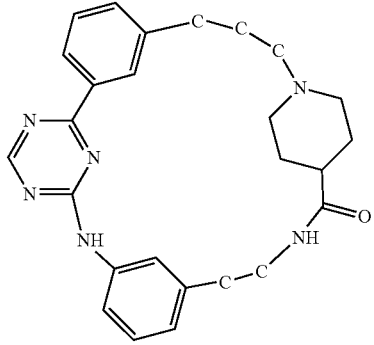

1,11,13,15,23,31-Hexaazapentacyclo[23.2.2.1~5,9~.1~10,14~.1~16,20~]dotriaconta-5(32),6,8,10(31),11,13,16(30),17,19-nonaen-24-one. Referred to herein as "Compound 31".

In one embodiment, the cyclic aniline-pyridinotriazine is a compound of the Formula (34).

Formula (34):

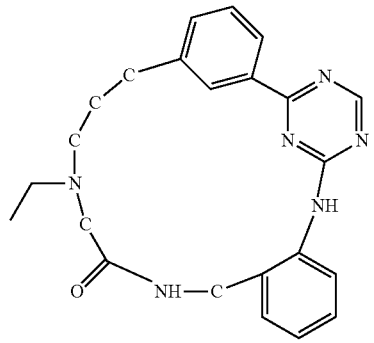

15-Ethyl-13,14,15,16,18,19-hexahydro-1H-6,2-(azeno)-7,11-(metheno)-1,3,5,15,18-benzopentaazacyclohenicosin-17(12H)-one. Referred to herein as "Compound 32".

In one embodiment, the cyclic aniline-pyridinotriazine is a compound of the Formula (35).

Formula (35):

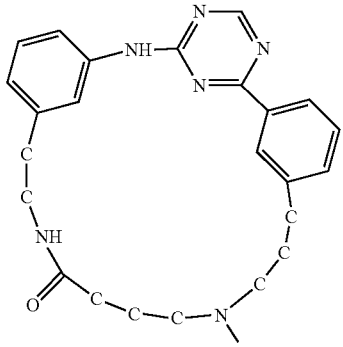

20-Methyl-3,5,7,15,20,30-hexaazatetracyclo[22.3.1.1~2,6~.1~8,12~]triaconta-1(28),2(30),3,5,8(29),9,11,24,26-nonaen-16-one. Referred to herein as "Compound 33".

In one embodiment, the cyclic aniline-pyridinotriazine is a compound of the Formula (36).

Formula (36):

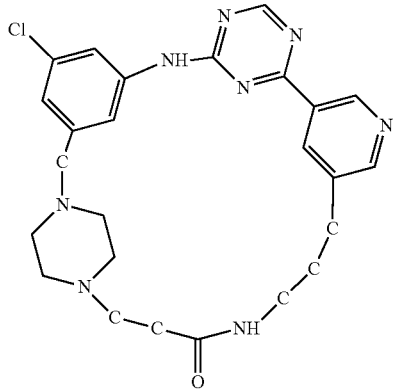

5-Chloro-1,8,10,12,16,22,26,32-octaazapentacyclo[24.2.2.1~3,7~.1~9,13~.1~14,18~]tritriaconta-3(33),4,6,9(32),10,12,14(31),15,17-nonaen-23-one. Referred to herein as "Compound 34".

In one embodiment, the cyclic aniline-pyridinotriazine is a compound of the Formula (37).

Formula (37):

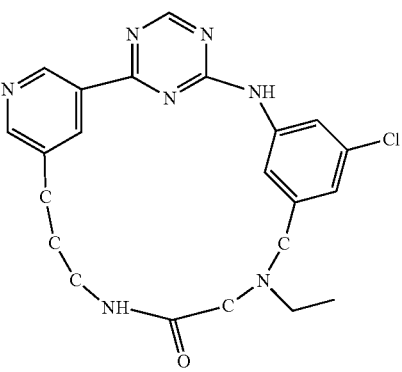

10-Chloro-14-ethyl-3,5,7,14,17,23,27-heptaazatetracyclo[19.3.1.1~2,6~.1~8,12~]heptacosa-1(25),2(27),3,5,8(26),9,11,21,23-nonaen-16-one. Referred to herein as "Compound 35".

In one embodiment, the cyclic aniline-pyridinotriazine is a compound of the Formula (38).

Formula (38):

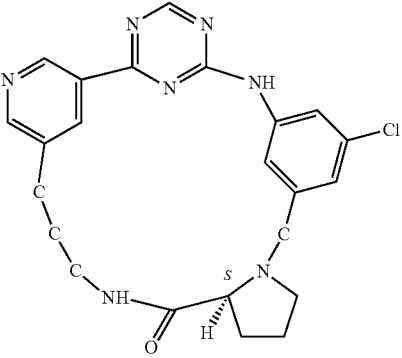

(18S)-10-Chloro-3,5,7,14,20,26,30-heptaazapentacyclo[22.3.1.1~2,6~.1~8,12~0.0~14,18~]triaconta-1(28),2(30),3,5,8(29),9,11,24,26-nonaen-19-one. Referred to herein as "Compound 36".

In one embodiment, the cyclic aniline-pyridinotriazine is a compound of the Formula, (39).

Formula (39):

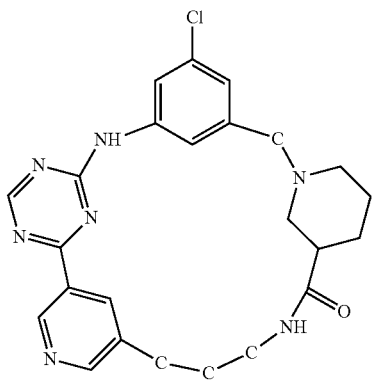

10-Chloro-3,5,7,14,20,26,31-heptaazapentacyclo[22.3.1.1~2,6~.1~8,12~.1~14,18~]hentriaconta-1(28),2(31),3,5,8(30),9,11,24,26-nonaen-19-one. Referred to herein as "Compound 37".

In one embodiment, the cyclic aniline-pyridinotriazine is a compound of the Formula (40).

Formula (40):

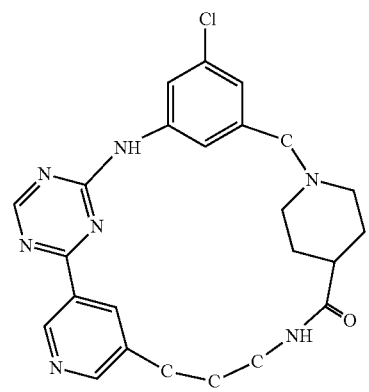

5-Chloro-1,8,10,12,16,22,30-heptaazapentacyclo[22.2.2.1~3,7~.1~9,13~.1~14,18~]hentriaconta-3(31),4,6,9(30),10,12,14(29),15,17-nonaen-23-one. Referred to herein as "Compound 38".

In one embodiment, the cyclic aniline-pyridinotriazine is a compound of the Formula (41).

Formula (41):

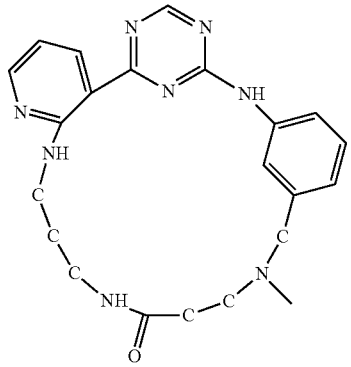

9-Methyl-2,3,4,5,7,8,9,10-octahydro-16H-17,21-(azeno)-11,15-(metheno)pyrido[3,2-g][1,3,5,9,13,17]hexaazacyclotricosin-6(1H)-one. Referred to herein as "Compound 39".

In one embodiment, the cyclic aniline-pyridinotriazine is a compound of the Formula (42).

Formula (42):

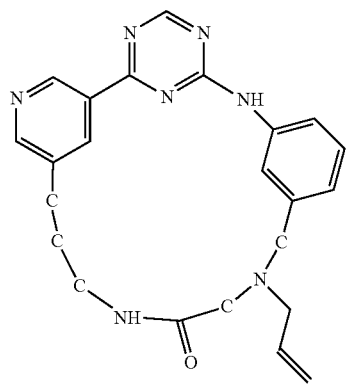

14-Prop-2-en-1-yl-3,5,7,14,17,23,27-heptaazatetracyclo[19.3.1.1~2,6~1~8,12~]heptacosa-1(25),2(27),3,5,8(26),9,11,21,23-nonaen-16-one. Referred to herein as "Compound 40".

In one embodiment, the cyclic aniline-pyridinotriazine is a compound of the Formula (43).

Formula (43):

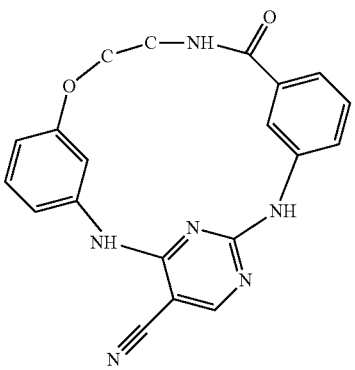

18-Oxo-14-oxa-2,4,8,17,25-pentaazatetracyclo[17.3.1.1~3,7~.1~9,13~]pentacosa-1(23),3(25),4,6,9(24),10,12,19,21-nonaene-6-carbonitrile. Referred to herein as "Compound 41".

In one embodiment, the cyclic aniline-pyridinotriazine is a compound of the Formula (44).

Formula (44):

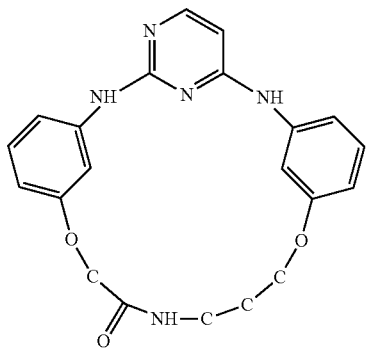

14,21-Dioxa-2,4,8,18,28-pentaazatetracyclo[20.3.1.1~3, 7~.1~9,13~]octacosa-1(26),3(28),4,6,9(27),10,12,22,24-nonaen-19-one. Referred to herein as "Compound 42".

In one embodiment, the cyclic aniline-pyridinotriazine is a compound of the Formula (45).

Formula (45):

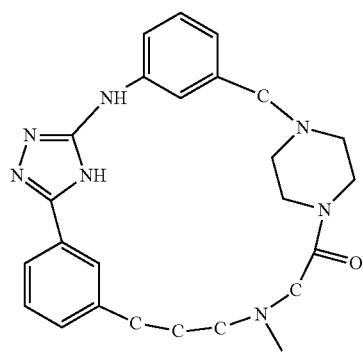

21-Methyl-1,8,10,11,21,24,30-heptaazapentacyclo [22.2.2.1~3,7~.1~9,12~.1~13,17~]hentriaconta-3(31),4,6,9, 11,13(29),14,16-octaen-23-one. Referred to herein as "Compound 43".

In one embodiment, the cyclic aniline-pyridinotriazine is a compound of the Formula (46).

Formula (46):

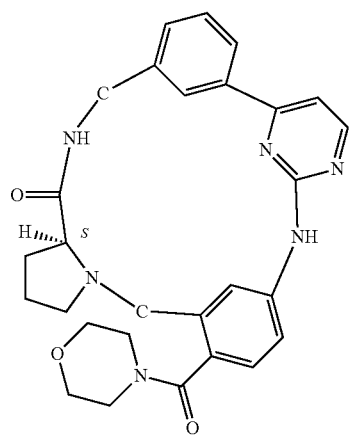

(18S)-11-(Morpholin-4-ylcarbonyl)-5,7,14,20,28-pentaaza-pentacyclo[20.3.1.1~2,6~.1f8,12~0.0~14,18~]octacosa-1 (26),2(28),3,5,8(27),9,11,22,24-nonaen-19-one. Referred to herein as "Compound 44".

In one embodiment, the cyclic aniline-pyridinotriazine is a compound of the Formula (47).

Formula (47):

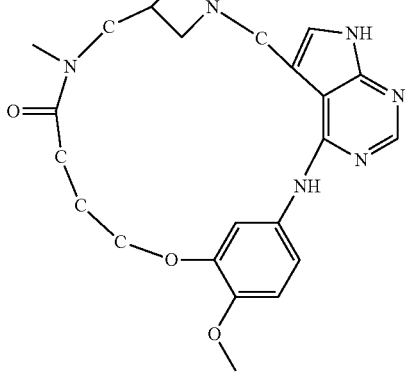

10-Methoxy-17-methyl-2,14,15,17,18,19,20,22-octahydro-6H-19,21-methano-7,11-(metheno)-12-oxa-2,3,5,6,17,21-hexaazacycloicosa[1,2,3-cd]inden-16(13H)-one. Referred to herein as "Compound 45".

In one embodiment, the at least one other factor is a compound of the Formula (48):

Formula (48)

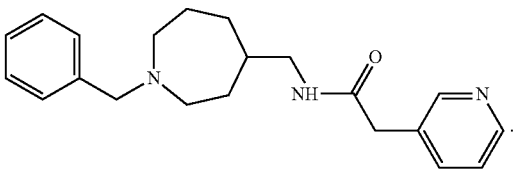

N-{[1-(Phenylmethyl)azepan-4-yl]methyl}-2-pyridin-3-ylacetamide. Referred herein as "Compound 46".

In one embodiment, the at least one other factor is a compound of the Formula (49):

Formula (49)

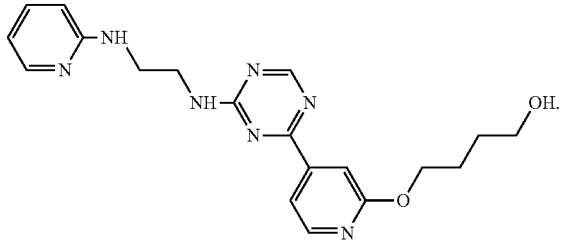

4-{[4-(4-{[2-(Pyridin-2-ylamino)ethyl]amino}-1,3,5-tri-azin-2-yl)pyridin-2-yl]oxy}butan-1-ol. Referred herein as "Compound 47".

In one embodiment, the at least one other factor is a compound of the Formula (50):

Formula (50)

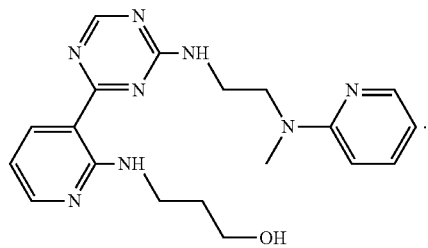

3-({3-[4-({2-[Methyl(pyridin-2-yl)amino]ethyl}amino)-1,3,5-triazin-2-yl]pyridin-2-yl}amino)propan-1-ol. Referred herein as "Compound 48".

In one embodiment, the at least one other factor is a compound of the Formula (51):

Formula (51)

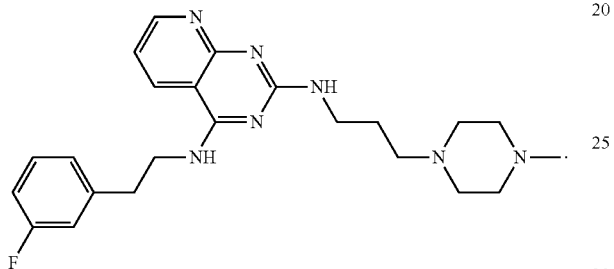

N~4~-[2-(3-Fluorophenyl)ethyl]-N~2~-[3-(4-methylpiperazin-1-yl)propyl]pyrido[2,3-d]pyrimidine-2,4-diamine. Referred herein as "Compound 49".

In one embodiment, the at least one other factor is a compound of the Formula (52):

Formula (52)

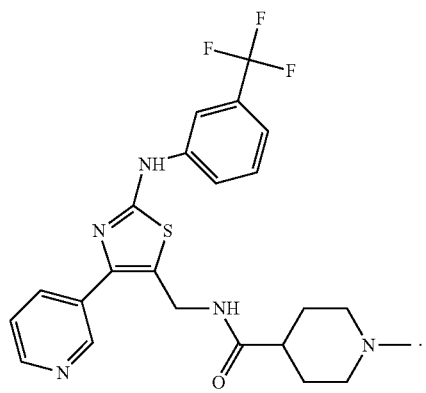

1-Methyl-N-[(4-pyridin-3-yl-2-{[3-(trifluoromethyl)phenyl]amino}-1,3-thiazol-5-yl)methyl]piperidine-4-carboxamide. Referred herein as "Compound 50".

In one embodiment, the at least one other factor is a compound of the Formula (53):

Formula (53)

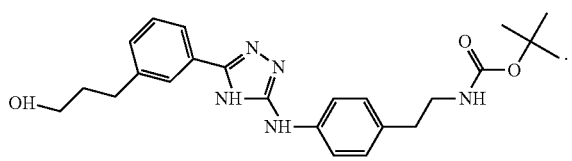

1,1-Dimethylethyl {2-[4-({5-[3-(3-hydroxypropyl)phenyl]-4H-1,2,4-triazol-3-yl}amino)phenyl]ethyl}carbamate. Referred herein as "Compound 51".

In one embodiment, the at least one other factor is a compound of the Formula (54):

Formula (54)

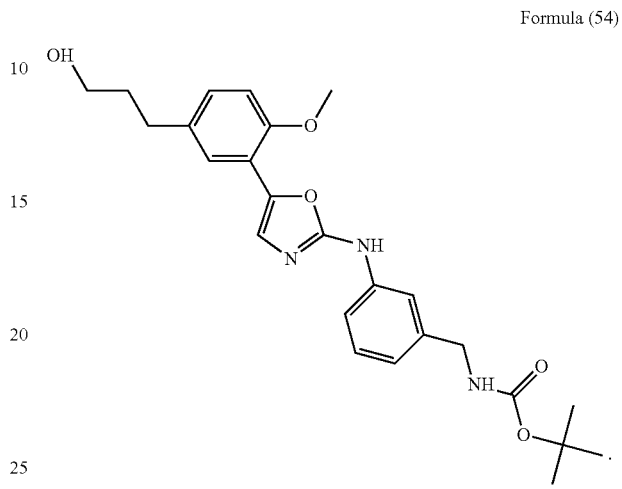

1,1-Dimethylethyl {[3-({5-[5-(3-hydroxypropyl)-2-(methyloxy)phenyl]-1,3-oxazol-2-yl}amino)phenyl]methyl}carbamate. Referred herein as "Compound 52".

In one embodiment, the at least one other factor is a compound of the Formula (55):

Formula (55)

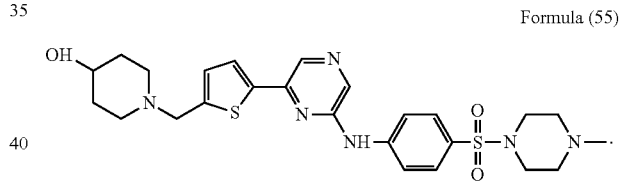

1-({5-[6-({4-[(4-Methylpiperazin-1-yl)sulfonyl]phenyl}amino)pyrazin-2-yl]thiophen-2-yl}methyl)piperidin-4-ol. Referred herein as "Compound 53".

In one embodiment, the at least one other factor is a compound of the Formula (56):

Formula (56)

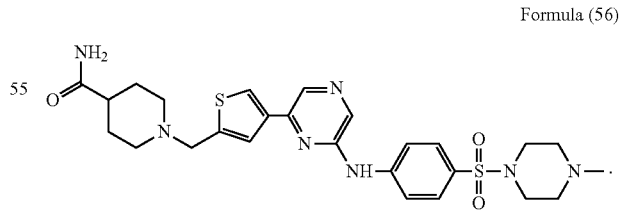

1-({4-[6-({4-[(4-Methylpiperazin-1-yl)sulfonyl]phenyl}amino)pyrazin-2-yl]thiophen-2-yl}methyl)piperidine-4-carboxamide. Referred herein as "Compound 54".

In one embodiment, the at least one other factor is a compound of the Formula (57):

Formula (57)

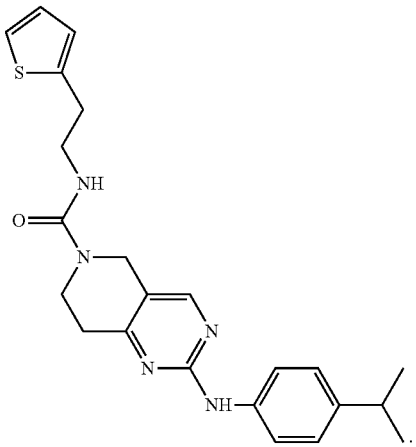

2-{[4-(1-Methylethyl)phenyl]amino}-N-(2-thiophen-2-yl-ethyl)-7,8-dihydropyrido[4,3-d]pyrimidine-6(5H)-carboxamide. Referred herein as "Compound 55".

In one embodiment, the at least one other factor is a compound of the Formula (58):

Formula (58)

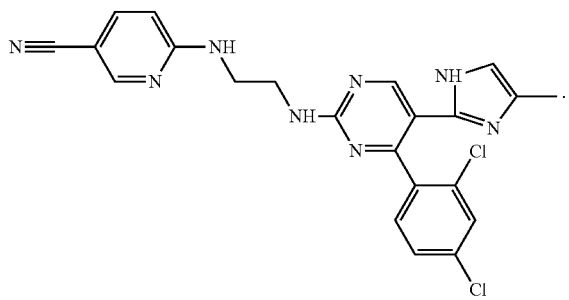

6-[(2-{[4-(2,4-Dichlorophenyl)-5-(4-methyl-1H-imidazol-2-yl)pyrimidin-2-yl]amino}ethyl)amino]pyridine-3-carbonitrile. Referred herein as "Compound 56".

In one embodiment, the at least one other factor is a compound of the Formula (59):

Formula (59)

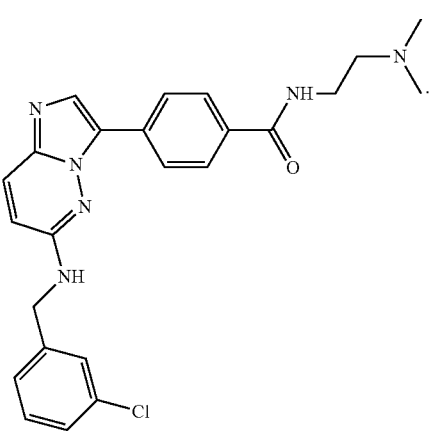

4-(6-{[(3-Chlorophenyl)methyl]amino}imidazo[1,2-b]pyridazin-3-yl)-N-[2-(dimethylamino)ethyl]benzamide. Referred herein as "Compound 57".

Detection of Cells Expressing Markers Characteristic of the Definitive Endoderm Lineage Formation of cells expressing markers characteristic of the definitive endoderm lineage may be determined by testing for the presence of the markers before and after following a particular protocol. Pluripotent stem cells typically do not express such markers. Thus, differentiation of pluripotent cells is detected when cells begin to express them.

The efficiency of differentiation may be determined by exposing a treated cell population to an agent (such as an antibody) that specifically recognizes a protein marker expressed by cells expressing markers characteristic of the definitive endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g. Harlow and Lane, Using Antibodies: A Laboratory Manual, New York: Cold Spring Harbor Laboratory Press (1998)).

For example, characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, Connexin43, Connexin45, OCT4, SOX2, Nanog, hTERT, UTF-1, ZFP42, SSEA-3, SSEA-4, Tra1-60, or Tra1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Formation of Cells Expressing Markers Characteristic of the Pancreatic Endoderm Lineage Cells expressing markers characteristic of the definitive endoderm lineage may be differentiated into cells expressing markers characteristic of the pancreatic endoderm lineage by any method in the art or by any method proposed in this invention.

For example, cells expressing markers characteristic of the definitive endoderm lineage may be differentiated into cells expressing markers characteristic of the pancreatic endoderm lineage according to the methods disclosed in D'Amour et al, Nature Biotechnology 24, 1392-1401 (2006).

For example, cells expressing markers characteristic of the definitive endoderm lineage are further differentiated into cells expressing markers characteristic of the pancreatic endoderm lineage, by treating the cells expressing markers characteristic of the definitive endoderm lineage with a fibroblast growth factor and the hedgehog signaling pathway inhibitor KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in Nature Biotechnology 24, 1392-1401 (2006).

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/736,908, assigned to LifeScan, Inc.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/779,311, assigned to LifeScan, Inc.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage according to the methods disclosed in U.S. patent application Ser. No. 60/990,529.

Cells expressing markers characteristic of the definitive endoderm lineage may be treated with at least one other additional factor that may enhance the formation of cells expressing markers characteristic of the pancreatic endoderm lineage. Alternatively, the at least one other additional factor may enhance the proliferation of the cells expressing markers characteristic of the pancreatic endoderm lineage formed by the methods of the present invention. Further, the at least one other additional factor may enhance the ability of the cells expressing markers characteristic of the pancreatic endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (such as, for example, GDF-5, -6, -8, -10, -11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valproic acid, trichostatin A, sodium butyrate, hepatocyte growth factor (HGF), sphingosine-1, VEGF, MG132 (EMD, CA). N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687). HPAF-II (ATCC No: CRL-1997), hepatic cell lines such as, for example, HepG2 (ATCC No: HTB-8065), and intestinal cell lines such as, for example, FHs 74 (ATCC No: CCL-241).

Detection of Cells Expressing Markers Characteristic of the Pancreatic Endoderm Lineage Markers characteristic of the pancreatic endoderm lineage are well known to those skilled in the art, and additional markers characteristic of the pancreatic endoderm lineage continue to be identified. These markers can be used to confirm that the cells treated in accordance with the present invention have differentiated to acquire the properties characteristic of the pancreatic endoderm lineage. Pancreatic endoderm lineage specific markers include the expression of one or more transcription factors such as, for example, Hlxb9, PTF-1a, PDX-1, HNF-6, HNF-1beta.

The efficiency of differentiation may be determined by exposing a treated cell population to an agent (such as an antibody) that specifically recognizes a protein marker expressed by cells expressing markers characteristic of the pancreatic endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Formation of Cells Expressing Markers of the Pancreatic Endocrine Lineage

Cells expressing markers characteristic of the pancreatic endoderm lineage may be differentiated into cells expressing markers characteristic of the pancreatic endocrine lineage by any method in the art or by any method disclosed in this invention.

For example, cells expressing markers characteristic of the pancreatic endoderm lineage may be differentiated into cells expressing markers characteristic of the pancreatic endocrine lineage according to the methods disclosed in D'Amour et al., Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4, then removing the medium containing DAPT and exendin 4 and subsequently culturing the cells in medium containing exendin 1, IGF-1 and HGF. An example of this method is disclosed in Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4, then removing the medium containing exendin 4 and subsequently culturing the cells in medium containing exendin 1, IGF-1 and HGF. An example of this method is disclosed in D' Amour et al, Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4. An example of this method is disclosed in D'Amour et al, Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4. An example of this method is disclosed in D'Amour et al, Nature Biotechnology, 2006.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/736,908, assigned to LifeScan. Inc.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/779,311, assigned to LifeScan, Inc.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 60/953,178, assigned to LifeScan, Inc.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage according to the methods disclosed in U.S. patent application Ser. No. 60/990,529.

Cells expressing markers characteristic of the pancreatic endoderm lineage may be treated with at least one other additional factor that may enhance the formation of cells expressing markers characteristic of the pancreatic endocrine lineage. Alternatively, the at least one other additional factor may enhance the proliferation of the cells expressing markers characteristic of the pancreatic endocrine lineage formed by the methods of the present invention. Further, the at least one other additional factor may enhance the ability of the cells expressing markers characteristic of the pancreatic endocrine lineage formed by the methods of the present invention to form other cell types or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (such as, for example, GDF-5, -6, -8, -10, -11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin. Na-Butyrate, activin, betacellulin. ITS, noggin, neurite growth factor, nodal, valproic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Detection of Cells Expressing Markers Characteristic of the Pancreatic Endocrine Lineage Markers characteristic of cells of the pancreatic endocrine lineage are well known to those skilled in the art, and additional markers characteristic of the pancreatic endocrine lineage continue to be identified. These markers can be used to confirm that the cells treated in accordance with the present invention have differentiated to acquire the properties characteristic of the pancreatic endocrine lineage. Pancreatic endocrine lineage specific markers include the expression of one or more transcription factors such as, for example, NGN3, NEURO, or ISL1.

Markers characteristic of cells of the β cell lineage are well known to those skilled in the art, and additional markers characteristic of the β cell lineage continue to be identified. These markers can be used to confirm that the cells treated in accordance with the present invention have differentiated to acquire the properties characteristic of the β-cell lineage. β cell lineage specific characteristics include the expression of one or more transcription factors such as, for example, PDX1, NKX2.2, NKX6.1, ISL1, PAX6, PAX4, NEUROD, HNF1 beta, HNF6, HNF3 beta, or MAFA, among others. These transcription factors are well established in the art for identification of endocrine cells. See, e.g., Edlund (Nature Reviews Genetics 3: 524-632 (2002)).

The efficiency of differentiation may be determined by exposing a treated cell population to an agent (such as an antibody) that specifically recognizes a protein marker expressed by cells expressing markers characteristic of the pancreatic endocrine lineage. Alternatively, the efficiency of differentiation may be determined by exposing a treated cell population to an agent (such as an antibody) that specifically recognizes a protein marker expressed by cells expressing markers characteristic of the β cell lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

In one aspect of the present invention, the efficiency of differentiation is determined by measuring the percentage of insulin positive cells in a given cell culture following treatment. In one embodiment, the methods of the present invention produce about 100% insulin positive cells in a given culture. In an alternate embodiment, the methods of the present invention produce about 90% insulin positive cells in a given culture. In an alternate embodiment, the methods of the present invention produce about 80% insulin positive cells in a given culture. In an alternate embodiment, the methods of the present invention produce about 70% insulin positive cells in a given culture. In an alternate embodiment, the methods of the present invention produce about 60% insulin positive cells in a given culture. In an alternate embodiment, the methods of the present invention produce about 50% insulin positive cells in a given culture. In an alternate embodiment, the methods of the present invention produce about 40% insulin positive cells in a given culture. In an alternate embodiment, the methods of the present invention produce about 30% insulin positive cells in a given culture. In an alternate embodiment, the methods of the present invention produce about 20% insulin positive cells in a given culture. In an alternate embodiment, the methods of the present invention produce about 10% insulin positive cells in a given culture. In an alternate embodiment, the methods of the present invention produce about 5% insulin positive cells in a given culture.

In one aspect of the present invention, the efficiency of differentiation is determined by measuring glucose-stimulated insulin secretion, as detected by measuring the amount of C-peptide released by the cells. In one embodiment, cells produced by the methods of the present, invention produce about 1000 ng C-peptide/pg DNA. In an alternate embodiment, cells produced by the methods of the present invention produce about 900 ng C-peptide/pg DNA. In an alternate embodiment, cells produced by the methods of the present invention produce about 800 ng C-peptide/pg DNA. In an alternate embodiment, cells produced by the methods of the present invention produce about 700 ng C-peptide/pg DNA. In an alternate embodiment, cells produced by the methods of the present invention produce about 600 ng C-peptide/pg DNA. In an alternate embodiment, cells produced by the methods of the present invention produce about 500 ng C-peptide/pg DNA. In an alternate embodiment, cells produced by the methods of the present invention produce about 400 ng C-peptide/pg DNA. In an alternate embodiment, cells produced by the methods of the present invention produce about 500 ng C-peptide/pg DNA. In an alternate embodiment, cells produced by the methods of the present invention produce about 400 ng C-peptide/pg DNA. In an alternate embodiment, cells produced by the methods of the present invention produce about 300 ng C-peptide/pg DNA. In an alternate embodiment, cells produced by the methods of the present invention produce about 200 ng C-peptide/pg DNA. In an alternate embodiment, cells produced by the methods of the present invention produce about 100 ng C-peptide/pg DNA. In an alternate embodiment, cells produced by the methods of the present invention produce about 90 ng C-peptide/pg DNA. In an alternate embodiment, cells produced by the methods of the present invention produce about 80 ng C-peptide/pg DNA. In an alternate embodiment, cells produced by the methods of the present invention produce about 70 ng C-peptide/pg DNA. In an alternate embodiment, cells produced by the methods of the present invention produce about 60 ng C-peptide/pg DNA. In an alternate embodiment, cells produced by the methods of the present invention produce about 50 ng C-peptide/pg DNA). In an alternate embodiment, cells produced by the methods of the present invention produce about 40 ng C-peptide/pg DNA. In an alternate embodiment, cells produced by the methods of the present invention produce about 30 ng C-peptide/pg DNA. In an alternate embodiment, cells produced by the methods of the present invention produce about 20 ng C-peptide/pg DNA. In an alternate embodiment, cells produced by the methods of the present invention produce about 10 ng C-peptide/pg DNA.

Therapies

In one aspect, the present invention provides a method for treating a patient suffering from, or at risk of developing, Type 1 diabetes. This method involves culturing pluripotent stem cells, differentiating the pluripotent stem cells in vitro into a β-cell lineage, and implanting the cells of a β-cell lineage into a patient.

In yet another aspect, this invention provides a method for treating a patient suffering from, or at risk of developing, Type 2 diabetes. This method involves culturing pluripotent stem cells, differentiating the cultured cells in vitro into a β-cell lineage, and implanting the cells of a β-cell lineage into the patient.

If appropriate, the patient can be further treated with pharmaceutical agents or bioactives that facilitate the survival and function of the transplanted cells. These agents may include, for example, insulin, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (such as, for example, GDF-5, -6, -7, -8, -10, -15), vascular endothelial cell-derived growth factor (VEGF), pleiotrophin, endothelin, among others. Other pharmaceutical compounds can include, for example, nicotinamide, glucagon like peptide-I (GLP-1) and II, GLP-1 and -2 mimetibody, Exendin-4, retinoic acid, parathyroid hormone, MAPK inhibitors, such as, for example, compounds disclosed in U.S. Published Application 2004/0209901 and U.S. Published Application 2004/0132729.

The pluripotent stem cells may be differentiated into an insulin-producing cell prior to transplantation into a recipient. In a specific embodiment, the pluripotent stem cells are fully differentiated into β-cells prior to transplantation into a recipient. Alternatively, the pluripotent stem cells may be transplanted into a recipient in an undifferentiated or partially differentiated state. Further differentiation may take place in the recipient.

Definitive endoderm cells or, alternatively, pancreatic endoderm cells, or, alternatively, β cells, may be implanted as dispersed cells or formed into clusters that may be infused into the hepatic portal vein. Alternatively, cells may be provided in biocompatible degradable polymeric supports, porous non-degradable devices or encapsulated to protect from host immune response. Cells may be implanted into an appropriate site in a recipient. The implantation sites include, for example, the liver, natural pancreas, renal subcapsular space, omentum, peritoneum, subserosal space, intestine, stomach, or a subcutaneous pocket.

To enhance further differentiation, survival or activity of the implanted cells, additional factors, such as growth factors, antioxidants or anti-inflammatory agents, can be administered before, simultaneously with, or after the administration of the cells. In certain embodiments, growth factors are utilized to differentiate the administered cells in vivo. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In one aspect, this invention provides a method for treating a patient suffering from, or at risk of developing diabetes. This method involves culturing pluripotent stem cells, differentiating the cultured cells in vitro into a β-cell lineage, and incorporating the cells into a three-dimensional support. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, for example, the materials disclosed in U.S. Pat. No. 5,770,417, U.S. Pat. No. 6,022,743, U.S. Pat. No. 5,567,612, U.S. Pat. No. 5,759,830, U.S. Pat. No. 6,626,950, U.S. Pat. No. 6,534,084, U.S. Pat. No. 6,306,424, U.S. Pat. No. 6,365,149, U.S. Pat. No. 6,599,323, U.S. Pat. No. 6,656,488, U.S. Published Application 2004/0062753 A1, U.S. Pat. No. 4,557,264 and U.S. Pat. No. 6,333,029.

To form a support incorporated with a pharmaceutical agent, the pharmaceutical agent can be mixed with the polymer solution prior to forming the support. Alternatively, a pharmaceutical agent could be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example, compounds disclosed in U.S. Pat. No. 6,509,369.

The support may be incorporated with at least one pharmaceutical compound that is an anti-apoptotic compound, such as, for example, compounds disclosed in U.S. Pat. No. 6,793,945.

The support may also be incorporated with at least one pharmaceutical compound that is an inhibitor of fibrosis, such as, for example, compounds disclosed in U.S. Pat. No. 6,331,298.

The support may also be incorporated with at least one pharmaceutical compound that is capable of enhancing angiogenesis, such as, for example, compounds disclosed in U.S. Published Application 2004/0220393 and U.S. Published Application 2004/0209901.

The support may also be incorporated with at least one pharmaceutical compound that is an immunosuppressive compound, such as, for example, compounds disclosed in U.S. Published Application 2004/0171623.

The support may also be incorporated with at least one pharmaceutical compound that is a growth factor, such as, for example, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (such as, for example, GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-I (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, MAPK inhibitors, such as, for example, compounds disclosed in U.S. Published Application 2004/0209901 and U.S. Published Application 2004/0132729.

The incorporation of the cells of the present invention into a scaffold can be achieved by the simple depositing of cells onto the scaffold. Cells can enter into the scaffold by simple diffusion (J. Pediatr. Surg. 23 (1 Pt 2): 3-9 (1988)). Several other approaches have been developed to enhance the efficiency of cell seeding. For example, spinner flasks have been used in seeding of chondrocytes onto polyglycolic acid scaffolds (Biotechnol. Prog. 14(2): 193-202 (1998)). Another approach for seeding cells is the use of centrifugation, which yields minimum stress to the seeded cells and enhances seeding efficiency. For example, Yang et al. developed a cell seeding method (J. Biomed. Mater. Res. 55(3): 379-86 (2001)), referred to as Centrifugational Cell Immobilization (CCI).

The present invention is further illustrated, but not limited by, the following examples.

EXAMPLES

For clarity of disclosure, and not by way of limitation, the detailed description of the invention is divided into the following subsections that describe or illustrate certain features, embodiments, or applications of the present invention.

Example 1

Human Embryonic Stem Cell Culture

The human embryonic stem cell lines H1, H7, and H9 were obtained from WiCell Research Institute, Inc., (Madison, Wis.) and cultured according to instructions provided by the source institute. The human embryonic stem cells were also seeded on plates coated with a 1:30 dilution of reduced growth factor MATRIGEL™ (BD Biosciences; Cat #356231) and cultured in MEF-conditioned medium supplemented with 8 ng/ml bFGF (R&D Systems; Cat #233-FB). The cells cultured on MATRIGEL™ were routinely passaged as clusters using collagenase IV (Invitrogen/GIBCO; Cat #17104-019), Dispase (Invitrogen; Cat #7105-041), or Liberase CI enzyme (Roche; Cat #11814435001). In some instances, the cells were passaged as single cells using ACCUTASE (Sigma; Cat # A6964).

Human embryonic stem cells used in these examples were maintained in an undifferentiated, pluripotent state with passage on average every four-days. Passage was performed by exposing cell cultures to a solution of collagenase (1 or 10 mg/ml; Sigma-Aldrich) for 10 to 30 minutes at 37° C. followed by gentle scraping with a pipette tip to recover cell clusters. Clusters were allowed to sediment by gravity, followed by washing to remove residual collagenase. Cell clusters were split at a 1:3 ratio for routine maintenance culture or a 1:1 ratio for later assay. All human ES cell lines were maintained at passage numbers less than 50 and routinely evaluated for normal karyotypic phenotype and absence of mycoplasma contamination.

Example 2

Bioassay for the Formation of Cells Expressing Markers Characteristic of the Definitive Endoderm Lineage Activin A is an important mediator of differentiation in a broad range of cell types, including differentiation of embryonic stem cells to definitive endoderm. When human embryonic stem cells are treated with a combination of activin A and Wnt3a various genes representative of definitive endoderm are up-regulated. A bioassay that measures this differentiation in human embryonic stem cells was adapted in miniaturized format to 96-well plates for screening purposes. Validation was completed using treatment with commercial sources of activin A and Wnt3a recombinant proteins and measuring protein expression of the transcription factor SOX17, considered to be a representative marker of definitive endoderm.

Live Cell Assay:

Briefly, clusters of H1 human embryonic stem cells were grown on reduced growth factor MATRIGEL™ (Invitrogen; Cat #356231)-coated tissue culture plastic. Cells were passaged using collagenase (Invitrogen; Cat #17104-019) treatment and gentle scraping, washed to remove residual enzyme, and plated in a ratio of 1:1 (surface area) on reduced growth factor MATRIGEL™-coated 96-well black plates (Packard ViewPlates; Perkin Elmer; Cat #6005182). Cells were allowed to attach as clusters and then recover log phase growth over a 1 to 3 day period, feeding daily with 100 µl per well mouse embryonic fibroblast (MEF) conditioned medium supplemented with 8 ng/ml bFGF (R&D Systems; Cat #233-FB).

The assay was initiated by washing the wells of each plate twice in PBS (Invitrogen; Cat #14190), followed by adding an aliquot (100 µl) of test sample in DMEM:F12 basal medium (Invitrogen; Cat #11330-032) to each well. Test conditions were performed in triplicate, feeding on alternate days by aspirating and replacing the medium from each well with test samples over a total four-day assay period. On the first and second day of assay, test samples added to the assay wells were diluted in DMEM:F12 with 0.5% FCS (HyClone; Cat # SH30070.03) and 20 ng/ml Wnt3a (R&D Systems; Cat #1324-WN). On the third and fourth day of assay, test samples added to the assay wells were diluted in DMEM:F12 with 2% FCS, without any Wnt3a. Positive control samples consisted of recombinant human activin A (PeproTech; Cat #120-14) added at a concentration of 100 ng/ml throughout assay plus Wnt3a (20 ng/ml) on days 1 and 2. Negative control samples omitted treatment with both activin A and Wnt3a.

High Content Analysis:

At the conclusion of four-days of culture, assay plates were washed twice with PBS (Invitrogen; Cat #14190), fixed with 4% paraformaldehyde (Alexis Biochemical; Cat # ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; Cat # AF1924) was diluted 1:100 in 4% chicken serum and added to each well for one hour at room temperature. Alexa Fluor 488 conjugated secondary antibody (chicken anti-goat IgG; Molecular Probes; Cat # AZ1467) was diluted 1:200 in PBS and added to each sample well after washing three times with PBS. To counter stain nuclei, 4 µg/ml Hoechst 33342 (Invitrogen; Cat # H3570) was added for ten minutes at room temperature. Plates were washed once with PBS and left in 100 µl well PBS for imaging.

Imaging was performed using an IN Cell Analyzer 1000 (GE Healthcare) utilizing the 51008bs dichroic for cells stained with Hoechst 33342 and Alexa Fluor 488. Exposure times were optimized from positive control wells and from untreated negative control wells stained with secondary antibody alone. Images from 15 fields per well were acquired to compensate for any cell loss during the bioassay and subsequent staining procedures. Measurements for total cell number and total SOX17 intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total SOX17 protein expression was reported as total intensity or integrated intensity, defined as total fluorescence of the cell multiplied by the area of the cell. Background was eliminated based on acceptance criteria of gray-scale ranges between 200 to 3500. Total intensity data were normalized by dividing total intensities for each well by the average total intensity for the positive control. Normalized data were calculated for averages and standard deviations for each replicate set.

Figure 1B:
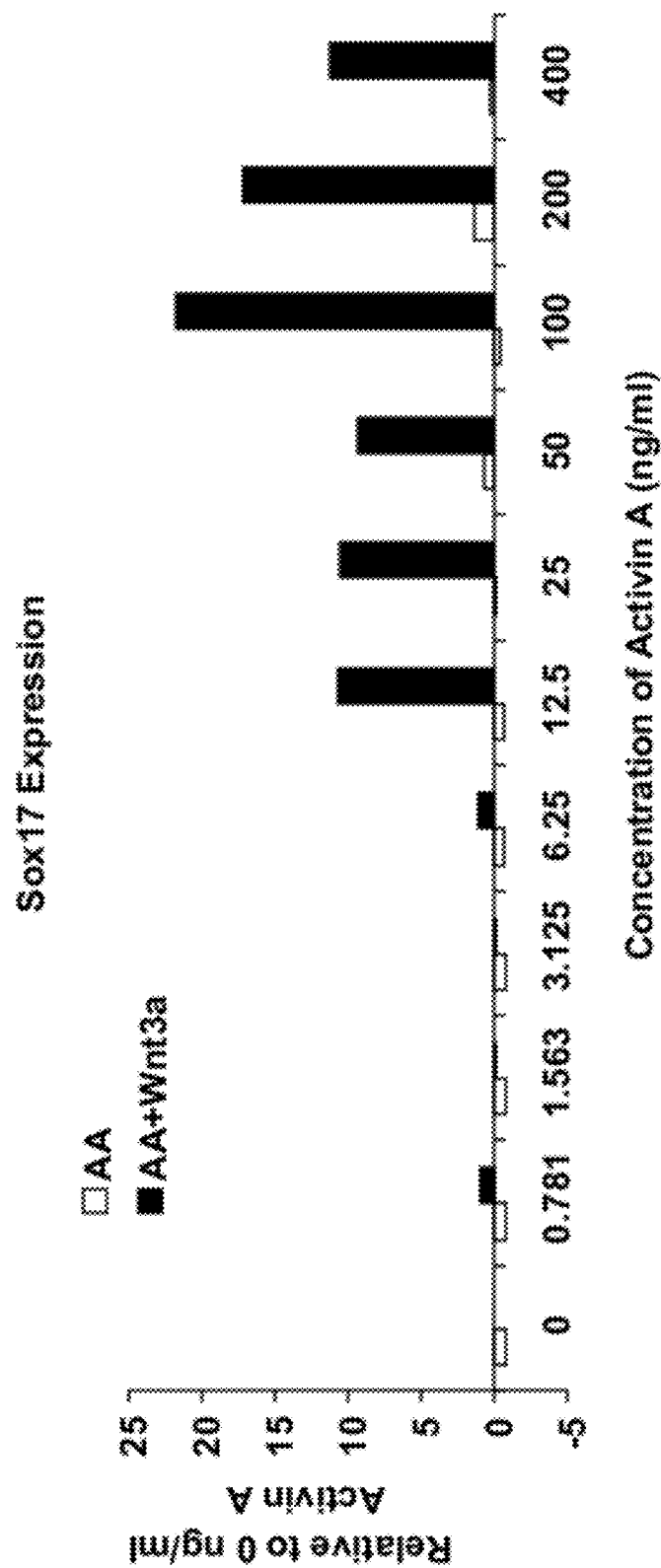

FIG. 1 shows validation of the screening assay, testing a two-fold dilution curve of a commercial source of activin A (PeproTech) and measuring both cell number (FIG. 1A) and SOX17 intensity (FIG. 1B). Optimal activin A effects for induction of SOX17 expression were generally observed in the 100-200 ng/ml range with an $EC_{50}$ of 30-50 ng/ml. Omitting Wnt3a from treatment on days 1 and 2 of assay failed to produce measurable SOX17 expression (FIG. 1B, white bars). Absence of activin A also failed to yield SOX17 expression (FIG. 1B).

Example 3

Primary Screening: Effects of the Compounds of the Present Invention on the Differentiation of Human Embryonic Stem Cells into Cells Expressing Markers Characteristic of the Definitive Endoderm Lineage in the Absence of Activin A Differentiation of pluripotent stem cells into cells expressing markers characteristic of the definitive endoderm lineage is mediated through a series of receptor-ligand interactions that in turn activate receptor kinases leading to phosphorylation and nuclear translocation of downstream substrates, eventually regulating expression of specific target genes. Optimal activation of these signaling cascades in some cell types may require inhibition of opposing default pathways. In other cases, redundant pathways involving alternative members of a larger kinase family may substitute in part for one or more signaling molecules. In other cases, canonical and non-canonical pathways may diverge with different initiating stimuli but may lead to a similar functional outcome.

Cell-based functional screens are one approach to identify novel targets and methods that can impact specific cellular responses. One very powerful approach involves a series of iterative screens whereby leads or hits from one screen are integrated into a subsequent screen. Alternatively, a series of different variables are integrated in a combinatorial fashion (for example, growth factors with kinase inhibitors) to identify novel effects on cellular differentiation. In this case, a library of small molecules comprising aniline-pyridinotriazines, cyclic aniline-pyridinotriazines and intermediate structures in their synthesis was tested for properties important during definitive endoderm differentiation of human embryonic stem cells, specifically for effects to retain or enhance cell number at the conclusion of a 'first' differentiation step in low serum and in the absence of the growth factor activin A.

Screening Assay

Cell Assay Seeding:

Briefly, clusters of H1 human embryonic stem cells were grown on reduced growth factor MATRIGEL™ (Invitrogen; Cat #356231)-coated tissue culture plastic. Cells were passaged using collagenase (Invitrogen; Cat #17104-019) treatment and gentle scraping, washed to remove residual enzyme, and plated with even dispersal at a ratio of 1:1 (surface area) on reduced growth factor MATRIGEL™-coated 96-well black plates (Packard ViewPlates; PerkinElmer; Cat #6005182) using volumes of 100 µl/well. Cells were allowed to attach as clusters and then recover log phase growth over a 1 to 3 day period, feeding daily with MEF conditioned medium supplemented with 8 ng/ml bFGF (R&D Systems; Cat #233-FB). Plates were maintained at 37° C., 5% $CO_2$ in a humidified box throughout the duration of assay.

Preparation of Compounds and Assay:

The compounds tested were made available as 5 mM stocks in 96-well plate format, solubilized in 100% DMSO (Sigma; Cat # D2650) and stored at −80° C. The library compounds were further diluted to an intermediate concentration of 0.2 mM in 50 mM HEPES (Invitrogen; Cat #15630-080), 20% DMSO and stored at 4° C. Test conditions were performed in triplicate, feeding on alternate days over a four-day assay period. Primary screening assays were initiated by aspirating culture medium from each well followed by three washes in PBS (Invitrogen; Cat #14190) to remove residual growth factors and serum. On the first day of assay, test volumes of 200 µl per well were added back containing DMEM:F12 base medium (Invitrogen; Cat #11330-032) supplemented with 0.5% FCS (HyClone; Cat # SH30070.03) and 20 ng/ml Wnt3a (R&D Systems; Cat #1324-WN) plus 2.5 µM test compound. On the third day of assay, test volumes of 200 µl per well were added back containing DMEM:F12 base medium supplemented with 2% FCS plus 2.5 µM test compound, without Wnt3a. Positive control samples contained the same base medium supplemented with FCS, substituting 100 ng/ml recombinant human activin A (PeproTech; Cat #120-14) for the test compound throughout the four-day assay along with Wnt3a (20 ng/ml) added only on days 1 and 2. Negative control samples contained DMEM:F12 base medium supplemented with FCS, adding Wnt3a on days 1 and 2 but omitting activin A.

High Content Analysis:

At the conclusion of four-days of culture, assay plates were washed twice with PBS (Invitrogen; Cat #14190), fixed with 4% paraformaldehyde (Alexis Biochemical; Cat # ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; Cat # AF1924) was diluted 1:100 in 4% chicken serum and added to each well for one hour at room temperature. Alexa Fluor 488 conjugated secondary antibody (chicken anti-goat IgG; Molecular Probes; Cat # AZ1467) was diluted 1:200 in PBS and added to each sample well after washing three times with PBS. To counter stain nuclei, 4 µg/ml Hoechst 33342 (Invitrogen; Cat # H3570) was added for ten minutes at room temperature. Plates were washed once with PBS and left in 100 µl/well PBS for imaging.

Imaging was performed using an IN Cell Analyzer 1000 (GE Healthcare) utilizing the 51008bs dichroic for cells stained with Hoechst 33342 and Alexa Fluor 488. Exposure times were optimized from positive control wells and from untreated negative control wells stained with secondary antibody alone. Images from 15 fields per well were acquired to compensate for any cell loss during the bioassay and subsequent staining procedures. Measurements for total cell number and total SOX17 intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total SOX17 protein expression was reported as total intensity or integrated intensity, defined as total fluorescence of the cell multiplied by the area of the cell. Background was eliminated based on acceptance criteria of gray-scale ranges between 200 to 3500. Total intensity data were normalized by dividing total intensities for each well by the average total intensity for the positive control. Normalized data were calculated for averages and standard deviations for each replicate set.

Table 1 shows results of primary screening for the compounds tested, showing their effects on the differentiation of human embryonic stem cells to cells expressing markers characteristic of the definitive endoderm lineage in the absence of activin A. The results include quantitative measures of both cell number and SOX17 intensity, where respective data points were averaged from triplicate wells and analyzed for each parameter using identical fields in each well. Expression of the transcription factor SOX17 is considered indicative of definitive endoderm differentiation. Primary screening results were captured from eight 96-well screening plates. Plate to plate variability was reduced with inclusion of individual positive and negative controls on each plate. Results are normalized and expressed as a percentage of the positive control. Emphasis was placed on retention or amplification of cell number at the conclusion of assay.

Table 2 lists a subset of 27 compounds and their analyzed results from the primary screening, where these hits appeared to retain cell number at a level equivalent to or better than the positive control despite the absence of activin A in the screening assay.

In some cases, SOX17 expression was induced in the absence of activin A (for example, the cyclic aniline-pyridinotriazines Compound 35 and Compound 22.

The compounds shown in Table 2 were selected for further evaluation for effects on the differentiation of human embryonic stem cells to cells expressing markers characteristic of the definitive endoderm lineage in the absence of activin A.

Example 4

Secondary Screening: Effects of the Compounds of the Present Invention on the Differentiation of Human Embryonic Stem Cells into Cells Expressing Markers Characteristic of the Definitive Endoderm Lineage with EGF/FGF4 in the Absence of Activin A A titration curve for activin A with a constant amount of Wnt3a showed at least two effects during DE differentiation: 1) maintaining cell numbers or preventing cell loss; and 2) inducing a marker of DE, for example, SOX17 expression (Example 2). Primary screening from Example 3 identified compounds that could maintain similar or improved cell numbers in assay relative to addition of activin A/Wnt3a alone. A secondary screening assay was conducted to evaluate the effect of combinations of the identified compounds with other growth factors, specifically EGF and FGF4, on the generation of definitive endoderm.

Cell Assay Seeding:

Clusters of H1 human embryonic stem cells were grown on reduced growth factor MATRIGEL™ (Invitrogen; Cat #356231)-coated tissue culture plastic. Cells were passaged using collagenase (Invitrogen; Cat # Cat #17104-019) treatment and gentle scraping, washed to remove residual enzyme, and plated with even dispersal at a ratio of 1:1 (surface area) on reduced growth factor MATRIGEL™-coated 96-well black plates (Packard ViewPlates; PerkinElmer; Cat #6005182) using volumes of 100 µl/well. Cells were allowed to attach as clusters and then recover log phase growth over a 1 to 3 day period, feeding daily with MEF conditioned medium supplemented with 8 ng/ml bFGF (R&D Systems; Cat #233-FB). Plates were maintained at 37° C., 5% $CO_2$ in a humidified box throughout the duration of assay.

Preparation of Compounds and Growth Factors:

Stock concentrations for EGF (R&D Systems; Cat #236-EG) and FGF4 (R&D Systems; Cat #235-F4) were 250 ng/ml, each solubilized in PBS with 0.1% BSA (Sigma; Cat #A7888). Compounds were available as 5 mM stocks in 96-well plate format, solubilized in 100% DMSO (Sigma; Cat # D2650) and stored at −80° C. The compounds were further diluted to an intermediate concentration of 0.2 mM in 50 mM HEPES (Invitrogen; Cat #15630-080), 20% DMSO and stored at 4° C. All growth factors and inhibitors were prepared in a deep well, 96-well polypropylene plate, diluted to 5× intermediate stocks in DMEM:F12 base medium at the beginning of assay and stored at 4° C.

A secondary screening assay was conducted, testing in triplicate and feeding on alternate days over the four-day assay timeframe. Assays were initiated by aspirating culture medium from each well followed by three washes in PBS to remove residual growth factors and serum. Test volumes of 80 µl per well were added back containing DMEM:F12 base medium (Invitrogen; Cat #11330-032) supplemented with 0.625% FCS (HyClone; Cat # SH30070.03), 25 ng/ml Wnt3a (R&D Systems), and 3.1241M compound plus 20 µl 5× stock of growth factors to yield a final concentration of 0.5% FCS, 20 ng/ml Wnt3a, and 2.5 µM compound plus 50 ng/ml EGF and 50 ng/ml FGF4 in the assay. Positive control wells (100 µl/well) contained the same base medium supplemented with 0.5% FCS, 20 ng/ml Wnt3a and 100 ng/ml activin A. Negative control wells (100 µl/well) contained the same base medium with 0.5% FCS and 20 ng/ml Wnt3a, omitting activin A.

On day 3, wells were aspirated and fed with 80 µl DMEM:F12 base medium supplemented with 2.5% FCS (HyClone) and 3.125 µM compound plus 20 µl 5× stock of growth factors per well to yield a final concentration of 2% FCS and 2.41M compound (omitting Wnt3a) plus 50 ng/ml EGF and FGF4 in the assay. Positive control wells (100 µl/well) contained the same base medium supplemented with 2% FCS and 100 ng/ml activin A, omitting Wnt3a. Negative control wells (100 µl/well) contained the same base medium with 2% FCS, omitting both activin A and Wnt3a.

High Content Analysis:

At the conclusion of four-days of culture, assay plates were washed twice with PBS, fixed with 4% paraformaldehyde (Alexis Biochemical; Cat # ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; cat # AF1924) was diluted 1:100 in 4% chicken serum and added to each well for one hour at room temperature. Alexa Fluor 488 conjugated secondary antibody (chicken anti-goat IgG; Molecular Probes; Cat # AZ1467) was diluted 1:200 in PBS and added to each sample well after washing three times with PBS. To counterstain nuclei, 4 µg/ml Hoechst 33342 (Invitrogen; Cat # H3570) was added for ten minutes at room temperature. Plates were washed once with PBS and left in 100 µl/well PBS for imaging.

Imaging was performed using an IN Cell Analyzer 1000 (GE Healthcare) utilizing the 51008bs dichroic for cells stained with Hoechst 33342 and Alexa Fluor 488. Exposure times were optimized from positive control wells and from untreated negative control wells stained with secondary antibody alone. Images from 15 fields per well were acquired to compensate for any cell loss during the bioassay and subsequent staining procedures. Measurements for total cell number and total SOX17 intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total SOX17 protein expression was reported as total intensity or integrated intensity, defined as total fluorescence of the cell multiplied by the area of the cell. Background was eliminated based on acceptance criteria of gray-scale ranges between 200 to 3500. Total intensity data were normalized by dividing total intensities for each well by the average total intensity for the positive control. Normalized data were calculated for averages and standard deviations for each replicate set.

Table 3A shows the results for two growth factors, EGF and FGF 4 (50 ng/ml each) tested in combination with the aniline-pyridinotriazine compounds shown in Table 2 for their effects on the differentiation of human embryonic stem cells into cells expressing markers characteristic of the definitive endoderm lineage in the absence of activin A. Results are ranked in descending order for best effects on SOX17 expression. Although the effects of these compounds on SOX17 expression were considered weak relative to the activin A/Wnt3a positive control, the responses for some of these compounds were considered significant. For example a selection of the compounds appear to have unique properties with respect to retaining high cell numbers per well during assay, presumably either by preventing apoptosis or by modulating cell cycle. In addition, these compounds appear to synergize with EGF and FGF4 to promote modest definitive endoderm differentiation, as measured by SOX17 expression. The most potent compounds are listed in Table 3B. Other compounds tested in combination with EGF and FGF4 in this assay were ineffective at inducing SOX17 expression but could retain cell numbers in assay (e.g. Compound 90: 85% cell number; 2% SOX17 expression).

Example 5

Effects of Compounds of the Present Invention in Combination with Other Factors on the Differentiation of Human Embryonic Stem Cells to Cells Expressing Markers Characteristic of the Definitive Endoderm Lineage in the Absence of Activin A A secondary assay was conducted to evaluate the effect of the compounds of the present invention with combinations of other individual growth factors or compounds known from the literature to regulate definitive endoderm differentiation.

Cell Assay Seeding:

Clusters of H1 human embryonic stem cells were grown on reduced growth factor MATRIGEL™ (Invitrogen; Cat #356231)-coated tissue culture plastic. Cells were passaged using collagenase (Invitrogen; Cat # Cat #17104-019) treatment and gentle scraping, washed to remove residual enzyme, and plated with even dispersal at a ratio of 1:1 (surface area) on reduced growth factor MATRIGEL™-coated 96-well black plates (Packard ViewPlates; PerkinElmer; Cat #6005182) using volumes of 100 μl/well. Cells were allowed to attach as clusters and then recover log phase growth over a 1 to 3 day period, feeding daily with MEF conditioned medium supplemented with 8 ng/ml bFGF (R&D Systems; Cat #233-FB). Plates were maintained at 37° C., 5% $CO_2$ in a humidified box throughout the duration of assay.

Preparation of Compounds and Growth Factors:

Stocks of growth factors purchased from R&D Systems were EGF (Cat #236-EG), FGF4 (Cat #235-F4), PDGF-A (Cat #221-AA), PDGF-B (Cat #220-BB), PDGF-C (Cat #1687-CC), PDGF-D (Cat #1159-SB), PDGF-A/B (Cat #222-AB), VEGF (Cat #293-VE), BMP-1 (Cat #1927-ZN) BMP-2 (Cat #355-BM), BMP-4 (Cat #314-BP), BMP-6 (Cat #507-BP). BMP-7 (Cat 14222-AB), BMP-2/7 (Cat #3229-BM). Other agents tested were purchased as follows: BMP-7 (Sigma; Cat #B1434), LY294002 (Cayman; Cat 70920), PD98059, U0126, U0124 (EMD Biosciences; Cat #453710), muscimol (Tocris; Cat #0289), biuculline (Tocris; Cat #0130), sodium butyrate (Sigma; Cat #B5887). All growth factors were solubilized in PBS with 0.1% BSA (Sigma; Cat #A7888) and stored frozen at −80° C. Small molecules were solubilized in 100% DMSO (Sigma; Cat #2650) and stored frozen at −80° C. The compounds were available as 5 mM stocks in 96-well plate format, solubilized in 100% DMSO and stored at −80° C. The compounds of the present invention were further diluted to an intermediate concentration of 0.2 mM in 50 mM HEPES (Invitrogen; Cat #15630-080), 20% DMSO and stored at 4° C. All growth factors and inhibitors were prepared in a deep well, 96-well polypropylene plate, diluted to 5× intermediate stocks in DMEM:F12 base medium at the beginning of assay and stored at 4° C.

A secondary screening assay was conducted, testing in triplicate and feeding on alternate days over the four-day assay timeframe. Assays were initiated by aspirating culture medium from each well followed by three washes in PBS to remove residual growth factors and serum. Test volumes of 80 μl per well were added back containing DMEM:F12 base medium (Invitrogen; Cat #11330-032) supplemented with 0.625% FCS (HyClone; Cat # SH30070.03), 25 ng/ml Wnt3a (R&D Systems), and 3.125 μM compound plus 20 μl 5× stock of growth factor or small molecule to yield a final concentration of 0.5% FCS, 20 ng/ml Wnt3a, and 2.5 μM compound. All remaining growth factors were tested at a final assay concentration of 50 ng/ml (EGF, FGF4, PDGF-A, PDGF-B, PDGF-C, PDGF-D, PDGF-A/B, VEGF, BMP-1, BMP-2, BMP-4, BMP-6, BMP-7, BMP-2/7). Final assay concentrations of small molecules tested were as follows: muscimol (20 μM), PD98059 (1 μM), LY294002 (2.5 μM), U0124 (1 μM), U0126 (1 μM), sodium butyrate (0.5 mM). Positive control wells (100 μl/well) contained the same base medium supplemented with 0.5% FCS, 20 ng/ml Wnt3a and 100 ng/ml activin A. Negative control wells (100 μl/well) contained the same base medium with 0.5% FCS and 20 ng/ml Wnt3a, omitting activin A.

On day 3, wells were aspirated and fed with 80 μl DMEM:F12 base medium supplemented with 2.5% FCS (HyClone) and 3.125 μM cyclic aniline-pyridinotriazine compound plus 20 μl 5× stock of growth factors or small molecules per well to yield a final concentration of 2% FCS and 2.5 μM compound (omitting Wnt3a) and as denoted on day one for all remaining growth factors or small molecules. Positive control wells (100 μl/well) contained the same base medium supplemented with 2% FCS and 100 ng/ml activin A, omitting Wnt3a. Negative control wells (100 μl/well) contained the same base medium with 2% FCS, omitting both activin A and Wnt3a.

High Content Analysis:

At the conclusion of four-days of culture, assay plates were washed twice with PBS, fixed with 4% paraformaldehyde (Alexis Biochemical; Cat # ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; cat AF1924) was diluted 1:100 in 4% chicken serum and added to each well for one hour at room temperature. Alexa Fluor 488 conjugated secondary antibody (chicken anti-goat IgG; Molecular Probes; Cat # AZ1467) was diluted 1:200 in PBS and added to each sample well after washing three times with PBS. To counterstain nuclei, 4 μg/ml Hoechst 33342 (Invitrogen; Cat # H3570) was added for ten minutes at room temperature. Plates were washed once with PBS and left in 100 μl/well PBS for imaging.

Imaging was performed using an IN Cell Analyzer 1000 (GE Healthcare) utilizing the 51008bs dichroic for cells stained with Hoechst 33342 and Alexa Fluor 488. Exposure times were optimized from positive control wells and from untreated negative control wells stained with secondary antibody alone. Images from 15 fields per well were acquired to compensate for any cell loss during the bioassay and subsequent staining procedures. Measurements for total cell number and total SOX17 intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total SOX17 protein expression was reported as total intensity or integrated intensity, defined as total fluorescence of the cell multiplied by the area of the cell. Background was eliminated based on acceptance criteria of gray-scale ranges between 200 to 3500. Total intensity data were normalized by dividing total intensities for each well by the average total intensity for the positive control. Normalized data were calculated for averages and standard deviations for each replicate set.

Table 4 shows the results for the differentiation of human embryonic stem cells into cells expressing markers characteristic of the definitive endoderm lineage following treatment with the compounds of the present invention in combination with individual growth factors or other small molecules. In general, members of the BMP family (BMP-1, BMP-2, BMP-4, BMP-6, BMP-7, BMP-2/7) inhibited or had negligible effects on SOX17 expression. The same was true for most of the small molecule enzyme inhibitors tested in this assay (LY294002, PD98059, U0126, U0124, sodium butyrate). However, some members of the PDGF family (PDGF-A, -AB, -C, and -D) provided an increase in SOX17 expression (10-25% of the activin A/Wnt3a control). Other growth factors showing similar increases in SOX17 expression included EGF (34%), VEGF (18%), and FGF4 (17%), although FGF4 was not able to support retention of cell numbers. The small molecule muscimol (GABA$_A$ receptor agonist) tested in combination with Compound 35 also provided a modest increase in SOX17 expression; the GABA$_A$ antagonist bicuculline had no effect on SOX17 expression. EGF, FGF4, PDGF-A, PDGF-B, PDGF-AB, PDGF-C, and PDGF-D and muscimol were selected for additional evaluation during definitive endoderm differentiation.

Example 6

Effects of the Compounds of the Present Invention in Combination with Other Factors on the Differentiation of Human Embryonic Stem Cells into Cells Expressing Markers Characteristic of the Definitive Endoderm Lineage in the Absence of Activin A A secondary assay was conducted to evaluate the effects of combinations of different compounds with other individual agents on definitive endoderm differentiation. The other agents selected for this screen had previously shown a modest increase in definitive endoderm formation, as tested with Compound 17 and as denoted in Table 5. In this screen, a broader panel of compounds was evaluated in with these agents, either in single pair-wise comparisons or pooled combinations.

Cell Assay Seeding:

Clusters of H1 human embryonic stem cells were grown on reduced growth factor MATRIGEL™ (Invitrogen; Cat #356231)-coated tissue culture plastic. Cells were passaged using collagenase (Invitrogen; Cat #17104-019) treatment and gentle scraping, washed to remove residual enzyme, and plated with even dispersal at a ratio of 1:1 (surface area) on reduced growth factor MATRIGEL™-coated 96-well black plates (Packard ViewPlates; PerkinElmer; Cat #6005182) using volumes of 100 µl/well. Cells were allowed to attach as clusters and then recover log phase growth over a 1 to 3 day period, feeding daily with MEF-conditioned medium supplemented with 8 ng/ml bFGF (R&D Systems; Cat #233-FB). Plates were maintained at 37° C., 5% CO$_2$ in a humidified box throughout the duration of the assay.

Preparation of Compounds and Growth Factors:

Stocks of growth factors purchased from R&D Systems were EGF (Cat #236-EG), FGF4 (Cat #235-F4), PDGF-A (Cat #221-AA), PDGF-D (Cat #1159-SB), PDGF-A/B (Cat #222-AB), and VEGF (Cat #293-VE). Muscimol was purchased from Tocris (Cat #0289). All growth factors were solubilized in PBS with 0.1% BSA (Sigma; Cat #A7888) and stored frozen at −80° C. Muscimol was solubilized in 100% DMSO (Sigma; Cat #D2650) and stored frozen at −80° C. Compounds were available as 5 mM stocks in 96-well plate format, solubilized in 100% DMSO and stored at −80° C. Compounds were further diluted to an intermediate concentration of 0.2 mM in 50 mM HEPES (Invitrogen; Cat #15630-080), 20% DMSO and stored at 4° C. All growth factors and inhibitors were prepared in a deep well, 96-well polypropylene plate, diluted to 5× intermediate stocks in DMEM:F12 base medium at the beginning of assay and stored at 4° C.

A secondary screening assay was conducted, testing in triplicate and feeding on alternate days over the four-day assay timeframe. Assays were initiated by aspirating culture medium from each well followed by three washes in PBS to remove residual growth factors and serum. Test volumes of 80 µl per well were added back containing DMEM:F12 base medium (Invitrogen; Cat #11330-032) supplemented with 0.625% FCS (HyClone; Cat # SH30070.03), 25 ng/ml Wnt3a (R&D Systems), and 3.125 µM compound plus 20 µl 5× stock of growth factor or small molecule to yield a final concentration of 0.5% FCS, 20 ng/ml Wnt3a, and 2.5 µM. All remaining growth factors were tested at a final assay concentration of 50 ng/ml (EGF, FGF4, PDGF-A, PDGF-A/B, VEGF). Final assay concentration of muscimol was 20 µM. Positive control wells (100 µl/well) contained the same base medium supplemented with 0.5% FCS, 20 ng/ml Wnt3a and 100 ng/ml activin A. Negative control wells (100 µl/well) contained the same base medium with 0.5% FCS and 20 ng/ml Wnt3a, omitting activin A.

On day 3, wells were aspirated and fed with 80 µl DMEM:F12 base medium supplemented with 2.5% FCS (HyClone) and 3.125 µM compound plus 20 µl 5× stock of growth factors or small molecules per well to yield a final concentration of 2% FCS and 2.5 µM compound (omitting Wnt3a) and as denoted on day one for all remaining growth factors or small molecules. Positive control wells (100 µl/well) contained the same base medium supplemented with 2% FCS and 100 ng/ml activin A, omitting Wnt3a. Negative control wells (100 µl/well) contained the same base medium with 2% FCS, omitting both activin A and Wnt3a.

High Content Analysis:

At the conclusion of four-days of culture, assay plates were washed twice with PBS, fixed with 4% paraformaldehyde (Alexis Biochemical; Cat # ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat 16110082) in PBS for 30 minutes at room temperature. Primary antibody (goat anti-human SOX17; R&D Systems; cat # AF1924) was diluted 1:100 in 4% chicken serum and added to each well for one hour at room temperature. Alexa Fluor 488 conjugated secondary antibody (chicken anti-goat IgG; Molecular Probes; Cat # AZ1467) was diluted 1:200 in PBS and added to each sample well after washing three times with PBS. To counterstain nuclei, 4 μg/ml Hoechst 33342 (Invitrogen; Cat # H3570) was added for ten minutes at room temperature. Plates were washed once with PBS and left in 100 μl/well PBS for imaging.

Imaging was performed using an IN Cell Analyzer 1000 (GE Healthcare) utilizing the 51008bs dichroic for cells stained with Hoechst 33342 and Alexa Fluor 488. Exposure times were optimized from positive control wells and from untreated negative control wells stained with secondary antibody alone. Images from 15 fields per well were acquired to compensate for any cell loss during the bioassay and subsequent staining procedures. Measurements for total cell number and total SOX17 intensity were obtained from each well using IN Cell Developer Toolbox 1.7 (GE Healthcare) software. Segmentation for the nuclei was determined based on grayscale levels (baseline range 100-300) and nuclear size. Averages and standard deviations were calculated for each replicate data set. Total SOX17 protein expression was reported as total intensity or integrated intensity, defined as total fluorescence of the cell multiplied by the area of the cell. Background was eliminated based on acceptance criteria of gray-scale ranges between 200 to 3500. Total intensity data were normalized by dividing total intensities for each well by the average total intensity for the positive control. Normalized data were calculated for averages and standard deviations for each replicate set.

Table 5 shows compounds previously identified as hits (Table 2) tested in a definitive endoderm bioassay in various combinations with growth factors and muscimol, without activin A. Some compounds had minimal or weak effects on SOX17 expression with all growth factor combinations tested. However, some compounds were able to induce significant SOX17 expression with some but not all growth factor combinations. One compound in particular, Compound 34, had significant synergistic responses with all growth factors tested and mediated increases in both cell numbers as well as SOX17 expression in this assay: Compound 39 with 1) EGF+FGF4=77% of positive control response; or 2) EGF+FGF4+PDGF-AB=68% of positive control response; or 3) EGF+FGF4+PDGF-A+VEGF=31% of positive control response.

Example 7

Effects of Compound 34 in Combination with Other Factors on the Differentiation of Human Embryonic Stem Cells into Cells Expressing Markers Characteristic of the Definitive Endoderm Lineage in the Absence of Activin A In this example, an effort was made to analyze the minimum number of growth factors required in combination with the best cyclic aniline-pyridinotriazine compound, Compound 34 to yield a robust SOX17 response in the absence of activin A. Also in this example, a new growth factor, GDF-8, was added for evaluation. GDF-8, also known as myostatin, is a member of the TGF-β family and has been shown to use the activin type II and TGF-β type I receptors (ALK4/5) to induce SMAD 2/3 phosphorylation.

Cell Assay Seeding:

Clusters of H1 human embryonic stem cells were grown on reduced growth factor MATRIGEL™ (Invitrogen; Cat #356231)-coated tissue culture plastic. Cells were passaged using collagenase (Invitrogen; Cat #17104-019) treatment and gentle scraping, washed to remove residual enzyme, and plated with even dispersal at a ratio of 1:1 (surface area) on reduced growth factor MATRIGEL™-coated 96-well black plates (Packard ViewPlates; PerkinElmer; Cat #6005182) using volumes of 100 μl/well. Cells were allowed to attach as clusters and then recover log phase growth over a 1 to 3 day period, feeding daily with MEF conditioned medium supplemented with 8 ng/ml bFGF (R&D Systems; Cat #233-FB). Plates were maintained at 37° C., 5% $CO_2$ in a humidified box throughout the duration of assay.

Preparation of Compounds and Growth Factors:

Stocks of growth factors purchased from R&D Systems were EGF (Cat #236-EG), FGF4 (Cat #235-F4), PDGF-A (Cat #221-AA), PDGF-D (Cat #1159-SB), PDGF-A/B (Cat #222-AB), VEGF (Cat #293-VE), and GDF-8 (Cat #788-G8). Muscimol was purchased from Tocris (Cat #0289). All growth factors were solubilized in PBS with 0.1% BSA (Sigma; Cat # A7888) and stored frozen at −80° C. Muscimol was solubilized in 100% DMSO (Sigma; Cat #D2650) and stored frozen at −80° C. Cyclic aniline-pyridinotriazine compounds were available as 5 mM stocks in 96-well plate format, solubilized in 100% DMSO and stored at −80° C. Compound 34 was further diluted to an intermediate concentration of 0.2 mM in 50 mM HEPES (Invitrogen; Cat #15630-080), 20% DMSO and stored at 4° C. All growth factors and inhibitors were prepared in a deep well, 96-well polypropylene plate, diluted to 5× intermediate stocks in DMEM:F12 base medium at the beginning of assay and stored at 4° C.

A secondary screening assay was conducted, testing in triplicate and feeding on alternate days over the four-day assay timeframe. Assays were initiated by aspirating culture medium from each well followed by three washes in PBS to remove residual growth factors and serum. Test volumes of 80 μl per well were added back containing DMEM:F12 base medium (Invitrogen; Cat #11330-032) supplemented with 0.625% FCS (HyClone; Cat # SH30070.03), 25 ng/ml Wnt3a (R&D Systems), and 3.125 μM Compound 27 plus 20 μl 5× stock of growth factor or small molecule to yield a final concentration of 0.5% FCS, 20 ng/ml Wnt3a, and 2.5 μM Compound 34. All remaining growth factors were tested at a final assay concentration of 50 ng/ml (EGF, FGF4, PDGF-A, PDGF-A/B, VEGF) with the exception of GDF-8 tested at 25 ng/ml. Final assay concentration of muscimol was 20 μM. Positive control wells (100 μl/well) contained the same base medium supplemented with 0.5% FCS, 20 ng/ml Wnt3a and 100 ng/ml activin A. Negative control wells (100 μl/well) contained the same base medium with 0.5% FCS and 20 ng/ml Wnt3a, omitting activin A.

On day 3, wells were aspirated and fed with 80 μl DMEM:F12 base medium supplemented with 2.5% FCS (HyClone) and 3.125 μM Compound 34 plus 20 μl 5× stock of growth factors or small molecules per well to yield a final concentration of 2% FCS and 2.5 μM Compound 34 (omitting Wnt3a) and as denoted on day one for all remaining growth factors or small molecules. Positive control wells (100 μl/well) contained the same base medium supplemented with 2% FCS and 100 ng/ml activin A, omitting Wnt3a. Negative control wells (100 μl/well) contained the same base medium with 2% FCS, omitting both activin A and Wnt3a.

High Content Analysis:

At the conclusion of four-days of culture, assay plates were washed twice with PBS, fixed with 4% paraformaldehyde (Alexis Biochemical; Cat # ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; cat # AF1924) was diluted 1:100 in 4% chicken serum and added to each well for one hour at room temperature. Alexa Fluor 488 conjugated secondary antibody (chicken anti-goat IgG; Molecular Probes; Cat # AZ1467) was diluted 1:200 in PBS and added to each sample well after washing three times with PBS. To counterstain nuclei, 4 μg/ml Hoechst 33342 (Invitrogen; Cat # H3570) was added for ten minutes at room temperature. Plates were washed once with PBS and left in 100 μl/well PBS for imaging.

Imaging was performed using an IN Cell Analyzer 1000 (GE Healthcare) utilizing the 51008bs dichroic for cells stained with Hoechst 33342 and Alexa Fluor 488. Exposure times were optimized from positive control wells and from untreated negative control wells stained with secondary antibody alone. Images from 15 fields per well were acquired to compensate for any cell loss during the bioassay and subsequent staining procedures. Measurements for total cell number and total SOX17 intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total SOX17 protein expression was reported as total intensity or integrated intensity, defined as total fluorescence of the cell multiplied by the area of the cell. Background was eliminated based on acceptance criteria of gray-scale ranges between 200 to 3500. Total intensity data were normalized by dividing total intensities for each well by the average total intensity for the positive control. Normalized data were calculated for averages and standard deviations for each replicate set.

Table 6 shows results of this assay. Where GDF-8 was present in any combination with the Compound 34, a substantial increase in SOX17 expression was observed. Furthermore, GDF-8 and Wnt3a with Compound 34 were sufficient to yield SOX17 expression (88% of control) in a range similar to that seen with 100 ng/ml activin A/Wnt3a treatment. It appears that the growth factor GDF-8 can serve as a replacement for activin A during definitive endoderm differentiation of human embryonic stem cells.

Example 8

Additional Screening for Compounds Capable of Differentiating Pluripotent Stem Cells into Cells Expressing Markers Characteristic of the Definitive Endoderm Lineage Based on the compound structures for hits identified thus far, an analog search was conducted to find additional related compounds to test in the definitive endoderm bioassay. The substructure search yielded compounds for screening. Screening parameters for this assay were designed with the combination of factors that had yielded optimal results in previous assays, specifically combining EGF, FGF, PDGF-A, VEGF, PDGF-D, muscimol, and GDF-8 with the small molecule compound.

Cell Assay Seeding:

Briefly, clusters of H1 human embryonic stem cells were grown on reduced growth factor MATRIGEL™ (Invitrogen; Cat #356231)-coated tissue culture plastic. Cells were passaged using collagenase (Invitrogen; Cat #17104-019) treatment and gentle scraping, washed to remove residual enzyme, and plated with even dispersal at a ratio of 1:1 (surface area) on reduced growth factor MATRIGEL™-coated 96-well black plates (Packard ViewPlates; Perki-nElmer; Cat #6005182) using volumes of 100 μl/well. Cells were allowed to attach as clusters and then recover log phase growth over a 1 to 3 day period, feeding daily with MEF conditioned medium supplemented with 8 ng/ml bFGF (R&D Systems; Cat #233-FB). Plates were maintained at 37° C., 5% $CO_2$ in a humidified box throughout the duration of assay.

Preparation of Compounds and Assay:

Growth factors purchased from R&D Systems were EGF (Cat #236-EG), FGF4 (Cat #235-F4). PDGF-A (Cat #22'-AA), PDGF-D (Cat #1159-SB), PDGF-A/B (Cat #222-AB). VEGF (Cat #293-VE), and GDF-8 (Cat #788-G8). Muscimol was purchased from Tocris (Cat #0289). Screening was conducted using a library of compounds that were made available as 5 mM stocks in 96-well plate format, solubilized in 100% DMSO (Sigma; Cat #D2650) and stored at −80° C. The compounds were further diluted to an intermediate concentration of 0.2 mM in 50 mM HEPES (Invitrogen; Cat #15630-080), 20% DMSO and stored at 4° C. Test conditions were performed in single wells, feeding on alternate days over a four-day assay period. Primary screening assays were initiated by aspirating culture medium from each well followed by three washes in PBS (Invitrogen; Cat #14190) to remove residual growth factors and serum. On the first day of assay, test volumes of 200 μl per well were added back containing DMEM:F12 base medium (Invitrogen; Cat #11330-032) supplemented with 0.5% FCS (HyClone; Cat # SH30070.03) and 20 ng/ml Wnt3a (R&D Systems; Cat #1324-WN) plus 2.5 μM compound. All remaining growth factors were tested at a final assay concentration of 50 ng/ml (EGF, FGF4, PDGF-A, PDGF-A/B, VEGF) with the exception of GDF-8 tested at 25 ng/ml. Final assay concentration of muscimol was 20 μM. Positive control samples contained the same base medium supplemented with 0.5% FCS plus 20 ng/ml Wnt3a and 100 ng/ml recombinant human activin A (PeproTech; Cat #120-14). Negative control samples contained DMEM:F12 base medium supplemented with 0.5% FCS and 20 ng/ml Wnt3a. On the third day of assay, test volumes of 200 μl per well were added back containing DMEM:F12 base medium supplemented with 2% FCS plus 2.5 μM compound, without Wnt3a. All remaining growth factors were tested at a final assay concentration of 50 ng/ml (EGF, FGF4, PDGF-A, PDGF-A/B, VEGF) with the exception of GDF-8 tested at 25 ng/ml. Final assay concentration of muscimol was 20 μM. Positive control samples contained the same base medium supplemented with 2% FCS and 100 ng/ml recombinant human activin A (PeproTech; Cat #120-14). Negative control samples contained DMEM:F12 base medium supplemented with 2% FCS. Positive control samples contained the same base medium supplemented with FCS, substituting 100 ng/ml recombinant human activin A (PeproTech; Cat #120-14) for the aniline-pyridinotriazine compound throughout the four-day assay along with Wnt3a (20 ng/ml) on days 1 and 2. Negative control samples contained DMEM:F12 base medium supplemented with FCS, adding Wnt3a on days 1 and 2 but omitting treatment with activin A.

High Content Analysis:

At the conclusion of four-days of culture, assay plates were washed twice with PBS (Invitrogen; Cat #14190), fixed with 4% paraformaldehyde (Alexis Biochemical; Cat # ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; Cat # AF1924) was diluted 1:100 in 4% chicken serum and added to each well for one hour at room temperature. Alexa Fluor 488 conjugated secondary antibody (chicken anti-goat IgG; Molecular Probes; Cat #1 AZ1467) was diluted 1:200 in PBS and added to each sample well after washing three times with PBS. To counterstain nuclei, 4 µg/ml Hoechst 33342 (Invitrogen; Cat # H3570) was added for ten minutes at room temperature. Plates were washed once with PBS and left in 100 µl/well PBS for imaging.

Imaging was performed using an IN Cell Analyzer 1000 (GE Healthcare) utilizing the 51008bs dichroic for cells stained with Hoechst 33342 and Alexa Fluor 488. Exposure times were optimized from positive control wells and from untreated negative control wells stained with secondary antibody alone. Images from 15 fields per well were acquired to compensate for any cell loss during the bioassay and subsequent staining procedures. Measurements for total cell number and total SOX17 intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total SOX17 protein expression was reported as total intensity or integrated intensity, defined as total fluorescence of the cell times area of the cell. Background was eliminated based on acceptance criteria of gray-scale ranges between 200 to 3500. Total intensity data were normalized by dividing total intensities for each well by the average total intensity for the positive control. Normalized data were calculated for averages and standard deviations for each replicate set.

In Table 7, GDF-8 and a combination of growth factors/agonists (EGF, FGF, PDGF-A, VEGF, PDGF-D, muscimol) were tested with a new set of aniline-pyridinotriazine compounds. Results from two assay plates in this single experiment are ranked with respect to SOX17 responses (as a percentage of the positive control treatment with activin A and Wnt3a). Additional compounds were identified that show significant synergistic activity with the growth factor/agonist pool. These compounds were effective in both retaining assay cell number and yielding SOX17 expression during human embryonic stem cell differentiation in the absence of activin A. A list of these hits with greater than 25% activity of the positive control is shown in Table 8.

Of note, four hits from the initial primary screening (Table 2) were duplicated in the analog library. Two of these compounds repeated as hits with the analog screening (Compound 34 and Compound 35; shown boxed in Table 8); one was a weak hit in the analog screening, and one compound did not repeat.

Example 9

Effects of the Compounds of the Present Invention on the Differentiation of Human Embryonic Stem Cells to Cells Expressing Markers Characteristic of the Definitive Endoderm Lineage in the Presence of Low Concentrations of Activin A It was important to determine if the compounds that had been identified as hits in the definitive endoderm bioassays above could also show synergistic activity with very low doses of activin A. An initial evaluation was performed using the short hit list of cyclic aniline-pyridinotriazine compounds denoted in Table 3B.

Cell Assay Seeding:

Clusters of H1 human embryonic stem cells were grown on reduced growth factor MATRIGEL™ (Invitrogen; Cat #356231)-coated tissue culture plastic. Cells were passaged using collagenase (Invitrogen; Cat #17104-019) treatment and gentle scraping, washed to remove residual enzyme, and plated with even dispersal at a ratio of 1:1 (surface area) on reduced growth factor MATRIGEL™-coated 96-well black plates (Packard ViewPlates; PerkinElmer; Cat #6005182) using volumes of 100 µl/well. Cells were allowed to attach as clusters and then recover log phase growth over a 1 to 3 day period, feeding daily with MEF conditioned medium supplemented with 8 ng/ml bFGF (R&D Systems; Cat #233-FB). Plates were maintained at 37° C., 5% $CO_2$ in a humidified box throughout the duration of assay.

Preparation of Compounds and Growth Factors:

Stocks of growth factors purchased from R&D Systems were EGF (Cat #236-EG), FGF4 (Cat #235-F4), PDGF-A (Cat #221-AA), PDGF-D (Cat #1159-SB), PDGF-A/B (Cat #222-AB), VEGF (Cat #293-VE), and GDF-8 (Cat #788-G8). Activin A was purchased from PeproTech (Cat #). Muscimol was purchased from Tocris (Cat #0289). All growth factors were solubilized in PBS with 0.1% BSA (Sigma; Cat #A7888) and stored frozen at −80° C. Muscimol was solubilized in 100% DMSO (Sigma; Cat #D2650) and stored frozen at −80° C. The compounds were available as 5 mM stocks in 96-well plate format, solubilized in 100% DMSO and stored at −80° C. The compounds were further diluted to an intermediate concentration of 0.2 mM in 50 mM HEPES (Invitrogen; Cat #15630-080), 20% DMSO and stored at 4° C. All growth factors and inhibitors were prepared in a deep well, 96-well polypropylene plate, diluted to 5× intermediate stocks in DMEM:F12 base medium at the beginning of assay and stored at 4° C.

A secondary screening assay was conducted, testing in triplicate and feeding on alternate days over the four-day assay timeframe. Assays were initiated by aspirating culture medium from each well followed by three washes in PBS to remove residual growth factors and serum. Test volumes of 80 µl per well were added back containing DMEM:F12 base medium (Invitrogen; Cat #11330-032) supplemented with 0.625% FCS (HyClone; Cat 11 SH30070.03), 25 ng/ml Wnt3a (R&D Systems), 12.5 ng/ml activin A, and 3.125 µM compound plus 20 µl 5× stock of growth factor or small molecule to yield a final concentration of 0.5% FCS, 20 ng/ml Wnt3a. 10 ng/ml activin A, and 2.5 µM compound. All remaining growth factors were tested at a final assay concentration of 50 ng/ml (EGF, FGF4, PDGF-A, PDGF-A/13, VEGF), with the exception of GDF-8 used at 25 ng/ml. Final assay concentration of muscimol was 20 µM. Positive control wells (100 µl/well) contained the same base medium supplemented with 0.5% FCS, 20 ng/ml Wnt3a and 10 ng/ml (low dose) or 100 ng/ml (high dose) activin A. Negative control wells (100 μl/well) contained the same base medium with 0.5% FCS and 20 ng/ml Wnt3a, omitting activin A.

On day 3, wells were aspirated and fed with 80W DMEM:F12 base medium supplemented with 2.5% FCS (HyClone), 12.5 ng/ml activin A, and 3.125 μM compound plus 20 μl 5× stock of growth factors or small molecules per well to yield a final concentration of 2% FCS, 10 ng/ml activin A, and 2.5 μM compound (omitting Wnt3a) and as denoted on day one for all remaining growth factors or small molecules. Positive control wells (100 μl/well) contained the same base medium supplemented with 2% FCS and 10 ng/ml or 100 ng/ml activin A, omitting Wnt3a. Negative control wells (100 μl/well) contained the same base medium with 2% FCS, omitting both activin A and Wnt3a.

High Content Analysis:

At the conclusion of four-days of culture, assay plates were washed twice with PBS, fixed with 4% paraformaldehyde (Alexis Biochemical; Cat # ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; cat # AF1924) was diluted 1:100 in 4% chicken serum and added to each well for one hour at room temperature. Alexa Fluor 488 conjugated secondary antibody (chicken anti-goat IgG; Molecular Probes; Cat # AZ1467) was diluted 1:200 in PBS and added to each sample well after washing three times with PBS. To counterstain nuclei, 4 μg/ml Hoechst 33342 (Invitrogen; Cat # H3570) was added for ten minutes at room temperature. Plates were washed once with PBS and left in 100 μl/well PBS for imaging.

Imaging was performed using an IN Cell Analyzer 1000 (GE Healthcare) utilizing the 51008bs dichroic for cells stained with Hoechst 33342 and Alexa Fluor 488. Exposure times were optimized from positive control wells and from untreated negative control wells stained with secondary antibody alone. Images from 15 fields per well were acquired to compensate for any cell loss during the bioassay and subsequent staining procedures. Measurements for total cell number and total SOX17 intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total SOX17 protein expression was reported as total intensity or integrated intensity, defined as total fluorescence of the cell multiplied by the area of the cell. Background was eliminated based on acceptance criteria of gray-scale ranges between 200 to 3500. Total intensity data were normalized by dividing total intensities for each well by the average total intensity for the positive control. Normalized data were calculated for averages and standard deviations for each replicate set.

Table 9 shows results from assay of various compounds and different combinations of growth factors with low doses of activin A. Some compounds showed robust synergistic responses with various growth factors. In other cases, the synergistic effects were more modest but significant relative to a low dose activin A control. Other compounds had no activity relative to the low dose activin A control.

Example 10

Effects of the Compounds of the Present Invention on the Differentiation of Single Human Embryonic Stem Cells to Cells Expressing Markers of the Definitive Endoderm Lineage in the Absence of Activin A Cyclic aniline-pyridinotriazine compounds were also tested in a screening format using cells dispersed through enzymatic treatment to single cells and plated in monolayer for assay. The assay also made changes to eliminate serum that can provide growth factors even at low doses. To that end the basal medium was changed and serum was replaced with fatty acid free BSA. The assay was shortened from four days to three days to provide a more narrow timeframe to measure results. Finally, the assay included two growth factors, EGF and FGF4 that had previously shown significant but sub-optimal effects on definitive endoderm differentiation in the absence of activin A.

Screening Assay

Cell Assay Seeding:

Briefly, clusters of H1 human embryonic stem cells were grown on reduced growth factor MATRIGEL™ (Invitrogen; Cat #356231)-coated tissue culture plastic. Cultures were treated with Accutase (Sigma; Cat #A6964), using equivalent volumes of 10 ml per 10 cm$^2$ surface area for 5 minutes at 37° C., then gently resuspended, pelleted by centrifugation, and resuspended in MEF conditioned medium for counting. For assay seeding, cells were plated at 50,000 cells/cm$^2$ on reduced growth factor MATRIGEL™-coated 96-well black plates (Packard ViewPlates; Cat #6005182) using volumes of 100 μl/well. Cells were allowed to attach and recover log phase growth over a 3 to 5 day period, feeding daily with MEF conditioned medium supplemented with 8 ng/ml bFGF (R&D Systems; Cat #233-FB). Plates were maintained at 37° C., 5% $CO_2$ in a humidified box throughout the duration of assay.

Preparation of Compounds and Assay:

Stocks of EGF and FGF4 were prepared in a 96-well polypropylene plate (Corning, Inc.; Cat #3960). Compound 22 was available as a 5 mM stock solubilized in 100% DMSO (Sigma; Cat #D2650) and stored at −80° C. Assays were initiated by aspirating culture medium from each well followed by three washes in PBS to remove residual growth factors and serum. Test volumes of 80 μl per well were added back containing RPMI 1640 base medium (Invitrogen; Cat #22400-089) supplemented with 2.5% fatty acid free BSA (MP Biomedicals LLC; Cat #152401), 10 ng/ml bFGF (PeproTech Inc; Cat #100-18B), 25 ng/ml Wnt3a (R&D Systems; Cat #1324-WN) and 3.125 μM Compound 22 plus 20W 5× stock of growth factors to yield a final concentration of 2% fatty acid free BSA, 8 ng/ml bFGF (PeproTech Inc; Cat #100-18B), 20 ng/ml Wnt3a, and 2.5 μM Compound 22 in assay. Positive control wells contained the same base medium supplemented with 2% fatty acid free BSA, 8 ng/ml bFGF, 20 ng/ml Wnt3a, and 100 ng/ml recombinant human activin A (PeproTech; Cat #120-14). Negative control wells contained the same base medium supplemented with 2% fatty acid free BSA, 8 ng/ml bFGF, 20 ng/ml Wnt3a but omitted treatment with activin A.

On the second day of assay, wells were again aspirated and fed with 80 μl per well were added back containing RPMI 1640 base medium supplemented with 2.5% fatty acid free BSA, 10 ng/ml bFGF, and 3.125 μM Compound 22 plus 20 µl 5× stock of growth factors to yield a final concentration of 2% fatty acid free BSA, 8 ng/ml bFGF and 2.5 µM Compound 22 in assay. Positive control wells contained the same base medium supplemented with 2% fatty acid free BSA, 8 ng/ml bFGF and 100 ng/ml recombinant human activin A. Negative control samples contained the same base medium supplemented with 2% fatty acid free BSA and 8 ng/ml bFGF but omitted treatment with activin A.

High Content Analysis:

At the conclusion of four-days of culture, assay plates were washed twice with PBS, fixed with 4% paraformaldehyde (Alexis Biochemical; Cat #ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; cat AF1924) was diluted 1:100 in 4% chicken serum and added to each well for one hour at room temperature. Alexa Fluor 488 conjugated secondary antibody (chicken anti-goat IgG; Molecular Probes; Cat # AZ1467) was diluted 1:200 in PBS and added to each sample well after washing three times with PBS. To counterstain nuclei, 4 µg/ml Hoechst 33342 (Invitrogen; Cat # H3570) was added for ten minutes at room temperature. Plates were washed once with PBS and left in 100 µl/well PBS for imaging.

Imaging was performed using an IN Cell Analyzer 1000 (GE Healthcare) utilizing the 51008bs dichroic for cells stained with Hoechst 33342 and Alexa Fluor 488. Exposure times were optimized from positive control wells and from untreated negative control wells stained with secondary antibody alone. Images from 15 fields per well were acquired to compensate for any cell loss during the bioassay and subsequent staining procedures. Measurements for total cell number and total SOX17 intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total SOX17 protein expression was reported as total intensity or integrated intensity, defined as total fluorescence of the cell multiplied by the area of the cell. Background was eliminated based on acceptance criteria of gray-scale ranges between 200 to 3500. Total intensity data were normalized by dividing total intensities for each well by the average total intensity for the positive control. Normalized data were calculated for averages and standard deviations for each replicate set.

Table 10 shows results of this assay with Compound 34. Control samples with EGF and/or FGF4 alone without the Compound 34 had low SOX17 expression. Addition of Compound 34 added significant enhancement of SOX17 expression.

Example 11

A Comparison of the Ability of Activin A and GDF-8 to Differentiate Human Embryonic Stem Cells to Cells Expressing Markers Characteristic of the Definitive Endoderm Lineage A previous example showed that GDF-8 is able to replace activin A to differentiate human embryonic stem cells to cells expressing markers characteristic of the definitive endoderm lineage. It was important to know the relative potencies of GDF-8GDF-8 and activin A with respect their ability to differentiate human embryonic stem cells to cells expressing markers characteristic of the definitive endoderm lineage. A dose response assay was conducted using equivalent concentrations of each growth factor to compare results during embryonic stem cell differentiation.

Preparation of Cells for Assay:

Stock cultures of human embryonic stem cells (H1 human embryonic stem cell line) were maintained in an undifferentiated, pluripotent state on reduced growth factor MATRIGEL-coated dishes in MEF conditioned medium with passage on average every four days. Passage was performed by exposing cell cultures to a solution of 1 mg/ml dispase (Invitrogen, Cat #: 17105-041) for 5 to 7 minutes at 37° C. followed by rinsing the monolayer with MEF conditioned culture medium and gentle scraping to recover cell clusters. Clusters were centrifuged at low speed to collect a cell pellet and remove residual dispase. Cell clusters were split at a 1:3 or 1:4 ratio for routine maintenance culture or a 1:1 ratio for immediate assay. All human embryonic stem cell lines were maintained at passage numbers less than 50 and routinely evaluated for normal karyotypic phenotype and for absence of mycoplasma contamination.

Cell clusters used in the assay were evenly resuspended in MEF conditioned medium supplemented with 8 ng/ml bFGF and seeded onto reduced growth factor MATRIGEL™-coated 96-well Packard VIEWPLATES (PerkinElmer; Cat #6005182) in volumes of 100 µl/well. MEF conditioned medium supplemented with 8 ng/ml bFGF was used for initial plating and expansion. Daily feeding was conducted by aspirating spent culture medium from each well and replacing with an equal volume of fresh medium. Plates were maintained at 37° C., 5% $CO_2$ in a humidified box throughout the duration of assay.

Assay:

The assay was initiated by aspirating the culture medium from each well and adding back an aliquot (104 µl) of test medium. Test conditions were performed in quadruplicate over a total three-day assay period, feeding on day 1 and day 2 by aspirating and replacing the medium from each well with fresh test medium. Two 12-channel polypropylene basins (Argos technologies, Inc, Cat #: B3135) were used to make the test media containing different concentrations of Activin A (PeproTech; Cat #120-14) or GDF-8 (R&D Systems, Cat #788-G8). Channels numbered 2 through 12 of each basin contained 1 ml assay medium composed of RPMI-1640 medium (Invitrogen; Cat #: 22400) supplemented with 2% Albumin Bovine Fraction V, Fatty Acid Free (FAF BSA) (MP Biomedicals, Inc; Cat #152401) and 8 ng/ml bFGF (PeproTech Inc.; Cat #: 100-18B), and with 20 ng/ml Wnt3a (R&D Systems; Cat #1324-WN/CF) added on day 1, omitted on day 2 and 3. Channel number 1 of each basin contained 1600 ng/ml Activin A or 1600 ng/ml GDF-8, diluted into the same assay medium. One ml of medium was transferred from channel number 1 to channel number 2 and mixed well. A fresh pipette tip was used to transfer one ml of medium from channel number 2 to channel number 3, followed by thorough mixing. The same procedure was repeated in sequence through channel number 11 for each respective basin. Channel number 12 of each basin contained medium without Activin A or GDF-8. By doing this, a series of two-fold test dilutions was created, containing Activin A or GDF-8 at concentrations ranging from 1.6 ng/ml to 1600 ng/ml, for addition to the respective assay wells.

High Content Analysis:

At the conclusion of three days of culture, assay plates were washed once with PBS (Invitrogen; Cat #14190), fixed with 4% paraformaldehyde (Alexis Biochemical; Cat # ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; Cat # AF1924) was diluted 1:100 in 4% chicken serum and added to each well for two hours at room temperature. After washing three times with PBS, Alexa Fluor 488 conjugated secondary antibody (chicken anti-goat IgG; Invitrogen; Cat #A21467) diluted 1:200 in PBS was added to each well. To counterstain nuclei, 5 µg/ml Hoechst 33342 (Invitrogen; Cat # H3570) was added for fifteen minutes at room temperature. Plates were washed once with PBS and left in 100 µl/well PBS for imaging.

Figure 2:
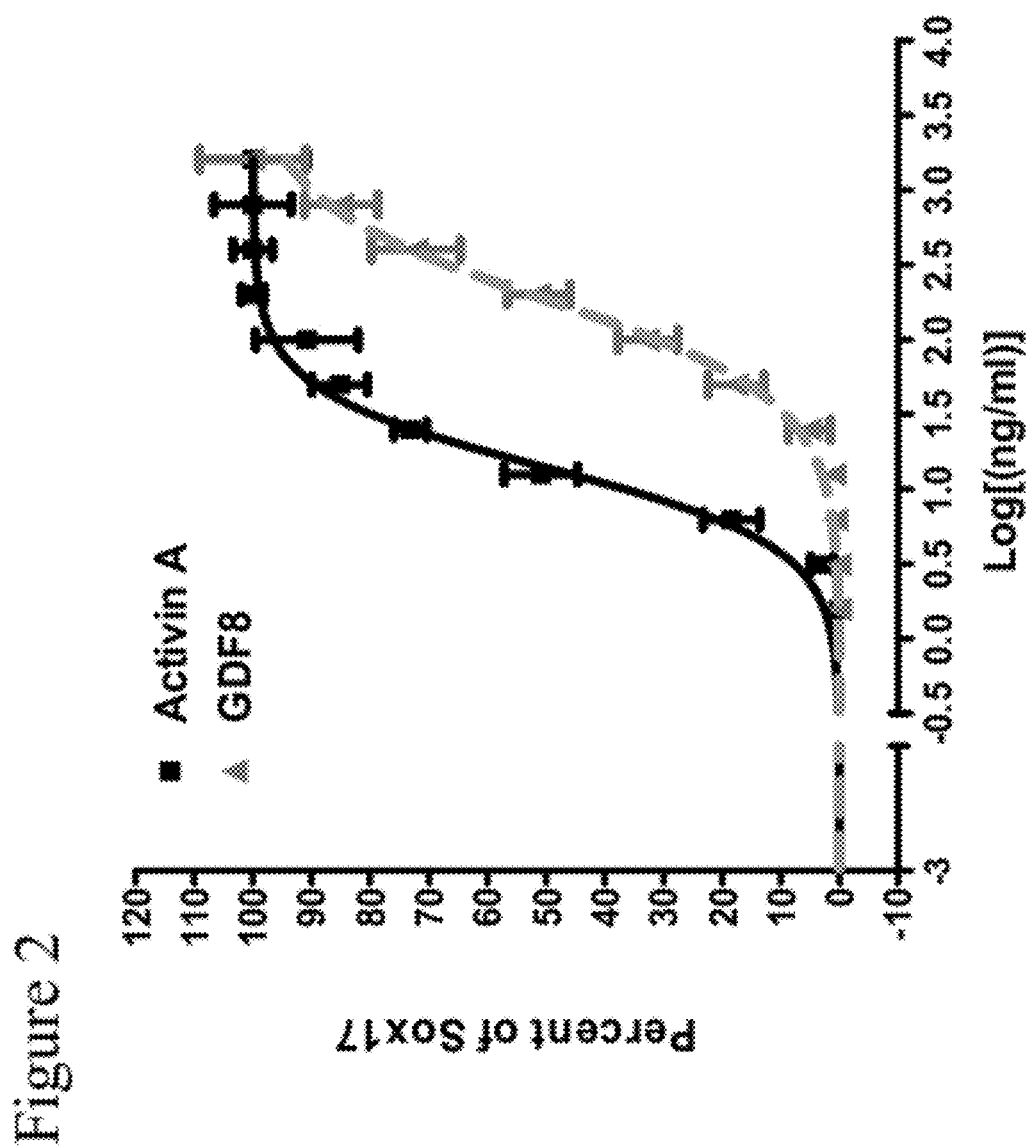
FIG. 2 shows the dose response relationship of activin A and GDF8 used to differentiate cells of the human embryonic stem cell line H1 toward cells expressing markers characteristic of the definitive endoderm lineage. Cells were treated for a total of three days with activin A or GDF8 at the concentrations shown in combination with 20 ng/ml Wnt3a on the first day of assay. Differentiation was determined by measuring SOX17 intensity using a fluorescent antibody probe and high content analysis on a GE Healthcare IN Cell Analyzer.

Imaging was performed using an IN Cell Analyzer 1000 (GE Healthcare) utilizing the 51008bs dichroic for cells stained with Hoechst 33342 and Alexa Fluor 488. Images were acquired from 25 fields per well. Measurements for total SOX17 intensity in each well were obtained using IN Cell Developer Toolbox 1.7 (GE Healthcare) software. Segmentation for the nuclei was determined based on gray-scale levels (baseline range 100-300) and nuclear size. Averages and standard deviations were calculated for each quadruplicate data set. Total SOX17 protein expression was reported as total intensity or integrated intensity, defined as total fluorescence of the cell multiplied by area of the cell. Background was eliminated based on acceptance criteria for gray-scale ranges between 200 to 4500. Total SOX17 intensity data were calculated using GraphPad Prism 4.02 (GraphPad Software, Inc., Lo Jolla, Calif.). Data were normalized to define the smallest and largest values in each data set as 0% and 100%, respectively. Table 11 shows the normalized values for each of the activin A and GDF-8 data sets. Two sigmoidal dose-response curves are shown in FIG. 2 as generated using the normalized values shown in Table 11. The $R^2$ values, indicating curve fit, were calculated using GraphPad Prism and determined to be 0.9944 for activin A and 0.9964 for GDF-8. Using GraphPad Prism, $EC_{50}$ values for each growth factor were calculated and determined to be 13.9 ng/ml for activin A and 184.8 ng/ml for GDF-8. These data indicate that GDF-8 is less potent than activin A with respect to inducing human embryonic stem cells to differentiate to cells expressing markers characteristic of the definitive endoderm lineage. Nonetheless, GDF-8 can substitute for activin A and at specific concentrations, can induce an equivalent population of definitive endoderm cells, as denoted by SOX17 expression.

Example 12

Cells Expressing Markers Characteristic of the Definitive Endoderm Lineage that were Formed According to the Methods of the Present Invention are Able to Further Differentiate into Cells Expressing Markers Characteristic of the Pancreatic Endocrine Lineage Parallel populations of human embryonic stem cells were differentiated to cells expressing markers characteristic of the definitive endoderm lineage using GDF-8 in combination with either Compound 34 or Compound 56. Thereafter, a step-wise differentiation protocol was applied to treated cells to promote differentiation toward pancreatic endoderm and endocrine lineages. A parallel control consisting of cells treated with Activin A and Wnt3a was maintained for comparison purposes throughout the step-wise differentiation process. Samples were taken at every stage of the differentiation to determine the appearance of proteins and mRNA biomarkers representative of the various stages of differentiation.

Preparation of Cells for Assay:

Stock cultures of human embryonic stem cells (H1 human embryonic stem cell line) were maintained in an undifferentiated, pluripotent state on reduced growth factor MATRIGEL™-coated dishes in MEF conditioned medium with passage on average every four days. Passage was performed by exposing cell cultures to a solution of 1 mg/ml dispase (Invitrogen; Cat #17105-041) for 5 to 7 minutes at 37° C. followed by rinsing the monolayer with MEF conditioned culture medium and gentle scraping to recover cell clusters. Clusters were centrifuged at low speed to collect a cell pellet and remove residual dispase. Cell clusters were split at a 1:3 or 1:4 ratio for routine maintenance culture or a 1:1 ratio for immediate assay. All human ES cell lines were maintained at passage numbers less than 50 and routinely evaluated for normal karyotype and absence of mycoplasma.

Cell clusters were evenly resuspended in MEF conditioned medium supplemented with 8 ng/ml bFGF and seeded onto reduced growth factor MATRIGEL™-coated 24-well, black wall culture plates (Arctic White; Cat #AWLS-303012) in volumes of 0.5 ml/well. Daily feeding was conducted by aspirating spent culture medium from each well and replacing with an equal volume of fresh medium. Plates were maintained at 37° C., 5% $CO_2$ throughout the duration of assay.

Assay:

The assay was initiated by aspirating the culture medium from each well and adding back an aliquot (0.5 ml) of test medium. Test conditions for the first step of differentiation were conducted over a three-day period, feeding daily by aspirating and replacing the medium from each well with fresh test medium. On the first day of assay, 100 ng/ml activin A (PeproTech; Cat #120-14) or 200 ng/ml GDF-8 (R&D Systems, Cat #788-G8) was added to respective assay wells where each growth factor was diluted into RPMI-1640 medium (Invitrogen; Cat #22400) with 1% Albumin Bovine Fraction V, Fatty Acid Free (FAF BSA) (MP Biomedicals, Inc; Cat #152401), 1% Probumin (Millipore; Cat #81-068-3) and 20 ng/ml Wnt3a (R&D Systems; Cat #1324-WN/CF). On the second day of assay, 100 ng/ml activin A or 200 ng/ml GDF-8 was diluted into RPMI-1640 medium supplemented with 2% FAF BSA without Wnt3a. In some test samples using GDF-8, Wnt3a was replaced with a either Compound 34 or Compound 56 at a concentration of 2.5 µM, and either Compound 34 or Compound 56 was added daily during all three days of definitive endoderm differentiation. At the conclusion of the first step of differentiation, cells from some wells were harvested for flow cytometry analysis to evaluate levels of CXCR4, a marker of definitive endoderm formation. Additional wells were harvested for RT-PCR analysis to measure other markers of differentiation.

At the conclusion of the first step of differentiation, replicate sets of parallel wells from each treatment group were subjected to further step-wise differentiation. It is important to note that after the first differentiation step, all wells undergoing continuing culture and differentiation received the same treatment. The protocol for this continuing differentiation is described below.

Step 2 of the differentiation protocol was carried out over two days. Cells were fed daily by aspirating the medium from each well and replacing with a fresh aliquot (0.5 ml) of DMEM:F12 medium (Invitrogen; Cat #11330-032) containing 2% Albumin Bovine Fraction V, Fatty Acid Free (FAF BSA) (MP Biomedicals, Inc; Cat #152401), 50 ng/ml FGF7 (PeproTech; Cat #100-19), and 250 nM cyclopamine (Calbiochem; Cat #239804).

Step 3 of the differentiation protocol was carried out over four days. Cells were fed daily by aspirating medium from each well and replacing with a fresh aliquot (0.5 ml) of DMEM-high glucose (Invitrogen; Cat #10569) supplemented with 1% B27 (Invitrogen; Cat #17504-044), 50 ng/ml FGF7, 100 ng/ml Noggin (R&D Systems; Cat #3344-NG), 250 nM KAAD-cyclopamine (Calbiochem; Cat #239804), and 2 µM all-trans retinoic acid (RA) (Sigma-Aldrich; Cat #R2625). At the conclusion of the third step of differentiation, cells from some wells were harvested for analysis by RT-PCR to measure markers of differentiation. Other culture wells were subjected to high content image analysis for protein expression levels of Pdx1, a transcription factor associated with pancreatic endoderm, and Cdx2, a transcription factor associated with intestinal endoderm.

Step 4 of the differentiation protocol was carried out over three days. Cells were fed daily by aspirating the medium from each well and replacing with a fresh aliquot (0.5 ml) of DMEM-high glucose supplemented with 1% 1327, 100 ng/ml Noggin, 100 ng/ml Netrin-4, 1 µM DAPT (EMD Biosciences; Cat #565770), and 1 µM Alk 5 inhibitor (Axxora; Cat # ALX-270-445). At the conclusion of the fourth step of differentiation, cells from some wells were harvested for analysis by RT-PCR to measure markers of differentiation. Other culture wells were subjected to high content image analysis for protein expression levels of PDX1.

Step 5 of the differentiation protocol was carried out over seven days in DMEM-high glucose with 1% B27, and 1 µM Alk 5 inhibitor. Medium in each well was aspirated and replaced with a fresh aliquot (0.5 ml) on all days. At the conclusion of the fifth step of differentiation, cells from some wells were harvested for analysis by RT-PCR to measure markers of differentiation. Other culture wells were subjected to high content image analysis for protein expression levels of insulin and glucagon.

Step 6 of the differentiation protocol was carried out over seven days in DMEM-high glucose with 1% B27. Medium in each well was aspirated and replaced with a fresh aliquot (0.5 ml) on alternating days. At the conclusion of the sixth step of differentiation, cells from some wells were harvested for analysis by RT-PCR to measure markers of differentiation.

FACS Analysis:

Cells for FACS analysis were blocked in a 1:5 solution of 0.5% human gamma-globulin (Sigma; Cat# G-4386) in PBS (Invitrogen; Cat #14040-133): BD FACS staining buffer—BSA (BD; Cat #554657) for 15 minutes at 4° C. Cells were then stained with antibodies for CD9 PE (BD; Cat #555372), CD99 PE (Caltag; Cat #MHCD9904) and CXCR4 APC (R&D Systems; Cat# FAB173A) for 30 minutes at 4° C. After a series of washes in BD FACS staining buffer, the cells were stained for viability with 7-AAD (BD; Cat #559925) and run on a BD FACSArray. A mouse IgG1K Isotype control antibody for both PE and APC was used to gate percent positive cells.

RT-PCR Analysis:

RNA samples were purified by binding to a silica-gel membrane (Rneasy Mini Kit, Qiagen, CA) in the presence of an ethanol-containing, high-salt buffer followed by washing to remove contaminants. The RNA was further purified using a TURBO DNA-free kit (Ambion, INC), and high-quality RNA was then eluted in water. Yield and purity were assessed by A260 and A280 readings on a spectrophotometer. CDNA copies were made from purified RNA using an ABI (ABI, CA) high capacity cDNA archive kit.

Unless otherwise stated, all reagents were purchased from Applied Biosystems. Real-time PCR reactions were performed using the ABI PRISM® 7900 Sequence Detection System. TAQMAN® UNIVERSAL PCR MASTER MIX® (ABI, CA) was used with 20 ng of reverse transcribed RNA in a total reaction volume of 20 µl. Each cDNA sample was run in duplicate to correct for pipetting errors. Primers and FAM-labeled TAQMAN® probes were used at concentrations of 200 nM. The level of expression for each target gene was normalized using a human glyceraldehyde-3-phosphate dehydrogenase (GAPDH) endogenous control previously developed by Applied Biosystems. Primer and probe sets are listed in Table 12. After an initial incubation at 50° C. for 2 min followed by 95° C. for 10 min, samples were cycled 40 times in two stages—a denaturation step at 95° C. for 15 sec followed by an annealing/extension step at 60° C. for 1 min. Data analysis was carried out using GENEAMP®7000 Sequence Detection System software. For each primer/probe set, a Ct value was determined as the cycle number at which the fluorescence intensity reached a specific value in the middle of the exponential region of amplification. Relative gene expression levels were calculated using the comparative Ct method. Briefly, for each cDNA sample, the endogenous control Ct value was subtracted from the gene of interest Ct to give the delta Ct value ($\Delta$Ct). The normalized amount of target was calculated as 2-$\Delta$Ct, assuming amplification to be 100% efficiency. Final data were expressed relative to a calibrator sample.

High Content Analysis:

At the conclusion of culture, assay plates were washed once with PBS (Invitrogen; Cat #14190), fixed with 4% paraformaldehyde (Alexis Biochemical; Cat # ALX-350-011) at room temperature for 20 minutes, then washed three times with PBS and permeabilized with 0.5% Triton X-100 (Sigma; Cat #T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; Cat # AF1924) was diluted 1:100 in 4% chicken serum and added to each well for two hours at room temperature. After washing three times with PBS, Alexa Fluor 488 conjugated secondary antibody (chicken anti-goat IgG; Invitrogen; Cat #A21467) diluted 1:200 in PBS was added to each well. To counterstain nuclei, 5 µg/ml Hoechst 33342 (Invitrogen; Cat # H3570) was added for fifteen minutes at room temperature. Plates were washed once with PBS and left in 100 µl/well PBS for imaging. Other primary antibodies used for analysis included 1:100 dilution mouse anti-human CDX2 (Invitrogen; Cat #397800), 1:100 dilution goat anti-human Pdx1 (Santa Cruz Biotechnology; Cat # SC-14664), 1:200 dilution rabbit anti-human insulin (Cell Signaling; Cat # C27C9), and 1:1500 dilution mouse anti-human glucagon (Sigma-Aldrich; Cat #G2654). Secondary antibodies used for analysis included 1:400 dilution Alexa Fluor 647 chicken anti-mouse IgG (Invitrogen; Cat #A-21463), 1:200 dilution Alexa Fluor 488 donkey anti-goat IgG (Invitrogen; Cat

A11055), 1:1000 dilution Alexa Fluor 647 chicken anti-rabbit IgG (Invitrogen; Cat #A21443), and 1:1000 dilution Alexa Fluor 488 chicken anti-mouse IgG (Invitrogen; Cat #A21200).

Imaging was performed using an IN Cell Analyzer. 1000 (GE Healthcare) utilizing the 51008bs dichroic for cells stained with Hoechst 33342 and Alexa Fluor 488. Images were acquired from 25 fields per well. Measurements for total intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total protein expression was reported as total intensity or integrated intensity, defined as total fluorescence of the cell multiplied by the area of the cell. Background was eliminated based on acceptance criteria for gray-scale ranges between 200 and 4500. Total intensity data were normalized by dividing total intensities for each well by the average total intensity for the positive control.

PCR results for representative differentiation markers are shown in Table 13 for cells harvested from each step of differentiation. Samples treated with GDF-8 and Wnt3a or with GDF-8 and either Compound 34 or Compound 56 showed similar, or in some instances, improved expression levels of expression markers associated with endodermal and endocrine differentiation.

Figure 3:
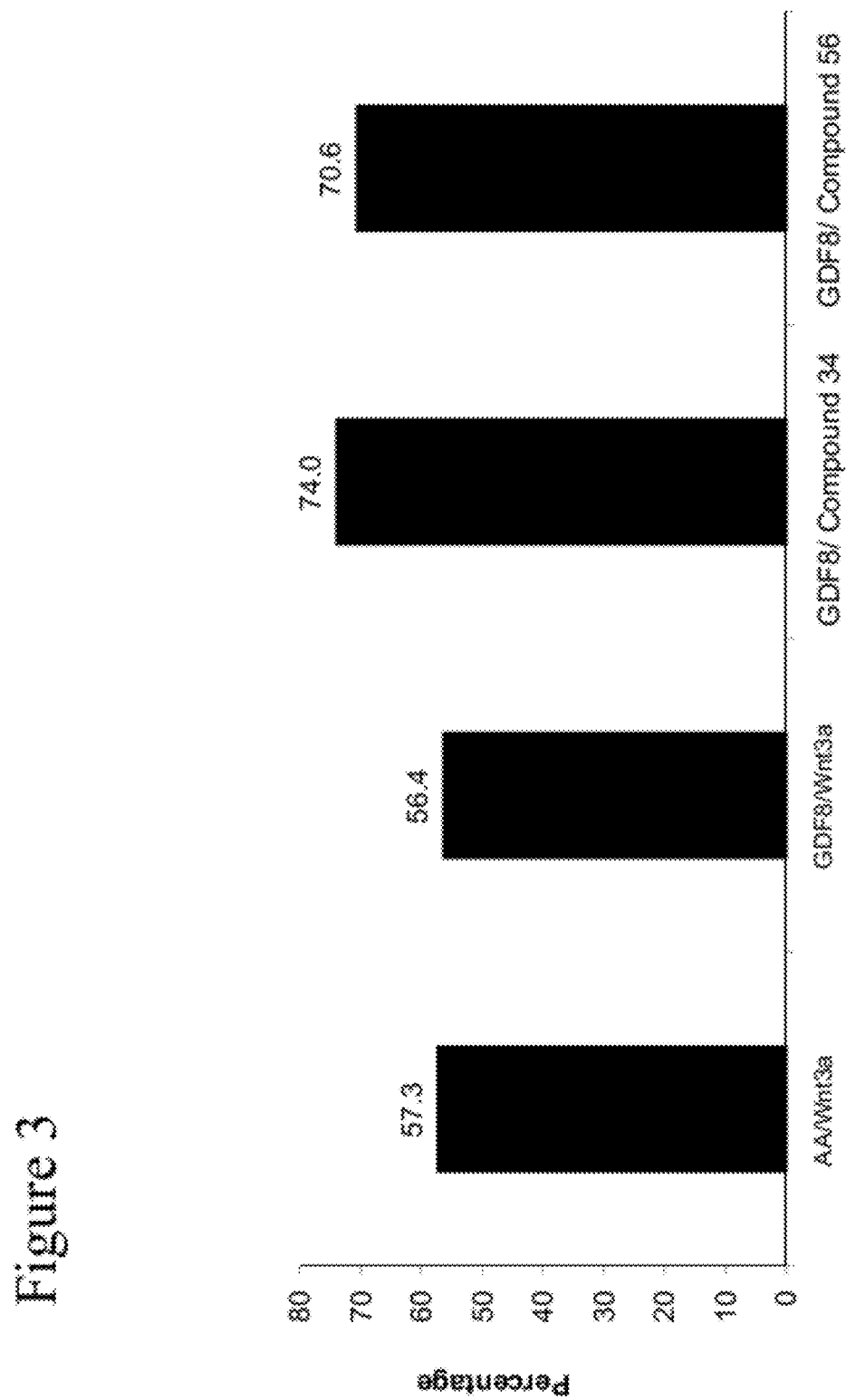
FIG. 3 shows the expression of CXCR4 in cells following the first step of differentiation, according to the methods described in Example 12. H1 cells were treated with 100 ng/ml activin A or 200 ng/ml GDF-8 for a total of three days in combination with 20 ng/ml Wnt3a for the first day or 2.5 µM Compound 34 or 2.5 µM Compound 56 for all three days. CXCR4 expression was measured using a fluorescent antibody probe and flow cytometry, yielding the percentages of positive cells shown.
Figure 4:
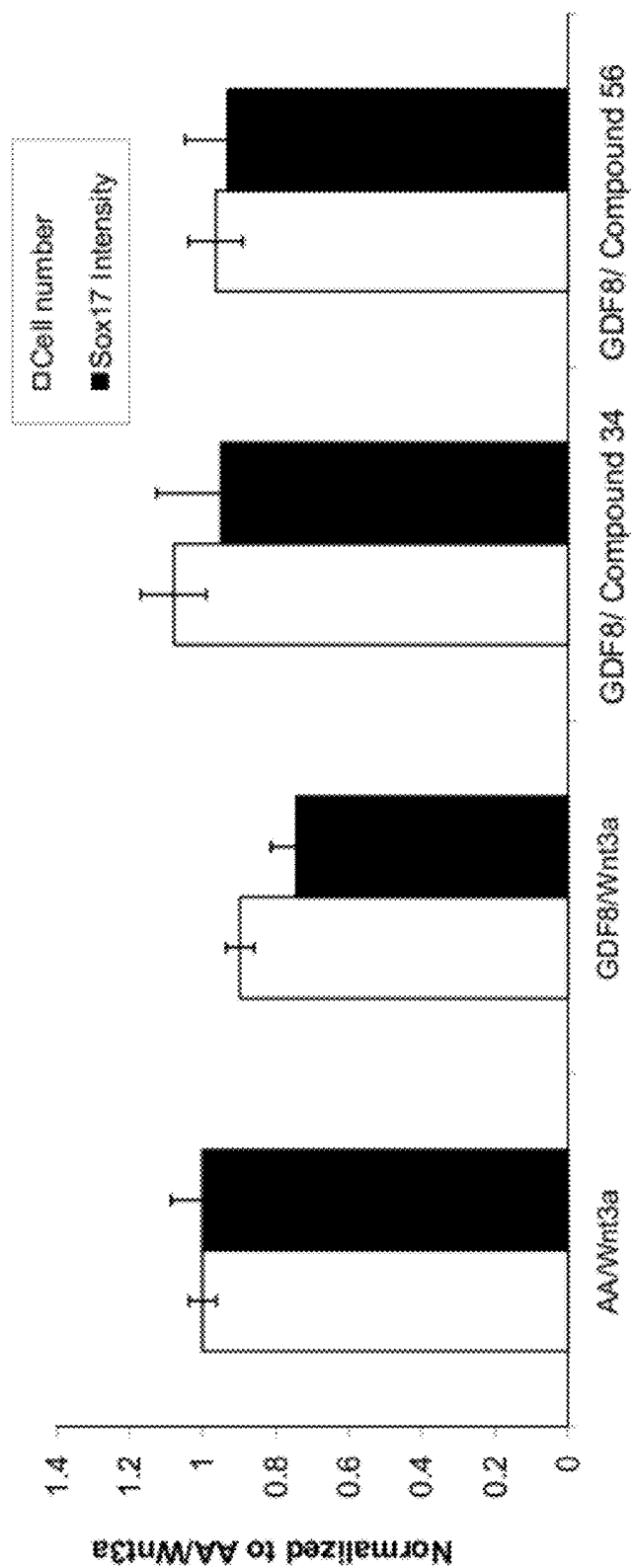
FIG. 4 shows the expression of SOX17 in cells after three days differentiation to definitive endoderm according to the methods described in Example 12. H1 cells were treated for a total of three days with 100 ng/ml activin A or 200 ng/ml GDF-8 in combination with 20 ng/ml Wnt3a for the first day or 2.5 µM Compound 34 or 2.5 µM Compound 56 for all three days. Differentiation was determined by measuring SOX17 intensity (black bars) and resulting cell number (white bars) with fluorescent antibody probes and high content analysis on a GE Healthcare IN Cell Analyzer.

FIG. 3 shows the results of the FACS analysis, showing the expression of the definitive endoderm marker, CXCR4, after the first step of differentiation. Treatment of human embryonic stem cells with GDF-8 and Wnt3a yielded an equivalent percentage of CXCR4 positive cells compared to treatment with activin A and Wnt3a. Similarly, treatment of human embryonic stem cells with GDF-8 and a small molecule (Compound 34 or Compound 56) also yielded an equivalent or higher percentage of CXCR4 positive cells. FIG. 4 shows high content image analysis for normalized SOX17 protein expression in human embryonic stem cells after three days differentiation to definitive endoderm. Levels of expression for treatment groups using GDF-8 with Wnt3a or GDF-8 with a small molecule are similar to treatment with activin A and Wnt3a.

Figure 5:
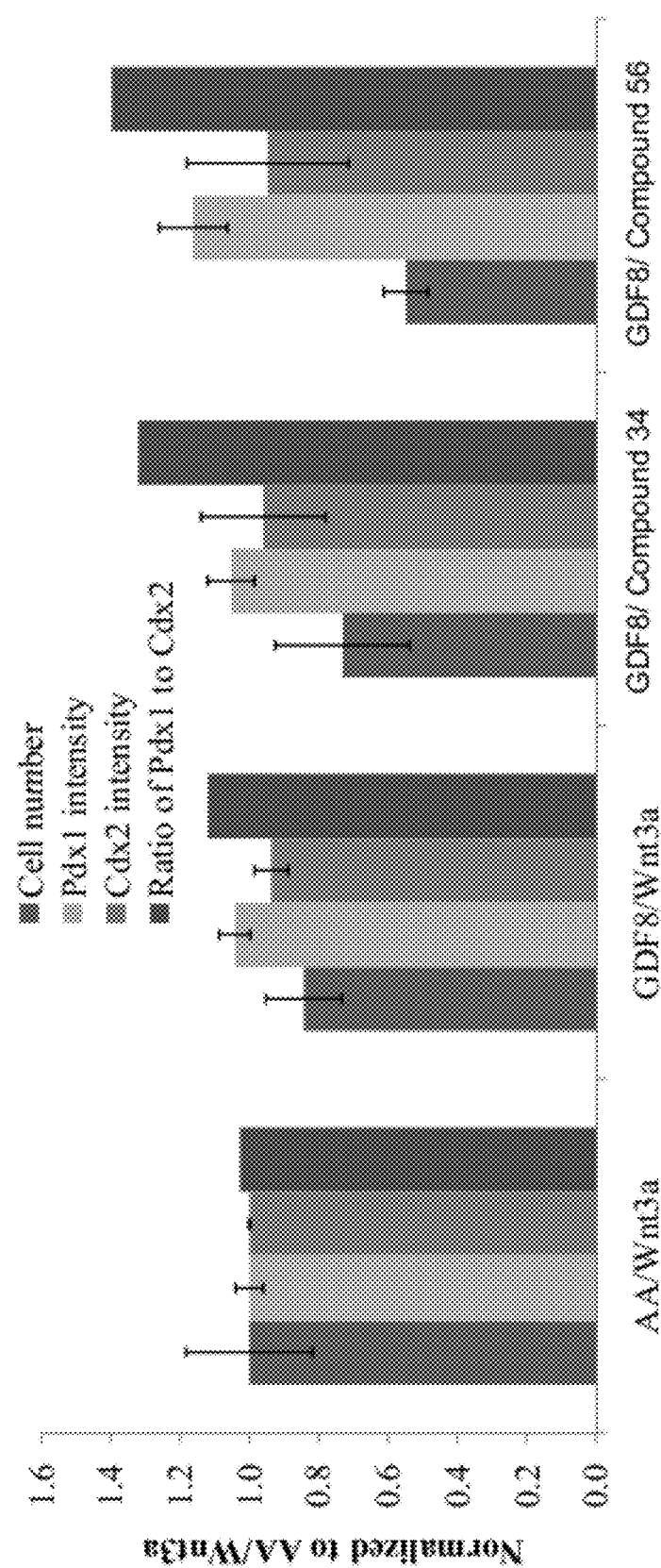
Figure 6:
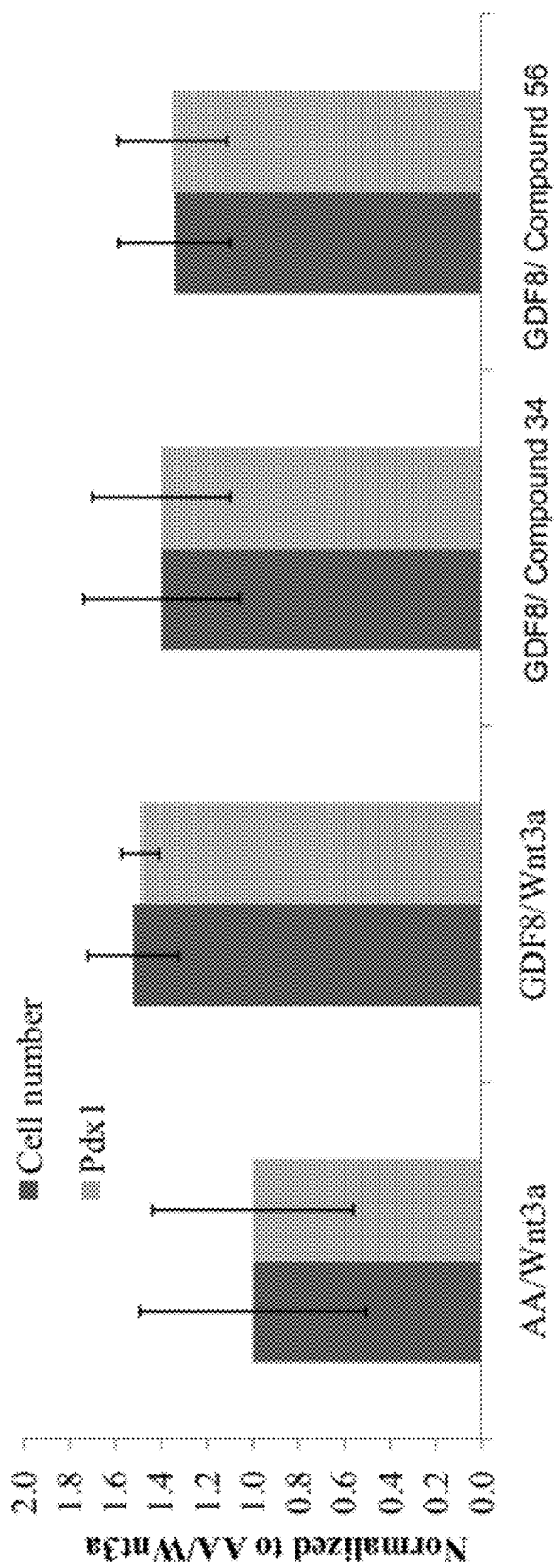
Figure 7:
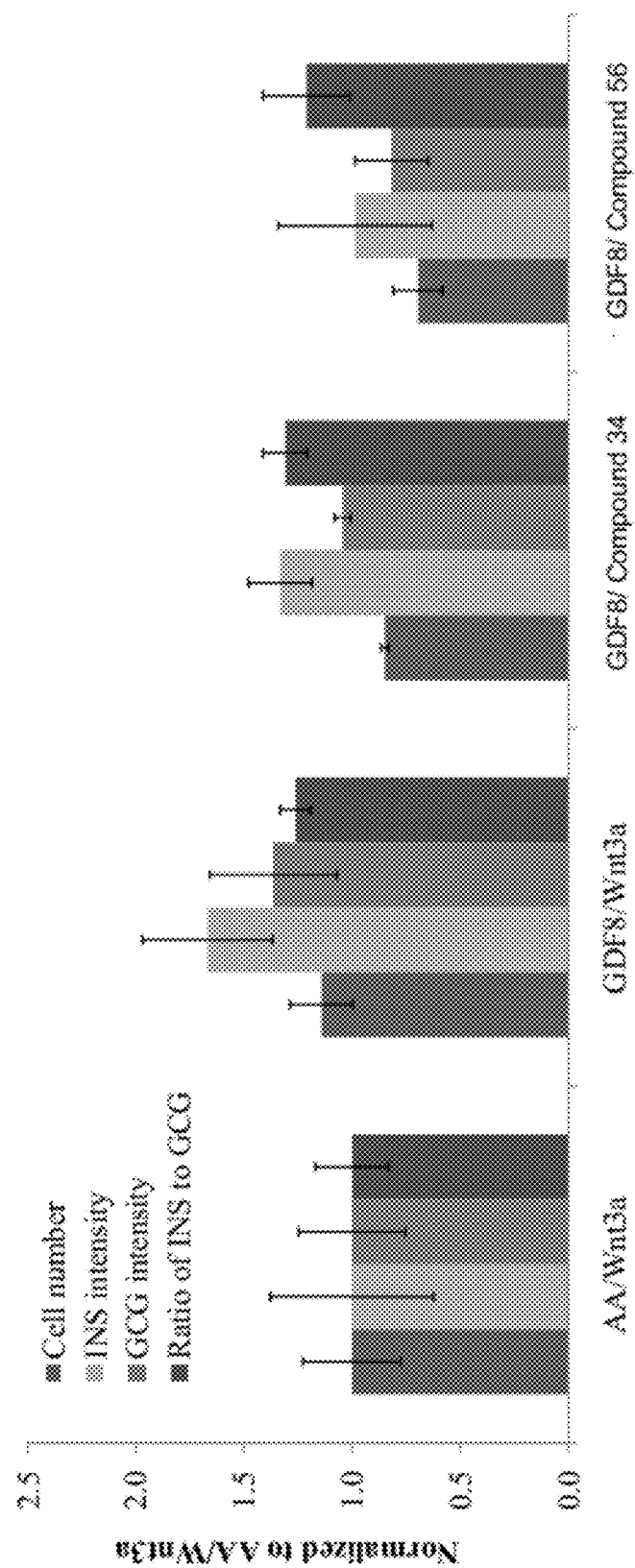
Figure 8A:
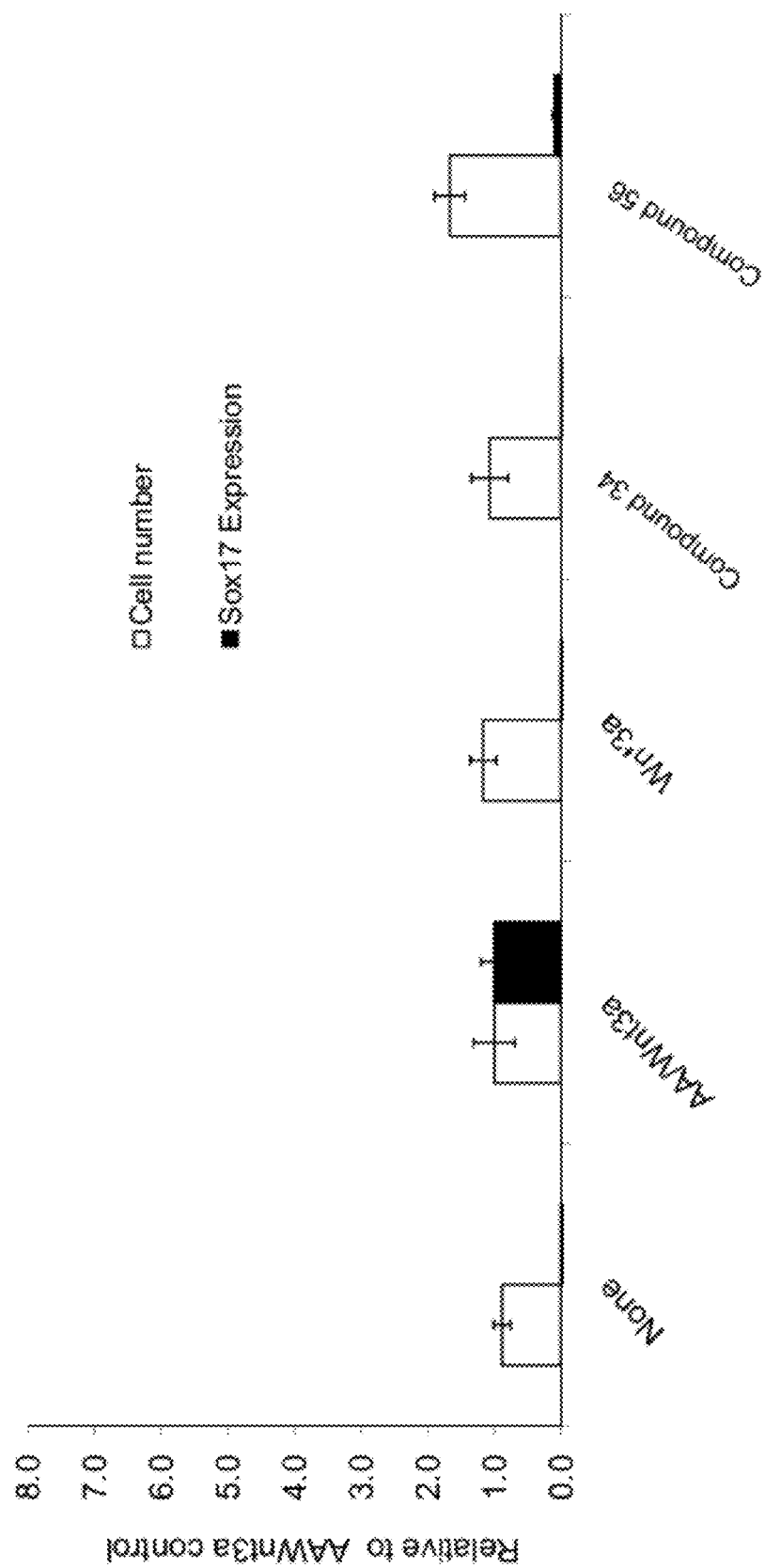
FIG. 8 shows SOX17 protein expression and cell number in human embryonic stem cells after differentiation to definitive endoderm, according to the methods described in Example 13. H1 cells were treated for a total of four days with 100 ng/ml of activin A or 100 ng/ml of a GDF-growth factor in combination with 20 ng/ml Wnt3a for the first day or 2.5 μM Compound 34 or 2.5 μM Compound 56 for the first two days of assay. SOX17 protein expression (black bars) and cell numbers (white bars), as determined with fluorescent antibody probes and high content analysis, are depicted for each treatment group. For comparative purposes, values are normalized relative to treatment with activin A/Wnt3a. Panel 8A shows a series of control conditions for differentiation in the absence of any growth factors (NONE), or with activin A/Wnt3a treatment (AA/Wnt3a) or with individual reagents alone. Panel 8B shows differentiation with GDF-3, alone or in multiple combinations with Wnt3a, Compound 34, or Compound 56. Panel 8C shows differentiation with GDF-5, alone or in multiple combinations with Wnt3a, Compound 34, or Compound 56. Panel 8D shows differentiation with GDF-8, alone or in multiple combinations with Wnt3a, Compound 34, or Compound 56. Panel 8E shows differentiation with GDF-10, alone or in multiple combinations with Wnt3a, Compound 34, or Compound 56. Panel 8F shows differentiation with GDF-11, alone or in multiple combinations with Wnt3a, Compound 34, or Compound 56. Panel 8G shows differentiation with GDF-15, alone or in multiple combinations with Wnt3a, Compound 34, or Compound 56.
Figure 8B:
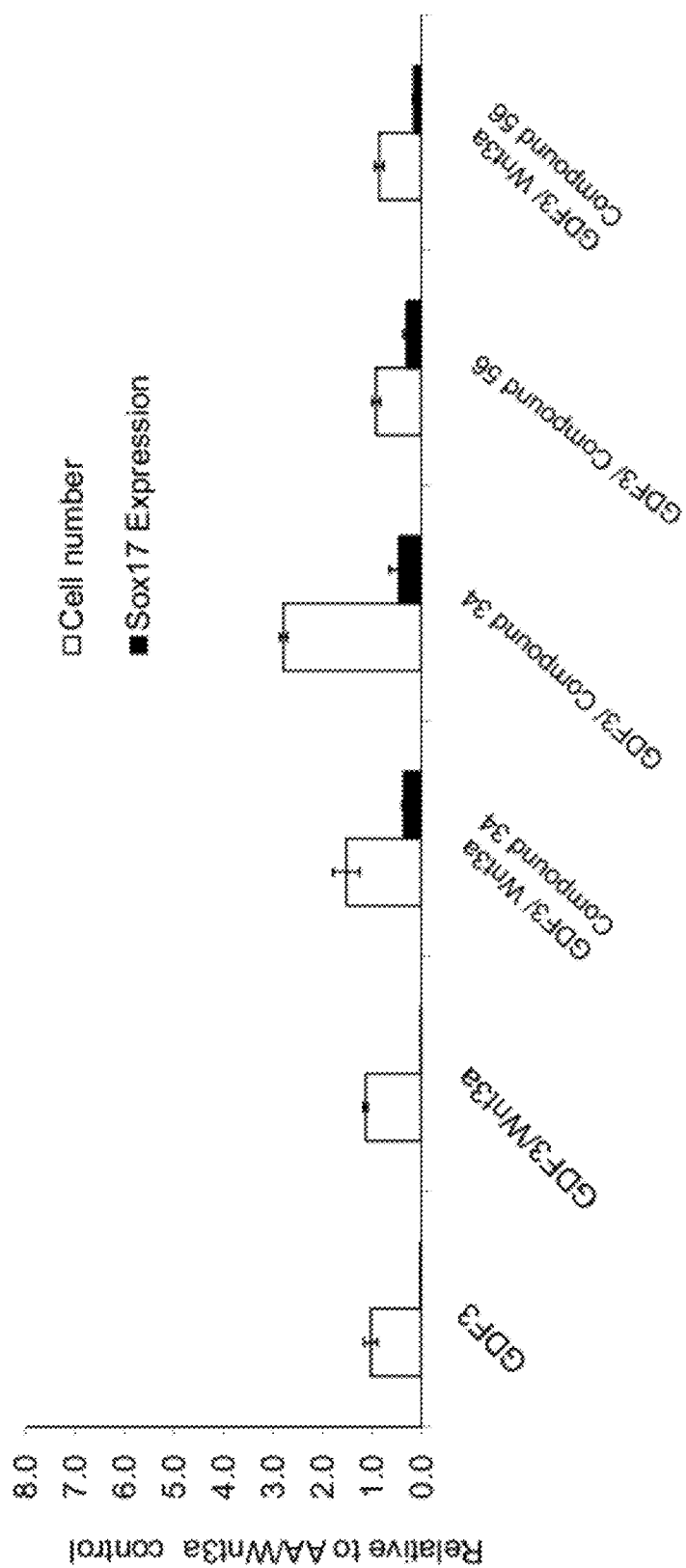
Figure 8C:
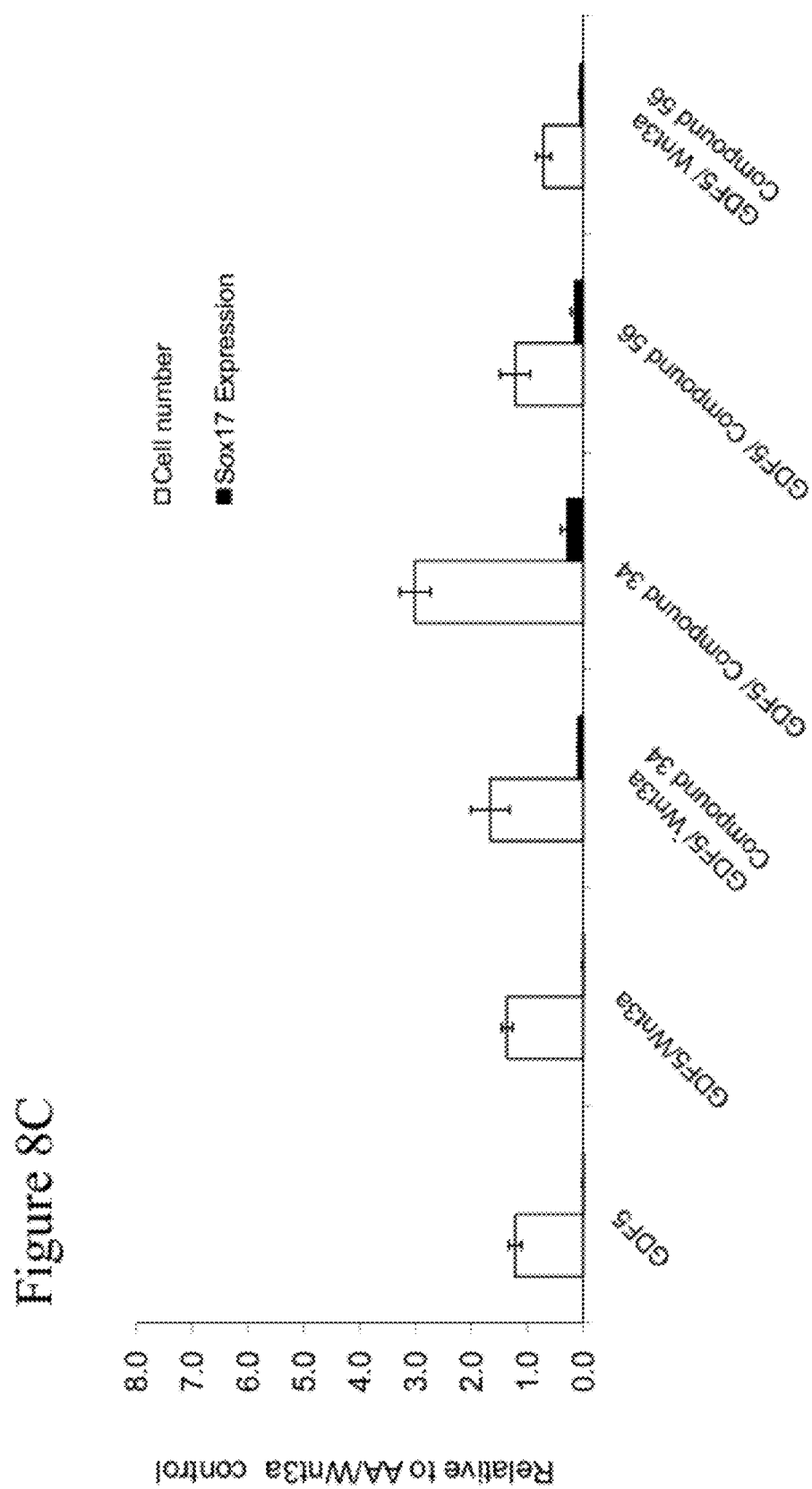
Figure 8D:
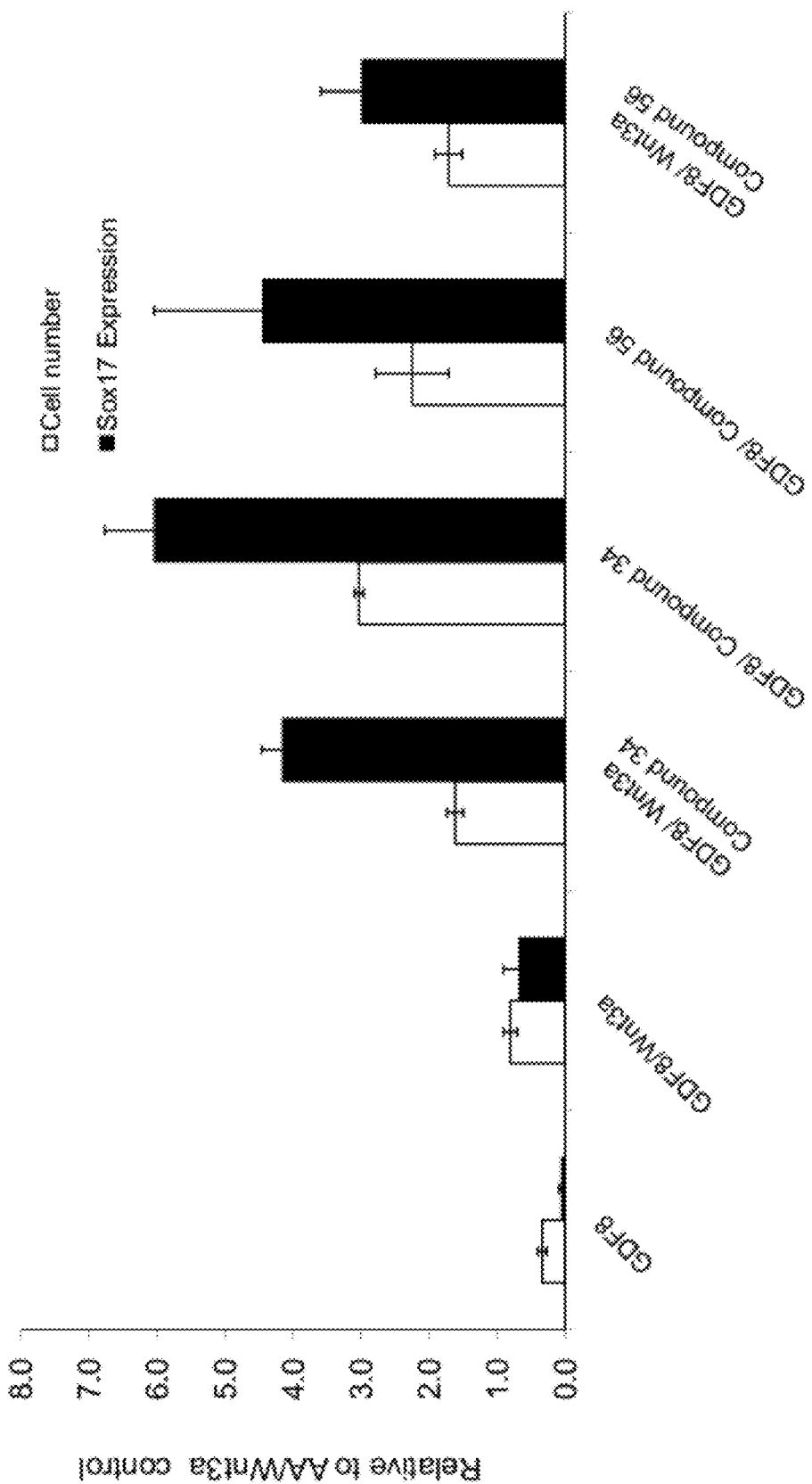
Figure 8E:
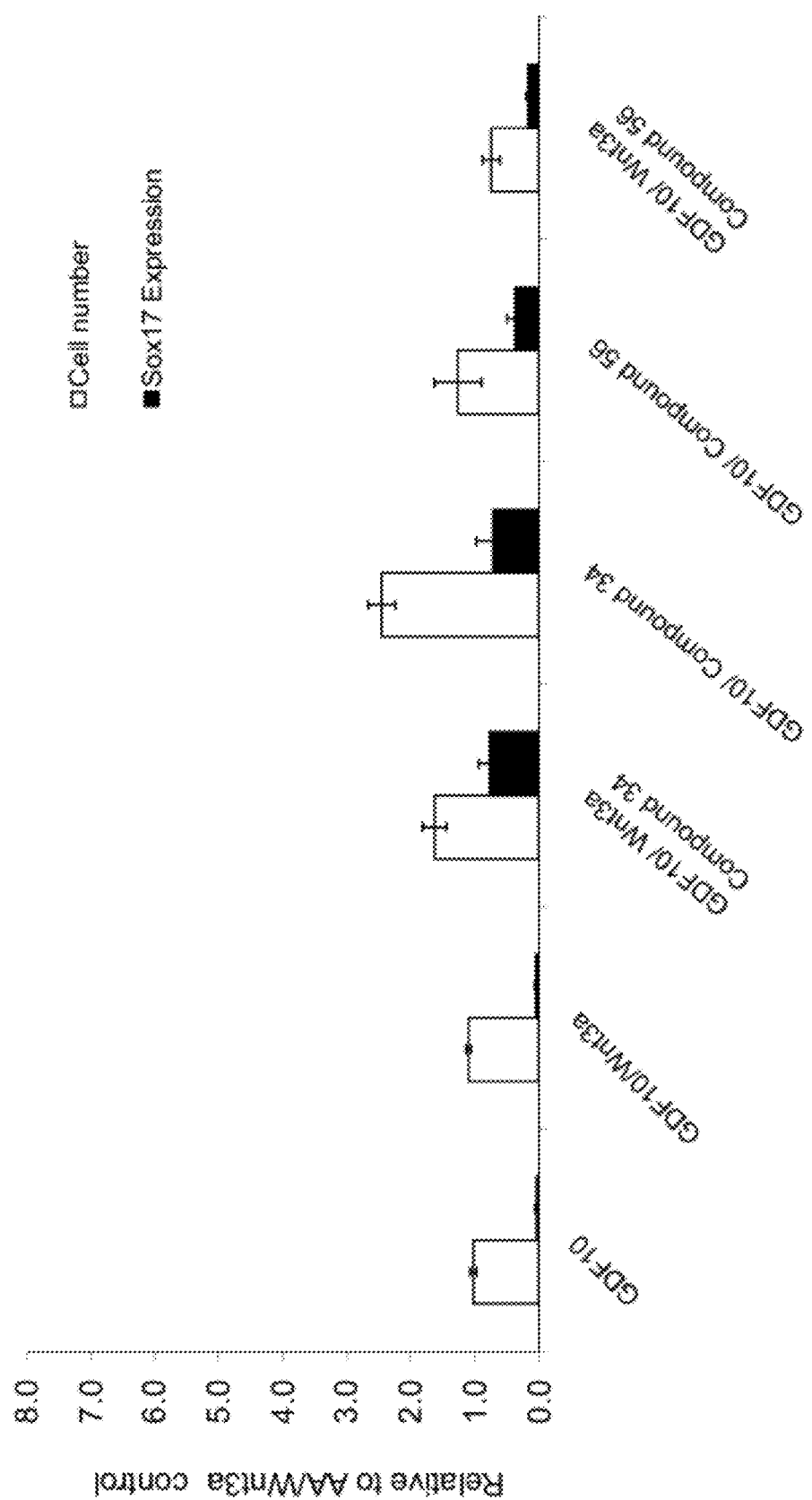
Figure 9A:
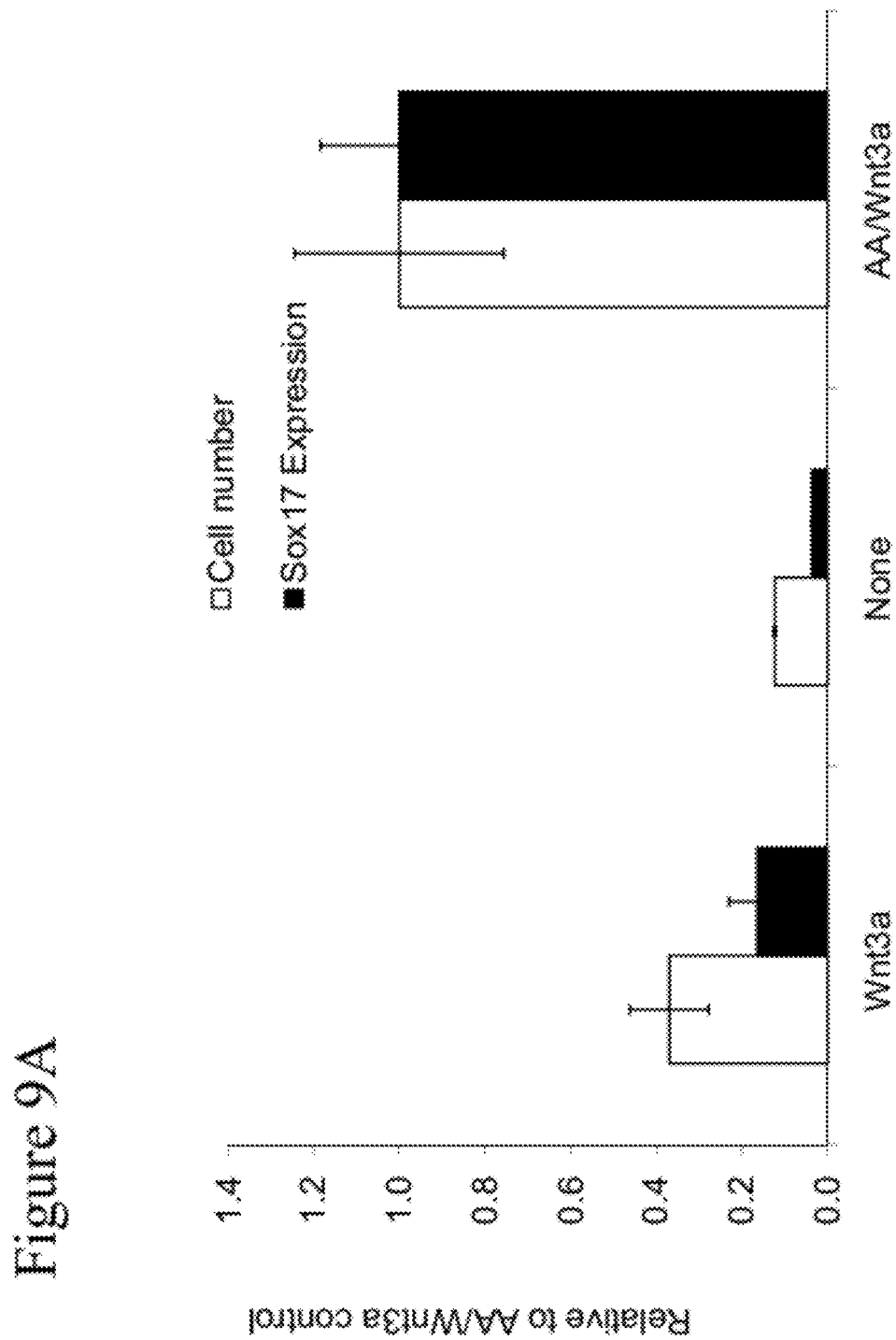
FIG. 9 shows SOX17 protein expression in human embryonic stem cells after differentiation to definitive endoderm, according to the methods described in Example 14. H1 cells were treated for a total of three days with 100 ng/ml of activin A or various growth factors at the concentrations shown in combination with 20 ng/ml Wnt3a or 2.5 μM Compound 34 for the first day of assay. SOX17 protein expression (black bars) and cell numbers (white bars), as determined with fluorescent antibody probes and high content analysis, are depicted for each treatment group. For comparative purposes, values are normalized relative to treatment with activin A/Wnt3a. Panel 9A shows a series of control conditions for differentiation with Wnt3a alone or in the absence of any growth factors (None) or with activin A/Wnt3a treatment (AA/Wnt3a). Panel 9B shows differentiation with GDF-8 (Vendor PeproTech), at the concentrations shown, in combination with 20 ng/ml Wnt3a. Panel 9C shows differentiation with GDF-8 (Vendor Shenendoah), at the concentrations shown, in combination with 20 ng/ml Wnt3a. Panel 9D shows differentiation with TGFβ1, at the concentrations shown, in multiple combinations with Wnt3a or Compound 34. Panel 9E shows differentiation with BMP2, at the concentrations shown, in multiple combinations with Wnt3a or Compound 34. Panel 9F shows differentiation with BMP3, at the concentrations shown, in multiple combinations with Wnt3a or Compound 34. Panel 9G shows differentiation with BMP4, at the concentrations shown, in multiple combinations with Wnt3a or Compound 34.
Figure 9C:
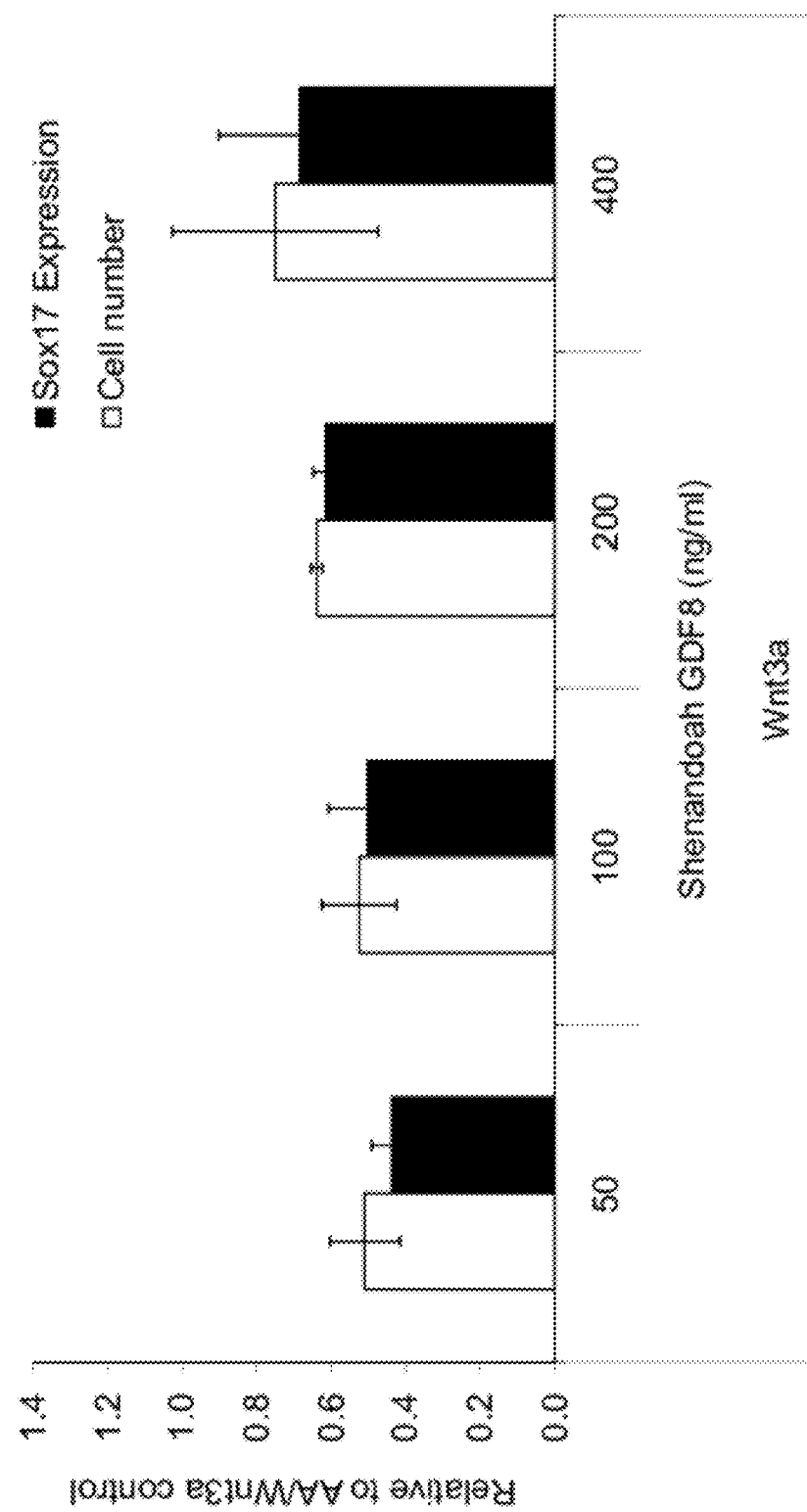
Figure 9D:
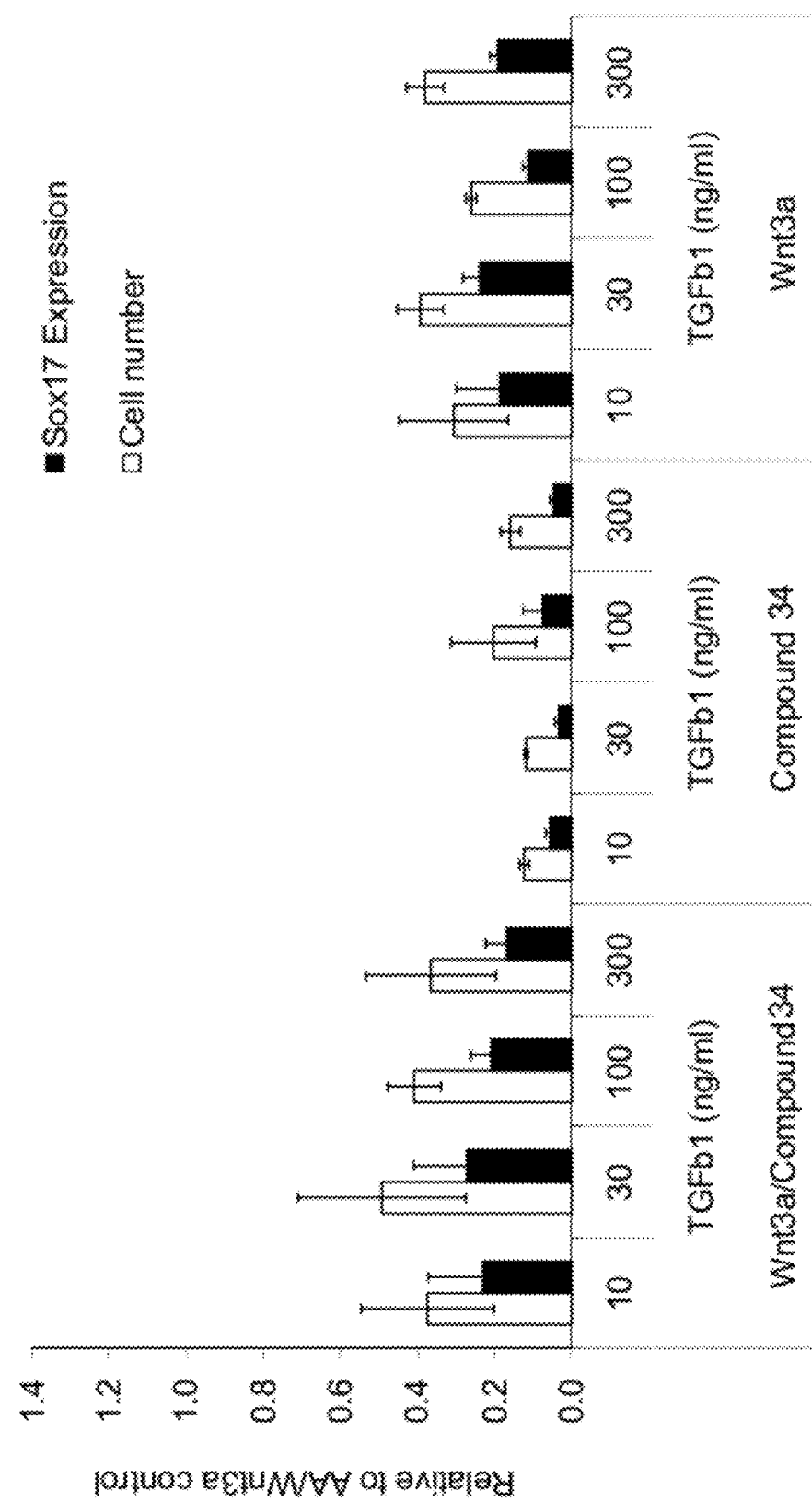
Figure 9G:
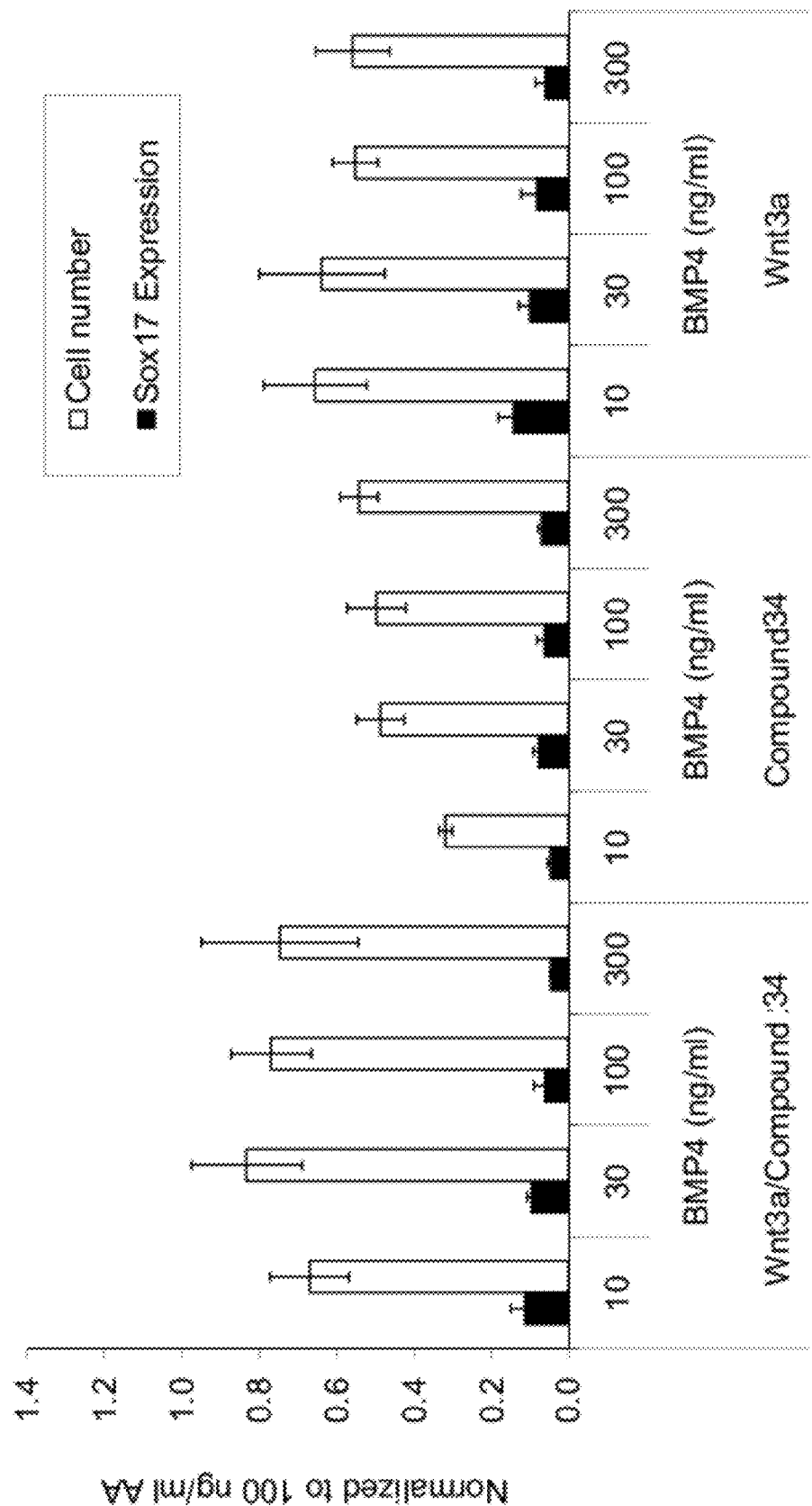
Figure 11C:
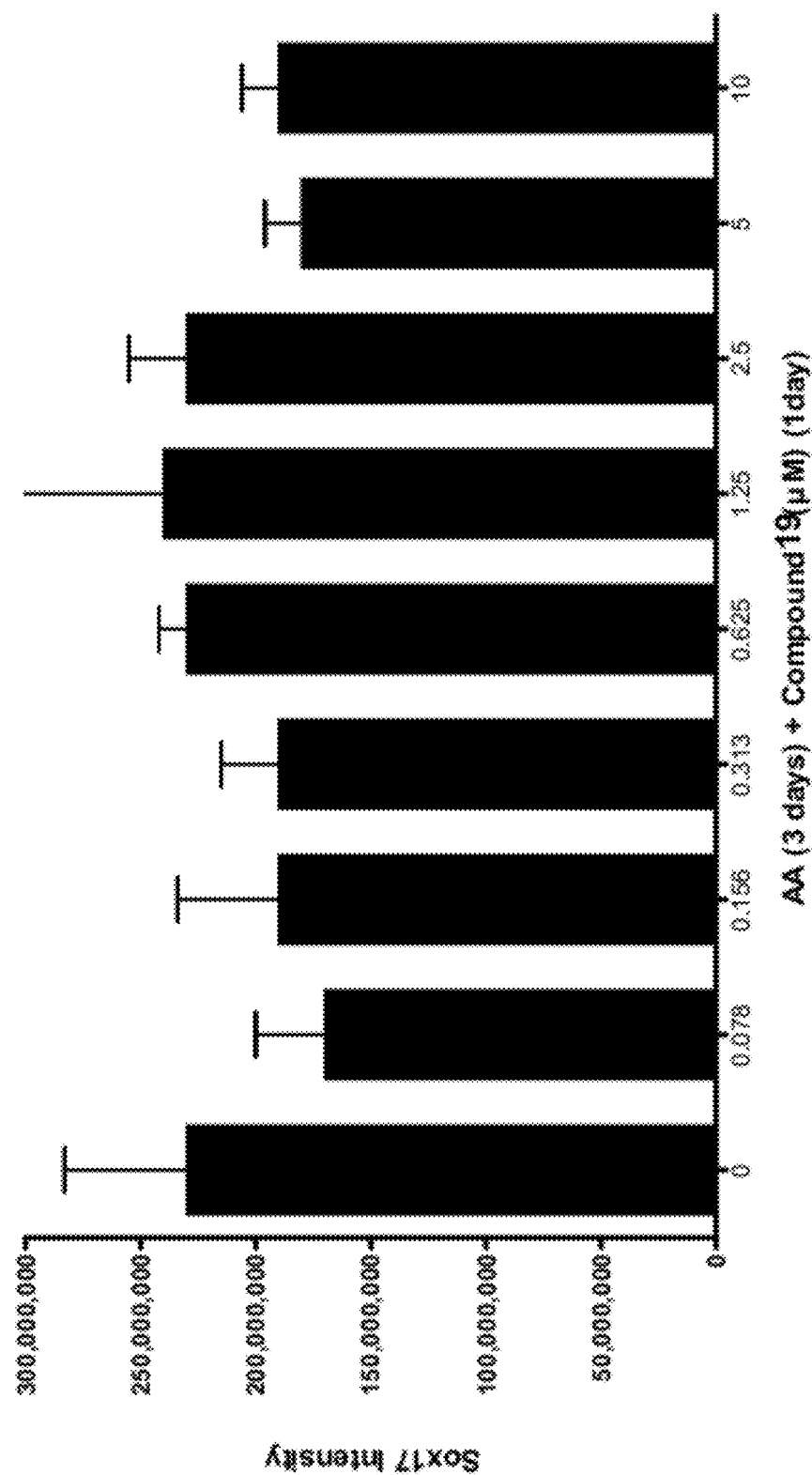
FIG. 11 shows SOX17 protein expression in human embryonic stem cells after differentiation to definitive endoderm, according to the methods described in Example 15. H1 cells were treated for a total of three days in various timed exposures with 100 ng/ml of activin A in combination with test compound (Compound 181 (Panel A), Compound 180 (Panel B), Compound 19 (Panel C), Compound 202 (Panel D), Compound 40 (Panel E), Compound 34 (Panel F), or GSK3 inhibitor BIO (Panel G)) at the concentrations shown, where test compound was added only on the first day of assay. Protein expression for SOX17, as determined with fluorescent antibody probes and high content analysis, is depicted by total intensity values.
Figure 11D:
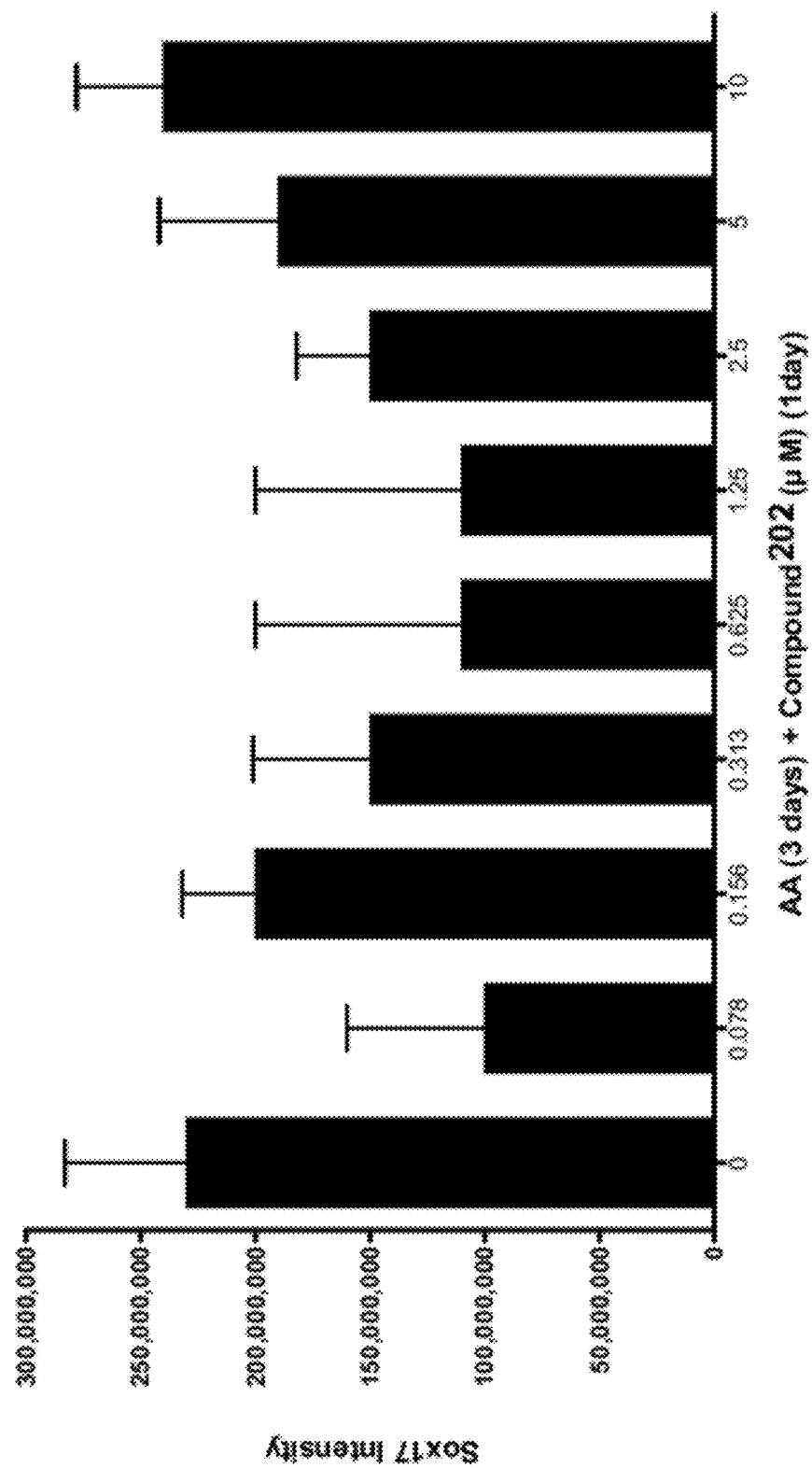
Figure 11E:
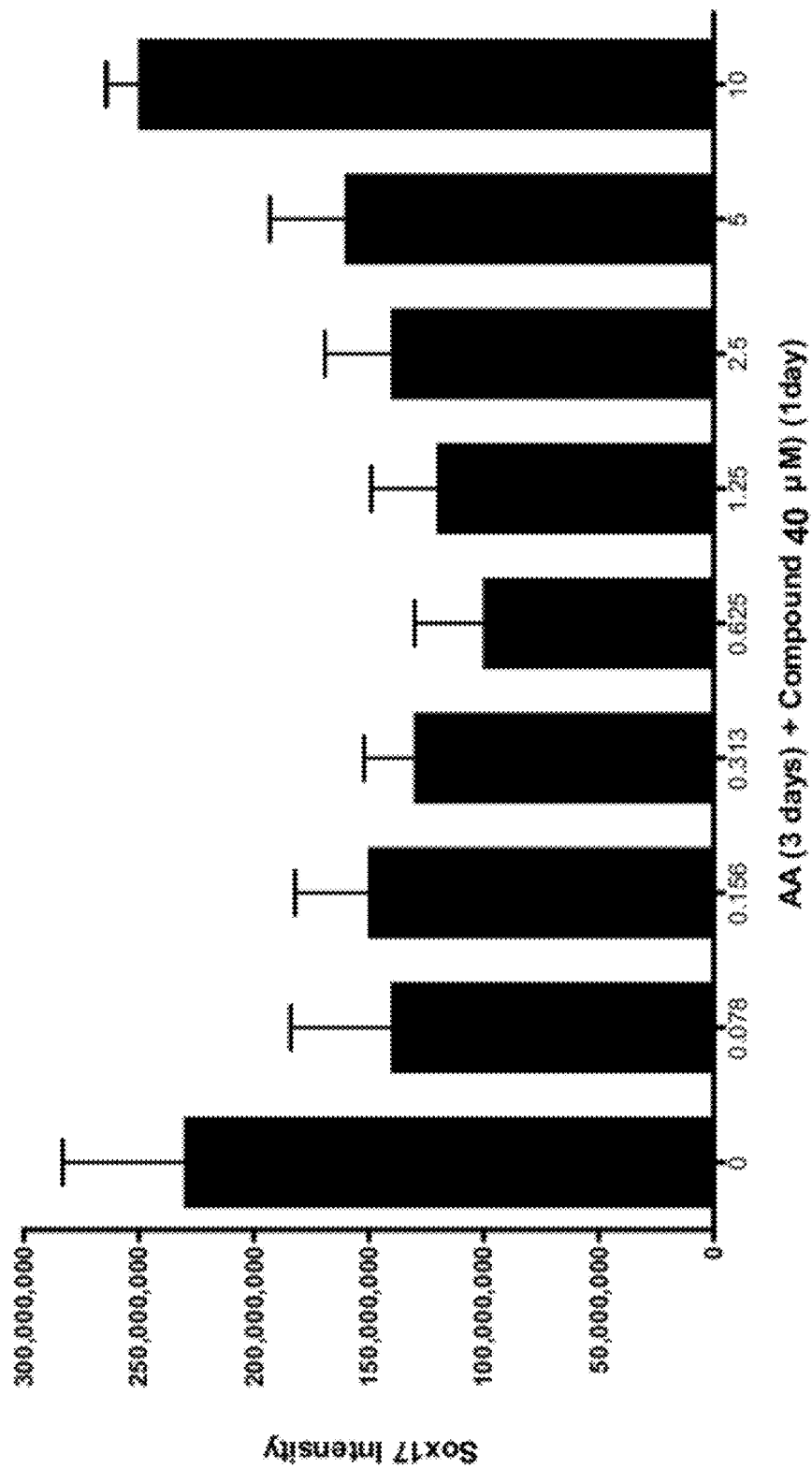
Figure 11F:
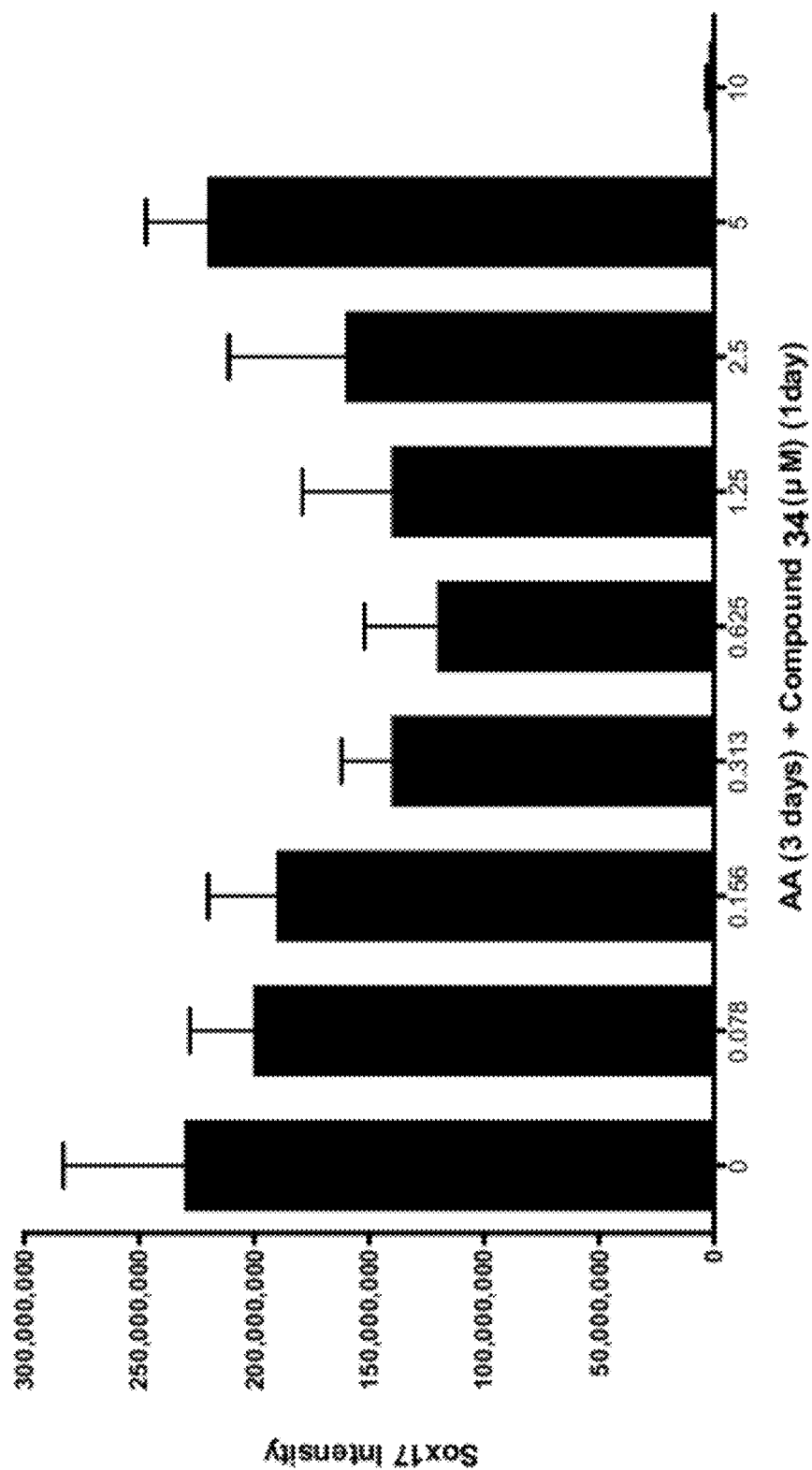
Figure 11G:
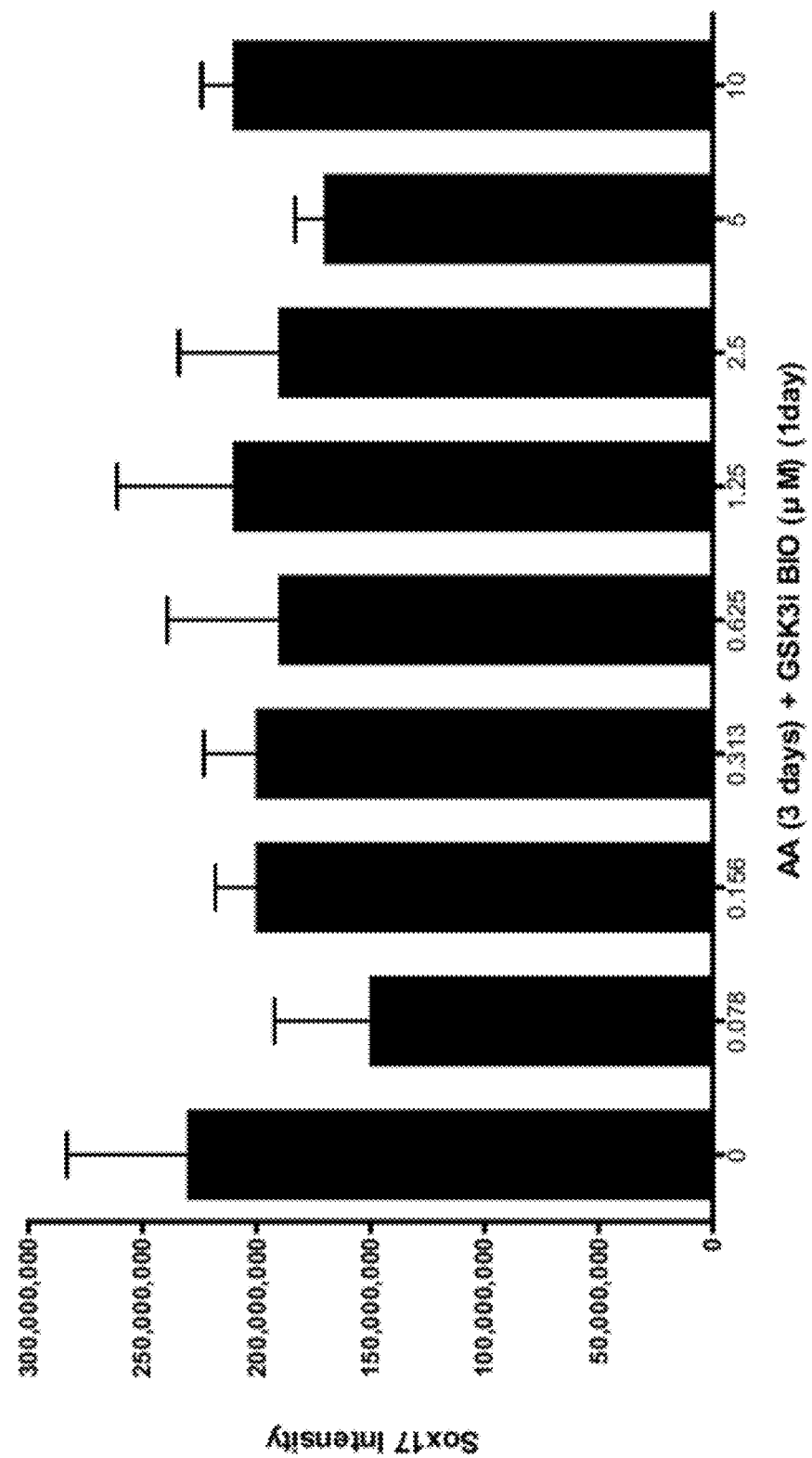
Figure 12B:
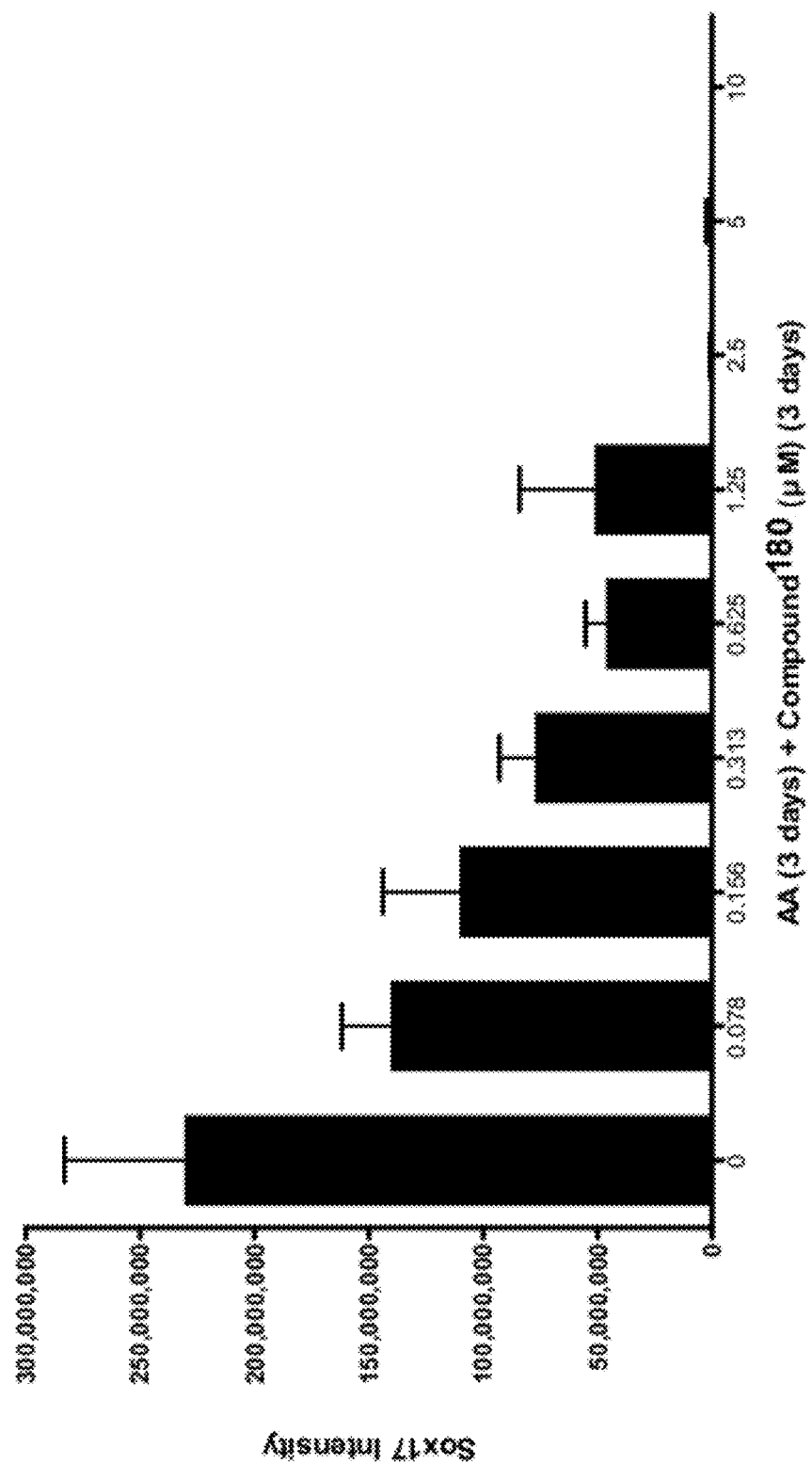
FIG. 12 shows SOX17 protein expression in human embryonic stem cells after differentiation to definitive endoderm, according to the methods described in Example 15. H1 cells were treated for a total of three days in various timed exposures with 100 ng/ml of activin A in combination with test compound (Compound 181 (Panel A), Compound 180 (Panel B), Compound 19 (Panel C), Compound 202 (Panel D), Compound 40 (Panel E), Compound 34 (Panel F), or GSK3 inhibitor BIO (Panel G)) at the concentrations shown, where test compound was added for all three days of assay. Protein expression for SOX17, as determined with fluorescent antibody probes and high content analysis, is depicted by total intensity values.
Figure 12C:
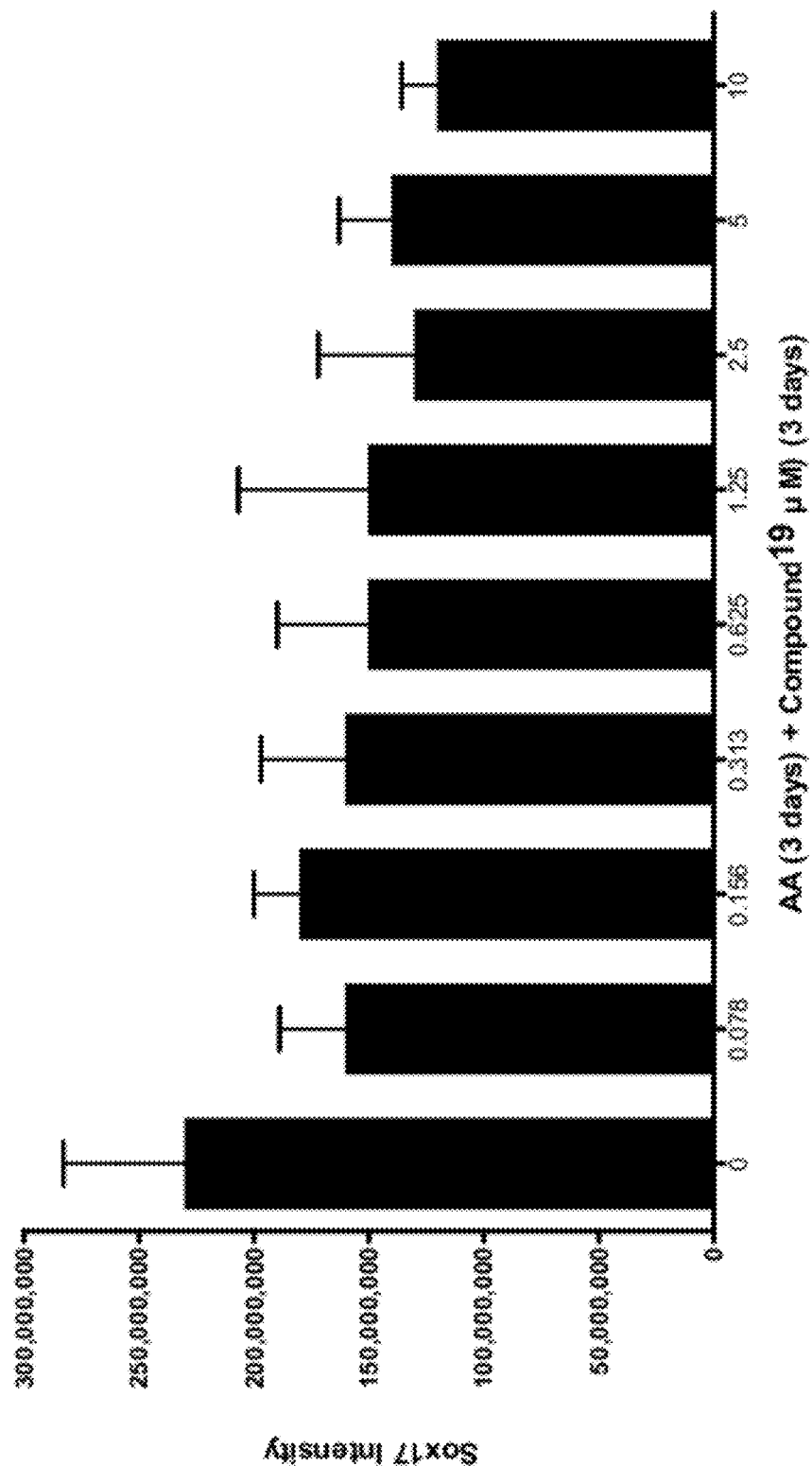
Figure 12D:
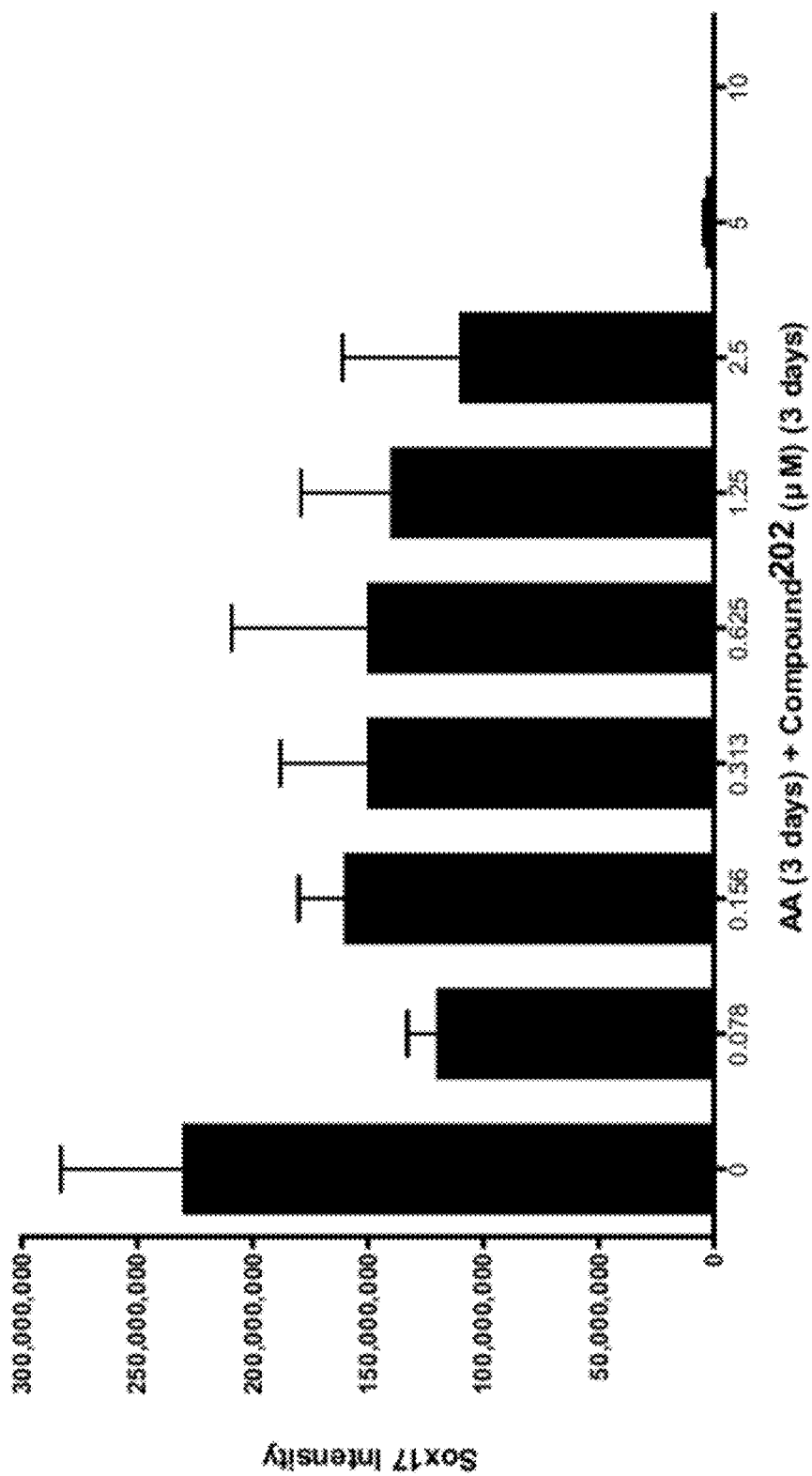
Figure 12F:
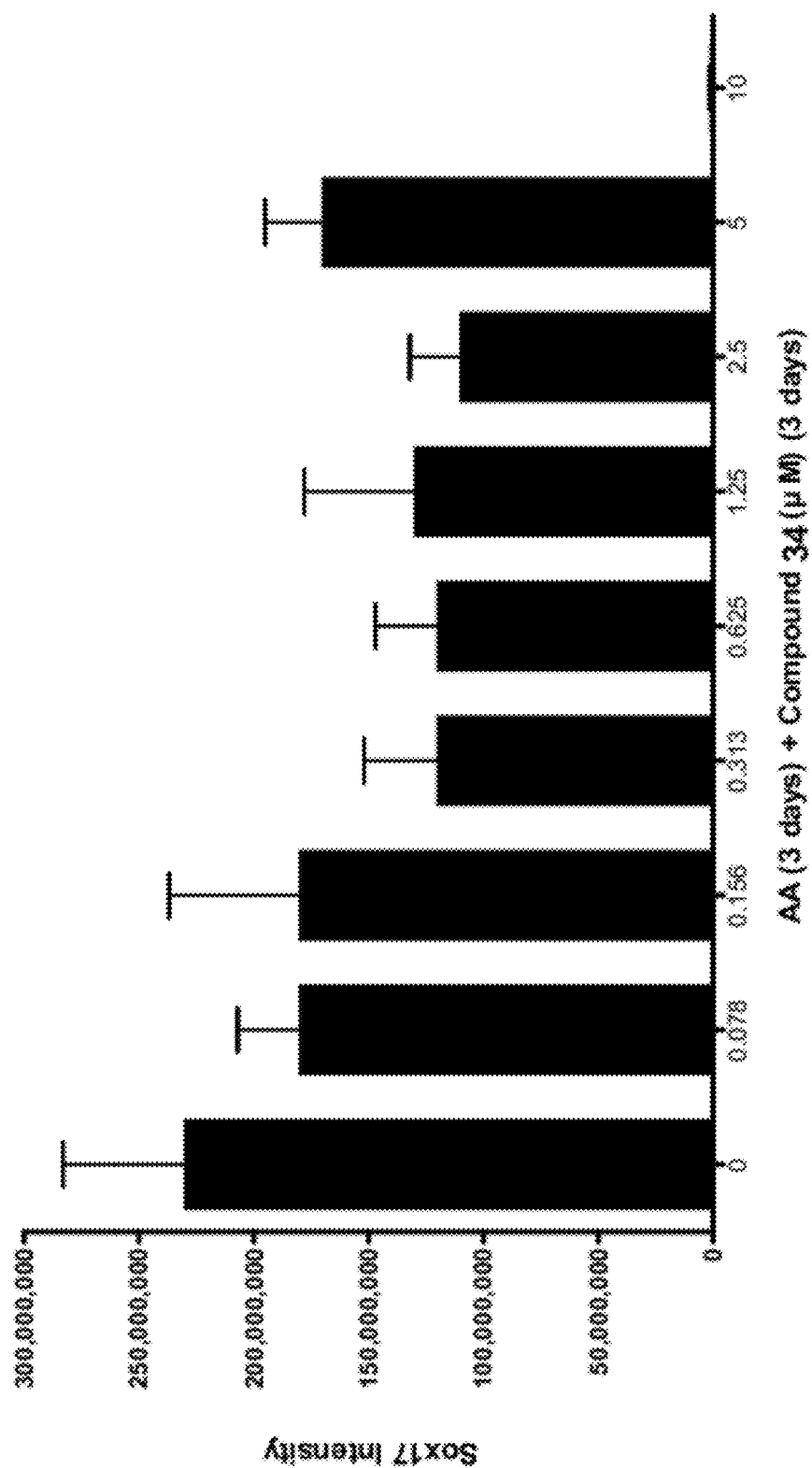
Figure 12G:
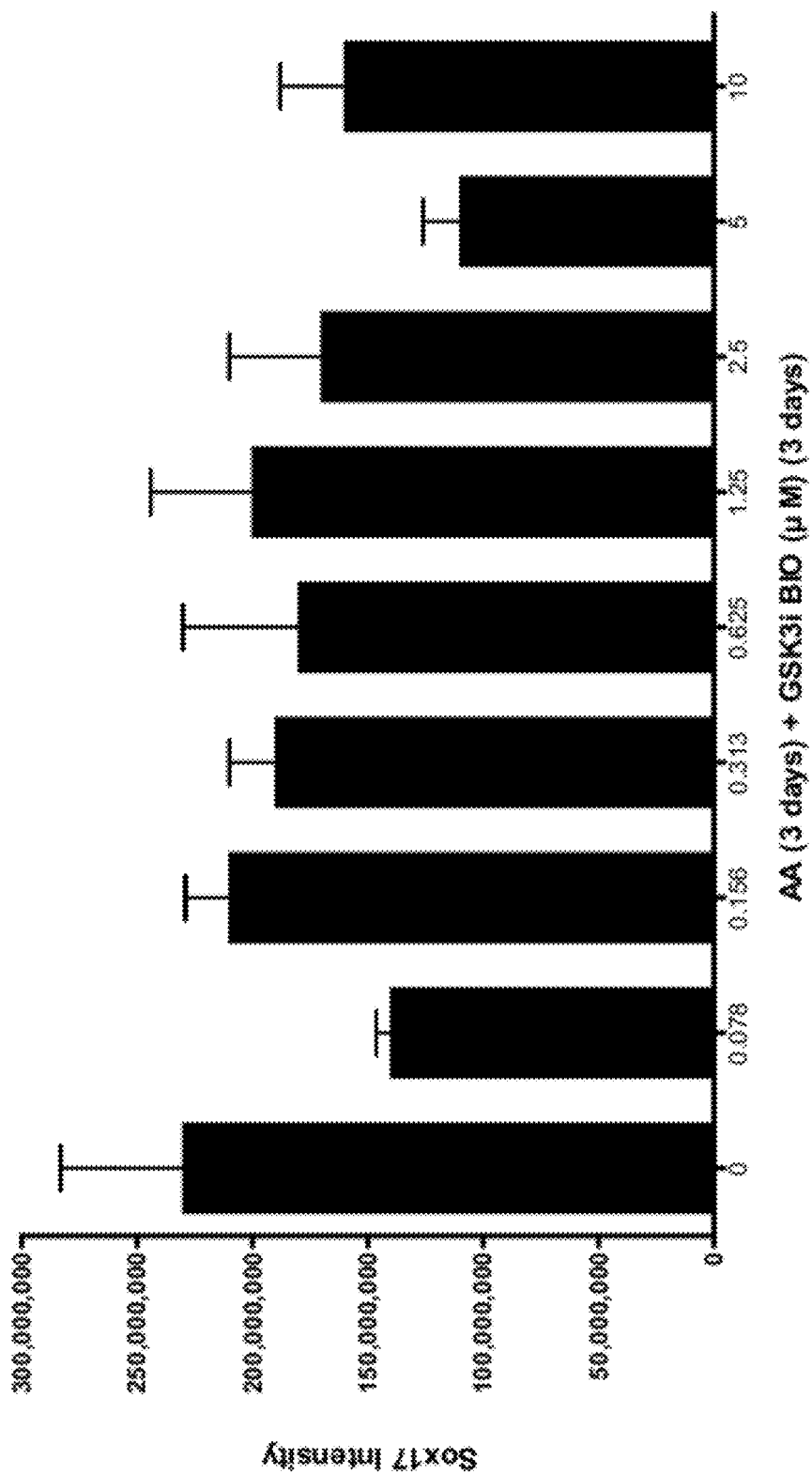
Figure 13B:
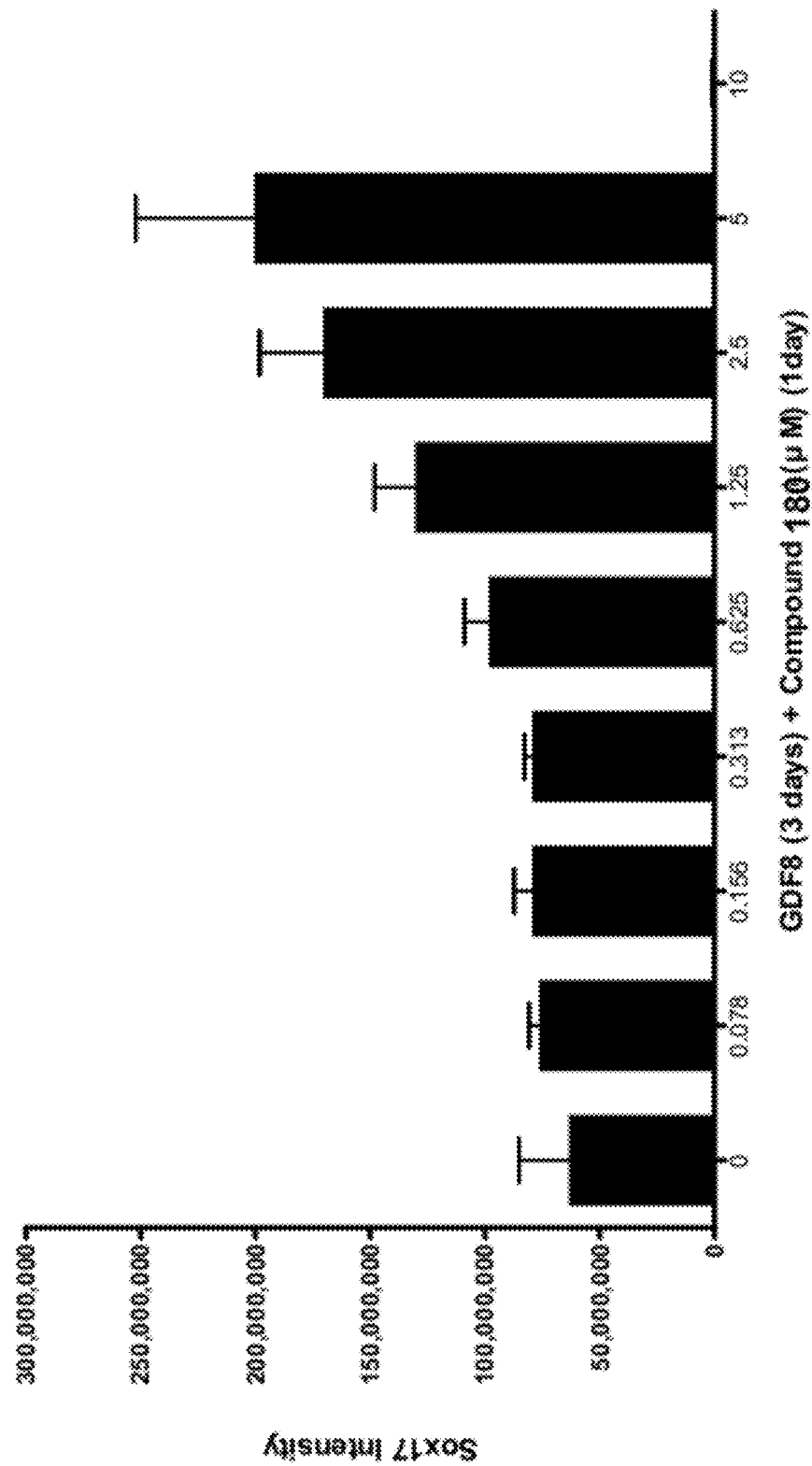
FIG. 13 shows SOX17 protein expression in human embryonic stem cells after differentiation to definitive endoderm, according to the methods described in Example 15. H1 cells were treated for a total of three days in various timed exposures with 100 ng/ml of GDF-8 in combination with test compound (Compound 181 (Panel A), Compound 180 (Panel B), Compound 19 (Panel C), Compound 202 (Panel D), Compound 40 (Panel E), Compound 34 (Panel F), or GSK3 inhibitor BIO (Panel G)) at the concentrations shown, where test compound was added only on the first day of assay. Protein expression for SOX17, as determined with fluorescent antibody probes and high content analysis, is depicted by total intensity values.
Figure 13C:
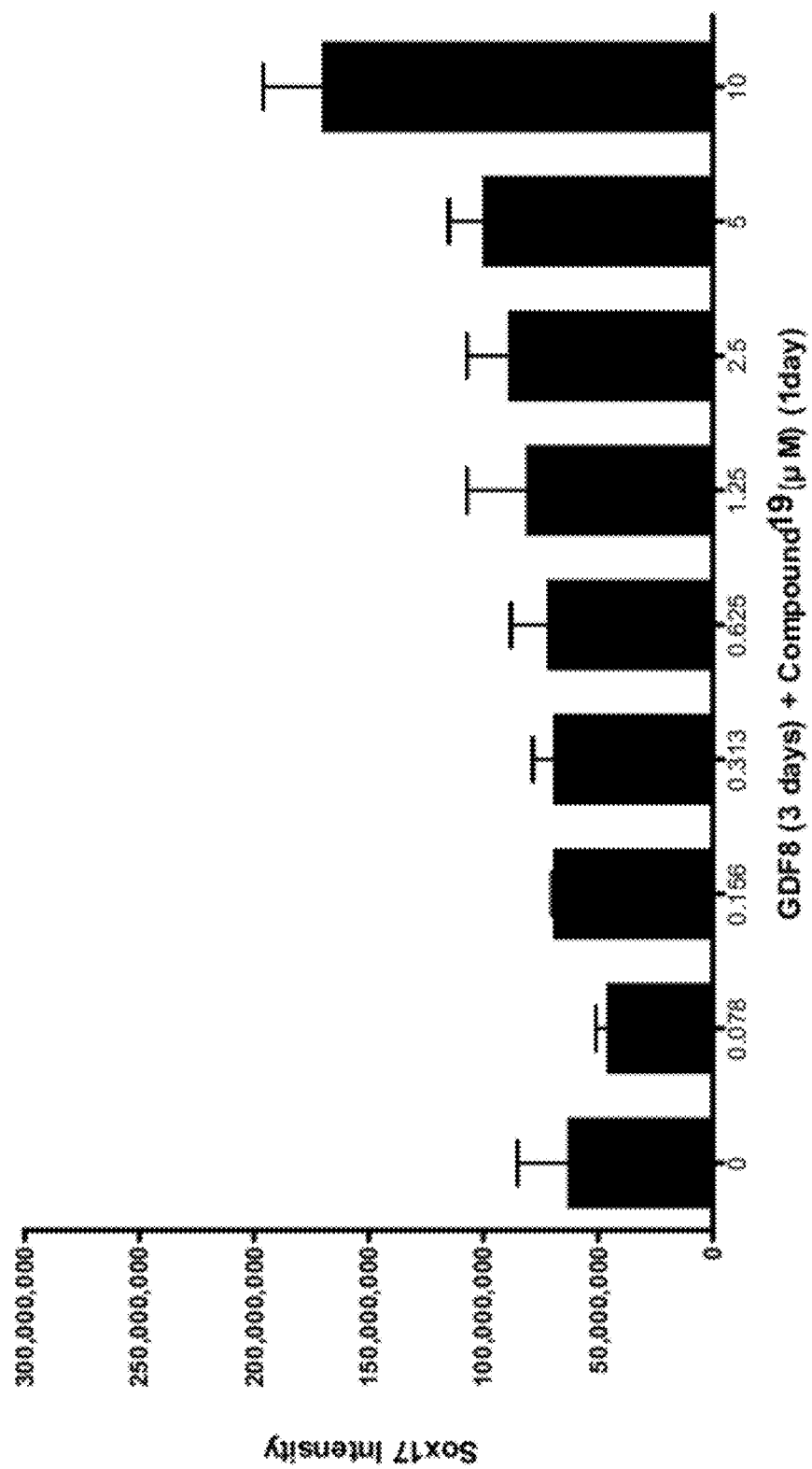
Figure 13D:
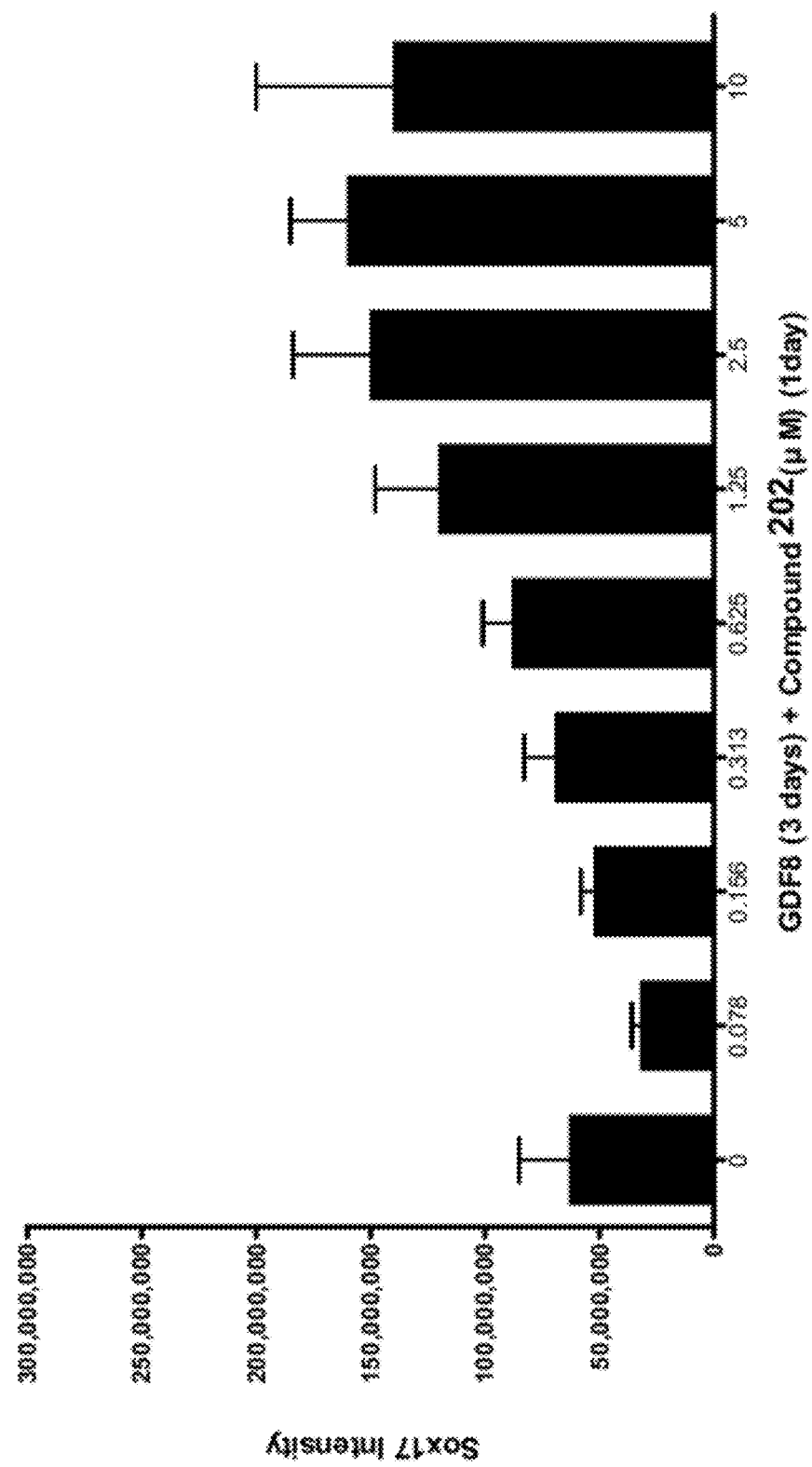
Figure 13E:
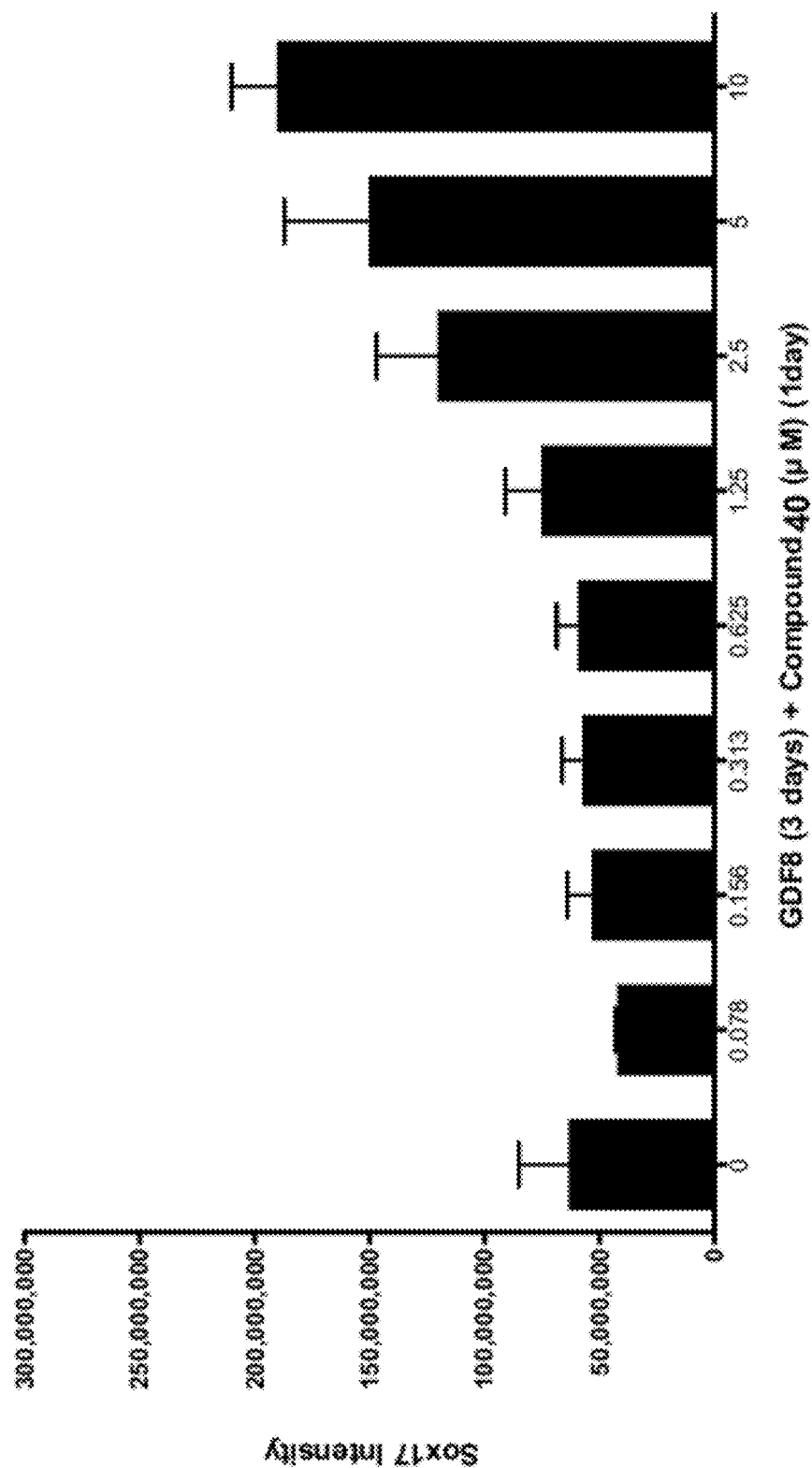
Figure 13F:
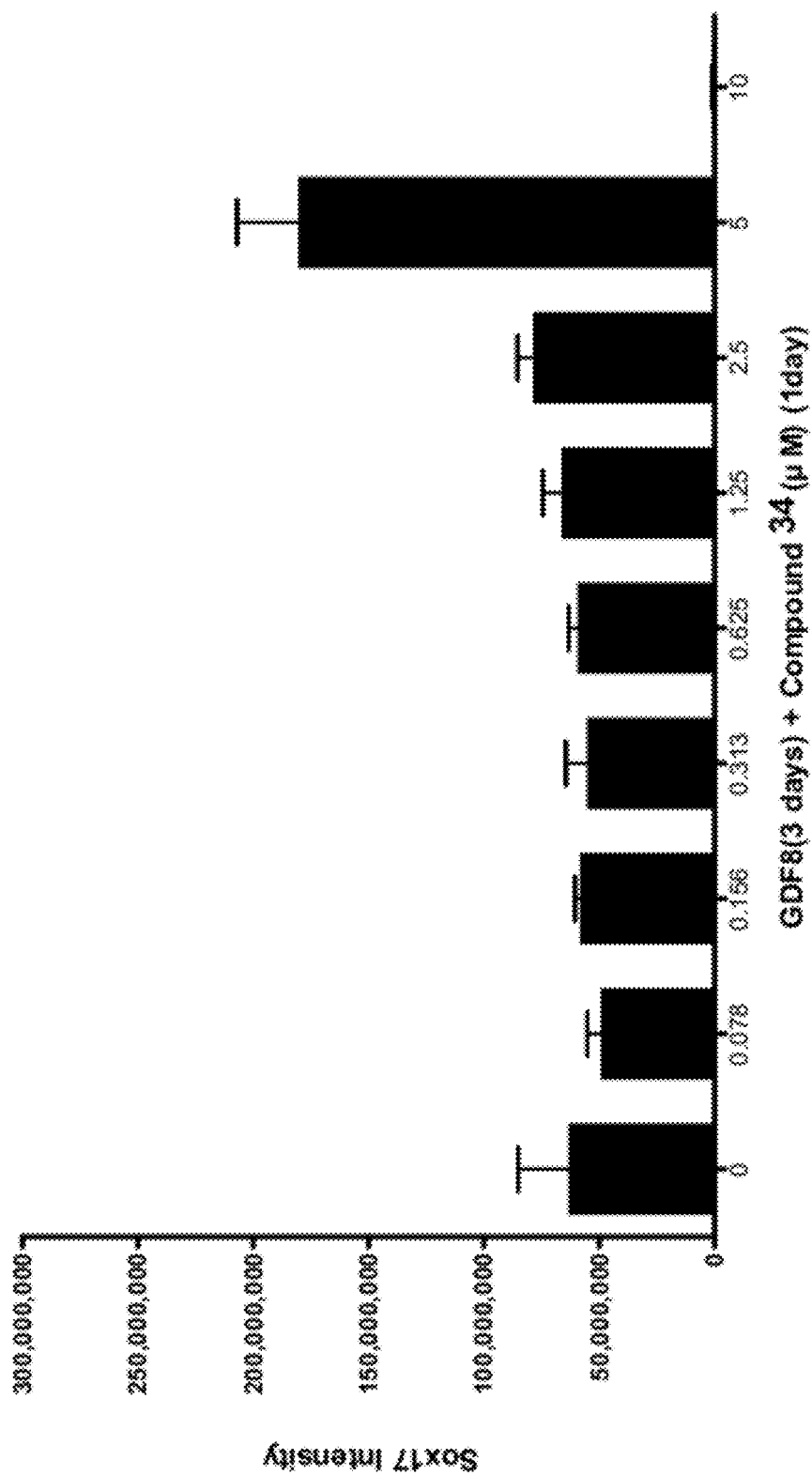
Figure 13G:
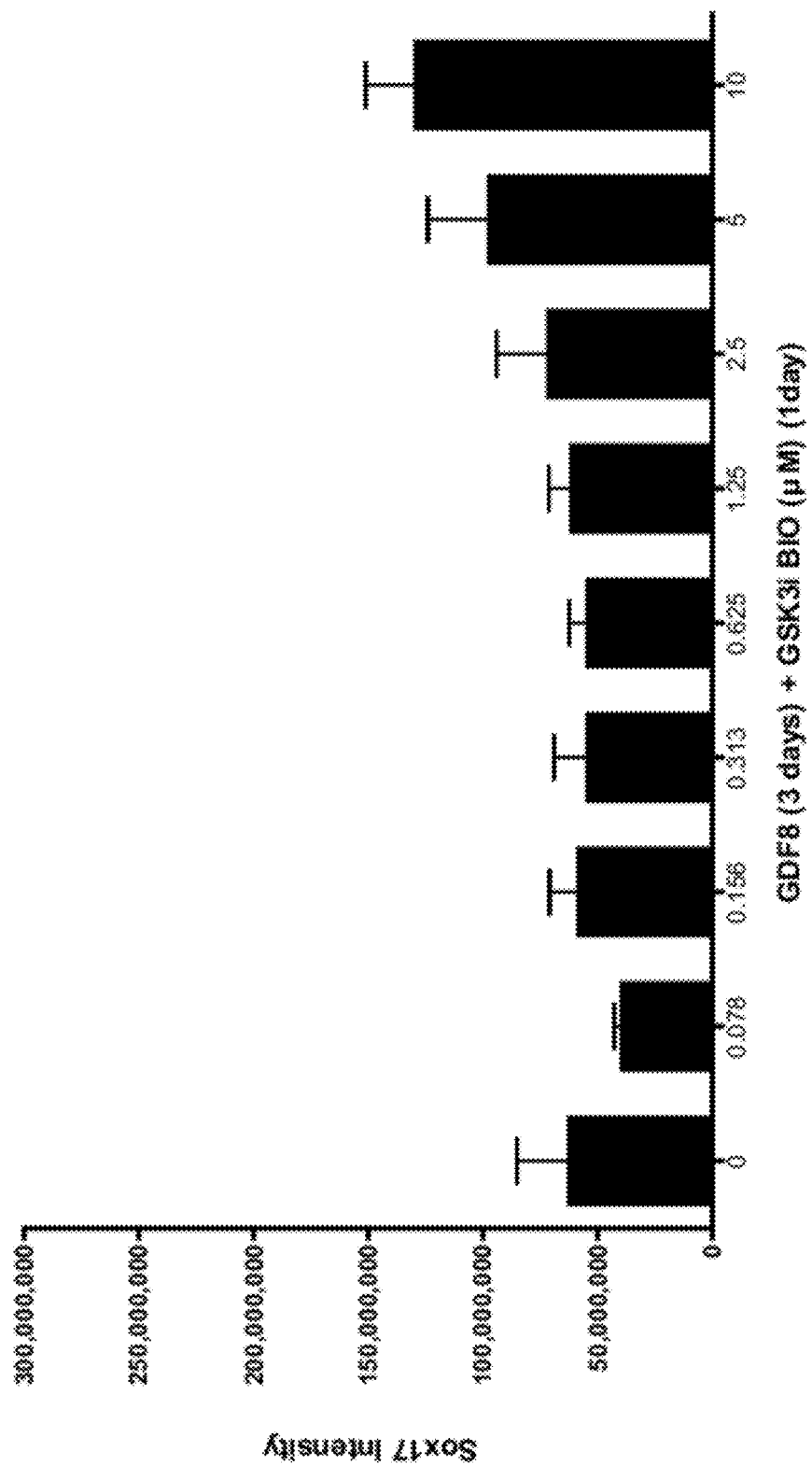
Figure 14A:
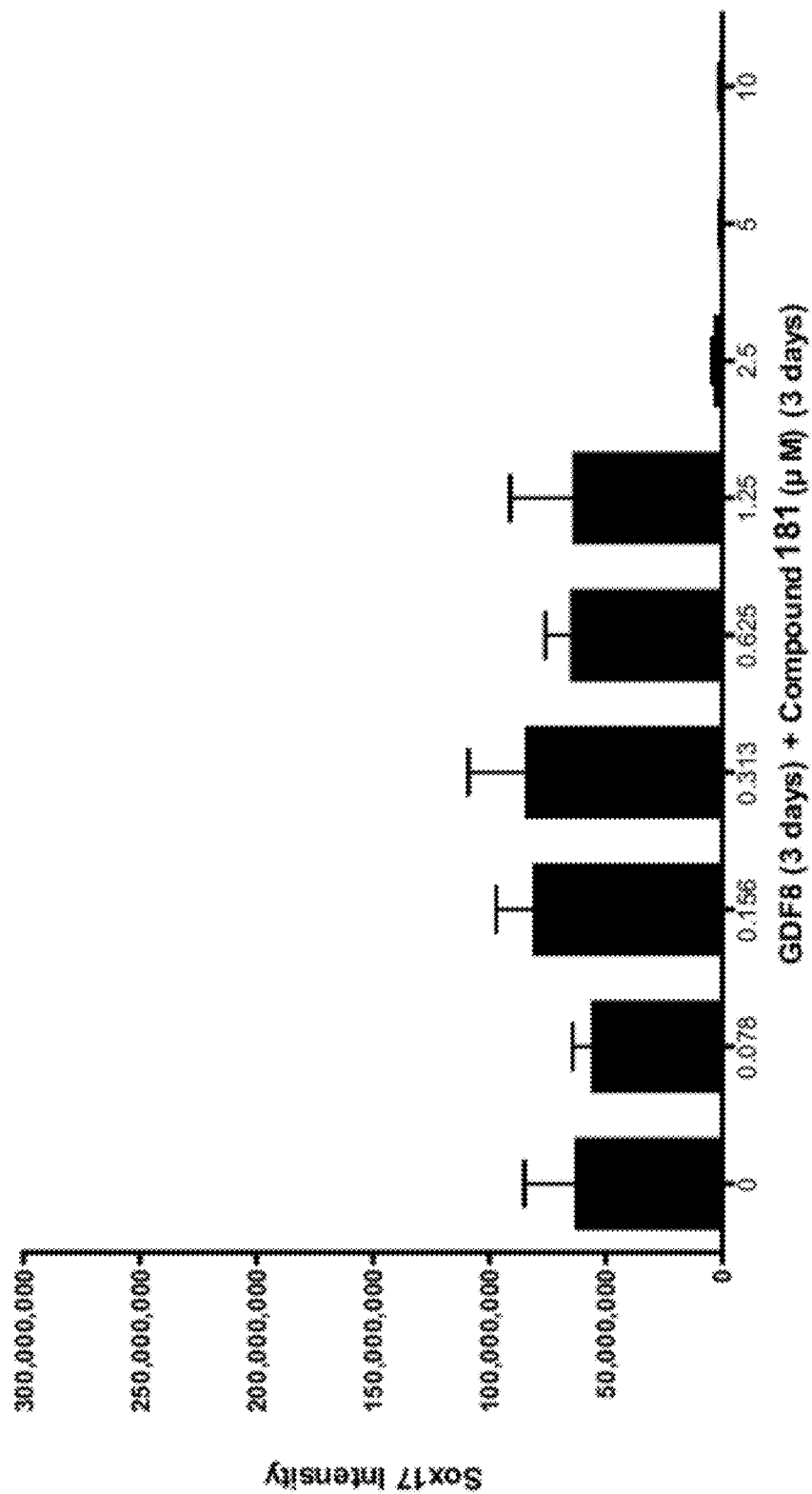
FIG. 14 shows SOX17 protein expression in human embryonic stem cells after differentiation to definitive endoderm, according to the methods described in Example 15. H1 cells were treated for a total of three days in various timed exposures with 100 ng/ml of GDF-8 in combination with test compound (Compound 181 (Panel A), Compound 180 (Panel B), Compound 19 (Panel C), Compound 202 (Panel D), Compound 40 (Panel E), Compound 34 (Panel F), or GSK3 inhibitor BIO (Panel G)) at the concentrations shown, where test compound was added for all three days of assay. Protein expression for SOX17, as determined with fluorescent antibody probes and high content analysis, is depicted by total intensity values.
Figure 14B:
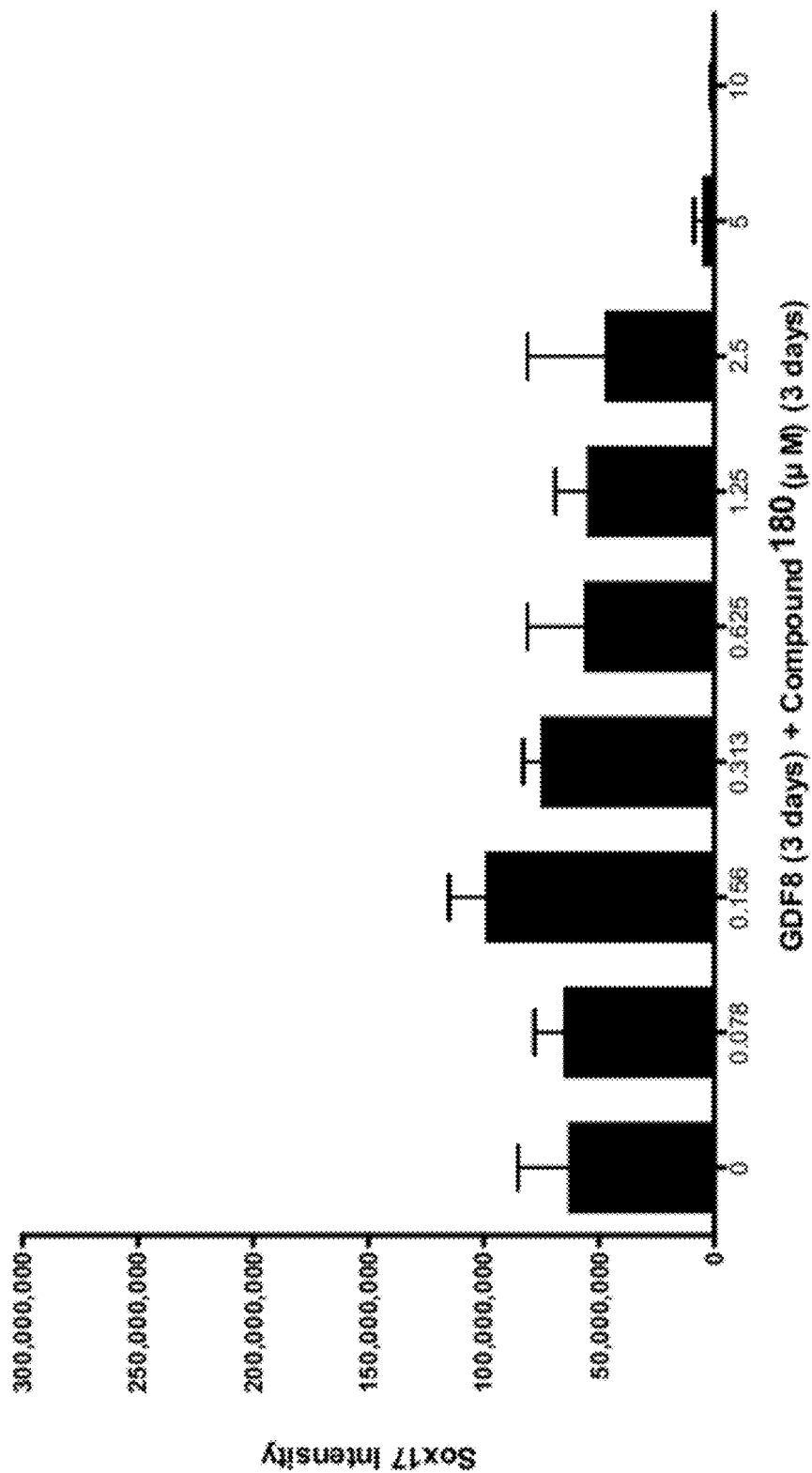
Figure 14D:
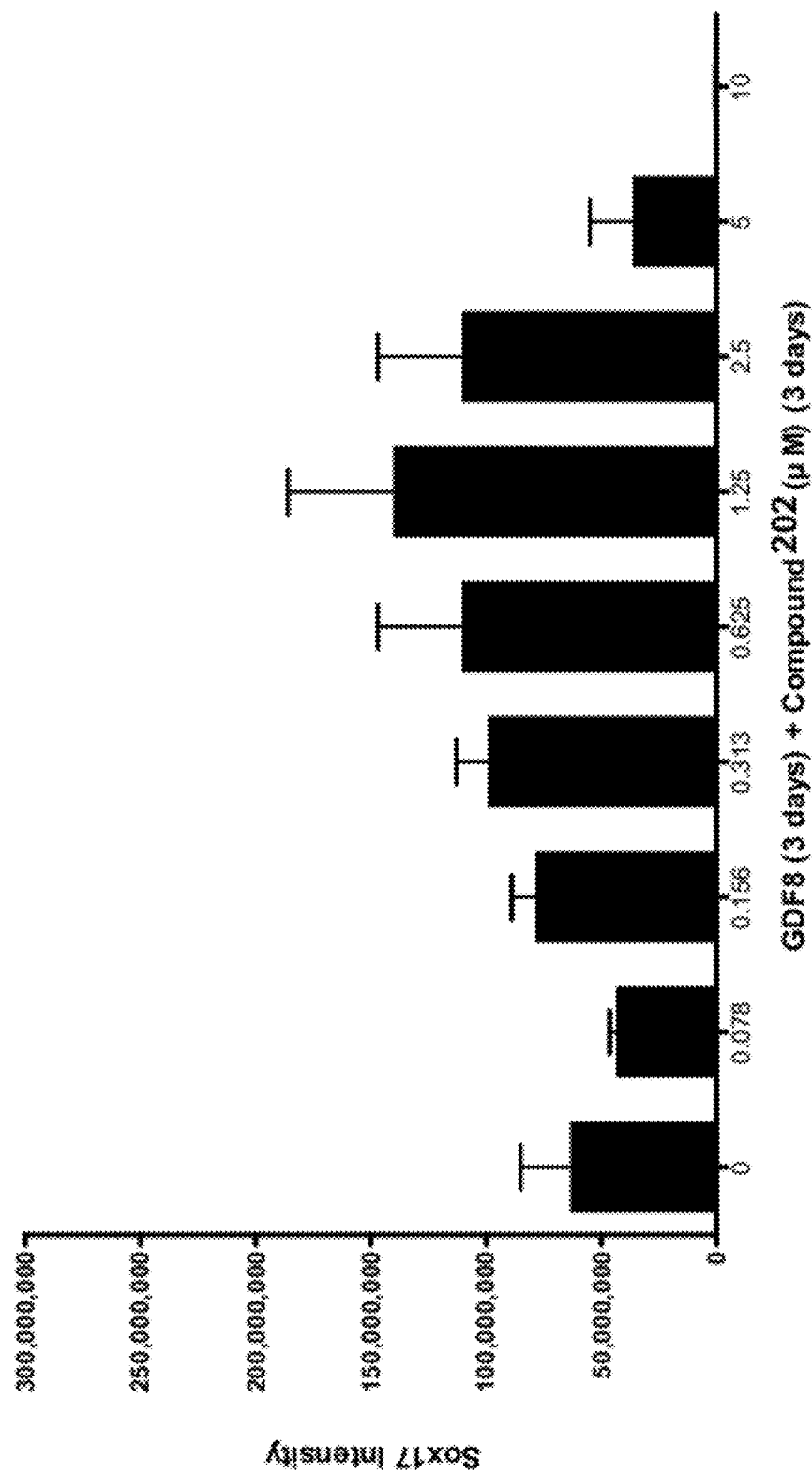
Figure 14E:
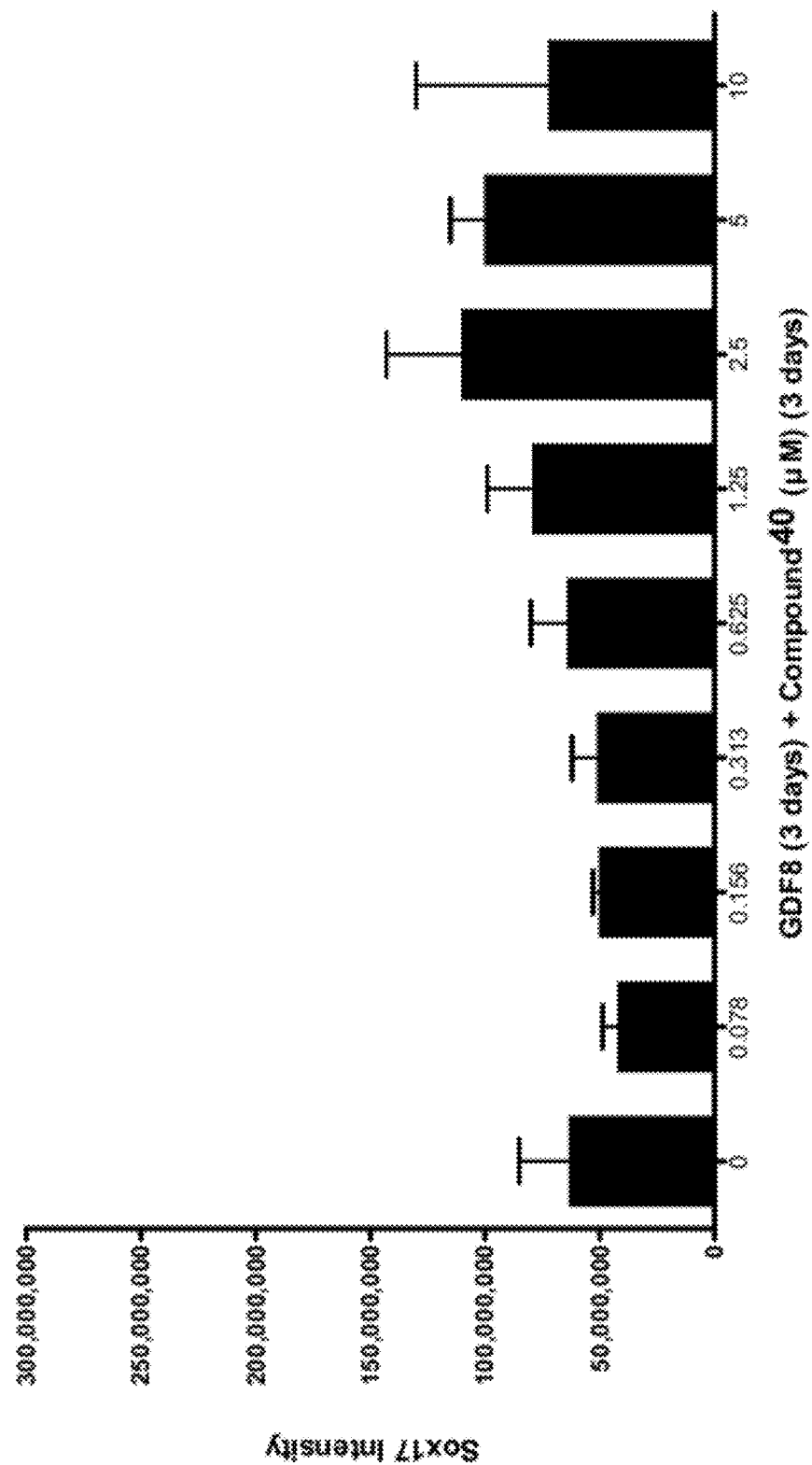
Figure 14F:
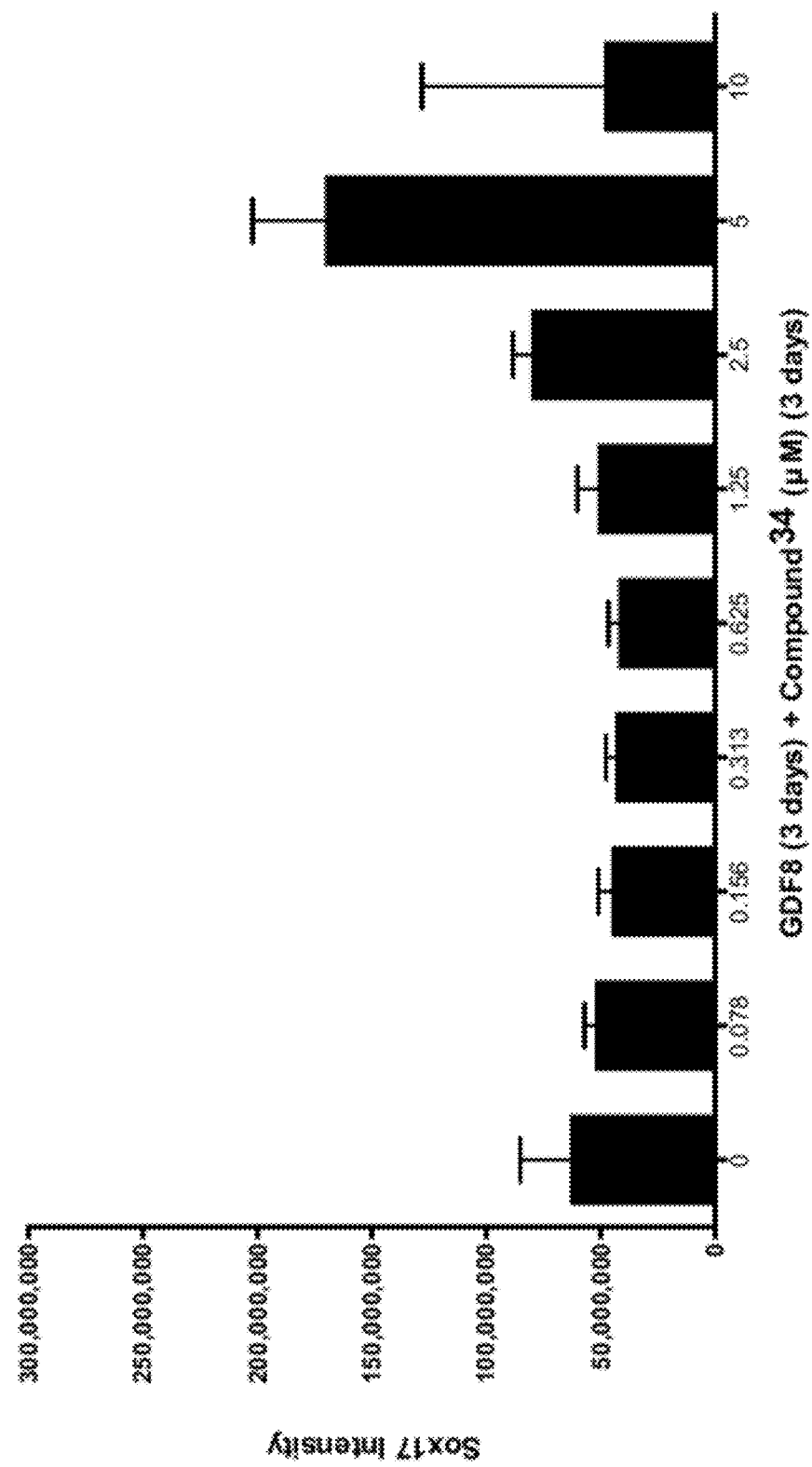

FIG. 5 shows high content image analysis for normalized Pdx1 and Cdx2 protein expression in human embryonic stem cells after the third step of differentiation to pancreatic endoderm. Levels of expression for treatment groups using GDF-8 with Wnt3a or GDF-8 with Wnt3a or GDF-8 with a compound of the present invention show equivalent levels of PDX1 and CDX2. In some treatment groups the cell number retained after differentiation decreased thereby increasing the ratio of PDX1 expressing cells. Similar results were obtained showing equivalent normalized PDX1 expression in all treatment groups after the fourth step of differentiation as shown in FIG. 6. In FIG. 7, normalized protein levels of insulin and glucagon are shown, demonstrating equivalent expression between the Activin A and GDF-8 treatment groups.

These collective results demonstrate that GDF-8, in combination with Wnt3a or Compound 34 or Compound 56, can substitute for activin A during definitive endoderm differentiation and subsequent pancreatic endoderm and endocrine differentiation.

Example 13

Formation of Cells Expressing Markers Characteristic of the Definitive Endoderm Lineage with Other Members of the GDF Family of Proteins It was important to determine if treating human embryonic stem cells with other GDF family members could the formation of cells expressing markers characteristic of the definitive endoderm lineage. Wnt3a in combination with either Compound 34 or Compound 56 were tested on human embryonic stem cells in combination with six different GDF growth factors [GDF-3, GDF-5, GDF-8, GDF-10, GDF-11, and GDF-15] to determine the ability of members of the GDF family of proteins to differentiate human embryonic stem cells toward cells expressing markers characteristic of the definitive endoderm lineage. A parallel control of cells treated with activin A and Wnt3a was maintained for comparison purposes.

Preparation of Cells for Assay:

Stock cultures of human embryonic stem cells (H1 human embryonic stem cell line) were maintained in an undifferentiated, pluripotent state on reduced growth factor MATRIGEL™ (BD Biosciences; Cat #356231)-coated dishes in MEF conditioned medium with passage on average every four days. Passage was performed by exposing cell cultures to a solution of 1 mg/ml dispase (Invitrogen; Cat #17105-041) for 5 to 7 minutes at 37° C. followed by rinsing the monolayer with MEF conditioned culture medium and gentle scraping to recover cell clusters. Clusters were centrifuged at low speed to collect a cell pellet and remove residual dispase. Cell clusters were split at a 1:3 or 1:4 ratio for routine maintenance culture or a 1:1 ratio for immediate assay. All human ES cell lines were maintained at passage numbers less than 50 and routinely evaluated for normal karyotype and absence of mycoplasma.

Cell clusters were evenly resuspended in MEF conditioned medium supplemented with 8 ng/ml bFGF and seeded onto reduced growth factor MATRIGEL™-coated 96-well Packard VIEWPLATES (PerkinElmer; Cat #6005182) in volumes of 0.1 ml/well. Daily feeding was conducted by aspirating spent culture medium from each well and replacing with an equal volume of fresh medium. Plates were maintained at 37° C., 5% $CO_2$ throughout the duration of assay.

Assay:

The assay was initiated by aspirating the culture medium from each well and adding back aliquots (100 µl) of test medium. Test conditions were performed in triplicate over a total four-day assay period, feeding on day 1 and day 3 by aspirating and replacing the medium from each well with fresh test medium. Various members of the GDF family of proteins were obtained for testing as follows: GDF-3 (PeproTech; Cat #120-22); GDF-5 (DePuy Orthopaedics, Inc., a Johnson & Johnson company); GDF-8 (R&D Systems; Cat #788-G8); GDF-10 (R&D Systems; Cat #1543-BP); GDF11 (PeproTech; Cat #120-11); GDF-15 (R&D Systems; Cat #957-GD). On the first day of assay, all wells received an aliquot (80 µl) of basal medium DMEM:F12 medium (Invitrogen; Cat #11330-032) supplemented with 0.5% fetal bovine serum (Hyclone; Cat # SH30070.03). A series of five different control or experimental test samples was created to evaluate activin A or various GDFs in combination with Wnt3a or Compound 34 or Compound 56. These test samples were added in 20 µl aliquots (5× concentrated) to appropriately matched assay wells to yield a final assay volume of 100 μl in each well at the final assay conditions indicated. In the first set of control samples, the following conditions were tested: 1) no additive (i.e. no supplementary growth factor or small molecule); 2) 100 ng/ml activin A (PeproTech; Cat #120-14) in combination with 20 ng/ml Wnt3a (R&D Systems; Cat #1324-WN/CF); 3) 20 ng/ml Wnt3a alone; 4) Compound 34 alone (2.5 μM) without any growth factor or small molecule; 5) Compound 56 alone (2.5 μM) without any growth factor or small molecule. In the second set of test samples, the following conditions were tested in combination with 100 ng/ml GDF3: 1) no additive (i.e. GDF-3 alone); 2) 20 ng/ml Wnt3a; 3) 20 ng/ml Wnt3a with Compound 34 (2.5 μM); 4) Compound 34 (2.5 μM); 5) Compound 56 (2.5 μM); and 6) 20 ng/ml Wnt3a with Compound 56 (2.5 μM). In the third set of test samples, each of the six conditions was combined with 100 ng/ml GDF-5. In the fourth set of test samples, each of the six conditions was combined with 100 ng/ml GDF-8. In the fifth set of test samples, each of the six conditions was combined with 100 ng/ml GDF-10. In the sixth set of test samples, each of the six conditions was combined with 100 ng/ml GDF-11. In the seventh set of test samples, each of the six conditions was combined with 100 ng/ml GDF-15. On the third day of assay, all wells for all test samples, received 100 ng/ml Activin A or 100 ng/ml respective GDF growth factor, without Wnt3a or Compound 34 or Compound 56, diluted into DMEM:F12 medium supplemented with 2% FBS.

High Content Analysis:

At the conclusion of culture, assay plates were washed once with PBS (Invitrogen; Cat #14190), fixed with 4% paraformaldehyde (Alexis Biochemical; Cat # ALX-350-011) at room temperature for 20 minutes, then washed three times with PBS and permeabilized with 0.5% Triton X-100 (Sigma; Cat #T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; Cat # AF1924) was diluted 1:100 in 4% chicken serum and added to each well for two hours at room temperature. After washing three times with PBS, Alexa Fluor 488 conjugated secondary antibody (chicken anti-goat IgG; Invitrogen; Cat #A21467) diluted 1:200 in PBS was added to each well. To counterstain nuclei, 5 μg/ml Hoechst 33342 (Invitrogen; Cat # H3570) was added for fifteen minutes at room temperature. Plates were washed once with PBS and left in 100 μl/well PBS for imaging.

Imaging was performed using an IN Cell Analyzer 1000 (GE Healthcare) utilizing the 51008bs dichroic for cells stained with Hoechst 33342 and Alexa Fluor 488. Images were acquired from 25 fields per well. Measurements for total intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total protein expression was reported as total intensity or integrated intensity, defined as total fluorescence of the cell multiplied by the area of the cell. Background was eliminated based on acceptance criteria for gray-scale ranges between 200 and 4500. Total intensity data were normalized by dividing total intensities for each well by the average total intensity for the positive control.

FIG. 8 shows high content image analysis for SOX17 protein expression in human embryonic stem cells after four days differentiation to definitive endoderm. In each case, results are normalized to the positive control treatment with activin A and Wnt3a. In FIG. 8A, only the positive control treatment yielded significant expression of SOX17; treatment with Wnt3a alone or either Compound 34 or Compound 56 alone failed to induce SOX17 expression. In FIG. 8, panels B through G, normalized SOX17 expression levels are shown for each GDF growth factor substituting for activin A in the respective treatments. GDF-3 (FIG. 8B) and GDF-5 (FIG. 8C) induced weak expression of SOX17 and only in test samples where one of the compounds of the present invention was present. GDF10 (FIG. 8D), GDF11 (FIG. 8E) and GDF5 (FIG. 8G) induced significant levels of SOX17 expression, more than observed with GDF3 or 5 treatments but less than observed that observed with activin A and Wnt3a treatment. In general, SOX17 expression was negligible when GDF-10, GDF-11, or GDF-15 was combined with Wnt3a, but improved in combination with one of the compounds of the present invention; in particular when combined with Compound 34. FIG. 8D shows results for treatment groups using GDF-8 where GDF-8 in combination with either Compound 34 or Compound 56 caused a robust induction of SOX17, exceeding results seen with the activin A/Wnt3a positive control. In some of these examples, the presence of Compound 34 or Compound 56 combined with a GDF growth factor also caused an increase in cell number during differentiation.

These collective results demonstrate that GDF-8 was superior to all other GDF family members tested when used in combination with Compound 34 or Compound 56, and could substitute for activin A during definitive endoderm differentiation.

Example 14

Formation of Cells Expressing Markers Characteristic of the Definitive Endoderm Lineage with Other Members of the TGF Superfamily of Proteins It was important to determine if treating human embryonic stem cells with other TGF superfamily members could facilitate the formation of cells expressing markers characteristic of the definitive endoderm lineage. Compound 34 and Wnt3a were tested on human embryonic stem cells in combination with either TGFβ-1, BMP2, BMP3, or BMP4 to determine the ability of members of the TGF superfamily members to differentiate human embryonic stem cells toward cells expressing markers characteristic of the definitive endoderm lineage. In parallel, two different commercial sources of GDF-8 were tested with Wnt3a for their ability to differentiate human embryonic stem cells toward cells expressing markers characteristic of the definitive endoderm lineage. A positive control using activin A with Wnt3a was maintained for comparison purposes.

Preparation of Cells for Assay:

Stock cultures of human embryonic stem cells (H1 human embryonic stem cell line) were maintained in an undifferentiated, pluripotent state on reduced growth factor MATRIGEL™-(BD Biosciences; Cat #356231)-coated dishes in MEF conditioned medium with passage on average every four days. Passage was performed by exposing cell cultures to a solution of 1 mg/ml dispase (Invitrogen; Cat #17105-041) for 5 to 7 minutes at 37° C. followed by rinsing the monolayer with MEF conditioned culture medium and gentle scraping to recover cell clusters. Clusters were centrifuged at low speed to collect a cell pellet and remove residual dispase. Cell clusters were split at a 1:3 or 1:4 ratio for routine maintenance culture or a 1:1 ratio for immediate assay. All human embryonic stem cell lines were maintained at passage numbers less than 50 and routinely evaluated for normal karyotype and absence of mycoplasma.

Cell clusters were evenly resuspended in MEF conditioned medium supplemented with 8 ng/ml bFGF and seeded onto reduced growth factor-MATRIGEL™-coated 96-well Packard VIEWPLATES (PerkinElmer; Cat #6005182) in volumes of 0.1 ml/well. Daily feeding was conducted by aspirating spent culture medium from each well and replacing with an equal volume of fresh medium. Plates were maintained at 37° C., 5% $CO_2$ throughout assay.

Assay:

The assay was initiated by aspirating the culture medium from each well and adding back aliquots (100 µl) of test medium. Test conditions were performed in triplicate over a total three day assay period, feeding on day 1 and day 2 by aspirating and replacing the medium from each well with fresh test medium. Various growth factor proteins were obtained for testing as follows: BMP-2 (R&D Systems; Cat #355-BM); BMP-3 (R&D Systems; Cat #113-BP); BMP-4 (R&D Systems; Cat #314-BP); TGFβ-1 (R&D Systems; Cat #240-B); GDF-8 (PeproTech; Cat #120-00); GDF-8 (Shenandoah; Cat #100-22); and activin A (PeproTech; Cat #120-14). On the first day of assay, each well was treated with 80 µl of growth medium [RPMI-1640 (Invitrogen; Cat #: 22400) containing 2.5% Albumin Bovine Fraction V, Fatty Acid Free (FAF BSA) (MP Biomedicals, Inc; Cat #152401), and 10 ng/ml bFGF]. In some wells, 25 ng/ml Wnt3a (R&D Systems; Cat #1324-WN/CF) was added to the growth medium to yield a final assay concentration of 20 ng/ml. In some wells, activin A was added to the growth medium to yield a final assay concentration of 100 ng/ml. In some wells, 3.125 µM Compound 34w as added to the growth medium to yield a final assay concentration of 2.5 µM. A dose titration of additional growth factors (5× concentrated, diluted in RPMI-1640) was also added to respective test wells to yield a final assay volume of 100 µl in each well for all treatment conditions. On the second day of assay, Wnt3a and Compound 34 were omitted from assay. All wells received 80 µl of growth medium [RPMI-1640 containing 2.5% FAF BSA, and 10 ng/ml bFGF] and 20 µl of respective growth factor dilution (5× concentrated, diluted in RPMI-1640). Comparative controls for this assay included: 1) no added growth factors; 2) Wnt3a alone; and 3) activin A with Wnt3a. Each commercial source of GDF-8 was tested in combination with Wnt3a. Each of the BMP growth factors, as well as TGFβ-1, was tested in combination with Wnt3a, with Compound 34, and with both Wnt3a in combination with Compound 34.

High Content Analysis:

At the conclusion of culture, assay plates were washed once with PBS (Invitrogen; Cat #14190), fixed with 4% paraformaldehyde (Alexis Biochemical; Cat # ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; Cat # AF1924) was diluted 1:100 in 4% chicken serum and added to each well for two hours at room temperature. After washing three times with PBS, Alexa Fluor 488 conjugated secondary antibody (chicken anti-goat IgG; Invitrogen; Cat #A21467) diluted 1:200 in PBS was added to each well. To counterstain nuclei, 5 µg/ml Hoechst 33342 (Invitrogen; Cat # H3570) was added for fifteen minutes at room temperature. Plates were washed once with PBS and left in 100 µl/well PBS for imaging.

Imaging was performed using an IN Cell Analyzer 1000 (GE Healthcare) utilizing the 51008bs dichroic for cells stained with Hoechst 33342 and Alexa Fluor 488. Images were acquired from 25 fields per well. Measurements for total intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total protein expression was reported as total intensity or integrated intensity, defined as total fluorescence of the cell multiplied by the area of the cell. Background was eliminated based on acceptance criteria for gray-scale ranges between 200 and 4500. Total intensity data were normalized by dividing total intensities for each well by the average total intensity for the positive control.

FIG. 9 shows high content image analysis for SOX17 protein expression in human embryonic stem cells after three days differentiation to definitive endoderm. In each case, results are normalized to the positive control treatment for activin A with Wnt3a. The results in FIG. 9A, show that treatment with growth medium alone, or Wnt3a alone failed to induce SOX17 expression; only the addition of activin A caused a robust expression of SOX17. In FIG. 9, panels B and C, results for each of the commercial sources of GDF-8 are depicted, showing differences in potency between the two vendors. Although less potent than activin A, there was significant induction of SOX17 expression in cells treated with GDF-8 in combination with Wnt3a. In FIG. 9, panels D, E, F and G, results are shown for definitive endoderm differentiation using BMP2, BMP3, BMP4, and TGFβ-1, incorporating a dose titration for each growth factor in combination with Wnt3a, or Compound 34, or both Wnt3a with Compound 34. Although some treatments had a significant effect on cell numbers at the conclusion of assay (e.g. BMP2 and BMP4), induction of SOX17 expression resulting from any of these growth factors and treatment combinations was weak or negligible compared to the Wnt3a treatment alone.

Example 15

Dose Ranging Studies for Formation of Cells Expressing Markers Characteristic of the Definitive Endoderm Lineage with a Selection of the Compounds of the Present Invention It was important to know the optimal working concentrations for Compound 181, Compound 180, Compound 19, Compound 202, Compound 40, and Compound 34 that would mediate the formation of cells expressing markers characteristic of the definitive endoderm lineage. In conjunction, side-by-side comparisons were performed for titrations of each compound in combination with activin A or GDF-8 in the definitive endoderm assay. Finally, the duration of exposure for each compound was tested in assay, also in combination with activin A or GDF-8, adding compound only on the first day of assay or throughout all three days of definitive endoderm formation.

Preparation of Cells for Assay:

Stock cultures of human embryonic stem cells (H1 human embryonic stem cell line) were maintained in an undifferentiated, pluripotent state on reduced growth factor MATRIGEL™ (BD Biosciences; Cat #356231)-coated dishes in MEF conditioned medium supplemented with 8 ng/ml bFGF (PeproTech Inc.; Cat #100-18B) with passage on average every four days. Passage was performed by exposing cell cultures to a solution of 1 mg/ml dispase (Invitrogen; Cat #17105-041) for 5 to 7 minutes at 37° C. followed by rinsing the monolayer with MEF conditioned culture medium and gentle scraping to recover cell clusters. Clusters were centrifuged at low speed to collect a cell pellet and remove residual dispase. Cell clusters were split at a 1:3 or 1:4 ratio for routine maintenance culture or a 1:1 ratio for immediate assay. All human embryonic stem cell lines were maintained at passage numbers less than 50 and routinely evaluated for normal karyotype and absence of mycoplasma.

Cell clusters were evenly resuspended in MEF conditioned medium supplemented with 8 ng/ml bFGF and seeded onto reduced growth factor MATRIGEL™-coated 96-well Packard VIEWPLATES (PerkinElmer; Cat #6005182) in volumes of 0.1 ml/well. Daily feeding was conducted by aspirating spent culture medium from each well and replacing with an equal volume of fresh medium. Plates were maintained at 37° C., 5% $CO_2$ throughout the duration of assay.

Assay:

Assay was initiated by aspirating the culture medium from each well and adding back aliquots (100 µl) of test medium. Test conditions were performed in quadruplicate over a total four-day assay period, feeding daily by aspirating and replacing the medium from each well with fresh test medium. Each well was treated with 80 µl of growth medium [RPMI-1640 (Invitrogen; Cat #: 22400) containing 2.5% Albumin Bovine Fraction V, Fatty Acid Free (FAF BSA) (MP Biomedicals, Inc; Cat #152401), 10 ng/ml bFGF, and additional growth factors (1.25× concentrated)] and 24.1 of test compound (5× concentrated diluted in RPMI-1640) to yield a final assay volume of 100 µl in each well. Test compounds in this assay included six of the compounds of the present invention: Compound 181, Compound 180, Compound 19, Compound 202, Compound 40, and Compound 34, and a commercial GSK31 inhibitor BIO (EMD Chemicals, Inc.; Cat #361550). On the first day of assay, wells were treated with various control or experimental conditions. Control conditions, with final assay concentrations as indicated, were as follows: 1) growth medium alone; 2) 20 ng/ml Wnt3a only R&D Systems; Cat #1324-WN/CF); 3) 100 ng/ml activin A (PeproTech; Cat #120-14); 4) 100 ng/ml activin A and 20 ng/ml Wnt3a; 5) 100 ng/ml GDF-8 (R&D Systems, Cat #788-G8); 6) 100 ng/ml GDF-8 and 20 ng/ml Wnt3a. Test compounds were diluted two-fold in series to yield a concentration range from 78 nM to 10 µM in the final assay. Experimental test samples combined each individual compound dilution series with 100 ng/ml activin A or 100 ng/ml GDF-8, both treatment sets in the absence of Wnt3a. On the second and third day of assay, some wells continued to be treated with 20 ng/ml Wnt3a or diluted test compound in combination with either activin A or GDF-8. In other wells, activin A or GDF-8 treatment continued on the second and third day of assay, but Wnt3a or diluted test compound was removed.

High Content Analysis:

At the conclusion of culture, assay plates were washed once with PBS (Invitrogen; Cat #14190), fixed with 4% paraformaldehyde (Alexis Biochemical; Cat # ALX-350-011) at room temperature for 20 minutes, then washed three times with PBS and permeabilized with 0.5% Triton X-100 (Sigma; Cat #T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; Cat # AF1924) was diluted 1:100 in 4% chicken serum and added to each well for two hours at room temperature. After washing three times with PBS, Alexa Fluor 488 conjugated secondary antibody (chicken anti-goat IgG; Invitrogen; Cat #A21467) diluted 1:200 in PBS was added to each well. To counterstain nuclei, 5 µg/ml Hoechst 33342 (Invitrogen; Cat # H3570) was added for fifteen minutes at room temperature. Plates were washed once with PBS and left in 100 µl/well PBS for imaging.

Imaging was performed using an IN Cell Analyzer 1000 (GE Healthcare) utilizing the 51008bs dichroic for cells stained with Hoechst 33342 and Alexa Fluor 488. Images were acquired from 25 fields per well. Measurements for total intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total protein expression was reported as total intensity or integrated intensity, defined as total fluorescence of the cell multiplied by the area of the cell. Background was eliminated based on acceptance criteria for gray-scale ranges between 200 and 4500. Total intensity data were normalized by dividing total intensities for each well by the average total intensity for the positive control.

Figure 15:
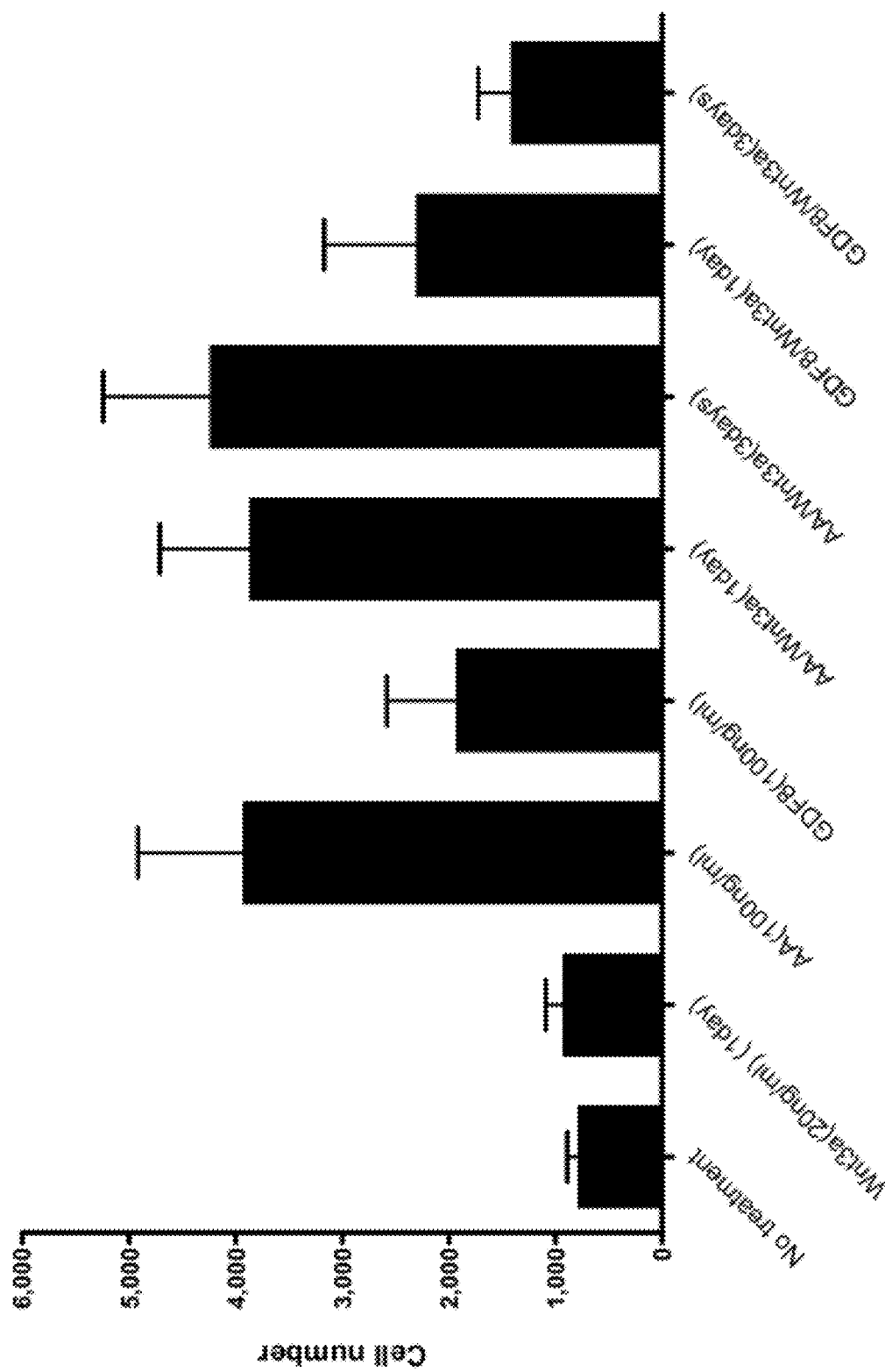
FIG. 15 shows cell number yields after differentiation of human embryonic stem cells to definitive endoderm, according to the methods described in Example 15. H1 cells were treated for a total of three days in various timed exposures with 100 ng/ml of activin A or 100 ng/ml GDF-8 in combination with 20 ng/ml Wnt3a. Cell numbers, as determined with a fluorescent nuclear probe and high content analysis are shown for each treatment group, testing control conditions for differentiation with no growth factors added (no treatment), with Wnt3a alone, with activin A or GDF-8 alone, or with activin A/Wnt3a treatment or GDF-8/Wnt3a treatment, where Wnt3a was added only for the first day of assay or for all three days of assay as shown.
Figure 16A:
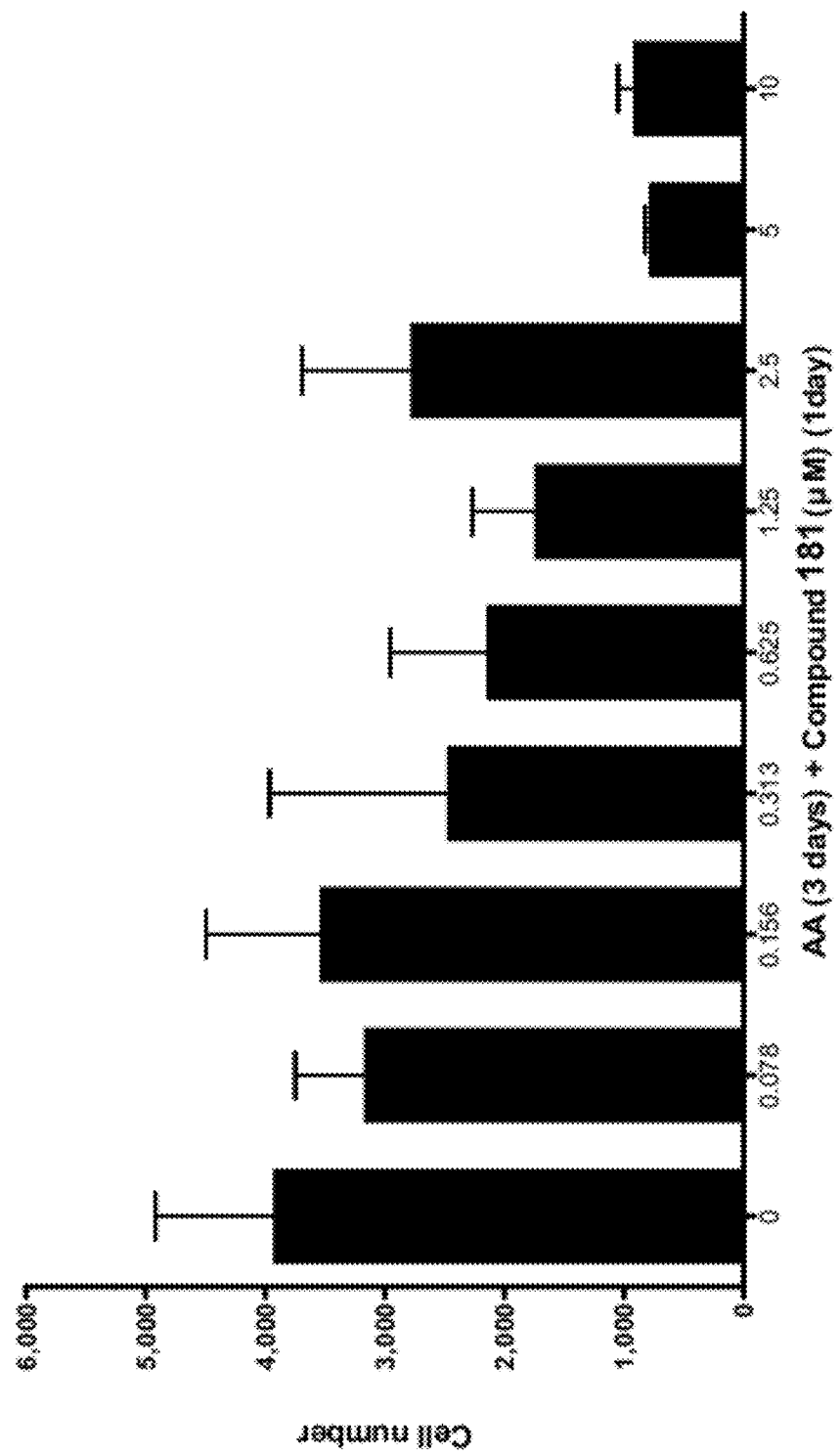
FIG. 16 shows cell number yields after differentiation of human embryonic stem cells to definitive endoderm, according to the methods described in Example 15. H1 cells were treated for a total of three days in various timed exposures with 100 ng/ml of activin A in combination with test compound (Compound 181 (Panel A), Compound 180 (Panel B), Compound 19 (Panel C), Compound 202 (Panel D), Compound 40 (Panel E), Compound 34 (Panel F), or GSK3 inhibitor BIO (Panel G)) at the concentrations shown, where test compound was added only on the first day of assay. Cell number yields, as determined with a fluorescent nuclear probe and high content analysis, are shown.
Figure 16D:
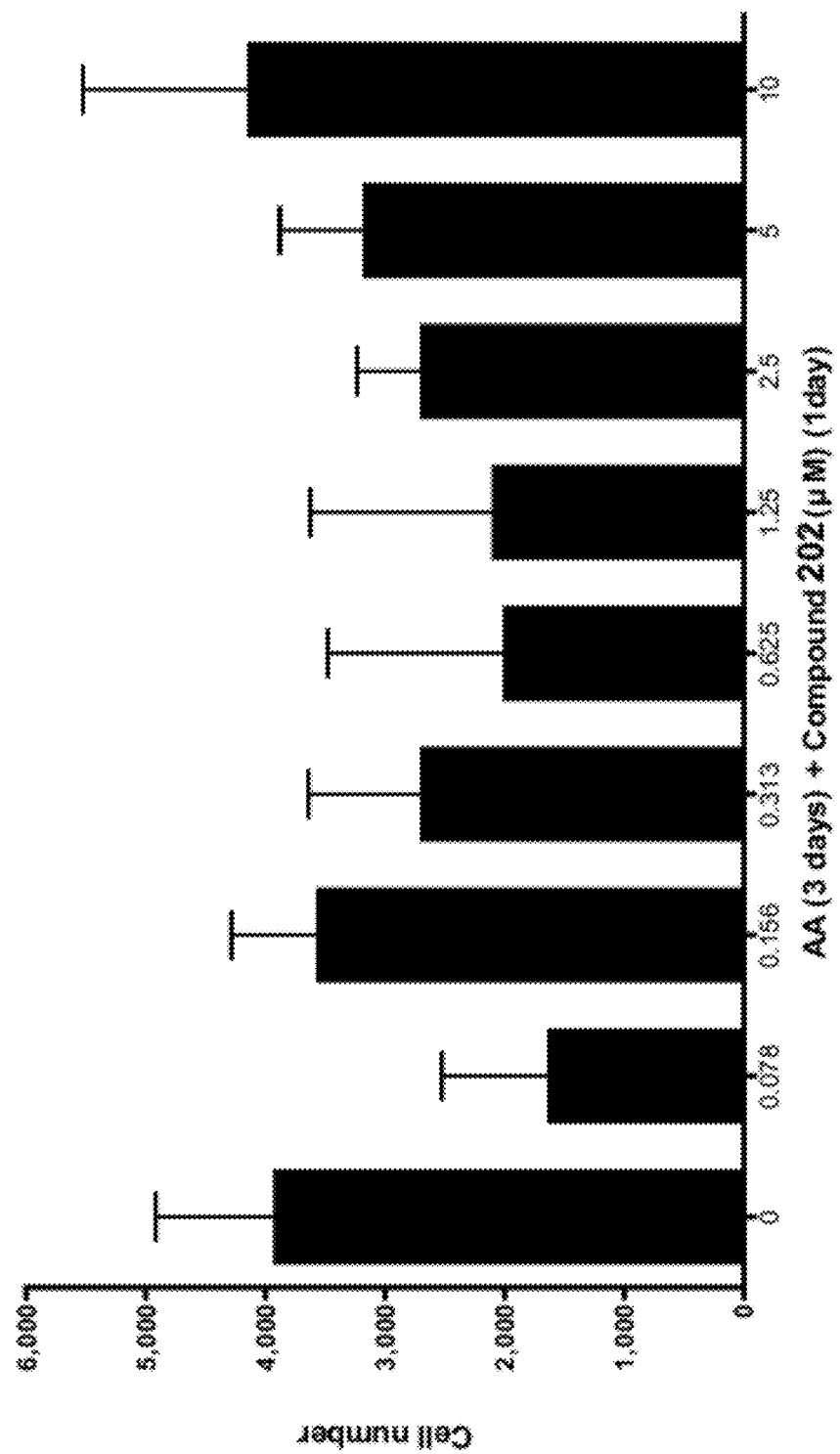
Figure 16E:
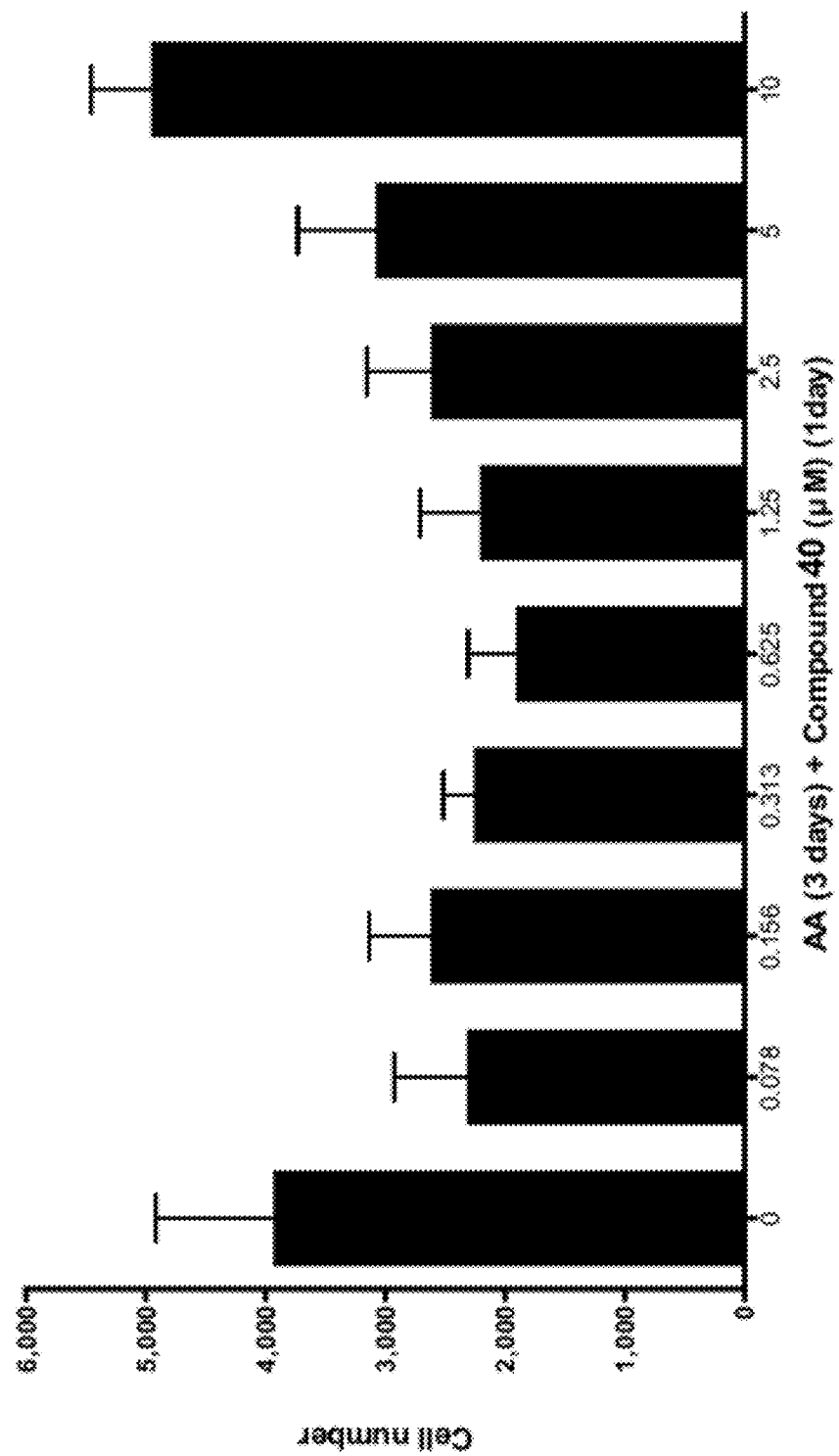
Figure 16F:
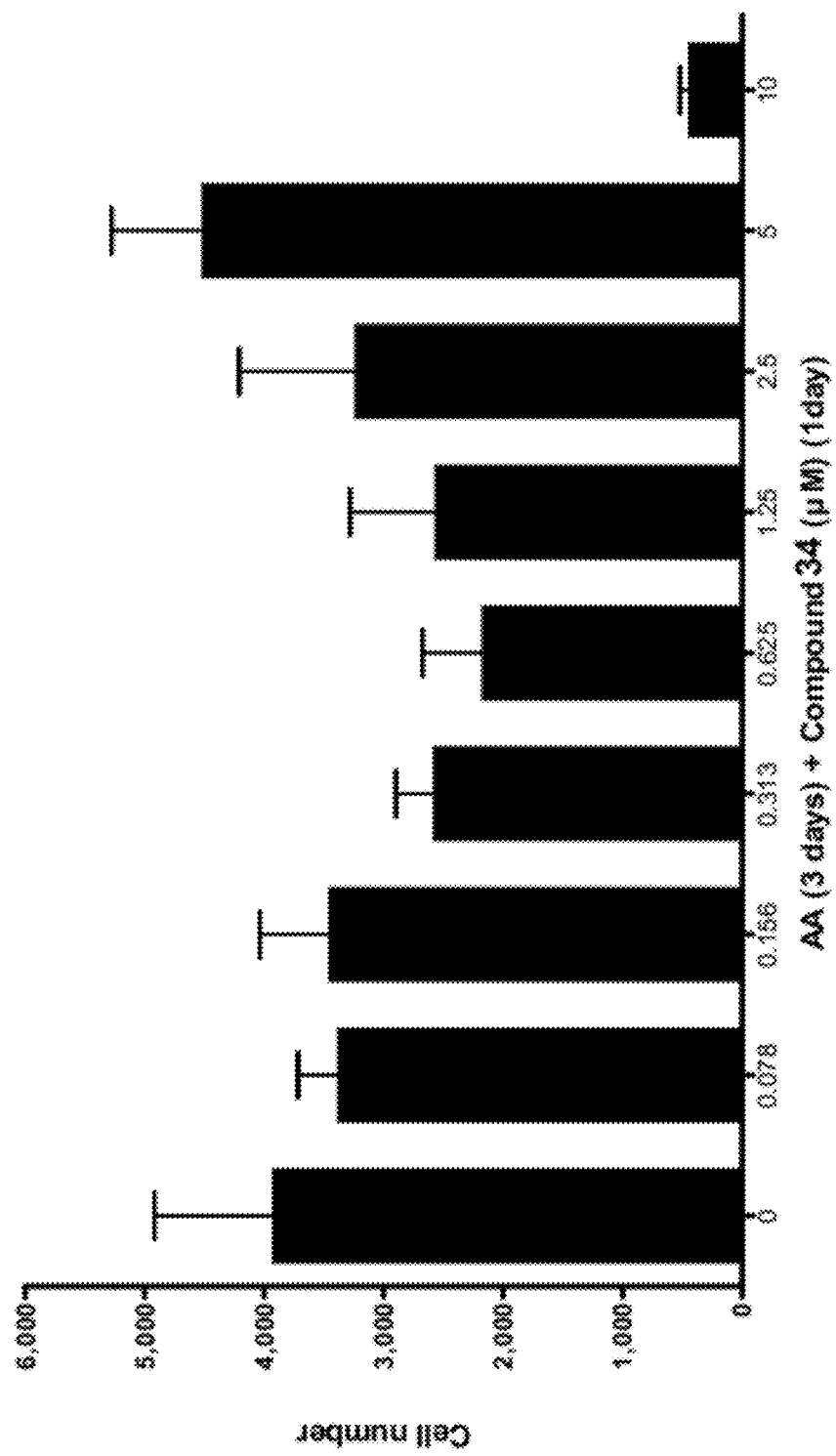
Figure 16G:
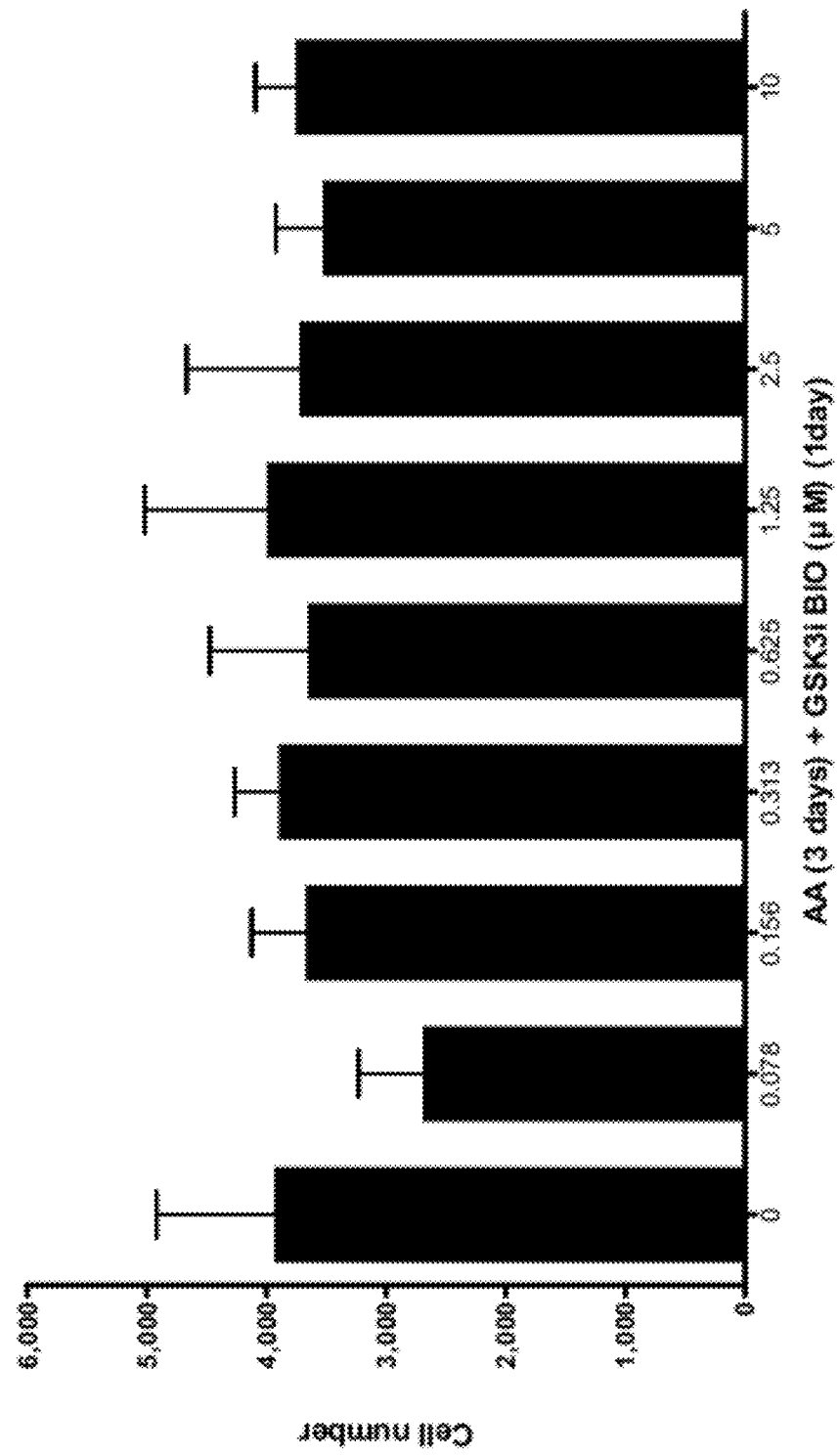
Figure 17A:
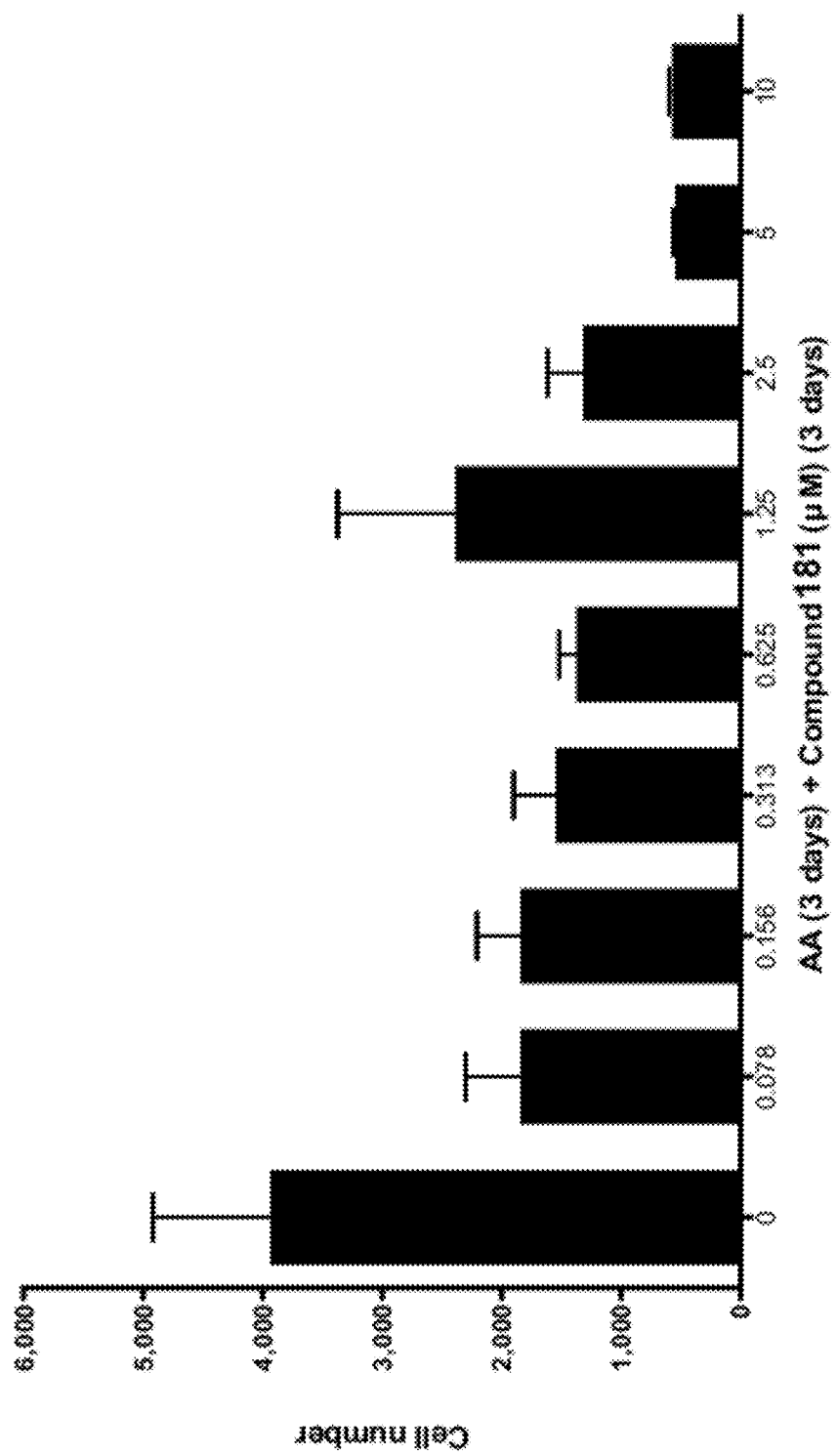
FIG. 17 shows cell number yields after differentiation of human embryonic stem cells to definitive endoderm, according to the methods described in Example 15. H1 cells were treated for a total of three days in various timed exposures with 100 ng/ml of activin A in combination with test compound (Compound 181 (Panel A), Compound 180 (Panel B), Compound 19 (Panel C), Compound 202 (Panel D), Compound 40 (Panel E), Compound 34 (Panel F), or GSK3 inhibitor BIO (Panel G)) at the concentrations shown, where test compound was added for all three days of assay. Cell number yields, as determined with a fluorescent nuclear probe and high content analysis, are shown.
Figure 17D:
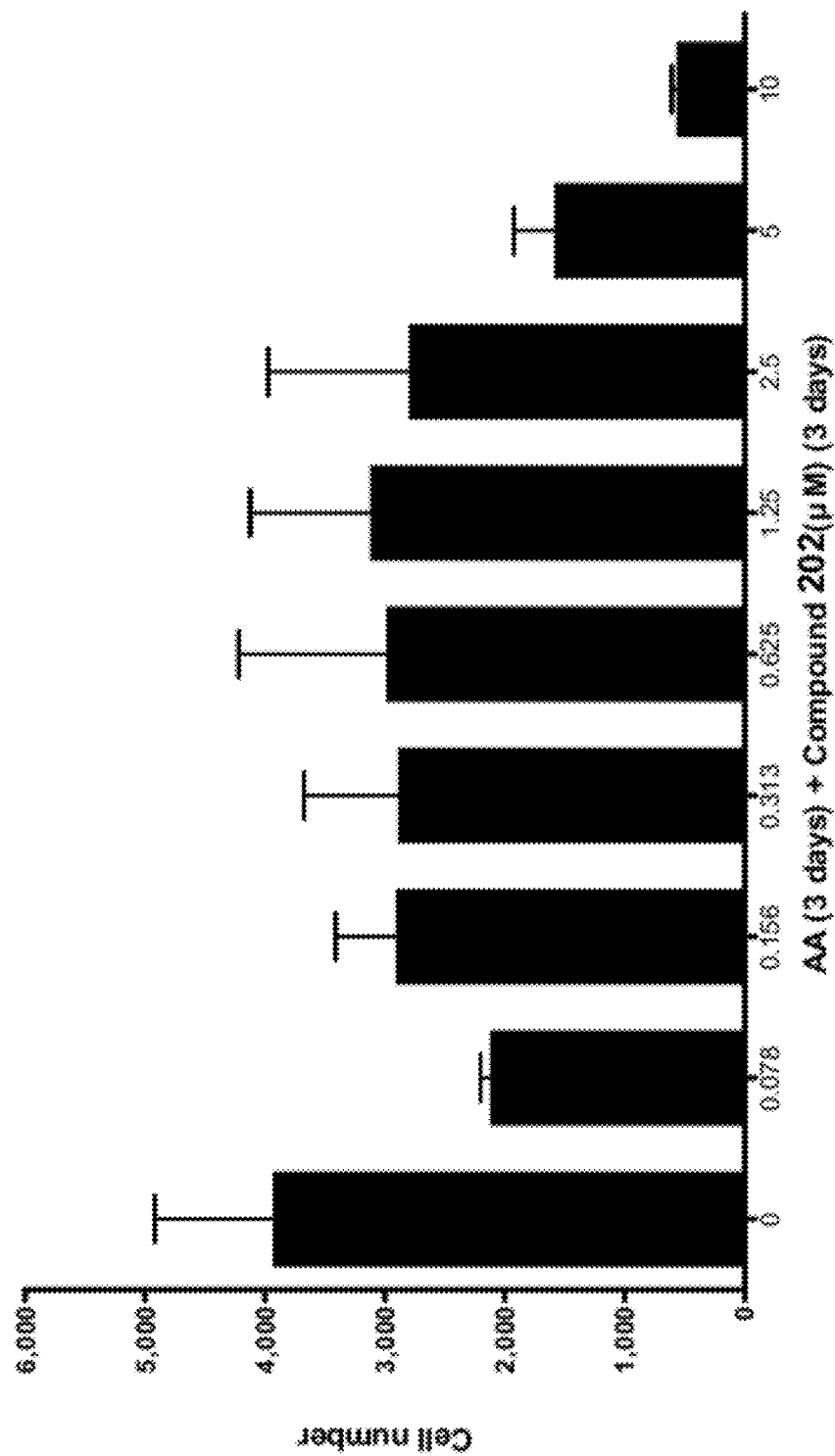
Figure 17E:
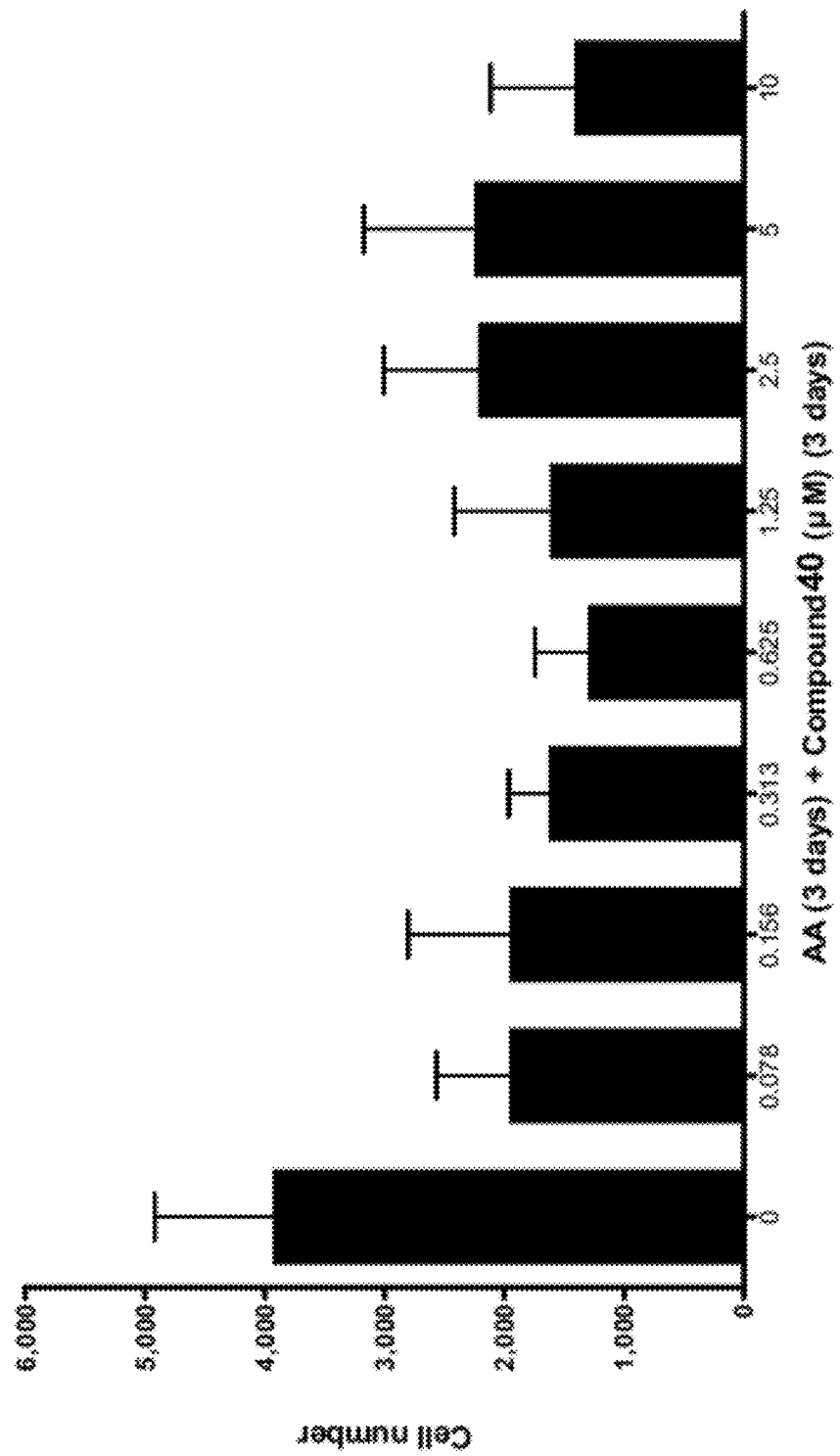
Figure 17F:
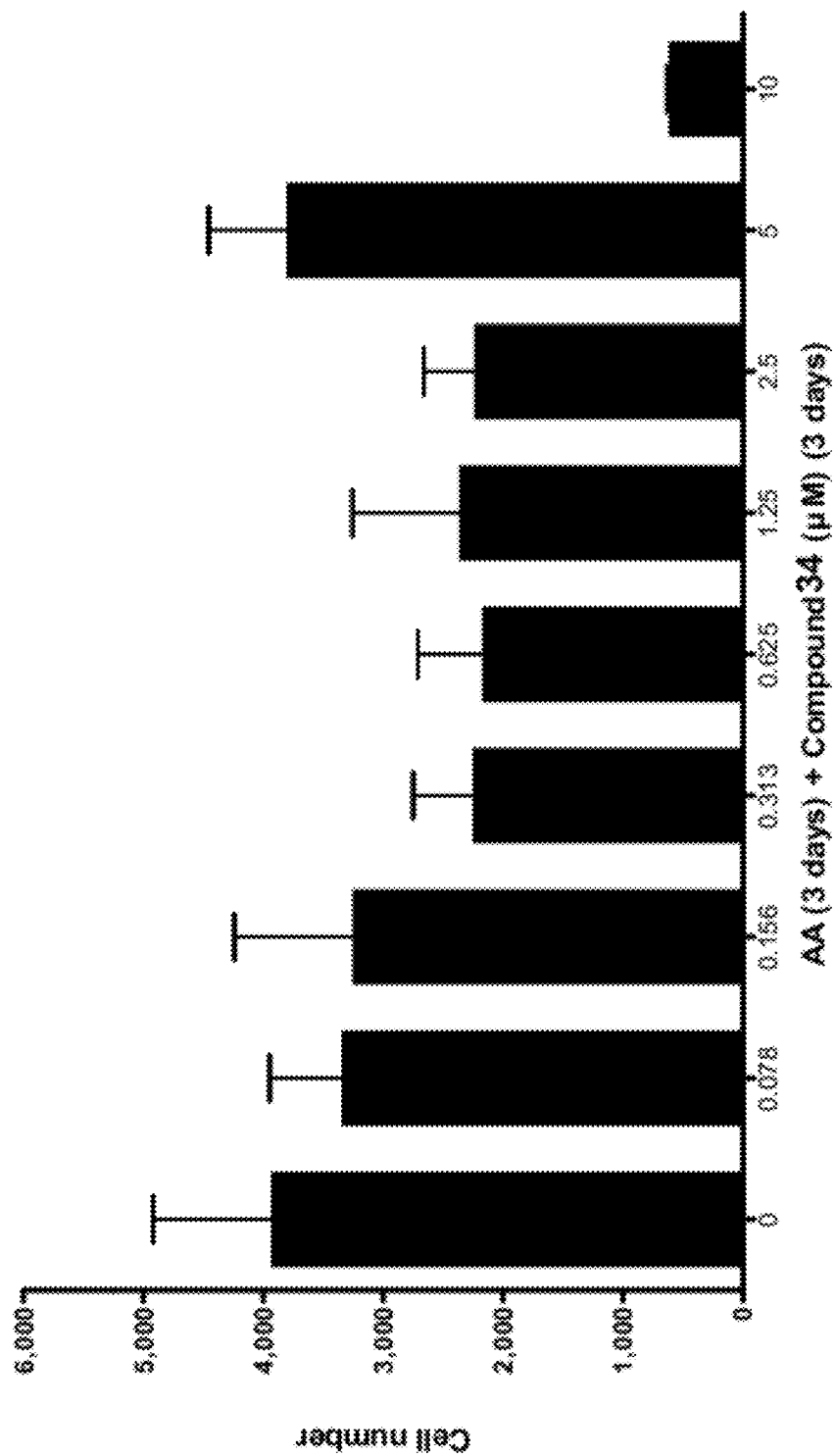
Figure 17G:
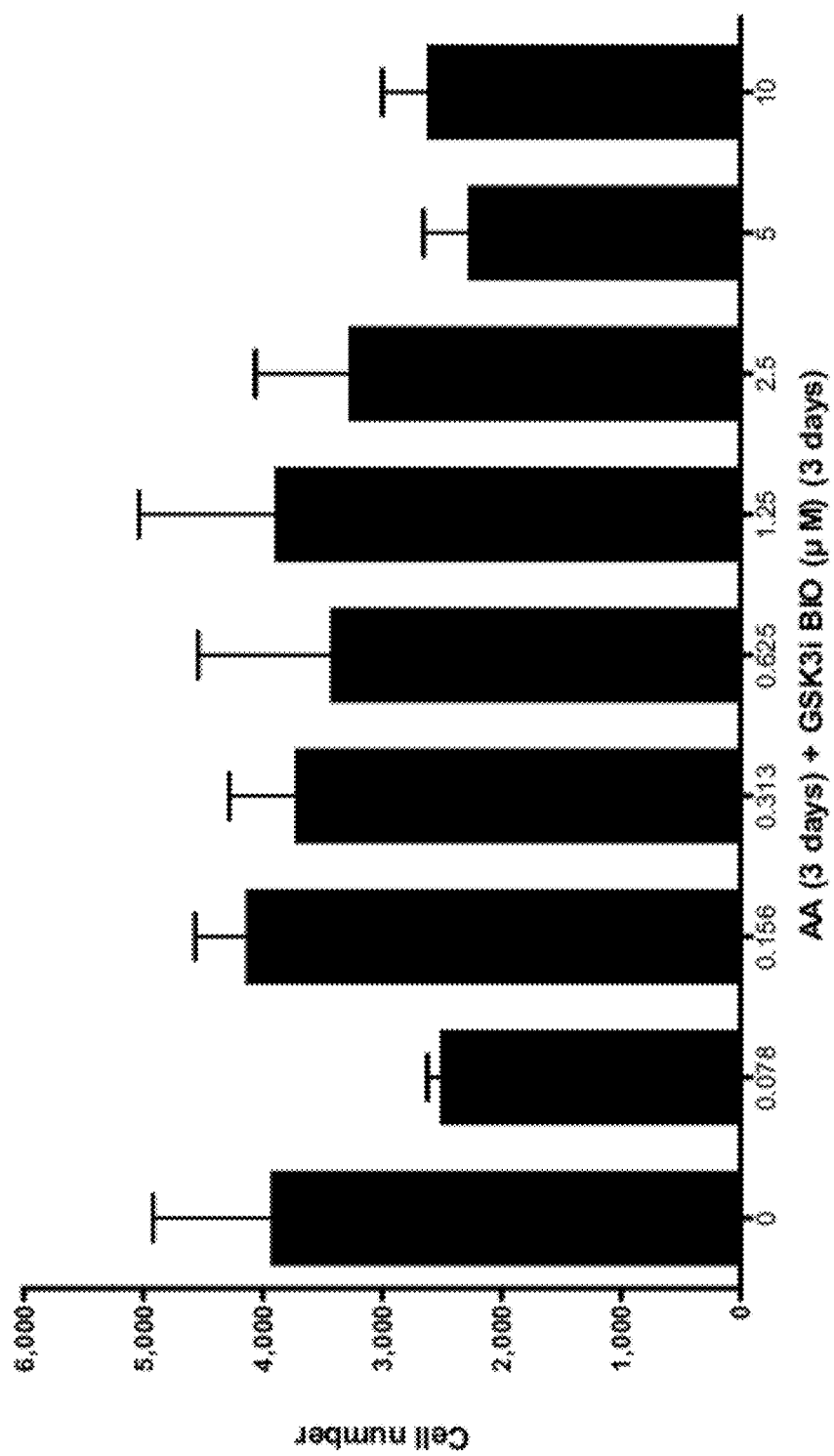
Figure 18A:
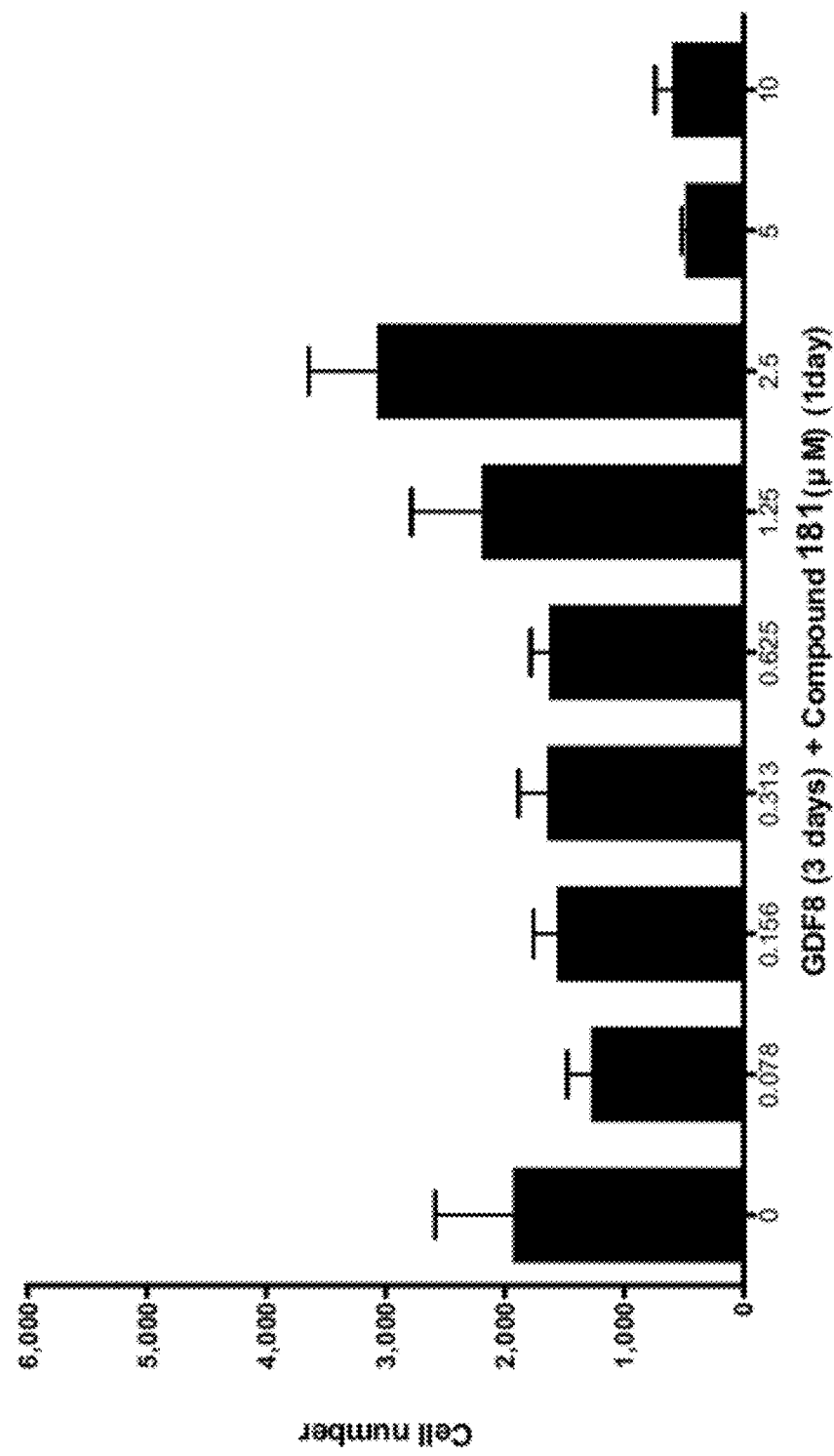
FIG. 18 shows cell number yields after differentiation of human embryonic stem cells to definitive endoderm, according to the methods described in Example 15. H1 cells were treated for a total of three days in various timed exposures with 100 ng/ml of GDF-8 in combination with test compound (Compound 181 (Panel A), Compound 180 (Panel B), Compound 19 (Panel C), Compound 202 (Panel D), Compound 40 (Panel E), Compound 34 (Panel F), or GSK3 inhibitor BIO (Panel G)) at the concentrations shown, where test compound was added only on the first day of assay. Cell number yields, as determined with a fluorescent nuclear probe and high content analysis, are shown.
Figure 18B:
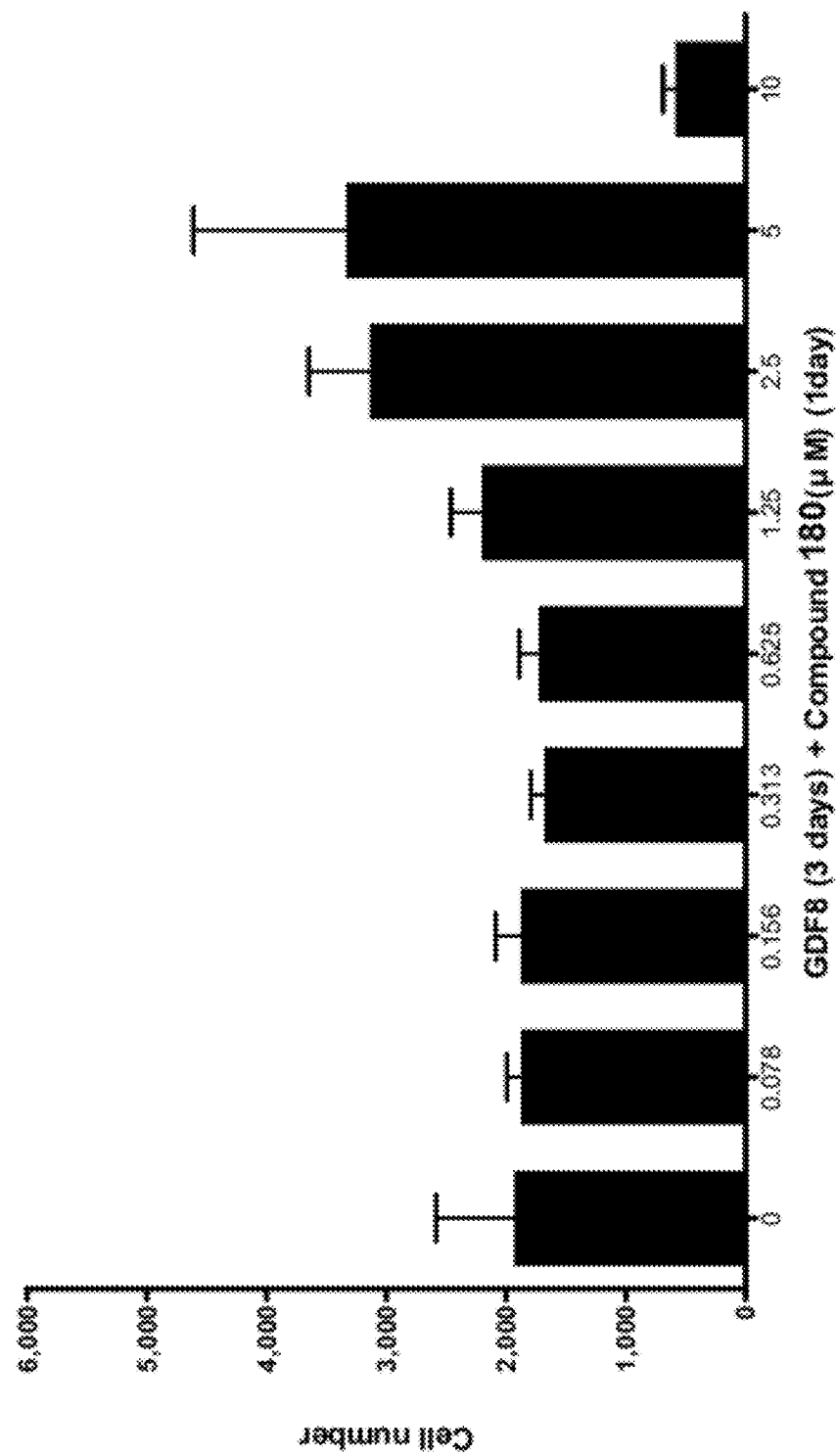
Figure 18C:
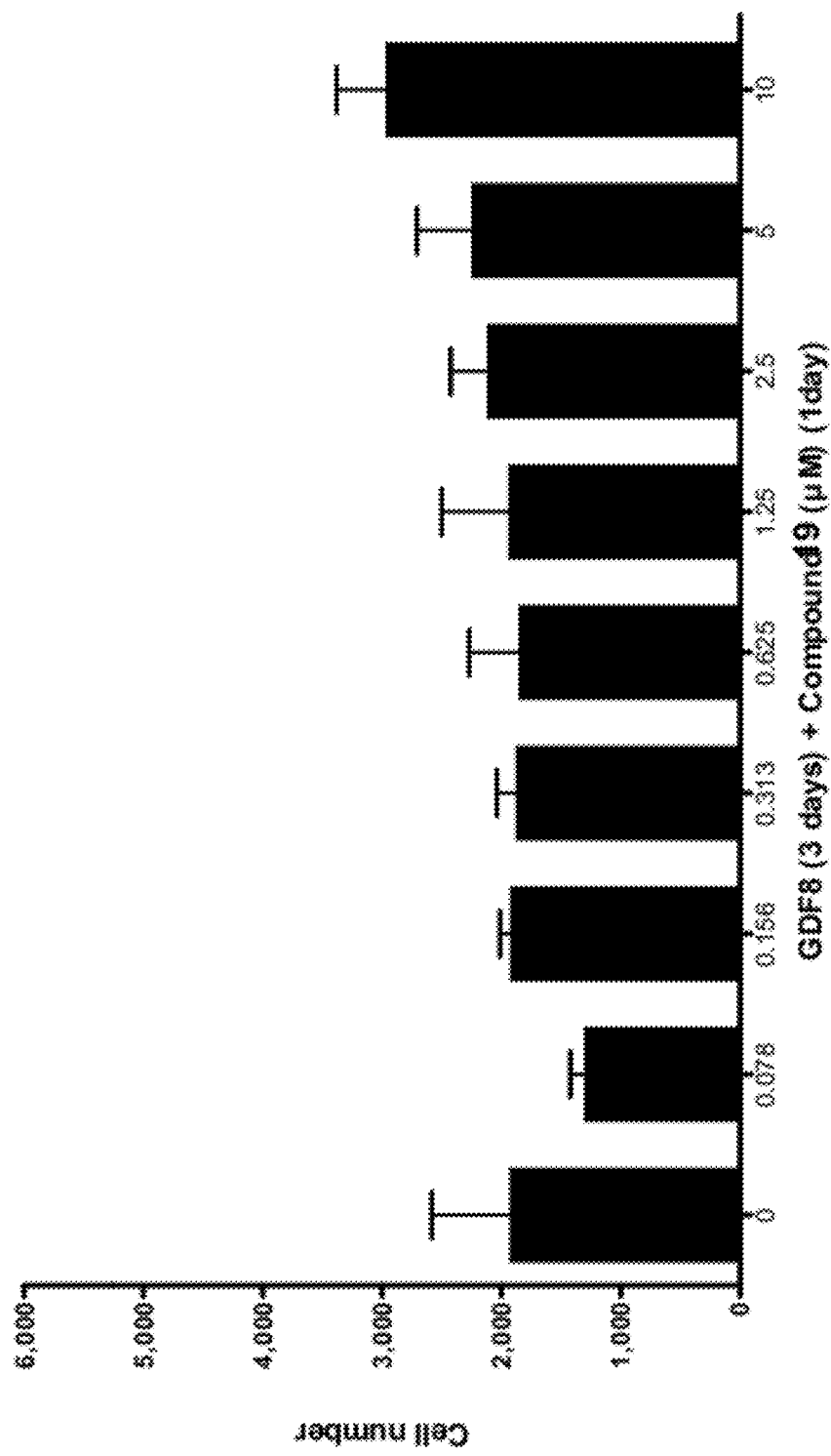
Figure 18D:
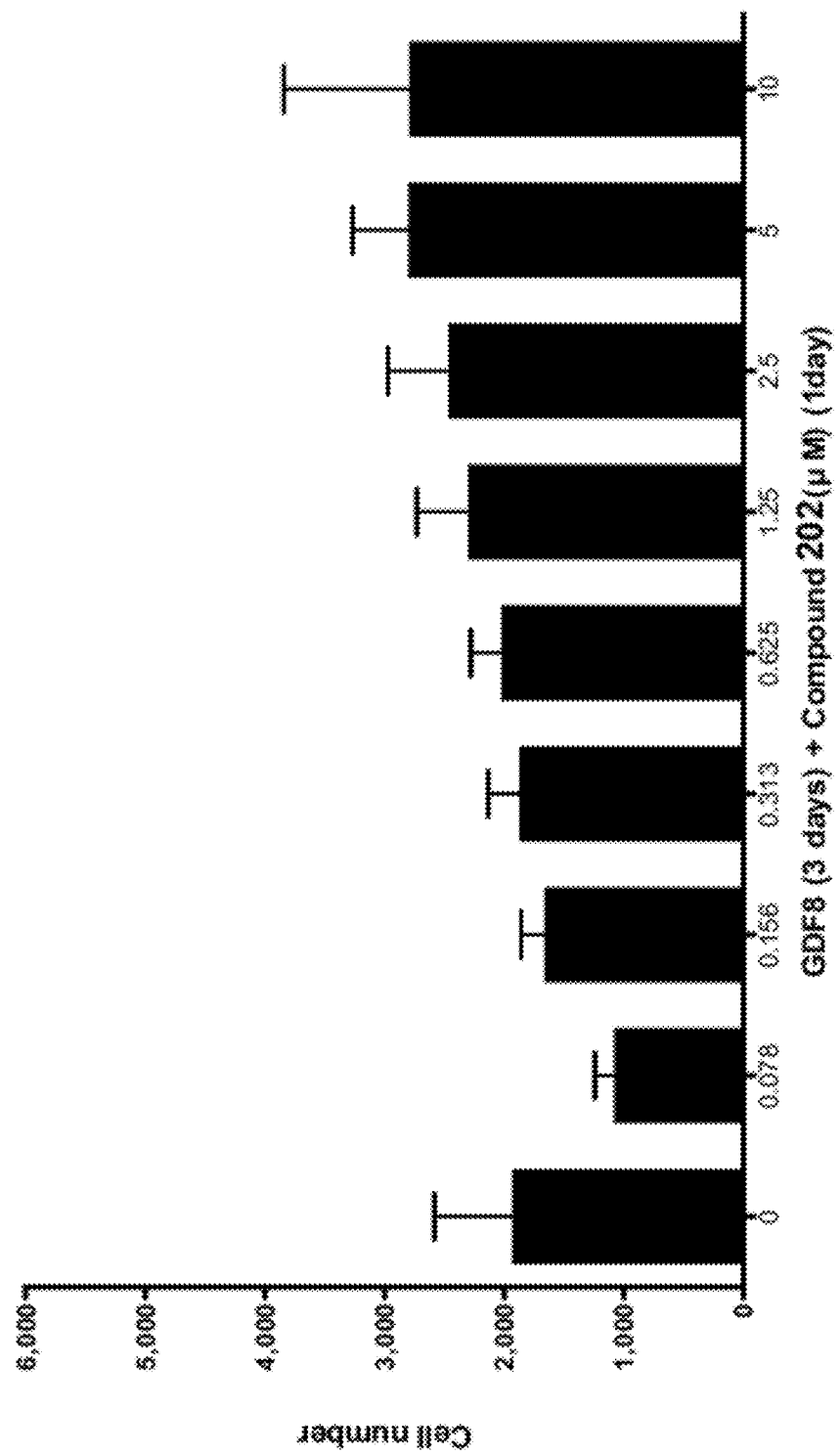
Figure 18E:
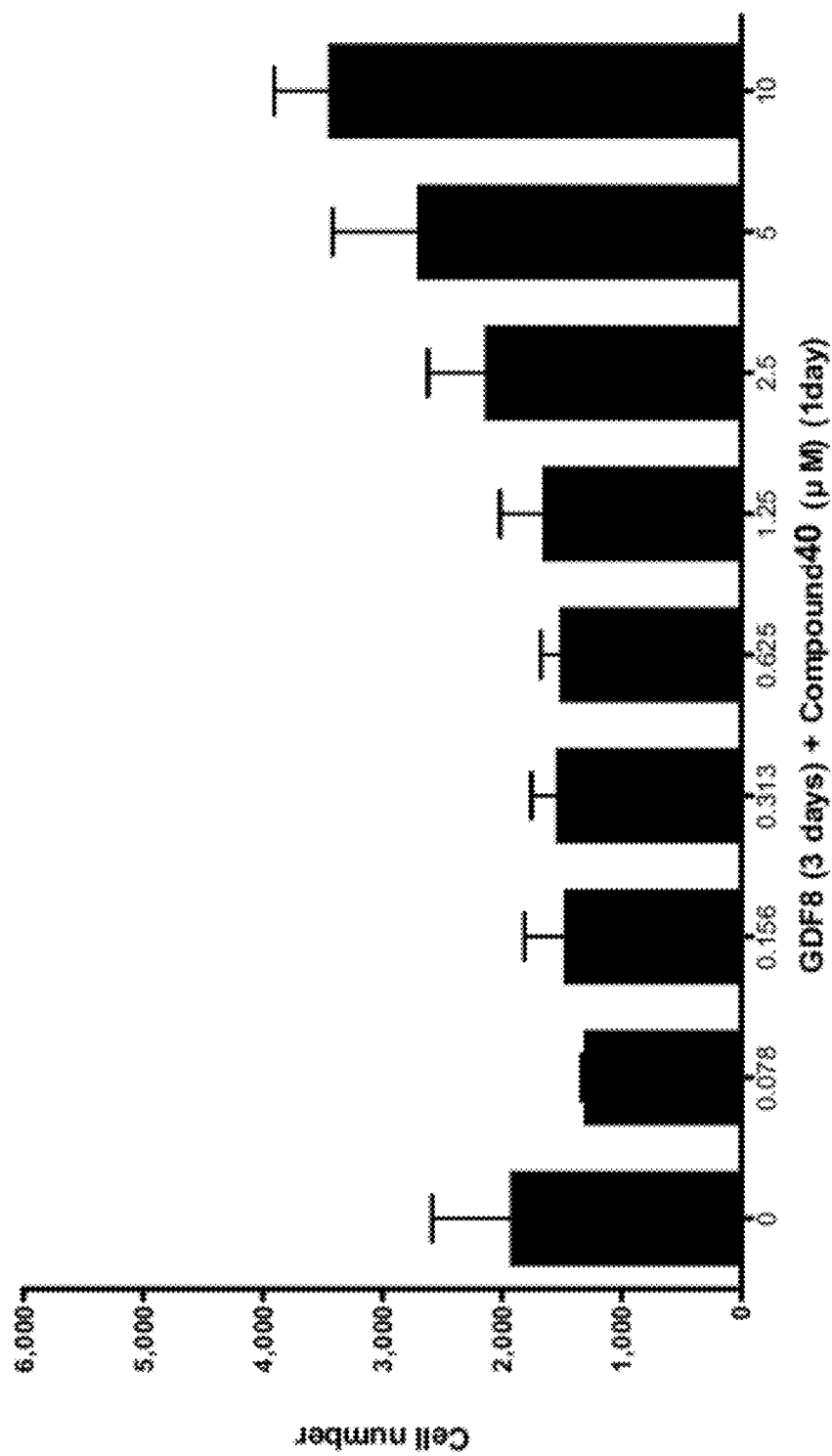
Figure 18F:
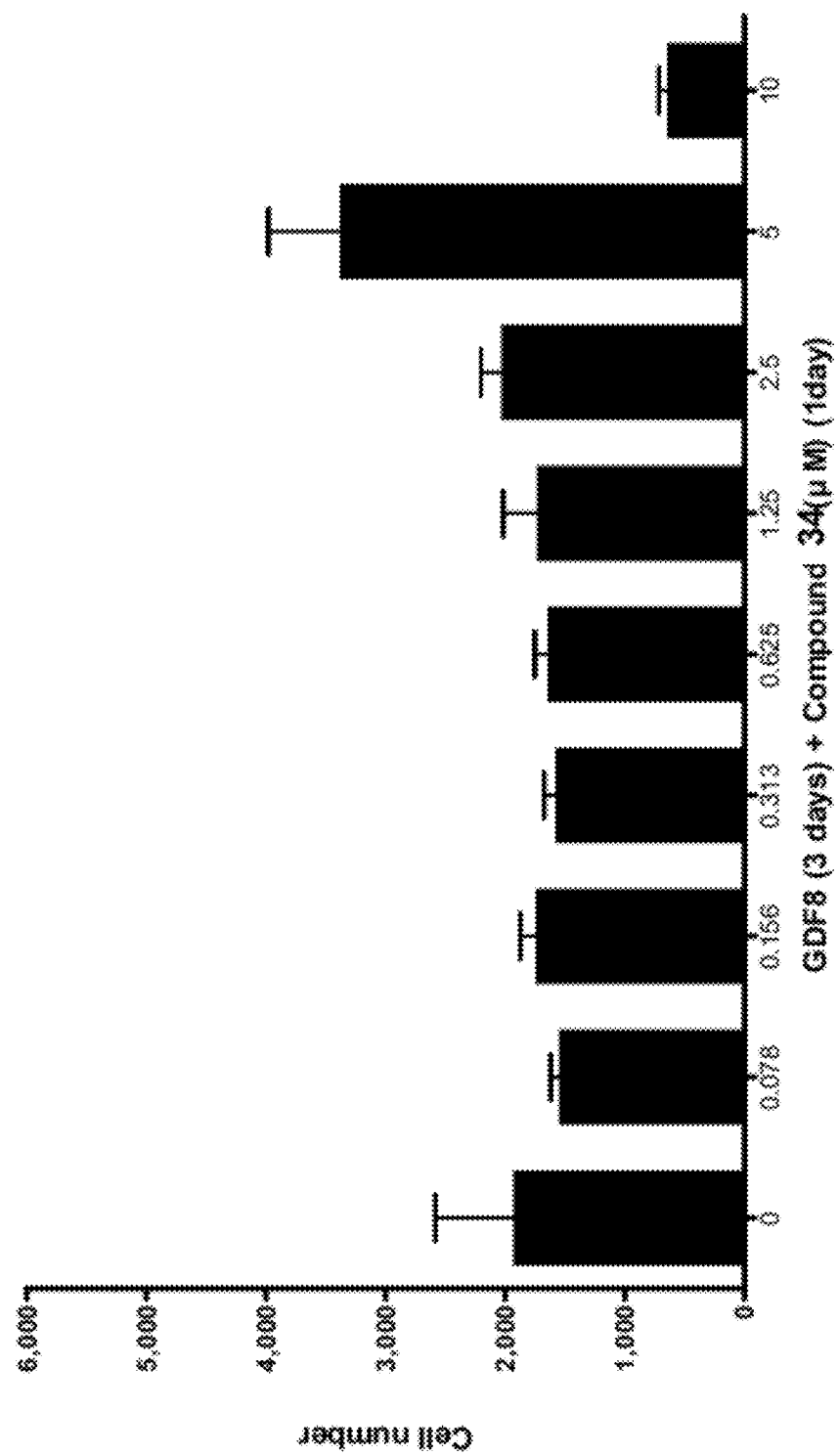
Figure 18G:
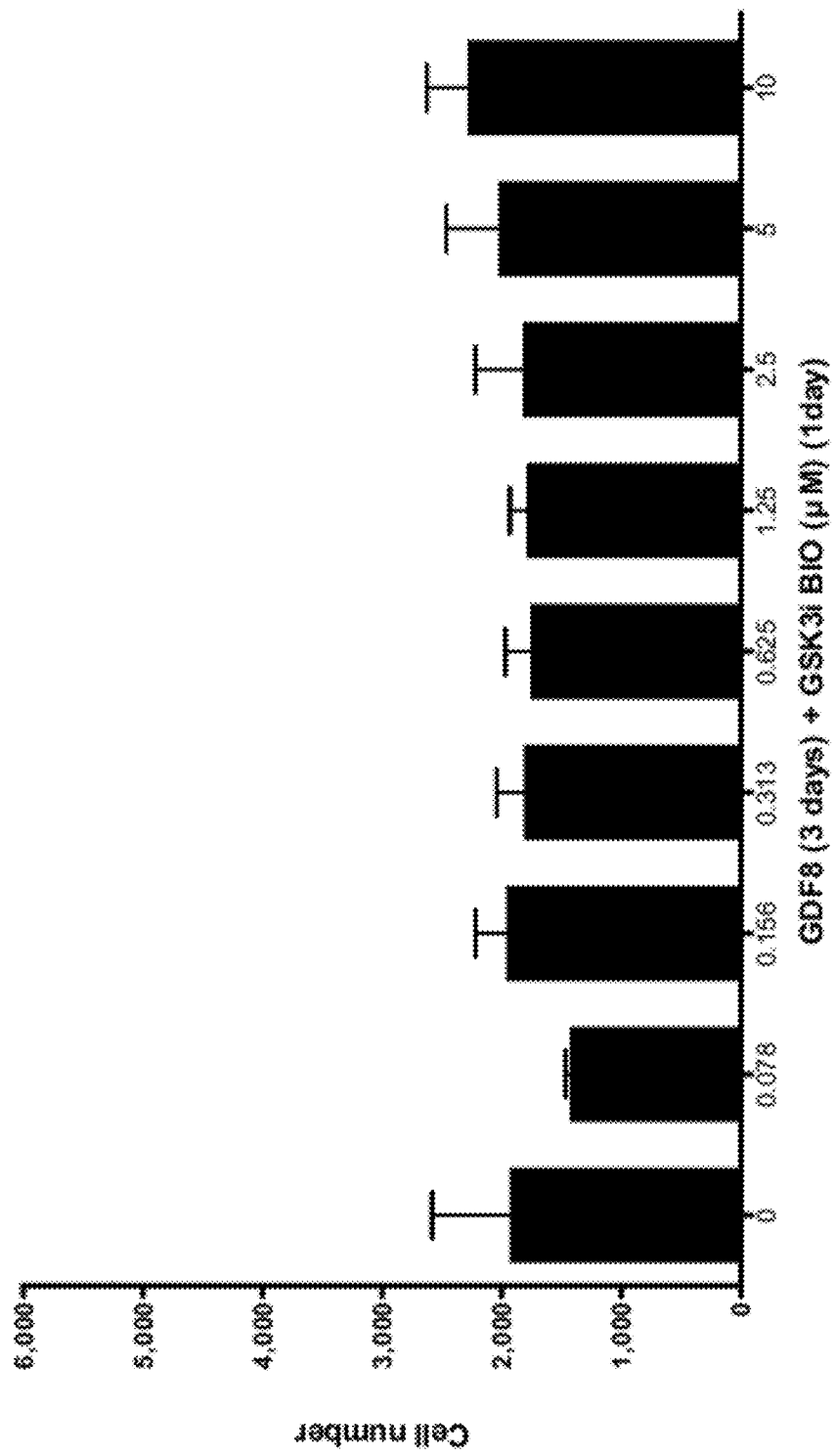
Figure 19A:
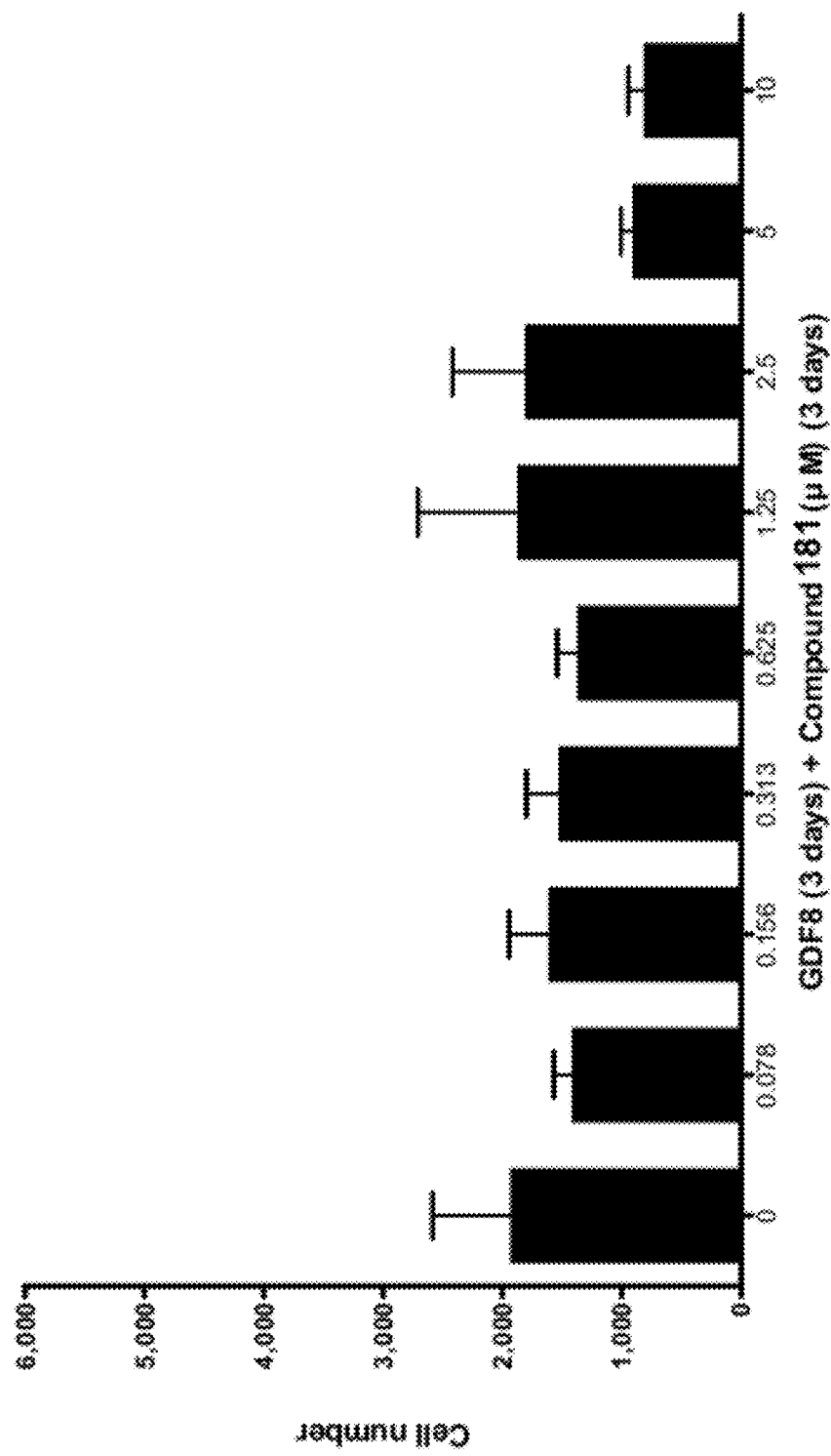
FIG. 19 shows cell number yields after differentiation of human embryonic stem cells to definitive endoderm, according to the methods described in Example 15. H1 cells were treated for a total of three days in various timed exposures with 100 ng/ml of GDF-8 in combination with test compound (Compound 181 (Panel A), Compound 180 (Panel B), Compound 19 (Panel C), Compound 202 (Panel D), Compound 40 (Panel E), Compound 34 (Panel F), or GSK3 inhibitor BIO (Panel G)) at the concentrations shown, where test compound was added for all three days of assay. Cell number yields, as determined with a fluorescent nuclear probe and high content analysis, are shown.
Figure 19B:
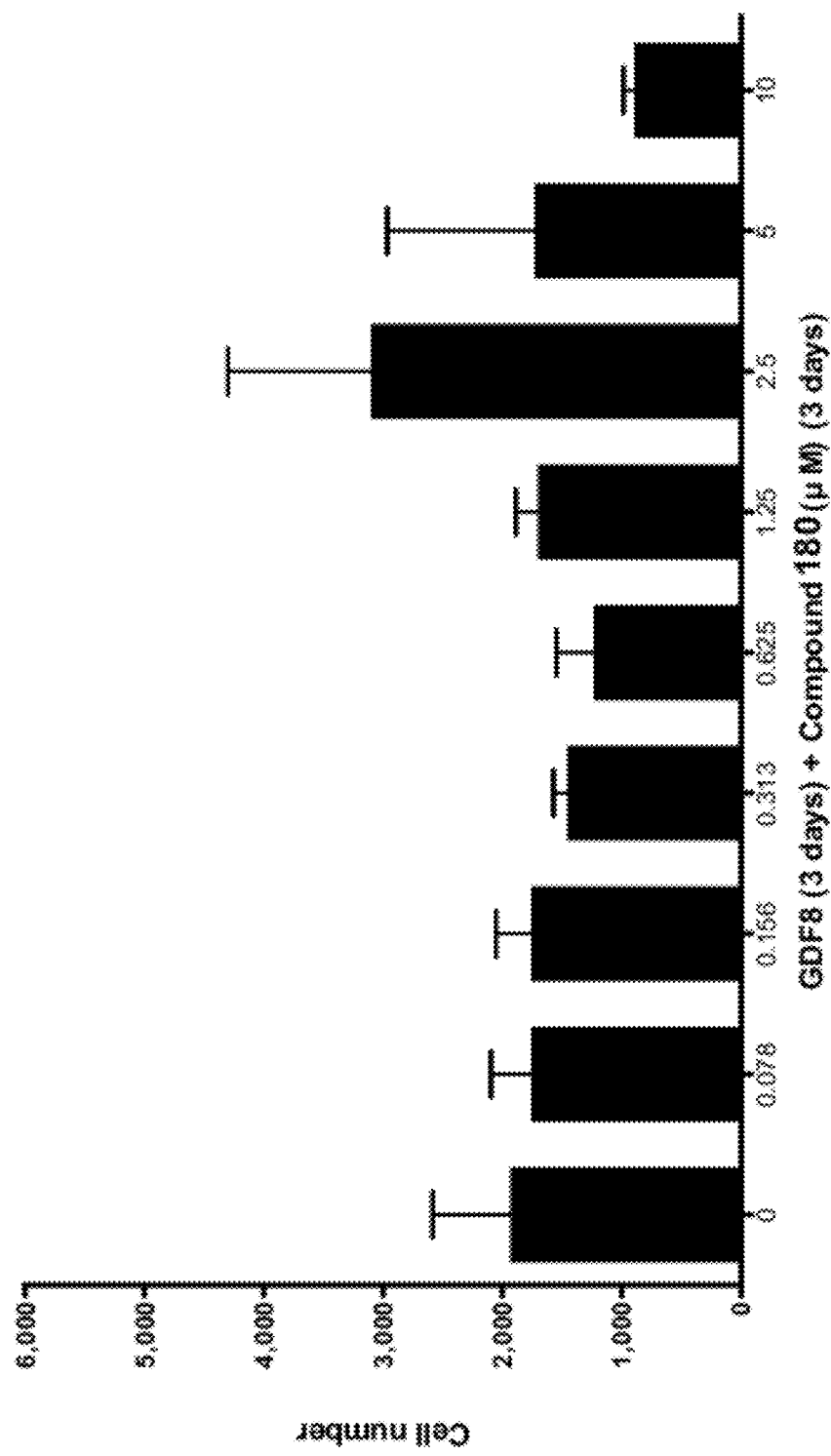
Figure 19C:
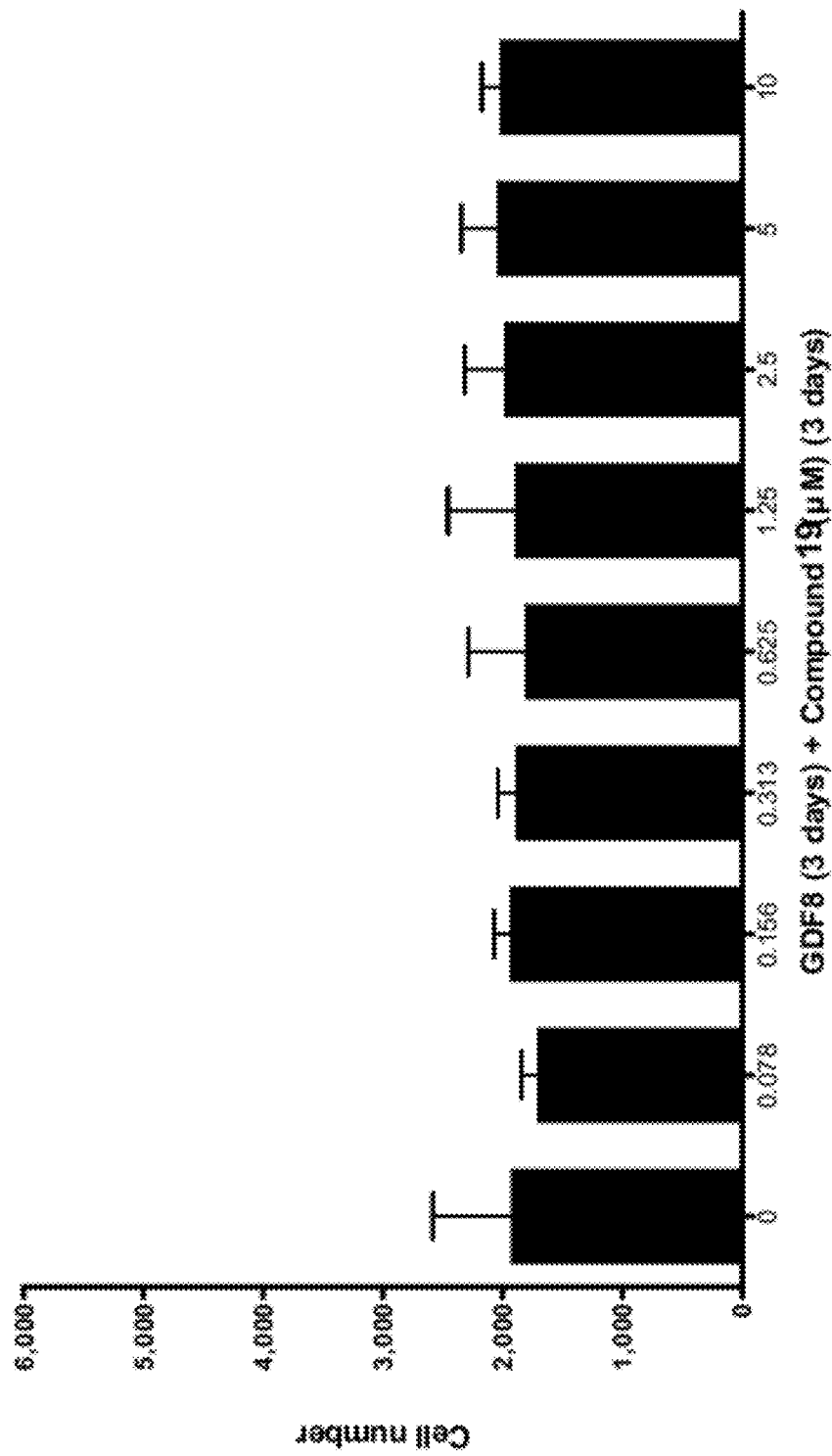
Figure 19D:
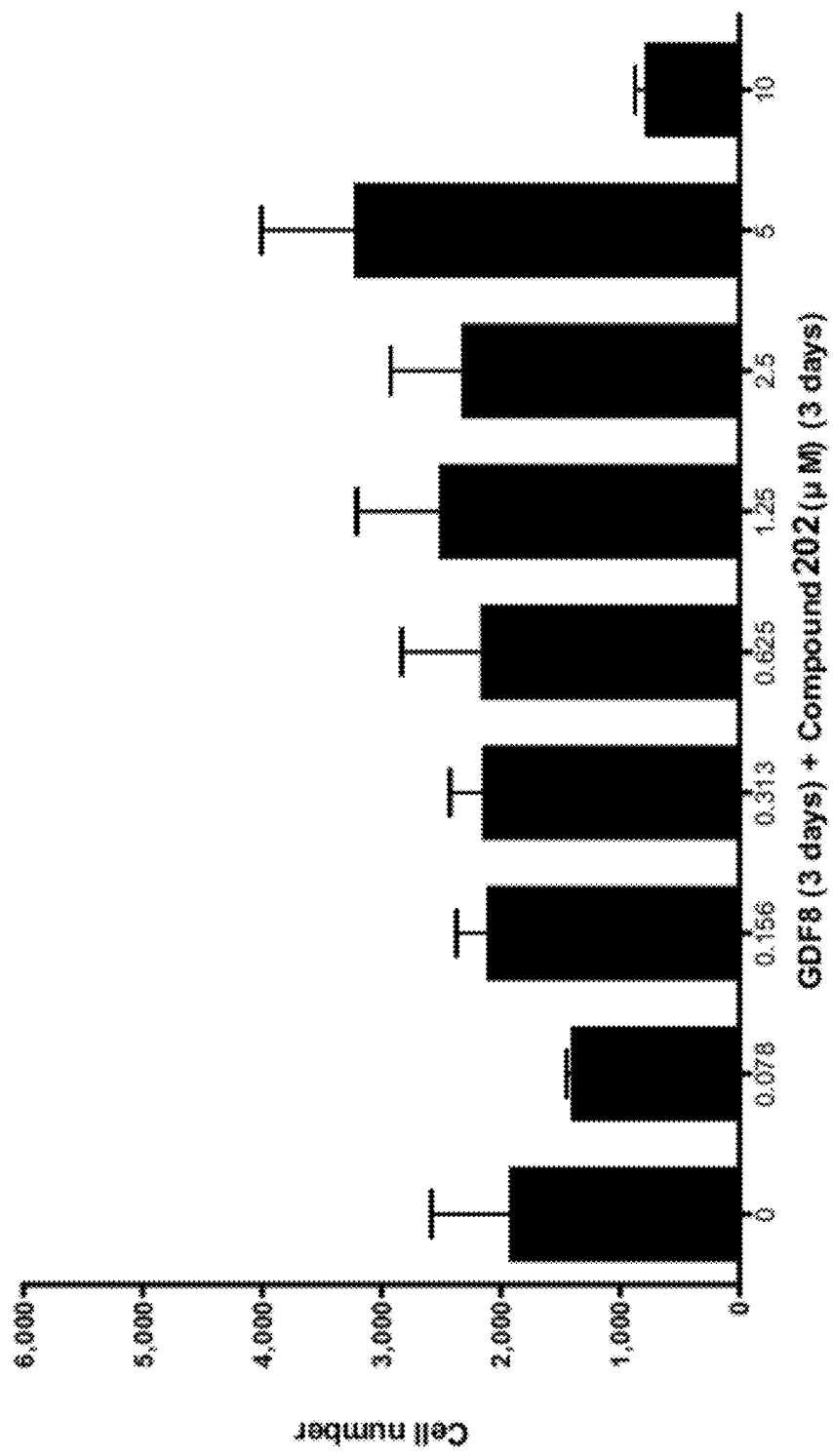
Figure 19E:
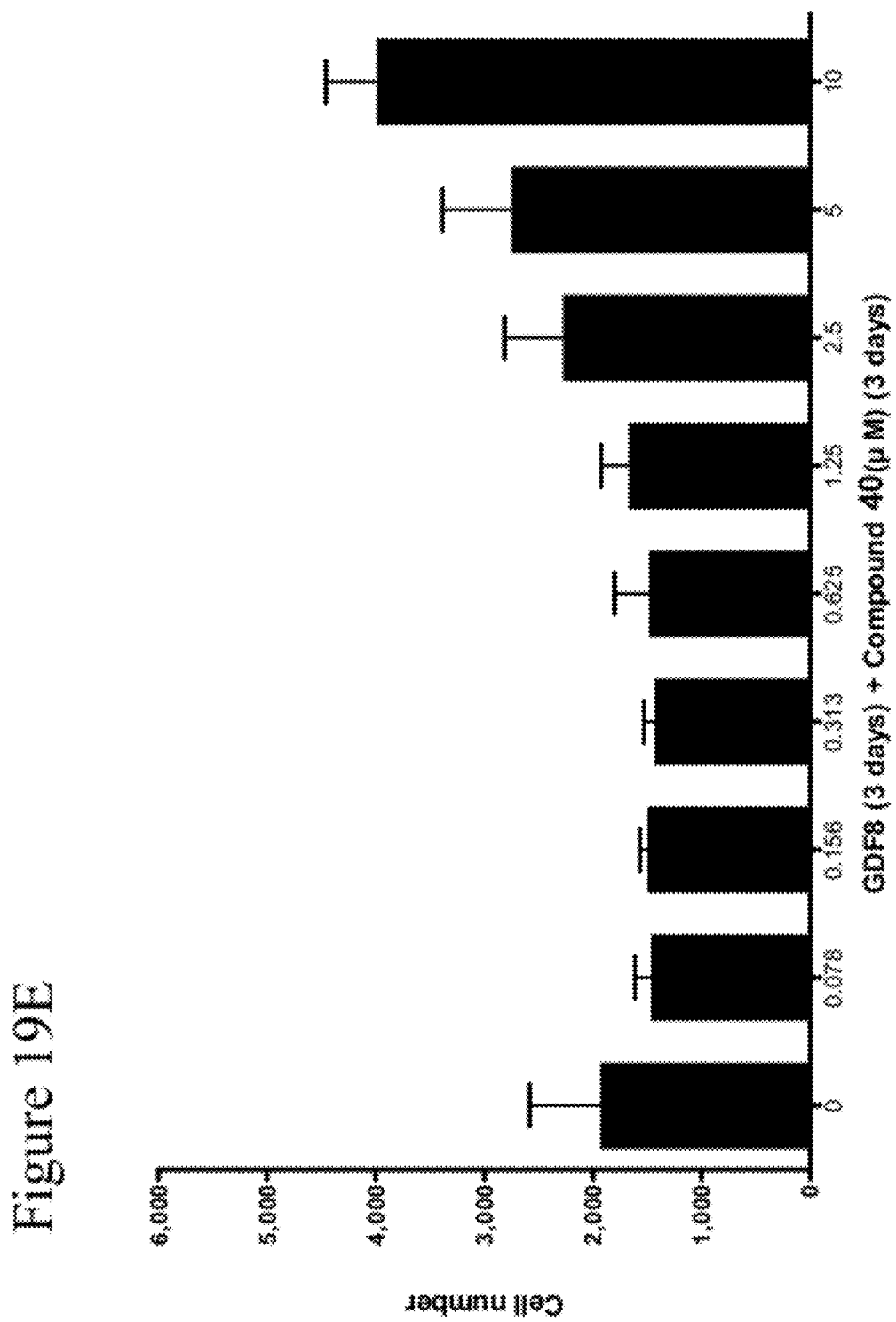
Figure 19F:
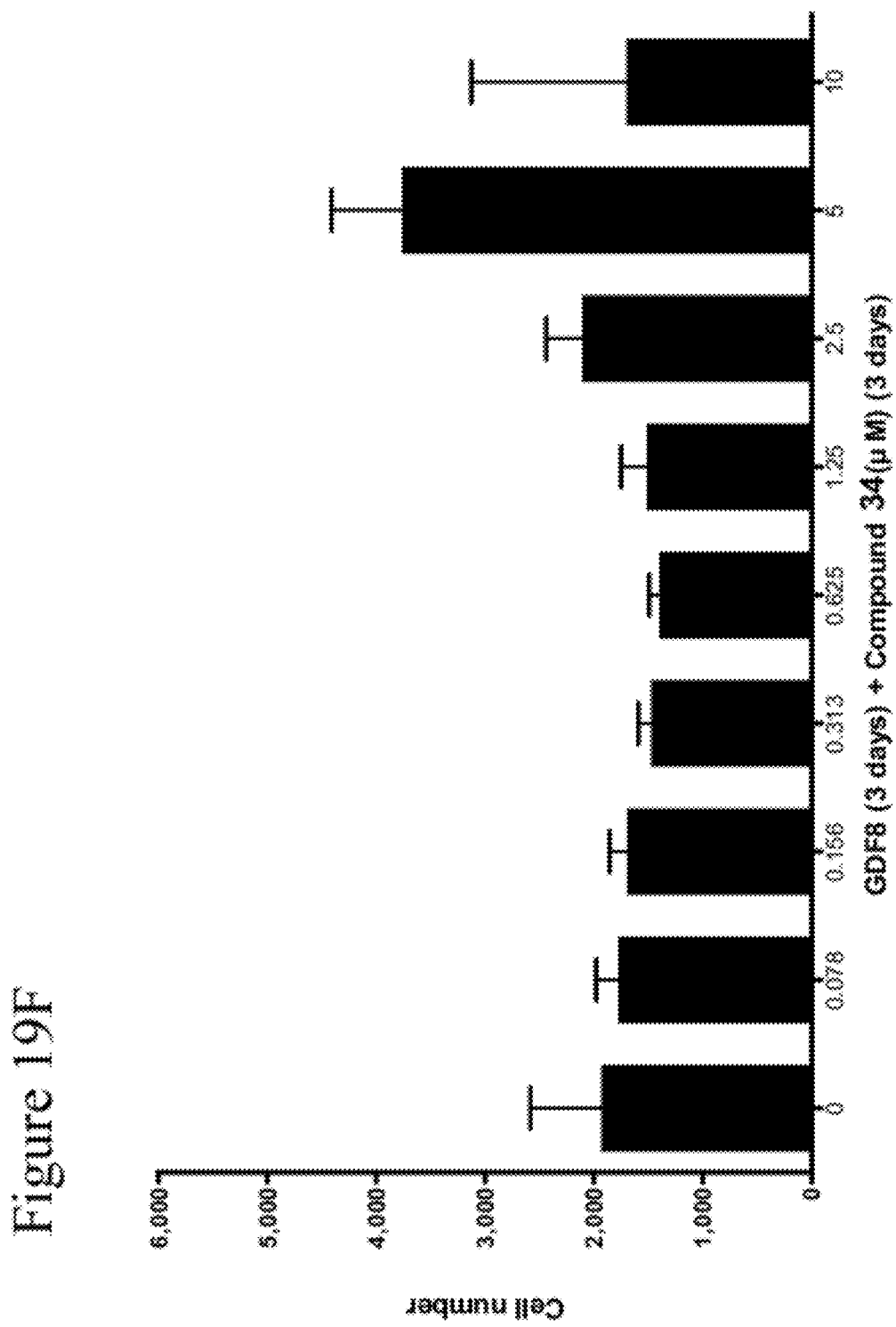
Figure 20A:
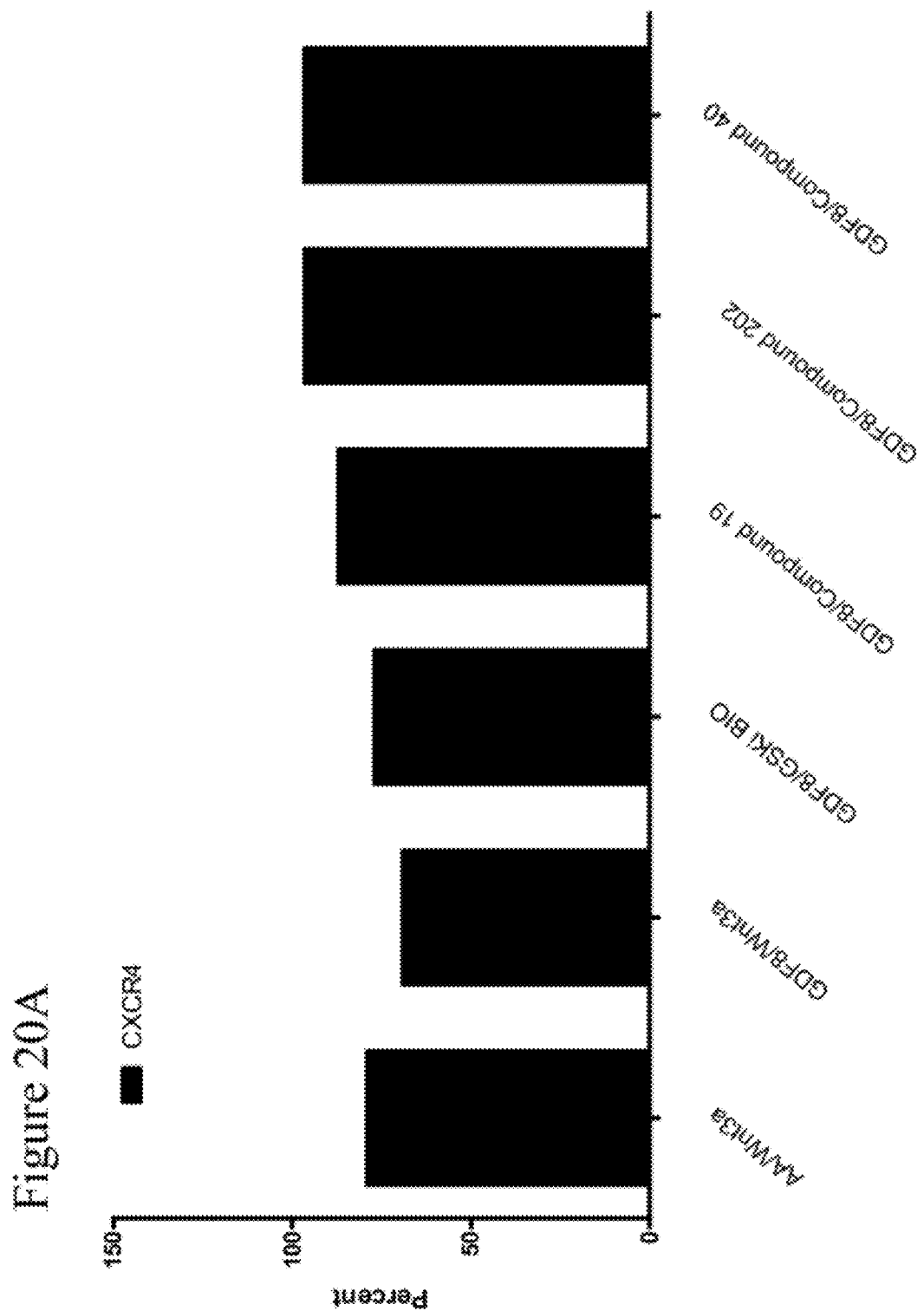
FIG. 20 shows the expression of various protein markers in cells throughout multiple steps of differentiation according to the methods described in Example 16. H1 cells were treated with 100 ng/ml activin A or 100 ng/ml GDF-8 for a total of three days in combination with 20 ng/ml Wnt3a for the first day or 2.5 µM various compounds (Compound 19, Compound 202, Compound 40, or GSK3 inhibitor BIO) added only on the first day.
Figure 20C:
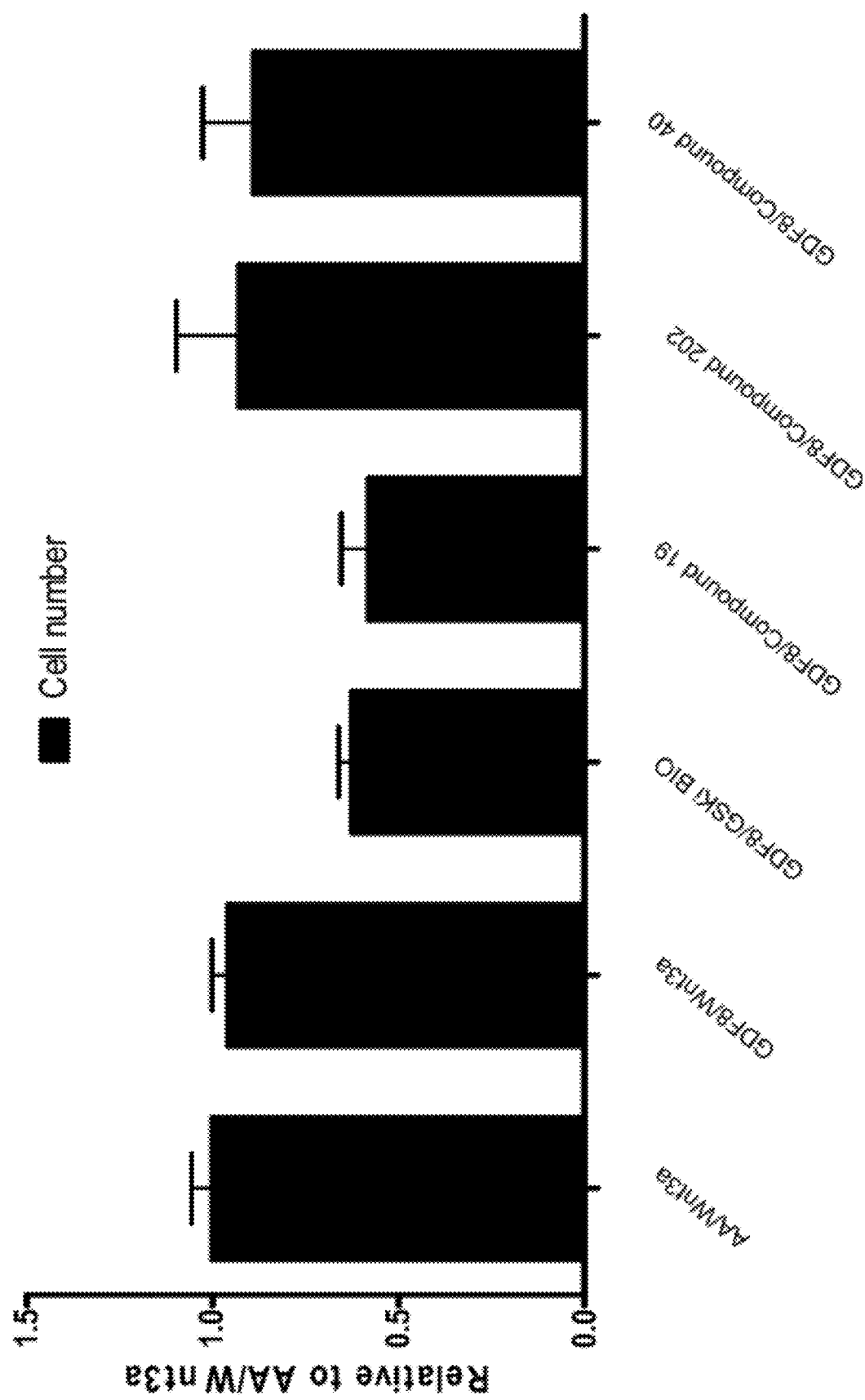
Figure 20D:
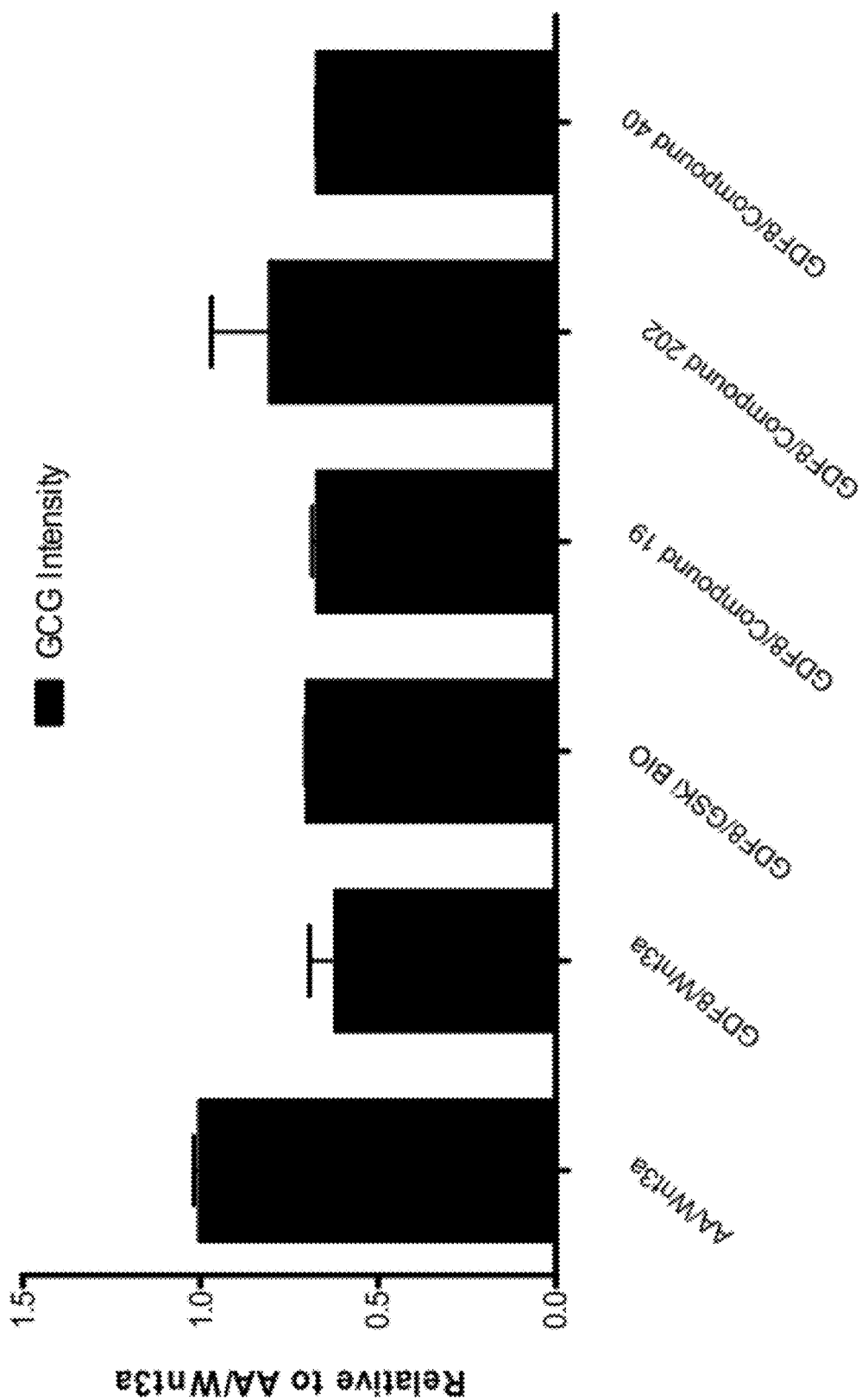
Figure 20E:
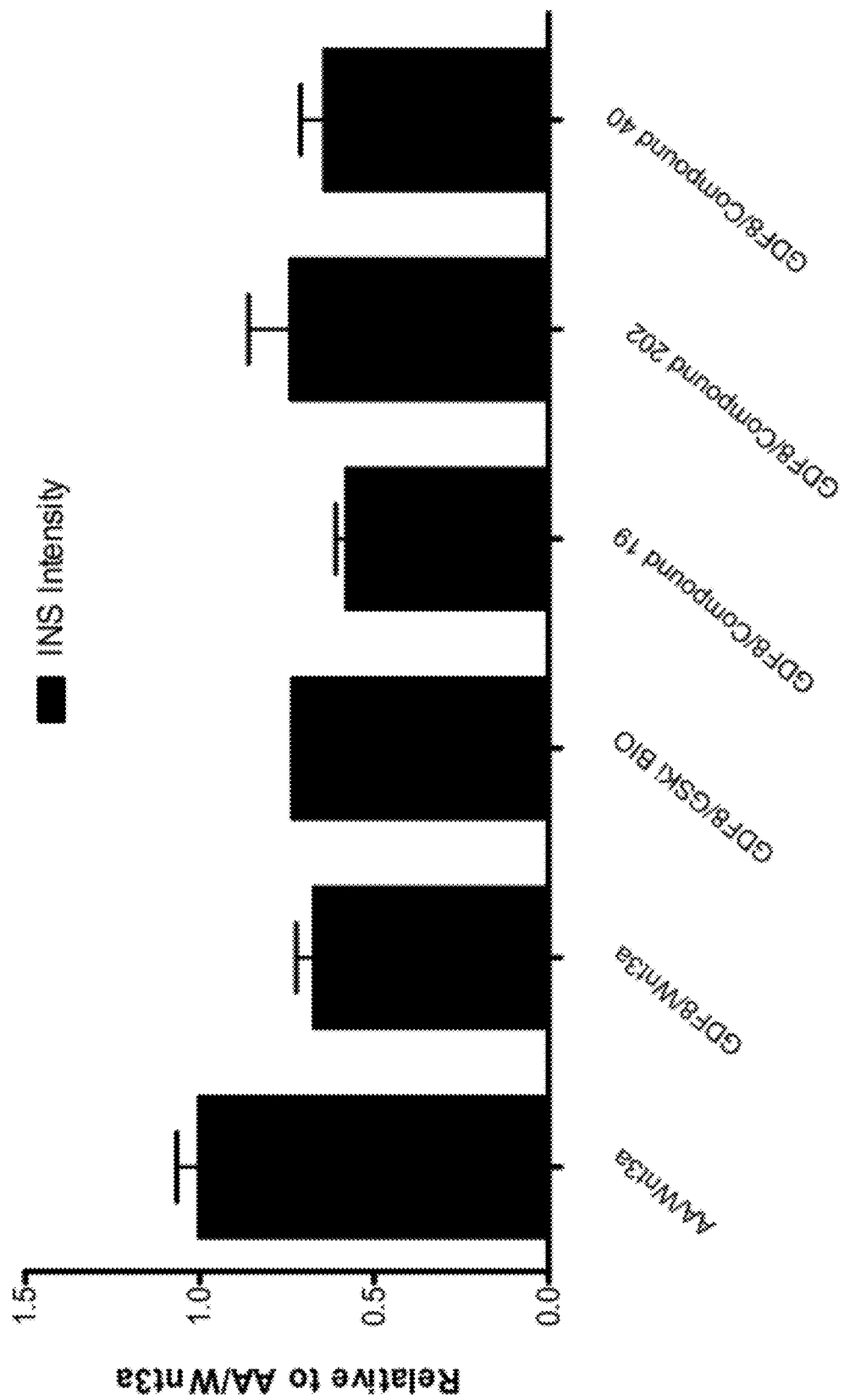
Figure 20F:
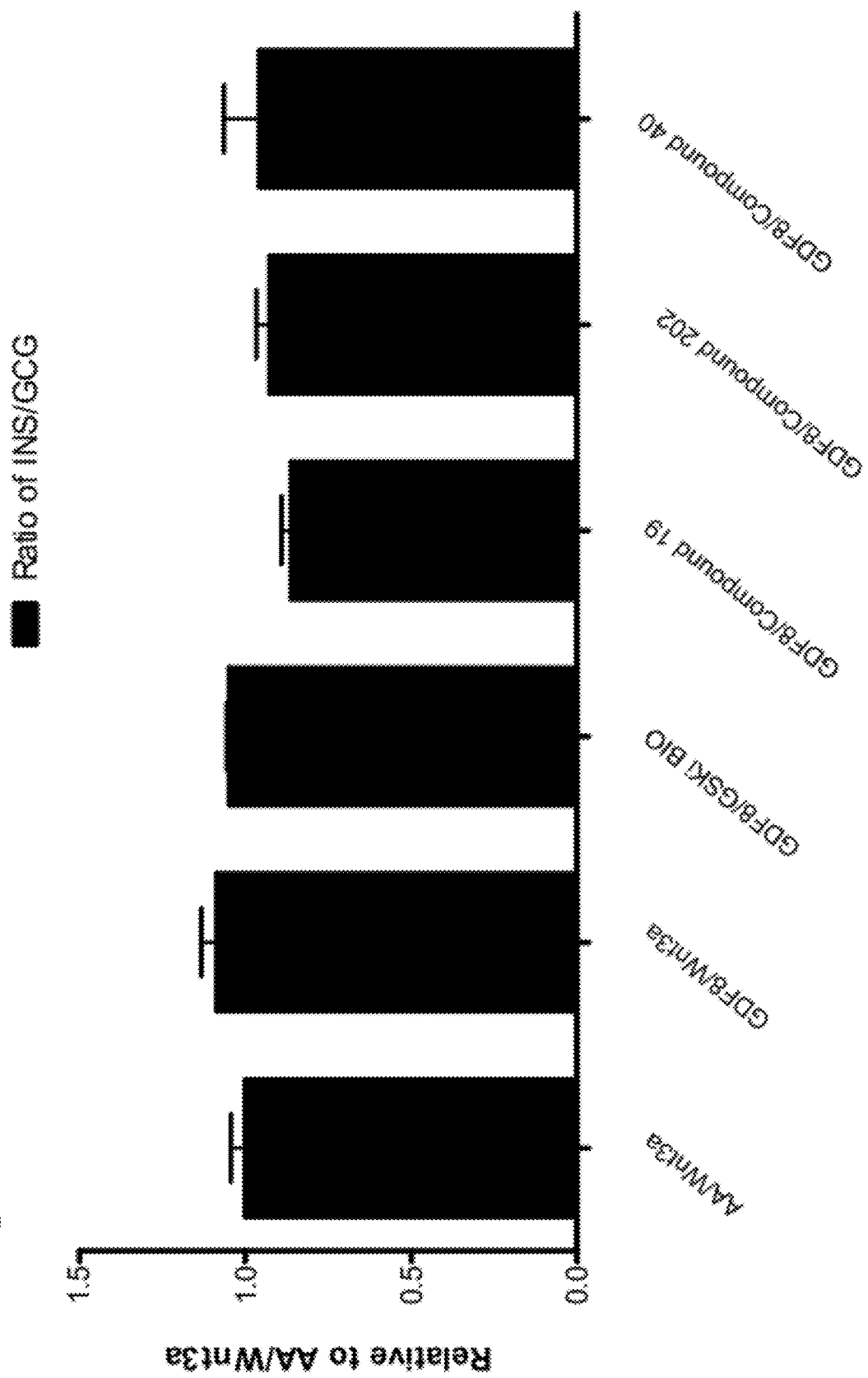

Results:

High content analysis results are shown for SOX17 expression in FIGS. 10-14 and resulting cell number at the conclusion of assay in FIGS. 15-19. In FIG. 10, results are shown for SOX17 expression resulting from control treatments using activin A or GDF-8, either alone or in combination with Wnt3a. Activin A treatments resulted in significantly higher SOX17 expression than was observed with GDF-8 treatment. Similarly, as seen in FIG. 15, activin A treatment resulted in a higher number of cells at the conclusion of assay than was seen with GDF-8 treatment, regardless of whether Wnt3a was present for one or three days during assay. Adding any of Compound 181, Compound 180, Compound 19, Compound 202, Compound 40, or Compound 34 with activin A treatment did not enhance SOX 17 expression (FIGS. 11-12) or increase cell numbers (FIGS. 17-18), regardless of whether the compound was present for one day at the initiation of assay or three days throughout the duration of assay. However, treatment with either Compound 181, Compound 180, Compound 19, Compound 202, Compound 40, or Compound 34 in combination with GDF-8 significantly improved SOX17 expression (FIGS. 13-14) and also enhanced cell numbers at the end of assay (FIGS. 18-19). When either Compound 181, Compound 180, Compound 19, Compound 202, Compound 40, or Compound 34 and GDF-8 were used in combination, the improvements to SOX17 expression and cell number in many cases were equivalent to results observed with activin A treatment. Improved differentiation in combination with GDF-8 was apparent in a dose titration effect for many of the compounds, although toxicity was sometimes observed at the highest concentrations. In most cases, optimal beneficial effects from treatment with the compound and GDF-8 were apparent with only one day of compound exposure at the initiation of assay. In some cases, presence of the compound throughout the duration of assay had no detrimental effect or had a slight beneficial effect. From these collective results an optimal working concentration range for each compound in combination with GDF8 treatment was determined. Results were compound specific, generally in the 1-10 µM range as tested in this assay.

Example 16

Cells Expressing Markers Characteristic of the Definitive Endoderm Lineage that were Formed without According to the Methods of the Present Invention are Able to Further Differentiate into Cells Expressing Markers Characteristic of the Pancreatic Endocrine Lineage Additional small molecules were tested in combination with GDF-8 for definitive endoderm differentiation. These included a commercial inhibitor of GSK3 as well as compounds of the present invention. A step-wise differentiation protocol was applied to cells treated with GDF-8 in combination with various small molecules. The efficacy of differentiation was determined by gene expression for biomarkers representative the pancreatic endoderm, or pancreatic endocrine lineages. A parallel control sample of cells treated with activin A and Wnt3a was maintained for comparison purposes throughout the step-wise differentiation process.

Preparation of Cells for Assay:

Stock cultures of human embryonic stem cells (H1 human embryonic stem cell line) were maintained in an undifferentiated, pluripotent state on reduced growth factor MATRIGEL™ (BD Biosciences; Cat #356231)-coated dishes in MEF conditioned medium with passage on average every four days. Passage was performed by exposing cell cultures to a solution of 1 mg/ml dispase (Invitrogen, Cat #: 17105-041) for 5 to 7 minutes at 37° C. followed by rinsing the monolayer with MEF conditioned culture medium and gentle scraping to recover cell clusters. Clusters were centrifuged at low speed to collect a cell pellet and remove residual dispase. Cell clusters were split at a 1:3 or 1:4 ratio for routine maintenance culture or a 1:1 ratio for immediate assay. All human embryonic stem cell lines were maintained at passage numbers less than 50 and routinely evaluated for normal karyotype and absence of mycoplasma.

Cell clusters were evenly resuspended in MEF conditioned medium supplemented with 8 ng/ml bFGF and plated onto reduced growth factor MATRIGEL-coated 24-well, black wall culture plates (Arctic White; Cat #AWLS-303012) in volumes of 0.5 ml/well. Daily feeding was conducted by aspirating spent culture medium from each well and replacing with an equal volume of fresh medium. Plates were maintained at 37° C., 5% $CO_2$ throughout the duration of assay.

Assay:

The assay was initiated by aspirating the culture medium from each well and adding back an aliquot (0.5 ml) of test medium. Test conditions for the first step of differentiation were conducted over a three-day period, feeding daily by aspirating and replacing the medium from each well with fresh test medium. On the first day of assay, 100 ng/ml activin A (PeproTech; Cat #120-14) or 100 ng/ml GDF-8 (R&D Systems, Cat #788-G8) was added to respective assay wells where each growth factor was diluted into RPMI-1640 medium (Invitrogen; Cat #: 22400) with 2% Albumin Bovine Fraction V, Fatty Acid Free (FAF BSA) (Proliant Inc. Cat #: SKU 68700), and 20 ng/ml Wnt3a (R&D Systems; Cat #1324-WN/CF). On the second day of assay, 100 ng/ml activin A or 100 ng/ml GDF-8 was diluted into RPMI-1640 medium supplemented with 2% FAF BSA without Wnt3a. In some test samples using GDF-8, Wnt3a was replaced with a small molecule compound, added only on the first day of definitive endoderm differentiation. These small molecules included Compound 19 (2.5 µM in assay), Compound 202 (2.5 µM in assay). Compound 40 (2.5 µM in assay), or a commercially available GSK3 inhibitor BIO (0.5 µM in assay) (EMD Chemicals, Inc.; Cat #361550). At the conclusion of the first step of differentiation, cells from some wells were harvested for flow cytometry analysis to evaluate levels of CXCR4, a marker of definitive endoderm formation. Additional wells were harvested for RT-PCR analysis to measure other markers of differentiation.

At the conclusion of the first step of definitive endoderm differentiation, replicate sets of parallel wells from each treatment group were subjected to further step-wise differentiation. It is important to note that after the first differentiation step, all wells undergoing subsequent culture and differentiation received the same treatment. The protocol for this continuing differentiation is described below.

Step 2 of the differentiation protocol was carried out over two days. Cells were fed daily by aspirating the medium from each well and replacing with a fresh aliquot (0.5 ml) of DMEM:F12 medium (Invitrogen; Cat #11330-032) containing 2% FAF BSA, 50 ng/ml FGF7 (PeproTech; Cat #100-19), and 250 nM cyclopamine-KAAD (Calbiochem; Cat #239804).

Step 3 of the differentiation protocol was carried out over seven days. Cells were fed daily by aspirating medium from each well and replacing with a fresh aliquot (0.5 ml) of DMEM-high glucose (Invitrogen; Cat #10569) supplemented with 0.1% Albumax (Invitrogen; Cat #: 11020-021), 0.5× Insulin-Transferrin-Selenium (ITS-X; Invitrogen; Cat #51500056), 50 ng/ml FGF7, 100 ng/ml Noggin (R&D Systems; Cat #3344-NG), 250 nM KAAD-cyclopamine, and 2 µM all-trans retinoic acid (RA) (Sigma-Aldrich; Cat #R2625). At the conclusion of the third step of differentiation, cells from some wells were harvested for analysis by RT-PCR to measure markers of differentiation. Other culture wells were subjected to high content image analysis for protein expression levels of Pdx1, and Cdx2.

Step 4 of the differentiation protocol was carried out over three days. Cells were fed daily by aspirating the medium from each well and replacing with a fresh aliquot (0.5 ml) of DMEM-high glucose supplemented with 0.1% Albumax, 0.5× Insulin-Transferrin-Selenium, 100 ng/ml Noggin, and 1 µM Alk 5 inhibitor (Axxora; Cat #ALX-270-445). At the conclusion of the fourth step of differentiation, cells from some wells were harvested for analysis by RT-PCR to measure markers of differentiation. Other culture wells were subjected to high content image analysis for protein expression levels of Pdx1.

Step 5 of the differentiation protocol was carried out over seven days in DMEM-high glucose with 0.1% Albumax, 0.5× Insulin-Transferrin-Selenium, and 1 µM Alk 5 inhibitor. Medium in each well was aspirated and replaced with a fresh aliquot (0.5 ml) on all days. At the conclusion of the fifth step of differentiation, cells from some wells were harvested for analysis by RT-PCR to measure markers of differentiation. Other culture wells were subjected to high content image analysis for protein expression levels of insulin and glucagon.

FACS Analysis:

Cells for FACS analysis were blocked in a 1:5 solution of 0.5% human gamma-globulin (Sigma; Cat #G-4386) in PBS (Invitrogen; Cat #14040-133): BD FACS staining buffer—BSA (BD; Cat #554657) for 15 minutes at 4° C. Cells were then stained with antibodies for CD9 PE (BD; Cat #555372), CD99 PE (Caltag; Cat #MHCD9904) and CXCR4 APC (R&D Systems; Cat# FAB173A) for 30 minutes at 4° C. After a series of washes in BD FACS staining buffer, the cells were stained for viability with 7-AAD (BD; Cat #559925) and run on a BD FACSArray. A mouse IgG1K Isotype control antibody for both PE and APC was used to gate percent positive cells.

RT-PCR Analysis:

RNA samples were purified by binding to a silica-gel membrane (Rneasy Mini Kit, Qiagen, CA) in the presence of an ethanol-containing, high-salt buffer followed by washing to remove contaminants. The RNA was further purified using a TURBO DNA-free kit (Ambion, INC), and high-quality RNA was then eluted in water. Yield and purity were assessed by A260 and A280 readings on a spectrophotometer. CDNA copies were made from purified RNA using an ABI (ABI, CA) high capacity cDNA archive kit.

Unless otherwise stated, all reagents were purchased from Applied Biosystems. Real-time PCR reactions were performed using the ABI PRISM® 7900 Sequence Detection System. TAQMAN® UNIVERSAL PCR MASTER MIX® (ABI, CA) was used with 20 ng of reverse transcribed RNA in a total reaction volume of 20 µl. Each cDNA sample was run in duplicate to correct for pipetting errors. Primers and FAM-labeled TAQMAN® probes were used at concentrations of 200 nM. The level of expression for each target gene was normalized using a human glyceraldehyde-3-phosphate dehydrogenase (GAPDH) endogenous control previously developed by Applied Biosystems. Primer and probe sets are listed in Table 12. After an initial incubation at 50° C. for 2 min followed by 95° C. for 10 min, samples were cycled 40 times in two stages—a denaturation step at 95° C. for 15 sec followed by an annealing/extension step at 60° C. for 1 min. Data analysis was carried out using GENEAMP®7000 Sequence Detection System software. For each primer/probe set, a Ct value was determined as the cycle number at which the fluorescence intensity reached a specific value in the middle of the exponential region of amplification. Relative gene expression levels were calculated using the comparative Ct method. Briefly, for each cDNA sample, the endogenous control Ct value was subtracted from the gene of interest Ct to give the delta Ct value ($\Delta$Ct). The normalized amount of target was calculated as 2-$\Delta$Ct, assuming amplification to be 100% efficiency. Final data were expressed relative to a calibrator sample.

High Content Analysis:

At the conclusion of culture, assay plates were washed once with PBS (Invitrogen; Cat #14190), fixed with 4% paraformaldehyde (Alexis Biochemical; Cat # ALX-350-011) at room temperature for 20 minutes, then washed three times with PBS and permeabilized with 0.5% Triton X-100 (Sigma; Cat #T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; Cat # AF1924) was diluted 1:100 in 4% chicken serum and added to each well for two hours at room temperature. After washing three times with PBS, Alexa Fluor 488 conjugated secondary antibody (chicken anti-goat IgG; Invitrogen; Cat #A21467) diluted 1:200 in PBS was added to each well. To counterstain nuclei, 5 µg/ml Hoechst 33342 (Invitrogen; Cat #1-13570) was added for fifteen minutes at room temperature. Plates were washed once with PBS and left in 100 µl/well PBS for imaging. Other primary antibodies used for analysis included 1:200 dilution rabbit anti-human insulin (Cell Signaling; Cat # C27C9), and 1:1500 dilution mouse anti-human glucagon (Sigma-Aldrich; Cat #G2654). Secondary antibodies used for analysis included 1:1000 dilution Alexa Fluor 647 chicken anti-rabbit IgG (Invitrogen; Cat #A21443), and 1:1000 dilution Alexa Fluor 488 chicken anti-mouse IgG (Invitrogen; Cat #A21200).

Imaging was performed using an IN Cell Analyzer 1000 (GE Healthcare) utilizing the 51008bs dichroic for cells stained with Hoechst 33342 and Alexa Fluor 488. Images were acquired from 25 fields per well. Measurements for total intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total protein expression was reported as total intensity or integrated intensity, defined as total fluorescence of the cell multiplied by the area of the cell. Background was eliminated based on acceptance criteria for gray-scale ranges between 200 and 4500. Total intensity data were normalized by dividing total intensities for each well by the average total intensity for the positive control.

PCR results for representative differentiation markers are shown in Table 14 for cells harvested from each step of differentiation. Samples treated with GDF-8 and Wnt3a or with GDF-8 and a small molecule showed similar expression levels of markers associated with endodermal and endocrine differentiation.

FIG. 20, panel A shows FACS analysis for the definitive endoderm marker, CXCR4, after the first step of differentiation. Treatment of human embryonic stem cells with GDF-8 and Wnt3a yielded a similar percentage of CXCR4 positive cells compared to treatment with activin A and Wnt3a. Treatment of human embryonic stem cells with GDF-8 and a compound of the present invention (Compound 19, Compound 202, Compound 40, or GSK3 inhibitor IX BIO) also yielded an equivalent or slightly higher percentage of CXCR4 positive cells. FIG. 20, panel B shows high content image analysis for normalized SOX17 protein expression in human embryonic stem cells after three days differentiation to definitive endoderm. In some cases, treatment with GDF-8 resulted in a lower cell number at the conclusion of the first step of differentiation. However, GDF-8 treatment in combination with Wnt3a or with the small molecule inhibitors clearly induced expression of SOX17, a marker of definitive endoderm. In one instance, treatment with GDF-8 and Compound 40 yielded cell numbers in culture and SOX17 expression equivalent to treatment with activin A and Wnt3a.

FIG. 20, panel C shows high content image analysis for relative cell numbers recovered from cultures treated through differentiation step 5. As observed earlier at the end of step 1, some treatments caused a drop in cell recovery relative to treatment with activin A and Wnt3a. This decrease in cell number was seen specifically with treatment groups using GDF-8 with GSK3 inhibitor BIO and also using GDF-8 with Compound 19. Additional GDF-8 treatment groups had cell recoveries similar to treatment with activin A and Wnt3a. In FIG. 20, panels D-F, normalized protein levels of insulin and glucagon are shown, along with their respective ratio for each treatment group. Similar levels of insulin and glucagon could be obtained with each of the GDF-8 treatments relative to treatment with activin A and Wnt3a, demonstrating that GDF-8, in combination with Wnt3a or a small molecule, can substitute for activin A during definitive endoderm differentiation and subsequent pancreatic endoderm and endocrine differentiation.

Example 17

Cells Expressing Markers Characteristic of the Definitive Endoderm Lineage that were Formed Using GDF-8 and a Compound of the Present Invention are Able to Further Differentiate into Cells Expressing Markers Characteristic of the Pancreatic Endocrine Lineage Additional small molecules were tested in combination with GDF-8 and activin A for definitive endoderm differentiation. These included a commercial inhibitor of GSK3 as well as the compounds of the present invention. A step-wise differentiation protocol was applied to cells treated with GDF-8 in combination with various small molecules. The efficacy of differentiation was determined by gene expression for biomarkers representative of the pancreatic endoderm and pancreatic endocrine lineages. A parallel control sample of cells treated with activin A and Wnt3a was maintained for comparison purposes throughout the step-wise differentiation process.

Preparation of Cells for Assay:

Stock cultures of human embryonic stem cells (H1 human embryonic stem cell line) were maintained in an undifferentiated, pluripotent state on reduced growth factor MATRIGEL™ (BD Biosciences; Cat #356231)-coated dishes in MEF conditioned medium supplemented with 8 ng/ml bFGF (PeproTech Inc.; Cat #100-18B) with passage on average every four days. Passage was performed by exposing cell cultures to a solution of 1 mg/ml dispase (Invitrogen; Cat #17105-041) for 5 to 7 minutes at 37° C. followed by rinsing the monolayer with MEF conditioned culture medium and gentle scraping to recover cell clusters. Clusters were centrifuged at low speed to collect a cell pellet and remove residual dispase. Cell clusters were split at a 1:3 or 1:4 ratio for routine maintenance culture or a 1:1 ratio for immediate assay. All human ES cell lines were maintained at passage numbers less than 50 and routinely evaluated for normal karyotype and absence of mycoplasma.

Cell clusters were evenly resuspended in MEF conditioned medium supplemented with 8 ng/ml bFGF and plated onto reduced growth factor MATRIGEL™-coated 24-well, black wall culture plates (Arctic White; Cat #AWLS-303012) in volumes of 0.5 ml/well. Daily feeding was conducted by aspirating spent culture medium from each well and replacing with an equal volume of fresh medium. Plates were maintained at 37° C., 5% $CO_2$ throughout assay.

Assay:

The assay was initiated by aspirating the culture medium from each well and adding back an aliquot (0.5 ml) of test medium. Test conditions for the first step of differentiation were conducted over a three-day period, feeding daily by aspirating and replacing the medium from each well with fresh test medium. On the first day of assay, 100 ng/ml activin A (PeproTech; Cat #120-14) or 100 ng/ml GDF-8 (R&D Systems, Cat #788-G8) was added to respective assay wells where each growth factor was diluted into RPMI-1640 medium (Invitrogen; Cat #: 22400) with 2% Albumin Bovine Fraction V, Fatty Acid Free (FAF BSA) (MP Biomedicals, Inc; Cat #152401). In some samples, 20 ng/ml Wnt3a (R&D Systems; Cat #1324-WN/CF) was also included. On the second day of assay, 100 ng/ml activin A or 100 ng/ml GDF-8 was diluted into RPMI-1640 medium supplemented with 2% FAF BSA, omitting Wnt3a from all samples. In some test samples using GDF-8, Wnt3a was replaced with a given concentration of small molecule compound, added only on the first day of definitive endoderm differentiation. These small molecules included: Compound 181 (1.25 µM in assay), Compound 180 (2.5 µM in assay), Compound 19 (10 µM in assay), Compound 202 (2.5 µM in assay), Compound 40 (5 µM in assay), Compound 34 (2.5 µM in assay), Compound 206 (2.5 µM in assay), and a commercially available GSK3 inhibitor IX BIO (10 µM in assay) (EMD Chemicals, Inc.; Cat #361550). At the conclusion of the first step of differentiation, cells from some wells were harvested for flow cytometry analysis to evaluate levels of CXCR4, a marker of definitive endoderm formation. Additional wells were harvested for RT-PCR analysis to measure other markers of differentiation.

At the conclusion of the first step of definitive endoderm differentiation, replicate sets of parallel wells from each treatment group were subjected to further step-wise differentiation. It is important to note that after the first differentiation step, all wells undergoing subsequent culture and differentiation received the same treatment. The protocol for this continuing differentiation is described below.

Step 2 of the differentiation protocol was carried out over two days. Cells were fed daily by aspirating the medium from each well and replacing with a fresh aliquot (0.5 ml) of DMEM:F12 medium (Invitrogen; Cat #11330-032) containing 2% FAF BSA, 50 ng/ml FGF7 (PeproTech; Cat #100-19), and 250 nM cyclopamine-KAAD (Calbiochem; Cat #239804).

Step 3 of the differentiation protocol was carried out over four days. Cells were fed daily by aspirating medium from each well and replacing with a fresh aliquot (0.5 ml) of DMEM-high glucose (Invitrogen; Cat #10569) supplemented with 0.1% Albumax (Invitrogen; Cat #: 11020-021), 0.5× Insulin-Transferrin-Selenium (ITS-X; Invitrogen; Cat #51500056), 50 ng/ml FGF7, 100 ng/ml Noggin (R&D Systems; Cat #3344-NG), 250 nM KAAD-cyclopamine, and 2 µM all-trans retinoic acid (RA) (Sigma-Aldrich; Cat #R2625). At the conclusion of the third step of differentiation, cells from some wells were harvested for analysis by RT-PCR to measure markers of differentiation.

Step 4 of the differentiation protocol was carried out over three days. Cells were fed daily by aspirating the medium from each well and replacing with a fresh aliquot (0.5 ml) of DMEM-high glucose supplemented with 0.1% Albumax, 0.5× Insulin-Transferrin-Selenium, 100 ng/ml Noggin, and MM Alk 5 inhibitor (Axxora; Cat 1/ALX-270-445). At the conclusion of the fourth step of differentiation, cells from some wells were harvested for analysis by RT-PCR to measure markers of differentiation.

Step 5 of the differentiation protocol was carried out over seven days in DMEM-high glucose with 0.1% Albumax, 0.5× Insulin-Transferrin-Selenium, and 1 µM Alk 5 inhibitor. Medium in each well was aspirated and replaced with a fresh aliquot (0.5 ml) on all days. At the conclusion of the fifth step of differentiation, cells from some wells were harvested for analysis by RT-PCR to measure markers of differentiation. Other culture wells were subjected to high content image analysis for protein expression levels of insulin and glucagon.

FACS Analysis:

Cells for FACS analysis were blocked in a 1:5 solution of 0.5% human gamma-globulin (Sigma; Cat# G-4386) in PBS (Invitrogen; Cat #14040-133): BD FACS staining buffer—BSA (BD; Cat #554657) for 15 minutes at 4° C. Cells were then stained with antibodies for CD9 PE (BD; Cat #555372), CD99 PE (Caltag; Cat #MHCD9904) and CXCR4 APC (R&D Systems; Cat# FAB173A) for 30 minutes at 4° C. After a series of washes in BD FACS staining buffer, the cells were stained for viability with 7-AAD (BD; Cat

559925) and run on a BD FACSArray. A mouse IgG1K Isotype control antibody for both PE and APC was used to gate percent positive cells.

RT-PCR Analysis:

RNA samples were purified by binding to a silica-gel membrane (Rneasy Mini Kit, Qiagen, CA) in the presence of an ethanol-containing, high-salt buffer followed by washing to remove contaminants. The RNA was further purified using a TURBO DNA-free kit (Ambion, INC), and high-quality RNA was then eluted in water. Yield and purity were assessed by A260 and A280 readings on a spectrophotometer. CDNA copies were made from purified RNA using an ABI (ABI, CA) high capacity cDNA archive kit.

Unless otherwise stated, all reagents were purchased from Applied Biosystems. Real-time PCR reactions were performed using the ABI PRISM® 7900 Sequence Detection System. TAQMAN® UNIVERSAL PCR MASTER MIX® (ABI, CA) was used with 20 ng of reverse transcribed RNA in a total reaction volume of 20 µl. Each cDNA sample was run in duplicate to correct for pipetting errors. Primers and FAM-labeled TAQMAN® probes were used at concentrations of 200 nM. The level of expression for each target gene was normalized using a human glyceraldehyde-3-phosphate dehydrogenase (GAPDH) endogenous control previously developed by Applied Biosystems. Primer and probe sets are listed in Table 12. After an initial incubation at 50° C. for 2 min followed by 95° C. for 10 min, samples were cycled 40 times in two stages—a denaturation step at 95° C. for 15 sec followed by an annealing/extension step at 60° C. for 1 min. Data analysis was carried out using GENEAMP®7000 Sequence Detection System software. For each primer/probe set, a Ct value was determined as the cycle number at which the fluorescence intensity reached a specific value in the middle of the exponential region of amplification. Relative gene expression levels were calculated using the comparative Ct method. Briefly, for each cDNA sample, the endogenous control Ct value was subtracted from the gene of interest Ct to give the delta Ct value ($\Delta$Ct). The normalized amount of target was calculated as 2-$\Delta$Ct, assuming amplification to be 100% efficiency. Final data were expressed relative to a calibrator sample.

High Content Analysis:

At the conclusion of culture, assay plates were washed once with PBS (Invitrogen; Cat #14190), fixed with 4% paraformaldehyde (Alexis Biochemical; Cat # ALX-350-011) at room temperature for 20 minutes, then washed three times with PBS and permeabilized with 0.5% Triton X-100 (Sigma; Cat #T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; Cat # AF1924) was diluted 1:100 in 4% chicken serum and added to each well for two hours at room temperature. After washing three times with PBS, Alexa Fluor 488 conjugated secondary antibody (chicken anti-goat IgG; Invitrogen; Cat #A21467) diluted 1:200 in PBS was added to each well. To counterstain nuclei, 5 µg/ml Hoechst 33342 (Invitrogen; Cat # H3570) was added for fifteen minutes at room temperature. Plates were washed once with PBS and left in 100 µl/well PBS for imaging. Other primary antibodies used for analysis included 1:100 dilution mouse anti-human CDX2 (Invitrogen; Cat #397800), 1:100 dilution goat anti-human Pdx1 (Santa Cruz Biotechnology; Cat # SC-14664), 1:200 dilution rabbit anti-human insulin (Cell Signaling; Cat # C27C9), and 1:1500 dilution mouse anti-human glucagon (Sigma-Aldrich; Cat # G2654). Secondary antibodies used for analysis included 1:400 dilution Alexa Fluor 647 chicken anti-mouse IgG (Invitrogen; Cat #A-21463), 1:200 dilution Alexa Fluor 488 donkey anti-goat IgG (Invitrogen; Cat #A11055), 1:1000 dilution Alexa Fluor 647 chicken anti-rabbit IgG (Invitrogen; Cat #A21443), and 1:1000 dilution Alexa Fluor 488 chicken anti-mouse IgG (Invitrogen; Cat #A21200).

Imaging was performed using an IN Cell Analyzer 1000 (GE Healthcare) utilizing the 51008bs dichroic for cells stained with Hoechst 33342 and Alexa Fluor 488. Images were acquired from 25 fields per well. Measurements for total intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total protein expression was reported as total intensity or integrated intensity, defined as total fluorescence of the cell multiplied by the area of the cell. Background was eliminated based on acceptance criteria for gray-scale ranges between 200 and 4500. Total intensity data were normalized by dividing total intensities for each well by the average total intensity for the positive control.

Results:

Results for representative differentiation markers are shown in FIG. 21 and Table 15 for cells harvested from each step of differentiation. In FIGS. 21A and B, flow cytometric results for CXCR4 are shown for various treatments during the first step of definitive endoderm differentiation. FIG. 21A shows the effects on CXCR4 expression from treatment with various compounds in combination with activin A. FIG. 21B shows the effects on CXCR4 from treatment with various compounds in combination with GDF-8. Compounds of the present invention in combination with activin A did not enhance CXCR4 expression. However, all of the compounds of the present invention tested in this Example enhanced CXCR4 expression in combination with GDF-8.

Figure 21A:
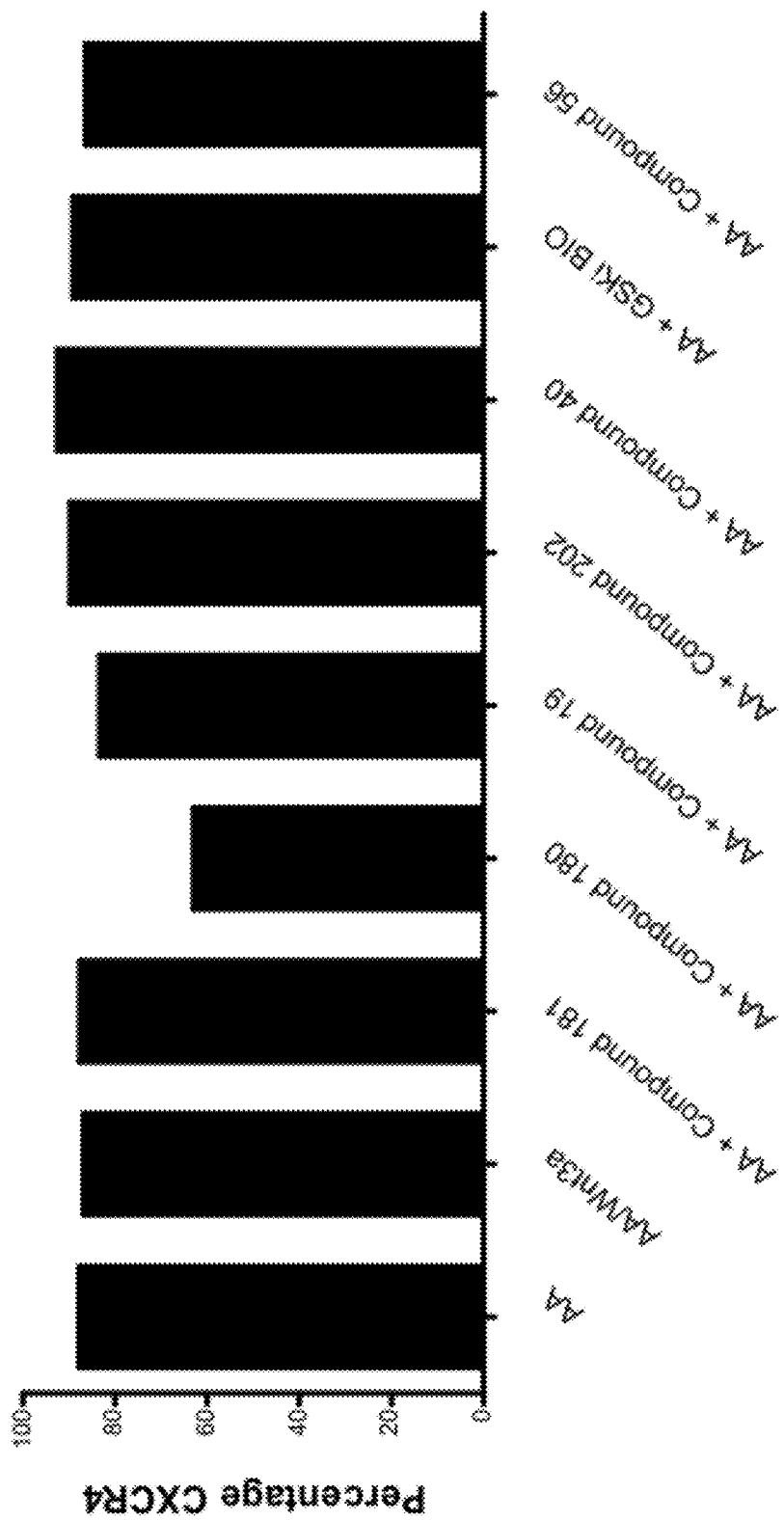
FIG. 21 shows the expression of various protein and RT-PCR markers in cells throughout multiple steps of differentiation according to the methods described in Example 17. H1 cells were treated with 100 ng/ml activin A or 100 ng/ml GDF-8 for a total of three days in combination with 20 ng/ml Wnt3a for the first day or various compounds at the following concentrations (Compound 181, Compound 180, Compound 19, Compound 202, Compound 40, Compound 56, or GSK3 inhibitor BIO) added only on the first day. FACS analysis for the definitive endoderm marker, CXCR4, is shown in cells after the first step of differentiation where treatment combined activin A (Panel A) or GDF-8 (Panel B) with Wnt3a or various compounds. CXCR4 expression was measured using a fluorescent antibody probe and flow cytometry, yielding the percentages of positive cells as shown. In subsequent panels of FIG. 21, normalized RT-PCR values for various differentiation markers are shown with respective treatments using activin A or GDF-8 during the first step of differentiation as follows: markers at the end of step one of differentiation for treatments combining activin A (Panel C) or GDF-8 (Panel D); markers at the end of step three of differentiation for treatments combining activin A (Panel E) or GDF-8 (Panel F); markers at the end of step four of differentiation for treatments combining activin A (Panel G) or GDF-8 (Panel H); markers at the end of step five of differentiation for treatments combining activin A (Panel I) or GDF-8 (Panel J). At the conclusion of step five of differentiation, high content analysis was performed to measure recovered cell numbers for corresponding treatments during the first step of differentiation using activin A (Panel K) or GDF-8 (Panel M). High content analysis was also used to measure glucagon and insulin intensity in recovered cell populations at the end of step five of differentiation, corresponding to treatment with activin A (Panel L) or GDF-8 (Panel N) during the first step of differentiation.
Figure 21B:
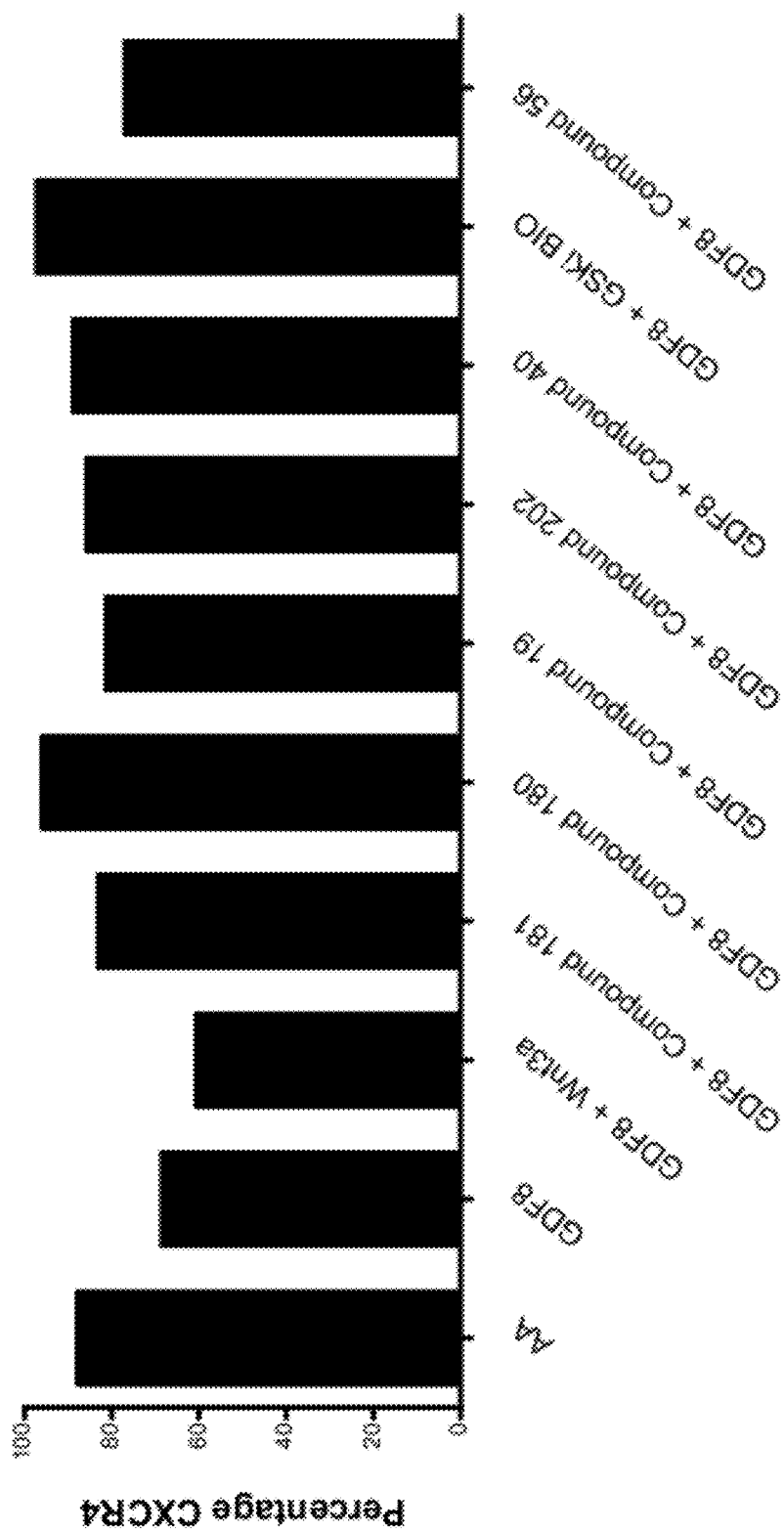
Figure 21D:
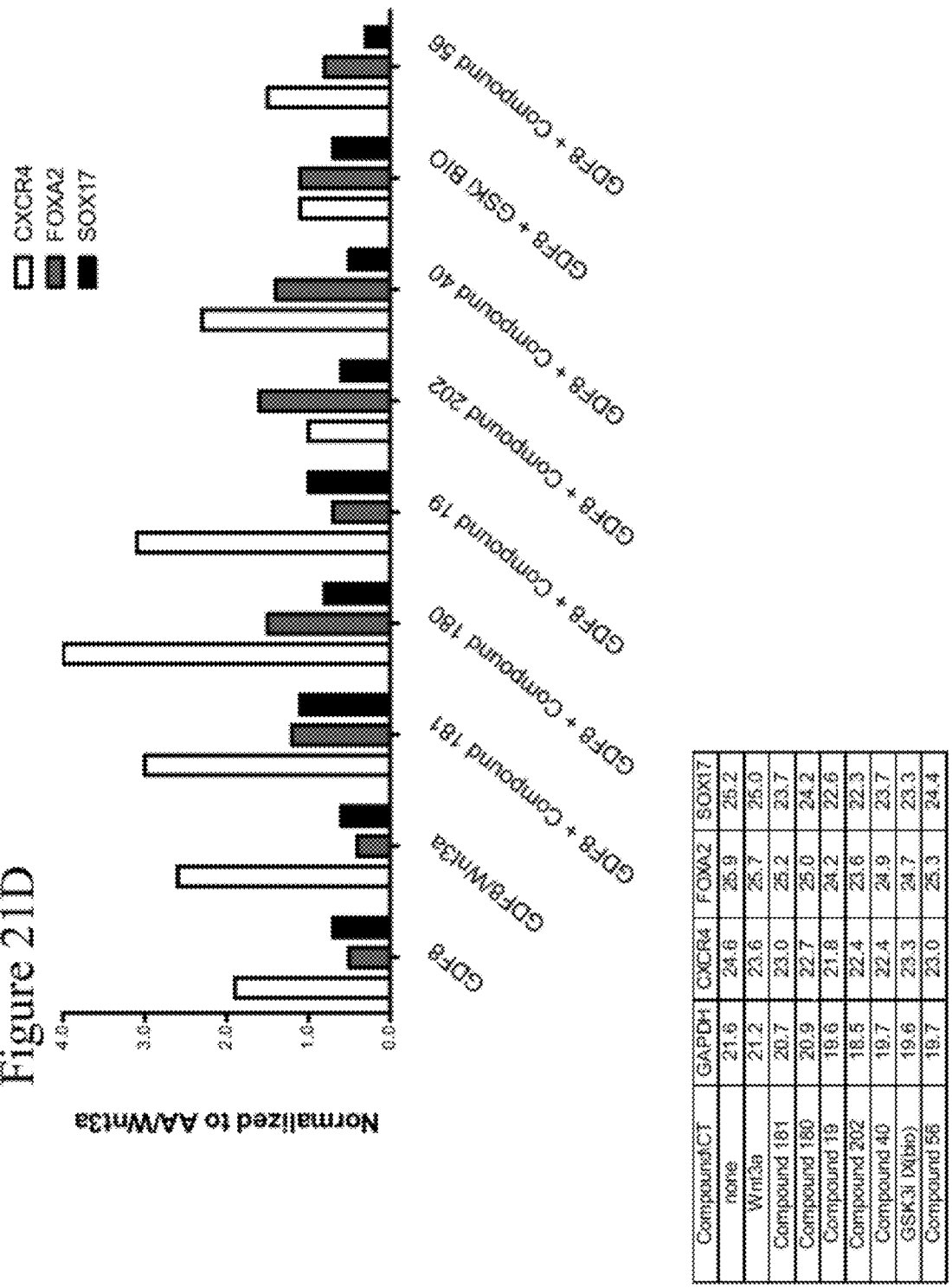
Figure 21E:
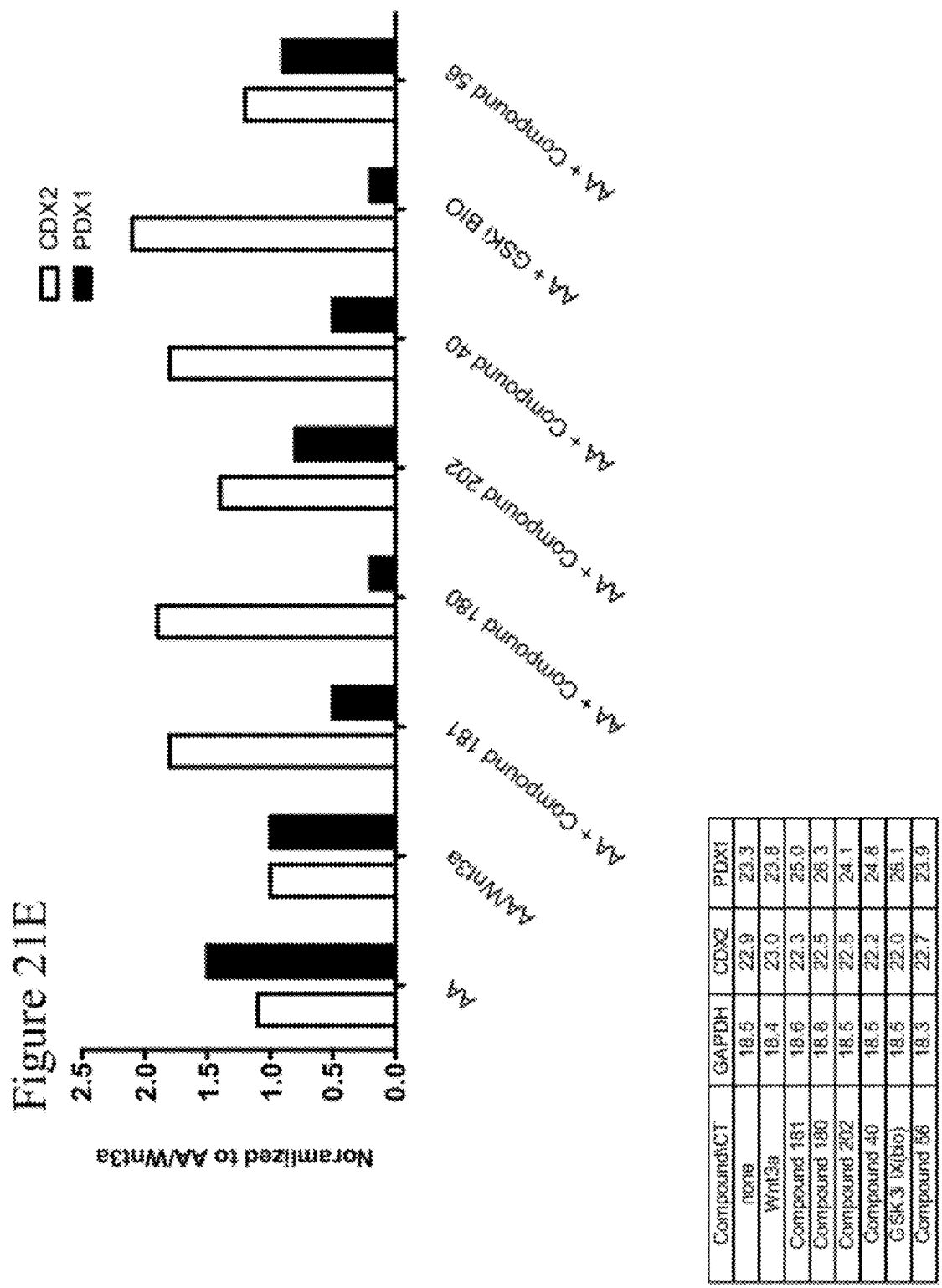
Figure 21F:
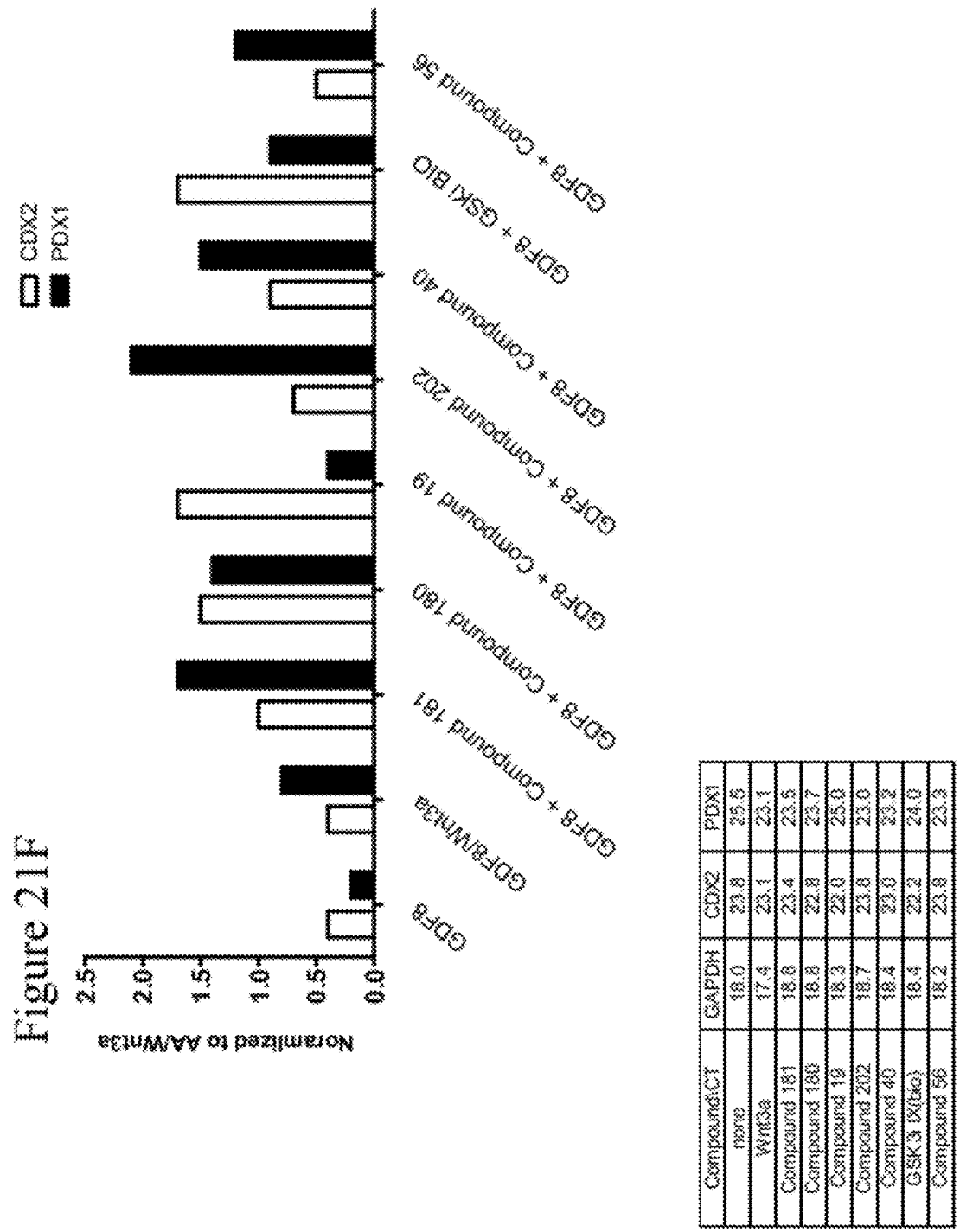
Figure 21H:
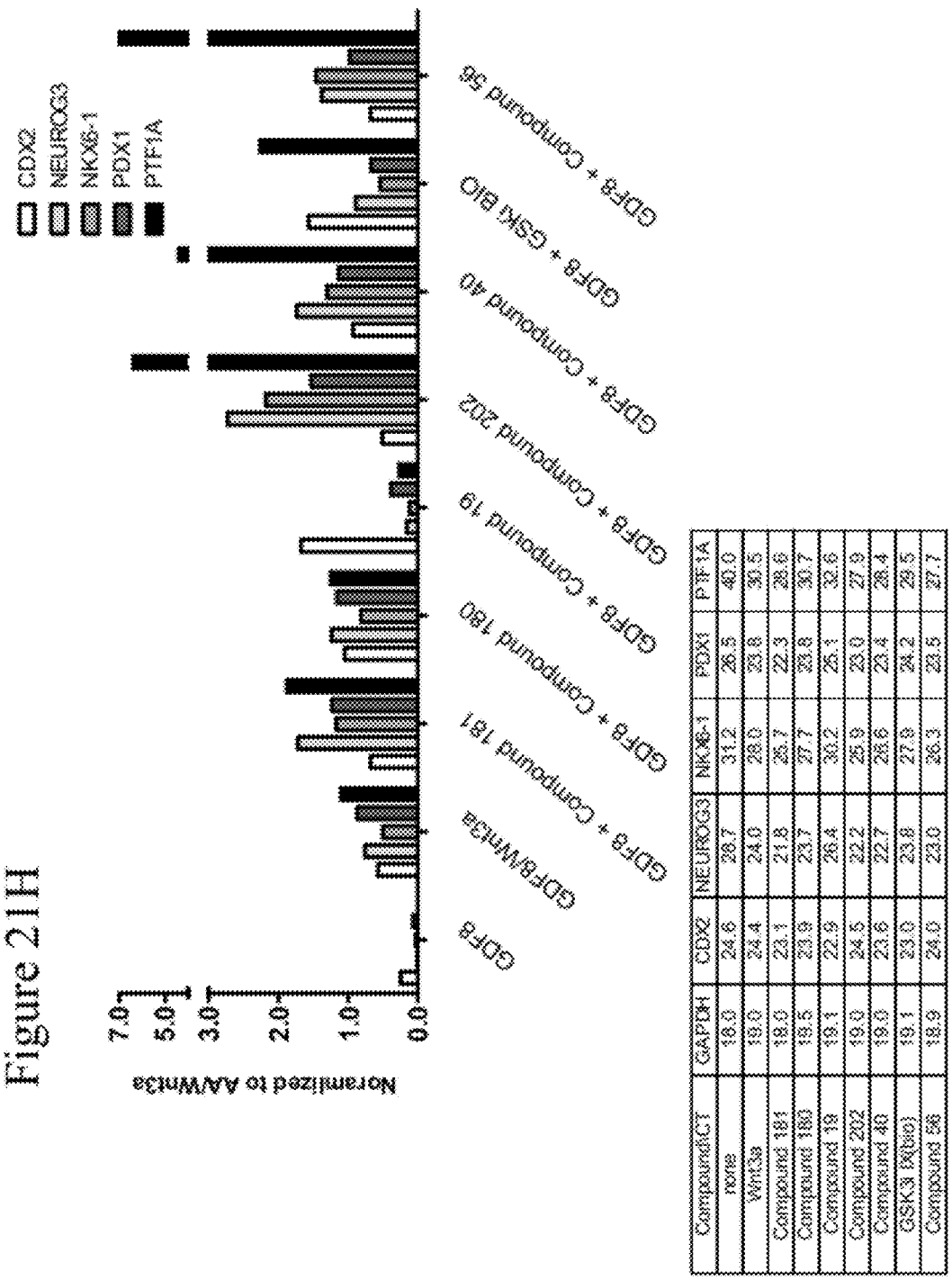
Figure 21I:
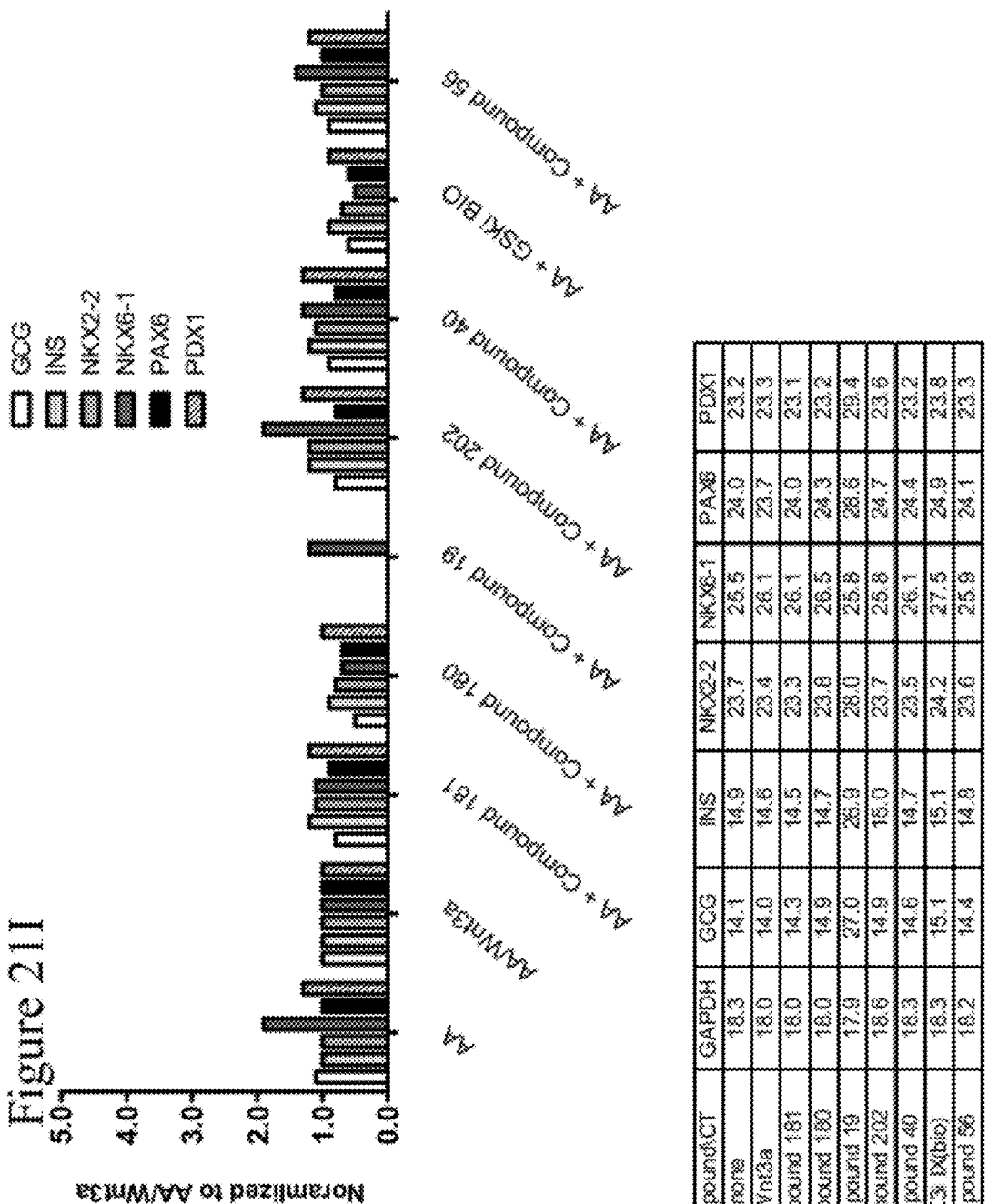
Figure 21J:
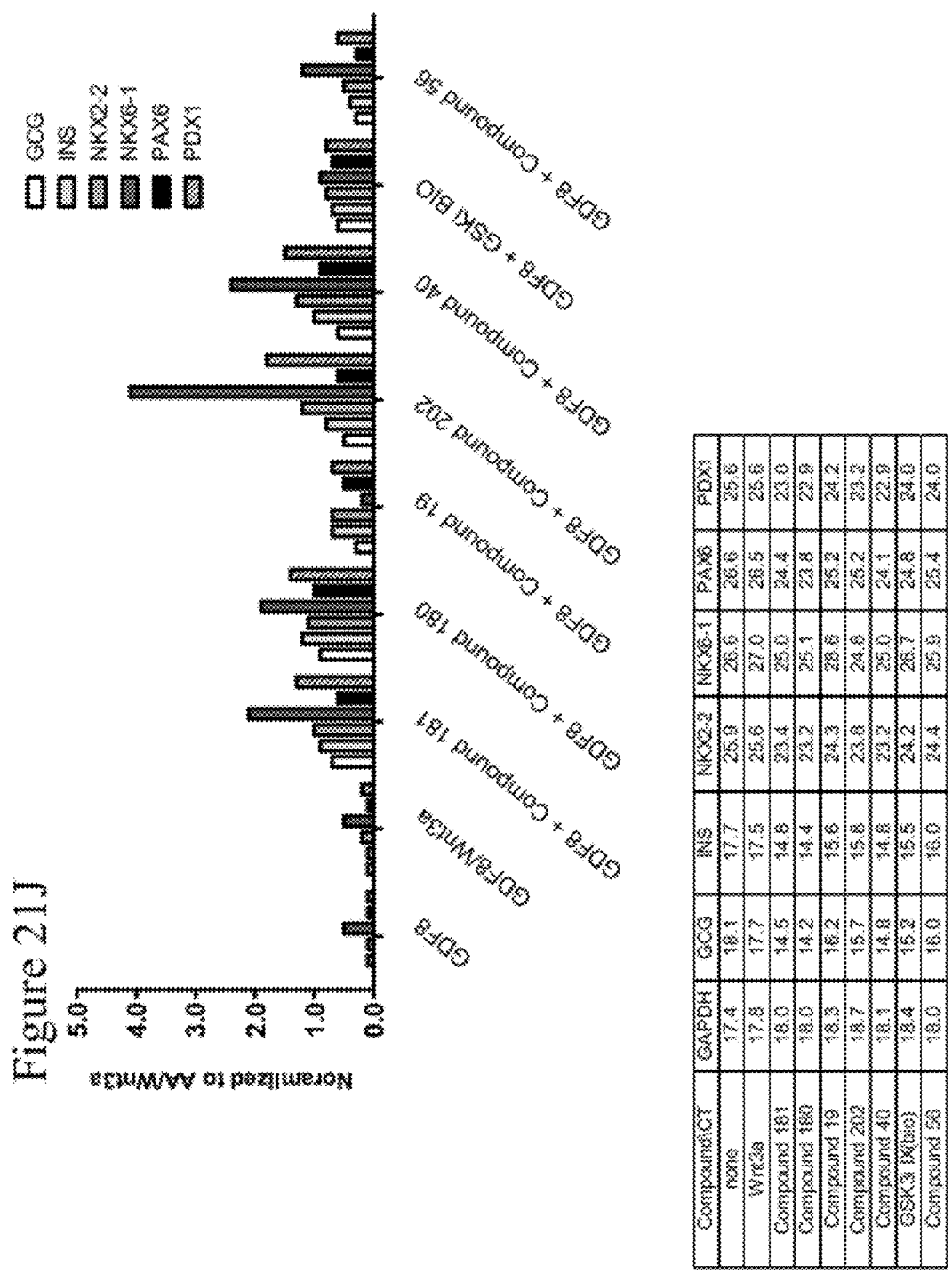
Figure 21K:
Figure 21L:
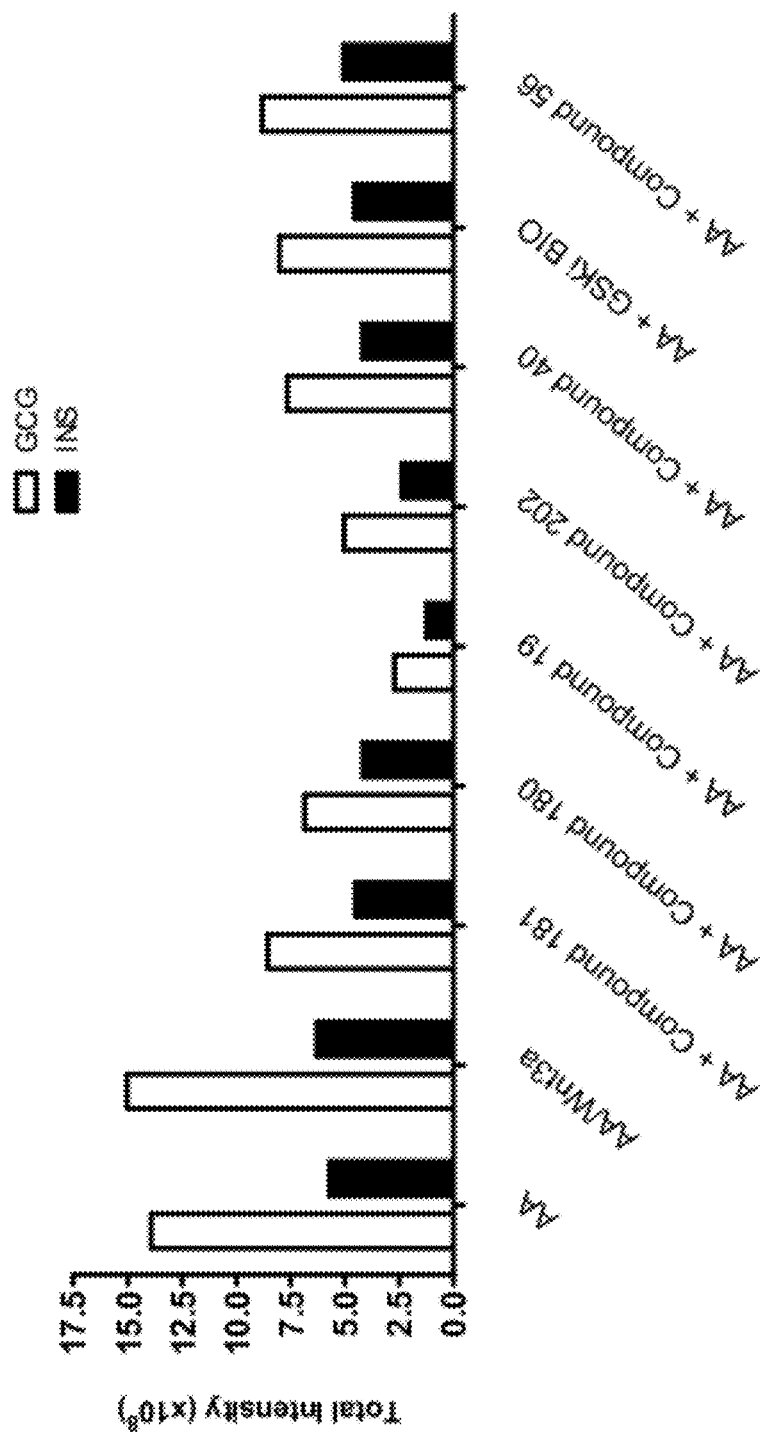
Figure 21M:
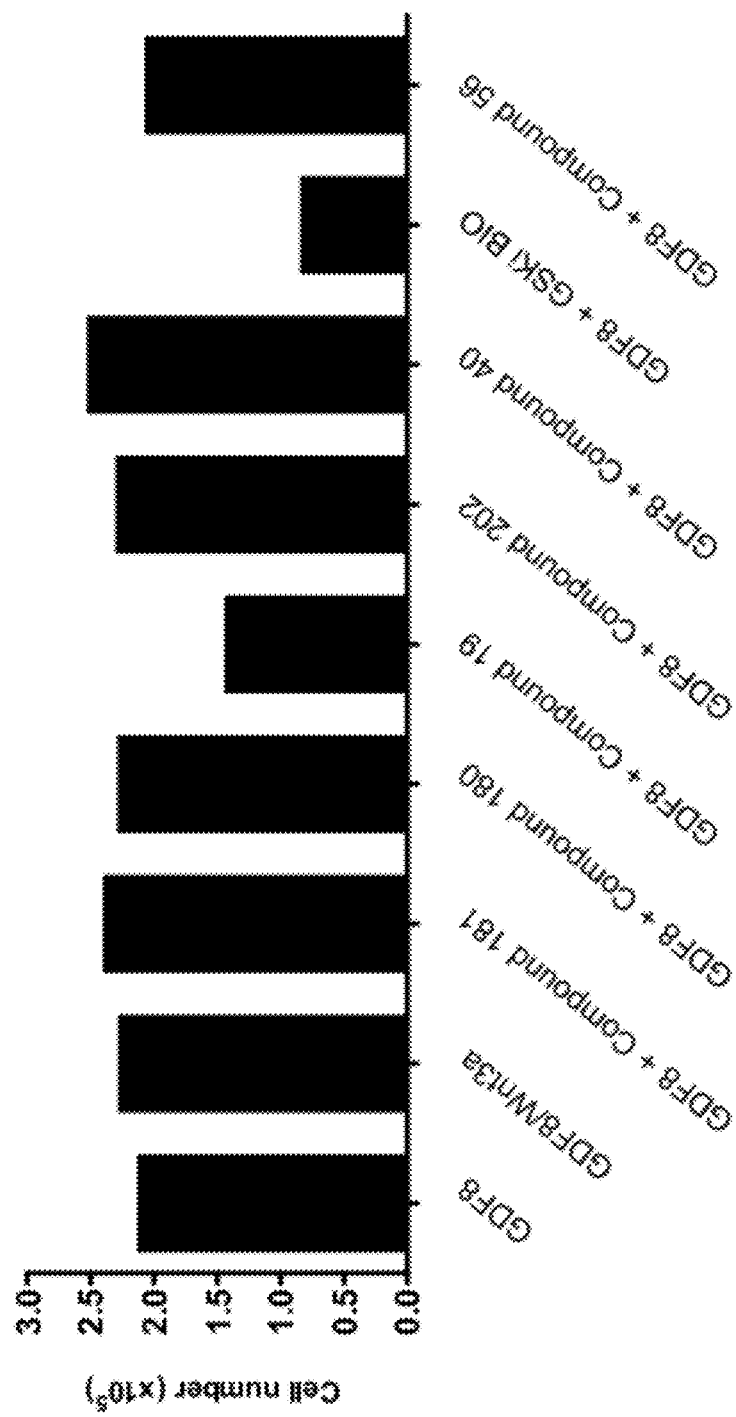
Figure 21N:
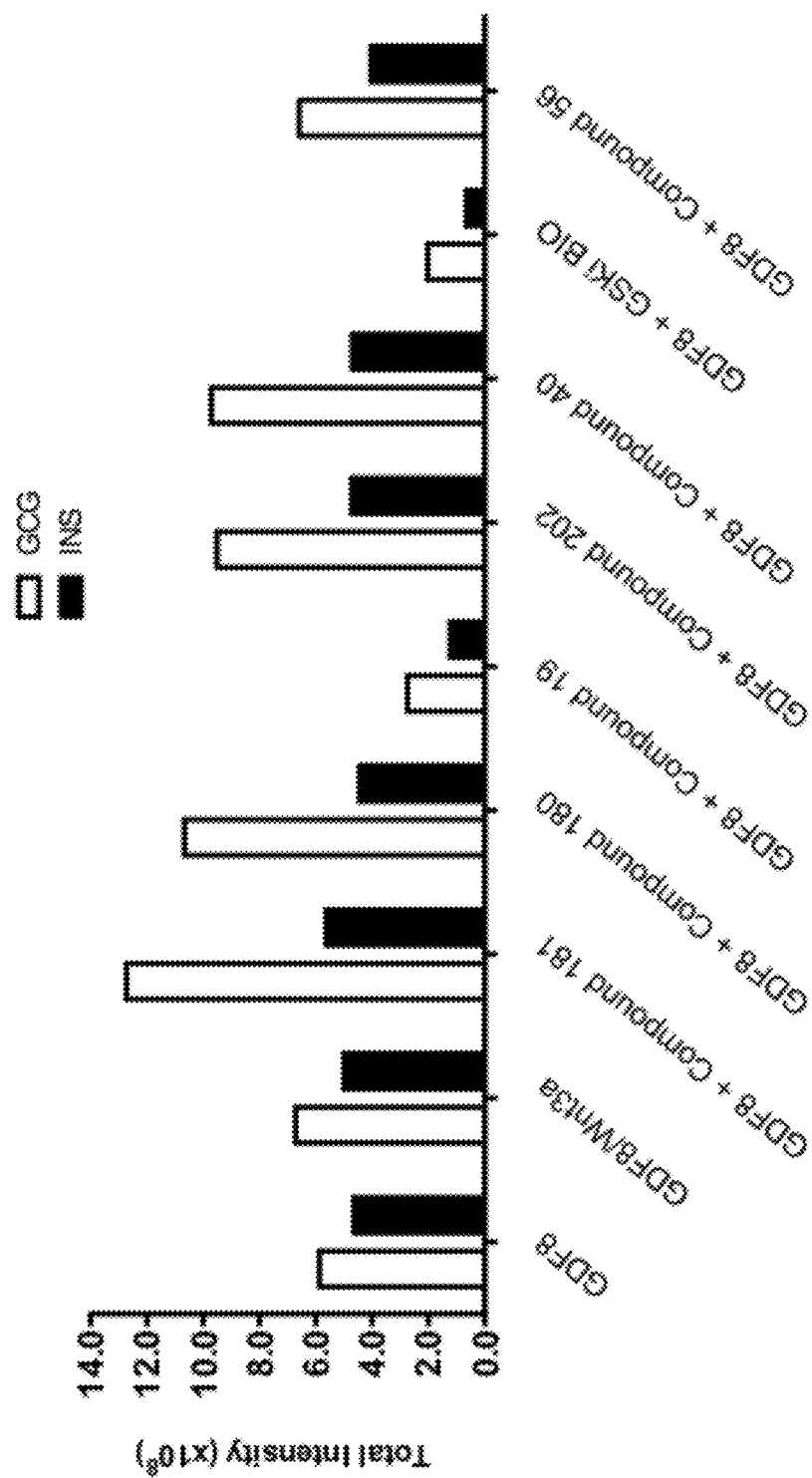

In FIGS. 21C and 21D, normalized RT-PCR values for various differentiation markers at the end of step one of differentiation are shown for treatments applied during step one of the protocol, using selected compounds of the present invention in combination with activin A (FIG. 21C) or in combination with GDF-8 (FIG. 21D). Similar normalized RT-PCR values were evaluated at the conclusion of step three of the differentiation protocol (FIGS. 21E and 21F) and at the end of step four of the differentiation protocol (FIGS. 21G and 21H) and at the end of step 5 of the differentiation protocol (FIGS. 21I and 21J). Treatments during differentiation step 1, which combined a compound of the present invention with GDF-8, had improved expression of various endoderm and pancreatic markers relative to GDF-8 treatment alone (FIGS. 21F and 21H and 21J). Treatments combining compounds of the present invention with activin A had minimal or no improvement in expression markers relative to treatment with activin A alone or activin A with Wnt3a (FIGS. 21E, and 21G and 21I). Table 15 summarizes comparative CT values for additional gene markers at the end of each differentiation step, comparing treatments during step one that combined activin A or GDF-8 with or without a compound of the present invention. At the conclusion of step five of differentiation, high content analysis was performed to measure cell numbers (FIGS. 21K and 21M) and protein expression of insulin and glucagon (FIGS. 21L and 21N). Treatment with GDF-8 during the first step of differentiation, alone or in combination with a compound of the present invention, resulted in insulin and glucagon expression at the conclusion of step five of differentiation, demonstrating that GDF-8 was able to substitute for activin A during the initiation of definitive endoderm formation and subsequently led to pancreatic hormonal cells. Collectively, these data show that addition of any of the respective small molecules had minimal effects on differentiation markers for treatments in combination with activin A. However, addition of a small molecule in combination with GDF8 treatment had significant improved effects on immediate definitive endoderm differentiation at the conclusion of step 1 differentiation and also on downstream differentiation markers at the conclusion of steps 3, 4, and 5. Variability was observed within the panel of small molecules, perhaps attributable to the concentration of compound used in assay and/or mechanism of action.

Example 18

Cells Expressing Markers Characteristic of the Definitive Endoderm Lineage that were Formed Using GDF-8 and a Compound of the Present Invention are Able to Release C-Peptide Following Transplantation into a Rodent It was important to determine whether cells expressing markers characteristic of the pancreatic endoderm lineage generated in vitro by treatment with GDF-8 and a small molecule could produce functional endocrine cells in vivo. An in vivo transplant study was done to compare cells differentiated by treatment with activin A and Wnt3a versus treatment with GDF-8 and small molecule compounds.

Preparation of Cells:

Clusters of H1 human embryonic stem cells were grown on reduced growth factor MATRIGEL™ (Invitrogen; Cat #356231)-coated tissue culture plastic with passage on average every four days. MEF conditioned medium supplemented with 8 ng/ml bFGF was used for initial seeding and expansion. All human ES cell lines were maintained at passage numbers less than 50 and routinely evaluated for normal karyotype and absence of mycoplasma contamination.

Cell passage was performed by exposing cell cultures to a solution of 1 mg/ml dispase (Invitrogen; Cat #17105-041) for 5 to 7 minutes at 37° C. followed by rinsing the cell monolayer with MEF conditioned medium and gentle scraping to recover cell clusters. Cell clusters were centrifuged at low speed in MEF conditioned medium to remove residual dispase and then evenly resuspended in MEF conditioned medium supplemented with 8 ng/ml bFGF (PeproTech Inc.; Cat #100-18B) for seeding on reduced growth factor MATRIGEL (BD Biosciences; Cat #356231)-coated 6-well plates (Nunc; Cat#140685) at a 1:3 ratio using volumes of 2.5 ml/well. Daily feeding was conducted by aspirating spent culture medium from each well and replacing with an equal volume of fresh medium. Plates were maintained at 37° C. 5% $CO_2$ throughout the time in culture.

Cell Differentiation:

The differentiation process was started three days after the cells were seeded onto 6-well plates coated with reduced growth factor MATRIGEL™. A four-step protocol was used for the in vitro differentiation of H1 human embryonic stem cells to cells expressing markers characteristic of the pancreatic endoderm lineage. Step 1 was conducted over three days to generate definitive endoderm cells. On the first day of step 1, differentiation was initiated by aspirating spent culture medium and adding an equal volume of RPMI-1640 basal medium (Invitrogen; Cat #22400) with 2% Albumin Bovine Fraction V. Fatty Acid Free (FAF BSA) (Proliant Biologicals; Cat #SKU 68700) and 8 ng/ml bFGF. In one treatment group, cells were exposed to 100 ng/ml activin A (PeproTech; Cat #120-14) with 20 ng/ml Wnt3a (R&D Systems; Cat #1324-WN/CF). In a second treatment group, cells were exposed to 100 ng/ml GDF-8 (R&D Systems; Cat #788-G8) with 2.5 µM Compound 40. In a third treatment group, cells were exposed to 100 ng/ml GDF-8 (R&D Systems; Cat #788-G8) with 2.5 µM Compound 202. On the second and third day of step 1 of differentiation, cells in all treatment groups were fed with RPMI-1640 containing 2% FAF BSA, 8 ng/ml bFGF and either 100 ng/ml activin A (treatment group 1) or 100 ng/ml GDF-8 (treatment groups 2 and 3), without the addition of Wnt3a or a compound of the present invention. At the end of the third day of culture, one well from each treatment group was collected for FACS analysis.

Step 2 of the differentiation protocol was conducted over three days. Cells for all treatment groups were fed daily with DMEM:F12 (Invitrogen; Cat #11330-032) supplemented with 2% FAF BSA and 50 ng/ml FGF7 (PeproTech; Cat #100-19).

Step 3 of the differentiation protocol was conducted over four days. Cells for all treatment groups were fed daily with DMEM-high glucose (Invitrogen; Cat #10569) supplemented with 1% B27 (Invitrogen; Cat #: 17504-044), 50 ng/ml FGF7, 100 ng/ml Noggin (R&D Systems; Cat #3344-NG), 250 nM KAAD-cyclopamine (Calbiochem; Cat #239804), and 2 µM all-trans retinoic acid (RA) (Sigma-Aldrich; Cat #R2625).

Step 4 of the differentiation protocol was conducted over three days. Cells for all treatment groups were fed daily for the first two days with DMEM-high glucose supplemented with 1% B27, 100 ng/ml Noggin, and 1 µM ALK5 inhibitor (Axxora; Cat # ALX-270-445). On the third day, cells were lifted from the substratum by using a 20 µl tip (Rainin; Cat #RT-L10F) and a cell scraper (Corning; Cat #3008), then transferred to a 50 ml tube. The cells were allowed to sediment by gravity, and the supernatant was aspirated without disturbing the cell pellet. Cells were resuspended in DMEM-high glucose supplemented with 1% B27, 100 ng/ml Noggin and 1 µM ALK5 inhibitor, then cultured overnight in six-well Costar Ultra Low Attachment Microplates (Corning Inc., Cat #3471). On the following day, cells in suspension culture were collected and counted. Aliquots of $10 \times 10^6$ cells/mouse were used for transplantation. Aliquots of $0.5 \times 10^6$ cells were collected for RT-PCR analysis.

Figure 22A:
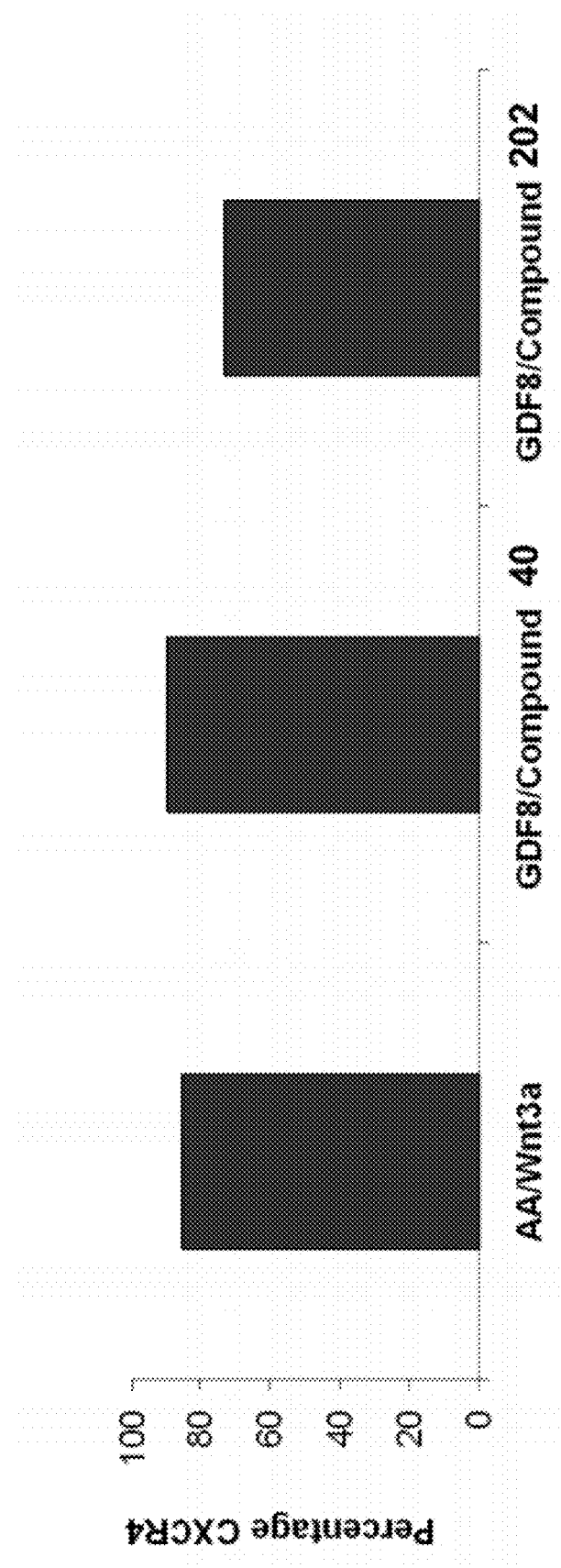
FIG. 22 shows the expression of various protein and RT-PCR markers in cells treated according to the methods described in Example 18. H1 cells were treated with 100 ng/ml activin A or 100 ng/ml GDF-8 for a total of three days in combination with 20 ng/ml Wnt3a for the first day or 2.5 µM Compound 40 or 2.5 µM Compound 202 only on the first day.
Figure 22B:
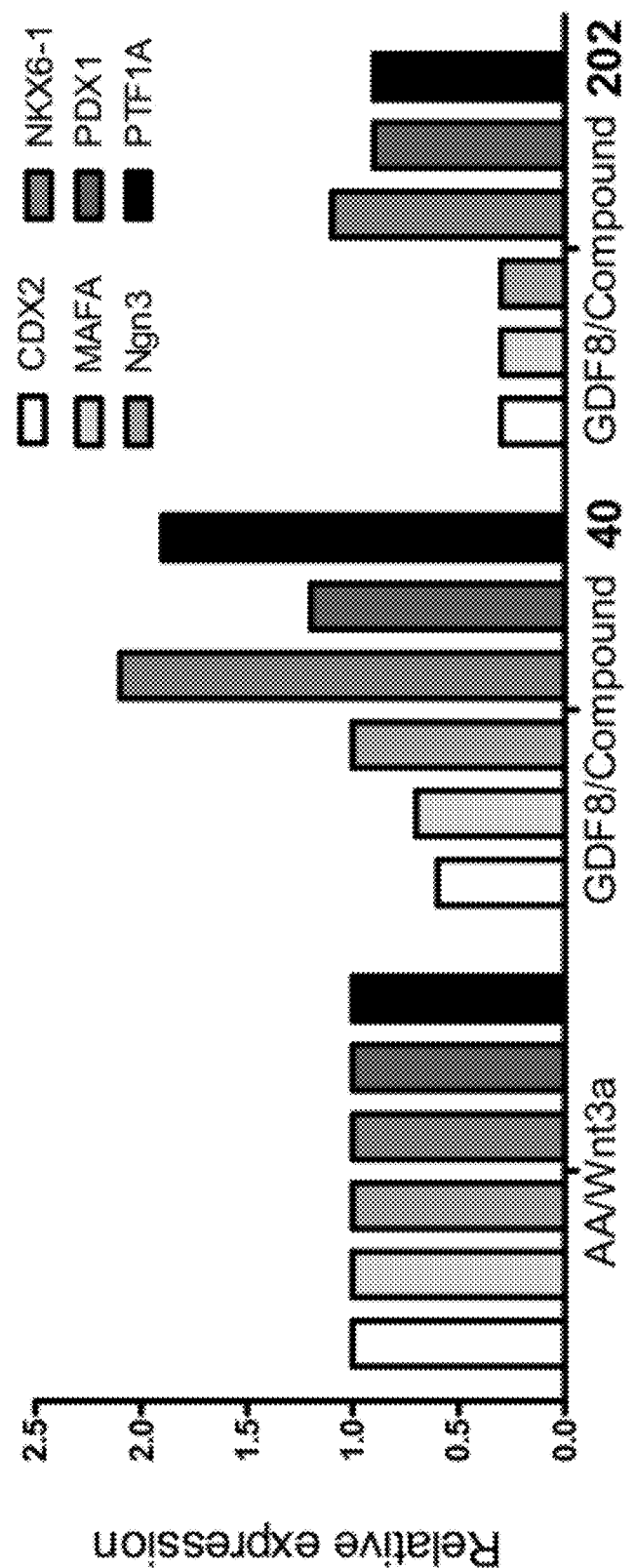

FIG. 22, panel A shows flow cytometric results for definitive endoderm cells generated at the end of step 1 for each of the respective treatment groups. Treatment with activin A and Wnt3a or treatment with GDF-8 and a compound of the present invention resulted in cells expressing similar levels of CXCR4 (greater than 85%) at the end of step 1, suggesting that an equivalent definitive endoderm population of cells was derived from each treatment group.

Results for RT-PCR analysis for cells from each treatment group at the conclusion of step 4 of the differentiation protocol are shown in FIG. 22, panel B. Cells differentiated to pancreatic endoderm (PE) using Activin A and Wnt3a or using GDF-8 and Compound 40 or using GDF-8 and Compound 202 expressed equivalent levels of PE markers: CDX2, MAFA, NGN3, NKX6.1, PDX1 and Ptf1 alpha. These results suggest that the differentiation protocol utilizing GDF-8 and a small molecule was equally effective in creating a pancreatic endoderm precursor population of cells.

Transplantation of Human Embryonic Stem Cells Treated According to the Methods of the Present Invention into Mice:

Five to six-week-old male scid-beige mice (C.B-Igh-1b/GbmsTac-Prkde$^{scid}$-Lyst$^{bg}$ N7) were purchased from Taconic Farms. Mice were housed in microisolator cages with free access to sterilized food and water. In preparation for surgery, mice were identified by ear tagging, their body weight was measured, and their blood glucose was determined using a hand held glucometer (LifeScan; One Touch). On the day of surgery, mice were anesthetized with a mixture of isoflurane and oxygen, and the surgical site was shaved with small animal clippers. Mice were dosed with 0.1 mg·kg Buprenex subcutaneously pre-operatively. The surgical site was prepared with successive washes of 70% isopropyl alcohol, 10% povidone-iodide, and 70% isopropyl alcohol, and a left lateral incision was made through the skin and muscle layers. The left kidney was externalized and kept moist with 0.9% sodium chloride. A 24 G×¾" I.V. catheter was used to penetrate the kidney capsule, and the needle was removed. The catheter was then advanced under the kidney capsule to the distal pole of the kidney. During preoperative preparation of the mice, cells for transplant were centrifuged in a 1.5 mL microfuge tube, and most of the supernatant was removed, leaving sufficient medium to collect the pellet of cells. The cells were collected into a Rainin Pos-D positive displacement pipette tip, and the pipette was inverted to allow the cells to settle by gravity. Excess medium was dispensed leaving a packed cell preparation for transplant. For transplantation, the Pos-D pipette tip was placed firmly in the hub of the catheter, and the cells were dispensed from the pipette through the catheter under the kidney capsule for delivery to the distal pole of the kidney. The lumen of the catheter was flushed with a small volume of culture medium to deliver any remaining cells, and the catheter was withdrawn. The kidney capsule was sealed with a low temperature cautery, and the kidney was returned to its original anatomical position. The muscle was closed with continuous sutures using 5-0. VICRYL sutures, and the skin was closed with wound clips. The mouse was removed from anesthesia and allowed to fully recover. Mice were dosed with 1.0 mg·kg Metacam subcutaneously post-operatively.

Following transplantation, mice were weighed once per week and blood glucose was measured twice per week. At various intervals following transplantation, mice were dosed with 3 g/kg glucose IP, and blood was drawn 60 minutes following glucose injection via the retro-orbital sinus into microfuge tubes containing a small amount of heparin. The blood was centrifuged, and the plasma was placed into a second microfuge tube, frozen on dry ice, for storage at −80° C. until the human C-peptide assay was performed. Human C-peptide levels were determined using the Mercodia/ALPCO Diagnostics Ultrasensitive C-peptide ELISA according to the manufacturer's instructions.

Figure 23B:
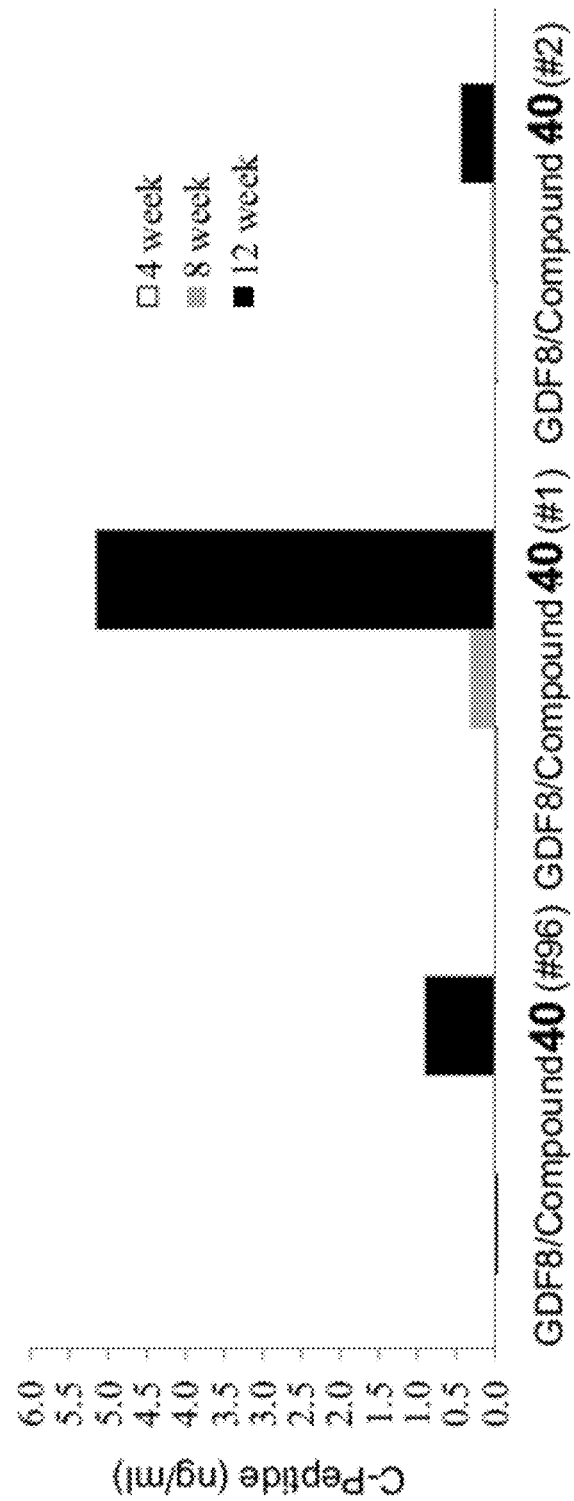
FIG. 23 shows the level of C-peptide detected in SCID-beige mice that received cells at the end of step four of the differentiation protocol as described in Example 18.
Figure 23C:
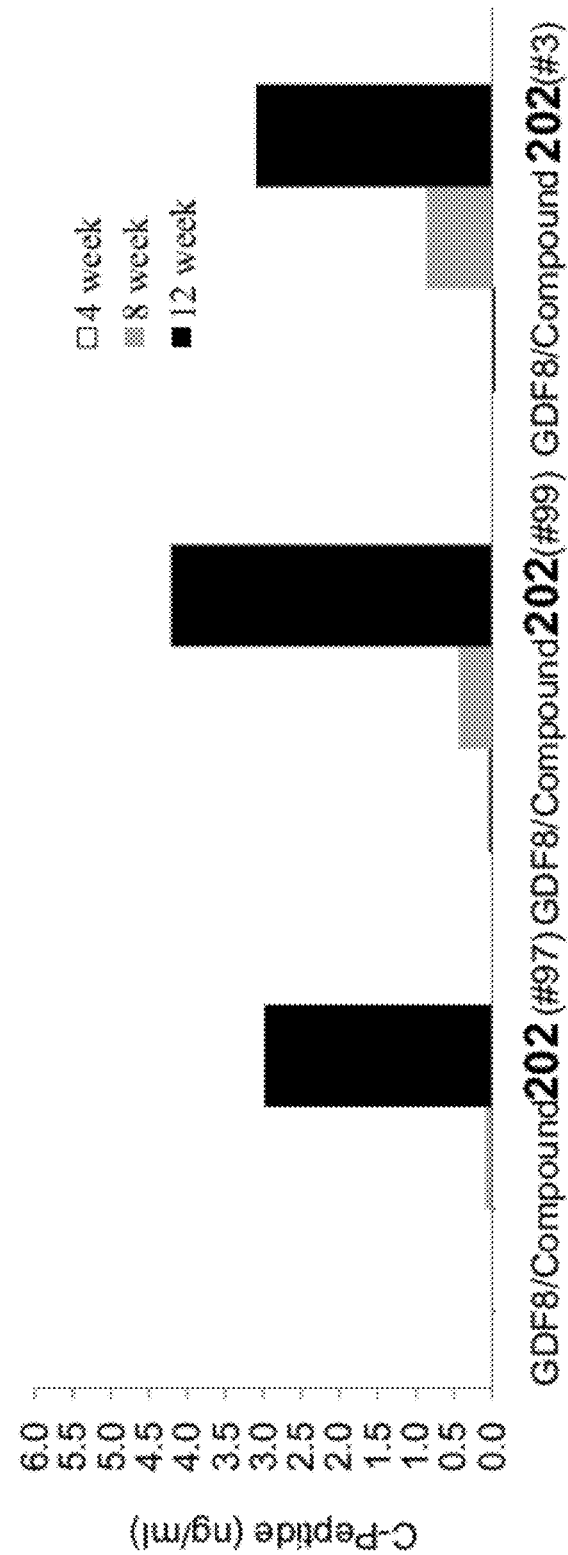

ELISA results for human C-peptide are shown in FIG. 23 for mice transplanted with cells from each of the respective treatment groups. No circulating human C-peptide was detected at four weeks post-transplant for any mice receiving cells from any of the treatment groups. At 8-weeks post-transplant, detectable C-peptide was found in one of two mice receiving cells treated with activin A and Wnt3a; one of three mice receiving cells treated with GDF-8 and Compound 40; and two of three mice receiving cells treated with GDF-8 and Compound 202. These results suggest that an equivalent endocrine precursor cell population could be derived from the differentiation protocol with GDF-8 and a small molecule and that the cells further matured in vivo to a glucose responsive, insulin secreting cell.

Example 19

Cells Expressing Markers Characteristic of the Definitive Endoderm Lineage that were Formed Using GDF-8 are Able to Release C-Peptide Following Transplantation into a Rodent It was important to demonstrate that cells differentiated with GDF-8 in the absence of activin A could also be further differentiated to an endocrine cell population capable of secreting human C-peptide in an in vivo rodent transplant model.

Preparation of Cells:

Clusters of H1 human embryonic stem cells were grown on reduced growth factor MATRIGEL™ (Invitrogen; Cat #356231)-coated tissue culture plastic with passage on average every four days. MEF conditioned medium supplemented with 8 ng/ml bFGF was used for initial seeding and expansion. All human ES cell lines were maintained at passage numbers less than 50 and routinely evaluated for normal karyotype and absence of mycoplasma contamination.

Cell passage was performed by exposing cell cultures to a solution of 1 mg/ml dispase (Invitrogen; Cat #17105-041) for 5 to 7 minutes at 37° C. followed by rinsing the cell monolayer with MEF conditioned medium and gentle scraping to recover cell clusters. Cell clusters were centrifuged at low speed in MEF conditioned medium to remove residual dispase and then evenly resuspended in MEF conditioned medium supplemented with 8 ng/ml bFGF (PeproTech Inc.; Cat #100-18B) for seeding on reduced growth factor MATRIGEL™ (BD Biosciences; Cat #356231)-coated 6-well plates (Nunc; Cat#140685) at a 1:3 ratio using volumes of 2.5 ml/well. Daily feeding was conducted by aspirating spent culture medium from each well and replacing with an equal volume of fresh medium. Plates were maintained at 37° C., 5% $CO_2$ throughout culture.

Cell Differentiation:

The differentiation process was started three days after the cells were seeded into 6-well plates. A four-step protocol was used for the in vitro differentiation of H1 human embryonic stem cells to cells expressing markers characteristic of the pancreatic endoderm lineage. Step 1 was conducted over three days to generate cells expressing markers characteristic of the definitive endoderm lineage. On the first day of step 1, differentiation was initiated by aspirating spent culture medium and adding an equal volume of RPMI-1640 basal medium (Invitrogen; Cat #22400) with 2% Albumin Bovine Fraction V, Fatty Acid Free (FAF BSA) (Proliant Biologicals; Cat #SKU 68700) and 8 ng/ml bFGF. In one treatment group, duplicate sets of cells were treated with 100 ng/ml GDF-8 (R&D Systems; Cat #788-G8) and 20 ng/ml Wnt3a (R&D Systems; Cat #1324-WN/CF). In a second treatment group, duplicate sets of cells were treated with 100 ng/ml GDF-8 and 2.5 µM Compound 40. On the second and third day of step 1 differentiation, cells in all treatment groups were fed with RPMI-1640 containing 2% FAF BSA, 8 ng/ml bFGF and 100 ng/ml GDF-8 but without the addition of Wnt3a or Compound 40. At the end of the third day of culture, one well from each treatment group was collected for FACS analysis.

Step 2 of the differentiation protocol was carried out over three days. Cells for all treatment groups were fed daily with DMEM:F12 (Invitrogen; Cat #11330-032) supplemented with 2% FAF BSA and 50 ng/ml FGF7 (PeproTech; Cat #100-19).

Step 3 of the differentiation protocol was carried out over four days. Cells for all treatment groups were fed daily with DMEM-high glucose (Invitrogen; Cat #10569) supplemented with 1% B27 (Invitrogen; Cat #: 17504-044), 50 ng/ml FGF7, 100 ng/ml Noggin (R&D Systems; Cat #3344-NG), 250 nM KAAD-cyclopamine (Calbiochem; Cat #239804), and 2 µM all-trans retinoic acid (RA) (Sigma-Aldrich; Cat #R2625).

Step 4 of the differentiation protocol was carried out over three days. Cells for all treatment groups were fed daily with DMEM-high glucose supplemented with 1% B27, 100 ng/ml Noggin and 1 µM ALK5 inhibitor (Axxora; Cat # ALX-270-445), and 100 ng/ml GDF-8 (R&D Systems; Cat #788-G8) during the first two days. On the third day of step 4, cells were harvested from the 6-well plates using a 20 µl tip (Rainin; Cat #RT-L10F) and a cell scraper (Corning; Cat #3008) and transferred to a 50 ml tube. Cells were allowed to sediment by gravity, and the supernatant was aspirated without disturbing the cell pellet. Cells were resuspended in DMEM-high glucose supplemented with 1% B27, 100 ng/ml Noggin, and 1 µM ALK5 inhibitor, then cultured overnight in six-well Costar Ultra Low Attachment Microplates (Corning Inc.; Cat #3471). On the following day, cells in suspension culture were collected and counted. Aliquots of $10 \times 10^6$ cells/mouse were used for transplantation. Aliquots of $0.5 \times 10^6$ cells were collected for RT-PCR analysis.

Figure 24A:
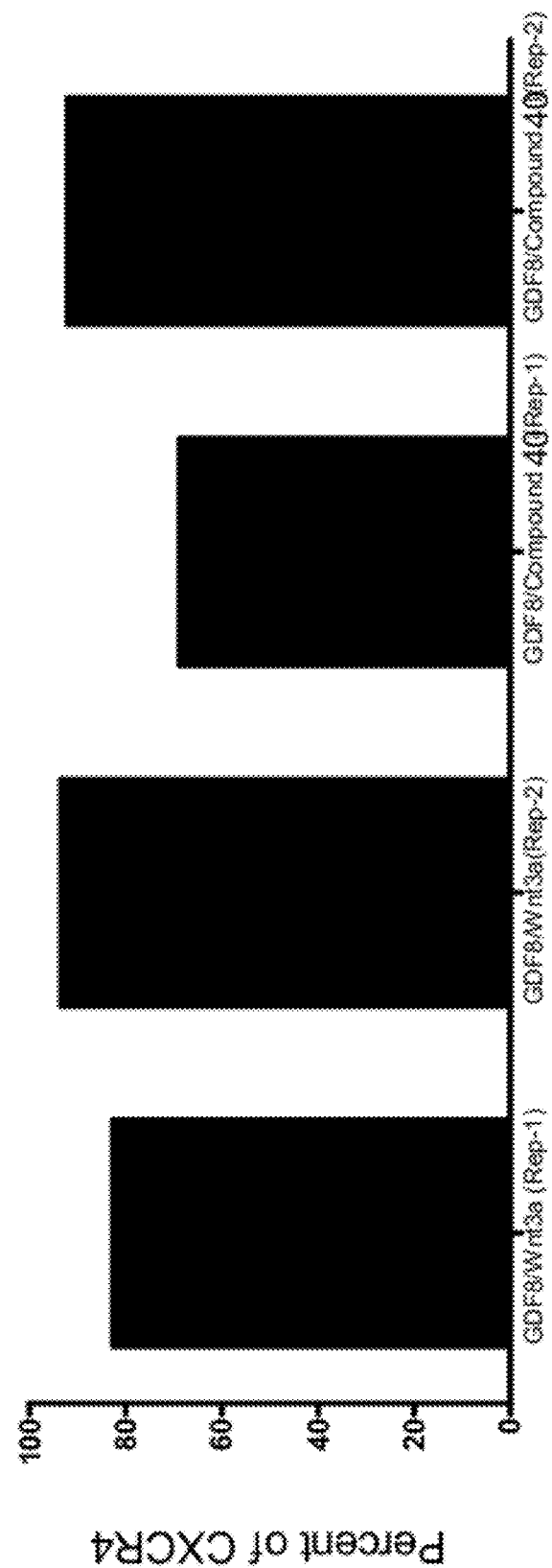
FIG. 24 panel A shows the expression of CXCR4, as determined by FACS in cells at the end of step one of the differentiation protocol described in Example 19. Panel B shows the expression of various genes, as determined by RT-PCR in cells at the end of step four of the differentiation protocol described in Example 19. Two different experimental replicates are shown (Rep-1 and Rep-2), each subjected to identical treatment protocols. Panel C shows the level of C-peptide detected in SCID-beige mice that received cells at the end of step four of the differentiation protocol as treated with GDF-8 and Wnt3a during the first step of in vitro differentiation. Panel D shows the level of C-peptide detected in SCID-beige mice that received cells at the end of step four of the differentiation protocol as treated with GDF-8 and Compound 28 during the first step of in vitro differentiation.
Figure 24B:
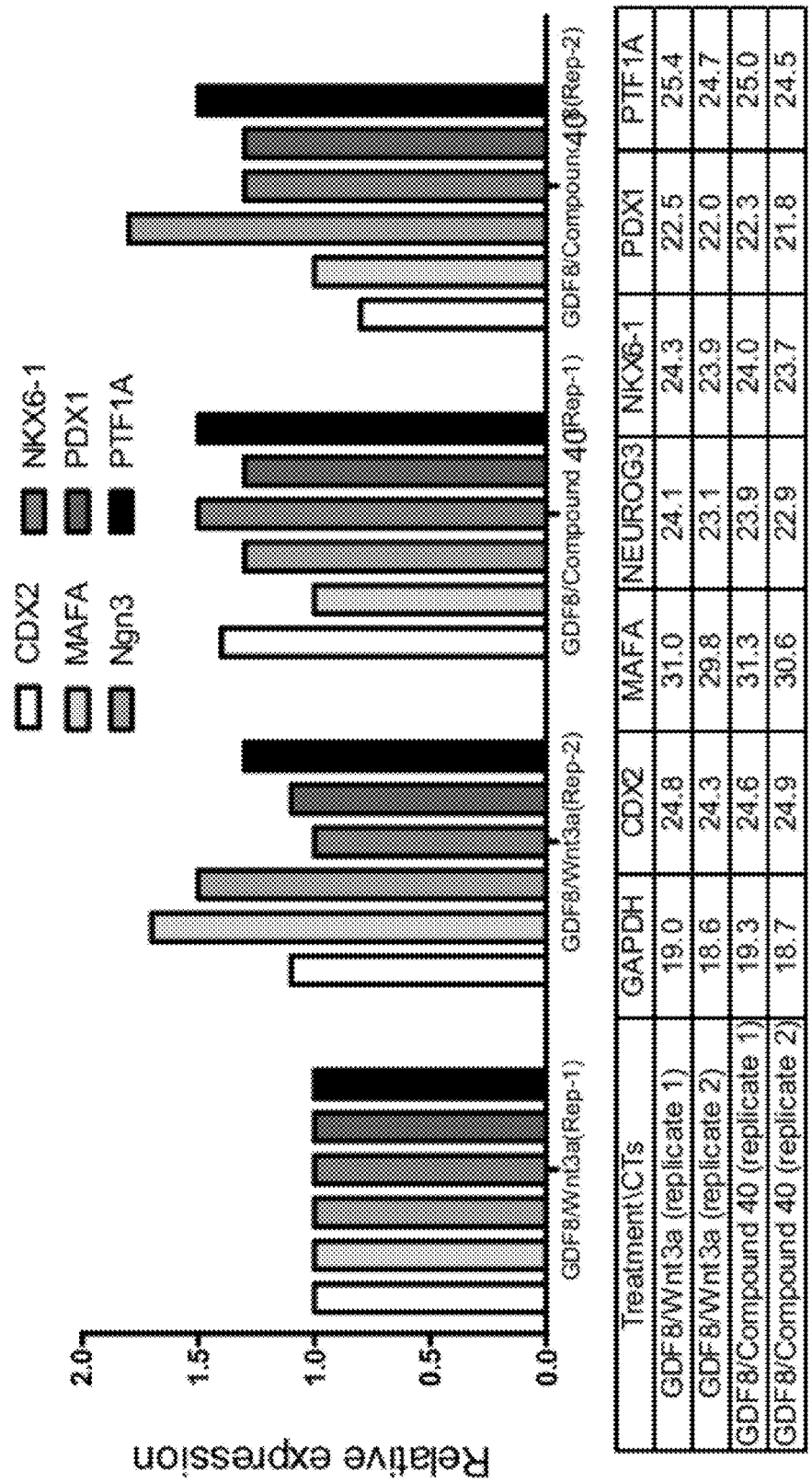
Figure 24D:
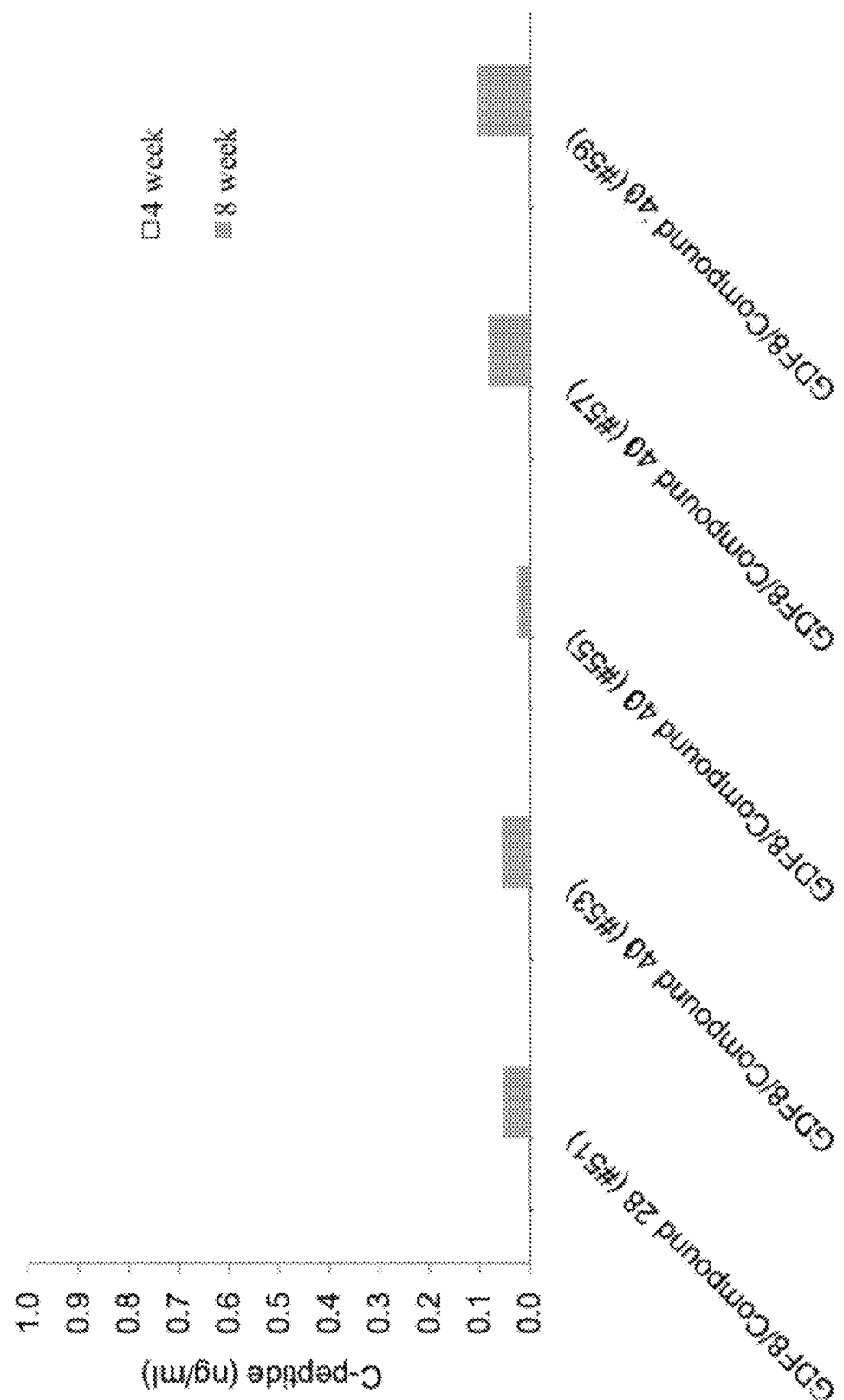

FIG. 24A shows flow cytometric results for definitive endoderm cells generated at the end of step 1 for each of the respective treatment groups. Results for treatment with GDF-8 and Wnt3a or treatment with GDF-8 and Compound 40 expressed similar levels of CXCR4 at the end of step 1, suggesting that an equivalent and robust definitive endoderm population of cells resulted from each treatment group. Duplicate treatment sets were in strong agreement. Results prior to transplant for RT-PCR analysis at the conclusion of step 4 of the differentiation protocol are shown in FIG. 24B. Cells differentiated to pancreatic endoderm (PE) using GDF-8 and Wnt3a or GDF-8 and Compound 40 expressed equivalent levels of markers characteristic of the pancreatic endoderm lineage, such as: CDX2, MafA, Ngn3, NKX6.1, Pdx-1 and Ptf1A. These results demonstrate that the differentiation protocol utilizing GDF-8 and Wnt3a or GDF-8 and a compound of the present invention was effective in creating a pancreatic endoderm precursor population of cells. The differentiation protocol was conducted in two independent but identical treatment sets. Results from duplicate treatment sets were in strong agreement as shown by RT-PCR analysis.

Human Embryonic Stem Cell Transplantation into Mice:

Five to six-week-old male scid-beige mice (C.B-Igh-1b/GbmsTac-Prkdc$^{scid}$-Lyst$^{hg}$ N7) were purchased from Taconic Farms. Mice were housed in microisolator cages with free access to sterilized food and water. In preparation for surgery, mice were identified by ear tagging, their body weight was measured, and their blood glucose was determined using a hand held glucometer (LifeScan; One Touch). On the day of surgery, mice were anesthetized with a mixture of isoflurane and oxygen, and the surgical site was shaved with small animal clippers. Mice were dosed with 0.1 mg·kg Buprenex subcutaneously pre-operatively. The surgical site was prepared with successive washes of 70% isopropyl alcohol, 10% povidone-iodide, and 70% isopropyl alcohol, and a left lateral incision was made through the skin and muscle layers. The left kidney was externalized and kept moist with 0.9% sodium chloride. A 24 G×¾" I.V. catheter was used to penetrate the kidney capsule, and the needle was removed. The catheter was then advanced under the kidney capsule to the distal pole of the kidney. During preoperative preparation of the mice, cells for transplant were centrifuged in a 1.5 mL microfuge tube, and most of the supernatant was removed, leaving sufficient medium to collect the pellet of cells. The cells were collected into a Rainin Pos-D positive displacement pipette tip, and the pipette was inverted to allow the cells to settle by gravity. Excess medium was dispensed leaving a packed cell preparation for transplant. For transplantation, the Pos-D pipette tip was placed firmly in the hub of the catheter, and the cells were dispensed from the pipette through the catheter under the kidney capsule for delivery to the distal pole of the kidney. The lumen of the catheter was flushed with a small volume of culture medium to deliver any remaining cells, and the catheter was withdrawn. The kidney capsule was sealed with a low temperature cautery, and the kidney was returned to its original anatomical position. The muscle was closed with continuous sutures using 5-0 vicryl, and the skin was closed with wound clips. The mouse was removed from anesthesia and allowed to fully recover. Mice were dosed with 1.0 mg·kg Metacam subcutaneously post-operatively.

Following transplantation, mice were weighed once per week and blood glucose was measured twice per week. At various intervals following transplantation, mice were dosed with 3 g/kg glucose IP, and blood was drawn 60 minutes following glucose injection via the retro-orbital sinus into microfuge tubes containing a small amount of heparin. The blood was centrifuged, and the plasma was placed into a second microfuge tube, frozen on dry ice, for storage at −80° C. until the human C-peptide assay was performed. Human C-peptide levels were determined using the Mercodia/ALPCO Diagnostics Ultrasensitive C-peptide ELISA according to the manufacturer's instructions. ELISA results for human C-peptide are shown in FIGS. 24C and D for mice transplanted with cells from each of the respective treatment groups. Similar levels of human C-peptide were detectable at 8 weeks post-transplant for each treatment category, indicating that an equivalent endocrine precursor cell population could be derived from the differentiation protocol using GDF-8 and Wnt3a or GDF-8 and a compound of the present invention.

Example 20

Evaluation of the Potential of Inhibitors of CDK, GSK3, and TRK to Differentiate Human Embryonic Stem Cells into Cells Expressing Markers Characteristic of the Definitive Endoderm Lineage A subset of 14 proprietary small molecules, known to have specificity for the CDK, GSK3, and/or TRK signaling pathways were evaluated for their potential to differentiate human embryonic stem cells to cells expressing markers characteristic of the definitive endoderm lineage.

Cell Assay Seeding:

Briefly, clusters of H1 human embryonic stem cells were grown on reduced growth factor Matrigel™ (Invitrogen; Cat #356231) coated tissue culture plastic. Cells were passaged using collagenase (Invitrogen; Cat #17104-019) treatment and gentle scraping, washed to remove residual enzyme, and plated with even dispersal at a ratio of 1:1 (surface area) on reduced growth factor MATRIGEL™ (BD Biosciences; Cat

356231)-coated 96-well black plates (Packard ViewPlates; PerkinElmer; Cat #6005182) using volumes of 100 Cells were allowed to attach and then recover log phase growth over a 1 to 3 day time period, feeding daily with MEF conditioned medium supplemented with 8 ng/ml bFGF (R&D Systems; Cat #233-FB). Plates were maintained at 37° C., 5% $CO_2$ in a humidified box throughout the duration of assay.

Preparation of Compounds and Assay:

Screening was conducted using the compounds described in Table 16. In addition Compound 34 was included as a positive control, as demonstrated in previous examples. Compounds were made available as 5 mM stocks in 96-well plate format, solubilized in 100% DMSO (Sigma; Cat #D2650) and stored at −80° C. The library compounds were further diluted to an intermediate concentration of 0.2 mM in 50 mM HEPES (Invitrogen; Cat #15630-080), 20% DMSO and stored at 4° C. Test conditions were performed in triplicate, feeding on alternating days over a four-day assay period. Assay was initiated by aspirating culture medium from each well followed by three washes in PBS (Invitrogen; Cat #14190) to remove residual growth factors. On the first day of assay, test volumes of 200 μl per well were added to each well using DMEM:F12 base medium (Invitrogen; Cat #11330-032) supplemented with 0.5% FCS (HyClone; Cat # SH30070.03) and 100 ng/ml GDF-8 (R&D Systems, Cat #788-G8) plus 2.5 μM compound. A parallel set of test samples were treated in an identical manner but omitting GDF-8 from the medium. On the third day of assay, test volumes of 100 μl per well were added to each well using DMEM:F12 base medium supplemented with 2% FCS plus 100 ng/ml GDF-8 (R&D Systems, Cat #788-G8). GDF-8 was omitted from test samples that did not get treated with GDF-8 on the first day of assay. Positive control samples contained the same base medium supplemented with FCS and 100 ng/ml recombinant human activin A (PeproTech; Cat #120-14) throughout the four day assay along with Wnt3a (20 ng/ml) addition on days 1 and 2. Negative control samples contained DMEM:F12 base medium supplemented with FCS.

High Content Analysis:

At the conclusion of four-days of culture, assay plates were washed twice with PBS (Invitrogen; Cat #14190), fixed with 4% paraformaldehyde (Alexis Biochemical; Cat 11 ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; Cat # AF1924) was diluted 1:100 in 4% chicken serum and added to each well for one hour at room temperature. Alexa Fluor 488 conjugated secondary antibody (chicken anti-goat IgG; Molecular Probes; Cat # AZ1467) was diluted 1:200 in PBS and added to each sample well after washing three times with PBS. To counterstain nuclei, 4 μg/ml Hoechst 33342 (Invitrogen; Cat # H3570) was added for ten minutes at room temperature. Plates were washed once with PBS and left in 100 μl/well PBS for imaging.

Imaging was performed using an IN Cell Analyzer 1000 (GE Healthcare) utilizing the 51008bs dichroic for cells stained with Hoechst 33342 and Alexa Fluor 488. Exposure times were optimized from positive control wells and from untreated negative control wells stained with secondary antibody alone. Images from 15 fields per well were acquired to compensate for any cell loss during the bioassay and subsequent staining procedures. Measurements for total cell number and total SOX17 intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total SOX17 protein expression was reported as total intensity or integrated intensity, defined as total fluorescence of the cell multiplied by area of the cell. Background was eliminated based on acceptance criteria of gray-scale ranges between 200 and 3500. Average data from triplicate wells were collected. The percentage of treated wells relative to the positive control was calculated.

Results for this screen are shown in Table 17. None of the small molecules induced significant SOX17 expression in the absence of GDF-8 during the four day differentiation process. Compound 34 served as an experimental control and induced significant SOX17 expression in the presence of GDF-8, equivalent to levels observed with the positive control using activin A and Wnt3a. The remaining compounds of the present invention tested in this example showed a range of activities with weak to moderate induction of SOX17 expression. Of note, differentiation activity in this subset of compounds was observed in association with selectivity for all three enzymatic signal pathways, making it difficult to conclusively determine a clear mechanism of action.

Example 21

Screening for Analogues of the Compounds of the Present Invention that are Capable of Mediating the Formation of Cells Expressing Markers Characteristic of the Definitive Endoderm Lineage Based on the structures for the compounds of the present invention, an analog search was conducted and 118 analogues were found. Initial screening determined that some analogues were able to induce definitive endoderm differentiation in the absence of activin A in combination with other growth factors. It was important to determine if these analogues could also induce definitive endoderm differentiation in combination with only GDF-8.

Cell Assay Seeding:

Briefly, clusters of H1 human embryonic stem cells were grown on reduced growth factor Matrigel™ (Invitrogen; Cat #356231)-coated tissue culture plastic. Cells were passaged using collagenase (Invitrogen; Cat #17104-019) treatment and gentle scraping, washed to remove residual enzyme, and plated with even dispersal at a ratio of 1:1 (surface area) on reduced growth factor MATRIGEL™ (BD Biosciences; Cat #356231)-coated 96-well black plates (Packard ViewPlates; PerkinElmer; Cat #6005182) using volumes of 100 μl/well. Cells were allowed to attach and then recover log phase growth over a 1 to 3 day time period, feeding daily with MEF conditioned medium supplemented with 8 ng/ml bFGF (R&D Systems; Cat #233-FB). Plates were maintained at 37° C., 5% $CO_2$ in a humidified box throughout the duration of assay.

Preparation of Compounds and Assay:

Screening was conducted using a library of the analogue compounds. Compounds from this library were made available as 5 mM stocks in 96-well plate format, solubilized in 100% DMSO (Sigma; Cat #D2650) and stored at −80° C. The library compounds were further diluted to an intermediate concentration of 0.2 mM in 50 mM HEPES (Invitrogen; Cat #15630-080), 20% DMSO and stored at 4° C. Test conditions were performed in triplicate, feeding on alternating days over a four-day assay period. Assays were initiated by aspirating culture medium from each well followed by three washes in PBS (Invitrogen; Cat #14190) to remove residual growth factors. On the first day of assay, test volumes of 200 µl per well were added to each well using DMEM:F12 base medium (Invitrogen; Cat #11330-032) supplemented with 0.5% FCS (HyClone; Cat # SH30070.03) and 200 ng/ml GDF-8 (R&D Systems, Cat #788-G8) plus 2.5 µM compound. On the third day of assay, test volumes of 100 µl per well were added to each well using DMEM:F12 base medium supplemented with 2% FCS plus 200 ng/ml GDF-8 (R&D Systems, Cat #788-G8). Positive control samples contained the same base medium supplemented with FCS and 100 ng/ml recombinant human activin A (PeproTech; Cat #120-14) throughout the four-day assay along with Wnt3a (20 ng/ml) on days 1 and 2. Negative control samples contained DMEM:F12 base medium supplemented with FCS, adding Wnt3a on days 1 and 2 but omitting treatment with activin A.

High Content Analysis:

At the conclusion of four-days of culture, assay plates were washed twice with PBS (Invitrogen; Cat #14190), fixed with 4% paraformaldehyde (Alexis Biochemical; Cat # ALX-350-011) at room temperature for 20 minutes, then washed three times with PBS and permeabilized with 0.5% Triton X-100 (Sigma; Cat # T8760-2) for 20 minutes at room temperature. Cells were washed again three times with PBS and blocked with 4% chicken serum (Invitrogen; Cat #16110082) in PBS for 30 minutes at room temperature. Primary antibody (goat anti-human SOX17; R&D Systems; Cat # AF1924) was diluted 1:100 in 4% chicken serum and added to each well for one hour at room temperature. Alexa Fluor 488 conjugated secondary antibody (chicken anti-goat IgG; Molecular Probes; Cat # AZ1467) was diluted 1:200 in PBS and added to each sample well after washing three times with PBS. To counterstain nuclei, 4 µg/ml Hoechst 33342 (Invitrogen; Cat # H3570) was added for ten minutes at room temperature. Plates were washed once with PBS and left in 100 µl/well PBS for imaging.

Imaging was performed using an IN Cell Analyzer 1000 (GE Healthcare) utilizing the 51008bs dichroic for cells stained with Hoechst 33342 and Alexa Fluor 488. Exposure times were optimized from positive control wells and from untreated negative control wells stained with secondary antibody alone. Images from 15 fields per well were acquired to compensate for any cell loss during the bioassay and subsequent staining procedures. Measurements for total cell number and total SOX17 intensity were obtained from each well using IN Cell Developer Toolbox 1.7 (GE Healthcare) software. Segmentation for the nuclei was determined based on gray-scale levels (baseline range 100-300) and nuclear size. Averages and standard deviations were calculated for each replicate data set. Total SOX17 protein expression was reported as total intensity or integrated intensity, defined as total fluorescence of the cell times area of the cell. Background was eliminated based on acceptance criteria of gray-scale ranges between 200 to 3500. Total intensity data were normalized by dividing total intensities for each well by the average total intensity for the positive control. Normalized data were calculated for averages and standard deviations for each replicate set.

Screening results are shown in Table 18 from four assay plates in this single experiment. Compounds are ranked with respect to SOX17 expression as a percentage of the positive control treatment with activin A and Wnt3a. This assay identified a list of 12 new analogue hits as shown in Table 19.

Example 22

Human Embryonic Stem Cells Grown on Microcarriers can be Differentiated into Cells Expressing Markers Characteristic of the Definitive Endoderm Lineage According to the Methods of the Present Invention For purposes of differentiation and production of large numbers of endocrine cells under scalable conditions, it was important to show that human embryonic stem cells could be grown and differentiated to definitive endoderm on microcarrier beads using the methods of the present invention.

Preparation of Cells for Assay and Differentiation:

H1 p49C3 cells were routinely grown on Cytodex3 beads (GE Healthcare Life Sciences, NJ) in a 125 ml spinner flask, according to the methods described in U.S. Patent Application No. 61/116,447. After seven days, cells and beads were transferred to a 6 well plate at a ratio of 30 cm$^2$ bead surface area per well, and the plate was placed on a rocking platform. Cells on beads in the positive control treatment well (designated AA/Wnt3a) were differentiated with addition of 100 ng/ml activin A (PeproTech; Cat #120-14) and 20 ng/ml Wnt3a (R&D Systems; Cat #1324-WN/CF) for two days followed by 100 ng/ml activin A and 8 ng/ml bFGF (PeproTech Inc.; Cat #: 100-18B) for one day in RPMI-1640 (Invitrogen; Cat #: 22400) with 2% Fatty Acid Free BSA (MP Biomedicals, Inc; Cat #152401) using volumes of 2 ml/well. Compound 34, at a final concentration of 2.5 µM was added to a negative control treatment well (designated CMP alone (JNJ alone)) in RPMI-1640 with 2% Fatty Acid Free BSA (2 ml/well) for three days in the absence of any other growth factor treatment. A third treatment well (designated CMP+8 (JNJ+8)) received Compound 34 at 2.5 µM plus 50 ng/ml GDF-8 (R&D Systems, Cat #788-G8) in RPMI-1640 with 2% Fatty Acid Free BSA (2 ml/well) for three days. A fourth treatment well (designated CMP+8+D (JNJ+8+D)) received Compound 34 at 2.5 µM with 50 ng/ml GDF-8 and 50 ng/ml PDGF-D in RPMI-1640 with 2% Fatty Acid Free BSA (2 ml/well) for three days. A fifth treatment well (designated CMP+8+D+V (JNJ+8+D+V)) received Compound 34 at 2.5 µM with 50 ng/ml GDF-8, 50 ng/ml PDGF-D, and 50 ng/ml VEGF in RPMI-1640 with 2% Fatty Acid Free BSA (2 ml/well) for three days. A sixth treatment well (designated CMP+8+D+V+M (JNJ+8+D+V+M)) received Compound 34 at 2.5 µM with 50 ng/ml GDF-8, 50 ng/ml PDGF-D, 50 ng/ml VEGF, and 20 ng/ml Muscimol in RPMI-1640 with 2% Fatty Acid Free BSA (2 ml/well) for three days. All media and treatments were exchanged daily.

At the conclusion of treatment and culture, cells were harvested from the beads, according to the methods described in U.S. Patent Application No. 61/116,447. The harvested cells were counted and analyzed by flow cytometry, according to the methods described above.

Figure 25B:
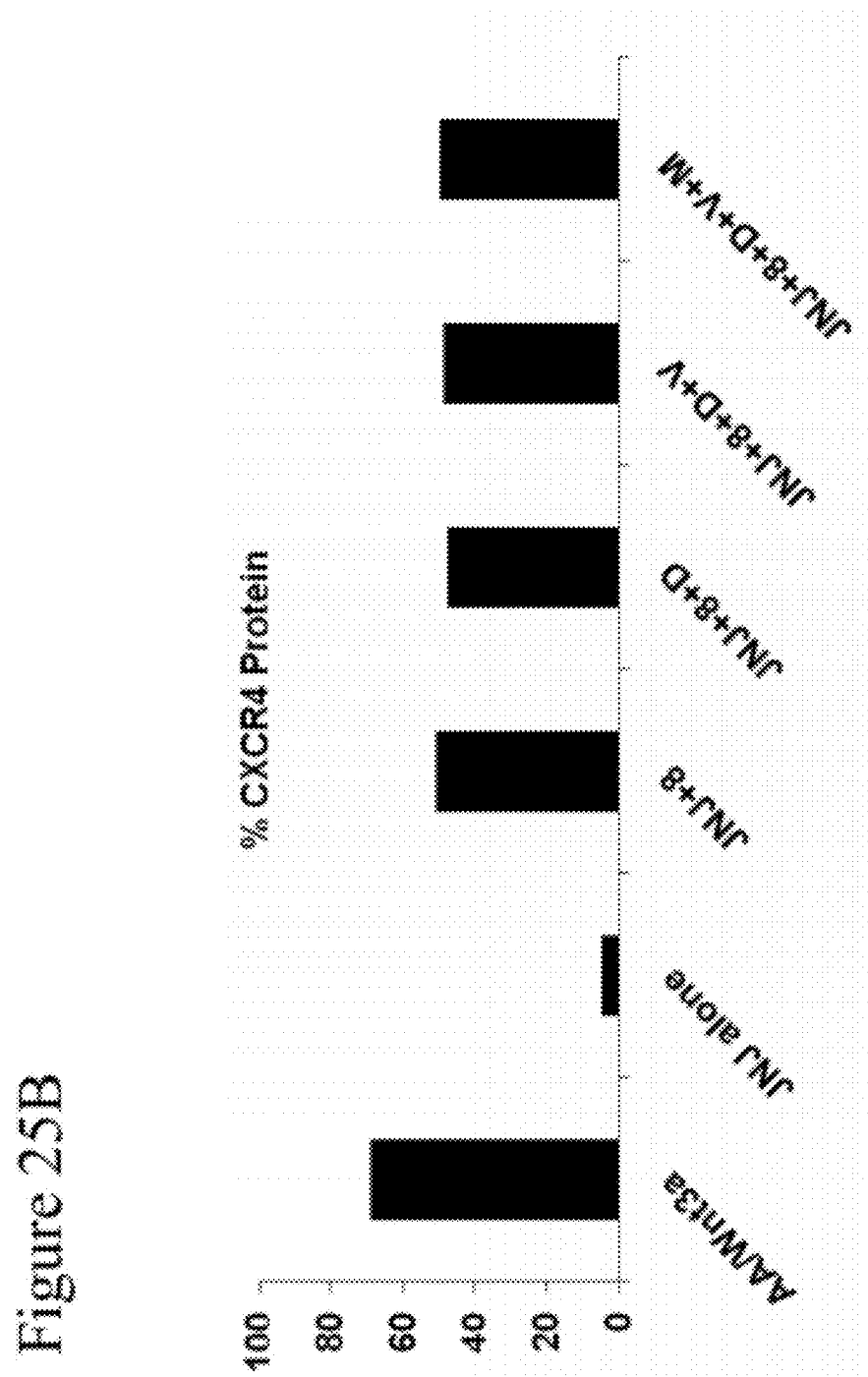
FIG. 25 shows the cell number (panel A) and expression of CXCR4 (panel B) from cells grown on microcarrier beads, treated according to the methods of the present invention as described in Example 22. Cells were grown on Cytodex3 beads without treatment (undifferentiated) or with treatment combining 100 ng/ml activin A with 20 ng/ml Wnt3a (AA/Wnt3a) or with various treatments combining GDF-8 as shown: 50 ng/ml GDF-8 with 2.5 µM Compound 34 (Cmp 34+8); or 50 ng/ml GDF-8 with 2.5 µM Compound 34 and 50 ng/ml PDGF (Cmp 34+8+D); or 50 ng/ml GDF-8 with 2.5 µM Compound 34 and 50 ng/ml PDGF and 50 ng/ml VEGF (Cmp 34+8+D+V); or 50 ng/ml GDF-8 with 2.5 µM Compound 34 and 50 ng/ml PDGF and 50 ng/ml VEGF and 20 ng/ml muscimol (Cmp 34+8+D+V+M).
Figure 26A:
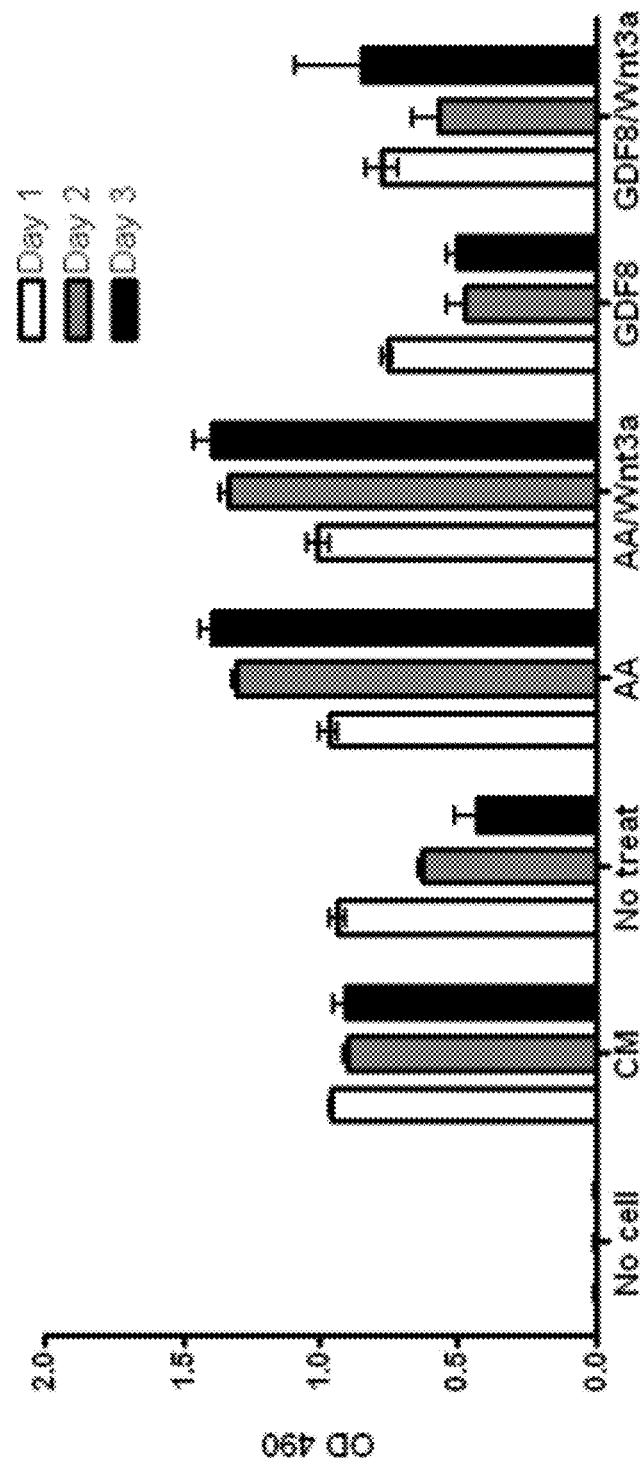
FIG. 26 shows the proliferation of cells following treatment of the compounds of the present invention as described in Example 23. Panels B through I show assay results for treatment using a compound in combination with GDF-8 and measuring MTS OD readings at 1 day, 2 days, and 3 days after initiating the differentiation assay.
Figure 26B:
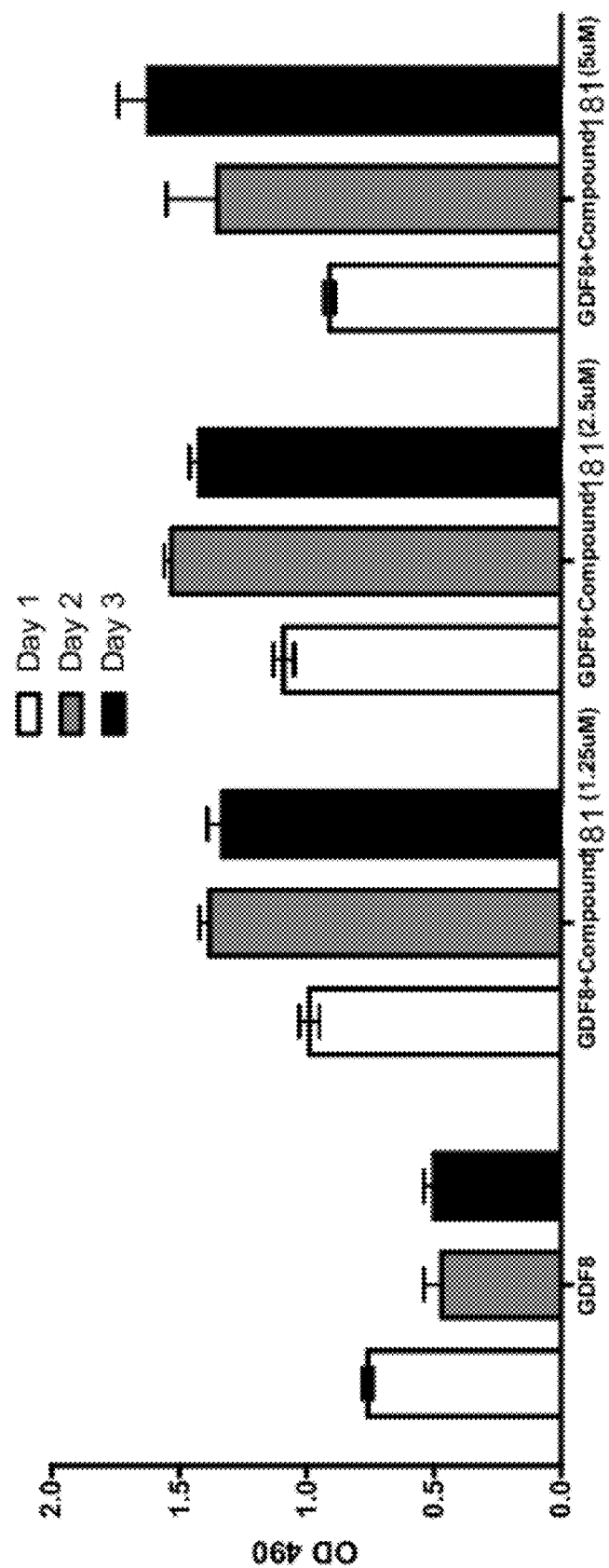
Figure 26C:
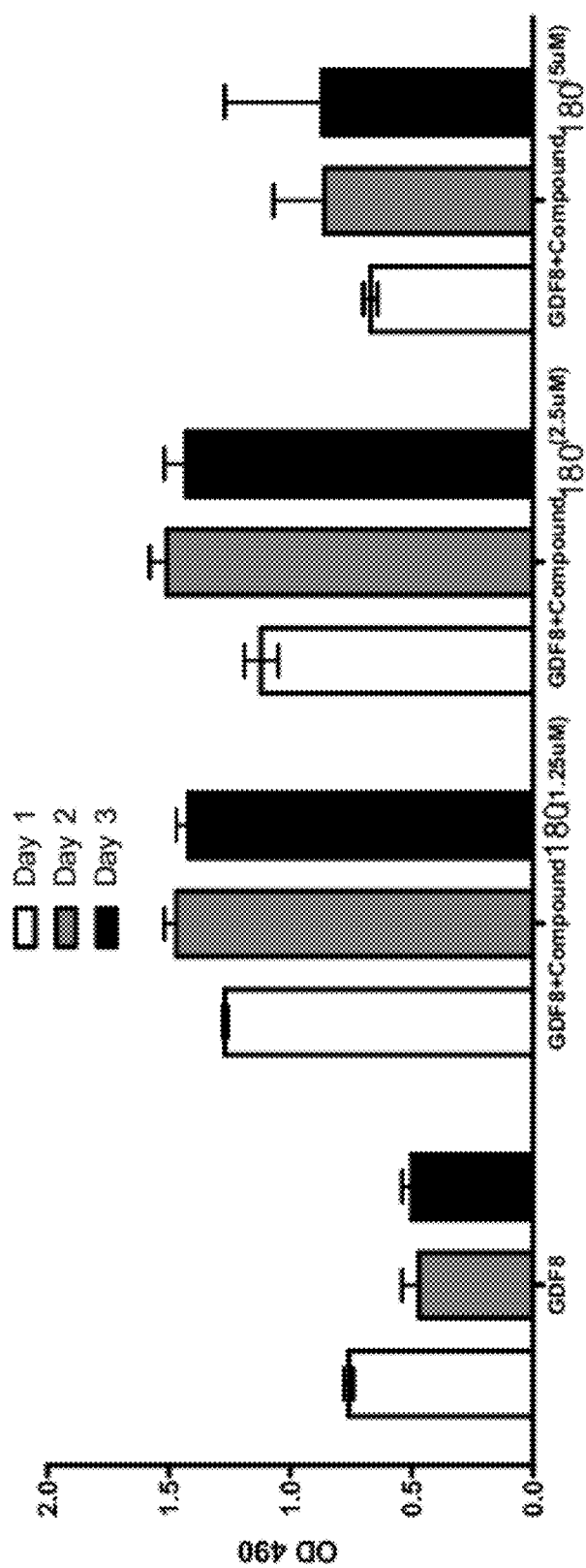
Figure 26E:
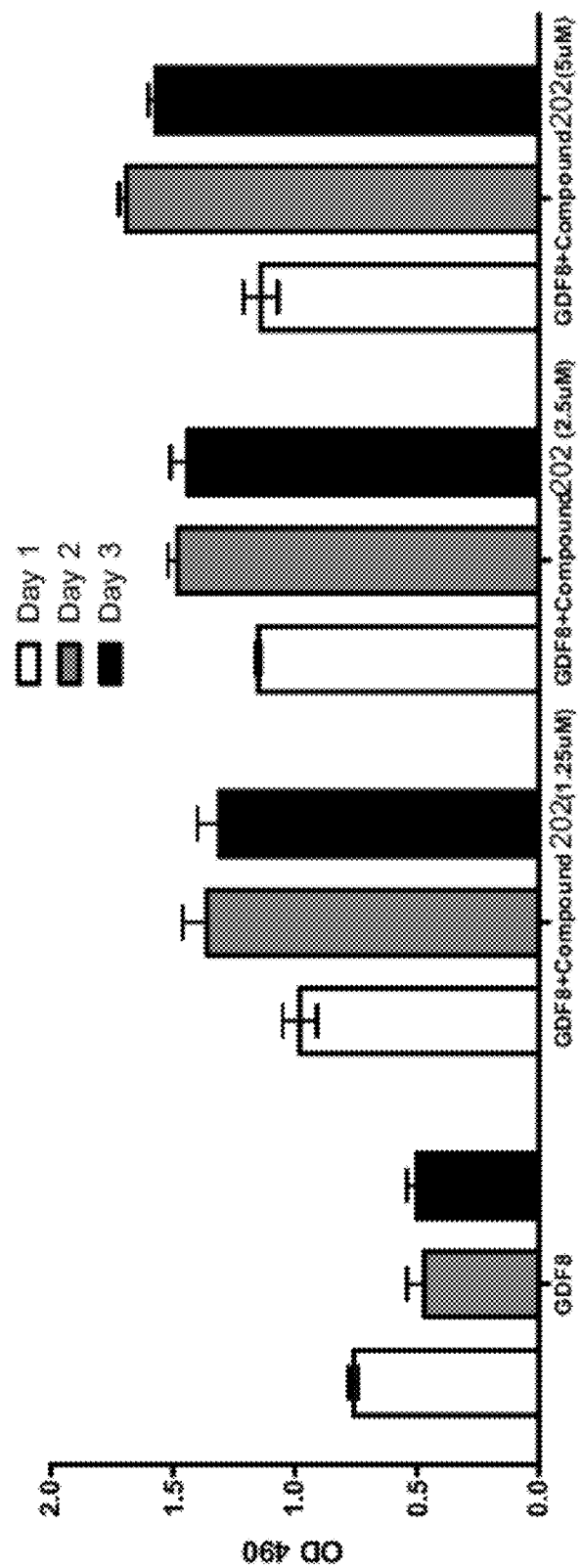
Figure 26F:
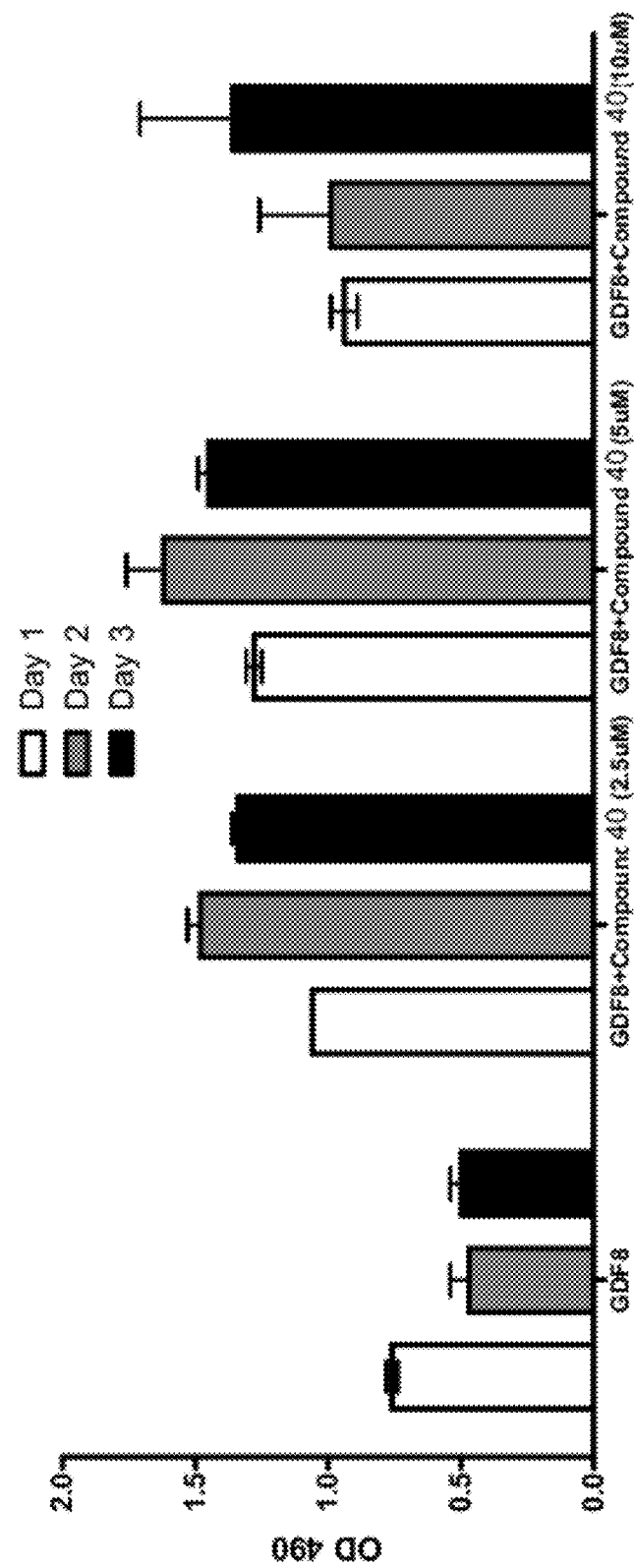
Figure 26G:
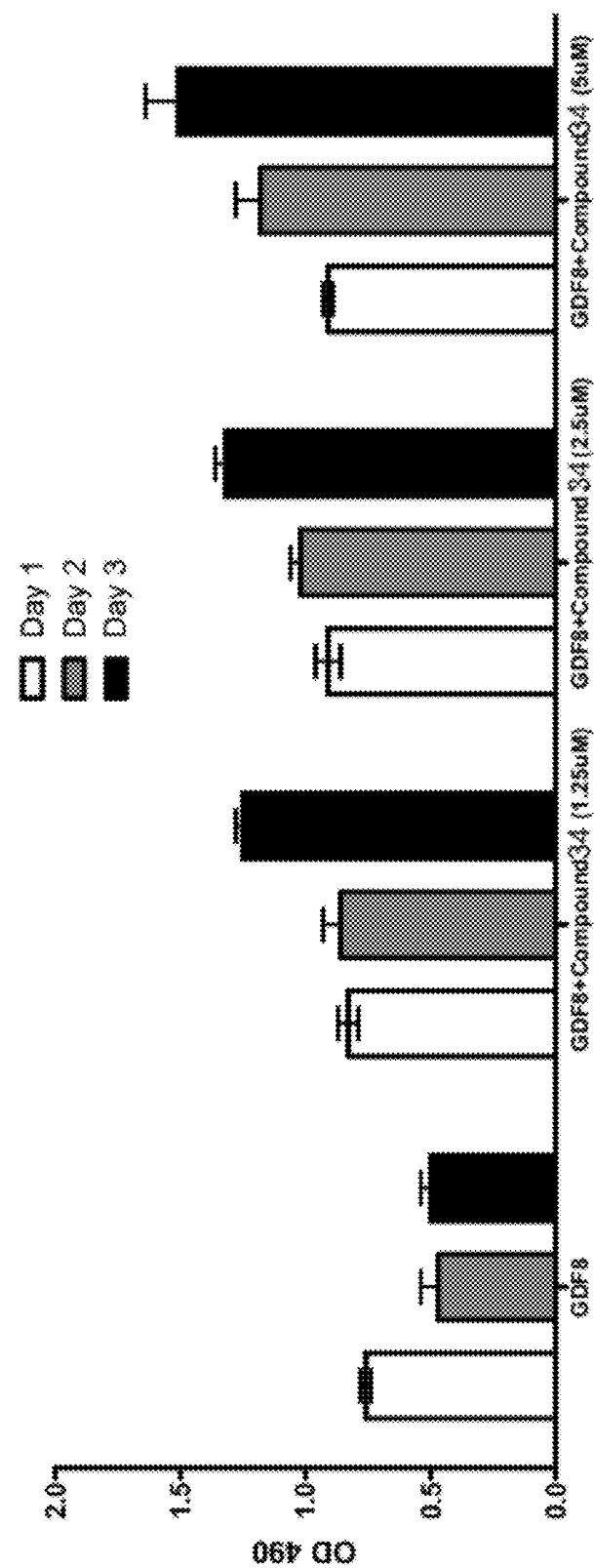
Figure 26H:
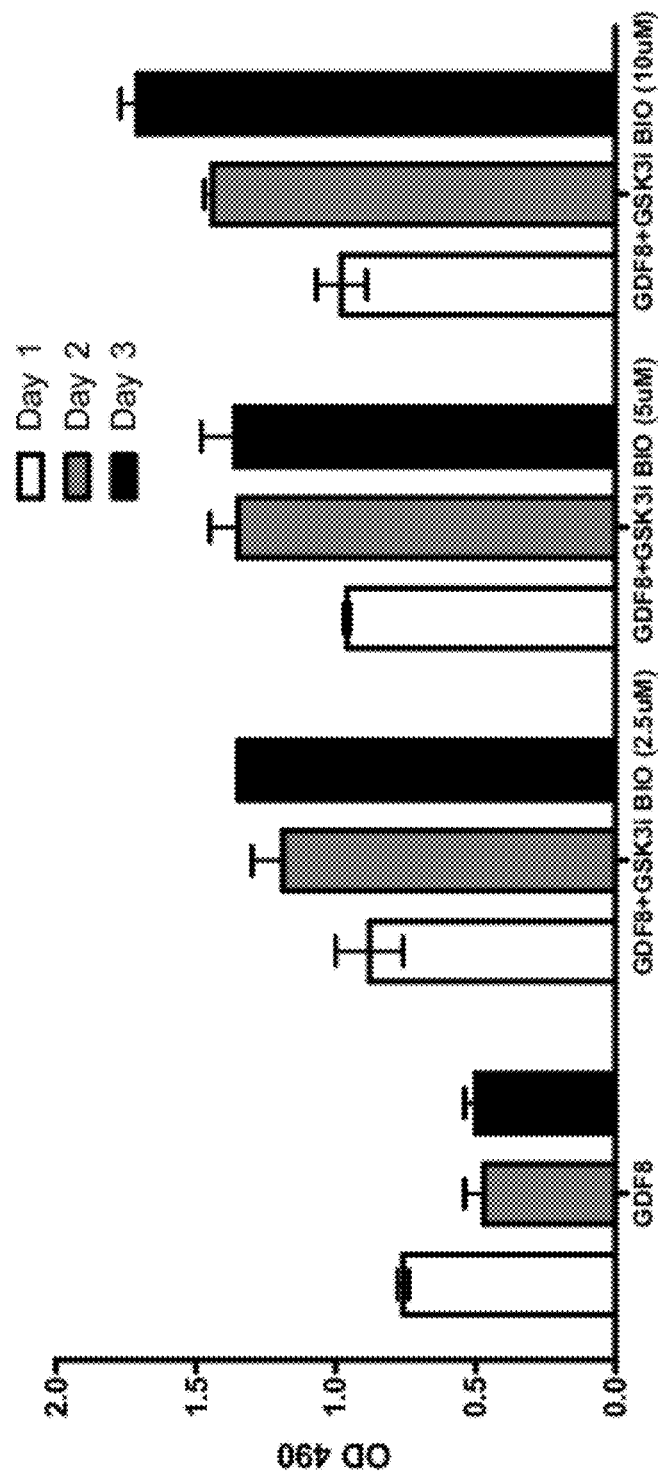
Figure 26I:
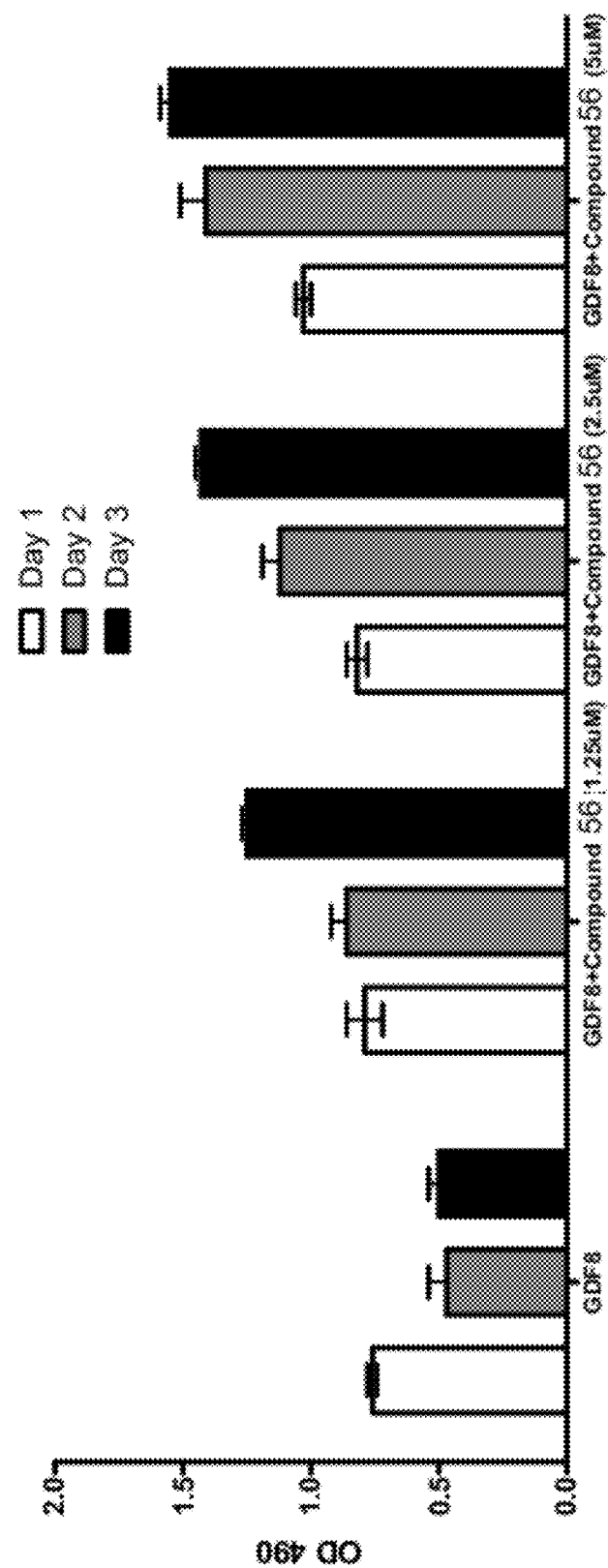

Results are shown in FIG. 25. As shown in panel A, similar numbers of cells were recovered for all treatment groups undergoing differentiation. As shown in panel B, cells treated with the Compound 34 (JNJ) alone did not differentiate into CXCR4 positive cells. The positive control treatment, adding activin A and Wnt3a during differentiation, induced expression of CXCR4 in 68% of the resulting cell population. Compound 34 added with the various growth factor combinations induced CXCR4 expression in 50% of the cells, on average. Of note, equivalent levels of CXCR4 expression were observed during treatment with Compound 34 in combination with a single growth factor, GDF-8, or in combination with multiple growth factors that included GDF-8. This proves that Compound 34 in combination with at least GDF-8 can substitute for activin A and Wnt3a to promote definitive endoderm differentiation. This example also shows that the treatment procedure is effective for cells grown and differentiated on microcarrier beads.

Example 23

The Compounds of the Present Invention, Together with GDF-8 Enhance Cell Proliferation A previous example showed that GDF-8 is able to replace activin A to differentiate human embryonic stem cells to cells expressing markers characteristic of the definitive endoderm lineage. It was important to know the relative potencies of GDF-8 and activin A with respect to definitive endoderm formation. A dose response assay was conducted using equivalent concentrations of each growth factor to compare results during human embryonic stem cell differentiation.

The compounds of the present invention used in combination with GDF-8 during definitive endoderm differentiation were evaluated for their ability to induce cell proliferation. Results were compared to treatment with activin A or GDF-8 alone.

Preparation of Cells for Assay:

Stock cultures of human embryonic stem cells (H1 human embryonic stem cell line) were maintained in an undifferentiated, pluripotent state on reduced growth factor MATRIGEL™ (BD Biosciences; Cat #356231)-coated dishes in MEF conditioned medium with passage on average every four days. Passage was performed by exposing cell cultures to a solution of 1 mg/ml dispase (Invitrogen, Cat #: 17105-041) for 5 to 7 minutes at 37° C. followed by rinsing the monolayer with MEF conditioned culture medium and gentle scraping to recover cell clusters. Clusters were centrifuged at low speed to collect a cell pellet and remove residual dispase. Cell clusters were split at a 1:3 or 1:4 ratio for routine maintenance culture or a 1:1 ratio for immediate assay. All human embryonic stem cell lines were maintained at passage numbers less than 50 and routinely evaluated for normal karyotypic phenotype and for absence of mycoplasma contamination.

Cell clusters used in the assay were evenly resuspended in MEF conditioned medium supplemented with 8 ng/ml bFGF and seeded onto reduced growth factor MATRIGEL™-coated 96-well Packard VIEWPLATES (PerkinElmer; Cat #6005182) in volumes of 100 µl/well. MEF conditioned medium supplemented with 8 ng/ml bFGF was used for initial seeding and expansion. Daily feeding was conducted by aspirating spent culture medium from each well and replacing with an equal volume of fresh medium. A background set of wells in each assay plate was not seeded with cells but was treated throughout assay with basal media conditions. Plates were maintained at 37° C., 5% $CO_2$ in a humidified box throughout the duration of assay.

Assay:

The assay was initiated by aspirating the culture medium from each well and adding back a final aliquot (100 µl) of test medium. Test conditions were performed in triplicate over a total three-day assay period, feeding daily by aspirating and replacing the medium from each well with fresh test medium. Identical assays were set up simultaneously in parallel for evaluation at the end of 24, 48, and 72 hours.

On the first day of assay, all wells containing cells received an aliquot (80 µl) of RPMI-1640 medium (Invitrogen; Cat #: 22400) supplemented with 2.5% Albumin Bovine Fraction V, Fatty Acid Free (FAF BSA; 2% in final assay) (Proliant Inc. Cat SKU 68700). Various control and test samples were created at 5× concentration to be added to appropriate wells (20 µl per well). Control conditions included the following, with final growth factor concentrations as indicated: 1) basal medium with 2% FAF BSA; 2) 100 ng/ml activin A (PeproTech; Cat #120-14) with 8 ng/ml bFGF (PeproTech; Cat #100-18B); 3) 100 ng/ml activin A with 8 ng/ml bFGF and 20 ng/ml Wnt3a (R&D Systems; Cat #1324-WN/CF); 4) 100 ng/ml GDF-8 (R&D Systems, Cat #788-G8) with 8 ng/ml bFGF; 5) GDF-8 with 8 ng/ml bFGF and 20 ng/ml Wnt3a. Cells in an additional set of control wells were treated with MEF conditioned medium throughout the assay. In some control samples using GDF-8, Wnt3a was replaced with a compound of the present invention. For experimental test samples, eight different compounds were diluted two-fold in series to create three different dose concentrations then combined with 100 ng/ml GDF-8 and 8 ng/ml bFGF. These small molecules included proprietary compounds Compound 181, Compound 180, Compound 19, Compound 202, Compound 40, Compound 34, Compound 56, and a commercially available GSK3 inhibitor BIO (EMD Chemicals, Inc.; Cat #361550). On the second and third day of assay, all wells for control and experimental samples were aspirated and fed again using identical treatment conditions except that Wnt3a was removed from some control wells.

MTS Assay:

At the conclusion of 24, 48, or 72 hours of culture, one set of assay plates was subjected to a MTS assay (Promega; Cat# G3581), following the manufacturer's instructions. In brief, 20 µl of MTS was added to each well, and assay plates were incubated at 37° C., 5% $CO_2$ for four hours prior to taking OD490 readings. Statistical measures were calculated minus background (i.e. treatment wells without cells) to determine mean values for each triplicate set in addition to a standard error of the mean.

The MTS assay is a measure of cellular metabolic activity in the enzymatic reduction of a tetrazolium compound to a formazan product. At a single time point, the MTS assay can be used as a comparative indicator of cell viability. MTS assays evaluated in parallel at sequential time points can add additional information regarding increases in cellular metabolic activity which in turn can be correlated with cell proliferation for each treatment condition. FIG. 26, panel A shows OD490 readings for all control treatments over the three day assay period. Cells treated with conditioned medium showed little change in OD490 over three days, indicating that cell numbers in this treatment group remained static. In contrast, cells cultured in basal medium without growth factors (no treatment), showed a steady decline in OD490 correlated with a loss in cell number over time. Activin A treatments during the differentiation process, with and without Wnt3a, showed incremental increases in OD490, indicating significant expansion of the cell population over time. GDF-8 treatment in the absence of Wnt3a resulted in a decrease in OD490 relative to activin A treatment; this was noticeable on the first day and sustained throughout all three days of culture. Addition of Wnt3a to the GDF-8 treatment group resulted in a recovery and increase in OD490 by the third day of culture.

FIG. 26, panel B through FIG. 26, panel I show MTS assay results for treatment with a small molecule inhibitor in combination with GDF-8. OD490 readings from treatments with a compound of the present invention and GDF-8 were equivalent to or exceeded results from treatment with activin A. In all cases, an optimal concentration of each small molecule combined with GDF-8 resulted in improved OD490 readings over the three day assay relative to treatment with GDF-8 alone. This suggests that the compounds of the present invention are important for inducing proliferation and expansion of a cell population during definitive endoderm differentiation.

Example 24

Human Embryonic Stem Cells Grown on Microcarriers can be Differentiated into Endocrine Progenitor Cells According to the Methods of the Present Invention For purposes of differentiation and production of large numbers of endocrine cells under industrial conditions, it was important to show that human embryonic stem cells could be grown and differentiated to endocrine progenitor cells on microcarrier beads using a protocol without activin A.

Preparation of Cells for Assay and Differentiation:

H1 p45 cells were grown on Cytodex3 beads (GE Healthcare; Cat #17-0485-01) in a 6 well ultra low attachment plate (Costar; Cat #3471) placed on a rocking platform at about 1 rotation every 10 seconds (Vari Mix, Thermo Scientific, Cat#M79735). MEF conditioned media was changed daily for six days. Then the media was changed to the following treatments to initiate endoderm differentiation. Cells on beads in the positive control treatment well (designated AA+Wnt) were differentiated with addition of 100 ng/ml activin A (PeproTech; Cat #120-14), 8 ng/ml bFGF (PeproTech Inc.; Cat #: 100-18B), and 20 ng/ml Wnt3a (R&D Systems; Cat #1324-WN/CF) for one day followed by 100 ng/ml activin A and 8 ng/ml bFGF (PeproTech Inc.; Cat #: 100-18B) for two days in RPMI-1640 (Invitrogen; Cat #: 22400) with 2% Fatty Acid Free BSA (Proliant Biomedicals, Inc; SKU #68700) using volumes of 2 ml/well. A second treatment well (designated GDF-8+MCX) received Compound 202 at 2.5 µM plus 200 ng/ml GDF-8 (R&D Systems, Cat #788-G8) and 8 ng/ml bFGF for one day followed by two days with 200 ng/ml GDF-8 and 8 ng/ml bFGF in RPMI-1640 with 2% Fatty Acid Free BSA (2 ml/well) media. A third treatment well (designated GDF-8+Wnt) received 200 ng/ml GDF-8 with 20 ng/ml Wnt3a and 8 ng/ml bFGF for one day followed by two days with 200 ng/ml GDF-8 and 8 ng/ml bFGF in RPMI-1640 with 2% Fatty Acid Free BSA (2 ml/well) media. All media and treatments were exchanged daily.

At the conclusion of treatment and culture, cells were harvested and counted to determine cell recovery and undergo flow cytometric analysis. High levels of CXCR4 and CD99 was seen following all three treatment regiments (FIG. 27A). Cell number varied between samples (FIG. 27B). A lower cell number was observed in samples treated with GDF-8 and at the definitive endoderm and fourth stage than the other treatment groups. This suggests that the compounds of the present invention may increase proliferation of the cells during differentiation.

Figure 27C:
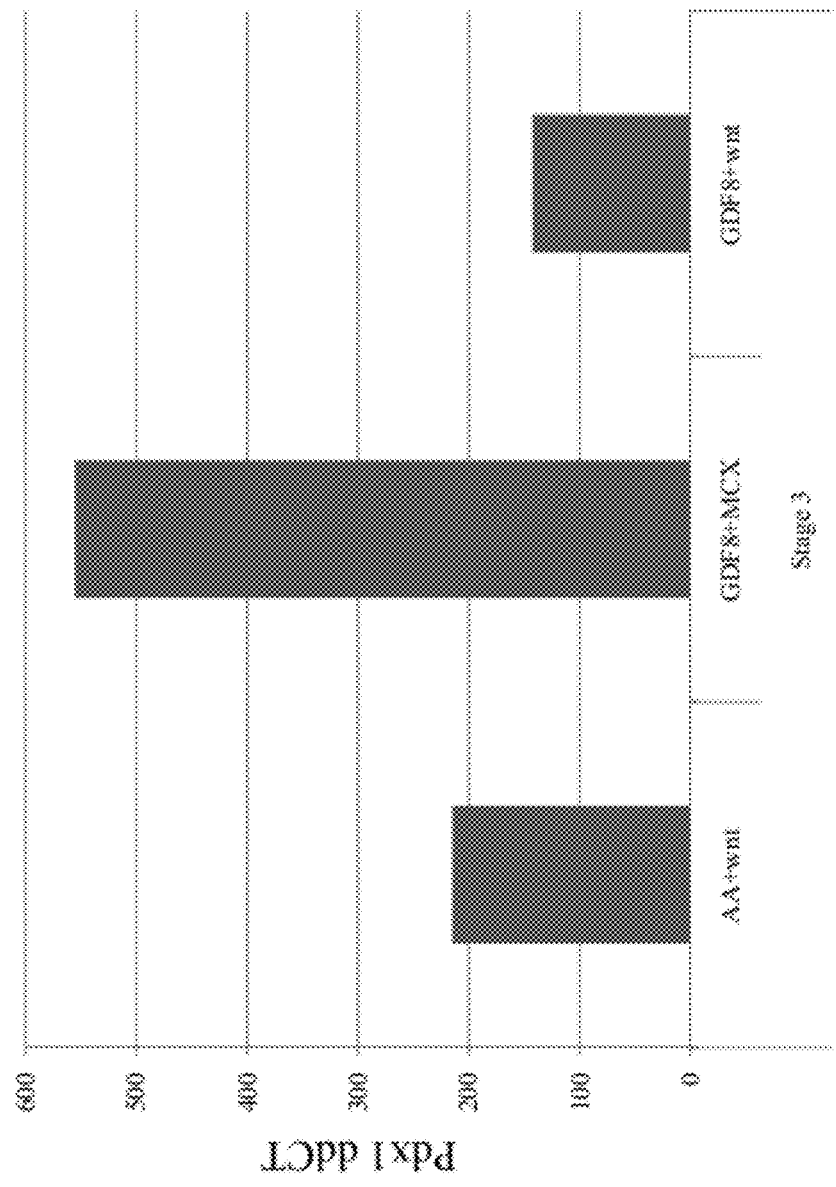
FIG. 27 shows the expression of various proteins and genes from cells grown on microcarrier beads, treated according to the methods of the present invention. Panel A shows the percent positive expression of CXCR4, CD99, and CD9 as determined by FACS in cells at the end of step one of the differentiation protocol described in Example 24. Panel B shows cells recovered from treatments as shown differentiated through step three of the differentiation protocol. Panel C shows ddCT values for various gene markers expressed in cells treated as shown in step and differentiated through step three of the protocol.
Figure 27E:
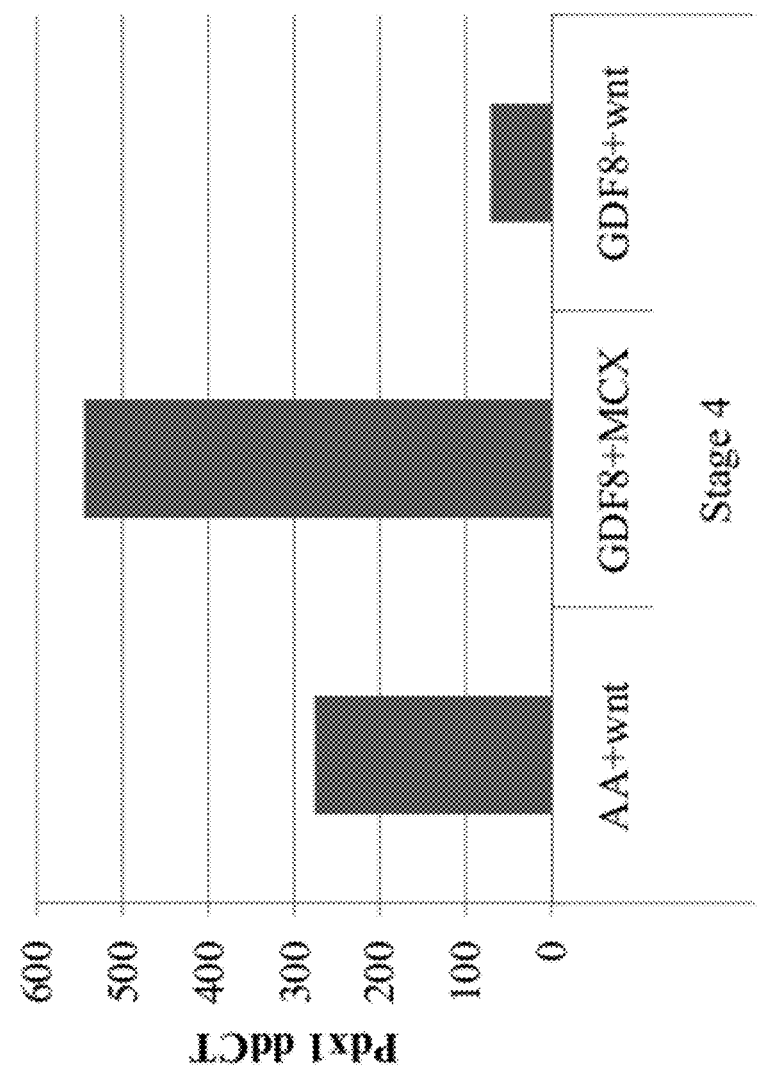

At the end of stage 3 the endodermal genes PDX1, HNF4 alpha, and CDX2 are expressed in the cells (FIGS. 27C, D). Treatment of the cells with GDF-8 and a compound of the present invention during stage one of differentiation resulted in better expression of Pdx1 than the control differentiation treatment. At the end of stage 4, endodermal genes were up regulated further (FIGS. 27E, F). These results conclude that GDF-8 plus Compound 202 can replace activin A and Wnt3a for definitive endoderm differentiation resulting in pancreatic endoderm formation.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under the principles of patent law.

TABLE 1

| | | Cell Number | | Sox17 Expression | |
| --- | --- | --- | --- | --- | --- |
| | | Average | | | |
| Plate # | Compound # | Total Cell Number | % of positive control | Average Total Intensity | % of positive control |
| plate 5 | no Activin A (with Wnt3a) | 7159 | 67.42 | 8.12E+06 | 2.51 |
| plate 5 | Activin A/Wnt3a | 10619 | 100.00 | 3.23E+08 | 100.00 |
| plate 5 | Compound 58 | 4848 | 45.66 | −1.60E+06 | −0.49 |
| plate 5 | Compound 59 | 20 | 0.19 | −4.62E+06 | −1.43 |
| plate 5 | Compound 60 | 3348 | 31.52 | −2.33E+05 | −0.07 |
| plate 5 | Compound 61 | 2931 | 27.60 | −3.05E+06 | −0.94 |
| plate 5 | Compound 62 | 7171 | 67.53 | −2.04E+06 | −0.63 |
| plate 5 | Compound 3 | 14211 | 133.82 | −2.34E+06 | −0.73 |
| plate 6 | no Activin A (with Wnt3a) | 3264 | 32.97 | 2.52E+06 | 0.80 |
| plate 6 | Activin A/Wnt3a | 9902 | 100.00 | 3.14E+08 | 100.00 |
| plate 6 | Compound 63 | 1917 | 19.36 | 4.75E+05 | 0.15 |
| plate 6 | Compound 26 | 5434 | 54.88 | −6.33E+05 | −0.20 |
| plate 6 | Compound 27 | 6288 | 63.50 | −1.13E+06 | −0.36 |
| plate 6 | Compound 28 | 4121 | 41.62 | −1.89E+06 | −0.60 |
| plate 6 | Compound 29 | 5164 | 52.15 | −1.66E+06 | −0.53 |
| plate 6 | Compound 30 | 4726 | 47.73 | −1.23E+06 | −0.39 |
| plate 7 | no Activin A (with Wnt3a) | 9545 | 47.57 | −4.87E+06 | −0.99 |
| plate 7 | Activin A/Wnt3a | 20064 | 100.00 | 4.92E+08 | 100.00 |
| plate 7 | Compound 31 | 7230 | 36.03 | −3.45E+06 | −0.70 |
| plate 7 | Compound 32 | 14655 | 73.04 | −3.03E+06 | −0.62 |
| plate 7 | Compound 33 | 13891 | 69.23 | −8.11E+06 | −1.65 |
| plate 7 | Compound 34 | 11674 | 58.18 | −2.24E+06 | −0.46 |
| plate 7 | Compound 35 | 15379 | 76.65 | −7.30E+06 | −1.48 |
| plate 7 | Compound 36 | 8356 | 41.65 | −4.57E+06 | −0.93 |
| plate 8 | no Activin A (with Wnt3a) | 6868 | 36.97 | −2.31E+06 | −0.52 |
| plate 8 | Activin A/Wnt3a | 18575 | 100.00 | 4.47E+08 | 100.00 |
| plate 8 | Compound 37 | 9048 | 48.71 | −3.51E+06 | −0.79 |
| plate 8 | Compound 38 | 11361 | 61.16 | −4.31E+06 | −0.96 |
| plate 8 | Compound 39 | 7054 | 37.98 | −3.83E+06 | −0.86 |
| plate 8 | Compound 40 | 8104 | 43.63 | −4.59E+06 | −1.03 |
| plate 1 | no Activin A (with Wnt3a) | 2972 | 27.98 | 1.64E+07 | 19.74 |
| plate 1 | Activin A/Wnt3a | 3126 | 29.44 | 8.33E+07 | 100.00 |
| plate 1 | Compound 64 | 2201 | 20.72 | 1.71E+07 | 20.52 |
| plate 1 | Compound 65 | 3030 | 28.53 | 2.83E+07 | 33.95 |
| plate 1 | Compound 66 | 1990 | 18.74 | 2.36E+07 | 28.30 |
| plate 1 | Compound 67 | 2074 | 19.53 | 2.63E+07 | 31.55 |
| plate 1 | Compound 68 | 1432 | 13.48 | 1.03E+07 | 12.39 |
| plate 1 | Compound 69 | 2593 | 24.42 | 2.62E+07 | 31.43 |
| plate 1 | Compound 70 | 2236 | 21.05 | 2.59E+07 | 31.11 |
| plate 1 | Compound 71 | 2996 | 28.22 | 3.07E+07 | 36.92 |
| plate 1 | Compound 72 | 2179 | 20.52 | 1.21E+07 | 14.50 |
| plate 1 | Compound 73 | 2817 | 26.53 | 2.93E+07 | 35.25 |
| plate 1 | Compound 74 | 2853 | 26.86 | 2.25E+07 | 27.01 |
| plate 1 | Compound 75 | 1689 | 15.91 | 1.42E+07 | 17.05 |
| plate 1 | Compound 76 | 2324 | 21.89 | 1.48E+07 | 17.81 |
| plate 1 | Compound 77 | 2306 | 21.71 | 2.04E+07 | 24.55 |
| plate 1 | Compound 78 | 3298 | 31.06 | 2.58E+07 | 31.00 |
| plate 1 | Compound 79 | 2855 | 26.88 | 2.79E+07 | 33.47 |

TABLE 1-continued

| Plate # | Compound # | Cell Number Average Total Cell Number | Cell Number % of positive control | Sox17 Expression Average Total Intensity | Sox17 Expression % of positive control |
|---|---|---|---|---|---|
| plate 1 | Compound 80 | 3603 | 33.93 | 3.22E+07 | 38.62 |
| plate 1 | Compound 81 | 2263 | 21.31 | 1.07E+07 | 12.91 |
| plate 1 | Compound 82 | 1210 | 11.39 | 1.36E+07 | 16.33 |
| plate 1 | Compound 83 | 1805 | 17.00 | 1.82E+07 | 21.87 |
| plate 1 | Compound 84 | 2024 | 19.06 | 2.48E+07 | 29.80 |
| plate 1 | Compound 85 | 2840 | 26.74 | 3.45E+07 | 41.44 |
| plate 1 | Compound 86 | 1447 | 13.63 | 8.43E+06 | 10.13 |
| plate 1 | Compound 87 | 5336 | 50.25 | 4.20E+07 | 50.38 |
| plate 2 | no Activin A (with Wnt3a) | 4033 | 35.50 | 2.14E+07 | 21.70 |
| plate 2 | Activin A/Wnt3a | 4292 | 37.78 | 9.86E+07 | 100.00 |
| plate 2 | Compound 88 | 3416 | 30.06 | 4.17E+07 | 42.28 |
| plate 2 | Compound 89 | 4751 | 41.82 | 2.11E+07 | 21.40 |
| plate 2 | Compound 90 | 4542 | 39.98 | 3.03E+07 | 30.70 |
| plate 2 | Compound 91 | 1401 | 12.33 | 1.29E+06 | 1.31 |
| plate 2 | Compound 92 | 4210 | 37.06 | 2.95E+07 | 29.90 |
| plate 2 | Compound 93 | 4157 | 36.59 | 2.29E+07 | 23.26 |
| plate 2 | Compound 94 | 4046 | 35.61 | 2.85E+07 | 28.91 |
| plate 2 | Compound 95 | 8368 | 73.66 | 4.02E+07 | 40.72 |
| plate 2 | Compound 96 | 3695 | 32.53 | 2.92E+07 | 29.57 |
| plate 2 | Compound 97 | 3437 | 30.26 | 2.41E+07 | 24.44 |
| plate 2 | Compound 98 | 4178 | 36.77 | 3.75E+07 | 38.07 |
| plate 2 | Compound 99 | 3739 | 32.91 | 2.10E+07 | 21.29 |
| plate 2 | Compound 100 | 2275 | 20.02 | 1.27E+07 | 12.86 |
| plate 2 | Compound 101 | 3496 | 30.77 | 2.98E+07 | 30.17 |
| plate 2 | Compound 102 | 4874 | 42.90 | 2.10E+07 | 21.32 |
| plate 2 | Compound 103 | 4228 | 37.22 | 2.69E+07 | 27.32 |
| plate 2 | Compound 104 | 6115 | 53.82 | 4.93E+07 | 49.99 |
| plate 2 | Compound 105 | 6484 | 57.07 | 5.03E+07 | 50.95 |
| plate 2 | Compound 106 | 4211 | 37.06 | 3.94E+07 | 40.00 |
| plate 2 | Compound 107 | 2853 | 25.11 | 1.78E+07 | 18.04 |
| plate 2 | Compound 108 | 3779 | 33.27 | 2.39E+07 | 24.26 |
| plate 2 | Compound 108 | 2869 | 25.26 | 2.04E+07 | 20.71 |
| plate 2 | Compound 110 | 4398 | 38.71 | 2.53E+07 | 25.65 |
| plate 3 | no Activin A (with Wnt3a) | 2589 | 91.17 | 1.17E+07 | 5.89 |
| plate 3 | Activin A/Wnt3a | 6933 | 244.13 | 1.98E+08 | 100.00 |
| plate 3 | Compound 111 | 6816 | 240.04 | 5.33E+07 | 26.90 |
| plate 3 | Compound 112 | 5357 | 188.66 | 3.52E+07 | 17.74 |
| plate 3 | Compound 113 | 6002 | 211.37 | 8.55E+07 | 43.11 |
| plate 3 | Compound 114 | 3308 | 116.49 | 3.85E+07 | 19.44 |
| plate 3 | Compound 115 | 5007 | 176.31 | 3.96E+07 | 19.95 |
| plate 3 | Compound 116 | 3802 | 133.89 | 3.12E+07 | 15.75 |
| plate 3 | Compound 117 | 6521 | 229.64 | 4.16E+07 | 20.97 |
| plate 3 | Compound 118 | 6128 | 215.81 | 5.53E+07 | 27.91 |
| plate 3 | Compound.119 | 4184 | 147.35 | 3.41E+07 | 17.21 |
| plate 3 | Compound 120 | 2489 | 87.66 | 2.87E+07 | 14.49 |
| plate 3 | Compound 121 | 4985 | 175.54 | 3.94E+07 | 19.87 |
| plate 3 | Compound 25 | 4151 | 146.17 | 4.03E+07 | 20.32 |
| plate 3 | Compound 122 | 6407 | 225.61 | 4.15E+07 | 20.95 |
| plate 3 | Compound 123 | 4465 | 157.24 | 5.35E+07 | 26.99 |
| plate 3 | Compound 124 | 4417 | 155.53 | 4.67E+07 | 23.55 |
| plate 3 | Compound 125 | 6367 | 224.23 | 5.73E+07 | 28.93 |
| plate 3 | Compound 126 | 6157 | 216.82 | 7.47E+07 | 37.70 |
| plate 3 | Compound 127 | 5593 | 196.97 | 5.61E+07 | 28.28 |
| plate 3 | Compound 128 | 4160 | 146.50 | 4.91E+07 | 24.77 |
| plate 3 | Compound 129 | 3778 | 133.03 | 3.54E+07 | 17.88 |
| plate 3 | Compound 130 | 4357 | 153.43 | 4.15E+07 | 20.92 |
| plate 3 | Compound 131 | 6135 | 216.05 | 4.28E+07 | 21.61 |
| plate 3 | Compound 132 | 4421 | 155.69 | 4.58E+07 | 23.12 |
| plate 3 | Compound 133 | 7069 | 248.94 | 6.52E+07 | 32.88 |
| plate 4 | no Activin A (with Wnt3a) | 3274 | 86.62 | 1.25E+07 | 12.79 |
| plate 4 | Activin A/Wnt3a | 4158 | 110.03 | 9.79E+07 | 100.00 |
| plate 4 | Compound 134 | 5277 | 139.62 | 3.43E+07 | 35.04 |
| plate 4 | Compound 64 | 5657 | 149.67 | 3.38E+07 | 34.48 |
| plate 4 | Compound 135 | 2790 | 73.83 | 1.63E+07 | 16.63 |
| plate 4 | Compound 34 | 4774 | 126.33 | 4.35E+07 | 44.47 |
| plate 4 | Compound 136 | 4881 | 129.16 | 3.20E+07 | 32.73 |
| plate 4 | Compound 137 | 1740 | 46.05 | 9.16E+06 | 9.35 |
| plate 4 | Compound 30 | 6367 | 168.46 | 4.22E+07 | 43.13 |
| plate 4 | Compound 37 | 5377 | 142.27 | 2.85E+07 | 29.14 |
| plate 4 | Compound 138 | 7722 | 204.32 | 3.07E+07 | 31.37 |
| plate 4 | Compound 139 | 3574 | 94.56 | 1.30E+07 | 13.32 |
| plate 4 | Compound 140 | 3893 | 103.00 | 1.12E+07 | 11.46 |
| plate 4 | Compound 39 | 6114 | 161.77 | 3.45E+07 | 35.22 |
| plate 4 | Compound 141 | 4310 | 114.04 | 1.61E+07 | 16.48 |
| plate 4 | Compound 142 | 5091 | 134.71 | 3.74E+07 | 38.22 |
| plate 4 | Compound 35 | 6601 | 174.65 | 8.50E+07 | 86.77 |
| plate 4 | Compound 143 | 3582 | 94.79 | 2.17E+07 | 22.14 |
| plate 4 | Compound 144 | 6787 | 179.57 | 5.45E+07 | 55.69 |
| plate 4 | Compound 145 | 3752 | 99.29 | 2.23E+07 | 22.81 |
| plate 4 | Compound 146 | 2554 | 67.59 | 1.83E+07 | 18.71 |
| plate 4 | Compound 112 | 3289 | 87.03 | 1.48E+07 | 15.11 |
| plate 4 | Compound 113 | 3819 | 101.06 | 2.34E+07 | 23.93 |
| plate 4 | Compound 114 | 1259 | 33.32 | 1.34E+07 | 13.67 |
| plate 4 | Compound 22 | 5517 | 145.98 | 7.09E+07 | 72.39 |
| plate 4 | Compound 150 | 5104 | 135.04 | 3.34E+07 | 34.11 |
| plate 5 | no Activin A (with Wnt3a) | 7159 | 116.70 | 8.12E+06 | 2.51 |
| plate 5 | Activin A/Wnt3a | 10619 | 173.09 | 3.23E+08 | 100.00 |
| plate 5 | Compound 151 | 2785 | 45.39 | −1.03E+06 | −0.32 |
| plate 5 | Compound 152 | 4693 | 76.50 | −3.08E+06 | −0.95 |
| plate 5 | Compound 153 | 9718 | 158.40 | −1.20E+06 | −0.37 |
| plate 5 | Compound 154 | 3479 | 56.70 | −1.97E+06 | −0.61 |
| plate 5 | Compound 155 | 9343 | 152.28 | −3.45E+06 | −1.07 |
| plate 5 | Compound 156 | 3813 | 62.16 | −2.58E+05 | −0.08 |
| plate 6 | no Activin A (with Wnt3a) | 3264 | 68.37 | 2.52E+06 | 0.80 |
| plate 6 | Activin A/Wnt3a | 9902 | 207.40 | 3.14E+08 | 100.00 |
| plate 6 | Compound 157 | 2480 | 51.94 | −1.22E+06 | −0.39 |
| plate 6 | Compound 158 | 5271 | 110.41 | −1.30E+06 | −0.41 |
| plate 6 | Compound 159 | 6478 | 135.68 | −1.84E+06 | −0.59 |
| plate 6 | Compound 160 | 4212 | 88.21 | 1.30E+05 | 0.04 |
| plate 6 | Compound 161 | 2439 | 51.09 | −9.20E+05 | −0.29 |
| plate 6 | Compound 162 | 1260 | 26.39 | −1.35E+06 | −0.43 |
| plate 7 | no Activin A (with Wnt3a) | 9545 | 156.12 | −4.87E+06 | −0.99 |
| plate 7 | Activin A/Wnt3a | 20064 | 328.17 | 4.92E+08 | 100.00 |
| plate 7 | Compound 163 | 16557 | 270.81 | −7.31E+06 | −1.49 |
| plate 7 | Compound 164 | 16472 | 269.42 | −7.37E+06 | −1.50 |
| plate 7 | Compound 165 | 3015 | 49.32 | −7.34E+06 | −1.49 |
| plate 7 | Compound 166 | 13845 | 226.45 | −7.98E+06 | −1.62 |
| plate 7 | Compound 167 | 10325 | 168.87 | −7.35E+06 | −1.49 |
| plate 7 | Compound 168 | 14139 | 231.26 | −6.49E+06 | −1.32 |
| plate 7 | Compound 169 | 4468 | 73.08 | −6.38E+06 | −1.30 |
| plate 8 | no Activin A (with Wnt3a) | 6868 | 179.83 | −2.31E+06 | −0.52 |
| plate 8 | Activin A/Wnt3a | 18575 | 486.35 | 4.47E+08 | 100.00 |
| plate 8 | Compound 170 | 13140 | 344.04 | −4.13E+06 | −0.93 |
| plate 8 | Compound 171 | 10894 | 285.22 | −2.61E+06 | −0.58 |
| plate 8 | Compound 172 | 3416 | 89.44 | −4.72E+06 | −1.06 |
| plate 8 | Compound 173 | 8815 | 230.81 | −4.25E+06 | −0.95 |
| plate 8 | Compound 174 | 11760 | 307.91 | −3.33E+06 | −0.75 |
| plate 8 | Compound 175 | 5 | 0.13 | −4.91E+06 | −1.10 |
| plate 8 | Compound 176 | 10139 | 265.47 | −4.73E+06 | −1.06 |
| plate 8 | Compound 177 | 9994 | 261.68 | −2.95E+06 | −0.66 |
| plate 8 | Compound 178 | 8998 | 235.58 | −3.74E+06 | −0.84 |
| plate 5 | no Activin A (with Wnt3a) | 7159 | 67.42 | 8.12E+06 | 2.51 |
| plate 5 | Activin A/Wnt3a | 10619 | 100.00 | 3.23E+08 | 100.00 |
| plate 5 | Compound 21 | 4719 | 44.44 | −1.96E+06 | −0.61 |
| plate 5 | Compound 22 | 2036 | 19.18 | −1.79E+06 | −0.55 |
| plate 5 | Compound 23 | 2563 | 24.13 | −1.56E+06 | −0.48 |
| plate 5 | Compound 24 | 4470 | 42.09 | −7.05E+05 | −0.22 |
| plate 5 | Compound 24 | 6085 | 57.30 | −3.08E+06 | −0.95 |
| plate 5 | Compound 26 | 7276 | 68.52 | −2.38E+06 | −0.74 |
| plate 5 | Compound 27 | 4588 | 43.20 | −5.63E+05 | −0.17 |
| plate 5 | Compound 28 | 2682 | 25.26 | −1.37E+06 | −0.43 |
| plate 5 | Compound 29 | 5778 | 54.41 | −1.94E+06 | −0.60 |
| plate 5 | Compound 30 | 620 | 5.84 | −5.05E+06 | −1.56 |
| plate 5 | Compound 31 | 3419 | 32.19 | −1.42E+06 | −0.44 |
| plate 6 | no Activin A (with Wnt3a) | 3264 | 69.07 | 2.52E+06 | 0.80 |

TABLE 1-continued

| Plate # | Compound # | Cell Number Average Total Cell Number | % of positive control | Sox17 Expression Average Total Intensity | % of positive control |
|---|---|---|---|---|---|
| plate 6 | Activin A/Wnt3a | 9902 | 209.51 | 3.14E+08 | 100.00 |
| plate 6 | Compound 32 | 2142 | 45.32 | −1.33E+06 | −0.42 |
| plate 6 | Compound 33 | 5564 | 117.73 | −8.63E+05 | −0.27 |
| plate 6 | Compound 34 | 5927 | 125.41 | −2.01E+06 | −0.64 |
| plate 6 | Compound 35 | 10068 | 213.01 | −2.15E+06 | −0.68 |
| plate 6 | Compound 36 | 5170 | 109.39 | −1.22E+06 | −0.39 |
| plate 6 | Compound 37 | 3098 | 65.55 | 1.91E+06 | 0.61 |
| plate 6 | Compound 38 | 1537 | 32.52 | 4.48E+04 | 0.01 |
| plate 6 | Compound 39 | 3650 | 77.23 | −2.01E+06 | −0.64 |
| plate 6 | Compound 40 | 5817 | 123.07 | 4.91E+05 | 0.16 |
| plate 6 | Compound 64 | 4359 | 92.23 | −1.07E+05 | −0.03 |
| plate 6 | Compound 30 | 4035 | 85.38 | 2.09E+06 | 0.66 |
| plate 6 | Compound 65 | 3279 | 69.37 | −5.63E+05 | −0.18 |
| plate 6 | Compound 67 | 2698 | 57.08 | −1.95E+06 | −0.62 |
| plate 7 | no Activin A (with Wnt3a) | 9545 | 321.22 | −4.87E+06 | −0.99 |
| plate 7 | Activin A/Wnt3a | 20064 | 675.20 | 4.92E+08 | 100.00 |
| plate 7 | Compound 68 | 10894 | 366.62 | −5.15E+06 | −1.05 |
| plate 7 | Compound 69 | 9734 | 327.58 | −3.97E+06 | −0.81 |
| plate 7 | Compound 70 | 16736 | 563.21 | −6.51E+06 | −1.32 |
| plate 7 | Compound 71 | 17999 | 605.71 | −7.38E+06 | −1.50 |
| plate 7 | Compound 72 | 7309 | 245.96 | −6.47E+06 | −1.32 |
| plate 7 | Compound 73 | 8888 | 299.10 | −3.03E+06 | −0.62 |
| plate 7 | Compound 74 | 11496 | 386.85 | −2.67E+06 | −0.54 |
| plate 7 | Compound 75 | 9739 | 327.74 | −7.75E+06 | −1.57 |
| plate 7 | Compound 76 | 14439 | 485.89 | −4.19E+06 | −0.85 |
| plate 7 | Conipound 77 | 12331 | 414.95 | −6.03E+06 | −1.22 |
| plate 7 | Compound 78 | 9702 | 326.49 | −6.57E+06 | −1.33 |
| plate 7 | Compound 79 | 8535 | 287.22 | −6.92E+06 | −1.41 |
| plate 8 | no Activin A (with Wnt3a) | 6868 | 295.49 | −2.31E+06 | −0.52 |
| plate 8 | Activin A/Wnt3a | 18575 | 799.17 | 4.47E+08 | 100.00 |
| plate 8 | Compound 80 | 13939 | 599.68 | −4.23E+06 | −0.95 |
| plate 8 | Compound 81 | 10466 | 450.29 | −4.91E+06 | −1.10 |
| plate 8 | Compound 82 | 10323 | 444.14 | −4.90E+06 | −1.10 |
| plate 8 | Compound 83 | 14619 | 628.95 | 1.48E+06 | 0.33 |
| plate 8 | Compound 84 | 14105 | 606.84 | −4.44E+06 | −0.99 |
| plate 8 | Compound 85 | 12172 | 523.66 | −3.48E+06 | −0.78 |
| plate 8 | Compound 86 | 7218 | 310.54 | −4.22E+06 | −0.94 |
| plate 8 | Compound 87 | 5383 | 231.58 | −4.07E+06 | −0.91 |
| plate 8 | Compound 88 | 10419 | 448.27 | −4.27E+06 | −0.96 |
| plate 8 | Compound 89 | 11780 | 506.83 | −3.94E+06 | −0.88 |
| plate 8 | Compound 90 | 7002 | 301.25 | −1.54E+06 | −0.35 |
| plate 8 | Compound 91 | 6224 | 267.78 | −4.53E+06 | −1.01 |

TABLE 2

| Compound # | Cell Number % of positive control | Sox17 Intensity % of positive control |
|---|---|---|
| Compound 17 | 133.8 | −0.7 |
| Compound 95 | 195.0 | 40.7 |
| Compound 138 | 185.7 | 31.4 |
| Compound 87 | 170.7 | 50.4 |
| Compound 144 | 163.2 | 55.7 |
| Compound 35 | 158.7 | 86.8 |
| Compound 30 | 153.1 | 43.1 |
| Compound 105 | 151.0 | 51.0 |
| Compound 39 | 147.0 | 35.2 |
| Compound 104 | 142.5 | 50.0 |
| Compound 29 | 136.0 | 34.5 |
| Compound 22 | 132.7 | 72.4 |
| Compound 37 | 129.3 | 29.1 |
| Compound 134 | 126.9 | 35.0 |
| Compound 150 | 122.7 | 34.1 |
| Compound 142 | 122.4 | 38.2 |
| Compound 136 | 117.4 | 32.7 |
| Compound 80 | 115.2 | 38.6 |
| Compound 34 | 114.8 | 44.5 |
| Compound 102 | 113.5 | 21.3 |
| Compound 89 | 110.7 | 21.4 |
| Compound 105 | 105.8 | 30.7 |
| Compound 78 | 105.5 | 31.0 |
| Compound 141 | 103.6 | 16.5 |
| Compound 110 | 102.5 | 25.7 |
| Compound 133 | 102.0 | 32.9 |

TABLE 3

| Compound # | Treatments | Cell Number Average Total Cell Number | % of positive control | Sox17 Expression Average Total Intensity | % of positive control |
|---|---|---|---|---|---|
| none | no Activin A, with Wnt3a | 23253 | 124.16 | 1.97E+07 | 10.59 |
| none | Activin A/Wnt3a | 18728 | 100.00 | 1.86E+08 | 100.00 |
| Compound 17 | no AA (with Wnt3a) EGF + FGF4 | 21445 | 114.51 | 3.43E+07 | 18.48 |
| none | no Activin A, with Wnt3a | 23253 | 124.16 | 1.97E+07 | 10.59 |
| none | Activin A/Wnt3a | 18728 | 100.00 | 1.86E+08 | 100.00 |
| Compound 22 | no AA (with Wnt3a) EGF + FGF4 | 18336 | 97.91 | 3.72E+07 | 20.05 |
| Compound 34 | no AA (with Wnt3a) EGF + FGF4 | 18891 | 100.87 | 3.26E+07 | 17.55 |
| Compound 29 | no AA (with Wnt3a) EGF + FGF4 | 20221 | 107.97 | 2.83E+07 | 15.27 |
| Compound 39 | no AA (with Wnt3a) EGF + FGF4 | 17095 | 91.28 | 2.82E+07 | 15.19 |
| Compound 37 | no AA (with Wnt3a) EGF + FGF4 | 15605 | 83.32 | 2.67E+07 | 14.37 |
| Compound 35 | no AA (with Wnt3a) EGF + FGF4 | 23823 | 127.20 | 2.54E+07 | 13.69 |
| Compound 80 | no AA (with Wnt3a) EGF + FGF4 | 19864 | 106.07 | 2.33E+07 | 12.54 |
| Compound 141 | no AA (with Wnt3a) EGF + FGF4 | 17719 | 94.61 | 2.24E+07 | 12.04 |
| Compound 30 | no AA (with Wnt3a) EGF + FGF4 | 18063 | 96.45 | 2.18E+07 | 11.73 |
| Compound 150 | no AA (with Wnt3a) EGF + FGF4 | 16833 | 89.88 | 2.16E+07 | 11.63 |
| Compound 144 | no AA (with Wnt3a) EGF + FGF4 | 17100 | 91.31 | 2.04E+07 | 11.01 |
| Compound 104 | no AA (with Wnt3a) EGF + FGF4 | 17863 | 95.38 | 1.89E+07 | 10.19 |
| Compound 142 | no AA (with Wnt3a) EGF + FGF4 | 18955 | 101.21 | 1.84E+07 | 9.90 |
| Compound 110 | no AA (with Wnt3a) EGF + FGF4 | 17534 | 93.62 | 1.76E+07 | 9.45 |
| Compound 78 | no AA (with Wnt3a) EGF + FGF4 | 17703 | 94.52 | 1.71E+07 | 9.23 |
| Compound 133 | no AA (with Wnt3a) EGF + FGF4 | 16521 | 88.22 | 1.67E+07 | 8.97 |
| Compound 87 | no AA (with Wnt3a) EGF + FGF4 | 16495 | 88.07 | 1.55E+07 | 8.33 |

TABLE 3-continued

|  |  | Cell Number | | Sox17 Expression | |
|---|---|---|---|---|---|
| Compound # | Treatments | AverageTotal Cell Number | % of positive control | Average Total Intensity | % of positive control |
| Compound 95 | no AA (with Wnt3a) EGF + FGF4 | 16900 | 90.24 | 1.43E+07 | 7.72 |
| Compound 136 | no AA (with Wnt3a) EGF + FGF4 | 19167 | 102.34 | 7.91E+06 | 4.26 |
| Compound 105 | no AA (with Wnt3a) EGF + FGF4 | 15217 | 81.25 | 7.45E+06 | 4.01 |
| Compound 134 | no AA (with Wnt3a) EGF + FGF4 | 17208 | 91.88 | 7.40E+06 | 3.99 |
| Compound 138 | no AA (with Wnt3a) EGF + FGF4 | 16695 | 89.14 | 6.65E+06 | 3.58 |
| Compound 89 | no AA (with Wnt3a) EGF + FGF4 | 14652 | 78.24 | 3.89E+06 | 2.10 |
| Compound 90 | no AA (with Wnt3a) EGF + FGF4 | 15903 | 84.92 | 3.53E+06 | 1.90 |
| Compound 102 | no AA (with Wnt3a) EGF + FGF4 | 12943 | 69.11 | 2.85E+05 | 0.15 |
| none | no Activin A, with Wnt3a | 23253 | 124.16 | 1.97E+07 | 10.59 |
| none | Activin A/Wnt3a | 18728 | 100.00 | 1.86E+08 | 100.00 |
| Compound 35 | no AA (with Wnt3a) EGF + FGF4 | 18294 | 97.68 | 1.99E+07 | 10.70 |

TABLE 3B

| Compound # | Cell Number % of positive control | Sox17 Intensity % of positive control |
|---|---|---|
| Compound 22 | 97.91 | 20.05 |
| Compound 34 | 100.87 | 17.55 |
| Compound 29 | 107.97 | 15.27 |
| Compound 39 | 91.28 | 15.19 |
| Compound 37 | 83.32 | 14.37 |
| Compound 35 | 127.20 | 13.69 |

TABLE 4

|  |  | Cell Number | | Sox17 Expression | |
|---|---|---|---|---|---|
| Compound # | Treatments | AverageTotal Cell Number | % of positive control | Average Total Intensity | % of positive control |
| none | no Activin A (with Wnt3a) | 7107 | 67.96 | −1.27E+07 | −7.94 |
| none | Activin A/Wnt3a | 10459 | 100.00 | 1.60E+08 | 100.00 |
| Compound 17 | no AA (with Wnt3a) EGF | 6942 | 73.43 | 1.27E+06 | 0.74 |
| Compound 17 | no AA (with Wnt3a) EGF + FGF4 | 5738 | 60.69 | 3.14E+06 | 1.83 |
| Compound 17 | no AA (with Wnt3a) EGF + FGF4 + PDG F-AB | 4453 | 47.10 | 9.30E+05 | 0.54 |
| Compound 17 | no AA (with Wnt3a) EGF + FGF4 + PDGF-AB + Muscimol | 10391 | 109.91 | 8.92E+06 | 5.20 |
| Compound 17 | no AA (with Wnt3a) EGF + PDGF-A + VEGF | 5728 | 60.59 | 2.14E+06 | 1.24 |
| Compound 17 | no AA (with Wnt3a) FGF4 + PDGF-A + VEGF | 13198 | 139.59 | 1.29E+07 | 7.54 |
| Compound 17 | no AA (with Wnt3a) EGF + FGF4 + PDGF-A + VEGF | 10480 | 110.85 | 8.97E+06 | 5.23 |
| Compound 17 | no AA (with Wnt3a) EGF + FGF4 + PDGF-A + Muscimol | 13649 | 144.37 | 1.45E+07 | 8.43 |
| none | no Activin A (with Wnt3a) | 3117 | 34.86 | −1.41E+06 | −0.72 |
| none | Activin A/Wnt3a | 8942 | 100.00 | 1.95E+08 | 100.00 |
| Compound 35 | no AA (with Wnt3a) EGF | 19334 | 216.23 | 6.62E+07 | 33.86 |
| Compound 35 | no AA (with Wnt3a) PDGF-AB | 16662 | 186.34 | 4.95E+07 | 25.33 |
| Compound 35 | no AA (with Wnt3a) PDGF-A | 16885 | 188.84 | 4.48E+07 | 22.94 |
| Compound 35 | no AA (with Wnt3a) VEGF | 18263 | 204.25 | 3.51E+07 | 17.98 |
| Compound 35 | no AA (with Wnt3a) FGF4 | 4410 | 49.32 | 3.33E+07 | 17.04 |
| Compound 35 | no AA (with Wnt3a) Muscimol | 18867 | 211.00 | 2.61E+07 | 13.35 |
| Compound 35 | no AA (with Wnt3a) PDGF-C | 16642 | 186.12 | 1.85E+07 | 9.46 |
| Compound 35 | no AA (with Wnt3a) PDGF-D | 17618 | 197.03 | 1.84E+07 | 9.41 |
| Compound 35 | no AA (with Wnt3a) PDGF-B | 14168 | 158.46 | 1.52E+07 | 7.76 |
| Compound 35 | no AA (with Wnt3a) PD98059 | 18877 | 211.11 | 1.30E+07 | 6.64 |
| Compound 35 | no AA (with Wnt3a) BMP1 | 18849 | 210.81 | 1.29E+07 | 6.59 |
| Compound 35 | no AA (with Wnt3a) LY294002 | 18374 | 205.49 | 1.03E+07 | 5.28 |
| Compound 35 | no AA (with Wnt3a) BMP4 | 16748 | 187.31 | 8.97E+06 | 4.59 |
| Compound 35 | no AA (with Wnt3a) BMP2 | 16218 | 181.38 | 8.89E+06 | 4.55 |
| Compound 35 | no AA (with Wnt3a) BMP7 | 20111 | 224.91 | 8.05E+06 | 4.12 |
| Compound 35 | no AA (with Wnt3a) U0124 | 16539 | 184.97 | 7.54E+06 | 3.86 |
| Compound 35 | no AA (with Wnt3a) BMP6 | 17838 | 199.50 | 7.32E+06 | 3.75 |
| Compound 35 | no AA (with Wnt3a) BMP2/7 | 12042 | 134.67 | 7.08E+06 | 3.62 |
| Compound 35 | no AA (with Wnt3a) bicuculline | 19312 | 215.98 | 1.95E+06 | 1.00 |
| Compound 35 | no AA (with Wnt3a) U0126 | 19961 | 223.24 | −5.75E+05 | −0.29 |
| Compound 35 | no AA (with Wnt3a) Butyrate | 14238 | 159.24 | −1.85E+06 | −0.94 |
| none | no Activin A (with Wnt3a) | 6049 | 45.2 | −1.31E+07 | −5.2 |
| none | Activin A/Wnt3a | 13392 | 100.0 | 2.50E+08 | 100.0 |
| Compound 20 | EGF, FGF, PDGF-A,VEGF, PDGF-D, muscimol, GDF8 | 9434 | 70.4 | 1.48E+08 | 59.1 |
| Compound 17 | EGF, FGF, PDGF-A,VEGF, PDGF-D, muscimol, GDF8 | 7988 | 59.6 | 1.13E+08 | 45.0 |
| Compound 16 | EGF, FGF, PDGF-A,VEGF, PDGF-D, muscimol, GDF8 | 8303 | 62.0 | 9.20E+07 | 36.7 |

TABLE 4-continued

|  |  | Cell Number | | Sox17 Expression | |
|---|---|---|---|---|---|
| Compound # | Treatments | Average Total Cell Number | % of positive control | Average Total Intensity | % of positive control |
| Compound 13 | EGF, FGF, PDGF-A,VEGF, PDGF-D, muscimol, GDF8 | 7045 | 52.6 | 7.22E+07 | 28.8 |
| Compound 19 | EGF, FGF, PDGF-A,VEGF, PDGF-D, muscimol, GDF8 | 7799 | 58.2 | 6.82E+07 | 27.2 |
| Compound 92 | EGF, FGF, PDGF-A,VEGF, PDGF-D, muscimol, GDF8 | 5886 | 44.0 | 5.63E+07 | 22.5 |
| Compound 93 | EGF, FGF, PDGF-A,VEGF, PDGF-D, muscimol, GDF8 | 5463 | 40.8 | 4.38E+07 | 17.5 |
| Compound 94 | EGF, FGF, PDGF-A,VEGF, PDGF-D, muscimol, GDF8 | 5100 | 38.1 | 4.18E+07 | 16.7 |
| Compound 95 | EGF, FGF, PDGF-A,VEGF, PDGF-D, muscimol, GDF8 | 4510 | 33.7 | 3.32E+07 | 13.3 |
| Compound 96 | EGF, FGF, PDGF-A,VEGF, PDGF-D, muscimol, GDF8 | 4570 | 34.1 | 3.09E+07 | 12.3 |
| Compound 97 | EGF, FGF, PDGF-A,VEGF, PDGF-D, muscimol, GDF8 | 4561 | 34.1 | 2.15E+07 | 8.6 |
| Compound 98 | EGF, FGF, PDGF-A,VEGF, PDGF-D, muscimol, GDF8 | 3176 | 23.7 | 9.86E+06 | 3.9 |
| Compound 99 | EGF, FGF, PDGF-A,VEGF, PDGF-D, muscimol, GDF8 | 1209 | 9.0 | −1.56E+07 | −6.2 |
| none | no Activin A (with Wnt3a) | 15494 | 98.0 | −1.25E+07 | −4.4 |
| none | Activin A/Wnt3a | 15807 | 100.0 | 2.86E+08 | 100.0 |
| Compound 18 | EGF, FGF, PDGF-A,VEGF, PDGF-D, muscimol, GDF8 | 8742 | 55.3 | 1.01E+08 | 35.4 |
| Compound 14 | EGF, FGF, PDGF-A,VEGF, PDGF-D, muscimol, GDF8 | 8464 | 53.5 | 8.33E+07 | 29.1 |
| Compound 15 | EGF, FGF, PDGF-A,VEGF, PDGF-D, muscimol, GDF8 | 7234 | 45.8 | 7.95E+07 | 27.8 |
| Compound 100 | EGF, FGF, PDGF-A,VEGF, PDGF-D, muscimol, GDF8 | 6805 | 43.0 | 5.88E+07 | 20.6 |
| Compound 101 | EGF, FGF, PDGF-A,VEGF, PDGF-D, muscimol, GDF8 | 5668 | 35.9 | 5.34E+07 | 18.7 |
| Compound 102 | EGF, FGF, PDGF-A,VEGF, PDGF-D, muscimol, GDF8 | 6195 | 39.2 | 5.29E+07 | 18.5 |
| Compound 103 | EGF, FGF, PDGF-A,VEGF, PDGF-D, muscimol, GDF8 | 7545 | 47.7 | 5.13E+07 | 18.0 |
| Compound 104 | EGF, FGF, PDGF-A,VEGF, PDGF-D, muscimol, GDF8 | 4757 | 30.1 | 4.58E+07 | 16.0 |
| Compound 105 | EGF, FGF, PDGF-A,VEGF, PDGF-D, muscimol, GDF8 | 6285 | 39.8 | 4.29E+07 | 15.0 |
| Compound 106 | EGF, FGF, PDGF-A,VEGF, PDGF-D, muscimol, GDF8 | 5622 | 35.6 | 2.86E+07 | 10.0 |
| Compound 107 | EGF, FGF, PDGF-A,VEGF, PDGF-D, muscimol, GDF8 | 3951 | 25.0 | 1.72E+07 | 6.0 |
| Compound 108 | EGF, FGF, PDGF-A,VEGF, PDGF-D, muscimol, GDF8 | 3226 | 20.4 | 1.58E+07 | 5.5 |
| Compound 109 | EGF, FGF, PDGF-A,VEGF, PDGF-D, muscimol, GDF8 | 3473 | 22.0 | 1.46E+07 | 5.1 |
| Compound 110 | EGF, FGF, PDGF-A,VEGF, PDGF-D, muscimol, GDF8 | 3703 | 23.4 | 1.32E+07 | 4.6 |
| Compound 111 | EGF, FGF, PDGF-A,VEGF, PDGF-D, muscimol, GDF8 | 2918 | 18.5 | 1.22E+07 | 4.3 |
| Compound 112 | EGF, FGF, PDGF-A,VEGF, PDGF-D, muscimol, GDF8 | 2975 | 18.8 | 1.04E+07 | 3.6 |
| Compound 113 | EGF, FGF, PDGF-A,VEGF, PDGF-D, muscimol, GDF8 | 2910 | 18.4 | 9.18E+06 | 3.2 |
| Compound 114 | EGF, FGF, PDGF-A,VEGF, PDGF-D, muscimol, GDF8 | 2734 | 17.3 | 6.13E+06 | 2.1 |
| Compound 115 | EGF, FGF, PDGF-A,VEGF, PDGF-D, muscimol, GDF8 | 2169 | 13.7 | 3.77E+06 | 1.3 |
| Compound 116 | EGF, FGF, PDGF-A,VEGF, PDGF-D, muscimol, GDF8 | 3107 | 19.7 | 3.52E+06 | 1.2 |
| Compound 117 | EGF, FGF, PDGF-A,VEGF, PDGF-D, muscimol, GDF8 | 3343 | 21.1 | 5.35E+05 | 0.2 |
| Compound 118 | EGF, FGF, PDGF-A,VEGF, PDGF-D, muscimol, GDF8 | 3034 | 19.2 | 2.37E+05 | 0.1 |
| Compound 119 | EGF, FGF, PDGF-A,VEGF, PDGF-D, muscimol, GDF8 | 2263 | 14.3 | −1.66E+06 | −0.6 |
| Compound 120 | EGF, FGF, PDGF-A,VEGF, PDGF-D, muscimol, GDF8 | 1771 | 11.2 | −5.57E+06 | −2.0 |
| Compound 121 | EGF, FGF, PDGF-A,VEGF, PDGF-D, muscimol, GDF8 | 1136 | 7.2 | −1.79E+07 | −6.3 |

TABLE 4-continued

|  |  | Cell Number | | Sox17 Expression | |
|---|---|---|---|---|---|
| Compound # | Treatments | Average Total Cell Number | % of positive control | Average Total Intensity | % of positive control |
| Compound 122 | EGF, FGF, PDGF-A, VEGF, PDGF-D, muscimol, GDF8 | 2021 | 12.8 | −2.09E+07 | −7.3 |

TABLE 5

|  |  |  | Cell Number | | Sox17 Expression | |
|---|---|---|---|---|---|---|
| Compound # | | Treatments | Average Total Cell Number | % of positive control | Average Total Intensity | % of positive control |
| none | | no Activin A (with Wnt3a) | 7107 | 67.96 | −1.27E+07 | −7.94 |
| none | | Activin A/Wnt3a | 10459 | 100.00 | 1.60E+08 | 100.00 |
| Compound 17 | no AA (with Wnt3a) | EGF | 6942 | 73.43 | 1.27E+06 | 0.74 |
| Compound 17 | no AA (with Wnt3a) | EGF + FGF4 | 5738 | 60.69 | 3.14E+06 | 1.83 |
| Compound 17 | no AA (with Wnt3a) | EGF + FGF4 + PDGF-AB | 4453 | 47.10 | 9.30E+05 | 0.54 |
| Compound 17 | no AA (with Wnt3a) | EGF + FGF4 + PDGF-AB + Muscimol | 10391 | 109.91 | 8.92E+06 | 5.20 |
| Compound 17 | no AA (with Wnt3a) | EGF + PDGF-A + VEGF | 5728 | 60.59 | 2.14E+06 | 1.24 |
| Compound 17 | no AA (with Wnt3a) | FGF4 + PDGF-A + VEGF | 13198 | 139.59 | 1.29E+07 | 7.54 |
| Compound 17 | no AA (with Wnt3a) | EGF + FGF4 + PDGF-A + VEGF | 10480 | 110.85 | 8.97E+06 | 5.23 |
| Compound 17 | no AA (with Wnt3a) | EGF + FGF4 + PDGF-A + Muscimol | 13649 | 144.37 | 1.45E+07 | 8.43 |
| none | | no Activin A (with Wnt3a) | 7107 | 67.96 | −1.27E+07 | −7.94 |
| none | | Activin A/Wnt3a | 10459 | 100.00 | 1.60E+08 | 100.00 |
| Compound 35 | no AA (with Wnt3a) | EGF | 23887 | 228.40 | −1.01E+07 | −6.32 |
| Compound 35 | no AA (with Wnt3a) | EGF + FGF4 | 21268 | 203.35 | 1.36E+06 | 0.85 |
| Compound 35 | no AA (with Wnt3a) | EGF + FGF4 + PDGF-AB | 17611 | 168.39 | 1.28E+07 | 8.03 |
| Compound 35 | no AA (with Wnt3a) | EGF + FGF4 + PDGF-AB + Muscimol | 17949 | 171.62 | 1.54E+06 | 0.96 |
| Compound 35 | no AA (with Wnt3a) | EGF + PDGF-A + VEGF | 23242 | 222.23 | 1.23E+07 | 7.72 |
| Compound 35 | no AA (with Wnt3a) | FGF4 + PDGF-A + VEGF | 16068 | 153.63 | 3.92E+07 | 24.57 |
| Compound 35 | no AA (with Wnt3a) | EGF + FGF4 + PDGF-A + VEGF | 16132 | 154.25 | 9.11E+07 | 57.04 |
| Compound 35 | no AA (with Wnt3a) | EGF + FGF4 + PDGF-A + Muscimol | 15457 | 147.80 | 6.89E+07 | 43.15 |
| Compound 29 | no AA (with Wnt3a) | EGF | 1971 | 18.84 | −1.44E+07 | −9.00 |
| Compound 29 | no AA (with Wnt3a) | EGF + FGF4 | 7436 | 71.10 | −4.35E+06 | −2.72 |
| Compound 29 | no AA (with Wnt3a) | EGF + FGF4 + PDGF-AB | 6535 | 62.48 | −7.52E+06 | −4.71 |
| Compound 29 | no AA (with Wnt3a) | EGF + FGF4 + PDGF-AB + Muscimol | 1376 | 13.15 | −1.42E+07 | −8.91 |
| Compound 29 | no AA (with Wnt3a) | EGF + PDGF-A + VEGF | 8880 | 84.91 | −8.53E+06 | −5.34 |
| Compound 29 | no AA (with Wnt3a) | FGF4 + PDGF-A + VEGF | 8146 | 77.89 | −4.82E+06 | −3.02 |
| Compound 29 | no AA (with Wnt3a) | EGF + FGF4 + PDGF-A + VEGF | 8858 | 84.70 | −7.15E+06 | −4.48 |
| Compound 29 | no AA (with Wnt3a) | EGF + FGF4 + PDGF-A + Muscimol | 10071 | 96.30 | 2.95E+06 | 1.85 |
| Compound 37 | no AA (with Wnt3a) | EGF | 7966 | 76.17 | −1.19E+07 | −7.42 |
| Compound 37 | no AA (with Wnt3a) | EGF + FGF4 | 6932 | 66.28 | −4.62E+06 | −2.89 |
| Compound 37 | no AA (with Wnt3a) | EGF + FGF4 + PDGF-AB | 7473 | 71.46 | −2.61E+06 | −1.63 |
| Compound 37 | no AA (with Wnt3a) | EGF + FGF4 + PDGF-AB + Muscimol | 7914 | 75.67 | −1.91E+06 | −1.20 |
| Compound 37 | no AA (with Wnt3a) | EGF + PDGF-A + VEGF | 12956 | 123.88 | −1.25E+07 | −7.82 |
| Compound 37 | no AA (with Wnt3a) | FGF4 + PDGF-A + VEGF | 6731 | 64.36 | −1.10E+07 | −6.89 |
| Compound 37 | no AA (with Wnt3a) | EGF + FGF4 + PDGF-A + VEGF | 8778 | 83.93 | 1.39E+05 | 0.09 |
| Compound 37 | no AA (with Wnt3a) | EGF + FGF4 + PDGF-A + Muscimol | 5821 | 55.66 | −1.22E+07 | −7.64 |
| Compound 34 | no AA (with Wnt3a) | EGF | 13062 | 124.89 | 2.78E+07 | 17.39 |
| Compound 34 | no AA (with Wnt3a) | EGF + FGF4 | 13133 | 125.58 | 1.23E+08 | 76.85 |
| Compound 34 | no AA (with Wnt3a) | EGF + FGF4 + PDGF-AB | 12532 | 119.83 | 1.09E+08 | 68.41 |
| Compound 34 | no AA (with Wnt3a) | EGF + FGF4 + PDGF-AB + Muscimol | 15811 | 151.18 | 6.90E+06 | 4.32 |
| Compound 34 | no AA (with Wnt3a) | EGF + PDGF-A + VEGF | 11801 | 112.84 | 4.04E+06 | 2.53 |
| Compound 34 | no AA (with Wnt3a) | FGF4 + PDGF-A + VEGF | 15262 | 145.93 | 1.15E+07 | 7.18 |
| Compound 34 | no AA (with Wnt3a) | EGF + FGF4 + PDGF-A + VEGF | 12901 | 123.36 | 5.01E+07 | 31.35 |
| Compound 34 | no AA (with Wnt3a) | EGF + FGF4 + PDGF-A + Muscimol | 12208 | 116.72 | 5.56E+07 | 34.83 |
| none | | no Activin A (with Wnt3a) | 10224 | 108.14 | 7.36E+05 | 0.43 |
| none | | Activin A/Wnt3a | 9455 | 100.00 | 1.72E+08 | 100.00 |
| Compound 39 | no AA (with Wnt3a) | EGF | 11615 | 122.85 | 1.49E+05 | 0.09 |
| Compound 39 | no AA (with Wnt3a) | EGF + FGF4 | 10456 | 110.59 | 5.11E+06 | 2.98 |
| Compound 39 | no AA (with Wnt3a) | EGF + FGF4 + PDGF-AB | 9972 | 105.47 | 1.62E+06 | 0.94 |
| Compound 39 | no AA (with Wnt3a) | EGF + FGF4 + PDGF-AB + Muscimol | 10540 | 111.48 | 2.22E+06 | 1.29 |
| Compound 39 | no AA (with Wnt3a) | EGF + PDGF-A + VEGF | 17050 | 180.34 | 4.84E+06 | 2.82 |
| Compound 39 | no AA (with Wnt3a) | FGF4 + PDGF-A + VEGF | 8856 | 93.67 | 7.01E+05 | 0.41 |
| Compound 39 | no AA (with Wnt3a) | EGF + FGF4 + PDGF-A + VEGF | 7973 | 84.33 | 5.30E+06 | 3.09 |
| Compound 39 | no AA (with Wnt3a) | EGF + FGF4 + PDGF-A + Muscimol | 9103 | 96.28 | 7.32E+05 | 0.43 |
| Compound 22 | no AA (with Wnt3a) | EGF | 14105 | 149.19 | 1.75E+06 | 1.02 |
| Compound 22 | no AA (with Wnt3a) | EGF + FGF4 | 12971 | 137.19 | 1.04E+07 | 6.05 |
| Compound 22 | no AA (with Wnt3a) | EGF + FGF4 + PDGF-AB | 16580 | 175.36 | 8.60E+06 | 5.01 |
| Compound 22 | no AA (with Wnt3a) | EGF + FGF4 + PDGF-AB + Muscimol | 14676 | 155.23 | 5.61E+06 | 3.27 |
| Compound 22 | no AA (with Wnt3a) | EGF + PDGF-A + VEGF | 20372 | 215.48 | 4.99E+06 | 2.91 |
| Compound 22 | no AA (with Wnt3a) | FGF4 + PDGF-A + VEGF | 12277 | 129.85 | 4.90E+06 | 2.86 |

TABLE 5-continued

|  |  | Cell Number | | Sox17 Expression | |
|---|---|---|---|---|---|
| Compound # | Treatments | Average Total Cell Number | % of positive control | Average Total Intensity | % of positive control |
| Compound 22 | no AA (with Wnt3a) EGF + FGF4 + PDGF-A + VEGF | 12522 | 132.44 | 7.88E+06 | 4.59 |
| Compound 22 | no AA (with Wnt3a) EGF + FGF4 + PDGF-A + Muscimol | 11610 | 122.80 | 1.33E+07 | 7.77 |

TABLE 6

|  |  | Cell Number | | Sox17 Expression | |
|---|---|---|---|---|---|
| Compound # | Treatments | Average Total Cell Number | % of positive control | Average Total Intensity | % of positive control |
| none | no Activin A (with Wnt3a) | 477 | 6.64 | 7.4E+04 | 0.09 |
| none | Activin A/Wnt3a | 7185 | 100.00 | 8.0E+07 | 100.00 |
| Compound 34 | no AA (with Wnt3a) none | 4611 | 64.18 | 1.4E+07 | 17.21 |
| Compound 34 | no AA (with Wnt3a) EGF | 6145 | 85.53 | 1.5E+07 | 19.18 |
| Compound 34 | no AA (with Wnt3a) FGF4 | 5323 | 74.09 | 2.7E+07 | 33.75 |
| Compound 34 | no AA (with Wnt3a) PDGF-D | 5017 | 69.84 | 1.5E+07 | 18.76 |
| Compound 34 | no AA (with Wnt3a) PDGF-A | 4175 | 58.11 | 1.1E+07 | 13.43 |
| Compound 34 | no AA (with Wnt3a) VEGF | 4713 | 65.60 | 1.0E+07 | 12.49 |
| Compound 34 | no AA (with Wnt3a) GDF8 | 6354 | 88.44 | 7.1E+07 | 88.59 |
| Compound 34 | no AA (with Wnt3a) Muscimol | 7286 | 101.41 | 3.1E+07 | 38.38 |
| Compound 34 | no AA (with Wnt3a) PDGF-D + VEGF | 5030 | 70.01 | 1.2E+07 | 14.58 |
| Compound 34 | no AA (with Wnt3a) VEGF + Muscimol | 776 | 10.81 | 1.3E+06 | 1.56 |
| Compound 34 | no AA (with Wnt3a) PDGF-D + Muscimol | 3490 | 48.57 | 6.5E+06 | 8.02 |
| Compound 34 | no AA (with Wnt3a) GDF8 + PDGF-D | 6889 | 95.88 | 5.8E+07 | 72.59 |
| Compound 34 | no AA (with Wnt3a) PDGF-D + Muscimol + VEGF | 2133 | 29.68 | 2.7E+06 | 3.32 |
| Compound 34 | no AA (with Wnt3a) GDF8 + PDGF-D + VEGF | 5585 | 77.74 | 6.6E+07 | 81.75 |
| Compound 34 | no AA (with Wnt3a) GDF8 + VEGF + Muscimol | 6083 | 84.67 | 5.6E+07 | 69.62 |
| Compound 34 | no AA (with Wnt3a) GDF8 + PDGF-D + VEGF + Muscimol | 9455 | 131.60 | 9.6E+07 | 119.24 |
| Compound 34 | no AA, no Wnt3a  EGF + FGF4 + PDGF-A + VEGF + PDGF-D + Muscimol + GDF8 | 4757 | 66.21 | 3.9E+07 | 48.77 |
| Compound 34 | no AA (with Wnt3a) EGF + FGF4 + PDGF-A + VEGF + PDGF-D + Muscimol + GDF8 | 6028 | 83.90 | 7.0E+07 | 87.44 |

TABLE 7

| Plate | Treatment | Compound # | Cell Number | | Sox17 Expression | |
|---|---|---|---|---|---|---|
|  |  |  | Average Total Cell Number | % of positive control | Average Total Intensity | % of positive control |
| 1 | no Activin A (with Wnt3a) | none | 6049 | 45.2 | −1.31E+07 | −5.2 |
| 1 | Activin A/Wnt3a | none | 13392 | 100.0 | 2.50E+08 | 100.0 |
| 1 | EGF, FGF, PDGF-A, VEGF, PDGF-D, muscimol, GDF8 | Compound 18 | 13037 | 97.3 | 1.63E+08 | 65.2 |
| 1 | EGF, FGF, PDGF-A, VEGF, PDGF-D, muscimol, GDF8 | Compound 14 | 9344 | 69.8 | 1.23E+08 | 49.0 |
| 1 | EGF, FGF, PDGF-A, VEGF, PDGF-D, muscimol, GDF8 | Compound 15 | 8448 | 63.1 | 8.64E+07 | 34.5 |
| 1 | EGF, FGF, PDGF-A, VEGF, PDGF-D, muscimol, GDF8 | Compound 16 | 5498 | 41.1 | 6.56E+07 | 26.2 |

TABLE 7-continued

| Plate | Treatment | Compound # | Cell Number Average Total Cell Number | % of positive control | Sox17 Expression Average Total Intensity | % of positive control |
|---|---|---|---|---|---|---|
| 1 | EGF, FGF, PDGF-A, VEGF, PDGF-D, muscimol, GDF8 | Compound 64 | 5063 | 37.8 | 5.88E+07 | 23.5 |
| 1 | EGF, FGF, PDGF-A, VEGF, PDGF-D, muscimol, GDF8 | Compound 65 | 4788 | 35.8 | 4.57E+07 | 18.2 |
| 1 | EGF, FGF, PDGF-A, VEGF, PDGF-D, muscimol, GDF8 | Compound 66 | 8129 | 60.7 | 3.53E+07 | 14.1 |
| 1 | EGF, FGF, PDGF-A, VEGF, PDGF-D, muscimol, GDF8 | Compound 67 | 6791 | 50.7 | 3.18E+07 | 12.7 |
| 1 | EGF, FGF, PDGF-A, VEGF, PDGF-D, muscimol, GDF8 | Compound 68 | 3456 | 25.8 | 2.30E+07 | 9.2 |
| 1 | EGF, FGF, PDGF-A, VEGF, PDGF-D, muscimol, GDF8 | Compound 69 | 3995 | 29.8 | 1.69E+07 | 6.8 |
| 1 | EGF, FGF, PDGF-A, VEGF, PDGF-D, muscimol, GDF8 | Compound 70 | 474 | 3.5 | −1.80E+07 | −7.2 |
| 2 | no Activin A (with Wnt3a) | none | 15494 | 98.0 | −1.25E+07 | −4.4 |
| 2 | Activin A/Wnt3a | none | 15807 | 100.0 | 2.86E+08 | 100.0 |
| 2 | EGF, FGF, PDGF-A, VEGF, PDGF-D, muscimol, GDF8 | Compound 19 | 8425 | 53.3 | 1.19E+08 | 41.6 |
| 2 | EGF, FGF, PDGF-A, VEGF, PDGF-D, muscimol, GDF8 | Compound 13 | 9123 | 57.7 | 1.13E+08 | 39.7 |
| 2 | EGF, FGF, PDGF-A, VEGF, PDGF-D, muscimol, GDF8 | Compound 71 | 6048 | 38.3 | 5.51E+07 | 19.3 |
| 2 | EGF, FGF, PDGF-A, VEGF, PDGF-D, muscimol, GDF8 | Compound 72 | 6060 | 38.3 | 5.46E+07 | 19.1 |
| 2 | EGF, FGF, PDGF-A, VEGF, PDGF-D, muscimol, GDF8 | Compound 73 | 5545 | 35.1 | 3.99E+07 | 14.0 |
| 2 | EGF, FGF, PDGF-A, VEGF, PDGF-D, muscimol, GDF8 | Compound 74 | 10898 | 68.9 | 3.91E+07 | 13.7 |
| 2 | EGF, FGF, PDGF-A, VEGF, PDGF-D, muscimol, GDF8 | Compound 75 | 4117 | 26.0 | 3.01E+07 | 10.5 |
| 2 | EGF, FGF, PDGF-A, VEGF, PDGF-D, muscimol, GDF8 | Compound 76 | 3825 | 24.2 | 2.74E+07 | 9.6 |
| 2 | EGF, FGF, PDGF-A, VEGF, PDGF-D, muscimol, GDF8 | Compound 77 | 5928 | 37.5 | 2.44E+07 | 8.5 |
| 2 | EGF, FGF, PDGF-A, VEGF, PDGF-D, muscimol, GDF8 | Compound 78 | 3303 | 20.9 | 2.03E+07 | 7.1 |
| 2 | EGF, FGF, PDGF-A, VEGF, PDGF-D, muscimol, GDF8 | Compound 79 | 4767 | 30.2 | 1.85E+07 | 6.5 |
| 2 | EGF, FGF, PDGF-A, VEGF, PDGF-D, muscimol, GDF8 | Compound 80 | 2194 | 13.9 | 1.22E+07 | 4.3 |
| 2 | EGF, FGF, PDGF-A, VEGF, PDGF-D, muscimol, GDF8 | Compound 81 | 2920 | 18.5 | 9.16E+05 | 0.3 |
| 2 | EGF, FGF, PDGF-A, VEGF, PDGF-D, muscimol, GDF8 | Compound 82 | 1819 | 11.5 | −1.05E+07 | −3.7 |
| 2 | EGF, FGF, PDGF-A, VEGF, PDGF-D, muscimol, GDF8 | Compound 83 | 2153 | 13.6 | −1.19E+07 | −4.2 |
| 2 | EGF, FGF, PDGF-A, VEGF, PDGF-D, muscimol, GDF8 | Compound 84 | 58 | 0.4 | −2.94E+07 | −10.3 |
| 2 | EGF, FGF, PDGF-A, VEGF, PDGF-D, muscimol, GDF8 | Compound 85 | 57 | 0.4 | −3.03E+07 | −10.6 |
| 1 | no Activin A (with Wnt3a) | none | 6049 | 45.2 | −1.31E+07 | −5.2 |
| 1 | Activin A/Wnt3a | none | 13392 | 100.0 | 2.50E+08 | 100.0 |
| 1 | EGF, FGF, PDGF-A, VEGF, PDGF-D, muscimol, GDF8 | Compound 20 | 9434 | 70.4 | 1.48E+08 | 59.1 |
| 1 | EGF, FGF, PDGF-A, VEGF, PDGF-D, muscimol, GDF8 | Compound 17 | 7988 | 59.6 | 1.13E+08 | 45.0 |
| 1 | EGF, FGF, PDGF-A, VEGF, PDGF-D, muscimol, GDF8 | Compound 16 | 8303 | 62.0 | 9.20E+07 | 36.7 |
| 1 | EGF, FGF, PDGF-A, VEGF, PDGF-D, muscimol, GDF8 | Compound 13 | 7045 | 52.6 | 7.22E+07 | 28.8 |
| 1 | EGF, FGF, PDGF-A, VEGF, PDGF-D, muscimol, GDF8 | Compound 19 | 7799 | 58.2 | 6.82E+07 | 27.2 |
| 1 | EGF, FGF, PDGF-A, VEGF, PDGF-D, muscimol, GDF8 | Compound 92 | 5886 | 44.0 | 5.63E+07 | 22.5 |
| 1 | EGF, FGF, PDGF-A, VEGF, PDGF-D, muscimol, GDF8 | Compound 93 | 5463 | 40.8 | 4.38E+07 | 17.5 |
| 1 | EGF, FGF, PDGF-A, VEGF, PDGF-D, muscimol, GDF8 | Compound 94 | 5100 | 38.1 | 4.18E+07 | 16.7 |
| 1 | EGF, FGF, PDGF-A, VEGF, PDGF-D, muscimol, GDF8 | Compound 95 | 4510 | 33.7 | 3.32E+07 | 13.3 |
| 1 | EGF, FGF, PDGF-A, VEGF, PDGF-D, muscimol, GDF8 | Compound 96 | 4570 | 34.1 | 3.09E+07 | 12.3 |
| 1 | EGF, FGF, PDGF-A, VEGF, PDGF-D, muscimol, GDF8 | Compound 97 | 4561 | 34.1 | 2.15E+07 | 8.6 |

TABLE 7-continued

| Plate | Treatment | Compound # | Cell Number | | Sox17 Expression | |
|---|---|---|---|---|---|---|
| | | | Average Total Cell Number | % of positive control | Average Total Intensity | % of positive control |
| 1 | EGF, FGF, PDGF-A, VEGF, PDGF-D, muscimol, GDF8 | Compound 98 | 3176 | 23.7 | 9.86E+06 | 3.9 |
| 1 | EGF, FGF, PDGF-A, VEGF, PDGF-D, muscimol, GDF8 | Compound 99 | 1209 | 9.0 | −1.56E+07 | −6.2 |
| 2 | no Activin A (with Wnt3a) | none | 15494 | 98.0 | −1.25E+07 | −4.4 |
| 2 | Activin A/Wnt3a | none | 15807 | 100.0 | 2.86E+08 | 100.0 |
| 2 | EGF, FGF, PDGF-A, VEGF, PDGF-D, muscimol, GDF8 | Compound 18 | 8742 | 55.3 | 1.01E+08 | 35.4 |
| 2 | EGF, FGF, PDGF-A, VEGF, PDGF-D, muscimol, GDF8 | Compound 14 | 8464 | 53.5 | 8.33E+07 | 29.1 |
| 2 | EGF, FGF, PDGF-A, VEGF, PDGF-D, muscimol, GDF8 | Compound 15 | 7234 | 45.8 | 7.95E+07 | 27.8 |
| 2 | EGF, FGF, PDGF-A, VEGF, PDGF-D, muscimol, GDF8 | Compound 100 | 6805 | 43.0 | 5.88E+07 | 20.6 |
| 2 | EGF, FGF, PDGF-A, VEGF, PDGF-D, muscimol, GDF8 | Compound 101 | 5668 | 35.9 | 5.34E+07 | 18.7 |
| 2 | EGF, FGF, PDGF-A, VEGF, PDGF-D, muscimol, GDF8 | Compound 102 | 6195 | 39.2 | 5.29E+07 | 18.5 |
| 2 | EGF, FGF, PDGF-A, VEGF, PDGF-D, muscimol, GDF8 | Compound 103 | 7545 | 47.7 | 5.13E+07 | 18.0 |
| 2 | EGF, FGF, PDGF-A, VEGF, PDGF-D, muscimol, GDF8 | Compound 104 | 4757 | 30.1 | 4.58E+07 | 16.0 |
| 2 | EGF, FGF, PDGF-A, VEGF, PDGF-D, muscimol, GDF8 | Compound 105 | 6285 | 39.8 | 4.29E+07 | 15.0 |
| 2 | EGF, FGF, PDGF-A, VEGF, PDGF-D, muscimol, GDF8 | Compound 106 | 5622 | 35.6 | 2.86E+07 | 10.0 |
| 2 | EGF, FGF, PDGF-A, VEGF, PDGF-D, muscimol, GDF8 | Compound 107 | 3951 | 25.0 | 1.72E+07 | 6.0 |
| 2 | EGF, FGF, PDGF-A, VEGF, PDGF-D, muscimol, GDF8 | Compound 108 | 3226 | 20.4 | 1.58E+07 | 5.5 |
| 2 | EGF, FGF, PDGF-A, VEGF, PDGF-D, muscimol, GDF8 | Compound 109 | 3473 | 22.0 | 1.46E+07 | 5.1 |
| 2 | EGF, FGF, PDGF-A, VEGF, PDGF-D, muscimol, GDF8 | Compound 110 | 3703 | 23.4 | 1.32E+07 | 4.6 |
| 2 | EGF, FGF, PDGF-A, VEGF, PDGF-D, muscimol, GDF8 | Compound 111 | 2918 | 18.5 | 1.22E+07 | 4.3 |
| 2 | EGF, FGF, PDGF-A, VEGF, PDGF-D, muscimol, GDF8 | Compound 112 | 2975 | 18.8 | 1.04E+07 | 3.6 |
| 2 | EGF, FGF, PDGF-A, VEGF, PDGF-D, muscimol, GDF8 | Compound 113 | 2910 | 18.4 | 9.18E+06 | 3.2 |
| 2 | EGF, FGF, PDGF-A, VEGF, PDGF-D, muscimol, GDF8 | Compound 114 | 2734 | 17.3 | 6.13E+06 | 2.1 |
| 2 | EGF, FGF, PDGF-A, VEGF, PDGF-D, muscimol, GDF8 | Compound 115 | 2169 | 13.7 | 3.77E+06 | 1.3 |
| 2 | EGF, FGF, PDGF-A, VEGF, PDGF-D, muscimol, GDF8 | Compound 116 | 3107 | 19.7 | 3.52E+06 | 1.2 |
| 2 | EGF, FGF, PDGF-A, VEGF, PDGF-D, muscimol, GDF8 | Compound 117 | 3343 | 21.1 | 5.35E+05 | 0.2 |
| 2 | EGF, FGF, PDGF-A, VEGF, PDGF-D, muscimol, GDF8 | Compound 118 | 3034 | 19.2 | 2.37E+05 | 0.1 |
| 2 | EGF, FGF, PDGF-A, VEGF, PDGF-D, muscimol, GDF8 | Compound 119 | 2263 | 14.3 | −1.66E+06 | −0.6 |
| 2 | EGF, FGF, PDGF-A, VEGF, PDGF-D, muscimol, GDF8 | Compound 120 | 1771 | 11.2 | −5.57E+06 | −2.0 |
| 2 | EGF, FGF, PDGF-A, VEGF, PDGF-D, muscimol, GDF8 | Compound 121 | 1136 | 7.2 | −1.79E+07 | −6.3 |
| 2 | EGF, FGF, PDGF-A, VEGF, PDGF-D, muscimol, GDF8 | Compound 122 | 2021 | 12.8 | −2.09E+07 | −7.3 |
| 1 | no Activin A (with Wnt3a) | none | 6049 | 45.2 | −1.31E+07 | −5.2 |
| 1 | Activin A/Wnt3a | none | 13392 | 100.0 | 2.50E+08 | 100.0 |
| 1 | EGF, FGF, PDGF-A, VEGF, PDGF-D, muscimol, GDF8 | Compound 19 | 15878 | 118.6 | 2.67E+08 | 106.5 |
| 1 | EGF, FGF, PDGF-A, VEGF, PDGF-D, muscimol, GDF8 | Compound 24 | 12714 | 94.9 | 2.46E+08 | 98.2 |
| 1 | EGF, FGF, PDGF-A, VEGF, PDGF-D, muscimol, GDF8 | Compound 23 | 12165 | 90.8 | 2.15E+08 | 86.0 |
| 1 | EGF, FGF, PDGF-A, VEGF, PDGF-D, muscimol, GDF8 | Compound 21 | 12640 | 94.4 | 1.65E+08 | 65.9 |
| 1 | EGF, FGF, PDGF-A, VEGF, PDGF-D, muscimol, GDF8 | Compound 13 | 11491 | 85.8 | 1.61E+08 | 64.3 |
| 1 | EGF, FGF, PDGF-A, VEGF, PDGF-D, muscimol, GDF8 | Compound 30 | 11396 | 85.1 | 1.34E+08 | 53.4 |
| 1 | EGF, FGF, PDGF-A, VEGF, PDGF-D, muscimol, GDF8 | Compound 36 | 7964 | 59.5 | 9.47E+07 | 37.8 |

TABLE 7-continued

|  |  |  | Cell Number | | Sox17 Expression | |
|---|---|---|---|---|---|---|
| Plate | Treatment | Compound # | Average Total Cell Number | % of positive control | Average Total Intensity | % of positive control |
| 1 | EGF, FGF, PDGF-A, VEGF, PDGF-D, muscimol, GDF8 | Compound 32 | 8066 | 60.2 | 9.29E+07 | 37.1 |
| 1 | EGF, FGF, PDGF-A, VEGF, PDGF-D, muscimol, GDF8 | Compound 26 | 7415 | 55.4 | 8.30E+07 | 33.1 |
| 1 | EGF, FGF, PDGF-A, VEGF, PDGF-D, muscimol, GDF8 | Compound 17 | 6994 | 52.2 | 7.76E+07 | 31.0 |
| 1 | EGF, FGF, PDGF-A, VEGF, PDGF-D, muscimol, GDF8 | Compound 31 | 6957 | 51.9 | 6.59E+07 | 26.3 |
| 1 | EGF, FGF, PDGF-A, VEGF, PDGF-D, muscimol, GDF8 | Compound 179 | 3573 | 26.7 | 2.43E+07 | 9.7 |
| 1 | EGF, FGF, PDGF-A, VEGF, PDGF-D, muscimol, GDF8 | Compound 180 | 922 | 6.9 | −2.20E+07 | −8.8 |
| 1 | EGF, FGF, PDGF-A, VEGF, PDGF-D, muscimol, GDF8 | Compound 181 | 8 | 0.1 | −2.68E+07 | −10.7 |
| 2 | no Activin A (with Wnt3a) | none | 15494 | 98.0 | −1.25E+07 | −4.4 |
| 2 | Activin A/Wnt3a | none | 15807 | 100.0 | 2.86E+08 | 100.0 |
| 2 | EGF, FGF, PDGF-A, VEGF, PDGF-D, muscimol, GDF8 | Compound 18 | 21102 | 133.5 | 4.18E+08 | 146.3 |
| 2 | EGF, FGF, PDGF-A, VEGF, PDGF-D, muscimol, GDF8 | Compound 15 | 15373 | 97.3 | 3.74E+08 | 130.8 |
| 2 | EGF, FGF, PDGF-A, VEGF, PDGF-D, muscimol, GDF8 | Compound 14 | 9008 | 57.0 | 2.62E+08 | 91.6 |
| 2 | EGF, FGF, PDGF-A, VEGF, PDGF-D, muscimol, GDF8 | Compound 38 | 9650 | 61.0 | 2.46E+08 | 86.2 |
| 2 | EGF, FGF, PDGF-A, VEGF, PDGF-D, muscimol, GDF8 | Compound 35 | 10461 | 66.2 | 1.59E+08 | 55.7 |
| 2 | EGF, FGF, PDGF-A, VEGF, PDGF-D, muscimol, GDF8 | Compound 16 | 9064 | 57.3 | 1.48E+08 | 51.8 |
| 2 | EGF, FGF, PDGF-A, VEGF, PDGF-D, muscimol, GDF8 | Compound 34 | 8907 | 56.3 | 9.99E+07 | 35.0 |
| 2 | EGF, FGF, PDGF-A, VEGF, PDGF-D, muscimol, GDF8 | Compound 20 | 7346 | 46.5 | 8.90E+07 | 31.2 |
| 2 | EGF, FGF, PDGF-A, VEGF, PDGF-D, muscimol, GDF8 | Compound 27 | 8044 | 50.9 | 8.81E+07 | 30.8 |
| 2 | EGF, FGF, PDGF-A, VEGF, PDGF-D, muscimol, GDF8 | Compound 28 | 7591 | 48.0 | 8.77E+07 | 30.7 |
| 2 | EGF, FGF, PDGF-A, VEGF, PDGF-D, muscimol, GDF8 | Compound 40 | 4049 | 25.6 | 8.23E+07 | 28.8 |
| 2 | EGF, FGF, PDGF-A, VEGF, PDGF-D, muscimol, GDF8 | Compound 33 | 7485 | 47.4 | 8.10E+07 | 28.3 |
| 2 | EGF, FGF, PDGF-A, VEGF, PDGF-D, muscimol, GDF8 | Compound 25 | 6571 | 41.6 | 7.60E+07 | 26.6 |
| 2 | EGF, FGF, PDGF-A, VEGF, PDGF-D, muscimol, GDF8 | Compound 182 | 7631 | 48.3 | 6.74E+07 | 23.6 |
| 2 | EGF, FGF, PDGF-A, VEGF, PDGF-D, muscimol, GDF8 | Compound 183 | 6777 | 42.9 | 5.93E+07 | 20.8 |
| 2 | EGF, FGF, PDGF-A, VEGF, PDGF-D, muscimol, GDF8 | Compound 184 | 5475 | 34.6 | 5.44E+07 | 19.0 |
| 2 | EGF, FGF, PDGF-A, VEGF, PDGF-D, muscimol, GDF8 | Compound 185 | 4093 | 25.9 | 4.92E+07 | 17.2 |
| 2 | EGF, FGF, PDGF-A, VEGF, PDGF-D, muscimol, GDF8 | Compound 186 | 5274 | 33.4 | 4.63E+07 | 16.2 |
| 2 | EGF, FGF, PDGF-A, VEGF, PDGF-D, muscimol, GDF8 | Compound 187 | 5342 | 33.8 | 4.02E+07 | 14.1 |
| 2 | EGF, FGF, PDGF-A, VEGF, PDGF-D, muscimol, GDF8 | Compound 188 | 5533 | 35.0 | 3.98E+07 | 13.9 |
| 2 | EGF, FGF, PDGF-A, VEGF, PDGF-D, muscimol, GDF8 | Compound 189 | 5928 | 37.5 | 3.96E+07 | 13.9 |
| 2 | EGF, FGF, PDGF-A, VEGF, PDGF-D, muscimol, GDF8 | Compound 190 | 4822 | 30.5 | 3.90E+07 | 13.7 |
| 2 | EGF, FGF, PDGF-A, VEGF, PDGF-D, muscimol, GDF8 | Compound 191 | 4249 | 26.9 | 3.81E+07 | 13.3 |
| 2 | EGF, FGF, PDGF-A, VEGF, PDGF-D, muscimol, GDF8 | Compound 192 | 5616 | 35.5 | 3.54E+07 | 12.4 |
| 2 | EGF, FGF, PDGF-A, VEGF, PDGF-D, muscimol, GDF8 | Compound 193 | 4158 | 26.3 | 3.23E+07 | 11.3 |
| 2 | EGF, FGF, PDGF-A, VEGF, PDGF-D, muscimol, GDF8 | Compound 194 | 3470 | 22.0 | 2.96E+07 | 10.4 |
| 2 | EGF, FGF, PDGF-A, VEGF, PDGF-D, muscimol, GDF8 | Compound 195 | 3800 | 24.0 | 2.95E+07 | 10.3 |
| 2 | EGF, FGF, PDGF-A, VEGF, PDGF-D, muscimol, GDF8 | Compound 196 | 4619 | 29.2 | 2.78E+07 | 9.7 |
| 2 | EGF, FGF, PDGF-A, VEGF, PDGF-D, muscimol, GDF8 | Compound 197 | 4011 | 25.4 | 2.45E+07 | 8.6 |

TABLE 7-continued

| Plate | Treatment | Compound # | Cell Number Average Total Cell Number | Cell Number % of positive control | Sox17 Expression Average Total Intensity | Sox17 Expression % of positive control |
|---|---|---|---|---|---|---|
| 2 | EGF, FGF, PDGF-A, VEGF, PDGF-D, muscimol, GDF8 | Compound 198 | 4367 | 27.6 | 1.92E+07 | 6.7 |
| 2 | EGF, FGF, PDGF-A, VEGF, PDGF-D, muscimol, GDF8 | Compound 199 | 3162 | 20.0 | 1.20E+07 | 4.2 |
| 2 | EGF, FGF, PDGF-A, VEGF, PDGF-D, muscimol, GDF8 | Compound 200 | 2087 | 13.2 | 4.43E+06 | 1.6 |
| 2 | EGF, FGF, PDGF-A, VEGF, PDGF-D, muscimol, GDF8 | Compound 201 | 1568 | 9.9 | −6.17E+06 | −2.2 |
| 2 | EGF, FGF, PDGF-A, VEGF, PDGF-D, muscimol, GDF8 | Compound 202 | 5213 | 33.0 | −1.41E+07 | −4.9 |
| 2 | EGF, FGF, PDGF-A, VEGF, PDGF-D, muscimol, GDF8 | Compound 203 | 7 | 0.0 | −3.04E+07 | −10.6 |
| 2 | EGF, FGF, PDGF-A, VEGF, PDGF-D, muscimol, GDF8 | Compound 204 | 11 | 0.1 | −3.18E+07 | −11.1 |
| 2 | EGF, FGF, PDGF-A, VEGF, PDGF-D, muscimol, GDF8 | Compound 205 | 10 | 0.1 | −3.20E+07 | −11.2 |

TABLE 8

| Compound # | Cell Number AverageTotal Cell Number | Cell Number % of positive control | Sox17 Expression Average Total Intensity | Sox17 Expression % of positive control |
|---|---|---|---|---|
| Compound 18 | 21102 | 133.5 | 4.18E+08 | 146.3 |
| Compound 15 | 15373 | 97.3 | 3.74E+08 | 130.8 |
| Compound 19 | 15878 | 118.6 | 2.67E+08 | 106.5 |
| Compound 24 | 12714 | 94.9 | 2.46E+08 | 98.2 |
| Compound 14 | 9008 | 57.0 | 2.62E+08 | 91.6 |
| Compound 38 | 9650 | 61.0 | 2.46E+08 | 86.2 |
| Compound 23 | 12165 | 90.8 | 2.15E+08 | 86.0 |
| Compound 21 | 12640 | 94.4 | 1.65E+08 | 65.9 |
| Compound 13 | 11491 | 85.8 | 1.61E+08 | 64.3 |
| Compound 35 | 10461 | 66.2 | 1.59E+08 | 55.7 |
| Compound 30 | 11396 | 85.1 | 1.34E+08 | 53.4 |
| Compound 16 | 9064 | 57.3 | 1.48E+08 | 51.8 |
| Compound 36 | 7964 | 59.5 | 9.47E+07 | 37.8 |
| Compound 32 | 8066 | 60.2 | 9.29E+07 | 37.1 |
| Compound 34 | 8907 | 56.3 | 9.99E+07 | 35.0 |
| Compound 26 | 7415 | 55.4 | 8.30E+07 | 33.1 |
| Compound 20 | 7346 | 46.5 | 8.90E+07 | 31.2 |
| Compound 17 | 6994 | 52.2 | 7.76E+07 | 31.0 |
| Compound 27 | 8044 | 50.9 | 8.81E+07 | 30.8 |
| Compound 28 | 7591 | 48.0 | 8.77E+07 | 30.7 |
| Compound 40 | 4049 | 25.6 | 8.23E+07 | 28.8 |
| Compound 33 | 7485 | 47.4 | 8.10E+07 | 28.3 |
| Compound 25 | 6571 | 41.6 | 7.60E+07 | 26.6 |
| Compound 31 | 6957 | 51.9 | 6.59E+07 | 26.3 |
| Compound 20 | 9434 | 70.4 | 1.48E+08 | 59.1 |
| Compound 17 | 7988 | 59.6 | 1.13E+08 | 45.0 |
| Compound 16 | 8303 | 62.0 | 9.20E+07 | 36.7 |
| Compound 18 | 8742 | 55.3 | 1.01E+08 | 35.4 |
| Compound 14 | 8464 | 53.5 | 8.33E+07 | 29.1 |
| Compound 13 | 7045 | 52.6 | 7.22E+07 | 28.8 |
| Compound 15 | 7234 | 45.8 | 7.95E+07 | 27.8 |
| Compound 19 | 7799 | 58.2 | 6.82E+07 | 27.2 |

TABLE 9

| Plate # | Activin A | Compound # | Growth Factors | Cell Number Average Total Cell Number | Cell Number % of positive control | Sox17 Expression Average Total Intensity | Sox17 Expression % of positive control |
|---|---|---|---|---|---|---|---|
| 1 | none | none | none | 9164 | 149.46 | −5.91E+06 | −5.17 |
| 1 | 10 ng/ml AA | none | none | 6132 | 100.00 | 1.52E+06 | 1.33 |
| 1 | 100 ng/ml AA | none | none | 9658 | 157.51 | 1.14E+08 | 100.00 |
| 1 | 10 ng/ml AA | Compound 22 | EGF + FGF4 + PDGF-A + VEGF + PDGF-D + Muscimol + GDF8 + Wnt3a | 8556 | 139.53 | 8.78E+07 | 76.82 |
| 1 | 10 ng/ml AA | Compound 22 | EGF + FGF4 + PDGF-AB + VEGF + Wnt3a | 7657 | 124.87 | 4.70E+07 | 41.09 |
| 1 | 10 ng/ml AA | Compound 22 | EGF + FGF4 + PDGF-A + Muscimol + Wnt3a | 8100 | 132.10 | 4.42E+07 | 38.65 |
| 1 | 10 ng/ml AA | Compound 22 | EGF + FGF4 + PDGF-AB + Wnt3a | 7975 | 130.06 | 3.43E+07 | 30.03 |
| 1 | 10 ng/ml AA | Compound 22 | EGF + FGF4 + Wnt3a | 9800 | 159.83 | 4.59E+07 | 40.13 |
| 1 | 10 ng/ml AA | Compound 22 | FGF4 + Wnt3a | 6490 | 105.84 | 4.28E+07 | 37.43 |
| 1 | 10 ng/ml AA | Compound 22 | EGF + Wnt3a | 5001 | 81.55 | 2.80E+07 | 24.45 |
| 1 | 10 ng/ml AA | Compound 22 | Wnt3a | 4543 | 74.09 | 3.05E+07 | 26.65 |
| 1 | 10 ng/ml AA | Compound 35 | EGF + FGF4 + PDGF-A + VEGF + PDGF-D + Muscimol + GDF8 + Wnt3a | 2522 | 41.14 | −4.86E+06 | −4.25 |
| 1 | 10 ng/ml AA | Compound 35 | EGF + FGF4 + PDGF-AB + VEGF + Wnt3a | 3479 | 56.74 | −3.96E+06 | −3.46 |
| 1 | 10 ng/ml AA | Compound 35 | EGF + FGF4 + PDGF-A + Muscimol + Wnt3a | 3820 | 62.29 | −1.67E+06 | −1.46 |
| 1 | 10 ng/ml AA | Compound 35 | EGF + FGF4 + PDGF-AB + Wnt3a | 3263 | 53.21 | −4.56E+06 | −3.99 |
| 1 | 10 ng/ml AA | Compound 35 | EGF + FGF4 + Wnt3a | 2704 | 44.10 | −4.17E+06 | −3.65 |

TABLE 9-continued

| | | | | Cell Number | | Sox17 Expression | |
|---|---|---|---|---|---|---|---|
| | | Treatments | | Average Total Cell | % of positive | Average Total | % of positive |
| Plate # | Activin A | Compound # | Growth Factors | Number | control | Intensity | control |
| 1 | 10 ng/ml AA | Compound 35 | FGF4 + Wnt3a | 284 | 4.64 | −7.54E+06 | −6.59 |
| 1 | 10 ng/ml AA | Compound 35 | EGF + Wnt3a | 155 | 2.53 | −7.82E+06 | −6.84 |
| 1 | 10 ng/ml AA | Compound 35 | Wnt3a | 173 | 2.83 | −7.61E+06 | −6.66 |
| 1 | 10 ng/ml AA | Compound 29 | EGF + FGF4 + PDGF-A + VEGF + PDGF-D + Muscimol + GDF8 + Wnt3a | 2737 | 44.63 | 2.41E+07 | 21.10 |
| 1 | 10 ng/ml AA | Compound 29 | EGF + FGF4 + PDGF-AB + VEGF + Wnt3a | 2283 | 37.23 | 5.59E+06 | 4.88 |
| 1 | 10 ng/ml AA | Compound 29 | EGF + FGF4 + PDGF-A + Muscimol + Wnt3a | 4676 | 76.26 | 2.41E+07 | 21.11 |
| 1 | 10 ng/ml AA | Compound 29 | EGF + FGF4 + PDGF-AB + Wnt3a | 3964 | 64.65 | 2.27E+07 | 19.89 |
| 1 | 10 ng/ml AA | Compound 29 | EGF + FGF4 + Wnt3a | 1736 | 28.31 | 1.98E+06 | 1.73 |
| 1 | 10 ng/ml AA | Compound 29 | FGF4 + Wnt3a | 2139 | 34.89 | 6.98E+06 | 6.10 |
| 1 | 10 ng/ml AA | Compound 29 | EGF + Wnt3a | 365 | 5.96 | −4.86E+06 | −4.25 |
| 1 | 10 ng/ml AA | Compound 29 | Wnt3a | 2090 | 34.09 | 4.89E+06 | 4.28 |
| 2 | none | none | none | 9325 | 121.89 | −3.35E+06 | −3.01 |
| 2 | 10 ng/ml AA | none | none | 5177 | 67.67 | 3.89E+06 | 3.49 |
| 2 | 100 ng/ml AA | none | none | 7650 | 100.00 | 1.11E+08 | 100.00 |
| 2 | 10 ng/ml AA | Compound 34 | EGF + FGF4 + PDGF-A + VEGF + PDGF-D + Muscimol + GDF8 + Wnt3a | 18362 | 240.02 | 3.45E+08 | 309.74 |
| 2 | 10 ng/ml AA | Compound 34 | EGF + FGF4 + PDGF-AB + VEGF + Wnt3a | 15574 | 203.58 | 2.59E+08 | 232.70 |
| 2 | 10 ng/ml AA | Compound 34 | EGF + FGF4 + PDGF-A + Muscimol + Wnt3a | 17890 | 233.85 | 2.88E+08 | 258.30 |
| 2 | 10 ng/ml AA | Compound 34 | EGF + FGF4 + PDGF-AB + Wnt3a | 17875 | 233.65 | 2.68E+08 | 241.07 |
| 2 | 10 ng/ml AA | Compound 34 | EGF + FGF4 + Wnt3a | 14158 | 185.07 | 2.40E+08 | 215.35 |
| 2 | 10 ng/ml AA | Compound 34 | FGF4 + Wnt3a | 13323 | 174.15 | 2.19E+08 | 196.86 |
| 2 | 10 ng/ml AA | Compound 34 | EGF + Wnt3a | 14527 | 189.89 | 2.28E+08 | 204.84 |
| 2 | 10 ng/ml AA | Compound 34 | Wnt3a | 3589 | 46.91 | 7.02E+07 | 63.08 |
| 2 | 10 ng/ml AA | Compound 39 | EGF + FGF4 + PDGF-A + VEGF + PDGF-D + Muscimol + GDF8 + Wnt3a | 5738 | 75.00 | 2.14E+07 | 19.24 |
| 2 | 10 ng/ml AA | Compound 39 | EGF + FGF4 + PDGF-AB + VEGF + Wnt3a | 2531 | 33.08 | 2.82E+06 | 2.53 |
| 2 | 10 ng/ml AA | Compound 39 | EGF + FGF4 + PDGF-A + Muscimol + Wnt3a | 2879 | 37.64 | 3.61E+06 | 3.24 |
| 2 | 10 ng/ml AA | Compound 39 | EGF + FGF4 + PDGF-AB + Wnt3a | 2989 | 39.07 | −1.78E+04 | −0.02 |
| 2 | 10 ng/ml AA | Compound 39 | EGF + FGF4 + Wnt3a | 734 | 9.59 | −3.93E+06 | −3.53 |
| 2 | 10 ng/ml AA | Compound 39 | FGF4 + Wnt3a | 521 | 6.81 | −4.46E+06 | −4.01 |
| 2 | 10 ng/ml AA | Compound 39 | EGF + Wnt3a | 211 | 2.75 | −4.54E+06 | −4.08 |
| 2 | 10 ng/ml AA | Compound 39 | Wnt3a | 518 | 6.78 | −2.37E+06 | −2.13 |
| 2 | 10 ng/ml AA | Compound 37 | EGF + FGF4 + PDGF-A + VEGF + PDGF-D + Muscimol + GDF8 + Wnt3a | 5711 | 74.65 | 1.21E+07 | 10.82 |
| 2 | 10 ng/ml AA | Compound 37 | EGF + FGF4 + PDGF-AB + VEGF + Wnt3a | 4767 | 62.31 | −5.16E+05 | −0.46 |
| 2 | 10 ng/ml AA | Compound 37 | EGF + FGF4 + PDGF-A + Muscimol + Wnt3a | 4540 | 59.34 | 9.23E+05 | 0.83 |
| 2 | 10 ng/ml AA | Compound 37 | EGF + FGF4 + PDGF-AB + Wnt3a | 4223 | 55.20 | −6.15E+05 | −0.55 |
| 2 | 10 ng/ml AA | Compound 37 | EGF + FGF4 + Wnt3a | 3501 | 45.77 | 5.60E+05 | 0.50 |
| 2 | 10 ng/ml AA | Compound 37 | FGF4 + Wnt3a | 3930 | 51.37 | −1.88E+06 | −1.69 |
| 2 | 10 ng/ml AA | Compound 37 | EGF + Wnt3a | 1431 | 18.70 | −2.75E+06 | −2.47 |
| 2 | 10 ng/ml AA | Compound 37 | Wnt3a | 791 | 10.34 | −2.99E+06 | −2.68 |

TABLE 10

| | | | | Cell Number | | Sox17 Expression | |
|---|---|---|---|---|---|---|---|
| Compound # | Treatments | | | Average Total Cell Number | % of positive control | Average Total Intensity | % of positive control |
| none | No Activin A (with Wnt3a) | | | 4273 | 33.70 | 4.75E+07 | 17.49 |
| none | Activin A (with Wnt3a) | | | 12676 | 100.00 | 2.72E+08 | 100.00 |
| Compound 34 | No AA (without Wnt3a) | FGF (50 ng/ml) | EGF (50 ng/ml) | 13317 | 105.06 | 2.01E+08 | 74.08 |
| Compound 34 | No AA (without Wnt3a) | FGF (50 ng/ml) | EGF (100 ng/ml) | 14189 | 111.93 | 2.01E+08 | 73.90 |
| Compound 34 | No AA (without Wnt3a) | FGF (100 ng/ml) | EGF (50 ng/ml) | 12616 | 99.52 | 1.80E+08 | 66.21 |
| Compound 34 | No AA (without Wnt3a) | FGF (100 ng/ml) | EGF (100 ng/ml) | 8269 | 65.23 | 1.13E+08 | 41.73 |
| Compound 34 | No AA (with Wnt3a) | none | none | 11711 | 92.38 | 1.65E+08 | 60.68 |
| Compound 34 | No AA (with Wnt3a) | none | EGF (25 ng/ml) | 16052 | 126.63 | 2.14E+08 | 78.82 |
| Compound 34 | No AA (with Wnt3a) | none | EGF (50 ng/ml) | 13593 | 107.23 | 1.94E+08 | 71.52 |
| Compound 34 | No AA (with Wnt3a) | none | EGF (100 ng/ml) | 13170 | 103.90 | 1.93E+08 | 71.04 |
| Compound 34 | No AA (with Wnt3a) | FGF (25 ng/ml) | none | 18433 | 145.41 | 2.49E+08 | 91.72 |
| Compound 34 | No AA (with Wnt3a) | FGF (25 ng/ml) | EGF (25 ng/ml) | 18841 | 148.63 | 2.60E+08 | 95.72 |
| Compound 34 | No AA (with Wnt3a) | FGF (25 ng/ml) | EGF (50 ng/ml) | 16232 | 128.05 | 2.30E+08 | 84.79 |
| Compound 34 | No AA (with Wnt3a) | FGF (25 ng/ml) | EGF (100 ng/ml) | 9309 | 73.44 | 1.39E+08 | 51.00 |
| Compound 34 | No AA (with Wnt3a) | FGF (50 ng/ml) | none | 12757 | 100.64 | 1.66E+08 | 61.10 |
| Compound 34 | No AA (with Wnt3a) | FGF (50 ng/ml) | EGF (25 ng/ml) | 17720 | 139.79 | 2.31E+08 | 85.01 |
| Compound 34 | No AA (with Wnt3a) | FGF (50 ng/ml) | EGF (50 ng/ml) | 16331 | 128.83 | 2.26E+08 | 83.11 |
| Compound 34 | No AA (with Wnt3a) | FGF (50 ng/ml) | EGF (100 ng/ml) | 16336 | 128.87 | 2.32E+08 | 85.24 |
| Compound 34 | No AA (with Wnt3a) | FGF (100 ng/ml) | none | 19853 | 156.61 | 2.59E+08 | 95.45 |

TABLE 10-continued

| Compound # | Treatments | | | Cell Number Average Total Cell Number | % of positive control | Sox17 Expression Average Total Intensity | % of positive control |
|---|---|---|---|---|---|---|---|
| Compound 34 | No AA (with Wnt3a) | FGF (100 ng/ml) | EGF (25 ng/ml) | 19880 | 156.83 | 2.59E+08 | 95.47 |
| Compound 34 | No AA (with Wnt3a) | FGF (100 ng/ml) | EGF (50 ng/ml) | 18166 | 143.30 | 2.35E+08 | 86.30 |
| Compound 34 | No AA (with Wnt3a) | FGF (100 ng/ml) | EGF (100 ng/ml) | 11241 | 88.68 | 1.55E+08 | 57.10 |
| none | No AA (with Wnt3a) | none | EGF (50 ng/ml) | 5558 | 43.85 | 5.01E+07 | 18.44 |
| none | No AA (with Wnt3a) | none | EGF (100 ng/ml) | 6818 | 53.79 | 6.42E+07 | 23.62 |
| none | No AA (with Wnt3a) | FGF (50 ng/ml) | none | 8494 | 67.01 | 6.62E+07 | 24.35 |
| none | No AA (with Wnt3a) | FGF (50 ng/ml) | EGF (50 ng/ml) | 10138 | 79.98 | 7.30E+07 | 26.87 |
| none | No AA (with Wnt3a) | FGF (50 ng/ml) | EGF (100 ng/ml) | 10219 | 80.62 | 7.75E+07 | 28.51 |
| none | No AA (with Wnt3a) | FGF (100 ng/ml) | none | 9944 | 78.45 | 6.68E+07 | 24.59 |
| none | No AA (with Wnt3a) | FGF (100 ng/ml) | EGF (50 ng/ml) | 11046 | 87.14 | 8.17E+07 | 30.07 |
| none | No AA (with Wnt3a) | FGF (100 ng/ml) | EGF (100 ng/ml) | 7695 | 60.71 | 6.87E+07 | 25.28 |

TABLE 11

| | Normalized SOX17 Intensity | | | |
|---|---|---|---|---|
| ng/ml | Activin A Average | SD | GDF8 Average | SD |
| 1600 | 100.00 | 9.20 | 100.00 | 9.00 |
| 800 | 100.00 | 6.60 | 84.90 | 6.30 |
| 400 | 100.00 | 3.30 | 72.20 | 7.50 |
| 200 | 100.00 | 1.90 | 51.30 | 5.30 |
| 100 | 90.70 | 8.70 | 32.70 | 5.10 |
| 50 | 85.20 | 4.70 | 17.60 | 4.80 |
| 25 | 73.10 | 2.80 | 5.10 | 3.60 |
| 12.50 | 50.90 | 6.20 | 0.90 | 0.80 |
| 6.25 | 18.40 | 4.80 | 0.70 | 1.40 |
| 3.13 | 3.00 | 1.90 | 0.10 | 0.20 |
| 1.56 | 0.10 | 0.00 | 0.00 | 0.20 |
| 0.00 | 0.00 | 0.20 | 0.30 | 0.30 |

TABLE 12

| Marker name | Catalog # * |
|---|---|
| AFP | Hs00173490_m1 |
| CD99 | Hs00365982_m1 |
| CD9 | Hs00233521_m1 |
| CDH1 | Hs00170423_m1 |
| CDH2 | Hs00169953_m1 |
| CDX2 | Hs00230919_m1 |
| CER1 | Hs00193796_m1 |
| CXCR4 | Hs00237052_m1 |
| FGF17 | Hs00182599_m1 |
| FGF4 | Hs00173564_m1 |
| FOXA2 | Hs00232764_m1 |
| GAPDH | Hs99999905_m1 |
| GATA4 | Hs00171403_m1 |
| GATA6 | Hs00232018_m1 |
| GSC | Hs00418279_m1 |
| HLXB9 | Hs00232128_m1 |
| KIT | Hs00174029_m1 |
| MIXL1 | Hs00430824_g1 |
| NANOG | Hs02387400_g1 |
| OTX2 | Hs00222238_m1 |
| POU5F1 | Hs00742896_s1 |
| SOX17 | Hs00751752_s1 |
| SOX7 | Hs00846731_s1 |
| T | Hs00610080_m1 |
| ALB | Hs00609411_m1 |
| AMY2A | Hs00420710_g1 |
| ARX | Hs00292465_m1 |
| CDX2 | Hs00230919_m1 |
| GAPDH | Hs99999905_m1 |
| GCG | Hs00174967_m1 |
| HNF4A | Hs00230853_m1 |
| INS | Hs00355773_m1 |
| ISL1 | Hs00158126_m1 |
| MAFA | Hs01651425_s1 |
| MAFB | Hs00534343_s1 |
| NEUROD1 | Hs00159598_m1 |
| NEUROG3 | Hs00360700_g1 |
| NKX2-2 | Hs00159616_m1 |
| NKX2-5 | Hs00231763_m1 |
| NKX6-1 | Hs00232355_m1 |
| PAX4 | Hs00173014_m1 |
| PAX6 | Hs00240871_m1 |
| PDX1 | Hs00236830_m1 |
| PECAM1 | Hs00169777_m1 |
| POU3F4 | Hs00264887_s1 |
| PTF1A | Hs00603586_g1 |
| SST | Hs00356144_m1 |
| ZIC1 | Hs00602749_m1 |

TABLE 13

| Differentiation Step 1 | CT Values | | | | | | | | | | | | |
|---|---|---|---|---|---|---|---|---|---|---|---|---|---|
| Treatment | GAPDH | AFP | CD9 | CD99 | CDH1 | CDH2 | CDX2 | CER1 | CXCR4 | FGF17 | FGF4 | FOXA2 | GATA4 |
| AA/Wnt3a | 19.5 | 34.7 | 23.8 | 24.1 | 24.5 | 21.5 | 36.8 | 18.4 | 22.7 | 20 | 33.5 | 24.7 | 23.7 |
| GDF8/Wnt3a | 18.7 | 36.1 | 23 | 23.5 | 23.3 | 21 | 36.2 | 17.8 | 21.9 | 19.9 | 33.1 | 23.8 | 23.7 |
| GDF8/Compound 34 | 18.5 | 33 | 23 | 23.1 | 23.6 | 20.9 | 35.3 | 17.9 | 21.3 | 19.7 | 32.6 | 24 | 23.2 |
| GDF8/Compound 56 | 17 | 31.2 | 20.8 | 20.9 | 21.2 | 18.4 | 35.3 | 15.5 | 19.4 | 17.2 | 29.7 | 21.1 | 20.8 |

TABLE 13-continued

| Differentiation Step 1 | CT Values | | | | | | | | | | |
|---|---|---|---|---|---|---|---|---|---|---|---|
| Treatment | GATA6 | GSC | KIT | MIXL1 | MNX1 | NANOG | OTX2 | POU5F1 | SOX17 | SOX7 | T |
| AA/Wnt3a | 22.1 | 22.3 | 25 | 23.4 | 28 | 23.8 | 22.6 | 31.4 | 23.5 | 32.2 | 32.3 |
| GDF8/Wnt3a | 21.9 | 22.1 | 23.9 | 23.1 | 28.6 | 23 | 21.9 | 29.6 | 23.4 | 31.9 | 32.2 |
| GDF8/Compound 34 | 21.7 | 21.9 | 24 | 23 | 27.5 | 23.2 | 21.5 | 30.1 | 23.2 | 31.7 | 32.1 |
| GDF8/Compound 56 | 19.6 | 20 | 21.5 | 21.5 | 25 | 21.1 | 19.3 | 27.9 | 21.8 | 31.1 | 30.3 |

| Differentiation Step 3 | CT Values | | | | | | | | | | | |
|---|---|---|---|---|---|---|---|---|---|---|---|---|
| Treatment\CTs | GAPDH | ALB | AMY2A | ARX | CDX2 | GCG | HNF4 | INS | ISL1 | MAFA | MAFB | NEUROD1 | NEUROG3 |
| AA/Wnt3a | 18.7 | 23.1 | 30.2 | 30.8 | 22.4 | 34.1 | 21.1 | 34.9 | 27.9 | 35.1 | 26.8 | 30.6 | 28 |
| GDF8/Wnt3a | 18.4 | 23.1 | 29.7 | 30.9 | 22.5 | 34.5 | 21.1 | 34.7 | 27.4 | 34.6 | 26.9 | 30.5 | 28 |
| GDF8/Compound 34 | 18.4 | 23.3 | 29.7 | 34.7 | 22.5 | 36.6 | 21.1 | 38.1 | 27.5 | 34.2 | 26.8 | 33.3 | 31 |
| GDF8/Compound 56 | 18.2 | 23.5 | 29.7 | 31.6 | 22.5 | 36.3 | 21.2 | 35.7 | 27.3 | 34.4 | 27 | 30.6 | 27.9 |

| Differentiation Step 3 | CT Values | | | | | | | | | | |
|---|---|---|---|---|---|---|---|---|---|---|---|
| Treatment\CTs | NKX2-2 | NKX2-5 | NKX6-1 | PAX4 | PAX6 | PDX1 | PECAM1 | POU3F4 | PTF1A | SST | ZIC1 |
| AA/Wnt3a | 29.3 | 33.1 | 38.5 | 30.6 | 36 | 25.6 | 28.3 | 29.5 | 38.4 | 30.3 | 32.7 |
| GDF8/Wnt3a | 30 | 36.4 | 36 | 31.1 | 33.5 | 25.4 | 30.4 | 30.1 | 38.5 | 27.9 | 32.4 |
| GDF8/Compound 34 | 32.2 | 33.8 | 37.8 | 33.2 | 36.5 | 26.3 | 28.1 | 31.1 | 36.4 | 27.6 | 33.2 |
| GDF8/Compound 56 | 30 | 33.8 | 38.2 | 30.8 | 32.7 | 25 | 28.9 | 30.4 | 34.8 | 27.5 | 32.7 |

| Differentiation Step 4 | CT Values | | | | | | | | | | | |
|---|---|---|---|---|---|---|---|---|---|---|---|---|
| Treatment\CTs | GAPDH | ALB | AMY2A | ARX | CDX2 | GCG | HNF4 | INS | ISL1 | MAFA | MAFB | NEUROD1 | NEUROG3 |
| AA/Wnt3a | 18.3 | 18.3 | 27.1 | 23.8 | 21.7 | 19.5 | 20.6 | 20.5 | 23.3 | 31 | 23.8 | 23 | 27.9 |
| GDF8/Wnt3a | 18.9 | 19.3 | 27.7 | 24.1 | 22.2 | 19.9 | 21.2 | 20.7 | 23.7 | 31.2 | 24.2 | 23.5 | 27.8 |
| GDF8/Compound 34 | 18.9 | 18.9 | 27.1 | 25 | 22.3 | 21.5 | 21 | 22.2 | 24.4 | 31.3 | 24.6 | 24.6 | 29.7 |
| GDF8/Compound 56 | 18.3 | 18.8 | 27.1 | 22.3 | 22.6 | 17.6 | 21.3 | 18.6 | 22.4 | 29.9 | 22.9 | 22.7 | 25.5 |

| Differentiation Step 4 | CT Values | | | | | | | | | | |
|---|---|---|---|---|---|---|---|---|---|---|---|
| Treatment\CTs | NKX2-2 | NKX2-5 | NKX6-1 | PAX4 | PAX6 | PDX1 | PECAM1 | POU3F4 | PTF1A | SST | ZIC1 |
| AA/Wnt3a | 24.6 | 31.5 | 31.5 | 27.5 | 26.4 | 24.1 | 26.9 | 27.6 | 40 | 25.2 | 31.4 |
| GDF8/Wnt3a | 25 | 35.4 | 31.5 | 27.7 | 26.3 | 24.5 | 29.5 | 29.3 | 38.2 | 24.9 | 31.4 |
| GDF8/Compound 34 | 25.8 | 31.6 | 29.6 | 27.9 | 26.4 | 23.9 | 27.5 | 28.1 | 37.1 | 24.7 | 29.5 |
| GDF8/Compound 56 | 23.2 | 32 | 27.9 | 25.5 | 23.8 | 23.2 | 27.8 | 27.5 | 30.9 | 22.8 | 32.1 |

| Differentiation Step 5 | CT Values | | | | | | | | | | | |
|---|---|---|---|---|---|---|---|---|---|---|---|---|
| Treatment\CTs | GAPDH | ALB | AMY2A | ARX | CDX2 | GCG | HNF4 | INS | ISL1 | MAFA | MAFB | NEUROD1 | NEUROG3 |
| AA/Wnt3a | 18.3 | 18.5 | 27.8 | 24 | 22.3 | 18.2 | 21.4 | 16.5 | 23.4 | 31.3 | 23.7 | 24.1 | 32.5 |
| GDF8/Wnt3a | 19.3 | 19.7 | 28.5 | 24.2 | 23.1 | 18.2 | 22 | 16.7 | 23.4 | 31.1 | 23.4 | 24.6 | 32.3 |
| GDF8/Compound 34 | 19.9 | 20.6 | 29 | 24.1 | 23.7 | 17.8 | 22.4 | 16.3 | 23.7 | 31.3 | 24 | 24.4 | 32.4 |
| GDF8/Compound 56 | 20 | 21.1 | 29 | 25.1 | 24.8 | 18.3 | 23.2 | 17.1 | 24.6 | 32.1 | 24.9 | 24.8 | 33.8 |

| Differentiation Step 5 | CT Values | | | | | | | | | | |
|---|---|---|---|---|---|---|---|---|---|---|---|
| Treatment\CTs | NKX2-2 | NKX2-5 | NKX6-1 | PAX4 | PAX6 | PDX1 | PECAM1 | POU3F4 | PTF1A | SST | ZIC1 |
| AA/Wnt3a | 25.4 | 29.7 | 32 | 28 | 25.1 | 24.2 | 26.9 | 29 | 37.5 | 22.5 | 29.9 |
| GDF8/Wnt3a | 25.6 | 29.9 | 30.5 | 28.1 | 25.4 | 24.6 | 29.9 | 29.9 | 33.4 | 22.1 | 32.1 |
| GDF8/Compound 34 | 25.8 | 31.3 | 32 | 28.4 | 25.6 | 24.6 | 29.7 | 30.7 | 34.5 | 21.6 | 35 |
| GDF8/Compound 56 | 26.3 | 34 | 30.2 | 29.7 | 27.3 | 25.9 | 29.7 | 31.5 | 34.7 | 22.1 | 33.3 |

| Differentiation Step 6 | CT Values | | | | | | | | | | | |
|---|---|---|---|---|---|---|---|---|---|---|---|---|
| Treatment\CTs | GAPDH | ALB | AMY2A | ARX | CDX2 | GCG | HNF4 | INS | ISL1 | MAFA | MAFB | NEUROD1 | NEUROG3 |
| AA/Wnt3a | 20.4 | 24.3 | 30.7 | 27.6 | 25.7 | 19.4 | 24.7 | 20.5 | 26.4 | 34.6 | 27.2 | 27.1 | 40 |
| GDF8/Wnt3a | 20.7 | 23.5 | 30.4 | 26.8 | 25.2 | 18.4 | 24.3 | 19.3 | 26.2 | 35.2 | 26.3 | 26.5 | 35 |
| GDF8/Compound 34 | 21.3 | 24.6 | 31.3 | 27.1 | 26 | 18.4 | 24.7 | 20.1 | 26.3 | 34.8 | 26.4 | 27 | 34.5 |
| GDF8/Compound 56 | 21.2 | 25 | 30.9 | 26 | 25.9 | 17.4 | 24.4 | 19.6 | 25.7 | 34.7 | 25.9 | 26.1 | 34.3 |

| Differentiation Step 6 | CT Values | | | | | | | | | | |
|---|---|---|---|---|---|---|---|---|---|---|---|
| Treatment\CTs | NKX2-2 | NKX2-5 | NKX6-1 | PAX4 | PAX6 | PDX1 | PECAM1 | POU3F4 | PTF1A | SST | ZIC1 |
| AA/Wnt3a | 29.6 | 30.7 | 33.4 | 30.9 | 28.6 | 29.2 | 31.3 | 32.8 | 38.4 | 22.2 | 34.8 |
| GDF8/Wnt3a | 29 | 32.3 | 30.5 | 30.7 | 27.8 | 28.5 | 32.3 | 31.5 | 33.9 | 22.4 | 27.4 |

TABLE 13-continued

| | | | | | | | | | | |
|---|---|---|---|---|---|---|---|---|---|---|
| GDF8/Compound 34 | 29.2 | 31.6 | 33.1 | 30.4 | 28.1 | 29 | 32.9 | 33.9 | 37.7 | 22.1 | 34.5 |
| GDF8/Compound 56 | 28.1 | 33.8 | 30.7 | 29.3 | 27.2 | 27.9 | 33.6 | 33.2 | 35.2 | 21 | 34.9 |

TABLE 14

| Differentiation Step 1 | Ct Value | | | | | | | | | | | | |
|---|---|---|---|---|---|---|---|---|---|---|---|---|---|
| Treatment | GAPDH | AFP | CD9 | CD99 | CDH1 | CDH | CDX2 | CER1 | CXCR4 | FGF17 | FGF4 | FOXA2 | GATA4 |
| AA/Wnt3a | 20 | 35.6 | 24.1 | 24.2 | 26 | 20.9 | 40 | 17.5 | 22.7 | 19.8 | 35.8 | 24.7 | 23.8 |
| GDF8/Wnt3a | 20.1 | 34 | 23.8 | 24.5 | 24.6 | 21.6 | 40 | 19.5 | 23.3 | 21 | 34.8 | 25.1 | 24.5 |
| GDF8/GSK3 inh BIO | 19 | 34.4 | 23.7 | 24.1 | 24.3 | 21.3 | 36 | 18.7 | 23 | 20.1 | 33.5 | 24.2 | 24.2 |
| GDF8/Compound 19 | 19.8 | 34.8 | 23.8 | 24 | 24.6 | 20.7 | 37.7 | 18.8 | 22.3 | 20 | 34.4 | 24.2 | 23.6 |
| GDF8/Compound 202 | 19.8 | 40 | 24.5 | 23.5 | 25.9 | 20.8 | 40 | 18.8 | 22.2 | 20.3 | 36.5 | 24.4 | 23.4 |
| GDF8/Compound 40 | 19.8 | 36.1 | 24.3 | 22.9 | 26.2 | 21.6 | 33.3 | 18.8 | 22.5 | 20.3 | 38.1 | 25.3 | 23.4 |

| Differentiation Step 1 | Ct Value | | | | | | | | | | |
|---|---|---|---|---|---|---|---|---|---|---|---|
| Treatment | GATA6 | GSC | HLXB9 | KIT | MIXL1 | NANOG | OTX2 | POU5F1 | SOX17 | SOX7 | T |
| AA/Wnt3a | 22.1 | 21.6 | 23.4 | 23.2 | 28.1 | 24.5 | 22 | 32.6 | 23.2 | 33 | 36.8 |
| GDF8/Wnt3a | 23.3 | 23.3 | 17.6 | 25.5 | 28.3 | 24.9 | 23 | 31 | 23.7 | 33.3 | 34.2 |
| GDF8/GSK3 inh BIO | 22.4 | 21.8 | 23.4 | 24.2 | 28.4 | 23.7 | 21.8 | 30.8 | 23 | 33.7 | 33.1 |
| GDF8/Compound 19 | 22.5 | 21.9 | 23.1 | 24.3 | 28 | 24.3 | 21.8 | 31.3 | 22.3 | 33 | 32.9 |
| GDF8/Compound 202 | 22.3 | 22.3 | 24 | 24.8 | 27.3 | 26 | 21.9 | 33.3 | 22.7 | 32.6 | 32.1 |
| GDF8/Compound 40 | 23 | 23 | 25 | 25.7 | 27.8 | 26 | 22.3 | 32.8 | 23.2 | 27.2 | 29.3 |

| Differentiation Step 3 | Ct Value | | | | | | | | | | | |
|---|---|---|---|---|---|---|---|---|---|---|---|---|
| Treatment | GAPDH | ALB | AMY2A | ARX | CDX2 | GCG | HNF4A | INS | ISL1 | MAFA | MAFB | NEUROD1 | NEUROG3 |
| AA/Wnt3a | 17.9 | 25.4 | 29.5 | 28.4 | 23.3 | 34.1 | 21.8 | 29.2 | 29.4 | 34 | 27 | 25.8 | 25.2 |
| GDF8/Wnt3a | 18.5 | 26.5 | 30.4 | 29.4 | 23.9 | 34.2 | 22.6 | 29 | 29 | 34.4 | 27.1 | 27.2 | 26.4 |
| GDF8/GSK3 inh BIO | 18.5 | 25.2 | 30.3 | 29.4 | 23.6 | 32.8 | 22.6 | 28.8 | 29.3 | 34.7 | 27.6 | 26.8 | 26.2 |
| GDF8/Compound 19 | 18.4 | 26.1 | 30.2 | 29.1 | 24 | 33.1 | 22.5 | 28.5 | 30 | 34.4 | 27.3 | 26.6 | 25.9 |
| GDF8/Compound 202 | 18.7 | 26.7 | 31.1 | 29.6 | 24 | 34.9 | 22.7 | 30.3 | 31.6 | 34.2 | 27.8 | 27.2 | 27 |
| GDF8/Compound 40 | 18.6 | 25.8 | 30.5 | 29.6 | 23.8 | 37.6 | 22.5 | 30 | 31.1 | 34.5 | 27.9 | 27.2 | 26.2 |

| Differentiation Step 3 | Ct Value | | | | | | | | | | |
|---|---|---|---|---|---|---|---|---|---|---|---|
| Treatment | NKX2-2 | NKX2-5 | NKX6-1 | PAX4 | PAX6 | PDX1 | PECAM | POU3F4 | PTF1A | SST | ZIC1 |
| AA/Wnt3a | 27.3 | 34.1 | 28.3 | 27.8 | 35.2 | 22.7 | 28.3 | 28.6 | 30.8 | 32.2 | 37.4 |
| GDF8/Wnt3a | 27.9 | 37.8 | 29 | 29.2 | 31.4 | 23.3 | 32.2 | 30.1 | 30.7 | 31 | 30.1 |
| GDF8/GSK3 inh BIO | 27.6 | 35 | 28.8 | 28.7 | 32.9 | 23.2 | 32.2 | 29.5 | 30.6 | 31.3 | 31.1 |
| GDF8/Compound 19 | 27.5 | 37.6 | 27.8 | 28.3 | 33.8 | 22.9 | 31.7 | 29.7 | 30 | 32.4 | 33.4 |
| GDF8/Compound 202 | 28 | 40 | 30 | 29 | 36.2 | 23.7 | 30.9 | 30.2 | 32.4 | 32.4 | 34.6 |
| GDF8/Compound 40 | 27.8 | 37.2 | 29.5 | 29 | 37.1 | 23.2 | 31.5 | 30.2 | 31.5 | 32.4 | 35.5 |

| Differentiation Step 4 | Ct Value | | | | | | | | | | | | |
|---|---|---|---|---|---|---|---|---|---|---|---|---|---|
| Treatment | GAPDH | ALB | AMY2A | ARX | CDX2 | GCG | HNF4A | INS | ISL1 | MAFA | MAFB | NEUROD1 | NEUROG3 |
| AA/Wnt3a | 18.9 | 21.3 | 28.8 | 24.6 | 23.4 | 21.7 | 21.9 | 21.6 | 25.2 | 32.4 | 24.9 | 23.7 | 23.8 |
| GDF8/Wnt3a | 18.3 | 21.3 | 28.5 | 25.3 | 23.1 | 22.6 | 21.9 | 21.9 | 25.7 | 33.1 | 24.9 | 24.3 | 24.2 |
| GDF8/GSK3 inh BIO | 19 | 21.2 | 28.3 | 25.3 | 22.3 | 22.3 | 21.9 | 22 | 25.7 | 32.5 | 25.4 | 24 | 24 |
| GDF8/Compound 19 | 18.9 | 21.7 | 28.9 | 25.2 | 23.5 | 22.4 | 22.2 | 22 | 25.6 | 34 | 25.4 | 24.1 | 23.9 |
| GDF8/Compound 202 | 19 | 20.9 | 29.2 | 25.1 | 23.6 | 22.4 | 22.1 | 22 | 25.5 | 33.3 | 25.5 | 23.9 | 24.1 |
| GDF8/Compound 40 | 19.2 | 21.1 | 29.4 | 25.5 | 23.7 | 22.8 | 22.3 | 22.3 | 26 | 33.5 | 25.8 | 24.2 | 24.2 |

| Differentiation Step 4 | Ct Value | | | | | | | | | | |
|---|---|---|---|---|---|---|---|---|---|---|---|
| Treatment | NKX2-2 | NKX2-5 | NKX6-1 | PAX4 | PAX6 | PDX1 | PECAM | POU3F4 | PTF1A | SST | ZIC1 |
| AA/Wnt3a | 24.2 | 33.9 | 25.6 | 25.6 | 27 | 23 | 29.2 | 27 | 28.1 | 25.3 | 32.6 |
| GDF8/Wnt3a | 24.7 | 35.4 | 25.8 | 26.2 | 27.3 | 23.2 | 31.2 | 27 | 28.7 | 24.7 | 24.6 |
| GDF8/GSK3 inh BIO | 24.7 | 35.4 | 26.1 | 26 | 27.7 | 23.2 | 30.7 | 27.4 | 28.5 | 25.6 | 31.5 |
| GDF8/Compound 19 | 24.6 | 35.9 | 25.7 | 25.7 | 27.8 | 23.1 | 31.4 | 27.1 | 28.6 | 25.5 | 31.4 |
| GDF8/Compound 202 | 24.5 | 35.7 | 26 | 25.8 | 27.6 | 23.4 | 30.2 | 27.5 | 28.8 | 26.1 | 35.7 |
| GDF8/Compound 40 | 24.6 | 37.3 | 25.9 | 25.9 | 28.4 | 23.1 | 30.4 | 27.6 | 28.4 | 26.3 | 34.4 |

| Differentiation Step 5 | Ct Value | | | | | | | | | | | | |
|---|---|---|---|---|---|---|---|---|---|---|---|---|---|
| Treatment | GAPDH | ALB | AMY2A | ARX | CDX2 | GCG | HNF4A | INS | ISL1 | MAFA | MAFB | NEUROD1 | NEUROG3 |
| AA/Wnt3a | 19.1 | 19.5 | 28.6 | 23.1 | 23.9 | 16.2 | 21.9 | 16.9 | 23.4 | 33.7 | 23.3 | 21.7 | 27.4 |
| GDF8/Wnt3a | 18.4 | 19.9 | 28.4 | 23.8 | 23.8 | 17.2 | 22.3 | 17.4 | 24 | 32.6 | 23.9 | 22.6 | 28.6 |

TABLE 14-continued

| | | | | | | | | | | | | | |
|---|---|---|---|---|---|---|---|---|---|---|---|---|---|
| GDF8/GSK3 inh BIO | 19.1 | 19.2 | 29.1 | 24 | 24.2 | 17.2 | 22.4 | 17.6 | 24 | 33.5 | 23.8 | 22.9 | 28.4 |
| GDF8/Compound 19 | 19 | 20 | 28.8 | 23.4 | 24.2 | 17 | 22.6 | 17.1 | 23.8 | 33.2 | 23.8 | 22.8 | 28.6 |
| GDF8/Compound 202 | 19.2 | 20 | 29 | 23 | 23.9 | 16.7 | 22.2 | 16.8 | 23.2 | 32.7 | 23.8 | 22.3 | 28.2 |
| GDF8/Compound 40 | 19.6 | 19.5 | 29 | 23.7 | 24.2 | 16.9 | 22.2 | 17.1 | 23.9 | 33.2 | 23.9 | 22.5 | 28.1 |

| Differentiation Step 5 | Ct Value | | | | | | | | | | |
|---|---|---|---|---|---|---|---|---|---|---|---|
| Treatment | NKX2-2 | NKX2-5 | NKX6-1 | PAX4 | PAX6 | PDX1 | PECAM | POU3F4 | PTF1A | SST | ZIC1 |
| AA/Wnt3a | 24 | 33.1 | 25 | 26.4 | 24.7 | 22.6 | 27.1 | 28.4 | 27.5 | 22 | 34.1 |
| GDF8/Wnt3a | 24.2 | 33.1 | 25.8 | 27.2 | 25.6 | 23.6 | 29.2 | 28.9 | 29.1 | 22.7 | 25.6 |
| GDF8/GSK3 inh BIO | 24.4 | 40 | 25.1 | 27.3 | 25.6 | 23.6 | 29.2 | 28.1 | 28.7 | 23 | 26.3 |
| GDF8/Compound 19 | 24.1 | 34.6 | 25 | 26.8 | 25.6 | 23.4 | 29.8 | 28.2 | 28.2 | 22.9 | 28.8 |
| GDF8/Compound 202 | 23.2 | 40 | 26 | 27.2 | 25.8 | 23.4 | 29.9 | 29.1 | 28.4 | 22.6 | 33.8 |
| GDF8/Compound 40 | 23.5 | 34.8 | 25 | 27.3 | 26.4 | 23.4 | 29.9 | 29.2 | 27.5 | 22.3 | 34.8 |

TABLE 15

| Step 1 | RT-PCR CT Values | | | | | | | | | | | | |
|---|---|---|---|---|---|---|---|---|---|---|---|---|---|
| Treatment | GAPDH | AFP | CD9 | CD99 | CDH1 | CDH | CDX2 | CER1 | CXCR4 | FGF17 | FGF4 | FOXA2 | GATA4 |
| AA | 19.4 | 32.8 | 25.2 | 24.0 | 26.1 | 21.8 | 36.0 | 18.3 | 20.4 | 20.7 | 34.0 | 25.1 | 25.0 |
| AA + Wnt3a | 18.2 | 40.0 | 23.5 | 22.0 | 24.1 | 20.9 | 40.0 | 17.1 | 22.0 | 18.7 | 33.4 | 22.9 | 23.1 |
| AA + Compound 181 | 20.1 | 40.0 | 24.5 | 23.3 | 26.0 | 20.7 | 35.9 | 18.2 | 22.0 | 20.1 | 35.1 | 25.6 | 24.7 |
| AA + Compound 180 | 18.4 | 34.2 | 23.6 | 21.6 | 25.9 | 21.4 | 35.2 | 17.2 | 22.0 | 18.9 | 34.0 | 24.0 | 23.1 |
| AA + Compound 19 | 20.1 | 35.4 | 24.4 | 24.9 | 26.3 | 20.8 | 40.0 | 17.9 | 17.7 | 20.5 | 32.8 | 25.6 | 25.1 |
| AA + Compound 202 | 20.3 | 40.0 | 25.1 | 23.7 | 25.9 | 21.4 | 40.0 | 18.3 | 22.0 | 20.4 | 36.0 | 25.7 | 24.5 |
| AA + Compound 40 | 19.9 | 40.0 | 24.6 | 23.6 | 25.8 | 20.4 | 40.0 | 17.7 | 22.7 | 20.2 | 35.1 | 25.5 | 24.6 |
| AA + GSK3 inhib BIO | 20.2 | 35.0 | 25.4 | 23.7 | 27.2 | 21.9 | 35.5 | 18.5 | 22.2 | 20.9 | 36.0 | 25.8 | 25.0 |
| AA + Compound 206 | 19.8 | 40.0 | 24.9 | 23.7 | 25.5 | 21.1 | 40.0 | 18.3 | 19.6 | 20.7 | 36.2 | 24.4 | 24.8 |
| GDF8 | 21.6 | 40.0 | 25.5 | 25.9 | 25.2 | 22.3 | 40.0 | 20.1 | 24.6 | 22.1 | 34.9 | 25.9 | 27.5 |
| GDF8 + Wnt3a | 21.2 | 40.0 | 25.0 | 25.8 | 25.1 | 22.6 | 40.0 | 19.7 | 23.6 | 22.0 | 34.8 | 25.7 | 27.3 |
| GDF8 + Compound 181 | 20.7 | 40.0 | 25.1 | 23.6 | 25.5 | 22.4 | 40.0 | 20.0 | 23.0 | 21.5 | 36.3 | 25.2 | 25.4 |
| GDF8 + Compound 180 | 20.9 | 40.0 | 25.6 | 24.0 | 26.9 | 22.1 | 34.7 | 19.9 | 22.7 | 21.1 | 36.6 | 25.0 | 25.2 |
| GDF8 + Compound 19 | 19.6 | 40.0 | 23.9 | 23.7 | 24.6 | 20.7 | 40.0 | 18.0 | 21.8 | 20.4 | 33.2 | 24.2 | 25.0 |
| GDF8 + Compound 202 | 18.5 | 30.6 | 22.1 | 20.2 | 22.8 | 19.7 | 35.8 | 18.5 | 22.4 | 19.9 | 34.3 | 23.6 | 22.7 |
| GDF8 + Compound 40 | 19.7 | 40.0 | 23.0 | 22.6 | 24.7 | 20.5 | 33.8 | 18.2 | 22.4 | 20.5 | 35.4 | 24.9 | 24.2 |
| GDF8 + GSK3 inhib BIO | 19.6 | 30.1 | 23.1 | 21.8 | 24.3 | 20.0 | 33.4 | 17.7 | 23.3 | 20.1 | 34.8 | 24.7 | 24.5 |
| GDF8 + Compound 206 | 19.7 | 40.0 | 22.7 | 22.5 | 23.2 | 21.0 | 29.9 | 18.4 | 23.0 | 20.3 | 34.5 | 25.3 | 24.9 |

| Step 1 | RT-PCR CT Values | | | | | | | | | | |
|---|---|---|---|---|---|---|---|---|---|---|---|
| Treatment | GATA6 | GSC | HLXB9 | KIT | MIXL1 | NANOG | OTX2 | POU5F1 | SOX17 | SOX7 | T |
| AA | 22.9 | 22.4 | 24.8 | 22.7 | 28.9 | 24.1 | 22.5 | 32.2 | 21.6 | 32.3 | 36.1 |
| AA + Wnt3a | 21.8 | 22.8 | 23.3 | 22.9 | 27.7 | 22.7 | 19.9 | 31.0 | 21.2 | 31.2 | 34.1 |
| AA + Compound 181 | 22.9 | 20.8 | 25.5 | 19.7 | 27.8 | 24.8 | 22.3 | 32.8 | 22.2 | 33.0 | 33.8 |
| AA + Compound 180 | 22.6 | 22.5 | 24.8 | 22.6 | 27.9 | 23.7 | 20.3 | 32.1 | 21.4 | 32.0 | 32.7 |
| AA + Compound 19 | 22.7 | 21.3 | 26.0 | 22.6 | 29.5 | 24.1 | 22.9 | 32.1 | 22.3 | 33.0 | 29.6 |
| AA + Compound 202 | 23.0 | 21.8 | 25.2 | 23.9 | 27.7 | 24.5 | 22.5 | 32.7 | 22.6 | 32.1 | 33.5 |
| AA + Compound 40 | 22.5 | 20.9 | 25.5 | 22.9 | 28.0 | 23.8 | 22.0 | 33.6 | 22.3 | 32.5 | 32.8 |
| AA + GSK3 inhib BIO | 23.2 | 22.2 | 25.2 | 23.7 | 28.5 | 24.9 | 22.8 | 34.3 | 23.4 | 32.7 | 33.5 |
| AA + Compound 206 | 22.7 | 22.6 | 24.1 | 23.7 | 27.6 | 23.9 | 22.0 | 33.2 | 23.3 | 32.4 | 34.6 |
| GDF8 | 24.8 | 24.2 | 25.3 | 25.4 | 30.6 | 25.0 | 24.3 | 29.5 | 25.2 | 29.8 | 32.9 |
| GDF8 + Wnt3a | 24.4 | 23.8 | 25.0 | 25.1 | 30.5 | 24.8 | 24.4 | 31.1 | 25.0 | 34.5 | 32.6 |
| GDF8 + Compound 181 | 23.9 | 23.6 | 24.3 | 26.3 | 28.1 | 25.4 | 23.3 | 31.8 | 23.7 | 32.8 | 31.9 |
| GDF8 + Compound 180 | 23.9 | 23.6 | 24.2 | 25.8 | 28.3 | 26.3 | 23.0 | 33.2 | 24.2 | 32.8 | 32.3 |
| GDF8 + Compound 19 | 22.8 | 22.1 | 24.0 | 22.6 | 28.5 | 23.1 | 22.7 | 30.3 | 22.6 | 32.1 | 29.3 |
| GDF8 + Compound 202 | 22.5 | 23.5 | 23.1 | 25.9 | 27.7 | 25.1 | 21.5 | 30.0 | 22.3 | 32.0 | 32.5 |
| GDF8 + Compound 40 | 22.6 | 23.4 | 23.4 | 25.4 | 28.5 | 24.0 | 22.2 | 31.6 | 23.7 | 31.2 | 32.7 |
| GDF8 + GSK3 inhib BIO | 22.4 | 22.7 | 24.1 | 25.0 | 29.3 | 24.8 | 21.8 | 31.7 | 23.3 | 33.7 | 34.6 |
| GDF8 + Compound 206 | 22.9 | 23.6 | 23.8 | 25.7 | 29.7 | 24.7 | 22.2 | 30.7 | 24.4 | 32.8 | 33.8 |

| Step 3 | RT-PCR CT Values | | | | | | | | | | | | |
|---|---|---|---|---|---|---|---|---|---|---|---|---|---|
| Treatment | GAPDH | ALB | AMY2A | ARX | CDX2 | GCG | HNF4A | INS | ISL1 | MAFA | MAFB | NEUROD1 | NEUROG3 |
| AA | 18.5 | 26.9 | 30.6 | 32.0 | 22.9 | 34.1 | 22.4 | 34.8 | 29.3 | 36.4 | 27.4 | 30.1 | 28.0 |
| AA + Wnt3a | 18.4 | 27.3 | 30.2 | 33.0 | 23.0 | 34.7 | 22.4 | 40.0 | 28.8 | 33.9 | 27.7 | 30.4 | 28.1 |
| AA + Compound 181 | 18.6 | 26.0 | 30.1 | 34.2 | 22.3 | 40.0 | 22.3 | 40.0 | 30.4 | 34.6 | 28.5 | 31.4 | 29.0 |
| AA + Compound 180 | 18.8 | 25.5 | 30.0 | 33.3 | 22.5 | 35.1 | 22.5 | 40.0 | 29.4 | 34.3 | 28.6 | 32.6 | 30.3 |
| AA + Compound 19 | 34.1 | 40.0 | 40.0 | 40.0 | 40.0 | 40.0 | 37.4 | 40.0 | 40.0 | 40.0 | 40.0 | 40.0 | 40.0 |
| AA + Compound 202 | 18.5 | 26.2 | 30.7 | 33.0 | 22.5 | 34.8 | 22.6 | 35.1 | 29.8 | 35.1 | 28.2 | 30.0 | 28.5 |
| AA + Compound 40 | 18.5 | 25.8 | 30.1 | 34.9 | 22.2 | 40.0 | 22.3 | 40.0 | 29.7 | 34.1 | 28.1 | 30.8 | 29.1 |
| AA + GSK3 inhib BIO | 18.5 | 24.9 | 30.1 | 34.6 | 22.0 | 40.0 | 21.5 | 40.0 | 30.2 | 34.9 | 27.8 | 34.0 | 31.0 |

TABLE 15-continued

| Treatment | | | | | | | | | | | | |
|---|---|---|---|---|---|---|---|---|---|---|---|---|
| AA + Compound 206 | 18.3 | 27.0 | 30.3 | 33.7 | 22.7 | 35.7 | 22.5 | 40.0 | 28.4 | 34.4 | 27.8 | 30.7 | 28.6 |
| GDF8 | 18.0 | 28.7 | 30.4 | 35.3 | 23.8 | 40.0 | 23.6 | 40.0 | 28.5 | 33.6 | 27.2 | 30.3 | 28.7 |
| GDF8 + Wnt3a | 17.4 | 27.0 | 29.5 | 33.8 | 23.1 | 35.1 | 22.4 | 40.0 | 26.3 | 30.5 | 26.1 | 30.1 | 27.5 |
| GDF8 + Compound 181 | 18.8 | 27.8 | 30.2 | 31.3 | 23.4 | 40.0 | 22.7 | 34.5 | 28.8 | 35.5 | 27.3 | 28.9 | 27.0 |
| GDF8 + Compound 180 | 18.8 | 27.3 | 30.6 | 32.4 | 22.8 | 34.9 | 22.7 | 40.0 | 29.5 | 35.9 | 27.7 | 30.0 | 27.5 |
| GDF8 + Compound 19 | 18.3 | 24.9 | 29.7 | 33.4 | 22.0 | 40.0 | 22.2 | 40.0 | 29.7 | 34.5 | 28.4 | 33.3 | 31.5 |
| GDF8 + Compound 202 | 18.7 | 27.8 | 30.4 | 32.8 | 23.8 | 40.0 | 22.9 | 34.6 | 28.5 | 34.2 | 27.6 | 29.6 | 27.1 |
| GDF8 + Compound 40 | 18.4 | 27.7 | 30.1 | 32.5 | 23.0 | 35.1 | 22.4 | 40.0 | 29.1 | 34.3 | 27.5 | 30.0 | 27.3 |
| GDF8 + GSK3 inhib BIO | 18.4 | 24.9 | 30.3 | 31.5 | 22.2 | 34.7 | 21.7 | 34.5 | 29.9 | 35.3 | 27.6 | 29.2 | 26.8 |
| GDF8 + Compound 206 | 18.2 | 27.6 | 30.2 | 33.5 | 23.8 | 40.0 | 22.9 | 40.0 | 27.9 | 35.1 | 27.1 | 29.9 | 27.7 |

| Step 3 | RT-PCR CT Values | | | | | | | | | | |
|---|---|---|---|---|---|---|---|---|---|---|---|
| Treatment | NKX2-2 | NKX2-5 | NKX6-1 | PAX4 | PAX6 | PDX1 | PECAM | POU3F4 | PTF1A | SST | ZIC1 |
| AA | 29.3 | 34.6 | 32.2 | 31.4 | 40.0 | 23.3 | 31.0 | 30.5 | 34.6 | 33.2 | 34.8 |
| AA + Wnt3a | 29.0 | 40.0 | 34.9 | 31.9 | 38.1 | 23.8 | 30.9 | 30.7 | 40.0 | 32.8 | 40.0 |
| AA + Compound 181 | 30.3 | 33.9 | 35.8 | 33.3 | 40.0 | 25.0 | 30.0 | 30.8 | 36.0 | 34.6 | 34.8 |
| AA + Compound 180 | 31.1 | 32.5 | 35.3 | 35.3 | 36.2 | 26.3 | 28.9 | 31.3 | 40.0 | 34.7 | 34.4 |
| AA + Compound 19 | 40.0 | 40.0 | 40.0 | 40.0 | 40.0 | 40.0 | 40.0 | 40.0 | 40.0 | 40.0 | 40.0 |
| AA + Compound 202 | 29.5 | 33.6 | 33.9 | 32.0 | 36.6 | 24.1 | 29.7 | 31.9 | 40.0 | 34.2 | 40.0 |
| AA + Compound 40 | 30.3 | 33.6 | 34.4 | 32.9 | 40.0 | 24.8 | 30.3 | 31.3 | 35.6 | 35.3 | 35.4 |
| AA + GSK3 inhib BIO | 31.8 | 32.6 | 40.0 | 34.9 | 40.0 | 26.1 | 31.0 | 32.4 | 40.0 | 35.2 | 34.9 |
| AA + Compound 206 | 29.8 | 32.8 | 35.0 | 31.5 | 30.4 | 23.9 | 29.7 | 31.2 | 35.0 | 31.9 | 40.0 |
| GDF8 | 30.3 | 34.4 | 35.0 | 32.4 | 24.8 | 25.5 | 30.0 | 30.8 | 34.2 | 29.5 | 26.1 |
| GDF8 + Wnt3a | 29.1 | 40.0 | 32.9 | 31.5 | 25.8 | 23.1 | 32.2 | 29.8 | 34.0 | 27.7 | 28.2 |
| GDF8 + Compound 181 | 28.0 | 35.4 | 32.5 | 30.5 | 35.4 | 23.5 | 29.4 | 30.5 | 33.9 | 32.4 | 34.5 |
| GDF8 + Compound 180 | 29.0 | 35.4 | 32.6 | 31.2 | 40.0 | 23.7 | 31.6 | 30.8 | 34.6 | 34.4 | 40.0 |
| GDF8 + Compound 19 | 32.2 | 34.4 | 35.2 | 34.4 | 35.0 | 25.0 | 29.4 | 31.6 | 40.0 | 34.1 | 33.5 |
| GDF8 + Compound 202 | 28.4 | 35.7 | 30.5 | 30.4 | 31.8 | 23.0 | 30.1 | 30.2 | 31.6 | 30.9 | 34.0 |
| GDF8 + Compound 40 | 28.8 | 35.3 | 32.9 | 31.5 | 40.0 | 23.2 | 29.2 | 30.5 | 36.3 | 33.7 | 40.0 |
| GDF8 + GSK3 inhib BIO | 27.9 | 34.6 | 33.9 | 30.6 | 35.1 | 24.0 | 30.4 | 30.0 | 34.8 | 33.6 | 40.0 |
| GDF8 + Compound 206 | 29.3 | 40.0 | 32.3 | 31.3 | 27.4 | 23.3 | 32.7 | 30.8 | 33.0 | 29.2 | 30.3 |

| Step 4 | RT-PCR CT Values | | | | | | | | | | | |
|---|---|---|---|---|---|---|---|---|---|---|---|---|
| Treatment | GAPDH | ALB | AMY2A | ARX | CDX2 | GCG | HNF4A | INS | ISL1 | MAFA | MAFB | NEUROD1 | NEUROG3 |
| AA | 19.0 | 22.4 | 28.6 | 23.9 | 23.7 | 22.8 | 22.1 | 23.6 | 24.1 | 30.6 | 23.5 | 23.7 | 23.3 |
| AA + Wnt3a | 19.5 | 23.5 | 29.3 | 24.6 | 24.1 | 25.1 | 22.7 | 25.2 | 25.1 | 31.1 | 24.4 | 24.4 | 24.1 |
| AA + Compound 181 | 18.0 | 21.0 | 27.7 | 24.0 | 22.1 | 24.5 | 21.0 | 24.6 | 24.5 | 31.6 | 24.0 | 24.2 | 24.6 |
| AA + Compound 180 | 19.4 | 21.0 | 27.3 | 26.3 | 21.6 | 25.4 | 20.6 | 26.7 | 26.1 | 34.7 | 24.6 | 25.5 | 25.8 |
| AA + Compound 19 | (insufficient RNA sample) | | | | | | | | | | | | |
| AA + Compound 202 | 19.2 | 20.7 | 29.1 | 24.0 | 23.3 | 21.8 | 21.9 | 22.7 | 24.4 | 31.1 | 23.9 | 24.0 | 24.1 |
| AA + Compound 40 | 19.2 | 20.8 | 29.4 | 24.7 | 22.9 | 22.2 | 21.8 | 23.5 | 25.3 | 31.5 | 24.7 | 24.7 | 25.3 |
| AA + GSK3 inhib BIO | 19.0 | 19.1 | 29.2 | 26.7 | 22.7 | 25.2 | 21.1 | 26.3 | 26.5 | 33.0 | 25.4 | 26.3 | 27.7 |
| AA + Compound 206 | 18.8 | 20.9 | 28.4 | 23.3 | 22.9 | 21.2 | 21.7 | 22.8 | 24.0 | 30.4 | 23.5 | 23.3 | 23.3 |
| GDF8 | 18.0 | 25.5 | 29.1 | 29.8 | 24.6 | 31.3 | 23.8 | 30.9 | 27.6 | 32.8 | 24.1 | 29.2 | 28.7 |
| GDF8 + Wnt3a | 19.0 | 24.3 | 29.0 | 25.4 | 24.4 | 27.7 | 23.0 | 25.5 | 25.4 | 32.7 | 25.1 | 25.4 | 24.0 |
| GDF8 + Compound 181 | 18.0 | 22.8 | 28.1 | 23.5 | 23.1 | 24.6 | 21.4 | 22.7 | 23.8 | 30.6 | 23.0 | 22.9 | 21.8 |
| GDF8 + Compound 180 | 19.5 | 24.0 | 29.3 | 24.4 | 23.9 | 25.7 | 22.5 | 24.5 | 24.7 | 31.4 | 24.4 | 24.3 | 23.7 |
| GDF8 + Compound 19 | 19.1 | 22.6 | 28.7 | 25.5 | 22.9 | 26.7 | 22.1 | 27.2 | 25.8 | 32.6 | 25.5 | 26.2 | 26.4 |
| GDF8 + Compound 202 | 19.0 | 22.0 | 28.9 | 23.7 | 24.5 | 21.8 | 22.3 | 21.7 | 24.3 | 30.3 | 23.5 | 22.9 | 22.2 |
| GDF8 + Compound 40 | 19.0 | 21.4 | 29.0 | 23.4 | 23.6 | 21.0 | 22.0 | 21.5 | 23.8 | 30.2 | 23.3 | 23.2 | 22.7 |
| GDF8 + GSK3 inhib BIO | 19.1 | 19.4 | 29.1 | 24.3 | 23.0 | 21.5 | 21.4 | 21.8 | 24.6 | 31.0 | 24.0 | 23.8 | 23.8 |
| GDF8 + Compound 206 | 18.9 | 21.6 | 28.9 | 24.4 | 24.0 | 22.6 | 22.3 | 22.7 | 24.9 | 30.9 | 24.2 | 23.7 | 23.0 |

TABLE 15-continued

| Step 4 Treatment | RT-PCR CT Values ||||||||||
|---|---|---|---|---|---|---|---|---|---|---|
| | NKX2-2 | NKX2-5 | NKX6-1 | PAX4 | PAX6 | PDX1 | PECAM | POU3F4 | PTF1A | SST | ZIC1 |
| AA | 24.0 | 31.9 | 27.4 | 25.7 | 27.1 | 23.7 | 29.8 | 26.5 | 29.6 | 24.3 | 32.5 |
| AA + Wnt3a | 24.5 | 31.8 | 27.5 | 26.1 | 27.9 | 24.1 | 30.4 | 27.2 | 31.1 | 25.9 | 32.4 |
| AA + Compound 181 | 24.6 | 30.9 | 28.1 | 26.3 | 28.0 | 24.0 | 27.9 | 27.5 | 31.0 | 25.5 | 31.2 |
| AA + Compound 180 | 25.0 | 29.4 | 28.9 | 27.7 | 28.9 | 24.0 | 26.7 | 28.5 | 32.6 | 27.1 | 31.2 |
| AA + Compound 19 | | | | | | | | | | | |
| AA + Compound 202 | 24.4 | 32.1 | 27.4 | 26.3 | 26.9 | 24.3 | 29.6 | 27.7 | 29.5 | 24.0 | 35.1 |
| AA + Compound 40 | 25.0 | 32.2 | 28.7 | 27.1 | 28.2 | 25.1 | 30.3 | 28.5 | 31.2 | 25.6 | 32.7 |
| AA + GSK3 inhib BIO | 26.2 | 31.5 | 32.9 | 29.4 | 30.0 | 26.5 | 29.6 | 30.5 | 33.7 | 27.2 | 32.4 |
| AA + Compound 206 | 23.8 | 31.9 | 27.2 | 25.5 | 26.3 | 23.6 | 29.7 | 26.6 | 29.3 | 23.6 | 32.9 |
| GDF8 | 29.0 | 32.3 | 31.2 | 31.1 | 27.9 | 26.5 | 29.4 | 29.4 | 40.0 | 26.0 | 22.8 |
| GDF8 + Wnt3a | 25.0 | 33.3 | 28.0 | 26.7 | 28.8 | 23.8 | 33.4 | 27.7 | 30.5 | 24.1 | 29.0 |
| GDF8 + Compound 181 | 23.2 | 32.1 | 25.7 | 24.2 | 27.0 | 22.3 | 27.6 | 25.4 | 28.6 | 24.2 | 31.6 |
| GDF8 + Compound 180 | 24.4 | 33.5 | 27.7 | 26.0 | 28.3 | 23.8 | 30.6 | 26.9 | 30.7 | 26.3 | 33.4 |
| GDF8 + Compound 19 | 25.6 | 34.0 | 30.2 | 28.2 | 30.0 | 25.1 | 30.2 | 29.2 | 32.6 | 27.9 | 31.1 |
| GDF8 + Compound 202 | 23.4 | 33.4 | 25.9 | 24.8 | 26.5 | 23.0 | 29.5 | 26.1 | 27.9 | 22.4 | 34.1 |
| GDF8 + Compound 40 | 23.7 | 33.2 | 26.6 | 24.8 | 26.1 | 23.4 | 29.3 | 26.4 | 28.4 | 22.7 | 32.6 |
| GDF8 + GSK3 inhib BIO | 24.2 | 33.3 | 27.9 | 26.1 | 27.0 | 24.2 | 30.0 | 27.8 | 29.5 | 23.4 | 32.7 |
| GDF8 + Compound 206 | 24.0 | 35.3 | 26.3 | 25.5 | 27.2 | 23.5 | 31.4 | 26.9 | 27.7 | 24.0 | 28.9 |

| Step 5 Treatment | RT-PCR CT Values |||||||||||||
|---|---|---|---|---|---|---|---|---|---|---|---|---|---|
| | GAPDH | ALB | AMY2A | ARX | CDX2 | GCG | HNF4A | INS | ISL1 | MAFA | MAFB | NEUROD1 | NEUROG3 |
| AA | 18.3 | 20.2 | 27.6 | 22.0 | 23.4 | 14.1 | 21.3 | 14.9 | 22.4 | 31.8 | 22.2 | 22.8 | 28.1 |
| AA + Wnt3a | 18.0 | 20.0 | 27.7 | 21.9 | 23.1 | 14.0 | 20.9 | 14.6 | 22.3 | 31.6 | 22.0 | 21.6 | 28.0 |
| AA + Compound 181 | 18.0 | 18.8 | 27.6 | 22.0 | 22.9 | 14.3 | 20.9 | 14.5 | 22.1 | 31.4 | 22.2 | 21.5 | 28.9 |
| AA + Compound 180 | 18.0 | 18.8 | 27.6 | 22.4 | 22.9 | 14.9 | 21.0 | 14.7 | 22.4 | 31.9 | 22.6 | 21.7 | 29.5 |
| AA + Compound 19 | 17.9 | 23.6 | 28.6 | 28.2 | 25.4 | 27.0 | 24.2 | 26.9 | 26.2 | 32.0 | 24.4 | 27.2 | 31.2 |
| AA + Compound 202 | 18.6 | 19.2 | 28.0 | 22.6 | 23.4 | 14.9 | 21.3 | 15.0 | 22.7 | 31.8 | 22.6 | 21.9 | 28.6 |
| AA + Compound 40 | 18.3 | 18.9 | 27.9 | 22.3 | 23.0 | 14.6 | 21.1 | 14.7 | 22.5 | 31.5 | 22.4 | 21.6 | 29.0 |
| AA + GSK3 inhib BIO | 18.3 | 17.1 | 28.0 | 23.0 | 22.6 | 15.1 | 20.5 | 15.1 | 22.8 | 31.8 | 22.8 | 22.1 | 29.5 |
| AA + Compound 206 | 18.2 | 19.5 | 27.9 | 22.2 | 23.4 | 14.4 | 21.3 | 14.8 | 22.5 | 31.1 | 22.4 | 21.7 | 28.0 |
| GDF8 | 17.4 | 20.5 | 28.2 | 25.2 | 24.4 | 18.1 | 22.9 | 17.7 | 24.3 | 31.8 | 23.3 | 24.2 | 30.1 |
| GDF8 + Wnt3a | 17.8 | 20.6 | 28.2 | 24.8 | 24.3 | 17.7 | 22.9 | 17.5 | 24.2 | 31.9 | 23.5 | 24.0 | 30.2 |
| GDF8 + Compound 181 | 18.0 | 19.1 | 27.6 | 22.4 | 23.4 | 14.5 | 21.2 | 14.8 | 22.5 | 31.5 | 22.6 | 21.7 | 27.4 |
| GDF8 + Compound 180 | 18.0 | 18.0 | 27.3 | 22.2 | 22.9 | 14.2 | 20.9 | 14.4 | 22.2 | 31.4 | 22.1 | 21.2 | 27.9 |
| GDF8 + Compound 19 | 18.3 | 18.5 | 27.8 | 23.4 | 23.0 | 16.2 | 21.2 | 15.6 | 23.2 | 32.2 | 23.2 | 22.6 | 31.2 |
| GDF8 + Compound 202 | 18.7 | 19.6 | 28.3 | 23.1 | 24.0 | 15.7 | 21.9 | 15.8 | 23.5 | 32.8 | 23.3 | 22.3 | 27.8 |
| GDF8 + Compound 40 | 18.1 | 18.7 | 27.9 | 22.3 | 23.0 | 14.8 | 21.1 | 14.8 | 22.6 | 31.5 | 22.5 | 21.5 | 27.3 |
| GDF8 + GSK3 inhib BIO | 18.4 | 17.1 | 27.6 | 23.2 | 22.8 | 15.2 | 20.6 | 15.5 | 23.1 | 32.6 | 22.6 | 22.1 | 28.2 |
| GDF8 + Compound 206 | 18.0 | 20.0 | 27.9 | 23.4 | 24.0 | 16.0 | 22.1 | 16.0 | 23.6 | 32.1 | 22.9 | 22.8 | 28.5 |

| Step 5 Treatment | RT-PCR CT Values ||||||||||
|---|---|---|---|---|---|---|---|---|---|---|
| | NKX2-2 | NKX2-5 | NKX6-1 | PAX4 | PAX6 | PDX1 | PECAM | POU3F4 | PTF1A | SST | ZIC1 |
| AA | 23.7 | 34.1 | 25.5 | 27.3 | 24.0 | 23.2 | 30.1 | 28.8 | 27.3 | 19.6 | 34.4 |
| AA + Wnt3a | 23.4 | 34.8 | 26.1 | 27.3 | 23.7 | 23.3 | 29.6 | 28.8 | 27.5 | 19.4 | 32.5 |
| AA + Compound 181 | 23.3 | 32.2 | 26.1 | 26.8 | 24.0 | 23.1 | 27.5 | 28.8 | 28.0 | 18.8 | 31.2 |
| AA + Compound 180 | 23.8 | 30.2 | 26.5 | 27.2 | 24.3 | 23.2 | 26.7 | 29.0 | 28.7 | 18.7 | 30.3 |
| AA + Compound 19 | 28.0 | 30.1 | 25.8 | 35.1 | 28.6 | 29.4 | 31.5 | 28.2 | 32.4 | 23.1 | 24.0 |
| AA + Compound 202 | 23.7 | 29.9 | 25.8 | 26.9 | 24.7 | 23.6 | 27.7 | 29.2 | 27.9 | 19.4 | 32.8 |
| AA + Compound 40 | 23.5 | 32.9 | 26.1 | 27.1 | 24.4 | 23.2 | 28.1 | 29.2 | 28.1 | 19.1 | 31.9 |
| AA + GSK3 inhib BIO | 24.2 | 33.8 | 27.5 | 27.4 | 24.9 | 23.8 | 28.3 | 29.9 | 29.7 | 19.5 | 32.0 |
| AA + Compound 206 | 23.6 | 35.8 | 25.9 | 27.1 | 24.1 | 23.3 | 29.0 | 28.7 | 27.5 | 19.7 | 32.7 |
| GDF8 | 25.9 | 31.4 | 26.6 | 29.4 | 26.6 | 25.6 | 29.7 | 27.8 | 29.5 | 21.1 | 22.5 |
| GDF8 + Wnt3a | 25.6 | 31.9 | 27.0 | 29.3 | 26.5 | 25.6 | 29.8 | 28.1 | 30.7 | 21.5 | 22.8 |
| GDF8 + Compound 181 | 23.4 | 33.8 | 25.0 | 26.8 | 24.4 | 23.0 | 27.5 | 28.8 | 27.3 | 19.5 | 31.9 |
| GDF8 + Compound 180 | 23.2 | 40.0 | 25.1 | 26.1 | 23.8 | 22.9 | 29.6 | 28.7 | 27.3 | 18.8 | 31.5 |
| GDF8 + Compound 19 | 24.3 | 33.9 | 28.6 | 27.3 | 25.2 | 24.2 | 29.0 | 30.1 | 31.0 | 20.5 | 31.9 |

TABLE 15-continued

| | | | | | | | | | | | |
|---|---|---|---|---|---|---|---|---|---|---|---|
| GDF8 + Compound 202 | 23.8 | 31.3 | 24.8 | 27.1 | 25.2 | 23.2 | 29.0 | 29.5 | 27.1 | 20.8 | 30.9 |
| GDF8 + Compound 40 | 23.2 | 33.2 | 25.0 | 26.6 | 24.1 | 22.9 | 27.3 | 28.9 | 27.4 | 20.4 | 32.0 |
| GDF8 + GSK3 inhib BIO | 24.2 | 35.0 | 26.7 | 27.3 | 24.8 | 24.0 | 28.1 | 30.1 | 28.5 | 19.3 | 32.4 |
| GDF8 + Compound 206 | 24.4 | 30.5 | 25.9 | 27.5 | 25.4 | 24.0 | 29.7 | 28.3 | 28.0 | 20.8 | 23.9 |

TABLE 16

| Compound # | Primary Selectivity |
|---|---|
| Compound 6 | Selective for GSK |
| Compound 7 | Selective for GSK |
| Compound 8 | Selective for GSK |
| Compound 9 | Selective for CDK |
| Compound 57 | Selective for Trk |
| Compound 41 | Selective for GSK |
| Compound 42 | Selective for CDK |
| Compound 10 | Selective for CDK |
| Compound 34 | Positive Control |
| Compound 11 | Selective for CDK |
| Compound 43 | Selective for Trk |
| Compound 44 | Selective for GSK |
| Compound 12 | Selective for CDK |
| Compound 45 | Selective for Trk |

TABLE 17

| | | | | Cell Number | | Sox17 Expression | |
|---|---|---|---|---|---|---|---|
| Plate | Treatment | Compound # | Compound Selectivity | Average Total Cell Number | % of positive control | Average Total Intensity | % of positive control |
| 1 | no Activin A | none | n/a | 9809 | 67.8 | −4.0E+05 | −0.2 |
| 1 | Activin A/Wnt3a | none | n/a | 14476 | 100.0 | 2.3E+08 | 100.0 |
| 1 | No GDF8 | Compound 11 | Selective for CDK | 565 | 3.9 | −1.1E+06 | −0.5 |
| 1 | No GDF8 | Compound 44 | Selective for GSK | 14 | 0.1 | −1.1E+06 | −0.5 |
| 1 | No GDF8 | Compound 43 | Selective for Trk | 8610 | 59.5 | −2.1E+05 | −0.1 |
| 1 | No GDF8 | Compound 42 | Selective for CDK | 8700 | 60.1 | −2.4E+05 | −0.1 |
| 1 | No GDF8 | Compound 57 | Selective for Trk | 1222 | 8.4 | −7.1E+05 | −0.3 |
| 1 | No GDF8 | Compound 10 | Selective for CDK | 7011 | 48.4 | −6.6E+05 | −0.3 |
| 1 | No GDF8 | Compound 41 | Selective for GSK | 9995 | 69.0 | 5.9E+04 | 0.0 |
| 1 | No GDF8 | Compound 7 | Selective for GSK | 3 | 0.0 | −1.4E+06 | −0.6 |
| 1 | No GDF8 | Compound 45 | Selective for Trk | 8857 | 61.2 | −4.5E+05 | −0.2 |
| 1 | No GDF8 | Compound 6 | Selective for GSK | 14827 | 102.4 | −1.8E+05 | −0.1 |
| 1 | No GDF8 | Compound 9 | Selective for CDK | 7156 | 49.4 | −4.2E+04 | 0.0 |
| 1 | No GDF8 | Compound 12 | Selective for GSK | 13124 | 90.7 | −2.3E+05 | −0.1 |
| 1 | No GDF8 | Compound 8 | Selective for GSK | 13235 | 91.4 | 3.8E+05 | 0.2 |
| 1 | GDF8 | Compound 34 | Positive Control | 13926 | 96.2 | 2.6E+08 | 111.8 |
| 1 | GDF8 | Compound 45 | Selective for Trk | 9540 | 65.9 | 1.1E+08 | 47.9 |
| 1 | GDF8 | Compound 7 | Selective for GSK | 5296 | 36.6 | 7.0E+07 | 30.4 |
| 1 | GDF8 | Compound 10 | Selective for CDK | 4627 | 32.0 | 6.6E+07 | 28.6 |
| 1 | GDF8 | Compound 6 | Selective for GSK | 5118 | 35.4 | 5.8E+07 | 25.2 |
| 1 | GDF8 | Compound 43 | Selective for Trk | 6682 | 46.2 | 5.4E+07 | 23.4 |
| 1 | GDF8 | Compound 42 | Selective for CDK | 5686 | 39.3 | 4.9E+07 | 21.2 |
| 1 | GDF8 | Compound 8 | Selective for GSK | 5018 | 34.7 | 4.7E+07 | 20.4 |
| 1 | GDF8 | Compound 9 | Selective for CDK | 4816 | 33.3 | 4.5E+07 | 19.4 |
| 1 | GDF8 | Compound 41 | Selective for GSK | 4455 | 30.8 | 3.4E+07 | 14.8 |
| 1 | GDF8 | n/a | n/a | 2856 | 19.7 | 2.2E+07 | 9.4 |
| 1 | GDF8 | Compound 57 | Selective for Trk | 2110 | 14.6 | 1.1E+07 | 4.8 |
| 1 | GDF8 | Compound 11 | Selective for CDK | 210 | 1.4 | −4.9E+05 | −0.2 |
| 1 | GDF8 | Compound 44 | Selective for GSK | 226 | 1.6 | −9.5E+05 | −0.4 |
| 1 | GDF8 | Compound 12 | Selective for CDK | 31 | 0.2 | −1.3E+06 | −0.6 |

TABLE 18

| | | | Cell Number | | | | Sox17 Expression | | | |
|---|---|---|---|---|---|---|---|---|---|---|
| Plate | Treatment | Compound # | Average Total Cell Number | SD | CV % | % of positive control | Average Total Intensity | SD | CV % | % of positive control |
| 1 | no Activin A (with Wnt3a) | none | 15489 | 0 | 0.00 | 103.2 | 3.75E+07 | 0.00E+00 | 0.00 | 10.9 |
| 1 | Activin A/Wnt3a | none | 15007 | 1991 | 13.27 | 100.0 | 3.45E+08 | 7.16E+07 | 20.75 | 100.0 |
| 1 | GDF8 | Compound 206 | 20568 | 1683 | 8.18 | 137.1 | 5.19E+08 | 4.41E+07 | 8.51 | 150.3 |
| 1 | GDF8 | Compound 207 | 19224 | 1091 | 5.68 | 128.1 | 2.54E+08 | 5.69E+07 | 22.41 | 73.6 |
| 1 | GDF8 | Compound 19 | 12569 | 1524 | 12.13 | 83.8 | 2.40E+08 | 6.34E+07 | 26.44 | 69.5 |

TABLE 18-continued

|  |  |  | Cell Number | | | | Sox17 Expression | | | |
| --- | --- | --- | --- | --- | --- | --- | --- | --- | --- | --- |
| Plate | Treatment | Compound # | Average Total Cell Number | SD | CV % | % of positive control | Average Total Intensity | SD | CV % | % of positive control |
| 1 | GDF8 | Compound 23 | 8758 | 474 | 5.41 | 58.4 | 1.16E+08 | 9.07E+06 | 7.80 | 33.7 |
| 1 | GDF8 | Compound 170 | 6460 | 2305 | 35.68 | 43.0 | 9.44E+07 | 6.98E+07 | 73.93 | 27.4 |
| 1 | GDF8 | Compound 208 | 4848 | 1225 | 25.27 | 32.3 | 2.26E+07 | 2.15E+07 | 94.96 | 23.6 |
| 1 | GDF8 | Compound 209 | 4831 | 1243 | 25.74 | 32.2 | 3.97E+07 | 1.61E+07 | 40.56 | 11.5 |
| 1 | GDF8 | Compound 32 | 4338 | 1520 | 35.04 | 28.9 | 3.63E+07 | 3.27E+07 | 90.14 | 10.5 |
| 1 | GDF8 | Compound 30 | 4679 | 435 | 9.29 | 31.2 | 3.47E+07 | 1.04E+07 | 30.03 | 10.1 |
| 1 | GDF8 | Compound 223 | 3704 | 1077 | 29.08 | 24.7 | 3.45E+07 | 2.74E+07 | 79.43 | 10.0 |
| 1 | GDF8 | Compound 2 | 4538 | 632 | 13.93 | 30.2 | 2.95E+07 | 2.81E+06 | 9.50 | 8.6 |
| 1 | GDF8 | Compound 210 | 2645 | 817 | 30.88 | 17.6 | 2.90E+07 | 2.45E+07 | 84.73 | 8.4 |
| 1 | GDF8 | Compound 24 | 5012 | 1263 | 25.21 | 33.4 | 2.64E+07 | 1.66E+07 | 62.95 | 7.7 |
| 1 | GDF8 | Compound 211 | 5165 | 796 | 15.41 | 34.4 | 2.61E+07 | 5.02E+06 | 19.23 | 7.6 |
| 1 | GDF8 | Compound 212 | 5476 | 1445 | 26.39 | 36.5 | 2.54E+07 | 1.18E+07 | 46.53 | 7.4 |
| 1 | GDF8 | Compound 224 | 5188 | 761 | 14.67 | 34.6 | 2.46E+07 | 8.26E+06 | 33.56 | 7.1 |
| 1 | GDF8 | Compound 225 | 4431 | 1149 | 25.92 | 29.5 | 2.45E+07 | 2.65E+07 | 108.19 | 7.1 |
| 1 | GDF8 | Compound 13 | 3123 | 1508 | 48.27 | 20.8 | 2.44E+07 | 2.30E+07 | 94.13 | 7.1 |
| 1 | GDF8 | Compound 213 | 1261 | 1028 | 81.49 | 8.4 | 2.07E+07 | 1.97E+07 | 95.03 | 6.0 |
| 1 | GDF8 | Compound 52 | 4932 | 386 | 7.82 | 32.9 | 1.99E+07 | 6.90E+06 | 34.67 | 5.8 |
| 1 | GDF8 | Compound 214 | 3345 | 335 | 10.01 | 22.3 | 1.93E+07 | 1.39E+07 | 72.18 | 5.6 |
| 1 | GDF8 | Compound 51 | 4289 | 940 | 21.91 | 28.6 | 1.70E+07 | 1.10E+07 | 64.86 | 4.9 |
| 1 | GDF8 | Compound 26 | 4896 | 545 | 11.14 | 32.6 | 1.65E+07 | 5.93E+06 | 36.02 | 4.8 |
| 1 | GDF8 | Compound 226 | 3617 | 577 | 15.94 | 24.1 | 1.59E+07 | 4.96E+06 | 31.21 | 4.6 |
| 1 | GDF8 | Compound 215 | 4326 | 165 | 3.81 | 28.8 | 1.45E+07 | 2.69E+06 | 18.53 | 4.2 |
| 1 | GDF8 | Compound 31 | 3619 | 1011 | 27.92 | 24.1 | 1.36E+07 | 4.63E+06 | 34.15 | 3.9 |
| 1 | GDF8 | Compound 216 | 3364 | 629 | 18.70 | 22.4 | 8.75E+06 | 2.30E+06 | 26.32 | 2.5 |
| 1 | GDF8 | Compound 217 | 2859 | 544 | 19.03 | 19.1 | 8.75E+06 | 1.94E+06 | 22.16 | 2.5 |
| 1 | GDF8 | Compound 218 | 1327 | 118 | 8.92 | 8.8 | 6.44E+06 | 9.70E+05 | 15.05 | 1.9 |
| 1 | GDF8 | Compound 219 | 368 | 168 | 45.67 | 2.5 | 1.79E+06 | 1.29E+06 | 72.17 | 0.5 |
| 2 | no Activin A (with Wnt3a) | none | 15778 | 0 | 0.00 | 103.2 | 2.24E+07 | 0.00E+00 | 0.00 | 6.7 |
| 2 | Activin A/Wnt3a | none | 15290 | 1119 | 7.32 | 100.0 | 3.37E+08 | 2.84E+07 | 8.44 | 100.0 |
| 2 | GDF8 | Compound 202 | 20177 | 987 | 4.89 | 132.0 | 4.85E+08 | 1.94E+07 | 4.00 | 144.0 |
| 2 | GDF8 | Compound 227 | 2911 | 4619 | 158.69 | 19.0 | 3.89E+07 | 6.69E+07 | 172.00 | 11.5 |
| 2 | GDF8 | Compound 15 | 4383 | 1775 | 40.49 | 28.7 | 3.57E+07 | 3.57E+07 | 100.03 | 10.6 |
| 2 | GDF8 | Compound 228 | 4043 | 1253 | 30.98 | 26.4 | 3.10E+07 | 2.53E+07 | 81.62 | 9.2 |
| 2 | GDF8 | Compound 229 | 3451 | 892 | 25.85 | 22.6 | 1.80E+07 | 1.46E+07 | 81.07 | 5.4 |
| 2 | GDF8 | Compound 4 | 3163 | 805 | 25.44 | 20.7 | 1.58E+07 | 3.54E+06 | 22.32 | 4.7 |
| 2 | GDF8 | Compound 220 | 2791 | 1453 | 52.05 | 18.3 | 1.40E+07 | 9.00E+06 | 64.28 | 4.2 |
| 2 | GDF8 | Compound 5 | 3137 | 1172 | 37.34 | 20.5 | 1.30E+07 | 7.52E+06 | 57.85 | 3.9 |
| 2 | GDF8 | Compound 230 | 2624 | 248 | 9.46 | 17.2 | 1.24E+07 | 1.55E+07 | 124.73 | 3.7 |
| 2 | GDF8 | Compound 231 | 4773 | 2651 | 55.55 | 31.2 | 1.22E+07 | 6.51E+06 | 53.37 | 3.6 |
| 2 | GDF8 | Compound 232 | 3273 | 1290 | 39.41 | 21.4 | 1.18E+07 | 1.51E+07 | 127.98 | 3.5 |
| 2 | GDF8 | Compound 221 | 1950 | 361 | 18.52 | 12.8 | 1.18E+07 | 1.54E+07 | 131.11 | 3.5 |
| 2 | GDF8 | Compound 233 | 3041 | 180 | 5.93 | 19.9 | 1.12E+07 | 1.09E+07 | 97.44 | 3.3 |
| 2 | GDF8 | Compound 147 | 3434 | 1199 | 34.91 | 22.5 | 1.12E+07 | 9.80E+06 | 87.75 | 3.3 |
| 2 | GDF8 | Compound 234 | 2835 | 623 | 21.98 | 18.5 | 9.47E+06 | 5.67E+06 | 59.84 | 2.8 |
| 2 | GDF8 | Compound 235 | 3391 | 2269 | 66.91 | 22.2 | 9.10E+06 | 6.51E+06 | 71.52 | 2.7 |
| 2 | GDF8 | Compound 236 | 2868 | 561 | 19.57 | 18.8 | 6.73E+06 | 6.32E+06 | 93.82 | 2.0 |
| 2 | GDF8 | Compound 33 | 2362 | 511 | 21.66 | 15.4 | 6.60E+06 | 2.45E+06 | 37.20 | 2.0 |
| 2 | GDF8 | Compound 1 | 3213 | 166 | 5.16 | 21.0 | 6.48E+06 | 3.09E+06 | 47.67 | 1.9 |
| 2 | GDF8 | Compound 53 | 2783 | 441 | 15.86 | 18.2 | 6.36E+06 | 2.89E+06 | 45.36 | 1.9 |
| 2 | GDF8 | Compound 237 | 2973 | 292 | 9.83 | 19.4 | 6.02E+06 | 3.00E+06 | 49.79 | 1.8 |
| 2 | GDF8 | Compound 238 | 2739 | 485 | 17.70 | 17.9 | 5.97E+06 | 6.10E+06 | 102.07 | 1.8 |
| 2 | GDF8 | Compound 239 | 3156 | 667 | 21.15 | 20.6 | 5.60E+06 | 2.42E+06 | 43.24 | 1.7 |
| 2 | GDF8 | Compound 240 | 3002 | 287 | 9.55 | 19.6 | 4.68E+06 | 3.13E+06 | 66.80 | 1.4 |
| 2 | GDF8 | Compound 200 | 2308 | 209 | 9.04 | 15.1 | 4.39E+06 | 1.88E+06 | 42.83 | 1.3 |
| 2 | GDF8 | Compound 222 | 1776 | 719 | 40.47 | 11.6 | 3.33E+06 | 2.52E+06 | 75.78 | 1.0 |
| 2 | GDF8 | Compound 241 | 2949 | 446 | 15.14 | 19.3 | 3.29E+06 | 1.55E+06 | 47.03 | 1.0 |
| 2 | GDF8 | Compound 242 | 385 | 184 | 47.83 | 2.5 | 1.08E+06 | 8.85E+05 | 81.61 | 0.3 |
| 2 | GDF8 | Compound 243 | 249 | 55 | 22.21 | 1.6 | 2.53E+05 | 3.07E+05 | 121.25 | 0.1 |
| 2 | GDF8 | Compound 204 | 250 | 21 | 8.38 | 1.6 | 1.36E+05 | 2.27E+04 | 16.66 | 0.0 |
| 3 | no Activin A (with Wnt3a) | none | 15796 | 0 | 0.00 | 99.6 | 2.82E+07 | 0.00E+00 | 0.00 | 8.0 |
| 3 | Activin A/Wnt3a | none | 15867 | 785 | 4.95 | 100.0 | 3.54E+08 | 2.40E+07 | 6.77 | 100.0 |
| 3 | GDF8 | Compound 34 | 6974 | 3723 | 53.38 | 44.0 | 2.07E+08 | 9.51E+07 | 45.85 | 58.6 |
| 3 | GDF8 | Compound 185 | 10892 | 1552 | 14.24 | 68.6 | 1.53E+08 | 4.08E+07 | 26.72 | 43.1 |
| 3 | GDF8 | Compound 35 | 7746 | 1873 | 24.17 | 48.8 | 1.35E+08 | 4.86E+07 | 36.08 | 38.0 |
| 3 | GDF8 | Compound 22 | 6727 | 1927 | 28.64 | 42.4 | 1.06E+08 | 5.04E+07 | 47.73 | 29.8 |
| 3 | GDF8 | Compound 34 | 4889 | 1152 | 23.57 | 30.8 | 4.31E+07 | 2.11E+07 | 48.95 | 12.2 |
| 3 | GDF8 | Compound 184 | 4173 | 1758 | 42.14 | 26.3 | 3.94E+07 | 2.24E+07 | 56.78 | 11.1 |
| 3 | GDF8 | Compound 223 | 4234 | 1604 | 37.88 | 26.7 | 3.55E+07 | 2.51E+07 | 70.56 | 10.0 |
| 3 | GDF8 | Compound 37 | 4187 | 338 | 8.06 | 26.4 | 3.11E+07 | 1.56E+07 | 50.18 | 8.8 |
| 3 | GDF8 | Compound 244 | 4479 | 1229 | 27.43 | 28.2 | 2.73E+07 | 1.52E+07 | 55.71 | 7.7 |
| 3 | GDF8 | Compound 245 | 4725 | 99 | 2.09 | 29.8 | 2.59E+07 | 1.03E+07 | 39.90 | 7.3 |
| 3 | GDF8 | Compound 246 | 3820 | 1091 | 28.57 | 24.1 | 2.30E+07 | 2.69E+07 | 117.08 | 6.5 |
| 3 | GDF8 | Compound 247 | 3730 | 966 | 25.90 | 23.5 | 2.14E+07 | 1.04E+07 | 48.63 | 6.1 |
| 3 | GDF8 | Compound 248 | 3875 | 445 | 11.48 | 24.4 | 2.13E+07 | 9.45E+06 | 44.45 | 6.0 |

TABLE 18-continued

| Plate | Treatment | Compound # | Cell Number | | | | Sox17 Expression | | | |
|---|---|---|---|---|---|---|---|---|---|---|
| | | | Average Total Cell Number | SD | CV % | % of positive control | Average Total Intensity | SD | CV % | % of positive control |
| 3 | GDF8 | Compound 25 | 3879 | 658 | 16.95 | 24.4 | 1.76E+07 | 1.21E+07 | 69.04 | 5.0 |
| 3 | GDF8 | Compound 195 | 3703 | 405 | 10.94 | 23.3 | 1.61E+07 | 3.27E+06 | 20.34 | 4.5 |
| 3 | GDF8 | Compound 227 | 2904 | 397 | 13.68 | 18.3 | 1.43E+07 | 1.35E+07 | 94.25 | 4.0 |
| 3 | GDF8 | Compound 183 | 3306 | 969 | 29.32 | 20.8 | 1.35E+07 | 1.14E+07 | 84.25 | 3.8 |
| 3 | GDF8 | Compound 187 | 2768 | 1426 | 51.51 | 17.4 | 1.35E+07 | 9.02E+06 | 66.67 | 3.8 |
| 3 | GDF8 | Compound 201 | 3213 | 1114 | 34.66 | 20.3 | 1.35E+07 | 1.69E+07 | 125.02 | 3.8 |
| 3 | GDF8 | Compound 197 | 3268 | 211 | 6.46 | 20.6 | 1.30E+07 | 5.25E+06 | 40.51 | 3.7 |
| 3 | GDF8 | Compound 249 | 3840 | 348 | 9.06 | 24.2 | 1.29E+07 | 6.79E+06 | 52.72 | 3.6 |
| 3 | GDF8 | Compound 141 | 2404 | 213 | 8.86 | 15.1 | 1.12E+07 | 4.95E+06 | 44.30 | 3.2 |
| 3 | GDF8 | Compound 194 | 3177 | 354 | 11.14 | 20.0 | 9.75E+06 | 2.11E+06 | 21.63 | 2.8 |
| 3 | GDF8 | Compound 250 | 3683 | 420 | 11.40 | 23.2 | 9.14E+06 | 4.78E+06 | 52.32 | 2.6 |
| 3 | GDF8 | Compound 251 | 3021 | 668 | 22.10 | 19.0 | 8.41E+06 | 4.59E+06 | 54.60 | 2.4 |
| 3 | GDF8 | Compound 20 | 2793 | 205 | 7.35 | 17.6 | 6.77E+06 | 1.86E+06 | 27.45 | 1.9 |
| 3 | GDF8 | Compound 252 | 2580 | 135 | 5.24 | 16.3 | 6.20E+06 | 2.31E+05 | 3.72 | 1.8 |
| 3 | GDF8 | Compound 253 | 2485 | 820 | 32.98 | 15.7 | 5.83E+06 | 1.47E+06 | 25.20 | 1.6 |
| 3 | GDF8 | Compound 202 | 2095 | 518 | 24.71 | 13.2 | 5.75E+06 | 2.62E+06 | 45.66 | 1.6 |
| 3 | GDF8 | Compound 21 | 371 | 294 | 79.19 | 2.3 | 2.36E+06 | 3.07E+06 | 129.78 | 0.7 |
| 4 | no Activin A (with Wnt3a) | none | 16629 | 0 | 0.00 | 119.3 | 2.42E+07 | 0.00E+00 | 0.00 | 7.8 |
| 4 | Activin A/Wnt3a | none | 13945 | 1535 | 11.01 | 100.0 | 3.09E+08 | 4.77E+07 | 15.46 | 100.0 |
| 4 | GDF8 | Compound 34 | 7416 | 6482 | 87.41 | 53.2 | 2.10E+08 | 1.82E+08 | 86.70 | 68.0 |
| 4 | GDF8 | Compound 240 | 11283 | 2023 | 17.93 | 80.9 | 1.61E+08 | 4.41E+07 | 27.34 | 52.2 |
| 4 | GDF8 | Compound 28 | 5236 | 1787 | 34.12 | 37.5 | 4.03E+07 | 3.08E+07 | 76.36 | 13.1 |
| 4 | GDF8 | Compound 198 | 3985 | 2674 | 67.10 | 28.6 | 3.89E+07 | 5.55E+07 | 142.91 | 12.6 |
| 4 | GDF8 | Compound 196 | 4861 | 1501 | 30.87 | 34.9 | 3.03E+07 | 1.98E+07 | 65.37 | 9.8 |
| 4 | GDF8 | Compound 18 | 1921 | 1759 | 91.56 | 13.8 | 2.94E+07 | 3.65E+07 | 123.90 | 9.5 |
| 4 | GDF8 | Compound 186 | 3486 | 425 | 12.19 | 25.0 | 2.34E+07 | 1.42E+07 | 60.78 | 7.6 |
| 4 | GDF8 | Compound 254 | 3960 | 1521 | 38.42 | 28.4 | 2.31E+07 | 2.27E+07 | 98.10 | 7.5 |
| 4 | GDF8 | Compound 168 | 3460 | 324 | 9.36 | 24.8 | 2.28E+07 | 7.13E+06 | 31.23 | 7.4 |
| 4 | GDF8 | Compound 190 | 3402 | 1318 | 38.74 | 24.4 | 1.87E+07 | 1.58E+07 | 84.61 | 6.1 |
| 4 | GDF8 | Compound 255 | 4006 | 1625 | 40.57 | 28.7 | 1.52E+07 | 1.05E+07 | 68.91 | 4.9 |
| 4 | GDF8 | Compound 50 | 2666 | 743 | 27.86 | 19.1 | 1.48E+07 | 8.30E+06 | 56.15 | 4.8 |
| 4 | GDF8 | Compound 27 | 3721 | 721 | 19.37 | 26.7 | 1.19E+07 | 9.69E+06 | 81.29 | 3.9 |
| 4 | GDF8 | Compound 256 | 2922 | 1275 | 43.64 | 21.0 | 9.41E+06 | 8.65E+06 | 92.01 | 3.0 |
| 4 | GDF8 | Compound 257 | 3182 | 705 | 22.14 | 22.8 | 8.06E+06 | 4.49E+06 | 55.75 | 2.6 |
| 4 | GDF8 | Compound 258 | 2731 | 472 | 17.29 | 19.6 | 7.89E+06 | 7.24E+06 | 91.70 | 2.6 |
| 4 | GDF8 | Compound 189 | 2350 | 1625 | 69.16 | 16.9 | 7.72E+06 | 5.36E+06 | 69.41 | 2.5 |
| 4 | GDF8 | Compound 259 | 2195 | 955 | 43.49 | 15.7 | 6.92E+06 | 2.58E+06 | 37.29 | 2.2 |
| 4 | GDF8 | Compound 260 | 2468 | 741 | 30.04 | 17.7 | 6.64E+06 | 3.33E+06 | 50.18 | 2.2 |
| 4 | GDF8 | Compound 261 | 2965 | 456 | 15.38 | 21.3 | 6.23E+06 | 2.10E+06 | 33.61 | 2.0 |
| 4 | GDF8 | Compound 192 | 2377 | 572 | 24.08 | 17.0 | 6.17E+06 | 2.76E+06 | 44.65 | 2.0 |
| 4 | GDF8 | Compound 262 | 2894 | 399 | 13.78 | 20.8 | 5.75E+06 | 3.00E+06 | 52.20 | 1.9 |
| 4 | GDF8 | Compound 188 | 3005 | 759 | 25.26 | 21.6 | 5.02E+06 | 3.97E+06 | 79.06 | 1.6 |
| 4 | GDF8 | Compound 263 | 2129 | 230 | 10.79 | 15.3 | 4.77E+06 | 1.14E+06 | 23.93 | 1.5 |
| 4 | GDF8 | Compound 264 | 2630 | 342 | 13.00 | 18.9 | 4.28E+06 | 2.17E+06 | 50.73 | 1.4 |
| 4 | GDF8 | Compound 265 | 2636 | 1372 | 52.04 | 18.9 | 4.27E+06 | 1.15E+06 | 26.86 | 1.4 |
| 4 | GDF8 | Compound 14 | 274 | 14 | 5.02 | 2.0 | 1.56E+05 | 9.51E+04 | 60.91 | 0.1 |
| 4 | GDF8 | Compound 205 | 241 | 3 | 1.20 | 1.7 | 1.36E+05 | 6.83E+04 | 50.42 | 0.0 |
| 4 | GDF8 | Compound 266 | 271 | 7 | 2.67 | 1.9 | 1.18E+05 | 3.34E+04 | 28.43 | 0.0 |
| 4 | GDF8 | Compound 203 | 253 | 4 | 1.49 | 1.8 | 1.09E+05 | 3.49E+04 | 32.09 | 0.0 |

TABLE 19

| Compound # | Sox17 Expression % of positive control |
|---|---|
| Compound 181 | 150.3 |
| Compound 202 | 144.0 |
| Compound 180 | 73.6 |
| Compound 19 | 69.5 |
| Compound 34 | 68.0 |
| Compound 40 | 52.2 |
| Compound 185 | 43.1 |
| Compound 185 | 38.0 |
| Compound 35 | 33.7 |
| Compound 23 | 29.8 |
| Compound 22 | 27.4 |
| Compound 17 | 23.6 |

What is claimed is:

1. A method to differentiate pluripotent stem cells into cells expressing markers characteristic of the definitive endoderm lineage, comprising treating the pluripotent stem cells with a medium lacking activin A, and containing GDF-8 and a cyclic analine-pyridinotriazine comprising 5-Chloro-1,8,10,12,16,22,26,32-octaazapentacyclo[24.2.2.1~3,7~.1~9,13~.1~14,18~]tritriaconta-3(33),4,6,9(32),10,12,14(31),15,17-nonaen-23-one, for a period of time sufficient for the pluripotent stem cells to differentiate into cells expressing markers characteristic of the definitive endoderm lineage.

2. The method of claim 1, wherein the method increases the percentage of cells expressing CXCR4.

3. The method of claim 1, wherein the medium further comprises EGF, FGF or EGF and FGF and wherein the method enhances expression of SOX17.

4. The method of claim 1, wherein the medium is further lacking Wnt3a.

5. The method of claim 1, wherein the medium further comprises at least one factor selected from the group consisting of: PDGF-A, PDGF-B, PDGF-C, PDGF-D, VEGF, muscimol, PD98059, LY294002, U0124, U0126, and sodium butyrate.

6. A method of enhancing the differentiation of pluripotent stem cells into definitive endoderm lineage cells comprising differentiating pluripotent stem cells into definitive endoderm cells by culturing the pluripotent stem cells for about one to about three days with a medium lacking activin A, and containing GDF-8 and 5-Chloro-1,8,10,12,16,22,26,32-octaazapentacyclo[24.2.2.1~3,7~.1~9,13~.1~14,18~]tritriaconta-3(33),4,6,9(32),10,12,14(31),15,17-nonaen-23-one.

7. The method of claim 6, wherein the medium further comprises at least one factor selected from the group consisting of: EGF, FGF4, PDGF-A, PDGF-B, PDGF-C, PDGF-D, VEGF, muscimol, PD98059, LY294002, U0124, U0126, and sodium butyrate.

8. The method of claim 6, wherein the method comprises culturing the pluripotent stem cells with a medium lacking activin A, and containing GDF-8 and 5-Chloro-1,8,10,12,16,22,26,32-octaazapentacyclo[24.2.2.1~3,7~.1~9,13~.1~14,18~]tritriaconta-3(33),4,6,9(32),10,12,14(31),15,17-nonaen-23-one for about one day.

9. A method of enhancing the yield of definitive endoderm cells in a population comprising definitive endoderm cells comprising: differentiating a population of pluripotent stem cells into the population comprising definitive endoderm cells by culturing the pluripotent stem cells in a medium lacking activin A, and containing GDF-8 and 5-Chloro-1,8,10,12,16,22,26,32-octaazapentacyclo[24.2.2.1~3,7~.1~9,13~.1~14,18~]tritriaconta-3(33),4,6,9(32),10,12,14(31),15,17-nonaen-23-one.

10. The method of claim 9, wherein the method comprises culturing in the medium from about one to about three days.

11. The method of claim 9, wherein the medium further comprises at least one factor selected from the group consisting of: EGF, FGF4, PDGF-A, PDGF-B, PDGF-C, PDGF-D, VEGF, muscimol, PD98059, LY294002, U0124, U0126, and sodium butyrate.

12. The method of claim 1, wherein said method enhances differentiation into the definitive endoderm lineage when compared to cells treated with a medium comprising activin A.

13. The method of claim 1, wherein the cells are cultured in the medium for about one to seven days.

* * * * *